(12) United States Patent
Dower et al.

(10) Patent No.: US 11,358,986 B2
(45) Date of Patent: *Jun. 14, 2022

(54) IL-2RBETA BINDING COMPOUNDS

(71) Applicant: MEDIKINE, INC., Menlo Park, CA (US)

(72) Inventors: William J. Dower, Menlo Park, CA (US); Michael C. Needels, Menlo Park, CA (US); Ronald W. Barrett, Menlo Park, CA (US); Alice V. Bakker, Menlo Park, CA (US); Steven E. Cwirla, Menlo Park, CA (US)

(73) Assignee: MEDIKINE, INC., Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/884,661

(22) Filed: May 27, 2020

(65) Prior Publication Data

US 2020/0291066 A1    Sep. 17, 2020

Related U.S. Application Data

(63) Continuation of application No. 16/531,954, filed on Aug. 5, 2019, now Pat. No. 10,703,776.

(60) Provisional application No. 62/785,754, filed on Dec. 28, 2018, provisional application No. 62/715,097, filed on Aug. 6, 2018.

(51) Int. Cl.
| | |
|---|---|
| *C07K 7/06* | (2006.01) |
| *C07K 14/00* | (2006.01) |
| *C07K 7/08* | (2006.01) |
| *A61K 38/00* | (2006.01) |

(52) U.S. Cl.
CPC .......... *C07K 7/06* (2013.01); *C07K 7/08* (2013.01); *C07K 14/001* (2013.01); *A61K 38/00* (2013.01)

(58) Field of Classification Search
CPC ................. C07K 7/06; C07K 14/001
See application file for complete search history.

(56) References Cited

U.S. PATENT DOCUMENTS

| | | | | |
|---|---|---|---|---|
| 5,635,597 | A * | 6/1997 | Barrett | C07K 7/08 530/300 |
| 9,861,705 | B2 | 1/2018 | Bossard et al. | |
| 10,689,417 | B2 | 6/2020 | Dower et al. | |
| 10,703,776 | B2 * | 7/2020 | Dower | C07K 7/06 |
| 2003/0166163 | A1 | 9/2003 | Gillies | |
| 2011/0243887 | A1 | 10/2011 | Lauder et al. | |
| 2013/0330296 | A1 | 12/2013 | Khaled | |
| 2017/0327555 | A1 | 11/2017 | Greve | |
| 2018/0125941 | A1 | 5/2018 | Greve | |
| 2018/0162919 | A1 | 6/2018 | Greve et al. | |
| 2018/0362655 | A1 | 12/2018 | Wang et al. | |
| 2019/0119346 | A1 | 4/2019 | Garcia et al. | |
| 2019/0153058 | A1 | 5/2019 | Greve | |
| 2019/0194255 | A1 | 6/2019 | Tagaya et al. | |
| 2019/0202881 | A1 | 7/2019 | Greve | |
| 2019/0202882 | A1 | 7/2019 | Greve | |
| 2020/0040034 | A1 | 2/2020 | Dower et al. | |
| 2020/0291067 | A1 | 9/2020 | Dower et al. | |
| 2021/0130424 | A1 | 5/2021 | Dower et al. | |
| 2021/0198336 | A1 | 7/2021 | Dower et al. | |
| 2021/0253669 | A1 | 8/2021 | Dower et al. | |
| 2021/0253670 | A1 | 8/2021 | Dower et al. | |

FOREIGN PATENT DOCUMENTS

| | | |
|---|---|---|
| WO | 2010/099084 | 9/2010 |
| WO | 2017/136818 A2 | 8/2017 |

OTHER PUBLICATIONS

Betts et al., 2003, Chapter 14: Amino Acid Properties and Consequences of Substitutions, Bioinformatics for Geneticists (Barnes and Gray eds.), 28 pages.*
Chen et al., 2013, Fusion Protein linkers: Property, Design and Functionality, Adv Drug Deliv Rev, 65(10): 1357-1369.*
Partial International Search for PCT Application No. PCT/US2019/045109, dated Nov. 5, 2019, 17 pages.
Klein et al., "Cergutuzumab amunaleukin (CEA-IL2v), a CEA-targeted IL-2 variant-based immunocytokine for combination cancer immunotherapy: Overcoming limitations of aldeslukin and conventional IL-2-based immunocytokines," OncoImmunology, 2017, vol. 6, No. 3, e1277306, 15 pages.
Levin et al., "Exploiting a natural conformational switch to engineer an interleukin-2 'superkine'," Nature, Apr. 2012, vol. 484, p. 529-533.
Mitra et al., "Interleukin-2 Activity can be Fine-Tuned with Engineered Receptor Signaling Clamps," Immunity, May 2015, vol. 42, No. 5, 29 pages.
Pulliam et al., "Common gamma chain cytokines in combinatorial immune strategies against cancer," Immunology Letters, 2016, vol. 169, p. 61-72.
International Search Report and Written Opinion for PCT Application No. PCT/US2019/045109, dated Jan. 14, 2020, 20 pages.
International Search Report and Written Opinion for PCT Application No. PCT/US2020/058963, dated Apr. 7, 2021, 12 pages.
International Search Report and written Opinion for PCT Application No. PCT/US2020/058969, dated Apr. 6, 2021, 14 pages.
UNIPROTKB Accession No. A0A227JM75, Oct. 25, 2017, retrieved from https://www.uniprot.org/uniprot/A0A227JM75, entire document retrieved on Mar. 22, 2021, 5 pages.
UNIPROTKB Accession No. A0A2D7IYS8, Apr. 25, 2018, retrieved from https://www.uniprot.org/uniprot/A0A2D7IYS8, entire document retrieved on Mar. 19, 2021, 3 pages.
UNIPROTKB Accession No. A0A1D1ZF92, Nov. 30, 2016, retrieved from https://www.uniprot.org/uniprot/A0A1D1ZF92, entire document retrieved on Mar. 19, 2021, 3 pages.

(Continued)

*Primary Examiner* — Amber D Steele

(57) ABSTRACT

IL-2Rβ ligands and IL-2Rγc ligands and compounds comprising the ligands are disclosed. The ligands and compounds such as heterodimers and fusion proteins comprising the IL-2Rβ ligands and/or the IL-2Rγc ligands can be IL-2 receptor agonists.

30 Claims, 12 Drawing Sheets

Specification includes a Sequence Listing.

(56) References Cited

OTHER PUBLICATIONS

International Search Report and Written Opinion for PCT Application No. PCT/US2021/016356, dated Jul. 13, 2021, 12 pages.
International Search Report and Written Opinion for PCT Application No. PCT/US2021/016361, dated Jul. 15, 2021, 12 pages.
Dower et al., "MDK/MDK-701: A potent fully efficacious peptidyl agonist of IL-7Rαγc, designed with no reference to cytokine or receptor structure and unrelated to IL-7, fused to an FC-domain for PK enhancement", Journal for ImmunoTherapy of Cancer, 2020, vol. 8, Issue 3, pp. A341-A342.
McElroy et al., "Structural reorganization of the interleukin-7 signaling complex", PNAS, 2012, vol. 109, No. 7, pp. 2503-2508.
Moors et al., "Interneukin-7 (IL-7) and IL-7 splice variants affect differentiation of human neural progenitor cells", Genes and Immunity, 2010, vol. 11, pp. 11-20.
UNIPROTKB Accession No. A0A444GHQ1, May 8, 2019, retrieved from https://www.uniprot.org/uniprot/A0A444GHQ1, entire document retrieved on Jun. 12, 2021.
UNIPROTKB Accession No. A0A0N1IMW7, Dec. 9, 2015, retrieved from https://www.uniprot.org/uniprot/A0A0N1IMW7, entire document retrieved on Jun. 12, 2021.

\* cited by examiner

| # | Cell line | Treatment |
|---|---|---|
| 1 | TF-1β | A 10µM |
| 2 | TF-1β | B 10µM |
| 3 | TF-1β | C 10µM |
| 4 | TF-1β | rhIL-2 1ng/mL |
| 5 | TF-1β | Starvation Medium (SM) |
| 6 | TF-1 | A 10µM |
| 7 | TF-1 | B 10µM |
| 8 | TF-1 | C 10µM |
| 9 | TF-1 | rhIL-2 1ng/mL |
| 10 | TF-1 | Starvation Medium (SM) |

| # | Peptide conc. (nM) |
|---|---|
| 1 | 10,000 |
| 2 | 3333.3 |
| 3 | 1111.1 |
| 4 | 370.4 |
| 5 | 123.5 |
| 6 | 41.15 |
| 7 | 13.72 |
| 8 | 4.572 |
| 9 | 1.524 |
| 10 | 0.508 |
| 11 | 0 |

```
                        SEQUENCE LISTING

<160> NUMBER OF SEQ ID NOS: 1103

<210> SEQ ID NO 1
  <211> LENGTH: 8
  <212> TYPE: PRT
  <213> ORGANISM: Artificial Sequence
  <220> FEATURE:
  <223> OTHER INFORMATION: Description of Artificial Sequence: Synthetic
        peptide
  <220> FEATURE:
  <221> NAME/KEY: MOD_RES
  <222> LOCATION: (1)..(1)
  <223> OTHER INFORMATION: A, D, E, F, G, H, M, N, Q, R, S, T, W, and Y
  <220> FEATURE:
  <221> NAME/KEY: MOD_RES
  <222> LOCATION: (2)..(2)
  <223> OTHER INFORMATION: A, D, E, F, G, I, K, L, M, N, Q, R, S, T, V,
        and Y
  <220> FEATURE:
  <221> NAME/KEY: MOD_RES
  <222> LOCATION: (3)..(3)
  <223> OTHER INFORMATION: A, G, I, Q, S, T, V, and W
  <220> FEATURE:
  <221> NAME/KEY: MOD_RES
  <222> LOCATION: (4)..(4)
  <223> OTHER INFORMATION: A, D, E, G, H, K, L, M, N, P, Q, R, S, T, and V
  <220> FEATURE:
  <221> NAME/KEY: MOD_RES
  <222> LOCATION: (5)..(5)
  <223> OTHER INFORMATION: F, I, K, L, Q, and V
  <220> FEATURE:
  <221> NAME/KEY: MOD_RES
  <222> LOCATION: (6)..(6)
  <223> OTHER INFORMATION: D, F, G, H, M, N, W, and Y
  <220> FEATURE:
  <221> NAME/KEY: MOD_RES
  <222> LOCATION: (7)..(7)
  <223> OTHER INFORMATION: A, D, E, M, P, Q, S, T, V, and W
  <220> FEATURE:
  <221> NAME/KEY: MOD_RES
  <222> LOCATION: (8)..(8)
  <223> OTHER INFORMATION: D, F, I, L, M, S, T, V, and Y

<400> SEQUENCE: 1

Xaa Xaa Xaa Xaa Xaa Xaa Xaa Xaa
  1               5

<210> SEQ ID NO 2
  <211> LENGTH: 12
  <212> TYPE: PRT
  <213> ORGANISM: Artificial Sequence
  <220> FEATURE:
  <223> OTHER INFORMATION: Description of Artificial Sequence: Synthetic
        peptide
  <220> FEATURE:
  <221> NAME/KEY: MOD_RES
  <222> LOCATION: (1)..(1)
  <223> OTHER INFORMATION: A, C, D, E, F, G, H, K, L, N, P, R, S, T, W,
        and Y
  <220> FEATURE:
  <221> NAME/KEY: MOD_RES
  <222> LOCATION: (3)..(3)
  <223> OTHER INFORMATION: A, D, E, F, G, H, M, N, Q, R, S, T, W, and Y
```

```
<220> FEATURE:
<221> NAME/KEY: MOD_RES
<222> LOCATION: (4)..(4)
<223> OTHER INFORMATION: A, D, E, F, G, I, K, L, M, N, Q, R, S, T, V,
      and Y
<220> FEATURE:
<221> NAME/KEY: MOD_RES
<222> LOCATION: (5)..(5)
<223> OTHER INFORMATION: A, G, I, Q, S, T, V, and W
<220> FEATURE:
<221> NAME/KEY: MOD_RES
<222> LOCATION: (6)..(6)
<223> OTHER INFORMATION: A, D, E, G, H, K, L, M, N, P, Q, R, S, T, and V
<220> FEATURE:
<221> NAME/KEY: MOD_RES
<222> LOCATION: (7)..(7)
<223> OTHER INFORMATION: F, I, K, L, Q, and V
<220> FEATURE:
<221> NAME/KEY: MOD_RES
<222> LOCATION: (8)..(8)
<223> OTHER INFORMATION: D, F, G, H, M, N, W, and Y
<220> FEATURE:
<221> NAME/KEY: MOD_RES
<222> LOCATION: (9)..(9)
<223> OTHER INFORMATION: A, D, E, M, P, Q, S, T, V, and W
<220> FEATURE:
<221> NAME/KEY: MOD_RES
<222> LOCATION: (10)..(10)
<223> OTHER INFORMATION: D, F, I, L, M, S, T, V, and Y
<220> FEATURE:
<221> NAME/KEY: MOD_RES
<222> LOCATION: (12)..(12)
<223> OTHER INFORMATION: D, E, F, H, I, L, M, Q, S, T, V, W, and Y

<400> SEQUENCE: 2

Xaa Cys Xaa Xaa Xaa Xaa Xaa Xaa Xaa Cys Xaa
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A, D, E, F, G, I, K, L, M, N, P, Q, S, T, V, W,
      and Y
<220> FEATURE:
<221> NAME/KEY: MOD_RES
<222> LOCATION: (2)..(2)
<223> OTHER INFORMATION: A, C, D, E, F, G, H, K, L, N, P, R, S, T, W,
      and Y
<220> FEATURE:
<221> NAME/KEY: MOD_RES
<222> LOCATION: (4)..(4)
<223> OTHER INFORMATION: A, D, E, F, G, H, M, N, Q, R, S, T, W, and Y
<220> FEATURE:
<221> NAME/KEY: MOD_RES
<222> LOCATION: (5)..(5)
<223> OTHER INFORMATION: A, D, E, F, G, I, K, L, M, N, Q, R, S, T, V,
      and Y
<220> FEATURE:
<221> NAME/KEY: MOD_RES
<222> LOCATION: (6)..(6)
<223> OTHER INFORMATION: A, G, I, Q, S, T, V, and W
<220> FEATURE:
<221> NAME/KEY: MOD_RES
<222> LOCATION: (7)..(7)
<223> OTHER INFORMATION: A, D, E, G, H, K, L, M, N, P, Q, R, S, T, and V
<220> FEATURE:
<221> NAME/KEY: MOD_RES
<222> LOCATION: (8)..(8)
<223> OTHER INFORMATION: F, I, K, L, Q, and V
<220> FEATURE:
```

```
<221> NAME/KEY: MOD_RES
<222> LOCATION: (9)..(9)
<223> OTHER INFORMATION: D, F, G, H, M, N, W, and Y
<220> FEATURE:
<221> NAME/KEY: MOD_RES
<222> LOCATION: (10)..(10)
<223> OTHER INFORMATION: A, D, E, M, P, Q, S, T, V, and W
<220> FEATURE:
<221> NAME/KEY: MOD_RES
<222> LOCATION: (11)..(11)
<223> OTHER INFORMATION: D, F, I, L, M, S, T, V, and Y
<220> FEATURE:
<221> NAME/KEY: MOD_RES
<222> LOCATION: (13)..(13)
<223> OTHER INFORMATION: D, E, F, H, I, L, M, Q, S, T, V, W, and Y
<220> FEATURE:
<221> NAME/KEY: MOD_RES
<222> LOCATION: (14)..(14)
<223> OTHER INFORMATION: F, I, L, M, N, S, V, W, and Y

<400> SEQUENCE: 3

Xaa Xaa Cys Xaa Xaa Xaa Xaa Xaa Xaa Xaa Cys Xaa Xaa
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Asp Cys Ser Ser Ala Ser Val Gly Thr Ile Cys Tyr Leu
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Glu Cys Gly Val Trp Asp Leu Trp Pro Asp Cys Trp Ile
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Phe Cys Asp Glu Ala Arg Val Gly Glu Leu Cys Val Met
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Asp Cys Ser Thr Ala Gln Val Gly Glu Leu Cys Val Met
```

```
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Thr Cys Ala Ile Ala Gln Leu Tyr Asp Leu Cys Asp Leu
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Tyr Cys Arg Asn Ser Asn Val Gly Asp Val Cys Tyr Leu
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Asp Cys Arg Tyr Ala Glu Val Gly Val Leu Cys Gln Met
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Asp Cys Gln Thr Ala Glu Leu Gly Asp Leu Cys Ile Val
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Phe Phe Cys Tyr Leu Ile Gly Gln Asp Glu Phe Cys Glu Phe
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
```

```
               peptide

<400> SEQUENCE: 13

Phe Pro Cys Gln Ile Ala Met Ile Gly Glu Tyr Cys Asp Trp
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Phe Arg Cys Trp Glu Ala Pro Val Gly Glu Ile Cys Glu Leu
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Ser Cys Asp Gln Ala Thr Leu Gly Gln Ile Cys Val Ile
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Asp Cys Tyr Phe Ser Gln Ile Gly Glu Leu Cys Met Leu
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Pro Cys Gln Gln Ala Lys Leu Gly Glu Leu Cys Asp Leu
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Asp Cys Ala Gln Ala Thr Val Gly Gln Tyr Cys Thr Leu
1               5                   10

<210> SEQ ID NO 19
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ile Asp Cys Ser Asp Ala Ala Val Gly Ala Leu Cys Thr Gln
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Asp Cys Thr Arg Ala Ser Leu Gly Asp Ile Cys Val Trp
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ile Glu Cys Glu Arg Ala Gln Ile Gly Glu Val Cys Gln Ile
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ile Phe Cys Gly Asp Ala Gln Leu Gly Glu Val Cys Ser Leu
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ile Phe Cys Gln Phe Ala Arg Leu Gly Gln Thr Cys Gln Leu
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24
```

```
Ile Pro Cys Ser Ile Ala Gln Leu Phe Ser Leu Cys Asp Val
1               5                   10
```

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Ile Pro Cys Tyr Leu Ala Glu Leu Gly Gln Val Cys Ser Leu
1               5                   10
```

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Lys Asn Cys Glu Val Ala Arg Leu Gly Asp Tyr Cys Glu Ile
1               5                   10
```

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Leu Ala Cys Ser Gln Ala Pro Leu Gly Thr Leu Cys Glu Ile
1               5                   10
```

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Leu Asp Cys Gly Ile Ala Leu Gln Gly Gln Leu Cys Asp Tyr
1               5                   10
```

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Leu Asp Cys Ser Leu Ser Ser Leu Gly Asp Tyr Cys Tyr Met
1               5                   10
```

<210> SEQ ID NO 30
<211> LENGTH: 14
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 30

Leu Gly Cys Phe Glu Ala Gln Ile Gly Met Ile Cys Asp Leu
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu His Cys Tyr Leu Ala Val Leu Gly Gln Leu Cys Asp Val
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Leu Cys Gln Val Ala Ser Leu Gly Asp Tyr Cys Thr Ile
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Pro Cys Asp Met Ala Asp Leu Phe Thr Leu Cys Asp Tyr
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Ser Cys Gly Ile Ala Gln Ile Gly Gln Val Cys Asp Met
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Trp Cys Gln Asp Ala Gln Ile Gly Asp Val Cys Trp Leu
1               5                   10

```
<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Met Glu Cys Phe Leu Ala Ala Val Gly Gln Ile Cys Glu Leu
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Met Phe Cys Gln Thr Ala Glu Val Gly Gln Met Cys Leu Leu
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Met Leu Cys Trp Glu Ala Pro Val Gly Asp Val Cys Thr Ile
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asn Phe Cys Ser Gly Ala Gly Leu Gly Glu Leu Cys Val Ile
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asn Leu Cys Glu Tyr Ser Lys Val Gly Glu Val Cys Val Phe
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41
```

Asn Tyr Cys Tyr Gln Ala Leu Leu Asp Thr Tyr Cys Ile Leu
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Pro Asp Cys Trp Tyr Ala Gly Leu Gly Gln Ile Cys Glu Phe
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Pro Ser Cys Trp Met Ala Gln Val Gly Asp Leu Cys Phe Ile
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Pro Thr Cys Asp Thr Ala Ala Val Gly Asp Leu Cys Glu Phe
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Asp Cys Phe Gln Ala Pro Ile Gly Ser Leu Cys Tyr Leu
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Trp Cys Tyr Met Thr Asp Val Gly Asp Leu Cys Glu Leu
1               5                   10

<210> SEQ ID NO 47
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 47

Ser Asp Cys His Leu Ala Gln Val Gly Glu Phe Cys Phe Leu
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Asp Cys Tyr Leu Ser Gln Val Gly Ser Leu Cys Asp Phe
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Pro Cys Ser Glu Ala Ser Leu Phe Gln Leu Cys Asp Leu
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Trp Cys Gln Val Gly Asp Phe Trp Asp Val Cys Thr Ser
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Glu Cys Trp Leu Gln Ala Leu Gly Glu Leu Cys Asp Phe
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Val Ala Cys Ser Ser Val Gln Val Gly Glu Leu Cys Asp Phe
1               5                   10
```

```
<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Val Glu Cys Met Met Ser Ser Leu Gly Asp Leu Cys Ser Phe
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Asn Cys Trp Glu Ala Gln Val Gly Trp Leu Cys Asp Trp
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Val Thr Cys Asp Lys Ala Thr Val Gly Gln Met Cys Ser Ile
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Ser Cys Asp Val Ala Ser Val Gly Ser Tyr Cys Met Leu
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 57

Xaa Asp Cys Ser Glu Ala Leu Leu Gly Gln Ile Cys Thr Tyr
1               5                   10

<210> SEQ ID NO 58
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 58

Tyr Asp Cys Arg Ile Ala Gln Val Gly Glu Leu Cys Asp Leu
1               5                   10

<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Tyr Glu Cys Phe Gln Ala Gln Val Gly Gln Leu Cys Asp Val
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Val Asp Cys Ser Arg Ala Val Val Gly Glu Leu Cys Val Asn
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Ala Cys Glu Val Ala Lys Val Gly Glu Leu Cys Asp Leu
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ile Arg Cys Glu Asp Ala Leu Leu Gly Asp Phe Cys Ile Phe
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Phe Cys His Gln Ala Gln Ile Gly Glu Leu Cys Ser Val
1               5                   10
```

```
<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Pro Asp Cys Ser Val Ala Leu Leu Gly Glu Ser Cys Ser Val
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Thr Gly Cys Asn Leu Ala Gln Ile Gly Asp Leu Cys Asp Leu
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ile Gly Cys Ser Leu Ala Arg Leu Gly Glu Tyr Cys Val Ile
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Leu Glu Cys Trp Gln Ala Gln Lys Gly Asp Leu Cys Asp Leu
1               5                   10

<210> SEQ ID NO 68
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Met Asp Cys Ser Asp Ala His Val Gly Gln Ile Cys Ser Ile
1               5                   10

<210> SEQ ID NO 69
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 69

Ala Leu Cys Gln Ala Ala Gln Val Gly Gln Leu Cys Asp Leu
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Leu Trp Cys Gly Asp Ala Ser Leu Gly Gln Leu Cys Trp Leu
1               5                   10

<210> SEQ ID NO 71
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp His Cys Ser Glu Ala Gln Ile Gly Gln Leu Asp His Leu
1               5                   10

<210> SEQ ID NO 72
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Asp Cys Phe Tyr Ala Thr Leu Gly Gln Val Cys Ser Leu
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Asp Cys Ser Glu Ala Leu Leu Gly Gln Ile Cys Thr Tyr
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Gly Cys Trp Gln Ala Pro Val Gly Ser Leu Cys Glu Leu
1               5                   10

<210> SEQ ID NO 75
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 75

Ser Gly Cys Glu Tyr Ala Thr Leu Gly Ser Leu Cys Asp Leu
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Leu Cys Ser Leu Ala Pro Leu Gly Ser Leu Cys Asp Leu
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Leu Cys Ser Met Val Gly Leu Gly Gln Leu Cys Asp Leu
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ile Pro Cys Ser Val Ala Arg Val Gly Trp Leu Cys Asp Leu
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asp Pro Cys Tyr Ala Ala Val Leu Asn Ser Leu Cys Asp Ile
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asp Ser Cys Gln Asn Ala Pro Leu Gly Ser Tyr Cys Val Leu
1               5                   10
```

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Leu Pro Cys Ser Leu Ala Lys Leu His Glu Leu Cys Asp Ile
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Ser Cys Ser Asp Ala Gln Leu Met Gln Leu Cys Glu Ile
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Cys Cys Tyr Gln Ala Met Val Gly Asp Leu Cys Asp Phe Cys
1               5                   10

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ser Ser Ala Ser Val Gly Thr Ile
1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Val Trp Asp Leu Trp Pro Asp
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 86

Asp Glu Ala Arg Val Gly Glu Leu
1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Thr Ala Gln Val Gly Glu Leu
1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Ile Ala Gln Leu Tyr Asp Leu
1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Asn Ser Asn Val Gly Asp Val
1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Tyr Ala Glu Val Gly Val Leu
1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Thr Ala Glu Leu Gly Asp Leu
1               5

<210> SEQ ID NO 92
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Tyr Leu Ile Gly Gln Asp Glu Phe
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Ile Ala Met Ile Gly Glu Tyr
1               5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Trp Glu Ala Pro Val Gly Glu Ile
1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Asp Gln Ala Thr Leu Gly Gln Ile
1               5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Tyr Phe Ser Gln Ile Gly Glu Leu
1               5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Gln Ala Lys Leu Gly Glu Leu
```

```
<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Gln Ala Thr Val Gly Gln Tyr
1               5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ser Asp Ala Ala Val Gly Ala Leu
1               5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Thr Arg Ala Ser Leu Gly Asp Ile
1               5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Glu Arg Ala Gln Ile Gly Glu Val
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Asp Ala Gln Leu Gly Glu Val
1               5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                         peptide

<400> SEQUENCE: 103

Gln Phe Ala Arg Leu Gly Gln Thr
1               5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Ile Ala Gln Leu Phe Ser Leu
1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Tyr Leu Ala Glu Leu Gly Gln Val
1               5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Glu Val Ala Arg Leu Gly Asp Tyr
1               5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ser Gln Ala Pro Leu Gly Thr Leu
1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Ile Ala Leu Gln Gly Gln Leu
1               5

<210> SEQ ID NO 109
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ser Leu Ser Ser Leu Gly Asp Tyr
1               5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Phe Glu Ala Gln Ile Gly Met Ile
1               5

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Tyr Leu Ala Val Leu Gly Gln Leu
1               5

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gln Val Ala Ser Leu Gly Asp Tyr
1               5

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Asp Met Ala Asp Leu Phe Thr Leu
1               5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114
```

```
Gly Ile Ala Gln Ile Gly Gln Val
1               5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gln Asp Ala Gln Ile Gly Asp Val
1               5

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Phe Leu Ala Ala Val Gly Gln Ile
1               5

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Thr Ala Glu Val Gly Gln Met
1               5

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Trp Glu Ala Pro Val Gly Asp Val
1               5

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ser Gly Ala Gly Leu Gly Glu Leu
1               5

<210> SEQ ID NO 120
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 120

Glu Tyr Ser Lys Val Gly Glu Val
1               5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Tyr Gln Ala Leu Leu Asp Thr Tyr
1               5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Trp Tyr Ala Gly Leu Gly Gln Ile
1               5

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Trp Met Ala Gln Val Gly Asp Leu
1               5

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Asp Thr Ala Ala Val Gly Asp Leu
1               5

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Phe Gln Ala Pro Ile Gly Ser Leu
1               5
```

```
<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Tyr Met Thr Asp Val Gly Asp Leu
1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

His Leu Ala Gln Val Gly Glu Phe
1               5

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Tyr Leu Ser Gln Val Gly Ser Leu
1               5

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ser Glu Ala Ser Leu Phe Gln Leu
1               5

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gln Val Gly Asp Phe Trp Asp Val
1               5

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131
```

```
Trp Leu Gln Ala Leu Gly Glu Leu
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ser Ser Val Gln Val Gly Glu Leu
1               5

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Met Met Ser Ser Leu Gly Asp Leu
1               5

<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Trp Glu Ala Gln Val Gly Trp Leu
1               5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Lys Ala Thr Val Gly Gln Met
1               5

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asp Val Ala Ser Val Gly Ser Tyr
1               5

<210> SEQ ID NO 137
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 137

Ser Glu Ala Leu Leu Gly Gln Ile
1               5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Arg Ile Ala Gln Val Gly Glu Leu
1               5

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Phe Gln Ala Gln Val Gly Gln Leu
1               5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ser Arg Ala Val Val Gly Glu Leu
1               5

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Glu Val Ala Lys Val Gly Glu Leu
1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Glu Asp Ala Leu Leu Gly Asp Phe
1               5
```

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

His Gln Ala Gln Ile Gly Glu Leu
1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ser Val Ala Leu Leu Gly Glu Ser
1               5

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Asn Leu Ala Gln Ile Gly Asp Leu
1               5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ser Leu Ala Arg Leu Gly Glu Tyr
1               5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Trp Gln Ala Gln Lys Gly Asp Leu
1               5

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 148

Ser Asp Ala His Val Gly Gln Ile
1               5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gln Ala Ala Gln Val Gly Gln Leu
1               5

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Asp Ala Ser Leu Gly Gln Leu
1               5

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ser Glu Ala Gln Ile Gly Gln Leu
1               5

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Phe Tyr Ala Thr Leu Gly Gln Val
1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ser Glu Ala Leu Leu Gly Gln Ile
1               5

<210> SEQ ID NO 154
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 154

Trp Gln Ala Pro Val Gly Ser Leu
1               5

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Glu Tyr Ala Thr Leu Gly Ser Leu
1               5

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ser Leu Ala Pro Leu Gly Ser Leu
1               5

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ser Met Val Gly Leu Gly Gln Leu
1               5

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Val Ala Arg Val Gly Trp Leu
1               5

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Tyr Ala Ala Val Leu Asn Ser Leu
1               5
```

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gln Asn Ala Pro Leu Gly Ser Tyr
1               5

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ser Leu Ala Lys Leu His Glu Leu
1               5

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ser Asp Ala Gln Leu Met Gln Leu
1               5

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Tyr Gln Ala Met Val Gly Asp Leu
1               5

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D, G, L, and N
<220> FEATURE:
<221> NAME/KEY: MOD_RES
<222> LOCATION: (2)..(2)
<223> OTHER INFORMATION: L, P, V, and Y
<220> FEATURE:
<221> NAME/KEY: MOD_RES
<222> LOCATION: (3)..(3)
<223> OTHER INFORMATION: F, G, and M
<220> FEATURE:
<221> NAME/KEY: MOD_RES

```
<222> LOCATION: (4)..(4)
<223> OTHER INFORMATION: A, D, N, and Q
<220> FEATURE:
<221> NAME/KEY: MOD_RES
<222> LOCATION: (5)..(5)
<223> OTHER INFORMATION: F, I, L, S, V, W, and Y
<220> FEATURE:
<221> NAME/KEY: MOD_RES
<222> LOCATION: (6)..(6)
<223> OTHER INFORMATION: D and W
<220> FEATURE:
<221> NAME/KEY: MOD_RES
<222> LOCATION: (7)..(7)
<223> OTHER INFORMATION: P and Y
<220> FEATURE:
<221> NAME/KEY: MOD_RES
<222> LOCATION: (8)..(8)
<223> OTHER INFORMATION: A, D, Q, and S

<400> SEQUENCE: 164

Xaa Xaa Xaa Xaa Xaa Xaa Xaa Xaa
1               5

<210> SEQ ID NO 165
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: E, F, I, L, M, and Q
<220> FEATURE:
<221> NAME/KEY: MOD_RES
<222> LOCATION: (3)..(3)
<223> OTHER INFORMATION: D, G, L, and N
<220> FEATURE:
<221> NAME/KEY: MOD_RES
<222> LOCATION: (4)..(4)
<223> OTHER INFORMATION: L, P, V, and Y
<220> FEATURE:
<221> NAME/KEY: MOD_RES
<222> LOCATION: (5)..(5)
<223> OTHER INFORMATION: F, G, and M
<220> FEATURE:
<221> NAME/KEY: MOD_RES
<222> LOCATION: (6)..(6)
<223> OTHER INFORMATION: A, D, N, and Q
<220> FEATURE:
<221> NAME/KEY: MOD_RES
<222> LOCATION: (7)..(7)
<223> OTHER INFORMATION: F, I, L, S, V, W, and Y
<220> FEATURE:
<221> NAME/KEY: MOD_RES
<222> LOCATION: (8)..(8)
<223> OTHER INFORMATION: D and W
<220> FEATURE:
<221> NAME/KEY: MOD_RES
<222> LOCATION: (9)..(9)
<223> OTHER INFORMATION: P and Y
<220> FEATURE:
<221> NAME/KEY: MOD_RES
<222> LOCATION: (10)..(10)
<223> OTHER INFORMATION: A, D, Q, and S
<220> FEATURE:
<221> NAME/KEY: MOD_RES
<222> LOCATION: (12)..(12)
<223> OTHER INFORMATION: I, L, Q, W, and Y

<400> SEQUENCE: 165

Xaa Cys Xaa Xaa Xaa Xaa Xaa Xaa Xaa Xaa Cys Xaa
1               5                   10
```

-continued

```
<210> SEQ ID NO 166
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A, D, E, G, N, Q, R, and V
<220> FEATURE:
<221> NAME/KEY: MOD_RES
<222> LOCATION: (2)..(2)
<223> OTHER INFORMATION: E, F, I, L, M, and Q
<220> FEATURE:
<221> NAME/KEY: MOD_RES
<222> LOCATION: (4)..(4)
<223> OTHER INFORMATION: D, G, L, and N
<220> FEATURE:
<221> NAME/KEY: MOD_RES
<222> LOCATION: (5)..(5)
<223> OTHER INFORMATION: L, P, V, and Y
<220> FEATURE:
<221> NAME/KEY: MOD_RES
<222> LOCATION: (6)..(6)
<223> OTHER INFORMATION: F, G, and M
<220> FEATURE:
<221> NAME/KEY: MOD_RES
<222> LOCATION: (7)..(7)
<223> OTHER INFORMATION: A, D, N, and Q
<220> FEATURE:
<221> NAME/KEY: MOD_RES
<222> LOCATION: (8)..(8)
<223> OTHER INFORMATION: F, I, L, S, V, W, and Y
<220> FEATURE:
<221> NAME/KEY: MOD_RES
<222> LOCATION: (9)..(9)
<223> OTHER INFORMATION: D and W
<220> FEATURE:
<221> NAME/KEY: MOD_RES
<222> LOCATION: (10)..(10)
<223> OTHER INFORMATION: P and Y
<220> FEATURE:
<221> NAME/KEY: MOD_RES
<222> LOCATION: (11)..(11)
<223> OTHER INFORMATION: A, D, Q, and S
<220> FEATURE:
<221> NAME/KEY: MOD_RES
<222> LOCATION: (13)..(13)
<223> OTHER INFORMATION: I, L, Q, W, and Y
<220> FEATURE:
<221> NAME/KEY: MOD_RES
<222> LOCATION: (14)..(14)
<223> OTHER INFORMATION: E, F, I, L, T, V, and W

<400> SEQUENCE: 166

Xaa Xaa Cys Xaa Xaa Xaa Xaa Xaa Xaa Xaa Xaa Cys Xaa Xaa
1               5                   10

<210> SEQ ID NO 167
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Glu Ile Cys Asn Val Gly Gln Val Trp Pro Asp Cys Leu Leu
1               5                   10

<210> SEQ ID NO 168
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 168

Gly Gln Cys Leu Pro Gly Asp Phe Trp Pro Ala Cys Tyr Glu
1               5                   10

<210> SEQ ID NO 169
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Asn Met Cys Leu Val Gly Asp Tyr Trp Pro Ser Cys Gln Ile
1               5                   10

<210> SEQ ID NO 170
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gln Ile Cys Asp Val Gly Gln Trp Trp Pro Asp Cys Gln Val
1               5                   10

<210> SEQ ID NO 171
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Val Leu Cys Asp Tyr Met Asn Ser Asp Tyr Gln Cys Ile Thr
1               5                   10

<210> SEQ ID NO 172
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ala Glu Cys Gly Val Gly Ala Ile Trp Pro Ser Cys Leu Trp
1               5                   10

<210> SEQ ID NO 173
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Arg Leu Cys Asp Leu Phe Ala Ile Trp Pro Asp Cys Leu Phe
1               5                   10
```

<210> SEQ ID NO 174
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Asp Phe Cys Leu Val Gly Asp Leu Trp Pro Ser Cys Trp Leu
1               5                   10

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Asn Val Gly Gln Val Trp Pro Asp
1               5

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Leu Pro Gly Asp Phe Trp Pro Ala
1               5

<210> SEQ ID NO 177
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Leu Val Gly Asp Tyr Trp Pro Ser
1               5

<210> SEQ ID NO 178
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Asp Val Gly Gln Trp Trp Pro Asp
1               5

<210> SEQ ID NO 179
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Asp Tyr Met Asn Ser Asp Tyr Gln
1               5

<210> SEQ ID NO 180
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Val Gly Ala Ile Trp Pro Ser
1               5

<210> SEQ ID NO 181
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Asp Leu Phe Ala Ile Trp Pro Asp
1               5

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Leu Val Gly Asp Leu Trp Pro Ser
1               5

<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: I and V
<220> FEATURE:
<221> NAME/KEY: MOD_RES
<222> LOCATION: (4)..(4)
<223> OTHER INFORMATION: D, E, and N
<220> FEATURE:
<221> NAME/KEY: MOD_RES
<222> LOCATION: (5)..(5)
<223> OTHER INFORMATION: F, L, and Y
<220> FEATURE:
<221> NAME/KEY: MOD_RES
<222> LOCATION: (6)..(6)
<223> OTHER INFORMATION: F, I, and V
<220> FEATURE:
<221> NAME/KEY: MOD_RES
<222> LOCATION: (7)..(7)

```
<223> OTHER INFORMATION: D and Q
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid

<400> SEQUENCE: 183

Xaa Xaa Gly Xaa Xaa Xaa Xaa Xaa Xaa Xaa
1               5                   10

<210> SEQ ID NO 184
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: I and V
<220> FEATURE:
<221> NAME/KEY: MOD_RES
<222> LOCATION: (6)..(6)
<223> OTHER INFORMATION: D, E, and N
<220> FEATURE:
<221> NAME/KEY: MOD_RES
<222> LOCATION: (7)..(7)
<223> OTHER INFORMATION: F, L, and Y
<220> FEATURE:
<221> NAME/KEY: MOD_RES
<222> LOCATION: (8)..(8)
<223> OTHER INFORMATION: F, I, and V
<220> FEATURE:
<221> NAME/KEY: MOD_RES
<222> LOCATION: (9)..(9)
<223> OTHER INFORMATION: D and Q
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid

<400> SEQUENCE: 184

Xaa Cys Xaa Xaa Gly Xaa Xaa Xaa Xaa Xaa Xaa Xaa Cys Xaa
1               5                   10

<210> SEQ ID NO 185
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Leu Cys His Val Gly Asp Tyr Ile Gln Asp Gly Ile Cys Met
1               5                   10

<210> SEQ ID NO 186
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ser Cys Gln Ile Gly Glu Leu Val Asp Leu Thr Asp Cys Ala
1               5                   10

<210> SEQ ID NO 187
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Thr Cys Gln Val Gly Asp Phe Phe Asp Trp Leu Ser Cys Ala
1               5                   10

<210> SEQ ID NO 188
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Tyr Ala Cys Ala Glu Asn Val Ile Asp Trp Leu Cys Thr
1               5                   10

<210> SEQ ID NO 189
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Leu Cys His Val Gly Asp Tyr Ile Gln Asp Gly Ile Cys Met
1               5                   10

<210> SEQ ID NO 190
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190
```

```
Ser Cys Gln Ile Gly Glu Leu Val Asp Leu Thr Asp Cys Ala
1               5                   10
```

```
<210> SEQ ID NO 191
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Thr Cys Gln Val Gly Asp Phe Phe Asp Trp Leu Ser Cys Ala
1               5                   10

<210> SEQ ID NO 192
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Tyr Ala Cys Ala Glu Asn Val Ile Asp Trp Leu Cys Thr
1               5                   10

<210> SEQ ID NO 193
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Cys Val Leu Leu Glu His Ser Ser Val Gly Asp Ile Ile Cys
1               5                   10

<210> SEQ ID NO 194
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D, E, F, N, Q, S, and T
<220> FEATURE:
<221> NAME/KEY: MOD_RES
<222> LOCATION: (2)..(2)
<223> OTHER INFORMATION: A, D, E, G, I, M, N, Q, R, S, and T
<220> FEATURE:
<221> NAME/KEY: MOD_RES
<222> LOCATION: (3)..(3)
<223> OTHER INFORMATION: D, E, F, Q, S, T, W, and Y
<220> FEATURE:
<221> NAME/KEY: MOD_RES
<222> LOCATION: (4)..(4)
<223> OTHER INFORMATION: D, E, F, G, L, M, N, Q, and Y
<220> FEATURE:
<221> NAME/KEY: MOD_RES
<222> LOCATION: (5)..(5)
<223> OTHER INFORMATION: E, G, N, S and Q
<220> FEATURE:
<221> NAME/KEY: MOD_RES
<222> LOCATION: (6)..(6)
<223> OTHER INFORMATION: I, K, M, P, T, and V
<220> FEATURE:
<221> NAME/KEY: MOD_RES
```

<222> LOCATION: (7)..(7)
<223> OTHER INFORMATION: I, L, M, S, T, and V
<220> FEATURE:
<221> NAME/KEY: MOD_RES
<222> LOCATION: (8)..(8)
<223> OTHER INFORMATION: F, I, and L

<400> SEQUENCE: 194

Xaa Xaa Xaa Xaa Xaa Xaa Xaa Xaa
1               5

<210> SEQ ID NO 195
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: G, I, K, L, Q, R, T, Y, and V
<220> FEATURE:
<221> NAME/KEY: MOD_RES
<222> LOCATION: (2)..(2)
<223> OTHER INFORMATION: A, D, E, H, I, L, M, R, S, T, V, and W
<220> FEATURE:
<221> NAME/KEY: MOD_RES
<222> LOCATION: (4)..(4)
<223> OTHER INFORMATION: D, E, F, N, Q, S, and T
<220> FEATURE:
<221> NAME/KEY: MOD_RES
<222> LOCATION: (5)..(5)
<223> OTHER INFORMATION: A, D, E, G, I, M, N, Q, R, S, and T
<220> FEATURE:
<221> NAME/KEY: MOD_RES
<222> LOCATION: (6)..(6)
<223> OTHER INFORMATION: D, E, F, Q, S, T, W, and Y
<220> FEATURE:
<221> NAME/KEY: MOD_RES
<222> LOCATION: (7)..(7)
<223> OTHER INFORMATION: D, E, F, G, L, M, N, Q, and Y
<220> FEATURE:
<221> NAME/KEY: MOD_RES
<222> LOCATION: (8)..(8)
<223> OTHER INFORMATION: E, G, N, S and Q
<220> FEATURE:
<221> NAME/KEY: MOD_RES
<222> LOCATION: (9)..(9)
<223> OTHER INFORMATION: I, K, M, P, T, and V
<220> FEATURE:
<221> NAME/KEY: MOD_RES
<222> LOCATION: (10)..(10)
<223> OTHER INFORMATION: I, L, M, S, T, and V
<220> FEATURE:
<221> NAME/KEY: MOD_RES
<222> LOCATION: (11)..(11)
<223> OTHER INFORMATION: F, I, and L
<220> FEATURE:
<221> NAME/KEY: MOD_RES
<222> LOCATION: (13)..(13)
<223> OTHER INFORMATION: F, T, and W
<220> FEATURE:
<221> NAME/KEY: MOD_RES
<222> LOCATION: (14)..(14)
<223> OTHER INFORMATION: A, E, F, G, I, K, L, M, N, P, Q, S, T, V, W,
      and Y

<400> SEQUENCE: 195

Xaa Xaa Cys Xaa Xaa Xaa Xaa Xaa Xaa Xaa Cys Xaa Xaa
1               5                   10

<210> SEQ ID NO 196
<211> LENGTH: 14
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 196

Gln Leu Cys Gln Ile Trp Gln Glu Val Leu Leu Cys Trp Pro
1               5                   10

<210> SEQ ID NO 197
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ile Glu Cys Asn Arg Asp Glu Cys Pro Met Ile Cys Trp Ala
1               5                   10

<210> SEQ ID NO 198
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Lys Val Cys Glu Met Trp Gly Gly Val Leu Leu Cys Trp Asn
1               5                   10

<210> SEQ ID NO 199
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Leu Glu Cys Asn Asn Ser Tyr Gly Val Leu Leu Cys Trp Ser
1               5                   10

<210> SEQ ID NO 200
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Arg Ile Cys Gln Asp Phe Gln Gly Val Ile Leu Cys Trp Leu
1               5                   10

<210> SEQ ID NO 201
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Arg Arg Cys Gln Asp Tyr Leu Gly Ile Leu Leu Cys Trp Glu
1               5                   10
```

<210> SEQ ID NO 202
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Arg Thr Cys Thr Glu Trp Glu Asn Val Val Leu Cys Trp Val
1               5                   10

<210> SEQ ID NO 203
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Thr Ser Cys Phe Asn Phe Asp Gly Val Leu Leu Cys Trp Gln
1               5                   10

<210> SEQ ID NO 204
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Val Ser Cys Glu Ser Trp Gln Gly Thr Leu Phe Cys Trp Gln
1               5                   10

<210> SEQ ID NO 205
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Val Thr Cys Gln Asp Trp Asn Gly Val Leu Leu Cys Phe Pro
1               5                   10

<210> SEQ ID NO 206
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Thr Cys Gln Glu Tyr Asn Gly Val Met Ile Cys Trp Gly
1               5                   10

<210> SEQ ID NO 207
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ile Ala Cys Ser Gln Glu Met Gly Ile Leu Leu Cys Trp Val
1               5                   10

<210> SEQ ID NO 208
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Lys Trp Cys Gln Asp Trp Phe Gly Val Leu Leu Cys Thr Val
1               5                   10

<210> SEQ ID NO 209
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Leu Thr Cys Gln Asn Trp Gln Gly Val Ser Leu Cys Trp Asn
1               5                   10

<210> SEQ ID NO 210
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Leu Val Cys Asp Asp Thr Leu Gly Val Thr Leu Cys Trp Trp
1               5                   10

<210> SEQ ID NO 211
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D, E, F, M, N, Q, S T, V, W, and Y
<220> FEATURE:
<221> NAME/KEY: MOD_RES
<222> LOCATION: (2)..(2)
<223> OTHER INFORMATION: D, E, F, G, I, L, M, P, R, S, T, and V
<220> FEATURE:
<221> NAME/KEY: MOD_RES
<222> LOCATION: (3)..(3)
<223> OTHER INFORMATION: F, H, L, W, and Y
<220> FEATURE:
<221> NAME/KEY: MOD_RES
<222> LOCATION: (4)..(4)
<223> OTHER INFORMATION: D, E, H, L, N, Q, S, and T
<220> FEATURE:
<221> NAME/KEY: MOD_RES
<222> LOCATION: (5)..(5)
<223> OTHER INFORMATION: G, T, Q, and E
<220> FEATURE:
<221> NAME/KEY: MOD_RES
<222> LOCATION: (6)..(6)

<223> OTHER INFORMATION: I, L, M, Q, and V
<220> FEATURE:
<221> NAME/KEY: MOD_RES
<222> LOCATION: (7)..(7)
<223> OTHER INFORMATION: D, E, N, Q, and R
<220> FEATURE:
<221> NAME/KEY: MOD_RES
<222> LOCATION: (8)..(8)
<223> OTHER INFORMATION: D, F, I, and L

<400> SEQUENCE: 211

Xaa Xaa Xaa Xaa Xaa Xaa Xaa Xaa
1               5

<210> SEQ ID NO 212
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: F, G, I, L, P, Q, R, T, and V
<220> FEATURE:
<221> NAME/KEY: MOD_RES
<222> LOCATION: (2)..(2)
<223> OTHER INFORMATION: A, D, E, I, M, R, S, T, and V
<220> FEATURE:
<221> NAME/KEY: MOD_RES
<222> LOCATION: (4)..(4)
<223> OTHER INFORMATION: D, E, F, M, N, Q, S T, V, W, and Y
<220> FEATURE:
<221> NAME/KEY: MOD_RES
<222> LOCATION: (5)..(5)
<223> OTHER INFORMATION: D, E, F, G, I, L, M, P, R, S, T, and V
<220> FEATURE:
<221> NAME/KEY: MOD_RES
<222> LOCATION: (6)..(6)
<223> OTHER INFORMATION: F, H, L, W, and Y
<220> FEATURE:
<221> NAME/KEY: MOD_RES
<222> LOCATION: (7)..(7)
<223> OTHER INFORMATION: D, E, H, L, N, Q, S, and T
<220> FEATURE:
<221> NAME/KEY: MOD_RES
<222> LOCATION: (8)..(8)
<223> OTHER INFORMATION: G, T, Q, and E
<220> FEATURE:
<221> NAME/KEY: MOD_RES
<222> LOCATION: (9)..(9)
<223> OTHER INFORMATION: I, L, M, Q, and V
<220> FEATURE:
<221> NAME/KEY: MOD_RES
<222> LOCATION: (10)..(10)
<223> OTHER INFORMATION: D, E, N, Q, and R
<220> FEATURE:
<221> NAME/KEY: MOD_RES
<222> LOCATION: (11)..(11)
<223> OTHER INFORMATION: D, F, I, and L
<220> FEATURE:
<221> NAME/KEY: MOD_RES
<222> LOCATION: (13)..(13)
<223> OTHER INFORMATION: F, I, L, R, T, W, and Y
<220> FEATURE:
<221> NAME/KEY: MOD_RES
<222> LOCATION: (14)..(14)
<223> OTHER INFORMATION: A, F, G, H, I, L, N, P, Q, S, T, and W

<400> SEQUENCE: 212

Xaa Xaa Cys Xaa Xaa Xaa Xaa Xaa Xaa Xaa Cys Xaa Xaa
1               5                   10

<210> SEQ ID NO 213

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ile Glu Cys Glu Phe Trp Asp Gly Met Gln Leu Cys Trp Gln
1               5                   10

<210> SEQ ID NO 214
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gln Ile Cys Gln Glu Trp Ser Gly Val Asn Leu Cys Trp His
1               5                   10

<210> SEQ ID NO 215
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ile Leu Cys Gln Asp Trp Ser Gly Ile Glu Ile Cys Trp Ser
1               5                   10

<210> SEQ ID NO 216
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Leu Ile Cys Tyr Thr Tyr Glu Gly Val Glu Leu Cys Trp Gln
1               5                   10

<210> SEQ ID NO 217
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Leu Val Cys Ser Met Phe Asn Gly Val Asp Leu Cys Trp Gln
1               5                   10

<210> SEQ ID NO 218
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218
```

```
Pro Arg Cys Glu Ile Trp Leu Gly Val Glu Leu Cys Arg Ile
1               5                   10

<210> SEQ ID NO 219
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Thr Glu Cys Gln Val Trp Asn Gly Val Glu Leu Cys Tyr Ile
1               5                   10

<210> SEQ ID NO 220
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Val Asp Cys Val Ile Trp Glu Gly Val Gln Leu Cys Thr Trp
1               5                   10

<210> SEQ ID NO 221
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Val Val Cys Thr Asp Tyr Leu Gly Val Gln Leu Cys Trp Thr
1               5                   10

<210> SEQ ID NO 222
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Val Met Cys Glu Arg Trp Gln Gly Val Glu Leu Cys Trp Leu
1               5                   10

<210> SEQ ID NO 223
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Val Val Cys Gln Gly Trp Ser Gly Val Asp Ile Cys Trp Gln
1               5                   10

<210> SEQ ID NO 224
<211> LENGTH: 12
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 224

Asp Cys Ser Met Trp Glu Gly Val Glu Leu Cys Trp
1               5                   10

<210> SEQ ID NO 225
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ile Val Cys Glu Glu Trp Ser Gly Val Arg Phe Cys Trp Asn
1               5                   10

<210> SEQ ID NO 226
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gln Thr Cys Trp Asp Tyr Glu Gly Met Glu Leu Cys Leu Ile
1               5                   10

<210> SEQ ID NO 227
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Pro Ala Cys Gln Asp Trp Asn Gly Val Glu Leu Cys Ile Leu
1               5                   10

<210> SEQ ID NO 228
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gln Glu Cys Thr Asp Trp Gln Gly Val Glu Leu Cys Leu Leu
1               5                   10

<210> SEQ ID NO 229
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Arg Ile Cys Asn Asp Trp Asn Gly Val Gln Leu Cys Trp Pro
1               5                   10

-continued

```
<210> SEQ ID NO 230
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Val Ile Cys Gln Ser Tyr Asp Gly Val Glu Phe Cys Trp Phe
1               5                   10

<210> SEQ ID NO 231
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Val Val Cys Glu Met Tyr Ser Gly Val Gln Ile Cys Trp Ala
1               5                   10

<210> SEQ ID NO 232
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Leu Asp Cys Met Asp Tyr Asn Gly Val Arg Leu Cys Trp Asn
1               5                   10

<210> SEQ ID NO 233
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Phe Thr Cys Trp Asp Tyr Asn Gly Val Asp Leu Cys Gln Ile
1               5                   10

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: C, D, F, P, and R
<220> FEATURE:
<221> NAME/KEY: MOD_RES
<222> LOCATION: (2)..(2)
<223> OTHER INFORMATION: A, D, L, Q, S, and W
<220> FEATURE:
<221> NAME/KEY: MOD_RES
<222> LOCATION: (3)..(3)
<223> OTHER INFORMATION: D, E, F, L, and V
<220> FEATURE:
<221> NAME/KEY: MOD_RES
<222> LOCATION: (4)..(4)
<223> OTHER INFORMATION: A, D, E, F, G, K, Q, and S
```

```
<220> FEATURE:
<221> NAME/KEY: MOD_RES
<222> LOCATION: (5)..(5)
<223> OTHER INFORMATION: E, L, M, and W
<220> FEATURE:
<221> NAME/KEY: MOD_RES
<222> LOCATION: (6)..(6)
<223> OTHER INFORMATION: G, I, L, W, and Y
<220> FEATURE:
<221> NAME/KEY: MOD_RES
<222> LOCATION: (7)..(7)
<223> OTHER INFORMATION: E, I, R, T, and V
<220> FEATURE:
<221> NAME/KEY: MOD_RES
<222> LOCATION: (9)..(9)
<223> OTHER INFORMATION: C, A, I, L, P, and V

<400> SEQUENCE: 234

Xaa Xaa Xaa Xaa Xaa Xaa Xaa Trp Xaa
1               5

<210> SEQ ID NO 235
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: C, D, E, and L
<220> FEATURE:
<221> NAME/KEY: MOD_RES
<222> LOCATION: (2)..(2)
<223> OTHER INFORMATION: C, L, M, R, S, V, and W
<220> FEATURE:
<221> NAME/KEY: MOD_RES
<222> LOCATION: (3)..(3)
<223> OTHER INFORMATION: C, D, F, P, and R
<220> FEATURE:
<221> NAME/KEY: MOD_RES
<222> LOCATION: (4)..(4)
<223> OTHER INFORMATION: A, D, L, Q, S, and W
<220> FEATURE:
<221> NAME/KEY: MOD_RES
<222> LOCATION: (5)..(5)
<223> OTHER INFORMATION: D, E, F, L, and V
<220> FEATURE:
<221> NAME/KEY: MOD_RES
<222> LOCATION: (6)..(6)
<223> OTHER INFORMATION: A, D, E, F, G, K, Q, and S
<220> FEATURE:
<221> NAME/KEY: MOD_RES
<222> LOCATION: (7)..(7)
<223> OTHER INFORMATION: E, L, M, and W
<220> FEATURE:
<221> NAME/KEY: MOD_RES
<222> LOCATION: (8)..(8)
<223> OTHER INFORMATION: G, I, L, W, and Y
<220> FEATURE:
<221> NAME/KEY: MOD_RES
<222> LOCATION: (9)..(9)
<223> OTHER INFORMATION: E, I, R, T, and V
<220> FEATURE:
<221> NAME/KEY: MOD_RES
<222> LOCATION: (11)..(11)
<223> OTHER INFORMATION: C, A, I, L, P, and V
<220> FEATURE:
<221> NAME/KEY: MOD_RES
<222> LOCATION: (12)..(12)
<223> OTHER INFORMATION: C, D, G, H
<220> FEATURE:
<221> NAME/KEY: MOD_RES
<222> LOCATION: (13)..(13)
<223> OTHER INFORMATION: C, D, E, H, S, and T
```

```
<400> SEQUENCE: 235

Xaa Xaa Xaa Xaa Xaa Xaa Xaa Xaa Trp Xaa Xaa Xaa
1               5                   10

<210> SEQ ID NO 236
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Met Cys Trp Leu Glu Trp Gly Glu Trp Val Gly Ser Cys Leu
1               5                   10

<210> SEQ ID NO 237
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Leu Cys Phe Ser Glu Phe Leu Gly Glu Trp Val Asp Cys Asn
1               5                   10

<210> SEQ ID NO 238
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Val Cys Ser Phe Asp Glu Ala Trp Gly Glu Trp Ile Cys Glu
1               5                   10

<210> SEQ ID NO 239
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Asp Cys Pro Gln Val Ser Trp Tyr Glu Trp Leu Asp Cys Tyr
1               5                   10

<210> SEQ ID NO 240
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Tyr Cys Leu Phe Asp Glu Gln Met Gly Glu Trp Leu Cys His
1               5                   10

<210> SEQ ID NO 241
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 241

Cys Glu Ser Phe Ser Glu Ala Leu Gly Thr Trp Ile Asp Cys
1               5                   10

<210> SEQ ID NO 242
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Cys Val Phe Leu Glu Asp Trp Trp Ile Trp Ala Gly Asp Cys
1               5                   10

<210> SEQ ID NO 243
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Glu Cys Asp Ala Phe Gly Trp Ile Ile Trp Pro His Cys Leu
1               5                   10

<210> SEQ ID NO 244
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Phe Cys Trp Asp Ser Asp Lys Met Leu Arg Trp Val Cys Ser
1               5                   10

<210> SEQ ID NO 245
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gln Cys Arg Arg Ser Asp Phe Glu Tyr Val Trp Leu Cys Thr
1               5                   10

<210> SEQ ID NO 246
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D, E, G, L, S, T, and Y
<220> FEATURE:
```

```
<221> NAME/KEY: MOD_RES
<222> LOCATION: (2)..(2)
<223> OTHER INFORMATION: E, L, P, and Q
<220> FEATURE:
<221> NAME/KEY: MOD_RES
<222> LOCATION: (4)..(4)
<223> OTHER INFORMATION: D, E, K, L, S, and T
<220> FEATURE:
<221> NAME/KEY: MOD_RES
<222> LOCATION: (5)..(5)
<223> OTHER INFORMATION: D, F, S, and W
<220> FEATURE:
<221> NAME/KEY: MOD_RES
<222> LOCATION: (6)..(6)
<223> OTHER INFORMATION: F, N, W, and Y

<400> SEQUENCE: 246

Xaa Xaa Cys Xaa Xaa Xaa
1               5

<210> SEQ ID NO 247
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D, G, I, and Q
<220> FEATURE:
<221> NAME/KEY: MOD_RES
<222> LOCATION: (2)..(2)
<223> OTHER INFORMATION: D, I, and L
<220> FEATURE:
<221> NAME/KEY: MOD_RES
<222> LOCATION: (3)..(3)
<223> OTHER INFORMATION: G, L, M, Q, R, S, and Y
<220> FEATURE:
<221> NAME/KEY: MOD_RES
<222> LOCATION: (4)..(4)
<223> OTHER INFORMATION: D, E, G, L, S, T, and Y
<220> FEATURE:
<221> NAME/KEY: MOD_RES
<222> LOCATION: (5)..(5)
<223> OTHER INFORMATION: E, L, P, and Q
<220> FEATURE:
<221> NAME/KEY: MOD_RES
<222> LOCATION: (7)..(7)
<223> OTHER INFORMATION: D, E, K, L, S, and T
<220> FEATURE:
<221> NAME/KEY: MOD_RES
<222> LOCATION: (8)..(8)
<223> OTHER INFORMATION: D, F, S, and W
<220> FEATURE:
<221> NAME/KEY: MOD_RES
<222> LOCATION: (9)..(9)
<223> OTHER INFORMATION: F, N, W, and Y
<220> FEATURE:
<221> NAME/KEY: MOD_RES
<222> LOCATION: (10)..(10)
<223> OTHER INFORMATION: F, I, L, R, and W
<220> FEATURE:
<221> NAME/KEY: MOD_RES
<222> LOCATION: (11)..(11)
<223> OTHER INFORMATION: A, E, L, and S
<220> FEATURE:
<221> NAME/KEY: MOD_RES
<222> LOCATION: (12)..(12)
<223> OTHER INFORMATION: H, I, K, N, Q, and V

<400> SEQUENCE: 247

Xaa Xaa Xaa Xaa Xaa Cys Xaa Xaa Xaa Xaa Xaa Xaa
1               5                   10
```

```
<210> SEQ ID NO 248
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Asp Leu Ser Asp Leu Cys Thr Phe Trp Leu Ser Gln
1               5                   10

<210> SEQ ID NO 249
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gly Leu Gln Glu Leu Cys Ser Phe Tyr Ile Ala Gln
1               5                   10

<210> SEQ ID NO 250
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Gln Ile Arg Gln Leu Cys Glu Phe Trp Leu Ser Gln
1               5                   10

<210> SEQ ID NO 251
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Gln Leu Gly Thr Leu Cys Asp Phe Phe Arg Glu Asn
1               5                   10

<210> SEQ ID NO 252
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Trp Cys Leu Ser Gln Glu Glu Phe Asn Phe Leu Val
1               5                   10

<210> SEQ ID NO 253
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 253

Tyr Ser Glu Glu Leu Ser Trp Ile Cys Lys Gln Leu
1               5                   10

<210> SEQ ID NO 254
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ile Asp Met Tyr Pro Gln Glu Trp Trp Phe Cys Asn
1               5                   10

<210> SEQ ID NO 255
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Cys Pro Leu Ser Leu Met Gly Ser Glu Arg Ile Phe Val Cys
1               5                   10

<210> SEQ ID NO 256
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Cys Thr Tyr Phe Gly Pro Asp Ala Phe Arg Met Leu Phe Cys
1               5                   10

<210> SEQ ID NO 257
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Cys Tyr Phe Asn Ser Ile Phe Leu Gly Glu Ser Pro Phe Cys
1               5                   10

<210> SEQ ID NO 258
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Cys Tyr Leu Ile Tyr Lys Asn Asn Gln Leu Ala Leu Gln Cys
1               5                   10

<210> SEQ ID NO 259
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 259

Cys Tyr Val Val Tyr Asn Tyr Gln Glu Phe Arg Tyr Leu Cys
1               5                   10

<210> SEQ ID NO 260
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Leu Tyr Cys Arg Asp Asn Asp Gly Thr Gln Tyr Cys Glu Thr
1               5                   10

<210> SEQ ID NO 261
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Tyr Tyr Cys Tyr Leu Asn Ile Trp Thr Met Lys Cys Glu Asp
1               5                   10

<210> SEQ ID NO 262
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Tyr Tyr Cys Tyr Leu Asn Ile Trp Pro Val Lys Cys Glu Asp
1               5                   10

<210> SEQ ID NO 263
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Leu Glu Cys Ala Thr Ser Glu Glu Pro Tyr Tyr Cys Tyr Leu
1               5                   10

<210> SEQ ID NO 264
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Cys Asp Cys Gln His His Arg Cys Arg Thr Gly Gly Leu Val
1               5                   10
```

```
<210> SEQ ID NO 265
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Cys Gly Ile Ala Tyr Arg Ser Gly Glu Phe Thr Met Ile Cys
1               5                   10

<210> SEQ ID NO 266
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Cys Pro Ser Met Leu Gln Gly Pro Glu Arg Thr Trp Val Cys
1               5                   10

<210> SEQ ID NO 267
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Trp Cys Ile Tyr Tyr Pro Phe Thr Asp Val Glu Ala Cys Thr
1               5                   10

<210> SEQ ID NO 268
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Ile Ser Ala Gly Arg Trp Gly Asp Val Gly Asp Leu Ile Pro
1               5                   10

<210> SEQ ID NO 269
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Gly Val Gln Ser Arg Trp Gly Asp Val Gly Asp Leu Ile Pro Trp
1               5                   10                  15

<210> SEQ ID NO 270
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 270

Phe Pro Val Pro Arg Trp Gly Asp Trp Gly Asp Leu Ile Glu Leu
1               5                   10                  15

<210> SEQ ID NO 271
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Arg Trp Gly Asp Val Gly Asp Leu Ile Gly
1               5                   10

<210> SEQ ID NO 272
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Arg Trp Gly Asp Val Gly Asp Leu Ile Trp
1               5                   10

<210> SEQ ID NO 273
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Arg Trp Gly Asp Val Gly Asp Leu Ile Gly
1               5                   10

<210> SEQ ID NO 274
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Arg Trp Gly Asp Val Gly Asp Leu Ile Val
1               5                   10

<210> SEQ ID NO 275
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Arg Trp Gly Asp Val Gly Asp Leu Val Ser
1               5                   10

<210> SEQ ID NO 276
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Arg Trp Gly Asp Val Gly Asp Leu Val Met
1               5                   10

<210> SEQ ID NO 277
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Arg Trp Gly Asp Val Gly Asp Met Val Glu
1               5                   10

<210> SEQ ID NO 278
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Arg Tyr Gly Glu Val Gly Asp Leu Leu Pro
1               5                   10

<210> SEQ ID NO 279
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Arg Trp Gly Asp Trp Gly Asp Leu Leu Pro
1               5                   10

<210> SEQ ID NO 280
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Arg Trp Gly Asp Trp Gly Asp Leu Ile Pro
1               5                   10

<210> SEQ ID NO 281
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Arg Trp Gly Asp Trp Gly Asp Leu Val Ala
```

```
1               5                  10

<210> SEQ ID NO 282
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Arg Trp Gly Asp Trp Gly Asp Leu Val Glu
1               5                  10

<210> SEQ ID NO 283
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Arg Trp Gly Asp Trp Gly Asp Leu Val Trp
1               5                  10

<210> SEQ ID NO 284
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Arg Trp Gly Asp Trp Gly Asp Leu Val Gly
1               5                  10

<210> SEQ ID NO 285
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Arg Trp Gly Asp Val Gly Asp Leu Val Pro
1               5                  10

<210> SEQ ID NO 286
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Arg Trp Gly Asp Trp Gly Asp Met Val Val
1               5                  10

<210> SEQ ID NO 287
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 287

Trp Ser Gly Pro Gly Ile Leu Gly Glu Tyr Met
1               5                   10

<210> SEQ ID NO 288
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Trp Asp Gly Pro Gly Leu Gly Glu Phe Phe
1               5                   10

<210> SEQ ID NO 289
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Trp Ser Gly Pro Gly Ile Leu Gly Glu Phe Met
1               5                   10

<210> SEQ ID NO 290
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Trp Tyr Gly Pro Gly Ile Leu Gly Glu Tyr Met
1               5                   10

<210> SEQ ID NO 291
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Trp Glu Gly Pro Gly Leu Gly Glu Tyr Met
1               5                   10

<210> SEQ ID NO 292
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Trp Glu Gly Pro Gly Ile Leu Gly Glu Tyr
1               5                   10

<210> SEQ ID NO 293

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ile Asp Cys Gly Val Ala Thr Val Gly Glu Leu Cys
1               5                   10

<210> SEQ ID NO 294
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Ile Ser Cys Ser Glu Ala Gly Leu Gly Glu Leu Cys
1               5                   10

<210> SEQ ID NO 295
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Ile Asp Cys Ser Gln Ala Met Leu Gly Glu Leu Cys
1               5                   10

<210> SEQ ID NO 296
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Ile Asp Cys Ser Glu Ala Trp Leu Gly Glu Leu Cys
1               5                   10

<210> SEQ ID NO 297
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Ile Asp Cys Ser Glu Ala Ala Leu Gly Thr Leu Cys
1               5                   10

<210> SEQ ID NO 298
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298
```

```
Leu Asp Cys Ser Ile Ala Ala Leu Gly Glu Leu Cys
1               5                   10

<210> SEQ ID NO 299
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Leu Asp Cys Ser Glu Ala Ile Leu Gly Gln Leu Cys
1               5                   10

<210> SEQ ID NO 300
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Leu Asp Cys Gly Glu Ala Ile Leu Gly Glu Leu Cys
1               5                   10

<210> SEQ ID NO 301
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Leu Asp Cys Arg Asp Ala Val Leu Gly Glu Leu Cys
1               5                   10

<210> SEQ ID NO 302
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Met Asp Cys Ser Glu Arg Ala Leu Gly Glu Leu Cys
1               5                   10

<210> SEQ ID NO 303
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Met Asp Cys Ser Gln Ala Gly Leu Gly Glu Leu Cys
1               5                   10

<210> SEQ ID NO 304
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 304

Met Asp Cys Arg Glu Ala Ala Leu Gly Glu Leu Cys
1               5                   10

<210> SEQ ID NO 305
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Met Asp Cys Trp Glu Ala Ala Leu Gly Glu Leu Cys
1               5                   10

<210> SEQ ID NO 306
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Met Asp Cys Ser Glu Ala Leu Leu Gly Glu Leu Cys
1               5                   10

<210> SEQ ID NO 307
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Met Asp Cys Tyr Asp Ala Arg Leu Gly Asp Leu Cys
1               5                   10

<210> SEQ ID NO 308
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Met Asp Ser Ser Gln Ala Ala Leu Gly Glu Leu Cys
1               5                   10

<210> SEQ ID NO 309
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Val Asp Cys Ser Glu Ala Val Leu Gly Gln Leu Cys
1               5                   10
```

```
<210> SEQ ID NO 310
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Leu Asp Cys Ser Arg Ala Ser Leu Gly Glu Leu Cys
1               5                   10

<210> SEQ ID NO 311
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Met Asp Cys Ser Gln Ala Gly Leu Gly Glu Leu Cys
1               5                   10

<210> SEQ ID NO 312
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Ile Asp Cys Ser Glu Ala Gly Leu Gly Glu Leu Cys
1               5                   10

<210> SEQ ID NO 313
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Ile Asp Cys Ser Glu Ala Ala Leu Gly Glu Leu Cys
1               5                   10

<210> SEQ ID NO 314
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Ile Asn Cys Ser Glu Ala Val Ile Gly Gln Leu Cys
1               5                   10

<210> SEQ ID NO 315
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315
```

```
Ile Asp Cys Ser Asn Ala Val Val Gly Gln Leu Cys
1               5                   10

<210> SEQ ID NO 316
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Ile Asp Cys Ser Ala Ala Gly Leu Gly Glu Leu Cys
1               5                   10

<210> SEQ ID NO 317
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Leu Asp Cys Ser Asn Ala Gly Trp Gly Asp Leu Cys
1               5                   10

<210> SEQ ID NO 318
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Leu Asp Cys Ser Glu Ala Val Leu Gly Glu Leu Cys
1               5                   10

<210> SEQ ID NO 319
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Leu Asp Cys His Leu Ala Val Leu Gly Glu Leu Cys
1               5                   10

<210> SEQ ID NO 320
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Leu Asp Cys Ser Val Ala Val Leu Gly Glu Leu Cys
1               5                   10

<210> SEQ ID NO 321
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 321

Leu Asp Cys Ser Glu Ala Trp Leu Gly His Leu Cys
1               5                   10

<210> SEQ ID NO 322
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Met Asp Cys Ser Gln Ala Ala Leu Gly Asp Leu Cys
1               5                   10

<210> SEQ ID NO 323
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Met Asp Cys Ser Trp Ala Trp Leu Gly Asp Leu Cys
1               5                   10

<210> SEQ ID NO 324
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Met Asp Cys Ser Asp Ala Val Leu Gly Asp Leu Cys
1               5                   10

<210> SEQ ID NO 325
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Met Asp Cys His Glu Ala Ala Leu Gly His Leu Cys
1               5                   10

<210> SEQ ID NO 326
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Met Asp Cys Ser Gln Ala Val Leu Gly Glu Leu Cys
1               5                   10
```

<210> SEQ ID NO 327
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Met Asp Cys Ser Ile Arg Ala Leu Gly Glu Leu Cys
1               5                   10

<210> SEQ ID NO 328
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Thr Glu Cys Ser Glu Ala Gly Leu Trp Glu Leu Cys
1               5                   10

<210> SEQ ID NO 329
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Thr Glu Cys Ser Glu Ala Gly Leu Trp Glu Leu Cys
1               5                   10

<210> SEQ ID NO 330
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Met Asp Cys Arg Trp Ala Ala Leu Gly Glu Leu Cys
1               5                   10

<210> SEQ ID NO 331
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Met Asp Cys Ser Lys Ala Ala Leu Gly Glu Leu Cys
1               5                   10

<210> SEQ ID NO 332
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 332

Met Asp Cys Ser Glu Ala Val Leu Gly Glu Leu Cys
1               5                   10

<210> SEQ ID NO 333
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Met Asp Cys Ser Ile Arg Ala Leu Gly Glu Leu Cys
1               5                   10

<210> SEQ ID NO 334
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Val Asp Cys Ser Glu Ala Val Leu Gly Gln Leu Cys
1               5                   10

<210> SEQ ID NO 335
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Met Asp Cys Ser Glu Arg Ala Leu Gly Glu Leu Cys
1               5                   10

<210> SEQ ID NO 336
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Ile Asp Cys Gly Val Ala Thr Val Gly Glu Leu Cys
1               5                   10

<210> SEQ ID NO 337
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Ile Asp Cys Ser Glu Ala Ala Leu Gly Glu Leu Cys
1               5                   10

<210> SEQ ID NO 338
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 338

Ile Asn Cys Ser Glu Ala Val Ile Gly Asp Leu Cys
1               5                   10

<210> SEQ ID NO 339
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Ile Asp Cys Ser Gln Ala Met Leu Gly Glu Leu Cys
1               5                   10

<210> SEQ ID NO 340
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Ile Asp Cys Ser Glu Ala Val Leu Gly Glu Leu Cys
1               5                   10

<210> SEQ ID NO 341
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Ile Asp Cys Ser Ala Ala Gly Leu Gly Glu Leu Cys
1               5                   10

<210> SEQ ID NO 342
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Ile Asp Cys Ser Glu Ala Ala Leu Gly Thr Leu Cys
1               5                   10

<210> SEQ ID NO 343
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Leu Asp Cys Ser Asn Ala Gly Val Gly Asp Leu Cys
1               5                   10
```

<210> SEQ ID NO 344
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Leu Asp Cys Ser Ile Ala Ala Leu Gly Glu Leu Cys
1               5                   10

<210> SEQ ID NO 345
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Leu Asp Cys Ser Glu Ala Ile Leu Gly Gln Leu Cys
1               5                   10

<210> SEQ ID NO 346
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Leu Asp Cys His Leu Ala Val Leu Gly Glu Leu Cys
1               5                   10

<210> SEQ ID NO 347
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Leu Asp Cys Ser Val Ala Val Leu Gly Glu Leu Cys
1               5                   10

<210> SEQ ID NO 348
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Leu Asp Cys Arg Asp Ala Val Leu Gly Glu Leu Cys
1               5                   10

<210> SEQ ID NO 349
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 349

Met Asp Cys Ser Glu Arg Ala Leu Gly Glu Leu Cys
1               5                   10

<210> SEQ ID NO 350
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Met Asp Cys Ser Gln Ala Ala Leu Gly Asp Leu Cys
1               5                   10

<210> SEQ ID NO 351
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Met Asp Cys Ser Val Ala Val Leu Gly Asp Leu Cys
1               5                   10

<210> SEQ ID NO 352
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Met Asp Cys Arg Glu Ala Ala Leu Gly Glu Leu Cys
1               5                   10

<210> SEQ ID NO 353
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Met Asp Cys Trp Glu Ala Ala Leu Gly Glu Leu Cys
1               5                   10

<210> SEQ ID NO 354
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Met Asp Cys His Glu Ala Ala Leu Gly His Leu Cys
1               5                   10

<210> SEQ ID NO 355
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Met Asp Cys Ser Gln Ala Val Leu Gly Glu Leu Cys
1               5                   10

<210> SEQ ID NO 356
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Met Asp Cys Tyr Asp Ala Arg Leu Gly Asp Leu Cys
1               5                   10

<210> SEQ ID NO 357
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Met Asp Ser Ser Gln Ala Ala Leu Gly Glu Leu Cys
1               5                   10

<210> SEQ ID NO 358
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Thr Glu Cys Ser Glu Ala Gly Leu Trp Glu Leu Cys
1               5                   10

<210> SEQ ID NO 359
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Met Asp Cys Ser Glu Ala Val Leu Gly Glu Leu Cys
1               5                   10

<210> SEQ ID NO 360
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Ile Ser Cys Ser Glu Ala Gly Leu Gly Glu Leu Cys
```

```
1               5                   10

<210> SEQ ID NO 361
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Met Asp Cys Ser Gln Ala Ala Leu Gly Asp Leu Cys
1               5                   10

<210> SEQ ID NO 362
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Met Asp Cys Ser Gln Ala Gly Leu Gly Glu Leu Cys
1               5                   10

<210> SEQ ID NO 363
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Ile Ser Cys Ser Glu Ala Gly Leu Gly Glu Leu Cys
1               5                   10

<210> SEQ ID NO 364
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Ile Asp Cys Ser Asn Ala Val Val Gly Gln Leu Cys
1               5                   10

<210> SEQ ID NO 365
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Leu Asp Cys Ser Glu Ala Val Leu Gly Glu Leu Cys
1               5                   10

<210> SEQ ID NO 366
<211> LENGTH: 12
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 366

Leu Asp Cys Gly Glu Ala Ile Leu Gly Glu Leu Cys
1               5                   10

<210> SEQ ID NO 367
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Leu Asp Cys Ser Glu Ala Val Leu Gly His Leu Cys
1               5                   10

<210> SEQ ID NO 368
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Met Asp Cys Ser Gln Ala Gly Leu Cys Glu Leu Cys
1               5                   10

<210> SEQ ID NO 369
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Met Asp Cys Ser Asp Ala Val Leu Gly Asp Leu Cys
1               5                   10

<210> SEQ ID NO 370
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Met Asp Cys Ser Glu Ala Leu Leu Gly Glu Leu Cys
1               5                   10

<210> SEQ ID NO 371
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

His Cys Leu Asp Met Gly Cys Thr Phe Pro Val Trp
1               5                   10

<210> SEQ ID NO 372

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Ala Arg Ser Asp Tyr Gly Leu Gly Ala Ile Trp Pro
1               5                   10

<210> SEQ ID NO 373
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Arg Ala Cys Arg Val Met Pro Cys Leu Pro Asp Leu
1               5                   10

<210> SEQ ID NO 374
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Ser Gly Cys Gly Arg Glu Leu Gly Trp Cys
1               5                   10

<210> SEQ ID NO 375
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Thr Gln Glu Val Tyr Tyr Ser Leu Leu
1               5

<210> SEQ ID NO 376
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Gly Thr Gln Glu Ala Cys Phe Gly Leu Leu
1               5                   10

<210> SEQ ID NO 377
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377
```

```
Gly Gly Phe Arg Cys Trp Glu Ala Pro Val Gly Glu Ile Cys Glu Leu
1               5                   10                  15

Gly Gly
```

<210> SEQ ID NO 378
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

```
Gly Gly Ile Glu Cys Glu Arg Ala Gln Ile Gly Glu Val Cys Gln Ile
1               5                   10                  15

Gly Gly
```

<210> SEQ ID NO 379
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

```
Gly Gly Met Glu Cys Phe Leu Ala Ala Val Gly Gln Ile Cys Glu Leu
1               5                   10                  15

Gly Gly
```

<210> SEQ ID NO 380
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

```
Gly Gly Tyr Asp Cys Arg Ile Ala Gln Val Gly Glu Leu Cys Asp Leu
1               5                   10                  15

Gly Gly
```

<210> SEQ ID NO 381
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

```
Gly Gly Glu Ile Cys Asn Val Gly Gln Val Trp Pro Asp Cys Leu Leu
1               5                   10                  15

Gly Gly
```

<210> SEQ ID NO 382
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

```
Gly Gly Asn Met Cys Leu Val Gly Asp Tyr Trp Pro Ser Cys Gln Ile
1               5                   10                  15

Gly Gly

<210> SEQ ID NO 383
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Gly Gly Gln Ile Cys Asp Val Gly Gln Trp Trp Pro Asp Cys Gln Val
1               5                   10                  15

Gly Gly

<210> SEQ ID NO 384
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Cys Tyr Glu Val Gly Asp Tyr Cys Gln Ser Phe Leu Gly Gly
1               5                   10

<210> SEQ ID NO 385
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Arg Trp Gly Asp Val Gly Asp Leu Leu Met Pro Leu Gly Gly
1               5                   10

<210> SEQ ID NO 386
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Asp Leu Ser Asp Leu Cys Thr Phe Trp Leu Ser Gln Gly Gly
1               5                   10

<210> SEQ ID NO 387
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Asp Leu Ser Asp Leu Ser Thr Phe Trp Leu Ser Gln Gly Gly
1               5                   10
```

-continued

```
<210> SEQ ID NO 388
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Asp Cys Ser Met Trp Glu Gly Val Glu Leu Cys Trp Gly Gly
1               5                   10

<210> SEQ ID NO 389
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Gly Gly Leu Cys Phe Ser Glu Phe Leu Gly Glu Trp Val Asp Cys Asn
1               5                   10                  15

Gly Gly

<210> SEQ ID NO 390
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Gly Gly Val Cys Ser Phe Asp Glu Ala Trp Gly Glu Trp Ile Cys Glu
1               5                   10                  15

Gly Gly

<210> SEQ ID NO 391
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Gly Gly Lys Val Cys Glu Met Trp Gly Gly Val Leu Leu Cys Trp Asn
1               5                   10                  15

Gly Gly Arg

<210> SEQ ID NO 392
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Gly Gly Arg Thr Cys Thr Glu Trp Glu Asn Val Val Leu Cys Trp Val
1               5                   10                  15

Gly Gly

<210> SEQ ID NO 393
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Gly Gly Ile Leu Cys Gln Asp Trp Ser Gly Ile Glu Ile Cys Trp Ser
1               5                   10                  15

Gly Gly Arg

<210> SEQ ID NO 394
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Gly Gly Leu Ile Cys Tyr Thr Tyr Glu Gly Val Glu Leu Cys Trp Gln
1               5                   10                  15

Gly Gly Arg

<210> SEQ ID NO 395
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Gly Gly Val Met Cys Glu Arg Trp Gln Gly Val Glu Leu Cys Trp Leu
1               5                   10                  15

Gly Gly

<210> SEQ ID NO 396
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Gly Gly Met Cys Trp Leu Glu Trp Gly Glu Trp Val Gly Ser Cys Leu
1               5                   10                  15

Gly Gly Arg

<210> SEQ ID NO 397
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Gly Gly Cys Tyr Val Val Tyr Asn Tyr Gln Glu Phe Arg Tyr Leu Cys
1               5                   10                  15

Gly Gly Arg
```

```
<210> SEQ ID NO 398
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Gly Gly Leu Tyr Cys Arg Asp Asn Asp Gly Thr Gln Tyr Cys Glu Thr
1               5                   10                  15

Gly Gly

<210> SEQ ID NO 399
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Gly Gly Val Val Cys Gln Asp Trp Glu Gly Val Glu Leu Cys Trp Gln
1               5                   10                  15

Gly Gly Arg

<210> SEQ ID NO 400
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Asp His Lys Thr Trp Ser Ala Asp Cys Arg Ile Ala Gln Val Gly Glu
1               5                   10                  15

Leu Cys Gln Leu
            20

<210> SEQ ID NO 401
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Arg Arg Ile Ala Gln Cys Ser Lys Ala Gln Val Gly Glu Leu Cys Glu
1               5                   10                  15

Leu

<210> SEQ ID NO 402
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Gly Val Lys Asp Gly Trp Glu Asp Cys Gly Ile Ala Gln Val Gly Glu
1               5                   10                  15

Leu Cys Val Leu
```

-continued

```
                20

<210> SEQ ID NO 403
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Glu Asp Cys Trp Met Ala Gln Val Gly Gln Leu Cys Asp Leu
1               5                   10

<210> SEQ ID NO 404
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Arg Thr Leu Glu His Val Glu Pro Cys Arg Ile Ala Gly Leu Gly Glu
1               5                   10                  15

Leu Cys Asp Leu
            20

<210> SEQ ID NO 405
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Glu Tyr Cys Gln Met Ala Gln Leu Gly Asp Leu Cys Asp Leu
1               5                   10

<210> SEQ ID NO 406
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

His Gly Thr Phe Ala Cys Ser Leu Ala Gln Val Gly Asp Leu Cys Glu
1               5                   10                  15

Leu Phe Gly Asn
            20

<210> SEQ ID NO 407
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Phe Asp Cys Arg Phe Ala Gln Leu Gly Gly Leu Cys Asp Leu
1               5                   10
```

```
<210> SEQ ID NO 408
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Ala Lys Phe Phe Asp Cys Ser Phe Ala Pro Val Gly Tyr Leu Cys Asp
1               5                   10                  15

Leu Ile Val Ile
            20

<210> SEQ ID NO 409
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Phe Glu Cys Arg Ile Ala Lys Val Gly Glu Leu Cys Asp Leu
1               5                   10

<210> SEQ ID NO 410
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Phe Glu Cys Arg Thr Ala Pro Val Gly Glu Leu Cys Asp Leu Trp Pro
1               5                   10                  15

Trp Glu Leu Asp
            20

<210> SEQ ID NO 411
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Phe Glu Cys Trp Ile Ala Gln Val Gly Glu Leu Cys Asp Leu
1               5                   10

<210> SEQ ID NO 412
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Phe Glu Cys Trp Arg Ala Gln Val Gly Glu Leu Cys Asp Leu
1               5                   10

<210> SEQ ID NO 413
<211> LENGTH: 20
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 413

Gly Asp Cys Arg Phe Ala His Leu Gly Asp Leu Cys Asp Leu Ser Gly
1               5                   10                  15

Thr Ser Gly Ala
            20

<210> SEQ ID NO 414
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Phe Val Val Asn Glu Leu Gly Asp Cys Arg Phe Ala Gln Leu Gly Glu
1               5                   10                  15

Leu Cys Asp Leu
            20

<210> SEQ ID NO 415
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Gly Asp Cys Arg Ile Ala Glu Val Gly Glu Leu Cys Asp Leu
1               5                   10

<210> SEQ ID NO 416
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

His Asp Cys Trp Phe Ala Lys Leu Gly Glu Leu Cys Asp Leu Arg Gln
1               5                   10                  15

Met Ser Phe Val
            20

<210> SEQ ID NO 417
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

His Asp Cys Tyr Ser Ala His Val Gly Glu Leu Cys Asp Leu Asn Glu
1               5                   10                  15

Pro Asp Gly Lys
            20
```

```
<210> SEQ ID NO 418
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

His Glu Cys Arg Phe Ala Gln Val Gly Glu Leu Cys Asp Leu
1               5                   10

<210> SEQ ID NO 419
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

His Gln Cys Arg Phe Ala His Val Gly Glu Leu Cys Asp Leu Phe Val
1               5                   10                  15

Phe Glu Ser Tyr
            20

<210> SEQ ID NO 420
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Ile Asp Cys Arg Phe Ala Arg Leu Gly Tyr Leu Cys Asp Leu Gln Thr
1               5                   10                  15

Asn Glu His Met
            20

<210> SEQ ID NO 421
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Lys Ala Cys Ser Ile Ala Gln Val Gly Asp Leu Cys Glu Ile Tyr Gly
1               5                   10                  15

Phe Asp Asp Ala
            20

<210> SEQ ID NO 422
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Arg Gln Ser Arg Met Trp Lys Ala Cys Ser Leu Ala His Leu Gly Glu
1               5                   10                  15

Leu Cys Asp Leu
```

```
                    20

<210> SEQ ID NO 423
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Lys Asp Cys Arg Leu Ala Tyr Val Gly Glu Leu Cys Asp Leu Asn Arg
1               5                   10                  15

Ser Asp Thr Ile
            20

<210> SEQ ID NO 424
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Ala Thr Phe Lys Asp Cys Arg Ser Ser Asp Val Gly Glu Leu Cys Asp
1               5                   10                  15

Met Thr Asn Met
            20

<210> SEQ ID NO 425
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Lys Asp Cys Arg Thr Ala Leu Ile Gly Asp Leu Cys Asp Leu Thr Leu
1               5                   10                  15

His Leu Gly Gly
            20

<210> SEQ ID NO 426
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Lys Asp Cys Ser Ile Ala Gln Val Gly Glu Leu Cys Glu Phe Ser Arg
1               5                   10                  15

Ser Gly Arg Thr
            20

<210> SEQ ID NO 427
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 427

Gln Asp Gly Ala Lys Leu Lys Glu Cys Arg Val Ala Gln Val Gly Glu
1               5                   10                  15

Leu Cys Glu Phe
            20

<210> SEQ ID NO 428
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Gln Val Leu Lys Asn Cys Arg Leu Ala His Ile Gly Glu Leu Cys Tyr
1               5                   10                  15

Leu Ser Glu Arg
            20

<210> SEQ ID NO 429
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Arg Thr Met Lys Gln Cys Ser Ile Ala Gln Val Gly Glu Leu Cys Asp
1               5                   10                  15

Leu Ala Val Thr
            20

<210> SEQ ID NO 430
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Lys Ser Cys Ala Arg Ala Gln Val Gly Glu Leu Cys Tyr Ile Glu Gly
1               5                   10                  15

Ala Glu Asp Ala
            20

<210> SEQ ID NO 431
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Met Asn Gln Lys Tyr Cys Lys Leu Ala Gln Val Gly Glu Leu Cys Asp
1               5                   10                  15

Leu Ser Met Asp
            20

<210> SEQ ID NO 432
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Leu Ala Cys Arg Ala Ala Gln Val Gly Gln Leu Cys Asp Leu
1               5                   10

<210> SEQ ID NO 433
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Leu Ala Cys Arg Met Ala Gln Val Gly Glu Leu Cys Asp Leu
1               5                   10

<210> SEQ ID NO 434
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Leu Ala Cys Trp Met Ala His Val Gly Gln Leu Cys Glu Leu Glu Ala
1               5                   10                  15

His Lys Val Val
            20

<210> SEQ ID NO 435
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Leu Asp Cys Arg Phe Ala Leu Leu Gly Gln Leu Cys Asp Leu Phe Phe
1               5                   10                  15

Gly Gln Arg Pro
            20

<210> SEQ ID NO 436
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Leu Asp Cys Arg Ile Ala Pro Leu Gly Glu Leu Cys Asp Met Phe Ile
1               5                   10                  15

Ser Ala Phe Asn
            20

<210> SEQ ID NO 437
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Leu Asp Cys Arg Met Ala Gln Val Gly Asp Leu Cys Asp Leu
1               5                   10

<210> SEQ ID NO 438
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Ser Asp Val Leu Asp Cys Arg Val Ala Gln Val Gly Ser Leu Cys Glu
1               5                   10                  15

Leu Tyr Glu

<210> SEQ ID NO 439
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Leu Asp Cys Ser Lys Ala Asp Val Gly Glu Leu Cys Asp Pro Trp Trp
1               5                   10                  15

Ser Arg Leu Lys
            20

<210> SEQ ID NO 440
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Ala Trp Asn Pro Leu Val Leu Asp Cys Ser Thr Ser Gln Val Gly Asp
1               5                   10                  15

Leu Cys Glu Leu
            20

<210> SEQ ID NO 441
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Phe Ser Gly Pro Asp Trp Leu Glu Cys Arg Phe Ala Gln Leu Gly Gln
1               5                   10                  15

Met Cys Asp Leu
            20
```

```
<210> SEQ ID NO 442
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Leu Glu Cys Arg Leu Ala His Leu Gly Glu Leu Cys Asp Leu
1               5                   10

<210> SEQ ID NO 443
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Leu Glu Cys Arg Leu Ala Arg Leu Gly Asp Leu Cys Tyr Leu
1               5                   10

<210> SEQ ID NO 444
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Leu Ile Met Leu Glu Cys Arg Met Ala Lys Leu Gly Glu Tyr Cys Tyr
1               5                   10                  15

Phe Asp Ala Glu
            20

<210> SEQ ID NO 445
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Leu Glu Cys Arg Met Ala Leu Val Gly Asp Leu Cys Asp Leu
1               5                   10

<210> SEQ ID NO 446
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Leu Glu Cys Arg Ser Ala Gln Met Gly Asp Leu Cys Asp Leu
1               5                   10

<210> SEQ ID NO 447
<211> LENGTH: 20
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 447

Leu Lys Cys Arg Met Ala Arg Leu Gly Asp Leu Cys Asp Leu Asp Ile
1               5                   10                  15

Gly Arg Asn Met
            20

<210> SEQ ID NO 448
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Leu Leu Cys Arg Met Ala His Leu Gly Glu Leu Cys Asp Leu
1               5                   10

<210> SEQ ID NO 449
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Leu Leu Cys Arg Asn Ala Gln Val Gly Gln Ile Cys Asp Leu Met Pro
1               5                   10                  15

Phe Met Leu Ser
            20

<210> SEQ ID NO 450
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Leu Leu Cys Ser Met Ala His Val Gly Glu Leu Cys Tyr Leu Leu Gln
1               5                   10                  15

Gly Thr Gln Glu
            20

<210> SEQ ID NO 451
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Lys Glu Phe Leu Asn Cys Arg Ile Ala Gln Val Gly Glu Leu Cys Glu
1               5                   10                  15

Met His Tyr Glu
            20

<210> SEQ ID NO 452
<211> LENGTH: 20
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 452

Ala Lys Ser Lys Gly Glu Leu Asn Cys Arg Tyr Ala His Val Gly Glu
1               5                   10                  15

Leu Cys Glu Leu
            20

<210> SEQ ID NO 453
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Leu Gln Cys Arg Leu Ala Gln Leu Gly Glu Leu Cys Val Phe
1               5                   10

<210> SEQ ID NO 454
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Leu Arg Cys Arg Met Ala Gln Val Gly Asp Leu Cys Asp Leu Asp Arg
1               5                   10                  15

Ala Trp Asp Trp
            20

<210> SEQ ID NO 455
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Leu Ser Cys Arg Met Ala Leu Val Gly Gln Leu Cys Glu Leu
1               5                   10

<210> SEQ ID NO 456
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Leu Ser Cys Ser Ile Ala Gln Val Gly Glu Leu Cys Asp Leu
1               5                   10

<210> SEQ ID NO 457
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 457

Leu Ser Cys Trp Val Ala His Leu Gly Asp Leu Cys Asp Leu Glu Arg
1               5                   10                  15

Asp Val Lys Glu
            20

<210> SEQ ID NO 458
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 458

Asn Asp Cys Arg Phe Ala His Leu Gly Glu Leu Cys Asp Leu Asp Leu
1               5                   10                  15

Glu Arg Ala Arg
            20

<210> SEQ ID NO 459
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Ala Ser Gly Asn Asp Cys Arg Met Ala Gln Val Gly Gln Leu Cys Asp
1               5                   10                  15

Leu Glu Trp Met
            20

<210> SEQ ID NO 460
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Ser Trp Val Asn Asn Cys Arg Met Ala Gln Val Gly Glu Leu Cys Asp
1               5                   10                  15

Leu Pro Asn Trp
            20

<210> SEQ ID NO 461
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Thr Tyr Ala Lys Leu Val Asn Tyr Cys Trp Thr Ala Gln Leu Gly Glu
1               5                   10                  15

Leu Cys Tyr Leu
            20

```
<210> SEQ ID NO 462
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Pro Asp Cys Ser Val Ala Val Leu Gly Glu Leu Cys Asp Leu
1               5                   10

<210> SEQ ID NO 463
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Gly Leu Asn Pro Met Ile Pro Gly Cys Gln Met Ala Gln Val Gly Glu
1               5                   10                  15

Leu Cys Glu Leu
            20

<210> SEQ ID NO 464
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Pro Gln Cys Arg Thr Ala Leu Leu Gly Glu Leu Cys Glu Leu
1               5                   10

<210> SEQ ID NO 465
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Pro Gln Cys Arg Thr Ala Gln Val Gly Glu Leu Cys Asp Leu
1               5                   10

<210> SEQ ID NO 466
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Lys Ala Gly Gln Ala Cys Arg Ile Ala His Val Gly Glu Leu Cys Asp
1               5                   10                  15

Leu Asn Glu Thr
            20

<210> SEQ ID NO 467
<211> LENGTH: 20
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 467

Gln Ala Cys Arg Met Ala Gln Val Gly Glu Leu Cys Asp Phe Tyr Gly
1               5                   10                  15

Thr Pro Glu Ser
            20

<210> SEQ ID NO 468
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Leu Glu Phe Met Trp Ile Gln Asp Cys Gly Met Ala Glu Val Gly Glu
1               5                   10                  15

Leu Cys Glu Leu
            20

<210> SEQ ID NO 469
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Gln Asp Cys Lys Phe Ala Gln Leu Trp Asp Leu Cys Asp Leu
1               5                   10

<210> SEQ ID NO 470
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Asp Glu Met Gln Asp Cys Gln Ile Ala Gln Val Gly Glu Leu Cys Asp
1               5                   10                  15

Leu Gly Leu Glu
            20

<210> SEQ ID NO 471
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Glu Tyr Phe Ser His Asp Gln Asp Cys Gln Thr Ala Gln Leu Gly Glu
1               5                   10                  15

Leu Cys Lys Met
            20

```
<210> SEQ ID NO 472
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Gln Asp Cys Arg Phe Ala Gln Leu Gly Asp Leu Cys Asp Leu
1               5                   10

<210> SEQ ID NO 473
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Gln Asp Cys Arg Phe Ala His Leu Gly Glu Leu Cys Asp Leu Thr Glu
1               5                   10                  15

Gly Gln Trp Trp
            20

<210> SEQ ID NO 474
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Gln Asp Cys Arg Phe Ala His Val Gly Asp Ile Cys Asp Leu
1               5                   10

<210> SEQ ID NO 475
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Gly Ile Pro Gln Asp Cys Arg Ile Ala Leu Val Gly Glu Leu Cys Asp
1               5                   10                  15

Leu Asp Ile Ala
            20

<210> SEQ ID NO 476
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Gln Asp Cys Arg Lys Ala Asn Val Gly Glu Leu Cys Tyr Leu Asp Trp
1               5                   10                  15

Asp Ser Pro Thr
            20
```

-continued

```
<210> SEQ ID NO 477
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Gln Asp Cys Arg Leu Ala His Leu Gly Asp Leu Cys Asp Leu Trp Ser
1               5                   10                  15

Pro Arg Gln Asn
            20

<210> SEQ ID NO 478
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Arg Val Phe Gln Asp Cys Arg Leu Ala Leu Val Gly Glu Leu Cys Glu
1               5                   10                  15

Leu Val Gly Pro
            20

<210> SEQ ID NO 479
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Ser Arg Ser Ile Arg Val Gln Asp Cys Arg Leu Ala Arg Val Gly Asp
1               5                   10                  15

Leu Cys Glu Leu
            20

<210> SEQ ID NO 480
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Gln Asp Cys Arg Met Ala His Leu Gly Glu Leu Cys Thr Leu
1               5                   10

<210> SEQ ID NO 481
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Gln Asp Cys Arg Met Ala Gln Val Gly His Leu Cys Asp Leu
1               5                   10
```

-continued

```
<210> SEQ ID NO 482
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Gln Asp Cys Arg Met Ala Gln Val Gly Glu Leu Cys Glu Leu Arg Gly
1               5                   10                  15

Gly Asp Ser Ser
            20

<210> SEQ ID NO 483
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Ser Tyr Leu Gln Asp Cys Arg Met Ala Gln Val Gly Gln Leu Cys Asp
1               5                   10                  15

Leu Asn Asp Ser
            20

<210> SEQ ID NO 484
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Asn Gln Phe Gln Asp Cys Arg Arg Ala Leu Val Gly Gln Leu Cys Asp
1               5                   10                  15

Met Tyr Ser Lys
            20

<210> SEQ ID NO 485
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Ala Val Lys Arg Phe Arg Gln Asp Cys Arg Thr Ala Pro Val Gly Thr
1               5                   10                  15

Leu Cys Asp Leu
            20

<210> SEQ ID NO 486
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Gln Asp Cys Arg Thr Ala Pro Val Gly Asp Leu Cys Asp Ile Met Gly
```

-continued

```
                1               5                  10                  15

Glu Asp Val Leu
            20

<210> SEQ ID NO 487
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Trp Thr Trp Gln Asp Cys Ser Leu Ala Gln Val Gly Asp Leu Cys Asp
1               5                  10                  15

Ile Gly Lys Lys
            20

<210> SEQ ID NO 488
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Gln Asp Cys Trp Met Ala Gln Leu Gly Glu Leu Cys Asp Leu Phe Ser
1               5                  10                  15

Asp His Lys Val
            20

<210> SEQ ID NO 489
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (11)..(11)
<223> OTHER INFORMATION: Any amino acid

<400> SEQUENCE: 489

Pro Gly Val Gln Asp Cys Xaa Ile Ala His Xaa Gly Glu Leu Cys Glu
1               5                  10                  15

Phe Val Trp Asn
            20

<210> SEQ ID NO 490
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Ser Trp Gly Glu Leu Leu Gln Glu Cys Arg Phe Ala His Leu Gly Glu
1               5                  10                  15

Leu Cys Ser Leu
```

```
                           20

<210> SEQ ID NO 491
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Trp Gly Arg Gln Glu Cys Arg Phe Ala Asn Val Gly Asp Leu Cys Asp
1               5                   10                  15

Val Ser Asn Tyr
            20

<210> SEQ ID NO 492
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Ala Val Asn Gln Glu Cys Arg Phe Ala Arg Leu Gly Glu Leu Cys Val
1               5                   10                  15

Leu Lys Asn Ile
            20

<210> SEQ ID NO 493
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Asn Gln Val Gln Glu Cys Arg Ile Ala Gln Leu Gly Asp Leu Cys Glu
1               5                   10                  15

Met Tyr Gln Ser
            20

<210> SEQ ID NO 494
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Val Leu Glu Val Leu Arg Gln Glu Cys Arg Met Ala Gln Val Gly Glu
1               5                   10                  15

Leu Cys Asp Leu
            20

<210> SEQ ID NO 495
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 495

Ser Val Trp Gln Glu Cys Ser Met Ala Gln Val Gly Asp Leu Cys Glu
1               5                   10                  15

Leu His Ile Gly
            20

<210> SEQ ID NO 496
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Lys Ile Arg Arg Asp Ser Gln Gly Cys Glu Ile Ala Gln Val Gly Glu
1               5                   10                  15

Leu Cys Glu Leu
            20

<210> SEQ ID NO 497
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Gln Gly Cys Trp Met Ala Gln Leu Gly Glu Leu Cys Asp Leu Ser Val
1               5                   10                  15

Gln Glu Tyr Leu
            20

<210> SEQ ID NO 498
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Gln Ile Cys Gln Thr Ala Leu Val Gly Glu Leu Cys Asp Leu Ile Ala
1               5                   10                  15

Asp Val Val Thr
            20

<210> SEQ ID NO 499
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499

Trp Pro Met Ser Gln Phe Gln Lys Cys Ala Thr Ala Gln Val Gly Glu
1               5                   10                  15

Leu Cys Glu Leu
            20

<210> SEQ ID NO 500
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Phe Ile Ala Gln Lys Cys Arg Leu Ala Lys Val Gly Glu Leu Cys Asp
1               5                   10                  15

Leu Gly Tyr Ser
            20

<210> SEQ ID NO 501
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Asn Leu Arg Gln Asn Cys Arg Asp Ala Pro Val Gly Glu Leu Cys Asp
1               5                   10                  15

Leu Glu Trp Ile
            20

<210> SEQ ID NO 502
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Gln Asn Cys Arg Phe Ala Gln Leu Gly Gln Leu Cys Asp Leu
1               5                   10

<210> SEQ ID NO 503
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

Gln Asn Cys Ser Thr Ala Lys Val Gly Glu Leu Cys Asp Leu Leu Met
1               5                   10                  15

Glu Gly Thr Glu
            20

<210> SEQ ID NO 504
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

Gln Pro Cys Arg Met Ala His Leu Phe Glu Leu Cys Asp Leu
1               5                   10

<210> SEQ ID NO 505
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

Gln Pro Cys Arg Asn Ala His Leu Gly Gln Leu Cys Asp Leu Gln Thr
1               5                   10                  15

Trp Thr Asn Ser
            20

<210> SEQ ID NO 506
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Gly Tyr Glu Pro Ile Met Arg Ala Cys Arg Asn Ala Gln Val Gly Asp
1               5                   10                  15

Leu Cys Asp Leu
            20

<210> SEQ ID NO 507
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Val Thr Gly Trp Thr Tyr Arg Asp Cys Arg Ile Ala Asn Val Gly Asp
1               5                   10                  15

Leu Cys Glu Leu
            20

<210> SEQ ID NO 508
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Tyr Gln Lys Gly Tyr Ser Arg Glu Cys Ser Thr Ala Gln Leu Gly Glu
1               5                   10                  15

Leu Cys Asp Leu
            20

<210> SEQ ID NO 509
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

Gly Ala Lys Gly Arg Leu Arg Glu Cys Tyr Met Ala Gln Val Gly Glu
1               5                   10                  15
```

Leu Cys Asp Leu
            20

<210> SEQ ID NO 510
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Arg Gly Cys Glu Thr Ala Gln Val Gly Glu Leu Cys Asp Glu Asp Met
1               5                   10                  15

Trp His Asp Arg
            20

<210> SEQ ID NO 511
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 511

Ser Asp Cys Arg Ile Ala Arg Val Gly Glu Leu Cys Asp Leu Leu Ser
1               5                   10                  15

Asp Glu Gly Lys
            20

<210> SEQ ID NO 512
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Ser Asp Cys Arg Leu Ala Gln Val Gly Gln Leu Cys Asp Arg Arg Arg
1               5                   10                  15

Phe Arg Gly Val
            20

<210> SEQ ID NO 513
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Leu Tyr Val Val Arg Asn Ser Asp Cys Arg Met Ala Asn Val Gly Glu
1               5                   10                  15

Leu Cys Asp Leu
            20

<210> SEQ ID NO 514
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 514

Glu Lys Ser Ser Asp Cys Arg Asn Ala Gln Val Gly Glu Leu Cys Asp
1               5                   10                  15

Leu

<210> SEQ ID NO 515
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Ser Asp Cys Ser Val Ala Asn Val Gly Asp Leu Cys Asn Leu
1               5                   10

<210> SEQ ID NO 516
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Asn Arg Leu Ser Phe Ser Ser Glu Cys Arg Leu Ala Gln Val Gly Glu
1               5                   10                  15

Leu Cys Asp Leu
            20

<210> SEQ ID NO 517
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

Ser Gly Cys Arg Phe Ala His Leu Gly Glu Leu Cys Asp Leu
1               5                   10

<210> SEQ ID NO 518
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Thr Asp Cys Arg Met Ala Gln Val Gly Glu Leu Cys Tyr Leu
1               5                   10

<210> SEQ ID NO 519
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 519

Thr Asn Cys Arg Leu Ala His Val Gly Asp Leu Cys Asp Leu
```

```
1               5                   10
```

<210> SEQ ID NO 520
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520

```
Trp Gln Arg Gly Gln Gly Thr Gln Cys Arg Phe Ala Leu Val Gly Glu
1               5                   10                  15

Leu Cys Asp Leu
            20
```

<210> SEQ ID NO 521
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

```
Leu Lys Lys Tyr Arg His Val Ala Cys Arg Met Ala Val Val Gly Glu
1               5                   10                  15

Leu Cys Asp Leu
            20
```

<210> SEQ ID NO 522
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

```
Pro Met Gly Met Asp Pro Val Ala Cys Arg Thr Ala Gln Val Gly Gln
1               5                   10                  15

Leu Cys Asp Leu
            20
```

<210> SEQ ID NO 523
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

```
Val Asp Cys Arg Gln Ala Gln Val Gly Asp Leu Cys Glu Leu Ser Asp
1               5                   10                  15

Glu Glu Ile Ser
            20
```

<210> SEQ ID NO 524
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 524

Val Asp Cys Trp Ile Ala Gln Leu Gly Glu Leu Cys Glu Leu Glu Asp
1               5                   10                  15

Gly Arg Arg Gln
            20

<210> SEQ ID NO 525
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

Met Trp Ile Gly His Ala Val Glu Cys Arg Phe Ala His Val Gly Asp
1               5                   10                  15

Leu Cys Asp Leu
            20

<210> SEQ ID NO 526
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Val Leu Cys Arg Ile Ala Gln Val Gly Gln Leu Cys Glu Leu
1               5                   10

<210> SEQ ID NO 527
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 527

Val Met Cys Arg Thr Ala Gln Val Gly Glu Leu Cys Asp Ile
1               5                   10

<210> SEQ ID NO 528
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Val Asn Cys Arg Gln Ala Gln Val Gly Asp Leu Cys Asp Phe Glu Gly
1               5                   10                  15

Ile Met Ser Asp
            20

<210> SEQ ID NO 529
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 529

Val Asn Cys Ser Ile Ala Lys Leu Gly Glu Leu Cys Tyr Val
1               5                   10

<210> SEQ ID NO 530
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Trp Glu Cys Arg Trp Ala Gln Val Gly Asp Leu Cys Asp Leu
1               5                   10

<210> SEQ ID NO 531
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 531

Trp Gln Cys Arg Trp Ala Gln Val Gly Glu Leu Cys Asp Leu Ser Ser
1               5                   10                  15

Glu Asn Asp Asn
            20

<210> SEQ ID NO 532
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

Trp Tyr Cys Trp Met Ala Gln Ile Gly Glu Leu Cys Asp Leu
1               5                   10

<210> SEQ ID NO 533
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Tyr Gln Cys Ser Ile Ala Arg Leu Gly Glu Leu Cys Asp Leu
1               5                   10

<210> SEQ ID NO 534
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Tyr Ala Cys Arg Phe Ala His Val Gly Asp Leu Cys Asp Leu
1               5                   10
```

-continued

```
<210> SEQ ID NO 535
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

Glu Gln Thr Arg Ser Gly Tyr Ala Cys Arg Thr Ala Gln Val Gly Glu
1               5                   10                  15

Leu Cys Asp Leu
            20

<210> SEQ ID NO 536
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 536

Tyr Asp Cys Gln Lys Ala Gln Leu Gly Glu Leu Cys Asp Leu Arg Tyr
1               5                   10                  15

Ser Val Arg Asp
            20

<210> SEQ ID NO 537
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Tyr Asp Cys Glu Met Ala Gln Val Gly Glu Leu Cys Asp Leu
1               5                   10

<210> SEQ ID NO 538
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Asp Ser Gln Tyr Lys Tyr Tyr Asp Cys Gly Arg Ala Gln Leu Gly Glu
1               5                   10                  15

Leu Cys Glu Leu
            20

<210> SEQ ID NO 539
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 539

Tyr Asp Cys Arg Phe Ala His Leu Gly Asp Leu Cys Asp Leu
1               5                   10
```

```
<210> SEQ ID NO 540
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

Tyr Asp Cys Arg Phe Ala His Leu Gly Asp Leu Cys Asp Leu
1               5                   10

<210> SEQ ID NO 541
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 541

Tyr Asp Cys Arg Phe Ala His Leu Gly Asp Leu Cys Asp Leu
1               5                   10

<210> SEQ ID NO 542
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 542

Tyr Asp Cys Arg Phe Ala Gln Val Gly Gln Leu Cys Asp Ile
1               5                   10

<210> SEQ ID NO 543
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 543

Tyr Asp Cys Arg Ile Ala Gln Val Gly Gln Leu Cys Asp Leu
1               5                   10

<210> SEQ ID NO 544
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 544

Tyr Asp Cys Arg Ile Ala Gln Val Gly Glu Leu Cys Asp Leu
1               5                   10

<210> SEQ ID NO 545
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 545
```

-continued

```
Tyr Asp Cys Arg Ile Ala Gln Val Gly Asp Leu Cys Asp Leu Ile Ser
1               5                   10                  15

Asn Ser Asn Arg
            20

<210> SEQ ID NO 546
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

Met Asn Asp Tyr Asp Cys Arg Ile Ala Arg Met Gly Glu Leu Cys Asp
1               5                   10                  15

Leu Leu Leu Asp
            20

<210> SEQ ID NO 547
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 547

Tyr Asp Cys Arg Leu Ala Arg Leu Gly Asp Leu Cys Asp Leu Arg Val
1               5                   10                  15

Leu Gly Val Glu
            20

<210> SEQ ID NO 548
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Tyr Asp Cys Arg Met Ala Lys Val Gly Asp Leu Cys Asp Leu Trp Ser
1               5                   10                  15

Val Trp Gly Arg
            20

<210> SEQ ID NO 549
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Ile Ser Gln His Arg Asn Tyr Asp Cys Arg Met Ala Gln Leu Gly Glu
1               5                   10                  15

Leu Cys Asp Leu
            20

<210> SEQ ID NO 550
<211> LENGTH: 20
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 550

Tyr Asp Cys Arg Ser Ala Pro Val Gly Glu Leu Cys Asp Leu Val Pro
1               5                   10                  15

Lys Asp Trp Ala
            20

<210> SEQ ID NO 551
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 551

Thr Trp Ala Tyr Asp Cys Arg Thr Ala Glu Val Gly Glu Leu Cys Asp
1               5                   10                  15

Leu Pro Val Gln
            20

<210> SEQ ID NO 552
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Thr Ile Ile Tyr Asp Cys Arg Thr Ala Gln Leu Gly Glu Leu Cys Glu
1               5                   10                  15

Ile Asn Tyr Asp
            20

<210> SEQ ID NO 553
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553

Tyr Asp Cys Arg Val Ala His Val Gly Glu Leu Cys Asp Leu Pro Phe
1               5                   10                  15

Val Gly Arg Ala
            20

<210> SEQ ID NO 554
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

Leu Ser Val Tyr Asp Cys Ser Lys Ala Arg Leu Gly Glu Leu Cys Asp
1               5                   10                  15

Leu Val Leu Glu

20

<210> SEQ ID NO 555
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 555

Asp Gly Tyr Asp Tyr Trp Tyr Asp Cys Thr Met Ala Tyr Val Gly Glu
1               5                   10                  15

Leu Cys Asp Phe
            20

<210> SEQ ID NO 556
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

Thr Gly Lys Tyr Asp Cys Trp Lys Ala Met Val Gly Glu Leu Cys Asp
1               5                   10                  15

Leu Arg Val Met
            20

<210> SEQ ID NO 557
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Met Lys Tyr Tyr Glu Cys Arg Phe Ala Pro Leu Gly Glu Leu Cys Glu
1               5                   10                  15

Leu Gly Val Ile
            20

<210> SEQ ID NO 558
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

Tyr Glu Cys Arg Ile Ala Gln Val Gly Glu Leu Cys Asp Leu
1               5                   10

<210> SEQ ID NO 559
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

Asn His Trp Tyr Glu Cys Arg Ile Ala Gln Val Gly Glu Val Cys Asp

```
1               5                   10                  15

Leu

<210> SEQ ID NO 560
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Tyr Glu Cys Arg Leu Ala His Val Gly Asp Leu Cys Asp Leu
1               5                   10

<210> SEQ ID NO 561
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Tyr Glu Cys Arg Met Ala Asn Val Gly Glu Leu Cys Asp Ile
1               5                   10

<210> SEQ ID NO 562
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Tyr Glu Cys Arg Asn Ala Gln Val Gly Asp Leu Cys Asp Leu Gly Ser
1               5                   10                  15

Tyr Val Gly Asn
            20

<210> SEQ ID NO 563
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Val Glu Glu Tyr Phe Cys Arg Ile Ala His Leu Gly Glu Leu Cys Asp
1               5                   10                  15

Leu Gly Leu Lys
            20

<210> SEQ ID NO 564
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Thr Ser Ser Tyr Phe Cys Arg Met Ala Glu Leu Phe His Leu Cys Asp
1               5                   10                  15
```

-continued

```
Leu Glu Glu Ser
            20

<210> SEQ ID NO 565
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Lys Gly Gly Tyr Gly Cys Arg Phe Ala Arg Leu Gly Glu Leu Cys Asp
1               5                   10                  15

Leu Asp Ser Thr
            20

<210> SEQ ID NO 566
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Tyr Leu Cys Gln Val Ala Gly Val Gly Glu Leu Cys Asp Leu Glu Glu
1               5                   10                  15

Ser Gly Arg Asn
            20

<210> SEQ ID NO 567
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Phe Glu Glu Tyr Asn Cys Arg Phe Ala Arg Leu Gly Glu Leu Cys Asp
1               5                   10                  15

Met Gly Ser Gln
            20

<210> SEQ ID NO 568
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Gly Arg Phe Tyr Pro Cys Asn Met Ala Gln Val Gly Glu Leu Cys Glu
1               5                   10                  15

Leu Met Glu Tyr
            20

<210> SEQ ID NO 569
<211> LENGTH: 14
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 569

Tyr Pro Cys Arg Met Ala Asp Val Gly Glu Leu Cys Asp Leu
1               5                   10

<210> SEQ ID NO 570
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Leu Leu Ser Tyr Pro Cys Arg Met Ala Gln Val Gly Glu Leu Cys Asp
1               5                   10                  15

Ile Ala Met Lys
            20

<210> SEQ ID NO 571
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Tyr Gln Cys Arg Phe Ala Leu Val Gly Gln Leu Cys Asp Leu
1               5                   10

<210> SEQ ID NO 572
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

Tyr Gln Cys Arg Leu Ala His Leu Gly Glu Leu Cys Asp Leu
1               5                   10

<210> SEQ ID NO 573
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

Tyr Gln Cys Arg Met Ala Gln Val Gly Glu Leu Cys Asp Leu
1               5                   10

<210> SEQ ID NO 574
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Gly Ile Asp Glu Asp Trp Tyr Ser Cys Trp Ile Ala Glu Val Gly Glu
1               5                   10                  15

Leu Cys Asp Leu
        20

<210> SEQ ID NO 575
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 575

Tyr Trp Cys Arg Met Ala Pro Val Gly Glu Leu Cys Asp Leu Pro Gly
1               5                   10                  15

Thr Val Leu

<210> SEQ ID NO 576
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Tyr Trp Cys Ser Val Ala Lys Val Gly Glu Leu Cys Asp Leu
1               5                   10

<210> SEQ ID NO 577
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

His Gly Leu Tyr Tyr Cys Arg Thr Ala His Leu Gly Glu Leu Cys Asp
1               5                   10                  15

Leu Gln Ser Ile
        20

<210> SEQ ID NO 578
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: an amino acid comprising a large hydrophobic
      side chain or an aromatic side chain
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: an amino acid comprising a large hydrophobic
      side chain or an aromatic side chain
<220> FEATURE:
<221> NAME/KEY: MOD_RES
<222> LOCATION: (4)..(4)
<223> OTHER INFORMATION: an amino acid comprising a large hydrophobic
      side chain or a basic side chain
<220> FEATURE:

```
<221> NAME/KEY: MOD_RES
<222> LOCATION: (5)..(5)
<223> OTHER INFORMATION: an amino acid comprising an acidic side chain
      or a small hydrophobic side chain
<220> FEATURE:
<221> NAME/KEY: MOD_RES
<222> LOCATION: (7)..(7)
<223> OTHER INFORMATION: an amino acid comprising a large hydrophobic
      side chain or a basic side chain
<220> FEATURE:
<221> NAME/KEY: MOD_RES
<222> LOCATION: (8)..(8)
<223> OTHER INFORMATION: an amino acid comprising a large hydrophobic
      side chain
<220> FEATURE:
<221> NAME/KEY: MOD_RES
<222> LOCATION: (9)..(9)
<223> OTHER INFORMATION: an amino acid comprising a small hydrophobic
      side chain
<220> FEATURE:
<221> NAME/KEY: MOD_RES
<222> LOCATION: (10)..(10)
<223> OTHER INFORMATION: an amino acid comprising a polar/neutral side
      chain or a basic side chain
<220> FEATURE:
<221> NAME/KEY: MOD_RES
<222> LOCATION: (11)..(11)
<223> OTHER INFORMATION: an amino acid comprising a large hydrophobic
      side chain
<220> FEATURE:
<221> NAME/KEY: MOD_RES
<222> LOCATION: (12)..(12)
<223> OTHER INFORMATION: an amino acid comprising a small hydrophobic
      side chain
<220> FEATURE:
<221> NAME/KEY: MOD_RES
<222> LOCATION: (13)..(13)
<223> OTHER INFORMATION: an amino acid comprising an acidic side chain
      or a polar/neutral side chain
<220> FEATURE:
<221> NAME/KEY: MOD_RES
<222> LOCATION: (14)..(14)
<223> OTHER INFORMATION: an amino acid comprising a large hydrophobic
      side chain
<220> FEATURE:
<221> NAME/KEY: MOD_RES
<222> LOCATION: (16)..(16)
<223> OTHER INFORMATION: an amino acid comprising an acidic side chain
<220> FEATURE:
<221> NAME/KEY: MOD_RES
<222> LOCATION: (17)..(17)
<223> OTHER INFORMATION: an amino acid comprising a large hydrophobic
      side chain
<220> FEATURE:
<221> NAME/KEY: MOD_RES
<222> LOCATION: (18)..(18)
<223> OTHER INFORMATION: an amino acid comprising an acidic side chain
      or an aromatic side chain
<220> FEATURE:
<221> NAME/KEY: MOD_RES
<222> LOCATION: (19)..(19)
<223> OTHER INFORMATION: an amino acid comprising an amino acid
<220> FEATURE:
<221> NAME/KEY: MOD_RES
<222> LOCATION: (20)..(20)
<223> OTHER INFORMATION: an amino acid comprising an acidic side chain

<400> SEQUENCE: 578

Xaa Xaa Xaa Xaa Xaa Cys Xaa Xaa Xaa Xaa Xaa Xaa Xaa Xaa Cys Xaa
1               5                   10                  15

Xaa Xaa Xaa Xaa
            20

<210> SEQ ID NO 579
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 579

Ile Tyr Cys Gly Phe Ala Pro Leu Gly Glu Leu Cys Ile Leu
1               5                   10

<210> SEQ ID NO 580
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 580

Leu Pro Cys Trp Ile Ala Gln Val Gly Glu Leu Cys Asp Leu
1               5                   10

<210> SEQ ID NO 581
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 581

Leu Pro Cys His Met Ala Gln Leu Gly Glu Leu Cys Asp Leu
1               5                   10

<210> SEQ ID NO 582
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

His Pro Cys Trp Met Ala Lys Val Gly Glu Leu Cys Asp Leu
1               5                   10

<210> SEQ ID NO 583
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

Tyr Pro Cys His Met Ala Asn Val Gly Glu Leu Cys Asp Leu
1               5                   10

<210> SEQ ID NO 584
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 584

Ser Gly Ser Asn Asp Val Pro His Cys Ser Met Ala Asp Leu Gly Asp
1               5                   10                  15
```

Leu Cys His Leu
            20

<210> SEQ ID NO 585
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

Trp His Gln Trp Leu Arg Lys Asp Cys Arg Phe Ala Lys Leu Gly Glu
1               5                   10                  15

Leu Cys Asp Leu
            20

<210> SEQ ID NO 586
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

Gly Arg Gly Val Glu Tyr Lys Glu Cys Trp Met Ala Ser Leu Gly Glu
1               5                   10                  15

Leu Cys Thr Leu
            20

<210> SEQ ID NO 587
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587

Gly Arg Ala Asp Gln Val Leu Pro Cys Trp Met Ala Gln Leu Gly Glu
1               5                   10                  15

Leu Cys Glu Leu
            20

<210> SEQ ID NO 588
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 588

Ile Asn Gln Ser Val Leu Trp Pro Cys His Leu Ala Ala Val Gly Asp
1               5                   10                  15

Leu Cys Asp Leu
            20

<210> SEQ ID NO 589
<211> LENGTH: 20
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 589

Leu Val Gly Trp Asn His Tyr Asp Cys Ser Val Ala Arg Val Gly Glu
1               5                   10                  15

Leu Cys Asp Leu
            20

<210> SEQ ID NO 590
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

Tyr Pro Cys Trp Met Ala Gln Ile Gly Glu Leu Cys Asp Leu
1               5                   10

<210> SEQ ID NO 591
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 591

Tyr Pro Cys His Ile Ala Leu Leu Gly Glu Leu Cys Asp Leu
1               5                   10

<210> SEQ ID NO 592
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 592

Leu Tyr Cys Trp Gln Ala Gln Leu Gly Gln Leu Cys Asp Leu
1               5                   10

<210> SEQ ID NO 593
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 593

Tyr Asp Cys Arg Phe Ala Gln Leu Gly Glu Leu Cys Asp Leu
1               5                   10

<210> SEQ ID NO 594
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 594

Leu Met Cys Trp Asn Ala Gln Leu Gly Asp Leu Cys Asp Leu
1               5                   10
```

<210> SEQ ID NO 595
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 595

Thr Met Ala Ser Asn Trp Tyr Asp Cys His Met Ala Gln Val Gly Glu
1               5                   10                  15

Leu Cys Asp Leu
            20

<210> SEQ ID NO 596
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 596

Leu Glu Tyr Asp Trp Asn Gln Ala Cys Ser Lys Ala His Leu Gly Glu
1               5                   10                  15

Leu Cys Val Leu
            20

<210> SEQ ID NO 597
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 597

Arg Ile Leu Tyr Glu Tyr Pro Asp Cys Trp Met Ala Gln Leu Gly Glu
1               5                   10                  15

Leu Cys Glu Leu
            20

<210> SEQ ID NO 598
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 598

Ala Gln Ala Arg Phe Trp His Asp Cys Ser Ile Ala His Val Gly Glu
1               5                   10                  15

Leu Cys Asp Leu
            20

<210> SEQ ID NO 599
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 599

Thr Ala Ala Glu Tyr Trp Tyr Pro Cys Trp Met Ala Gln Val Gly Glu
1               5                   10                  15

Leu Cys Asp Leu
            20

<210> SEQ ID NO 600
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 600

Gly Pro Ser Met Thr Tyr Lys Ala Cys Trp Met Ala Gln Leu Gly Glu
1               5                   10                  15

Leu Cys Glu Leu
            20

<210> SEQ ID NO 601
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 601

Tyr Phe Cys His Ile Ala Lys Leu Gly Glu Leu Cys Asp Leu
1               5                   10

<210> SEQ ID NO 602
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 602

Leu Ala Cys Arg Phe Ala Lys Leu Gly Glu Leu Cys Asp Leu
1               5                   10

<210> SEQ ID NO 603
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 603

Leu Pro Cys Trp Met Ala Gln Leu Gly Asp Leu Cys Asp Leu
1               5                   10

<210> SEQ ID NO 604
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 604

Leu Tyr Arg Pro Asn Tyr Ser Asp Cys Ser Met Ala Gln Leu Gly Glu
1               5                   10                  15

```
Leu Cys Glu Met
            20

<210> SEQ ID NO 605
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 605

Lys Leu Gly Lys Gly Trp His Asp Cys Ser Val Ala Gln Val Gly Glu
1               5                   10                  15

Leu Cys Asp Leu
            20

<210> SEQ ID NO 606
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 606

Asp Val Phe Lys Asn Trp Tyr Asp Cys Arg Ile Ala Lys Leu Gly Glu
1               5                   10                  15

Leu Cys Asp Leu
            20

<210> SEQ ID NO 607
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 607

Glu Tyr Val Leu Lys Trp Pro Asp Cys Ser Ser Ala Gln Leu Gly Glu
1               5                   10                  15

Leu Cys Glu Leu
            20

<210> SEQ ID NO 608
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 608

Arg Ala Leu Arg Lys Phe His Asp Cys Ser Thr Ala Arg Leu Gly Glu
1               5                   10                  15

Leu Cys Asp Leu
            20

<210> SEQ ID NO 609
<211> LENGTH: 20
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 609

Gln Val Glu Gly Ser Tyr Tyr Asp Cys Arg Trp Ala His Leu Gly Glu
1               5                   10                  15

Leu Cys Asp Leu
            20

<210> SEQ ID NO 610
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 610

Tyr Pro Cys Arg Met Ala Lys Leu Gly Glu Leu Cys Asp Leu
1               5                   10

<210> SEQ ID NO 611
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 611

Tyr Pro Cys Trp Leu Ala His Val Gly Glu Leu Cys Asp Leu
1               5                   10

<210> SEQ ID NO 612
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 612

Tyr Pro Cys Trp Met Ala Gln Leu Gly Glu Leu Cys Asp Leu
1               5                   10

<210> SEQ ID NO 613
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 613

Tyr Asp Cys Ser Ile Ala Gln Leu Gly Glu Leu Cys Asp Leu
1               5                   10

<210> SEQ ID NO 614
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Leu Tyr Cys Trp Ala Ala Gln Leu Gly Glu Leu Cys Asp Leu
1               5                   10

<210> SEQ ID NO 615
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 615

Leu Ala Cys Trp Met Ala His Leu Gly Asp Leu Cys Asp Leu
1               5                   10

<210> SEQ ID NO 616
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 616

Ser Ser Tyr Asp Met Asp Gln Asp Cys Arg Trp Ala Gln Leu Gly Gln
1               5                   10                  15

Leu Cys Ala Ile
            20

<210> SEQ ID NO 617
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 617

Met Glu Asn Lys Tyr Trp Tyr Asp Cys Ser Val Ala Leu Val Gly Glu
1               5                   10                  15

Leu Cys Asp Leu
            20

<210> SEQ ID NO 618
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 618

Lys Val Lys Leu Ser Trp Tyr Asp Cys Ser Val Ala Gln Val Gly Glu
1               5                   10                  15

Leu Cys Asp Leu
            20

<210> SEQ ID NO 619
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 619

Gly Phe Leu Leu Glu Trp Tyr Asp Cys Arg Ile Ala Gln Val Gly Glu
1               5                   10                  15

Leu Cys Asp Leu
            20

<210> SEQ ID NO 620
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 620

Tyr Asp Ser Arg Ser Tyr Leu Pro Cys His Met Ala Gln Leu Gly Asp
1               5                   10                  15

Leu Cys Asp Leu
            20

<210> SEQ ID NO 621
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 621

Glu Ser Met Gly Leu Gly Tyr Pro Cys Trp Arg Ala Gln Leu Gly Glu
1               5                   10                  15

Leu Cys Asp Leu
            20

<210> SEQ ID NO 622
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 622

Tyr Pro Cys Trp Met Ala Leu Val Gly Glu Leu Cys Asp Leu
1               5                   10

<210> SEQ ID NO 623
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 623

Tyr Asp Cys Arg Phe Ala Leu Leu Gly Glu Leu Cys Asp Leu
1               5                   10

<210> SEQ ID NO 624
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 624

Tyr Trp Cys Trp Met Ala Gln Leu Gly Glu Leu Cys Asp Leu
1               5                   10

<210> SEQ ID NO 625
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 625

Lys Trp Cys Trp Leu Ala His Leu Gly Glu Leu Cys Asp Leu
1               5                   10

<210> SEQ ID NO 626
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 626

Leu Pro Cys Trp Leu Ala Lys Val Gly Asp Leu Cys Asp Leu
1               5                   10

<210> SEQ ID NO 627
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 627

Asp His Leu Gln Arg Trp Trp Pro Cys Arg Leu Ala Arg Leu Gly Glu
1               5                   10                  15

Leu Cys Asp Leu
            20

<210> SEQ ID NO 628
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 628

Lys Ser Gly Gln Arg Tyr Tyr Asp Cys Ser Met Ala Gln Leu Gly Glu
1               5                   10                  15

Leu Cys Asp Leu
            20

<210> SEQ ID NO 629
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 629

Glu Leu Val Lys Thr Trp Tyr Pro Cys Trp Lys Ala His Val Gly Glu
1               5                   10                  15

Leu Cys Asp Leu
            20

```
<210> SEQ ID NO 630
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 630

Arg Ser Leu Phe Leu Trp His Asp Cys Ser Thr Ala Gln Leu Gly Glu
1               5                   10                  15

Leu Cys Asp Leu
            20

<210> SEQ ID NO 631
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 631

Leu Pro Arg Ser Gly Trp Tyr Asp Cys Ser Ile Ala His Val Gly Glu
1               5                   10                  15

Leu Cys Asp Leu
            20

<210> SEQ ID NO 632
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 632

Leu Ser Val Asn Lys Trp Tyr Pro Cys Trp Ile Ala Asp Val Gly Glu
1               5                   10                  15

Leu Cys Asp Trp
            20

<210> SEQ ID NO 633
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 633

Tyr Pro Cys Trp Ile Ala Gln Val Gly Glu Leu Cys Asp Leu
1               5                   10

<210> SEQ ID NO 634
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 634

Leu Lys Cys Trp Met Ala Gln Leu Gly Glu Leu Cys Asp Leu
1               5                   10
```

```
<210> SEQ ID NO 635
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 635

Leu Asp Cys Arg Phe Ala Gln Val Gly Asp Leu Cys Asp Ile
1               5                   10

<210> SEQ ID NO 636
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 636

Leu Trp Cys Trp Met Ala Gln Leu Gly Glu Leu Cys Asp Leu
1               5                   10

<210> SEQ ID NO 637
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 637

Tyr Pro Cys Trp Val Ala Lys Leu Gly Glu Leu Cys Asp Phe
1               5                   10

<210> SEQ ID NO 638
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 638

Trp Ser Ser Lys Val Val Lys Pro Cys His Ile Ala Arg Leu Gly Glu
1               5                   10                  15

Leu Cys Glu Leu
            20

<210> SEQ ID NO 639
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 639

Leu Asp Glu Thr Tyr Trp Tyr Asp Cys His Val Ala Gln Val Gly Glu
1               5                   10                  15

Leu Cys Asp Leu
            20

<210> SEQ ID NO 640
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 640

Thr Ser Leu Asp Ser Tyr Tyr Asp Cys Gly Met Ala Lys Val Gly Glu
1               5                   10                  15

Leu Cys Asp Leu
            20

<210> SEQ ID NO 641
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 641

Glu Ser Gly His Tyr Ile Lys His Cys Ser Ile Ala Leu Leu Gly Glu
1               5                   10                  15

Leu Cys His Leu
            20

<210> SEQ ID NO 642
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 642

Arg Thr Tyr Asp Pro Gly Gln Asp Cys Arg Leu Ala Gln Leu Gly Glu
1               5                   10                  15

Leu Cys Glu Leu
            20

<210> SEQ ID NO 643
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 643

Leu Met Cys Trp Leu Ala Gln Leu Gly Glu Leu Cys Glu Leu
1               5                   10

<210> SEQ ID NO 644
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 644

Tyr Pro Cys Trp Ile Ala Lys Val Gly Glu Leu Cys Asp Leu
1               5                   10

<210> SEQ ID NO 645
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 645

Tyr Trp Cys Trp Met Ala Gln Val Gly Glu Leu Cys Asp Leu
1               5                   10

<210> SEQ ID NO 646
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 646

Tyr Glu Cys His Leu Ala Lys Leu Gly Glu Leu Cys Asp Leu
1               5                   10

<210> SEQ ID NO 647
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 647

Arg Gly Arg Trp Glu Trp Tyr Asp Cys Ser Ile Ala Gln Val Gly Glu
1               5                   10                  15

Leu Cys Asp Val
            20

<210> SEQ ID NO 648
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 648

Arg Ser Phe Glu Asn Trp Tyr Asp Cys Arg Ile Ala Gln Leu Gly Glu
1               5                   10                  15

Leu Cys Asp Leu
            20

<210> SEQ ID NO 649
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 649

Pro Ser Ser Arg Gly Tyr Lys Pro Cys Trp Ser Ala Gln Val Gly Glu
1               5                   10                  15

Leu Cys Glu Leu
            20

<210> SEQ ID NO 650
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 650

Val Asp Val Ser Gly Trp Lys Pro Cys Tyr Met Ala His Leu Gly Glu
1               5                   10                  15

Leu Cys Asp Leu
            20

<210> SEQ ID NO 651
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 651

Val Glu Thr Thr Ala Trp Tyr Pro Cys Glu Leu Ala Gln Leu Gly Glu
1               5                   10                  15

Leu Cys Asp Leu
            20

<210> SEQ ID NO 652
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 652

Leu His Cys His Asn Ala Gln Val Gly Asp Leu Cys Asp Leu
1               5                   10

<210> SEQ ID NO 653
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 653

Leu Trp Cys His Met Ala Asn Leu Gly Asp Leu Cys Asp Leu
1               5                   10

<210> SEQ ID NO 654
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 654

Tyr Pro Cys His Ile Ala Gln Val Gly Glu Leu Cys Asp Leu
1               5                   10

<210> SEQ ID NO 655
<211> LENGTH: 14
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 655

Tyr Pro Cys His Val Ala Gln Leu Gly Glu Leu Cys Asp Leu
1               5                   10

<210> SEQ ID NO 656
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 656

Tyr Asp Cys Ser Met Ala Gln Leu Gly Glu Leu Cys Asp Leu
1               5                   10

<210> SEQ ID NO 657
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 657

Gln Trp Cys Trp Met Ala Arg Leu Gly Glu Leu Cys Asp Leu
1               5                   10

<210> SEQ ID NO 658
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 658

Leu Met Val Trp Asp Arg Arg Asp Cys Ser Thr Ala Gln Leu Gly Glu
1               5                   10                  15

Leu Cys Asp Leu
            20

<210> SEQ ID NO 659
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 659

Thr Arg Asn Glu Phe Val Tyr Pro Cys Trp Leu Ala Gln Val Gly Glu
1               5                   10                  15

Leu Cys Asp Leu
            20

<210> SEQ ID NO 660
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 660

Ala Val Arg Asn Val Trp Tyr Asp Cys Ser Phe Ala Arg Leu His Glu
1               5                   10                  15

Leu Cys Asp Val
            20

<210> SEQ ID NO 661
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 661

Glu Val Asn Trp Leu Tyr Tyr Asp Cys Arg Phe Ala His Leu Gly Glu
1               5                   10                  15

Leu Cys Asp Leu
            20

<210> SEQ ID NO 662
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 662

Arg Lys Thr Trp Ile Trp Lys Asp Cys Ser Ile Ala Arg Val Gly Glu
1               5                   10                  15

Leu Cys Asp Leu
            20

<210> SEQ ID NO 663
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 663

Tyr Asp Cys Arg Ile Ala Gln Val Gly Glu Leu Cys Asp Leu
1               5                   10

<210> SEQ ID NO 664
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 664

Tyr Pro Cys His Met Ala Gln Leu Gly Glu Leu Cys Asp Leu Trp Ser
1               5                   10                  15

Trp Gly Asp Ile
            20

<210> SEQ ID NO 665
<211> LENGTH: 20
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 665

Phe Asp Cys Arg Phe Ala Gln Val Gly Asp Leu Cys Asp Leu Trp Ser
1               5                   10                  15

Pro Glu His Ile
            20

<210> SEQ ID NO 666
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 666

Leu Pro Cys Trp Leu Ala Asn Val Gly Glu Leu Cys Asp Leu Pro Gly
1               5                   10                  15

Lys Phe Glu Arg
            20

<210> SEQ ID NO 667
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 667

Tyr Asp Cys Arg Asn Ala His Val Gly Glu Leu Cys Asp Leu Ile Asp
1               5                   10                  15

Val Pro Trp Glu
            20

<210> SEQ ID NO 668
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 668

Leu Lys Cys Trp Met Ala Gln Val Gly Glu Leu Cys Asp Leu Gly Val
1               5                   10                  15

Asp Asp Gly Gln
            20

<210> SEQ ID NO 669
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 669

Tyr Glu Cys Trp Met Ala Lys Leu Gly Glu Leu Cys Asp Met Tyr Leu
1               5                   10                  15

Glu Gly Glu Ile
            20
```

<210> SEQ ID NO 670
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 670

Gly Asp Val Tyr Phe Cys Trp Asn Ala Lys Leu Gly Glu Leu Cys Asp
1               5                   10                  15

Leu Phe Glu Met
            20

<210> SEQ ID NO 671
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 671

Val Gln Tyr Lys Lys Cys Trp Met Ala Gln Leu Gly Asp Leu Cys Glu
1               5                   10                  15

Leu Asp Pro Ser
            20

<210> SEQ ID NO 672
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 672

Pro Leu Cys Tyr Ser Cys Gln Met Ala Arg Val Gly Glu Leu Cys Asp
1               5                   10                  15

Leu Gly Cys Asp
            20

<210> SEQ ID NO 673
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 673

Ile Gly Tyr His Ala Cys Trp Met Ala Gln Leu Gly Asp Leu Cys Asp
1               5                   10                  15

Leu His Asp Asn
            20

<210> SEQ ID NO 674
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 674

```
Met Ser Trp Tyr Asp Cys Trp Met Ala Gln Val Gly Glu Leu Cys Asp
1               5                   10                  15

Leu His Val Leu
            20

<210> SEQ ID NO 675
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 675

Tyr Leu Cys Arg Phe Ala Gln Leu Gly Glu Leu Cys Asp Leu His Val
1               5                   10                  15

His Trp Glu Asp
            20

<210> SEQ ID NO 676
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 676

Tyr Tyr Cys Gly Ile Ala Asn Val Gly Glu Leu Cys Asp Leu Glu Met
1               5                   10                  15

Gly Gly Asn Ile
            20

<210> SEQ ID NO 677
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 677

Tyr His Cys Arg Phe Ala Gln Val Gly Glu Leu Cys Asp Leu Glu Pro
1               5                   10                  15

Gln Ile Thr Trp
            20

<210> SEQ ID NO 678
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 678

Leu Gly Cys Trp Leu Ala His Val Gly Glu Leu Cys Asp Leu Met Phe
1               5                   10                  15

Pro Gly Asp Glu
            20

<210> SEQ ID NO 679
<211> LENGTH: 20
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 679

Gly Trp His His Trp Cys His Met Ala Gln Val Gly Glu Leu Cys Asp
1               5                   10                  15

Leu Gln Val Thr
            20

<210> SEQ ID NO 680
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 680

Glu Thr Val Ser Asp Cys Arg Met Ala Gln Val Gly Glu Leu Cys Glu
1               5                   10                  15

Tyr His Ser Ala
            20

<210> SEQ ID NO 681
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 681

Trp Ser Trp Tyr Asp Cys Arg Ile Ala Gln Ile Gly Glu Leu Cys Asp
1               5                   10                  15

Leu Ile Ile Met
            20

<210> SEQ ID NO 682
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 682

Trp Leu Phe Tyr Asp Cys Arg Trp Ala Gln Val Gly Glu Leu Cys Asp
1               5                   10                  15

Leu Ser Gly Asp
            20

<210> SEQ ID NO 683
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 683

Tyr Pro Cys Trp Ile Ala Gln Ile Gly Glu Leu Cys Asp Met Asp Pro
1               5                   10                  15

Arg Ala Asn Met
```

20

<210> SEQ ID NO 684
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 684

Tyr Asp Cys Arg Phe Ala Gln Leu Gly Glu Leu Cys Asp Leu Tyr Glu
1               5                   10                  15

Thr Asp Gly Arg
            20

<210> SEQ ID NO 685
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 685

Tyr Trp Cys Arg Phe Ala Gln Val Gly Glu Leu Cys Asp Val Gln Met
1               5                   10                  15

Tyr Ala Ser Gln
            20

<210> SEQ ID NO 686
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 686

Leu Pro Cys Trp Met Ala Gln Val Gly Gln Leu Cys Tyr Leu Asp Thr
1               5                   10                  15

Glu Arg His Ser
            20

<210> SEQ ID NO 687
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 687

Tyr Ala Cys Tyr Ile Ala Lys Leu Gly Glu Leu Cys Asp Leu Glu Met
1               5                   10                  15

Thr Asp His Gly
            20

<210> SEQ ID NO 688
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 688

Pro Glu Trp Tyr Asp Cys Ser Thr Ala Gln Val Gly Glu Leu Cys Asp
1               5                   10                  15

Leu Phe Asp Asp
            20

<210> SEQ ID NO 689
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 689

Ser Ser Tyr Tyr Ser Cys Ser Met Ala Gln Leu Gly Glu Leu Cys Asp
1               5                   10                  15

Leu Lys Leu Ser
            20

<210> SEQ ID NO 690
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 690

Asp Arg Phe Asn Pro Cys His Met Ala Gln Leu Gly Glu Leu Cys Asp
1               5                   10                  15

Leu Ala Arg Asp
            20

<210> SEQ ID NO 691
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 691

Trp Leu Tyr Pro Glu Cys Arg Phe Ala Gln Val Gly Gln Leu Cys Glu
1               5                   10                  15

Phe Arg Asn Gln
            20

<210> SEQ ID NO 692
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 692

Ala Gly Trp His Pro Cys His Leu Ala Gln Val Gly Glu Leu Cys Asp
1               5                   10                  15

Leu Asp Ala Leu
            20

<210> SEQ ID NO 693
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 693

Tyr Ala Cys Trp Leu Ala Lys Val Gly Glu Leu Cys Asp Met Asp Glu
1               5                   10                  15
Asp Phe Thr Ile
            20

<210> SEQ ID NO 694
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 694

Tyr Ser Cys Gly Ile Ala Lys Val Gly Glu Leu Cys Asp Leu Val Asp
1               5                   10                  15
Gln Glu Pro Asp
            20

<210> SEQ ID NO 695
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 695

His Pro Cys His Met Ala Arg Leu Gly Glu Leu Cys Asp Leu His Ser
1               5                   10                  15
Gly Val Tyr Asp
            20

<210> SEQ ID NO 696
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 696

Leu Tyr Cys Gly Phe Ala Gln Val Gly Asp Leu Cys Asp Leu Asp Val
1               5                   10                  15
Glu Val Thr Tyr
            20

<210> SEQ ID NO 697
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 697

Leu Pro Cys Trp Lys Ala Tyr Val Gly Glu Leu Cys Asp Leu Asn Met
1               5                   10                  15
```

Pro Arg Leu Asp
            20

<210> SEQ ID NO 698
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 698

Ala Glu Val Lys Pro Cys His Met Ala Gln Val Gly Asp Leu Cys Asp
1               5                   10                  15

Leu Thr Gly Gly
            20

<210> SEQ ID NO 699
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 699

Thr Pro His Tyr Pro Cys Trp Met Ala His Met Gly Glu Leu Cys Asp
1               5                   10                  15

Leu Glu Trp Lys
            20

<210> SEQ ID NO 700
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 700

Pro Ile Tyr Gln Pro Cys His Met Ala Ala Leu Gly Glu Leu Cys Asp
1               5                   10                  15

Leu Gly Thr Ala
            20

<210> SEQ ID NO 701
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 701

Ser Lys Phe Tyr Asp Cys Arg Ile Ala Lys Leu Gly Glu Leu Cys Asp
1               5                   10                  15

Leu Arg Ser Gly
            20

<210> SEQ ID NO 702
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 702

Leu Asp Trp His Ala Cys Trp Glu Ala Gln Val Gly Glu Leu Cys Asp
1               5                   10                  15

Leu Arg Arg Ser
            20

<210> SEQ ID NO 703
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 703

Leu Trp Cys His Met Ala Asn Val Gly Glu Leu Cys Asp Ile Asp Trp
1               5                   10                  15

Thr Asn Gly Ser
            20

<210> SEQ ID NO 704
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 704

Leu Ala Cys His Val Ala Gln Leu Gly Glu Leu Cys Asp Leu Trp Pro
1               5                   10                  15

Asp Gly Val Asn
            20

<210> SEQ ID NO 705
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 705

Lys Pro Cys Tyr Met Ala Gln Val Gly Glu Leu Cys Asp Leu Pro Ala
1               5                   10                  15

Glu Ser Leu Ser
            20

<210> SEQ ID NO 706
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 706

Tyr Asp Cys Ser Ile Ala Gln Leu Gly Glu Leu Cys Asp Val Glu Pro
1               5                   10                  15

Trp Glu Ser Met
            20

<210> SEQ ID NO 707
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 707

Tyr Trp Cys Arg Trp Ala Gln Val Gly Glu Leu Cys Asp Leu Glu Val
1               5                   10                  15

Glu Asn Lys Asp
            20

<210> SEQ ID NO 708
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 708

Leu His Cys Tyr Asp Ala Gln Val Gly Glu Leu Cys Asp Leu Glu Asn
1               5                   10                  15

Trp Leu His Gln
            20

<210> SEQ ID NO 709
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 709

Ile Lys Met Ser Pro Cys His Leu Ala Gln Val Gly Glu Leu Cys Asp
1               5                   10                  15

Leu Gln Trp Glu
            20

<210> SEQ ID NO 710
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 710

Arg His Phe Leu Asp Cys Arg Ile Ala Gln Ile Gly Asp Leu Cys Asp
1               5                   10                  15

Leu Ile Gly Phe
            20

<210> SEQ ID NO 711
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 711

Pro Ala Tyr Tyr Asp Cys Ser Ile Ala Lys Val Gly Glu Leu Cys Asp
1               5                   10                  15
```

```
Leu Ser Met Met
            20

<210> SEQ ID NO 712
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 712

Val Arg Phe His Asp Cys Ser Ile Ala Leu Val Gly Asp Leu Cys Asp
1               5                   10                  15

Leu His Met Tyr
            20

<210> SEQ ID NO 713
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 713

Val Thr Pro Tyr Tyr Cys Trp Asn Ala Lys Leu Gly Glu Leu Cys Asp
1               5                   10                  15

Met Met Trp Asn
            20

<210> SEQ ID NO 714
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 714

Glu Tyr Ser Leu Asp Cys Arg Ile Ala Gln Leu Gly Gln Leu Cys Asp
1               5                   10                  15

Leu Met Arg Trp
            20

<210> SEQ ID NO 715
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 715

Tyr Asp Cys Arg Met Ala Lys Val Gly Glu Leu Cys Asp Leu Trp Trp
1               5                   10                  15

Asp Thr Leu Tyr
            20

<210> SEQ ID NO 716
<211> LENGTH: 20
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 716

Tyr Asp Cys His Met Ala Lys Leu Gly Glu Leu Cys Asp Leu Met Leu
1               5                   10                  15

Gly Asp Val Thr
            20

<210> SEQ ID NO 717
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 717

Tyr Pro Cys His Leu Ala His Val Gly Glu Leu Cys Asp Leu Glu Gly
1               5                   10                  15

Gly Thr Glu Phe
            20

<210> SEQ ID NO 718
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 718

Tyr Asp Cys Ser Ile Ala Arg Val Gly Glu Leu Cys Asp Leu Leu Gln
1               5                   10                  15

Asp Trp Trp Pro
            20

<210> SEQ ID NO 719
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 719

Leu Pro Cys Trp Leu Ala Gln Val Gly Glu Leu Cys Asp Leu Gln Glu
1               5                   10                  15

Glu Thr Gly Ser
            20

<210> SEQ ID NO 720
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 720

Asp Gly His Tyr Glu Cys Trp Lys Ala Gln Leu Gly Glu Leu Cys Asp
1               5                   10                  15

Leu Ala Gly Ala
            20

```
<210> SEQ ID NO 721
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 721

Ser Phe Val Gln Asp Cys Ser Leu Ala Gln Leu Trp Asp Leu Cys Glu
1               5                   10                  15

Ile Trp Thr Asp
            20

<210> SEQ ID NO 722
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 722

Glu Pro Phe Tyr His Cys Ser Ile Ala Gln Leu Gly Glu Leu Cys Asp
1               5                   10                  15

Leu Val Arg Ala
            20

<210> SEQ ID NO 723
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 723

Trp Pro Trp Gln Asp Cys Ser Thr Ala Gln Leu Gly Asp Leu Cys Asp
1               5                   10                  15

Leu Met Ser Tyr
            20

<210> SEQ ID NO 724
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 724

Gly Leu Thr Leu Pro Cys Trp Met Ala Gln Leu Gly Glu Leu Cys Asp
1               5                   10                  15

Leu Asn Asn Ala
            20

<210> SEQ ID NO 725
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 725

Asn Leu His Tyr Asp Cys Arg Ile Ala Gln Val Gly Glu Leu Cys Asp
```

-continued

```
                1               5                  10                  15

Leu Thr Tyr Glu
            20

<210> SEQ ID NO 726
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 726

Tyr His Cys Phe Leu Ala Gln Val Gly Asp Leu Cys Asp Leu Trp Asp
1               5                   10                  15

Ser Met Thr Thr
            20

<210> SEQ ID NO 727
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 727

Arg Trp Cys His Met Ala Gln Leu Gly Asp Leu Cys Glu Leu Tyr Ile
1               5                   10                  15

Phe Asp Lys His
            20

<210> SEQ ID NO 728
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 728

Leu Pro Cys His Leu Ala Gln Val Gly Glu Leu Cys Asp Leu Pro Ser
1               5                   10                  15

Ser Met Leu Thr
            20

<210> SEQ ID NO 729
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 729

Trp Ala Trp Leu Asp Cys His Asn Ala Gln Val Gly Glu Leu Cys Asp
1               5                   10                  15

Leu Leu Arg Asp
            20

<210> SEQ ID NO 730
<211> LENGTH: 20
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 730

Thr Ser Phe His Asp Cys Arg Ile Ala Asn Val Gly Glu Leu Cys Asp
1               5                   10                  15

Leu Ser Ile Leu
            20

<210> SEQ ID NO 731
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 731

Val Ser Trp Tyr Pro Cys His Met Ala Gln Val Gly Glu Leu Cys Asp
1               5                   10                  15

Leu Gly Phe Ser
            20

<210> SEQ ID NO 732
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 732

Gly Asn Phe Lys Gln Cys His Met Ala Ala Val Gly Glu Leu Cys Glu
1               5                   10                  15

Met Glu Asn Glu
            20

<210> SEQ ID NO 733
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 733

Ala Val Trp Tyr Asp Cys Arg Ile Ala Gln Val Gly Glu Leu Cys Asp
1               5                   10                  15

Leu Val His Pro
            20

<210> SEQ ID NO 734
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 734

Tyr Asp Cys Phe Phe Ala His Val Gly Glu Leu Cys Asp Leu Met Gly
1               5                   10                  15

Asn Ser Gly Thr
            20
```

<210> SEQ ID NO 735
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 735

Lys Ala Cys His Met Ala Gln Leu Gly Glu Leu Cys Asp Leu Tyr Gln
1               5                   10                  15

Gly Gly Ile Asn
            20

<210> SEQ ID NO 736
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 736

Tyr Pro Cys Trp Leu Ala Leu Pro Gly Glu Leu Cys Asp Leu Met Glu
1               5                   10                  15

Ser Thr Val Asn
            20

<210> SEQ ID NO 737
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 737

Tyr Asp Cys Ser Leu Ala Gln Leu Gly Glu Leu Cys Asp Leu Thr Gly
1               5                   10                  15

Pro Ser Tyr Gly
            20

<210> SEQ ID NO 738
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 738

Tyr Pro Cys His Val Ala Gln Val Gly Glu Leu Cys Asp Leu Ser Pro
1               5                   10                  15

Gly Leu His Gly
            20

<210> SEQ ID NO 739
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 739

His Met Phe Tyr Pro Cys Trp Arg Ala Gln Val Gly Glu Leu Cys Asp
1               5                   10                  15

Leu Ala Asn Tyr
            20

<210> SEQ ID NO 740
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 740

Ser Gly Trp Tyr Pro Cys Arg Ile Ala Arg Leu Gly Glu Leu Cys Asp
1               5                   10                  15

Leu Trp Glu Gly
            20

<210> SEQ ID NO 741
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 741

Gln Val His Tyr Asp Cys Ser Met Ala Gln Leu Gly Glu Leu Cys Asp
1               5                   10                  15

Leu Tyr Asp Glu
            20

<210> SEQ ID NO 742
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 742

Leu Trp Phe Tyr Asp Cys Arg Phe Ala His Val Gly Glu Leu Cys Asp
1               5                   10                  15

Leu Glu Gln Thr
            20

<210> SEQ ID NO 743
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 743

Val Gly Arg Gln Met Arg Lys Ala Cys His Met Ala Leu Leu Gly Glu
1               5                   10                  15

Leu Cys Asp Leu
            20

<210> SEQ ID NO 744
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 744

His Trp Cys Trp Met Ala Arg Leu Gly Glu Leu Cys Asp Leu
1               5                   10

<210> SEQ ID NO 745
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 745

Ser Val Leu Leu Ser Tyr Pro Leu Cys Arg Phe Ala Gln Leu Gly Glu
1               5                   10                  15

Leu Cys Asp Leu
            20

<210> SEQ ID NO 746
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 746

Tyr Phe Cys Trp Met Ala Lys Leu Gly Glu Leu Cys Asp Leu
1               5                   10

<210> SEQ ID NO 747
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 747

Leu His Ile Leu Lys Asn Tyr Pro Cys Tyr Leu Ala Gln Val Gly Glu
1               5                   10                  15

Leu Cys Asp Leu
            20

<210> SEQ ID NO 748
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 748

His Ile Met Arg Thr Trp Tyr Asp Cys Ser Ile Ala Gln Ile Gly Glu
1               5                   10                  15

Leu Cys Asp Leu
            20

<210> SEQ ID NO 749
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 749

Pro Glu Arg Gly Gly Trp Tyr Asp Cys Arg Phe Ala Lys Leu Gly Glu
1               5                   10                  15

Leu Cys Asp Leu
            20

<210> SEQ ID NO 750
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 750

Gly Gly Met Ala Lys Tyr Asn Pro Cys His Ile Ala Lys Leu Gly Glu
1               5                   10                  15

Leu Cys Asp Leu
            20

<210> SEQ ID NO 751
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 751

Tyr Phe Cys Trp Met Ala Gln Leu Gly Glu Leu Cys Asp Leu
1               5                   10

<210> SEQ ID NO 752
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 752

Ile Ser Gly Leu Gly Ile Tyr Pro Cys Trp Met Ala His Leu Gly Glu
1               5                   10                  15

Leu Cys Asp Leu
            20

<210> SEQ ID NO 753
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 753

Gly Val Thr Tyr Gln Trp Tyr Asp Cys Ser Ile Ala Leu Val Gly Glu
1               5                   10                  15

Leu Cys Asp Ile
            20

<210> SEQ ID NO 754
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 754

Tyr Pro Cys His Leu Ala Leu Leu Gly Glu Leu Cys Asp Leu
1               5                   10

<210> SEQ ID NO 755
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 755

Arg Pro Trp Arg Gln Trp Tyr Asp Cys Ser Ile Ala Arg Leu Gly Glu
1               5                   10                  15

Leu Cys Asp Ile
            20

<210> SEQ ID NO 756
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 756

Tyr Pro Cys Trp Met Ala Gln Val Gly Glu Leu Cys Asp Leu
1               5                   10

<210> SEQ ID NO 757
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 757

Tyr Asp Cys Ser Ile Ala Lys Leu Gly Glu Leu Cys Asp Leu
1               5                   10

<210> SEQ ID NO 758
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 758

Val Ser Val Trp Lys Asp Cys Ser Ile Ala Gln Leu Gly Glu Leu Cys
1               5                   10                  15

Asp Leu

<210> SEQ ID NO 759
<211> LENGTH: 20
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 759

Asn Glu Gln Met Ile Pro Trp Pro Cys His Leu Ala Gln Leu Gly Asp
1               5                   10                  15

Leu Cys Asp Leu
            20

<210> SEQ ID NO 760
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 760

Phe Pro Cys Trp Leu Ala Lys Leu Gly Asp Leu Cys Asp Leu
1               5                   10

<210> SEQ ID NO 761
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 761

Tyr Trp Cys His Ile Ala Gln Leu Gly Glu Leu Cys Asp Leu
1               5                   10

<210> SEQ ID NO 762
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 762

Asp Ser Asn Ala Pro Trp Tyr Asp Cys Ser Lys Ala Leu Leu Gly Glu
1               5                   10                  15

Leu Cys Asp Leu
            20

<210> SEQ ID NO 763
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 763

Trp Ser Ile Ala Asn Phe Tyr Asp Cys Arg Phe Ala His Leu Gly Glu
1               5                   10                  15

Leu Cys Asp Leu
            20

<210> SEQ ID NO 764
<211> LENGTH: 14
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 764

Leu Pro Cys His Met Ala Leu Leu Gly Gln Leu Cys Asp Leu
1               5                   10

<210> SEQ ID NO 765
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 765

Leu Met Cys Trp Phe Ala Gln Leu Gly Asp Leu Cys Asp Leu
1               5                   10

<210> SEQ ID NO 766
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 766

Tyr Pro Cys Trp Ile Ala Lys Leu Gly Glu Leu Cys Asp Phe
1               5                   10

<210> SEQ ID NO 767
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 767

Ala Tyr Arg Ala Met Pro Tyr Tyr Cys Trp Met Ala Gln Leu Gly Glu
1               5                   10                  15

Leu Cys Asp Leu
            20

<210> SEQ ID NO 768
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 768

Gly Ser Ser Val Glu Ile Lys Pro Cys Trp Met Ala Tyr Leu Gly Glu
1               5                   10                  15

Leu Cys His Leu
            20

<210> SEQ ID NO 769
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 769

Tyr Pro Cys Trp Leu Ala Arg Val Gly Glu Leu Cys Asp Leu Asp Ser
1               5                   10                  15

Gly Asp Val His
            20

<210> SEQ ID NO 770
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 770

Tyr Asp Cys Ser Met Ala Leu Leu Gly Glu Leu Cys Asp Leu Trp Met
1               5                   10                  15

Pro Ala Ile Lys
            20

<210> SEQ ID NO 771
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 771

Tyr Pro Cys Trp Met Ala His Val Gly Glu Leu Cys Asp Leu Glu Gly
1               5                   10                  15

Trp Phe Gly Val
            20

<210> SEQ ID NO 772
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 772

Gly Val Phe Tyr Asp Cys Arg Ile Ala Gln Leu Gly Glu Leu Cys Asp
1               5                   10                  15

Leu Trp Ala Ser
            20

<210> SEQ ID NO 773
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 773

Tyr Lys Phe Leu Pro Cys Trp Arg Ala Arg Val Gly Glu Leu Cys Asp
1               5                   10                  15

Leu Asp Thr Ala
            20

<210> SEQ ID NO 774
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 774

Ala Asn Phe Tyr Asp Cys Arg Tyr Ala Gln Leu Gly Glu Leu Cys Asp
1               5                   10                  15

Leu Met Asn Val
            20

<210> SEQ ID NO 775
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 775

Arg Arg Ala Ser Trp Cys His Leu Ala Gln Val Gly Glu Leu Cys Asp
1               5                   10                  15

Leu Leu Trp Glu
            20

<210> SEQ ID NO 776
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 776

His Pro Cys His Met Ala Gln Val Gly Glu Leu Cys Asp Leu Asn Phe
1               5                   10                  15

Pro Tyr Val Glu
            20

<210> SEQ ID NO 777
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 777

Thr Pro Cys Tyr Met Ala Lys Leu Gly Glu Leu Cys Asp Leu Glu Glu
1               5                   10                  15

Trp Ala Leu Glu
            20

<210> SEQ ID NO 778
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 778

Leu Trp Cys Trp Met Ala Gln Val Gly Glu Leu Cys Asp Leu Glu Glu
1               5                   10                  15
```

Arg Ser Phe Met
            20

<210> SEQ ID NO 779
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 779

Tyr Pro Cys His Met Ala Gln Leu Gly Glu Leu Cys Asp Leu Trp Ser
1               5                   10                  15

Trp Gly Asp Ile
            20

<210> SEQ ID NO 780
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 780

Leu Pro Cys Trp Lys Ala Asn Leu Gly Glu Leu Cys Asp Leu Tyr Asp
1               5                   10                  15

Met Gly His Ser
            20

<210> SEQ ID NO 781
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 781

Trp Ala Phe Tyr Asp Cys Phe Thr Ala Gln Val Gly Glu Leu Cys Asp
1               5                   10                  15

Leu Ser Ile Gly
            20

<210> SEQ ID NO 782
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 782

Lys Thr Trp Tyr Asp Cys Arg Phe Ala Gln Leu Gly Glu Leu Cys Asp
1               5                   10                  15

Leu Asn Met Asn
            20

<210> SEQ ID NO 783
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 783

Leu Pro Cys Trp Leu Ala Arg Leu Gly Glu Leu Cys Asp Leu Gln Tyr
1               5                   10                  15

Glu Tyr Asn Asp
            20

<210> SEQ ID NO 784
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 784

Phe Ser Phe Gln His Cys His Met Ala Gln Leu Gly Glu Leu Cys Asp
1               5                   10                  15

Leu Gly Tyr Glu
            20

<210> SEQ ID NO 785
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 785

Tyr Pro Cys Arg Ile Ala Lys Leu Gly Glu Leu Cys Asp Leu Ser Glu
1               5                   10                  15

Trp Gln Gln Leu
            20

<210> SEQ ID NO 786
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 786

Tyr Ala Cys Trp Phe Ala Gln Val Gly Glu Leu Cys Asp Leu Glu Glu
1               5                   10                  15

Asp Met Val Thr
            20

<210> SEQ ID NO 787
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 787

Gly Phe Ser His Phe Cys Trp Glu Ala Gln Val Gly Glu Leu Cys Asp
1               5                   10                  15

Leu Ile Tyr Gly
            20

<210> SEQ ID NO 788

-continued

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 788

Leu Tyr Cys Trp Met Ala Gln Leu Gly Glu Leu Cys Asp Leu Glu His
1               5                   10                  15

Val Asp Trp Asn
            20

<210> SEQ ID NO 789
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 789

Leu Trp Cys Gly Ile Ala Gln Leu Gly Glu Leu Cys Asp Leu Glu Leu
1               5                   10                  15

Gly Ile His Asp
            20

<210> SEQ ID NO 790
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 790

Leu Leu Cys Trp Met Ala Gln Leu Gly Glu Leu Cys Asp Leu Glu Gly
1               5                   10                  15

Glu Val Met Lys
            20

<210> SEQ ID NO 791
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 791

Lys Val Trp Tyr Pro Cys Arg Ile Ala Gln Val Gly Glu Leu Cys Asp
1               5                   10                  15

Leu Asp Gln Phe
            20

<210> SEQ ID NO 792
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 792

Gly Glu Trp Tyr Asp Cys Arg Ile Ala Gln Val Gly Glu Leu Cys Asp
1               5                   10                  15
```

-continued

Leu Trp Pro Val
        20

<210> SEQ ID NO 793
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 793

Tyr Pro Cys Trp Phe Ala Lys Leu Gly Glu Leu Cys Asp Leu Gly Leu
1               5                   10                  15

Thr Asp Thr Lys
        20

<210> SEQ ID NO 794
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 794

Val Ser Trp Val Asp Cys His Met Ala Gln Val Gly Glu Leu Cys Asp
1               5                   10                  15

Leu Arg Asp Ser
        20

<210> SEQ ID NO 795
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 795

Gln Phe Trp Leu Gly Cys Trp Met Ala Gln Val Gly Glu Leu Cys Asp
1               5                   10                  15

Leu Asp Gln Pro
        20

<210> SEQ ID NO 796
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 796

Tyr Thr Trp Leu Asp Cys Ser Val Ala Gln Leu Gly Gln Leu Cys Asp
1               5                   10                  15

Leu Trp Ser Met
        20

<210> SEQ ID NO 797
<211> LENGTH: 20
<212> TYPE: PRT
<213> ORGANISM: Artificial Sequence
<220> FEATURE:
<223> OTHER INFORMATION: Description of Artificial Sequence: Synthetic

```
                         peptide

<400> SEQUENCE: 797

Ala Leu Ser Trp Leu Trp Gln Asp Cys Ala Leu Ala Gln Leu Gly Glu
1               5                  10                  15

Leu Cys Asp Leu
            20

<210> SEQ ID NO 798
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 798

Gly Asp Leu Val Met Phe Tyr Asp Cys Arg Phe Ala Arg Val Gly Glu
1               5                  10                  15

Leu Cys Asp Leu
            20

<210> SEQ ID NO 799
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 799

Arg Leu Phe Asp Pro Asp Gln Asn Cys Arg Phe Ala Leu Leu Gly Glu
1               5                  10                  15

Leu Cys Leu Leu
            20

<210> SEQ ID NO 800
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 800

Gly Ser Val Trp Glu Phe Tyr Asp Cys Phe Ile Ala Arg Val Gly Glu
1               5                  10                  15

Leu Cys Asp Leu
            20

<210> SEQ ID NO 801
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 801

Ser Asp Leu Met Val Trp Lys Pro Cys Trp Thr Ala Gln Leu Gly Glu
1               5                  10                  15

Leu Cys Asp Leu
            20
```

```
<210> SEQ ID NO 802
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 802

Lys Tyr Cys Gly Phe Ala Gln Leu Gly Glu Leu Cys Val Leu
1               5                   10

<210> SEQ ID NO 803
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 803

Tyr Pro Cys Trp Met Ala Gln Val Gly Glu Leu Cys Asp Leu Phe Leu
1               5                   10                  15

Glu Ser Val Pro
            20

<210> SEQ ID NO 804
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 804

Met Gly Phe Tyr Pro Cys Trp Thr Ala Gln Leu Gly Glu Leu Cys Asp
1               5                   10                  15

Leu Ser Val Asp
            20

<210> SEQ ID NO 805
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 805

Pro Leu Asn Tyr Pro Cys Trp Ile Ala Gln Leu Gly Glu Leu Cys Asp
1               5                   10                  15

Leu Asp Leu Arg
            20

<210> SEQ ID NO 806
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 806

Trp Lys Phe Gln Asp Cys Arg Thr Ala Gln Val Gly Glu Leu Cys Asp
1               5                   10                  15

Leu Trp Pro Tyr
```

20

<210> SEQ ID NO 807
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 807

Leu Tyr Cys Gly Met Ala His Val Gly Gln Leu Cys Ile Leu Glu Asp
1               5                   10                  15

Trp Arg Gly Ala
            20

<210> SEQ ID NO 808
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 808

Trp Tyr Pro Cys Trp Met Ala Gln Leu Gly Glu Leu Cys Asp Leu Asp
1               5                   10                  15

<210> SEQ ID NO 809
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: an amino acid comprising an aromatic side chain
<220> FEATURE:
<221> NAME/KEY: MOD_RES
<222> LOCATION: (3)..(3)
<223> OTHER INFORMATION: an amino acid comprising a large hydrophobic
      side chain or an aromatic side chain
<220> FEATURE:
<221> NAME/KEY: MOD_RES
<222> LOCATION: (6)..(6)
<223> OTHER INFORMATION: an amino acid comprising an aromatic side chain
<220> FEATURE:
<221> NAME/KEY: MOD_RES
<222> LOCATION: (7)..(7)
<223> OTHER INFORMATION: an amino acid comprising a large hydrophobic
      side chain
<220> FEATURE:
<221> NAME/KEY: MOD_RES
<222> LOCATION: (9)..(9)
<223> OTHER INFORMATION: an amino acid comprising a basic side chain or
      a polar/neutral side chain
<220> FEATURE:
<221> NAME/KEY: MOD_RES
<222> LOCATION: (10)..(10)
<223> OTHER INFORMATION: an amino acid comprising a large hydrophobic
      side chain
<220> FEATURE:
<221> NAME/KEY: MOD_RES
<222> LOCATION: (12)..(12)
<223> OTHER INFORMATION: an amino acid comprising an acidic side chain
      or a polar/neutral side chain
<220> FEATURE:

```
<221> NAME/KEY: MOD_RES
<222> LOCATION: (16)..(16)
<223> OTHER INFORMATION: an amino acid comprising a large hydrophobic
      side chain
<220> FEATURE:
<221> NAME/KEY: MOD_RES
<222> LOCATION: (17)..(17)
<223> OTHER INFORMATION: an amino acid comprising an acidic side chain

<400> SEQUENCE: 809

Xaa Xaa Xaa Pro Cys Xaa Xaa Ala Xaa Xaa Gly Xaa Leu Cys Asp Xaa
1               5                   10                  15

Xaa

<210> SEQ ID NO 810
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 810

Gln Pro Cys Trp Leu Ala Gln Val Gly Asp Leu Cys Asp Leu Leu Trp
1               5                   10                  15

Pro Gly Pro Leu
            20

<210> SEQ ID NO 811
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 811

Trp Leu Pro Cys Trp Ile Ala Arg Leu Gly Asp Leu Cys Asp Leu Glu
1               5                   10                  15

<210> SEQ ID NO 812
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 812

Trp Tyr Pro Cys Trp Met Ala Leu Leu Gly Glu Leu Cys Asp Gln Glu
1               5                   10                  15

<210> SEQ ID NO 813
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 813

Trp Tyr Pro Cys Tyr Arg Ala Arg Leu Gly Glu Leu Cys Asp Leu Asp
1               5                   10                  15

<210> SEQ ID NO 814
<211> LENGTH: 22
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 814

Trp Gln Arg Glu Trp Arg Trp Phe Pro Cys Trp Met Ala Lys Leu Gly
1               5                   10                  15

Asp Met Cys Asp Leu Asp
            20

<210> SEQ ID NO 815
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 815

Gln Asp Glu Ala Val Glu Trp Phe Pro Cys Trp Met Ala Arg Leu Gly
1               5                   10                  15

Glu Leu Cys Asp Leu Glu
            20

<210> SEQ ID NO 816
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 816

Tyr Tyr Pro Cys Trp Met Ala Arg Leu Gly Glu Leu Cys Asp Leu Asp
1               5                   10                  15

<210> SEQ ID NO 817
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 817

Ser Val Val Val Asn Asn Trp Leu Pro Cys Trp Met Ala Gln Leu Gly
1               5                   10                  15

Glu Leu Cys Asp Leu Asp
            20

<210> SEQ ID NO 818
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 818

Trp Tyr Pro Cys Trp Leu Ala Gln Leu Gly Asp Leu Cys Asp Leu Asp
1               5                   10                  15

<210> SEQ ID NO 819
<211> LENGTH: 22
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 819

Val Met Ser Pro Thr Arg Trp Leu Pro Cys Trp Ile Ala Lys Leu Gly
1               5                   10                  15

Glu Leu Cys Asp Leu Glu
            20

<210> SEQ ID NO 820
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 820

Trp Phe Pro Cys Trp Met Ala Gln Leu Gly Gln Leu Cys Asp Leu Glu
1               5                   10                  15

<210> SEQ ID NO 821
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 821

Trp Arg Pro Cys Trp Arg Ala Tyr Leu Gly Glu Leu Cys Asp Leu Glu
1               5                   10                  15

Ala Met Pro Arg Ala Thr
            20

<210> SEQ ID NO 822
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 822

Ile Arg Ser Cys Ser Pro Cys Trp Ser Ala Asp Val Gly Glu Leu Cys
1               5                   10                  15

Asp Leu Glu Cys Glu Trp
            20

<210> SEQ ID NO 823
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 823

Ser Gly His Trp Tyr Pro Cys Trp Met Ala Arg Leu Gly Glu Leu Cys
1               5                   10                  15

Asp Met Glu Glu Arg Ala
            20
```

```
<210> SEQ ID NO 824
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 824

Trp Tyr Pro Cys Trp Met Ala Gln Leu Gly Glu Leu Cys Asp Leu Gln
1               5                   10                  15

Thr Met Gly Tyr Ser His
            20

<210> SEQ ID NO 825
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 825

Ala Gly Asp Trp Leu Pro Cys Trp Met Ala Glu Leu Gly Glu Leu Cys
1               5                   10                  15

Asp Leu Glu Gly Pro Thr
            20

<210> SEQ ID NO 826
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 826

Trp Leu Pro Cys Trp Ile Ala Ser Leu Gly Glu Leu Cys Asp Leu Asp
1               5                   10                  15

Thr Gly Lys Arg Gln Gly
            20

<210> SEQ ID NO 827
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 827

Trp Leu Pro Cys Trp Met Ala His Leu Gly Gln Leu Cys Asp Leu Asp
1               5                   10                  15

Leu Pro Gly Lys Ser Met
            20

<210> SEQ ID NO 828
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 828

Glu Gly Val Phe Phe Pro Cys Trp Ile Ala Arg Leu Gly Glu Leu Cys
```

```
1               5                   10                  15

Asp Leu Asp His Gly Leu
            20

<210> SEQ ID NO 829
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 829

Thr Gly Arg Trp Lys Pro Cys Trp Met Ala Gly Leu His Glu Leu Cys
1               5                   10                  15

Asp Leu Glu Gly Phe Arg
            20

<210> SEQ ID NO 830
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 830

Arg Lys His Phe Tyr Pro Cys Trp Met Ala Gln Leu Gly Glu Leu Cys
1               5                   10                  15

Asp Leu Glu Gly Met Pro
            20

<210> SEQ ID NO 831
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 831

Asp Ile Gly Tyr Tyr Pro Cys Trp Met Ala Gln Val Gly Asp Leu Cys
1               5                   10                  15

Asp Leu Asp Asp Glu Lys
            20

<210> SEQ ID NO 832
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 832

Asp Ser Asp Trp Trp Pro Cys Trp Met Ala Gln Leu Gly Glu Leu Cys
1               5                   10                  15

Asp Leu Glu Asp Ala Arg
            20

<210> SEQ ID NO 833
<211> LENGTH: 22
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 833

Gly Glu Arg Trp Lys Pro Cys Trp Ile Ala Gln Leu Gly Glu Leu Cys
1               5                   10                  15

Asp Leu Asp Phe Asn Trp
            20

<210> SEQ ID NO 834
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 834

Trp Trp Pro Cys Trp Met Ala Gln Leu Gly Glu Met Cys Asp Leu Glu
1               5                   10                  15

Tyr Pro Tyr Val Pro Gly
            20

<210> SEQ ID NO 835
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 835

Gln Thr Lys Leu Glu Gly Trp Tyr Pro Cys Trp Met Ala Gln Leu Gly
1               5                   10                  15

Glu Leu Cys Asp Leu Asp
            20

<210> SEQ ID NO 836
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 836

Trp Gly Arg Lys Glu Gln Trp Leu Pro Cys Trp Lys Ala Gln Leu Gly
1               5                   10                  15

Glu Leu Cys Asp Leu Glu
            20

<210> SEQ ID NO 837
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 837

Val Pro Arg Ala Asn Ala Trp His Pro Cys Trp Met Ala Gln Leu Gly
1               5                   10                  15

Glu Leu Cys Asp Leu Glu
            20

<210> SEQ ID NO 838
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 838

Gly Arg Gln Gln Lys Gly Trp Tyr Pro Cys Trp Leu Ala Gln Leu Gly
1               5                   10                  15

Glu Leu Cys Asp Met Glu
            20

<210> SEQ ID NO 839
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 839

Trp Leu Asn Arg His Leu Phe Asn Pro Cys Trp Met Ala Arg Leu Gly
1               5                   10                  15

Glu Leu Cys Asp Leu Glu
            20

<210> SEQ ID NO 840
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 840

Ala Gln Val Arg Arg Glu Trp Tyr Pro Cys Trp Met Ala Gln Leu Gly
1               5                   10                  15

Glu Leu Cys Asp Leu Thr
            20

<210> SEQ ID NO 841
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 841

Glu Thr Glu Gln Met Ser Trp Tyr Pro Cys Trp Val Ala Gln Leu Trp
1               5                   10                  15

Glu Leu Cys Asp Leu Asp
            20

<210> SEQ ID NO 842
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 842

```
Trp Leu Pro Cys Trp Leu Ala Lys Leu Gly Glu Leu Cys Asp Leu Glu
1               5                   10                  15

Trp Leu Pro Cys Trp
            20

<210> SEQ ID NO 843
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 843

Glu Arg Arg Pro Asp Thr Trp Phe Pro Cys Trp Arg Ala Leu Val Gly
1               5                   10                  15

Glu Leu Cys Asp Leu Glu
            20

<210> SEQ ID NO 844
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 844

Trp Gly Arg Asn Arg Ser Trp Tyr Pro Cys Trp Met Ala Gln Leu Gly
1               5                   10                  15

Glu Leu Cys Asp Leu Glu
            20

<210> SEQ ID NO 845
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 845

Gln Asp Arg Arg Ser Pro Trp Tyr Pro Cys Trp Met Ala Lys Leu Gly
1               5                   10                  15

Glu Leu Cys Asp Leu Ala
            20

<210> SEQ ID NO 846
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 846

Thr Arg Arg Trp Tyr Pro Cys Tyr Leu Ala Lys Leu Gly Glu Leu Cys
1               5                   10                  15

Asp Leu Phe Glu Gly Gly Thr Arg
            20

<210> SEQ ID NO 847
<211> LENGTH: 24
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 847

Ser Glu Gln Trp Trp Pro Cys Trp Ile Ala Arg Leu Gly Glu Leu Cys
1               5                   10                  15

Asp Leu Asp Arg Glu Leu Ser Glu
            20

<210> SEQ ID NO 848
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 848

Trp Tyr Pro Cys Trp Val Ala Gln Leu Gly Glu Ile Cys Asp Leu Glu
1               5                   10                  15

Met Thr Gly Pro Asp Ser Trp Tyr Pro
            20                  25

<210> SEQ ID NO 849
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 849

Gln Asp Gly Trp Leu Pro Cys Trp Met Ala Gln Leu Gly Glu Leu Cys
1               5                   10                  15

Asp Leu Glu Tyr Lys Arg
            20

<210> SEQ ID NO 850
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 850

Asn Arg Arg Trp Tyr Pro Cys Trp Met Ala Gln Leu Gly Glu Leu Cys
1               5                   10                  15

Asp Leu Asp Ser Arg Pro
            20

<210> SEQ ID NO 851
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 851

Phe Tyr Pro Cys Trp Met Ala His Leu Gly Glu Leu Cys Asp Leu Asp
1               5                   10                  15

Gly Asp Thr Asp Ser Met
            20
```

<210> SEQ ID NO 852
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 852

Lys Ser Asn Phe Phe Pro Cys Trp Ile Ala Gln Leu Gly Gln Leu Cys
1               5                   10                  15

Asp Leu Glu Pro Glu Thr
            20

<210> SEQ ID NO 853
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 853

Phe Tyr Pro Cys Trp Met Ala Asn Leu Gly Glu Leu Cys Asp Leu Asp
1               5                   10                  15

Phe Leu Arg Glu Leu Asn
            20

<210> SEQ ID NO 854
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 854

His Ala Ser Trp Leu Pro Cys Trp Leu Ala Gln Leu Gly Glu Leu Cys
1               5                   10                  15

Asp Leu Glu Pro Asn Pro
            20

<210> SEQ ID NO 855
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 855

Asn Gly Ala Trp Tyr Pro Cys Trp Met Ala Gln Val Gly Glu Leu Cys
1               5                   10                  15

Asp Leu Glu Glu Arg Trp
            20

<210> SEQ ID NO 856
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 856

```
Trp Arg Arg Trp Tyr Pro Cys Trp Val Ala Gln Val Gly Glu Leu Cys
1               5                   10                  15

Asp Leu Glu Ile Glu Ala
            20

<210> SEQ ID NO 857
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 857

Arg Gln Ala Trp Tyr Pro Cys Trp Met Ala Gln Leu Gly Glu Leu Cys
1               5                   10                  15

Asp Leu Glu Ala Glu Leu
            20

<210> SEQ ID NO 858
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 858

Arg Gln Arg Trp Tyr Pro Cys Trp Met Ala Arg Leu Gly Glu Leu Cys
1               5                   10                  15

Asp Leu Asp Glu Pro Thr
            20

<210> SEQ ID NO 859
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 859

Asn Asn Ser Arg Glu Gly Trp Phe Pro Cys Trp Leu Ala Lys Leu Gly
1               5                   10                  15

Asp Leu Cys Asp Leu Asp
            20

<210> SEQ ID NO 860
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 860

Tyr Tyr Pro Cys Trp Met Ala Gln Leu Gly Glu Leu Cys Asp Leu Glu
1               5                   10                  15

<210> SEQ ID NO 861
<211> LENGTH: 16
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 861

Trp Tyr Pro Cys Trp Leu Ala Gln Leu Gly Glu Leu Cys Asp Leu Asp
1               5                   10                  15

<210> SEQ ID NO 862
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 862

Ser Trp His Ala Glu Thr Trp Tyr Pro Cys Trp Leu Ala Gln Val Gly
1               5                   10                  15

Glu Leu Cys Asp Leu Asp
            20

<210> SEQ ID NO 863
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 863

Lys Met His Lys Ala Val Trp Leu Pro Cys Trp Met Ala Gln Val Gly
1               5                   10                  15

Glu Leu Cys Asp Leu Glu
            20

<210> SEQ ID NO 864
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 864

Asp Val Leu Gly Asp Arg Trp Tyr Pro Cys Trp Ile Ala Lys Leu Gly
1               5                   10                  15

Glu Leu Cys Asp Leu Asp
            20

<210> SEQ ID NO 865
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 865

Trp Tyr Pro Cys Trp Met Ala Gln Leu Gly Glu Leu Cys Asp Leu Asp
1               5                   10                  15

<210> SEQ ID NO 866
<211> LENGTH: 22
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 866

Lys Leu Gln Ser Trp Arg Trp Tyr Pro Cys Trp Met Ala Gln Leu Gly
1               5                   10                  15

Glu Leu Cys Asp Leu Asp
            20

<210> SEQ ID NO 867
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 867

Asn Glu Pro Glu Gly Gly Phe Tyr Pro Cys Trp Leu Ala Gln Leu Gly
1               5                   10                  15

Glu Leu Cys Asp Leu His
            20

<210> SEQ ID NO 868
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 868

Trp Tyr Pro Cys Trp Met Ala Arg Leu Gly Glu Leu Cys Asp Leu Glu
1               5                   10                  15

<210> SEQ ID NO 869
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 869

Phe Tyr Pro Cys Trp Thr Ala Leu Leu Gly Glu Leu Cys Asp Leu Glu
1               5                   10                  15

Pro Gly Pro Pro Ala Met
            20

<210> SEQ ID NO 870
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 870

Trp Gly Thr Thr Trp Arg Trp Tyr Pro Cys Trp Met Ala Gln Leu Gly
1               5                   10                  15

Glu Leu Cys Asp Leu Glu
            20

<210> SEQ ID NO 871
<211> LENGTH: 22
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 871

Ala Lys Gly Trp Asp Thr Trp Lys Pro Cys Trp Leu Ala Asn Leu Gly
1               5                   10                  15

Glu Leu Cys Asp Leu Glu
            20

<210> SEQ ID NO 872
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 872

Arg Asp Glu Ser Ala Gly Tyr Tyr Pro Cys Trp Ile Ala Gln Leu Gly
1               5                   10                  15

Glu Leu Cys Asp Leu Glu
            20

<210> SEQ ID NO 873
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 873

Trp Tyr Pro Cys Trp Ile Ala Lys Leu Gly Glu Leu Cys Asp Leu Glu
1               5                   10                  15

<210> SEQ ID NO 874
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 874

Trp Tyr Pro Cys Trp Ile Ala Gln Leu Gly Glu Leu Cys Asp Leu Asp
1               5                   10                  15

<210> SEQ ID NO 875
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 875

Trp Tyr Pro Cys Trp Leu Ala Lys Leu Gly Glu Leu Cys Asp Leu Asp
1               5                   10                  15

<210> SEQ ID NO 876
<211> LENGTH: 22
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 876

Gln Gly Pro Val Arg Leu Trp Tyr Pro Cys Trp Met Ala Gln Leu Gly
1               5                   10                  15

Glu Leu Cys Asp Leu Asp
            20

<210> SEQ ID NO 877
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 877

Trp Tyr Pro Cys Trp Met Ala Gln Pro Gly Glu Leu Cys Asp Val Asp
1               5                   10                  15

<210> SEQ ID NO 878
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 878

Trp His Pro Cys Trp Ile Ala Gln Leu Gly Glu Leu Cys Asp Leu Glu
1               5                   10                  15

<210> SEQ ID NO 879
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 879

Trp Tyr Pro Cys Trp Ile Ala Gln Leu Gly Glu Leu Cys Asp Leu Glu
1               5                   10                  15

<210> SEQ ID NO 880
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 880

Val Arg Pro Met Gly Val Trp Tyr Pro Cys Trp Ile Ala Gln Leu Gly
1               5                   10                  15

Glu Leu Cys Asp Leu Val
            20

<210> SEQ ID NO 881
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 881

-continued

```
Val Pro Arg Trp Tyr Pro Cys Trp Ile Ala Gln Leu Gly Glu Leu Cys
1               5                   10                  15

Asp Leu Asp Ser Asp Asp
            20

<210> SEQ ID NO 882
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 882

Tyr Arg Gly Trp Leu Pro Cys Trp Arg Ala Lys Leu Gly Asp Leu Cys
1               5                   10                  15

Asp Leu Gly Gln Pro Met
            20

<210> SEQ ID NO 883
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 883

Gly Glu Ala Trp Tyr Pro Cys Trp Leu Ala Arg Leu Gly Glu Leu Cys
1               5                   10                  15

Asp Met Asp Pro Arg Val
            20

<210> SEQ ID NO 884
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 884

Trp Tyr Pro Cys Trp Met Ala Gln Leu Gly Glu Leu Cys Asp Leu Asp
1               5                   10                  15

Glu Ser Thr Arg Leu Thr
            20

<210> SEQ ID NO 885
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 885

Ile Gly Ser Trp Trp Pro Cys Trp Met Ala Gln Leu Gly Glu Leu Cys
1               5                   10                  15

Asp Leu Glu Pro Glu Leu
            20

<210> SEQ ID NO 886
<211> LENGTH: 22
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 886

Gly Thr Thr Trp Tyr Pro Cys Trp Leu Ala Gln Leu Gly Glu Leu Cys
1               5                   10                  15

Asp Leu Asp Val Leu Glu
            20

<210> SEQ ID NO 887
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 887

Trp Trp Pro Cys Trp Met Ala Gln Leu Gly Asp Leu Cys Asp Leu Glu
1               5                   10                  15

Glu Thr Ser Gly Gly Thr
            20

<210> SEQ ID NO 888
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 888

Trp Tyr Pro Cys Trp Met Ala Gln Leu Gly Glu Leu Cys Asp Leu Gly
1               5                   10                  15

Pro Thr Glu Ser Asn Leu
            20

<210> SEQ ID NO 889
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 889

Trp Tyr Pro Cys Trp Met Ala Asn Leu Gly Glu Leu Cys Asp Leu Glu
1               5                   10                  15

Tyr Pro Ser Trp Ala Gln
            20

<210> SEQ ID NO 890
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 890

Arg Gly Met Cys Tyr Pro Cys Trp Phe Ala Arg Leu Gly Glu Leu Cys
1               5                   10                  15

Asp Leu Glu Cys Asp Gln
```

```
<210> SEQ ID NO 891
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 891

Trp Tyr Pro Cys Trp Met Ala Gln Leu Gly Glu Leu Cys Asp Leu Asp
1               5                   10                  15

Ala Gly Ala Arg His Leu
            20

<210> SEQ ID NO 892
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 892

Lys Ser Gly Trp Tyr Pro Cys Trp Met Ala Lys Leu Gly Glu Leu Cys
1               5                   10                  15

Asp Leu Glu Ala Gln Pro
            20

<210> SEQ ID NO 893
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 893

Gly Pro Arg Phe Tyr Pro Cys Trp Ile Ala Gln Leu Gly Glu Leu Cys
1               5                   10                  15

Asp Leu Glu Asp Met Gly
            20

<210> SEQ ID NO 894
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 894

Arg Val Thr Trp Tyr Pro Cys Trp Met Ala Gln Leu Gly Glu Leu Cys
1               5                   10                  15

Asp Leu Glu Glu Ser Val
            20

<210> SEQ ID NO 895
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 895

Trp Leu Pro Cys Trp Met Ala Gln Leu Gly Asp Leu Cys Asp Leu Glu
1               5                   10                  15

Gln Tyr Val Pro Leu Pro
            20

<210> SEQ ID NO 896
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 896

Tyr Leu Pro Cys Trp Met Ala His Leu Gly Glu Leu Cys Asp Leu Asp
1               5                   10                  15

Ser Pro Leu Lys Ala Arg
            20

<210> SEQ ID NO 897
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 897

Trp Tyr Pro Cys Trp Met Ala Gln Leu Gly Glu Leu Cys Asp Leu Asp
1               5                   10                  15

Asp His Trp Pro Ala Met
            20

<210> SEQ ID NO 898
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 898

Trp Tyr Pro Cys Trp Arg Ala Gln Leu Gly Glu Leu Cys Asp Leu Asp
1               5                   10                  15

Pro Pro Ile Ala Val Glu
            20

<210> SEQ ID NO 899
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 899

Trp Tyr Pro Cys Trp Met Ala Asn Leu Gly Glu Leu Cys Asp Leu Glu
1               5                   10                  15

Ala Glu Arg Ser Pro Val
            20

<210> SEQ ID NO 900
<211> LENGTH: 22
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 900

Arg Asp Gln Tyr Tyr Pro Cys Trp Met Ala Gln Leu Gly Glu Leu Cys
1               5                   10                  15

Asp Leu Asp Glu Val Phe
            20

<210> SEQ ID NO 901
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 901

Trp Tyr Pro Cys Trp Met Ala Gln Leu Gly Asp Leu Cys Asp Leu Glu
1               5                   10                  15

Lys Pro Val Thr Glu Arg
            20

<210> SEQ ID NO 902
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 902

Trp Tyr Pro Cys Trp Ile Ala Arg Leu Gly Glu Leu Cys Asp Leu Glu
1               5                   10                  15

Thr Ser Gly Gly Phe Pro
            20

<210> SEQ ID NO 903
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 903

Ser Gly His Cys Tyr Pro Cys Trp Leu Ala Gly Leu Gly Glu Leu Cys
1               5                   10                  15

Asp Leu Asn Cys Gly
            20

<210> SEQ ID NO 904
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 904

Ile His Cys Asn Ser Gln Met Gly Ile Leu Ile Cys Trp Tyr
1               5                   10
```

<210> SEQ ID NO 905
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 905

Ile Met Cys Asp Ser Ser Ser Gly Val Ser Ile Cys Trp Thr
1               5                   10

<210> SEQ ID NO 906
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 906

Ile Thr Cys Gln Thr Phe Asn Gly Val Pro Leu Cys Trp Lys
1               5                   10

<210> SEQ ID NO 907
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 907

Leu Glu Cys Asp Ala Ser Met Ser Val Met Ile Cys Trp Phe
1               5                   10

<210> SEQ ID NO 908
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 908

Arg Val Cys Gln Asp Trp Leu Gly Val Lys Leu Cys Trp Asn
1               5                   10

<210> SEQ ID NO 909
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 909

Val Ser Cys Asp Gly Ser Ser Gly Val Leu Leu Cys Trp Met
1               5                   10

<210> SEQ ID NO 910
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 910

Tyr Leu Cys Asp Glu Ser Met Gly Val Lys Leu Cys Trp Phe
1               5                   10

<210> SEQ ID NO 911
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 911

Val Thr Cys Gln Thr Trp Asn Gln Val Leu Leu Cys Trp Ser
1               5                   10

<210> SEQ ID NO 912
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 912

Leu Asp Cys Asp Thr Ser Met Gly Val Pro Leu Cys Trp Phe
1               5                   10

<210> SEQ ID NO 913
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 913

Val Met Cys Glu Asp Trp Gly Gly Val Pro Ile Cys Trp Ile
1               5                   10

<210> SEQ ID NO 914
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 914

Phe Ser Cys Phe Ile Leu Glu Thr Leu Glu Leu Ala Cys Trp Pro
1               5                   10                  15

<210> SEQ ID NO 915
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 915

Gly Ala Cys Asn Pro His Thr Gln Gln Glu Asp Cys Phe Gly
1               5                   10

<210> SEQ ID NO 916
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 916

Ile Glu Cys Gln Val Phe His Gly Leu Glu Leu Cys Trp Ile
1               5                   10

<210> SEQ ID NO 917
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 917

Val Met Cys Glu Leu Phe Asp Glu Val Glu Leu Cys Trp Phe
1               5                   10

<210> SEQ ID NO 918
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 918

Phe Val Cys Glu Leu Trp Asp Gly Ile Glu Leu Cys Ile Pro
1               5                   10

<210> SEQ ID NO 919
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 919

Leu Thr Cys Val Thr Tyr Glu Gly Val Asp Leu Cys Trp Gln
1               5                   10

<210> SEQ ID NO 920
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 920

Val Glu Cys Asp Val Tyr His Gly Val Glu Ile Cys Trp Ala
1               5                   10

<210> SEQ ID NO 921
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 921

Leu Ser Leu Gly Gln Lys Asp Trp Trp Leu Ile Leu
1               5                   10
```

```
<210> SEQ ID NO 922
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 922

Gln Leu Gln Gly Leu Cys Asp Phe Phe Trp Ala His
1               5                   10

<210> SEQ ID NO 923
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 923

Leu Phe Asn Phe Cys Gln Gly Asp Lys Thr Cys Met Gln Trp His
1               5                   10                  15

<210> SEQ ID NO 924
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 924

Glu Cys Gly Gly Ala Trp Ala Met Leu Leu Trp Pro His Cys Thr
1               5                   10                  15

<210> SEQ ID NO 925
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 925

Ile Cys Thr Arg Leu His Asp Val Val Pro Ile Trp Ser Cys Pro
1               5                   10                  15

<210> SEQ ID NO 926
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 926

Gln Cys Tyr Arg Pro Ser Arg Asp Ile Pro Leu Tyr Leu Cys Ser
1               5                   10                  15

<210> SEQ ID NO 927
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 927

Leu Phe Asn Phe Cys Gln Gly Asp Lys Thr Cys Met Gln Trp His
1               5                   10                  15

<210> SEQ ID NO 928
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 928

Val Cys Trp Leu Thr His Asn Arg Gln Ser Tyr Tyr Cys Asp
1               5                   10

<210> SEQ ID NO 929
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 929

Cys Asp Leu Trp Pro Leu Thr Ala Gln Asn Phe Tyr Gly Cys
1               5                   10

<210> SEQ ID NO 930
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 930

Cys Pro Gly Glu Leu Arg Gly Pro Glu Arg Ala Trp Val Cys
1               5                   10

<210> SEQ ID NO 931
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: an amino acid comprising a large hydrophobic
      side chain
<220> FEATURE:
<221> NAME/KEY: MOD_RES
<222> LOCATION: (3)..(3)
<223> OTHER INFORMATION: an amino acid comprising a large hydrophobic
      side chain
<220> FEATURE:
<221> NAME/KEY: MOD_RES
<222> LOCATION: (4)..(4)
<223> OTHER INFORMATION: an amino acid comprising a large hydrophobic
      side chain
<220> FEATURE:
<221> NAME/KEY: MOD_RES
<222> LOCATION: (5)..(5)
<223> OTHER INFORMATION: an amino acid comprising a large hydrophobic
      side chain or an aromatic side chain
<220> FEATURE:
<221> NAME/KEY: MOD_RES
<222> LOCATION: (6)..(6)

```
<223> OTHER INFORMATION: an amino acid comprising a basic side chain and
      an acidic or polar neutral side chain
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: an amino acid comprising a small hydrophobic
      side chain
<220> FEATURE:
<221> NAME/KEY: MOD_RES
<222> LOCATION: (9)..(9)
<223> OTHER INFORMATION: an amino acid comprising an acidic or a polar
      neutral side chain
<220> FEATURE:
<221> NAME/KEY: MOD_RES
<222> LOCATION: (10)..(10)
<223> OTHER INFORMATION: an amino acid comprising a large hydrophobic
      side chain or an aromatic side chain
<220> FEATURE:
<221> NAME/KEY: MOD_RES
<222> LOCATION: (11)..(11)
<223> OTHER INFORMATION: an amino acid comprising a small hydrophobic
      side chain or a hydroxyl-containing side chain
<220> FEATURE:
<221> NAME/KEY: MOD_RES
<222> LOCATION: (12)..(12)
<223> OTHER INFORMATION: an amino acid comprising a large hydrophobic
      side chain or an aromatic side chain
<220> FEATURE:
<221> NAME/KEY: MOD_RES
<222> LOCATION: (13)..(13)
<223> OTHER INFORMATION: an amino acid comprising a large hydrophobic
      side chain

<400> SEQUENCE: 931

Cys Xaa Xaa Xaa Xaa Xaa Xaa Xaa Xaa Xaa Xaa Xaa Cys
1               5                   10

<210> SEQ ID NO 932
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 932

Cys Ala Asn Leu His Asp Thr Gln Glu Trp Trp Tyr Tyr Cys
1               5                   10

<210> SEQ ID NO 933
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 933

Cys Glu Leu Leu Thr Gly Ile Pro Glu Tyr Asn Phe Leu Cys
1               5                   10

<210> SEQ ID NO 934
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 934

Cys Phe Ile Arg Phe Tyr Gln Asp Lys Tyr Asp Tyr Val Cys
1               5                   10

<210> SEQ ID NO 935
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 935

Cys Phe Ile Arg Tyr Leu Arg Gly Glu Phe Ser Phe Val Cys
1               5                   10

<210> SEQ ID NO 936
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 936

Cys Phe Leu Arg Phe Ile His Gly Glu Leu Asp Tyr Tyr Cys
1               5                   10

<210> SEQ ID NO 937
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 937

Cys Phe Val Met Tyr Lys Asn Asn Glu Phe Ser Leu Ile Cys
1               5                   10

<210> SEQ ID NO 938
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 938

Cys Gly Ile Ala Tyr Arg Ser Gly Glu Phe Thr Met Ile Cys
1               5                   10

<210> SEQ ID NO 939
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 939

Cys Leu Ile Tyr Lys Glu Gln Lys Phe Ala Leu Ile Glu Cys
1               5                   10

<210> SEQ ID NO 940
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 940

Cys Tyr Ile Ile Tyr Arg Leu Gly Thr Phe Ser Tyr Met Cys
1               5                   10

<210> SEQ ID NO 941
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: an amino acid comprising a large hydrophobic
      side chain
<220> FEATURE:
<221> NAME/KEY: MOD_RES
<222> LOCATION: (2)..(2)
<223> OTHER INFORMATION: an amino acid comprising a small hydrophobic
      side chain or a hydroxyl-containing side chain
<220> FEATURE:
<221> NAME/KEY: MOD_RES
<222> LOCATION: (3)..(3)
<223> OTHER INFORMATION: an amino acid comprising a small hydrophobic
      side chain
<220> FEATURE:
<221> NAME/KEY: MOD_RES
<222> LOCATION: (4)..(4)
<223> OTHER INFORMATION: an amino acid comprising a small hydrophobic
      side chain or a hydroxyl-containing side chain
<220> FEATURE:
<221> NAME/KEY: MOD_RES
<222> LOCATION: (5)..(5)
<223> OTHER INFORMATION: an amino acid comprising a small hydrophobic
      side chain or a hydroxyl-containing side chain

<400> SEQUENCE: 941

Xaa Xaa Xaa Xaa Xaa
1               5

<210> SEQ ID NO 942
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: an amino acid comprising a small hydrophobic
      side chain or a hydroxyl-containing side chain
<220> FEATURE:
<221> NAME/KEY: MOD_RES
<222> LOCATION: (2)..(2)
<223> OTHER INFORMATION: an amino acid comprising a large hydrophobic
      side chain
<220> FEATURE:
<221> NAME/KEY: MOD_RES
<222> LOCATION: (3)..(3)
<223> OTHER INFORMATION: an amino acid comprising an acidic or polar
      neutral side chain
<220> FEATURE:
<221> NAME/KEY: MOD_RES
<222> LOCATION: (4)..(4)
<223> OTHER INFORMATION: an amino acid comprising a basic side chain
<220> FEATURE:
<221> NAME/KEY: MOD_RES
<222> LOCATION: (6)..(6)
```

```
<223> OTHER INFORMATION: an amino acid comprising a large hydrophobic
      side chain
<220> FEATURE:
<221> NAME/KEY: MOD_RES
<222> LOCATION: (7)..(7)
<223> OTHER INFORMATION: an amino acid comprising a small hydrophobic
      side chain or a hydroxyl-containing side chain
<220> FEATURE:
<221> NAME/KEY: MOD_RES
<222> LOCATION: (8)..(8)
<223> OTHER INFORMATION: an amino acid comprising a small hydrophobic
      side chain
<220> FEATURE:
<221> NAME/KEY: MOD_RES
<222> LOCATION: (9)..(9)
<223> OTHER INFORMATION: an amino acid comprising a small hydrophobic
      side chain or a hydroxyl-containing side chain
<220> FEATURE:
<221> NAME/KEY: MOD_RES
<222> LOCATION: (10)..(10)
<223> OTHER INFORMATION: an amino acid comprising a small hydrophobic
      side chain or a hydroxyl-containing side chain
<220> FEATURE:
<221> NAME/KEY: MOD_RES
<222> LOCATION: (12)..(12)
<223> OTHER INFORMATION: an amino acid comprising a small hydrophobic
      side chain or a hydroxyl-containing side chain
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: an amino acid comprising a large hydrophobic
      side chain or a basic side chain
<220> FEATURE:
<221> NAME/KEY: MOD_RES
<222> LOCATION: (15)..(15)
<223> OTHER INFORMATION: an amino acid comprising a large hydrophobic
      side chain

<400> SEQUENCE: 942

Xaa Xaa Xaa Xaa Cys Xaa Xaa Xaa Xaa Xaa Cys Xaa Xaa Xaa Xaa
1               5                   10                  15

<210> SEQ ID NO 943
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 943

Lys Met Asn Lys Cys Ala Thr Pro Ser Gln Cys Ser Val Ile Phe
1               5                   10                  15

<210> SEQ ID NO 944
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 944

Asn Leu Asn Lys Cys Trp Asn Pro Arg Ser Cys Ser Ser Lys Phe
1               5                   10                  15

<210> SEQ ID NO 945
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 945

Thr Tyr Asn Lys Cys Arg Ser Pro Phe Glu Cys Ser Gly Ile Phe
1               5                   10                  15

<210> SEQ ID NO 946
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 946

Tyr Leu Asn Lys Cys Tyr Ser Pro Ser Ser Cys Gln Leu Arg Leu
1               5                   10                  15

<210> SEQ ID NO 947
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 947

Ser Leu Tyr Lys Cys Asn Ser Pro Leu Ser Cys Ser Asn Ile Phe
1               5                   10                  15

<210> SEQ ID NO 948
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 948

Ser Leu Leu Lys Cys Tyr Asn Ala Ser Thr Cys Ala Ser Val Phe
1               5                   10                  15

<210> SEQ ID NO 949
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: an amino acid comprising a basic side chain
<220> FEATURE:
<221> NAME/KEY: MOD_RES
<222> LOCATION: (2)..(2)
<223> OTHER INFORMATION: an amino acid comprising a hydroxyl-containing
      side chain
<220> FEATURE:
<221> NAME/KEY: MOD_RES
<222> LOCATION: (3)..(3)
<223> OTHER INFORMATION: an amino acid comprising an acidic side chain
      or a large hydrophobic side chain
<220> FEATURE:
<221> NAME/KEY: MOD_RES
<222> LOCATION: (4)..(4)
<223> OTHER INFORMATION: an amino acid comprising a large hydrophobic
      side chain
```

```
<220> FEATURE:
<221> NAME/KEY: MOD_RES
<222> LOCATION: (5)..(5)
<223> OTHER INFORMATION: an amino acid comprising an acidic side chain
      or a large hydrophobic side chain
<220> FEATURE:
<221> NAME/KEY: MOD_RES
<222> LOCATION: (7)..(7)
<223> OTHER INFORMATION: an amino acid comprising an acidic side chain
      or a polar/ neutral side chain
<220> FEATURE:
<221> NAME/KEY: MOD_RES
<222> LOCATION: (8)..(8)
<223> OTHER INFORMATION: an amino acid comprising an acidic side chain
<220> FEATURE:
<221> NAME/KEY: MOD_RES
<222> LOCATION: (9)..(9)
<223> OTHER INFORMATION: an amino acid comprising a large hydrophobic
      side chain or an aromatic side chain
<220> FEATURE:
<221> NAME/KEY: MOD_RES
<222> LOCATION: (10)..(10)
<223> OTHER INFORMATION: an amino acid comprising an acidic side chain
      or a polar/neutral side chain
<220> FEATURE:
<221> NAME/KEY: MOD_RES
<222> LOCATION: (17)..(17)
<223> OTHER INFORMATION: an amino acid comprising a large hydrophobic
      side chain
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (20)..(20)
<223> OTHER INFORMATION: an amino acid comprising an acidic side chain

<400> SEQUENCE: 949

Xaa Xaa Xaa Xaa Xaa Cys Xaa Xaa Xaa Xaa Gly Val Glu Leu Cys Trp
1               5                   10                  15

Xaa Glu Xaa Xaa
            20

<210> SEQ ID NO 950
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 950

Ile Glu Cys Asp Thr Ser Tyr Gly Val Tyr Ile Cys Trp Gln
1               5                   10

<210> SEQ ID NO 951
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 951

Ile Glu Cys Glu Glu Trp Arg Gly Val Glu Leu Cys Trp Gln
1               5                   10

<210> SEQ ID NO 952
<211> LENGTH: 20
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 952

Pro Glu Gly Arg Glu Val Val Cys Arg Asp Trp Tyr Gly Val Glu
1               5                   10                  15

Leu Cys Trp Gln
            20

<210> SEQ ID NO 953
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 953

Ile Trp Gly Arg Thr Val Val Glu Cys Gln Asp Trp Glu Gly Val Glu
1               5                   10                  15

Leu Cys Trp Gln
            20

<210> SEQ ID NO 954
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 954

Leu Ala Leu Arg Lys Glu Val Val Cys Gln Glu Tyr Tyr Gly Val Glu
1               5                   10                  15

Leu Cys Trp Ile
            20

<210> SEQ ID NO 955
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 955

His Glu Ala Arg Glu Val Val Cys Gln Asp Trp Tyr Gly Val Glu
1               5                   10                  15

Leu Cys Trp Gln
            20

<210> SEQ ID NO 956
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 956

Met Val Asn Arg Glu Val Val Val Cys Glu Asp Trp Tyr Gly Val Glu
1               5                   10                  15

Leu Cys Trp Gln
            20
```

```
<210> SEQ ID NO 957
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 957

Thr Ala Asn Gln Thr Val Val Glu Cys Gln Val Trp Gly Gly Val Glu
1               5                   10                  15

Leu Cys Trp Gln
            20

<210> SEQ ID NO 958
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 958

Val Glu Cys Gln Glu Trp Gly Gly Val Glu Leu Cys Trp Cys
1               5                   10

<210> SEQ ID NO 959
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 959

Asp Val Glu Cys Val Asp Trp Gly Gly Val Glu Leu Cys Trp His
1               5                   10                  15

<210> SEQ ID NO 960
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 960

Ile Val Cys Glu Glu Trp Arg Gly Val Glu Leu Cys Trp Leu
1               5                   10

<210> SEQ ID NO 961
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 961

Asp Phe Glu Arg Ser Tyr Val Val Cys Gln Asp Trp Asp Gly Val Glu
1               5                   10                  15

Leu Cys Trp Ile
            20

<210> SEQ ID NO 962
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 962

Ala His Ser Arg Gln Glu Val Val Cys Glu Glu Trp Tyr Gly Val Glu
1               5                   10                  15

Leu Cys Trp Ile
            20

<210> SEQ ID NO 963
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 963

Ser Ala Pro Glu Arg Trp Val Glu Cys Glu Asp Trp Gln Gly Val Glu
1               5                   10                  15

Leu Cys Trp Val
            20

<210> SEQ ID NO 964
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 964

Tyr Ser Arg Glu Leu Tyr Val Gln Cys Glu Asp Trp Glu Gly Val Glu
1               5                   10                  15

Leu Cys Trp Ile
            20

<210> SEQ ID NO 965
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 965

Val Val Cys Gln Asp Trp Glu Gly Val Glu Leu Cys Trp Gln
1               5                   10

<210> SEQ ID NO 966
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 966

Asp Val Val Cys Gln Asn Trp Glu Gly Val Asp Leu Cys Trp His
1               5                   10                  15

<210> SEQ ID NO 967
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 967

Ser Ala Gly Arg Gln Glu Val Val Cys Gln Asp Trp Asn Gly Val Glu
1               5                   10                  15

Leu Cys Trp Ile
            20

<210> SEQ ID NO 968
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 968

Gly Gln Gly Arg Glu Val Val Cys His Asp Trp Tyr Gly Val Glu
1               5                   10                  15

Leu Cys Trp Gln
            20

<210> SEQ ID NO 969
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 969

Asp Trp Arg Arg Ser Val Val Glu Cys Gln Asp Trp Tyr Gly Val Glu
1               5                   10                  15

Leu Cys Trp Gln
            20

<210> SEQ ID NO 970
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 970

Asp Val Val Cys Gln Asn Trp Asp Gly Val Asp Leu Cys Trp His
1               5                   10                  15

<210> SEQ ID NO 971
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 971

Thr Leu Gly Arg Thr Val Val Glu Cys Gln Asp Trp Gly Gly Val Glu
1               5                   10                  15

Leu Cys Trp Gln
            20
```

```
<210> SEQ ID NO 972
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 972

Arg Leu Leu Asn Ser Val Val Glu Cys Leu Asp Trp Glu Gly Val Glu
1               5                   10                  15

Leu Cys Trp Gln
            20

<210> SEQ ID NO 973
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 973

Ile Val Cys Glu Asp Trp Arg Gly Val Glu Leu Cys Trp Ile
1               5                   10

<210> SEQ ID NO 974
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 974

Val Val Cys Gln Glu Trp Glu Gly Val Glu Leu Cys Trp Cys
1               5                   10

<210> SEQ ID NO 975
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 975

Gly Asp Arg Pro Lys Glu Val Val Cys Glu Asp Trp Lys Gly Val Glu
1               5                   10                  15

Leu Cys Trp Ile
            20

<210> SEQ ID NO 976
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 976

Glu Arg Pro Arg Ser Phe Ile Glu Cys Gln Glu Trp Glu Gly Val Glu
1               5                   10                  15

Leu Cys Trp Leu
            20
```

```
<210> SEQ ID NO 977
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 977

Glu Gly Ser Thr Thr Thr Ile Glu Cys Glu Glu Trp Ala Gly Val Glu
1               5                   10                  15

Leu Cys Trp Leu
            20

<210> SEQ ID NO 978
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 978

Ala Asn Gln Asn Thr Val Val Glu Cys Gln Asp Trp His Gly Val Glu
1               5                   10                  15

Leu Cys Trp Gln
            20

<210> SEQ ID NO 979
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 979

Arg Ser Asp Asp Glu Val Val Val Cys Gln Glu Trp Glu Gly Val Glu
1               5                   10                  15

Leu Cys Trp Gln
            20

<210> SEQ ID NO 980
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 980

Ile Glu Cys Glu Glu Trp Ala Gly Val Glu Leu Cys Trp Leu
1               5                   10

<210> SEQ ID NO 981
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 981

Thr Trp Asn Met Ser Glu Leu Glu Cys Gln Asp Trp Asn Gly Val Glu
1               5                   10                  15
```

```
Ile Cys Trp His
            20

<210> SEQ ID NO 982
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 982

Gly Asn Asp Asp Ser Tyr Ile Val Cys Glu Glu Trp Lys Gly Val Glu
1               5                   10                  15

Leu Cys Trp Ile
            20

<210> SEQ ID NO 983
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 983

Phe Ala His His Gly Val Val Glu Cys Gln Glu Trp Tyr Gly Val Glu
1               5                   10                  15

Leu Cys Trp Gln
            20

<210> SEQ ID NO 984
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 984

Leu Asn Arg Ser Val Trp Ile Glu Cys Glu Glu Tyr Glu Gly Val Glu
1               5                   10                  15

Leu Cys Trp Leu
            20

<210> SEQ ID NO 985
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 985

Trp Ser Lys Lys Ala Glu Val Val Cys Glu Glu Trp Gly Gly Val Glu
1               5                   10                  15

Phe Cys Trp Ile
            20

<210> SEQ ID NO 986
<211> LENGTH: 20
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 986

Arg Ser Asn Gln Thr Val Val Glu Cys Gln Asp Trp Glu Gly Val Glu
1               5                   10                  15

Leu Cys Trp Gln
            20

<210> SEQ ID NO 987
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 987

Val Val Cys Gln Glu Trp Glu Gly Val Glu Leu Cys Trp Tyr Ala Gly
1               5                   10                  15

Glu Cys Met Gln
            20

<210> SEQ ID NO 988
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 988

Ile Leu Cys Gln Glu Phe Glu Gly Val Glu Leu Cys Trp Leu Glu Glu
1               5                   10                  15

Ser Leu Ala Glu
            20

<210> SEQ ID NO 989
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 989

Lys Ser Gln Val Glu Cys Gln Asp Trp Glu Gly Val Glu Leu Cys Trp
1               5                   10                  15

Val Val Ser Glu
            20

<210> SEQ ID NO 990
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 990

Lys Ile Thr Val Glu Cys Gln Asp Trp Asp Gly Val Glu Leu Cys Trp
1               5                   10                  15

Pro Thr Trp Ile
            20

```
<210> SEQ ID NO 991
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 991

Arg Pro Gln Ile Glu Cys Gln Glu Trp Gln Gly Val Glu Leu Cys Trp
1               5                   10                  15

Thr Arg Glu Glu
            20

<210> SEQ ID NO 992
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 992

Val Ser Cys Gln Glu Trp Asp Gly Val Glu Leu Cys Trp Val Asp Gly
1               5                   10                  15

Asp Leu Ala Ala
            20

<210> SEQ ID NO 993
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 993

Ile Met Cys Gln Glu Trp Asp Gly Val Glu Leu Cys Trp Leu Glu Arg
1               5                   10                  15

Asp Lys Ala Asn
            20

<210> SEQ ID NO 994
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 994

Gly Leu Glu Ile Ala Cys Glu Asp Trp Tyr Gly Val Glu Leu Cys Trp
1               5                   10                  15

Leu Arg Arg Ala
            20

<210> SEQ ID NO 995
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 995

Gly Tyr Gly Val Leu Cys Gln Glu Trp Gln Gly Val Glu Leu Cys Trp
```

```
1               5                   10                  15
Pro Val Gln Arg Glu Ala Gly Val
            20

<210> SEQ ID NO 996
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 996

Pro Tyr Gly Val Val Cys Gln Asp Trp Ala Gly Val Glu Leu Cys Trp
1               5                   10                  15

Val Glu Asn Arg
            20

<210> SEQ ID NO 997
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 997

Lys Leu Thr Val Glu Cys Gln Asp Trp Asp Gly Val Glu Leu Cys Trp
1               5                   10                  15

Val Gly Val Glu
            20

<210> SEQ ID NO 998
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 998

Ile Asn Cys Gln Thr Trp Asn Gly Val Glu Leu Cys Trp Val Asp Glu
1               5                   10                  15

Gly Leu Tyr Gln
            20

<210> SEQ ID NO 999
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 999

Val Val Cys Gln Glu Trp Glu Gly Val Glu Leu Cys Trp Val Glu Pro
1               5                   10                  15

Pro Leu Leu Pro
            20

<210> SEQ ID NO 1000
<211> LENGTH: 20
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 1000

Arg Val Gln Val Glu Cys Glu Asp Trp Asn Gly Val Glu Leu Cys Trp
1               5                   10                  15

Pro Val Arg Val
            20

<210> SEQ ID NO 1001
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1001

Asp Arg Gln Val Val Cys Glu Glu Trp Asp Gly Val Glu Leu Cys Trp
1               5                   10                  15

Ile Glu Glu Ser
            20

<210> SEQ ID NO 1002
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1002

Lys Thr Thr Val Ala Cys Gln Asp Trp Gly Gly Val Glu Leu Cys Trp
1               5                   10                  15

Val Glu Arg Val
            20

<210> SEQ ID NO 1003
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1003

Arg Pro Glu Val Val Cys Gln Glu Trp Gly Gly Val Glu Leu Cys Trp
1               5                   10                  15

Ile Ser Pro Leu
            20

<210> SEQ ID NO 1004
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1004

Arg Leu Gly Val Glu Cys Gln Glu Trp Glu Gly Val Asp Leu Cys Trp
1               5                   10                  15

Ile Ser Ala Phe
            20

<210> SEQ ID NO 1005
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1005

Lys Pro Val Val Cys Glu Glu Trp Gln Gly Val Glu Leu Cys Trp
1               5                   10                  15

Leu Glu Ile Gln
            20

<210> SEQ ID NO 1006
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1006

Val Val Cys Glu Val Phe Gln Gly Val Glu Leu Cys Trp Cys Glu Asn
1               5                   10                  15

Glu Glu Phe Thr
            20

<210> SEQ ID NO 1007
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1007

Thr Asp Glu Val Ser Cys Gln Glu Trp Glu Gly Val Glu Leu Cys Trp
1               5                   10                  15

Ile Glu Arg Gln
            20

<210> SEQ ID NO 1008
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1008

Pro Val Glu Val Arg Cys Gln Glu Trp Glu Gly Val Glu Leu Cys Trp
1               5                   10                  15

Val Val Gly Ile
            20

<210> SEQ ID NO 1009
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1009

```
Gly Pro Glu Val Val Cys Glu Glu Phe Asn Arg Val Glu Leu Cys Trp
1               5                   10                  15

Val Glu Tyr Asn
            20

<210> SEQ ID NO 1010
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1010

Lys Tyr Ile Val Glu Cys Gln Glu Trp Gly Gly Val Glu Leu Cys Trp
1               5                   10                  15

Pro Glu Met Val
            20

<210> SEQ ID NO 1011
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1011

Val Thr Cys Gln Glu Tyr Glu Gly Val Glu Leu Cys Trp Thr Val Gly
1               5                   10                  15

Cys Ala Tyr Ser
            20

<210> SEQ ID NO 1012
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1012

Val Val Cys Gln Glu Trp Glu Gly Val Glu Leu Cys Trp Gln Thr Gly
1               5                   10                  15

Pro Gly Ala His Ala
            20

<210> SEQ ID NO 1013
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1013

Ile Val Cys Glu Glu Tyr Asn Gly Val Glu Leu Cys Trp Val Glu Thr
1               5                   10                  15

Ser Val Lys Pro
            20

<210> SEQ ID NO 1014
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 1014

Glu Gln Gln Val Val Cys Gln Glu Trp Asn Gly Val Glu Leu Cys Trp
1               5                   10                  15

Ile Glu Ala Gly
            20

<210> SEQ ID NO 1015
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1015

Gln Leu Gly Val Glu Cys Gln Asn Trp Arg Gly Val Glu Leu Cys Trp
1               5                   10                  15

Val Ser Glu Ile
            20

<210> SEQ ID NO 1016
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1016

Thr Ala Glu Val Val Cys Gln Glu Trp Asp Gly Val Glu Leu Cys Trp
1               5                   10                  15

Ile Glu Val Leu
            20

<210> SEQ ID NO 1017
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1017

Ser Pro Ser Ile Val Cys Glu Glu Trp Ala Gly Val Glu Leu Cys Trp
1               5                   10                  15

Val Asp Tyr Ser
            20

<210> SEQ ID NO 1018
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1018

Ala Val Cys Gln Asp Trp Tyr Gly Val Glu Leu Cys Trp Cys Met Gln
1               5                   10                  15

Asp Ile Leu Asp
            20
```

<210> SEQ ID NO 1019
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1019

Val Glu Cys Glu Glu Trp Gly Gly Val Glu Leu Cys Trp Leu Ala Asp
1               5                   10                  15

Glu Val Met Trp
            20

<210> SEQ ID NO 1020
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1020

His Ser Thr Val Ile Cys Gln Asp Trp Asp Gly Val Glu Leu Cys Trp
1               5                   10                  15

Ile Glu Asn Asp
            20

<210> SEQ ID NO 1021
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1021

Lys Lys Ile Val Val Cys Gln Asp Trp Gly Gly Val Glu Leu Cys Trp
1               5                   10                  15

Thr Glu Asp Asp
            20

<210> SEQ ID NO 1022
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1022

Ser Val Glu Val Val Cys Glu Glu Trp His Gly Val Glu Leu Cys Trp
1               5                   10                  15

Pro Val Phe Ile
            20

<210> SEQ ID NO 1023
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1023

-continued

Arg Trp Ala Val Ser Cys Gln Asp Trp Gln Gly Ile Glu Leu Cys Trp
1               5                   10                  15

Pro Glu Trp Asp
            20

<210> SEQ ID NO 1024
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1024

Arg Thr Gly Val Glu Cys Gln Asp Trp His Gly Val Glu Leu Cys Trp
1               5                   10                  15

Pro Val Trp Glu
            20

<210> SEQ ID NO 1025
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1025

Gly Tyr Gly Val Val Cys Glu Asp Phe Arg Gly Val Glu Leu Cys Trp
1               5                   10                  15

Leu Glu Arg Lys
            20

<210> SEQ ID NO 1026
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1026

Arg Thr Glu Val Glu Cys Glu Asp Trp Glu Gly Val Glu Leu Cys Trp
1               5                   10                  15

Leu

<210> SEQ ID NO 1027
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1027

Ile Leu Cys Glu Glu Trp Gln Gly Val Glu Leu Cys Trp Leu Glu Gly
1               5                   10                  15

Gly Gly Ser

<210> SEQ ID NO 1028
<211> LENGTH: 12
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: an amino acid comprising an acidic side chain
<220> FEATURE:
<221> NAME/KEY: MOD_RES
<222> LOCATION: (4)..(4)
<223> OTHER INFORMATION: an amino acid comprising a large hydrophobic
      side chain
<220> FEATURE:
<221> NAME/KEY: MOD_RES
<222> LOCATION: (5)..(5)
<223> OTHER INFORMATION: an amino acid comprising a small hydrophobic
      side chain
<220> FEATURE:
<221> NAME/KEY: MOD_RES
<222> LOCATION: (6)..(6)
<223> OTHER INFORMATION: an amino acid comprising an acidic side chain
<220> FEATURE:
<221> NAME/KEY: MOD_RES
<222> LOCATION: (7)..(7)
<223> OTHER INFORMATION: an amino acid comprising a large hydrophobic
      side chain
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: an amino acid comprising an acidic side chain
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: an amino acid comprising a large hydrophobic
      side chain

<400> SEQUENCE: 1028

Xaa Xaa Xaa Xaa Xaa Xaa Xaa Xaa Xaa Xaa Xaa Xaa
1               5                   10

<210> SEQ ID NO 1029
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1029

Cys Gln Ser Val Gly Asp Trp Cys Asp Met
1               5                   10

<210> SEQ ID NO 1030
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 1030

Cys Asp Ala Val Gly Ser Trp Cys Asp Phe Cys
1               5                   10

<210> SEQ ID NO 1031
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1031

Cys Phe Thr Val Gly Asp Tyr Cys Gly Tyr
1               5                   10

<210> SEQ ID NO 1032
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1032

Trp Cys Ser Asp Ile Gly Gln Tyr Cys Asp Tyr
1               5                   10

<210> SEQ ID NO 1033
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1033

Cys Tyr Glu Val Gly Asp Tyr Cys Gln Ser
1               5                   10

<210> SEQ ID NO 1034
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1034

Cys Gly Met Ala Ile Gly Asp Leu Cys Met
1               5                   10

<210> SEQ ID NO 1035
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1035

Cys Leu Glu Val Gly Cys Ile Trp Asp Met Phe Val
1               5                   10
```

<210> SEQ ID NO 1036
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1036

Phe Cys Asp Met Gly Thr Val Trp Pro Asp Leu Ser
1               5                   10

<210> SEQ ID NO 1037
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1037

Asp Cys Met Leu Tyr Glu Leu Cys Asp Ile Asp Val Leu
1               5                   10

<210> SEQ ID NO 1038
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1038

Ser Cys Cys Val Gly Asp Ile Trp Asp Thr Phe
1               5                   10

<210> SEQ ID NO 1039
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1039

Arg Trp Gly Asp Val Gly Asp Leu Leu Met Pro Phe Leu
1               5                   10

<210> SEQ ID NO 1040
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1040

Phe Leu Val Cys Asp Asp His Tyr Cys Trp Leu Trp Thr
1               5                   10

<210> SEQ ID NO 1041
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1041

Trp Glu Ser Trp Asn Val Gly Asp Leu Val Asn Leu Val Asn Trp
1               5                   10                  15

<210> SEQ ID NO 1042
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1042

Cys Tyr Glu Val Gly Asp Tyr Cys Gln Ser Pro Leu
1               5                   10

<210> SEQ ID NO 1043
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1043

Arg Trp Gly Asp Val Gly Asp Leu Leu Met Pro Leu
1               5                   10

<210> SEQ ID NO 1044
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1044

Arg Ser Cys Tyr Tyr Lys Arg Pro Arg Leu Trp Cys Ser Glu
1               5                   10

<210> SEQ ID NO 1045
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1045

Ile Cys Tyr Tyr Ser Pro Ser Asp Asn Thr Thr Val Cys Glu
1               5                   10

<210> SEQ ID NO 1046
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 1046

Ala Ser Cys Xaa Trp Leu Val Ser Phe Gly Arg Ser Val Cys Leu
1               5                   10                  15
```

<210> SEQ ID NO 1047
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1047

Cys Leu Ser Ile Gly Phe Arg Asp Ile Cys Phe Tyr Arg Val
1               5                   10

<210> SEQ ID NO 1048
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1048

Asp Cys Met Leu Tyr Glu Leu Cys Asp Ile Asp Val Leu
1               5                   10

<210> SEQ ID NO 1049
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1049

Phe Leu Val Cys Asp Asp His Tyr Cys Trp Leu Trp Thr
1               5                   10

<210> SEQ ID NO 1050
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1050

Ile Cys Tyr Tyr Ser Pro Ser Asp Asn Thr Thr Val Cys Glu
1               5                   10

<210> SEQ ID NO 1051
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1051

Asp Leu Ser Asp Leu Ser Thr Phe Trp Leu Ser Gln
1               5                   10

<210> SEQ ID NO 1052
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: an amino acid comprising a small hydrophobic
      side chain
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: an amino acid comprising a large hydrophobic
      side chain
<220> FEATURE:
<221> NAME/KEY: MOD_RES
<222> LOCATION: (6)..(6)
<223> OTHER INFORMATION: an amino acid comprising a small hydrophobic
      side chain
<220> FEATURE:
<221> NAME/KEY: MOD_RES
<222> LOCATION: (7)..(7)
<223> OTHER INFORMATION: an amino acid comprising a polar-neutral or an
      acidic side chain
<220> FEATURE:
<221> NAME/KEY: MOD_RES
<222> LOCATION: (8)..(8)
<223> OTHER INFORMATION: an amino acid comprising a large hydrophobic
      side chain

<400> SEQUENCE: 1052

Xaa Xaa Xaa Xaa Xaa Xaa Xaa Xaa
1               5

<210> SEQ ID NO 1053
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: an amino acid comprising a small hydrophobic
      side chain
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: an amino acid comprising a large hydrophobic
      side chain
<220> FEATURE:
<221> NAME/KEY: MOD_RES
<222> LOCATION: (8)..(8)
```

```
<223> OTHER INFORMATION: an amino acid comprising a small hydrophobic
      side chain
<220> FEATURE:
<221> NAME/KEY: MOD_RES
<222> LOCATION: (9)..(9)
<223> OTHER INFORMATION: an amino acid comprising a polar-neutral or an
      acidic side chain
<220> FEATURE:
<221> NAME/KEY: MOD_RES
<222> LOCATION: (10)..(10)
<223> OTHER INFORMATION: an amino acid comprising a large hydrophobic
      side chain
<220> FEATURE:
<221> NAME/KEY: MOD_RES
<222> LOCATION: (12)..(12)
<223> OTHER INFORMATION: Any amino acid

<400> SEQUENCE: 1053

Xaa Cys Xaa Xaa Xaa Xaa Xaa Xaa Xaa Xaa Cys Xaa
1               5                   10

<210> SEQ ID NO 1054
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: an amino acid comprising a small hydrophobic
      side chain
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: an amino acid comprising a large hydrophobic
      side chain
<220> FEATURE:
<221> NAME/KEY: MOD_RES
<222> LOCATION: (9)..(9)
<223> OTHER INFORMATION: an amino acid comprising a small hydrophobic
      side chain
<220> FEATURE:
<221> NAME/KEY: MOD_RES
<222> LOCATION: (10)..(10)
<223> OTHER INFORMATION: an amino acid comprising a polar-neutral or an
      acidic side chain
<220> FEATURE:
<221> NAME/KEY: MOD_RES
<222> LOCATION: (11)..(11)
<223> OTHER INFORMATION: an amino acid comprising a large hydrophobic
      side chain
<220> FEATURE:
<221> NAME/KEY: MOD_RES
<222> LOCATION: (13)..(13)
<223> OTHER INFORMATION: Any amino acid
```

```
<220> FEATURE:
<221> NAME/KEY: MOD_RES
<222> LOCATION: (14)..(14)
<223> OTHER INFORMATION: an amino acid comprising a large hydrophobic
      side chain

<400> SEQUENCE: 1054

Xaa Xaa Cys Xaa Xaa Xaa Xaa Xaa Xaa Xaa Xaa Cys Xaa Xaa
1               5                   10

<210> SEQ ID NO 1055
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: an amino acid comprising a polar-neutral or an
      acidic side chain
<220> FEATURE:
<221> NAME/KEY: MOD_RES
<222> LOCATION: (7)..(7)
<223> OTHER INFORMATION: an amino acid comprising a polar-neutral or an
      acidic side chain
<220> FEATURE:
<221> NAME/KEY: MOD_RES
<222> LOCATION: (8)..(8)
<223> OTHER INFORMATION: Any amino acid

<400> SEQUENCE: 1055

Xaa Xaa Xaa Xaa Xaa Xaa Xaa Xaa
1               5

<210> SEQ ID NO 1056
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
```

```
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: an amino acid comprising a polar-neutral or an
      acidic side chain
<220> FEATURE:
<221> NAME/KEY: MOD_RES
<222> LOCATION: (9)..(9)
<223> OTHER INFORMATION: an amino acid comprising a polar-neutral or an
      acidic side chain
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 1056

Xaa Cys Xaa Xaa Xaa Xaa Xaa Xaa Xaa Xaa Cys Xaa
1               5                   10

<210> SEQ ID NO 1057
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: an amino acid comprising a large hydrophobic
      side chain
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: an amino acid comprising a polar-neutral or an
      acidic side chain
<220> FEATURE:
```

```
<221> NAME/KEY: MOD_RES
<222> LOCATION: (10)..(10)
<223> OTHER INFORMATION: an amino acid comprising a polar-neutral or an
      acidic side chain
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: Any amino acid

<400> SEQUENCE: 1057

Xaa Xaa Cys Xaa Xaa Xaa Xaa Xaa Xaa Xaa Xaa Cys Xaa Xaa
1               5                   10

<210> SEQ ID NO 1058
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: an amino acid comprising a large hydrophobic
      side chain
<220> FEATURE:
<221> NAME/KEY: MOD_RES
<222> LOCATION: (3)..(3)
<223> OTHER INFORMATION: an amino acid comprising a small hydrophobic
      side chain
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: an amino acid comprising a large hydrophobic
      side chain
<220> FEATURE:
<221> NAME/KEY: MOD_RES
<222> LOCATION: (7)..(7)
<223> OTHER INFORMATION: an amino acid comprising a small hydrophobic
      side chain
<220> FEATURE:
<221> NAME/KEY: MOD_RES
<222> LOCATION: (8)..(8)
<223> OTHER INFORMATION: Any amino acid

<400> SEQUENCE: 1058

Xaa Xaa Xaa Xaa Xaa Xaa Xaa Xaa
1               5

<210> SEQ ID NO 1059
<211> LENGTH: 12
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: MOD_RES
<222> LOCATION: (1)..(1)
<223> OTHER INFORMATION: an amino acid comprising a large hydrophobic
      side chain
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: an amino acid comprising a large hydrophobic
      side chain
<220> FEATURE:
<221> NAME/KEY: MOD_RES
<222> LOCATION: (5)..(5)
<223> OTHER INFORMATION: an amino acid comprising a small hydrophobic
      side chain
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: an amino acid comprising a large hydrophobic
      side chain
<220> FEATURE:
<221> NAME/KEY: MOD_RES
<222> LOCATION: (9)..(9)
<223> OTHER INFORMATION: an amino acid comprising a small hydrophobic
      side chain
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 1059

Xaa Cys Xaa Xaa Xaa Xaa Xaa Xaa Xaa Xaa Cys Xaa
1               5                   10

<210> SEQ ID NO 1060
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: an amino acid comprising a large hydrophobic
      side chain
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: an amino acid comprising a large hydrophobic
      side chain
<220> FEATURE:
```

```
<221> NAME/KEY: MOD_RES
<222> LOCATION: (6)..(6)
<223> OTHER INFORMATION: an amino acid comprising a small hydrophobic
      side chain
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: an amino acid comprising a large hydrophobic
      side chain
<220> FEATURE:
<221> NAME/KEY: MOD_RES
<222> LOCATION: (10)..(10)
<223> OTHER INFORMATION: an amino acid comprising a small hydrophobic
      side chain
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(14)
<223> OTHER INFORMATION: an amino acid comprising a large hydrophobic
      side chain

<400> SEQUENCE: 1060

Xaa Xaa Cys Xaa Xaa Xaa Xaa Xaa Xaa Xaa Xaa Cys Xaa Xaa
1               5                   10

<210> SEQ ID NO 1061
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: an amino acid comprising a large hydrophobic
      side chain
<220> FEATURE:
<221> NAME/KEY: MOD_RES
<222> LOCATION: (3)..(3)
<223> OTHER INFORMATION: an amino acid comprising a small hydrophobic
      side chain
<220> FEATURE:
<221> NAME/KEY: MOD_RES
<222> LOCATION: (4)..(4)
<223> OTHER INFORMATION: an amino acid comprising an acidic side chain
      or a polar neutral side chain
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
```

```
<223> OTHER INFORMATION: an amino acid comprising a polar-neutral side
      chain or an acidic side chain
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid

<400> SEQUENCE: 1061

Xaa Xaa Xaa Xaa Xaa Xaa Xaa Xaa Xaa Xaa
1               5                   10

<210> SEQ ID NO 1062
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: an amino acid comprising a large hydrophobic
      side chain
<220> FEATURE:
<221> NAME/KEY: MOD_RES
<222> LOCATION: (5)..(5)
<223> OTHER INFORMATION: an amino acid comprising a small hydrophobic
      side chain
<220> FEATURE:
<221> NAME/KEY: MOD_RES
<222> LOCATION: (6)..(6)
<223> OTHER INFORMATION: an amino acid comprising an acidic side chain
      or a polar neutral side chain
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: an amino acid comprising a polar-neutral side
      chain or an acidic side chain
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(14)
```

<223> OTHER INFORMATION: Any amino acid

<400> SEQUENCE: 1062

Xaa Cys Xaa Xaa Xaa Xaa Xaa Xaa Xaa Xaa Xaa Xaa Cys Xaa
1               5                   10

<210> SEQ ID NO 1063
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: I, L, M, V, F, Y, and W
<220> FEATURE:
<221> NAME/KEY: MOD_RES
<222> LOCATION: (3)..(3)
<223> OTHER INFORMATION: A, G, P, S, and T
<220> FEATURE:
<221> NAME/KEY: MOD_RES
<222> LOCATION: (4)..(4)
<223> OTHER INFORMATION: D, E, H, N, Q, S, T, and Y
<220> FEATURE:
<221> NAME/KEY: MOD_RES
<222> LOCATION: (5)..(5)
<223> OTHER INFORMATION: I, L, M, V, F, Y, and W
<220> FEATURE:
<221> NAME/KEY: MOD_RES
<222> LOCATION: (6)..(6)
<223> OTHER INFORMATION: I, L, M, V, F, Y, and W
<220> FEATURE:
<221> NAME/KEY: MOD_RES
<222> LOCATION: (7)..(7)
<223> OTHER INFORMATION: D, E, H, N, Q, T, and Y
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: Any amino acid

<400> SEQUENCE: 1063

Xaa Xaa Xaa Xaa Xaa Xaa Xaa Xaa Xaa Xaa
1               5                   10

<210> SEQ ID NO 1064
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES

```
<222> LOCATION: (4)..(4)
<223> OTHER INFORMATION: I, L, M, V, F, Y, and W
<220> FEATURE:
<221> NAME/KEY: MOD_RES
<222> LOCATION: (5)..(5)
<223> OTHER INFORMATION: A, G, P, S, and T
<220> FEATURE:
<221> NAME/KEY: MOD_RES
<222> LOCATION: (6)..(6)
<223> OTHER INFORMATION: D, E, H, N, Q, S, T, and Y
<220> FEATURE:
<221> NAME/KEY: MOD_RES
<222> LOCATION: (7)..(7)
<223> OTHER INFORMATION: I, L, M, V, F, Y, and W
<220> FEATURE:
<221> NAME/KEY: MOD_RES
<222> LOCATION: (8)..(8)
<223> OTHER INFORMATION: I, L, M, V, F, Y, and W
<220> FEATURE:
<221> NAME/KEY: MOD_RES
<222> LOCATION: (9)..(9)
<223> OTHER INFORMATION: D, E, H, N, Q, T, and Y
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid

<400> SEQUENCE: 1064

Xaa Cys Xaa Xaa Xaa Xaa Xaa Xaa Xaa Xaa Xaa Xaa Cys Xaa
1               5                   10

<210> SEQ ID NO 1065
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: an amino acid comprising a polar-neutral side
      chain or an acidic side chain
<220> FEATURE:
<221> NAME/KEY: MOD_RES
<222> LOCATION: (2)..(2)
<223> OTHER INFORMATION: an amino acid comprising a polar-neutral side
      chain or an acidic side chain
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: an amino acid comprising a small hydrophobic
      side chain
<220> FEATURE:
<221> NAME/KEY: MOD_RES
<222> LOCATION: (6)..(6)
<223> OTHER INFORMATION: an amino acid comprising a large hydrophobic
```

```
        side chain
<220> FEATURE:
<221> NAME/KEY: MOD_RES
<222> LOCATION: (7)..(7)
<223> OTHER INFORMATION: an amino acid comprising a large hydrophobic
        side chain
<220> FEATURE:
<221> NAME/KEY: MOD_RES
<222> LOCATION: (8)..(8)
<223> OTHER INFORMATION: an amino acid comprising a large hydrophobic
        side chain

<400> SEQUENCE: 1065

Xaa Xaa Xaa Xaa Xaa Xaa Xaa Xaa
1               5

<210> SEQ ID NO 1066
<211> LENGTH: 14
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: an amino acid comprising a polar-neutral side
        chain or an acidic side chain
<220> FEATURE:
<221> NAME/KEY: MOD_RES
<222> LOCATION: (5)..(5)
<223> OTHER INFORMATION: an amino acid comprising a polar-neutral side
        chain or an acidic side chain
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: an amino acid comprising a small hydrophobic
        side chain
<220> FEATURE:
<221> NAME/KEY: MOD_RES
<222> LOCATION: (9)..(9)
<223> OTHER INFORMATION: an amino acid comprising a large hydrophobic
        side chain
<220> FEATURE:
<221> NAME/KEY: MOD_RES
<222> LOCATION: (10)..(10)
<223> OTHER INFORMATION: an amino acid comprising a large hydrophobic
        side chain
<220> FEATURE:
<221> NAME/KEY: MOD_RES
<222> LOCATION: (11)..(11)
<223> OTHER INFORMATION: an amino acid comprising a large hydrophobic
        side chain
<220> FEATURE:
<221> NAME/KEY: MOD_RES
<222> LOCATION: (13)..(13)
<223> OTHER INFORMATION: an amino acid comprising a large hydrophobic
        side chain
<220> FEATURE:
<221> NAME/KEY: MOD_RES
<222> LOCATION: (14)..(14)
```

<223> OTHER INFORMATION: Any amino acid

<400> SEQUENCE: 1066

Xaa Xaa Cys Xaa Xaa Xaa Xaa Xaa Xaa Xaa Cys Xaa Xaa
1               5                   10

<210> SEQ ID NO 1067
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D, E, F, N, Q, S, and T
<220> FEATURE:
<221> NAME/KEY: MOD_RES
<222> LOCATION: (2)..(2)
<223> OTHER INFORMATION: D, E, I, M, N, Q, R, and S
<220> FEATURE:
<221> NAME/KEY: MOD_RES
<222> LOCATION: (3)..(3)
<223> OTHER INFORMATION: D, E, F, S, T, W, and Y
<220> FEATURE:
<221> NAME/KEY: MOD_RES
<222> LOCATION: (4)..(4)
<223> OTHER INFORMATION: D, E, F, G, L, M, N, Q, and Y
<220> FEATURE:
<221> NAME/KEY: MOD_RES
<222> LOCATION: (5)..(5)
<223> OTHER INFORMATION: E, G, and N
<220> FEATURE:
<221> NAME/KEY: MOD_RES
<222> LOCATION: (6)..(6)
<223> OTHER INFORMATION: I, P, T, and V
<220> FEATURE:
<221> NAME/KEY: MOD_RES
<222> LOCATION: (7)..(7)
<223> OTHER INFORMATION: I, L, M, S, T, and V
<220> FEATURE:
<221> NAME/KEY: MOD_RES
<222> LOCATION: (8)..(8)
<223> OTHER INFORMATION: F, I, and L

<400> SEQUENCE: 1067

Xaa Xaa Xaa Xaa Xaa Xaa Xaa Xaa
1               5

<210> SEQ ID NO 1068
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: G, I, K, L, Q, R, T, and V
<220> FEATURE:
<221> NAME/KEY: MOD_RES
<222> LOCATION: (2)..(2)
<223> OTHER INFORMATION: A, E, I, L, R, S, T, V, and W
<220> FEATURE:
<221> NAME/KEY: MOD_RES
<222> LOCATION: (4)..(4)
<223> OTHER INFORMATION: D, E, F, N, Q, S, and T
<220> FEATURE:
<221> NAME/KEY: MOD_RES
<222> LOCATION: (5)..(5)
<223> OTHER INFORMATION: D, E, I, M, N, Q, R, and S
<220> FEATURE:
<221> NAME/KEY: MOD_RES

```
<222> LOCATION: (6)..(6)
<223> OTHER INFORMATION: D, E, F, S, T, W, and Y
<220> FEATURE:
<221> NAME/KEY: MOD_RES
<222> LOCATION: (7)..(7)
<223> OTHER INFORMATION: D, E, F, G, L, M, N, Q, and Y
<220> FEATURE:
<221> NAME/KEY: MOD_RES
<222> LOCATION: (8)..(8)
<223> OTHER INFORMATION: E, G, and N
<220> FEATURE:
<221> NAME/KEY: MOD_RES
<222> LOCATION: (9)..(9)
<223> OTHER INFORMATION: I, P, T, and V
<220> FEATURE:
<221> NAME/KEY: MOD_RES
<222> LOCATION: (10)..(10)
<223> OTHER INFORMATION: I, L, M, S, T, and V
<220> FEATURE:
<221> NAME/KEY: MOD_RES
<222> LOCATION: (11)..(11)
<223> OTHER INFORMATION: F, I, and L
<220> FEATURE:
<221> NAME/KEY: MOD_RES
<222> LOCATION: (13)..(13)
<223> OTHER INFORMATION: F, T, and W
<220> FEATURE:
<221> NAME/KEY: MOD_RES
<222> LOCATION: (14)..(14)
<223> OTHER INFORMATION: A, E, G, M, L, N, P, Q, S, V, and W

<400> SEQUENCE: 1068

Xaa Xaa Cys Xaa Xaa Xaa Xaa Xaa Xaa Xaa Xaa Cys Xaa Xaa
1               5                   10

<210> SEQ ID NO 1069
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D, E, F, N, Q, S, and T
<220> FEATURE:
<221> NAME/KEY: MOD_RES
<222> LOCATION: (2)..(2)
<223> OTHER INFORMATION: A, D, E, G, I, M, N, Q, R, S, and T
<220> FEATURE:
<221> NAME/KEY: MOD_RES
<222> LOCATION: (3)..(3)
<223> OTHER INFORMATION: D, E, F, S, T, W, and Y
<220> FEATURE:
<221> NAME/KEY: MOD_RES
<222> LOCATION: (4)..(4)
<223> OTHER INFORMATION: D, E, F, G, L, M, N, Q, and Y
<220> FEATURE:
<221> NAME/KEY: MOD_RES
<222> LOCATION: (5)..(5)
<223> OTHER INFORMATION: E, G, N, S, and Q
<220> FEATURE:
<221> NAME/KEY: MOD_RES
<222> LOCATION: (6)..(6)
<223> OTHER INFORMATION: I, K, M, P, T, and V
<220> FEATURE:
<221> NAME/KEY: MOD_RES
<222> LOCATION: (7)..(7)
<223> OTHER INFORMATION: I, L, M, S, T, and V
<220> FEATURE:
<221> NAME/KEY: MOD_RES
<222> LOCATION: (8)..(8)
<223> OTHER INFORMATION: F, I, and L

<400> SEQUENCE: 1069
```

Xaa Xaa Xaa Xaa Xaa Xaa Xaa Xaa
1               5

<210> SEQ ID NO 1070
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: G, I, K, L, Q, R, T, Y, and V
<220> FEATURE:
<221> NAME/KEY: MOD_RES
<222> LOCATION: (2)..(2)
<223> OTHER INFORMATION: A, D, E, H, I, L, M, R, S, T, V, and W
<220> FEATURE:
<221> NAME/KEY: MOD_RES
<222> LOCATION: (4)..(4)
<223> OTHER INFORMATION: D, E, F, N, Q, S, and T
<220> FEATURE:
<221> NAME/KEY: MOD_RES
<222> LOCATION: (5)..(5)
<223> OTHER INFORMATION: A, D, E, G, I, M, N, Q, R, S, and T
<220> FEATURE:
<221> NAME/KEY: MOD_RES
<222> LOCATION: (6)..(6)
<223> OTHER INFORMATION: D, E, F, S, T, W, and Y
<220> FEATURE:
<221> NAME/KEY: MOD_RES
<222> LOCATION: (7)..(7)
<223> OTHER INFORMATION: D, E, F, G, L, M, N, Q, and Y
<220> FEATURE:
<221> NAME/KEY: MOD_RES
<222> LOCATION: (8)..(8)
<223> OTHER INFORMATION: E, G, N, S, and Q
<220> FEATURE:
<221> NAME/KEY: MOD_RES
<222> LOCATION: (9)..(9)
<223> OTHER INFORMATION: I, K, M, P, T, and V
<220> FEATURE:
<221> NAME/KEY: MOD_RES
<222> LOCATION: (10)..(10)
<223> OTHER INFORMATION: I, L, M, S, T, and V
<220> FEATURE:
<221> NAME/KEY: MOD_RES
<222> LOCATION: (11)..(11)
<223> OTHER INFORMATION: F, I, and L
<220> FEATURE:
<221> NAME/KEY: MOD_RES
<222> LOCATION: (13)..(13)
<223> OTHER INFORMATION: F, T, and W
<220> FEATURE:
<221> NAME/KEY: MOD_RES
<222> LOCATION: (14)..(14)
<223> OTHER INFORMATION: E, F, G, I, K, L, M, N, P, Q, S, T, V, W, and Y

<400> SEQUENCE: 1070

Xaa Xaa Cys Xaa Xaa Xaa Xaa Xaa Xaa Xaa Cys Xaa Xaa
1               5                   10

<210> SEQ ID NO 1071
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES

```
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: an amino acid comprising a large hydrophobic
      side chain
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: a small hydrophobic side chain
<220> FEATURE:
<221> NAME/KEY: MOD_RES
<222> LOCATION: (6)..(6)
<223> OTHER INFORMATION: an amino acid comprising a large hydrophobic
      side chain
<220> FEATURE:
<221> NAME/KEY: MOD_RES
<222> LOCATION: (7)..(7)
<223> OTHER INFORMATION: an amino acid comprising a basic side chain,
      an acidic side chain, or a polar-neutral side chain
<220> FEATURE:
<221> NAME/KEY: MOD_RES
<222> LOCATION: (8)..(8)
<223> OTHER INFORMATION: an amino acid comprising a large hydrophobic
      side chain

<400> SEQUENCE: 1071

Xaa Xaa Xaa Xaa Xaa Xaa Xaa Xaa
1               5

<210> SEQ ID NO 1072
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: an amino acid comprising a large hydrophobic
      side chain
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: a small hydrophobic side chain
<220> FEATURE:
<221> NAME/KEY: MOD_RES
<222> LOCATION: (9)..(9)
<223> OTHER INFORMATION: an amino acid comprising a large hydrophobic
      side chain
<220> FEATURE:
```

-continued

```
<221> NAME/KEY: MOD_RES
<222> LOCATION: (10)..(10)
<223> OTHER INFORMATION: an amino acid comprising a basic side chain, an
      acidic side chain, or a polar-neutral side chain
<220> FEATURE:
<221> NAME/KEY: MOD_RES
<222> LOCATION: (11)..(11)
<223> OTHER INFORMATION: an amino acid comprising a large hydrophobic
      side chain
<220> FEATURE:
<221> NAME/KEY: MOD_RES
<222> LOCATION: (13)..(13)
<223> OTHER INFORMATION: an amino acid comprising a large hydrophobic
      side chain
<220> FEATURE:
<221> NAME/KEY: MOD_RES
<222> LOCATION: (14)..(14)
<223> OTHER INFORMATION: Any amino acid

<400> SEQUENCE: 1072

Xaa Xaa Cys Xaa Xaa Xaa Xaa Xaa Xaa Xaa Cys Xaa Xaa
1               5                   10

<210> SEQ ID NO 1073
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: E, M, N, Q, S T, V, W, and Y
<220> FEATURE:
<221> NAME/KEY: MOD_RES
<222> LOCATION: (2)..(2)
<223> OTHER INFORMATION: D, E, F, G, I, M, R, S, T, and V
<220> FEATURE:
<221> NAME/KEY: MOD_RES
<222> LOCATION: (3)..(3)
<223> OTHER INFORMATION: F, W, and Y
<220> FEATURE:
<221> NAME/KEY: MOD_RES
<222> LOCATION: (4)..(4)
<223> OTHER INFORMATION: D, E, L, N, Q, and S
<220> FEATURE:
<221> NAME/KEY: MOD_RES
<222> LOCATION: (6)..(6)
<223> OTHER INFORMATION: I, M, and V
<220> FEATURE:
<221> NAME/KEY: MOD_RES
<222> LOCATION: (7)..(7)
<223> OTHER INFORMATION: D, E, N, Q, and R
<220> FEATURE:
<221> NAME/KEY: MOD_RES
<222> LOCATION: (8)..(8)
<223> OTHER INFORMATION: F, I, and L

<400> SEQUENCE: 1073

Xaa Xaa Xaa Xaa Gly Xaa Xaa Xaa
1               5

<210> SEQ ID NO 1074
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: I, L, P, Q, R, T, and V
<220> FEATURE:
```

```
<221> NAME/KEY: MOD_RES
<222> LOCATION: (2)..(2)
<223> OTHER INFORMATION: A, D, E, I, M, R, T, and V
<220> FEATURE:
<221> NAME/KEY: MOD_RES
<222> LOCATION: (4)..(4)
<223> OTHER INFORMATION: E, M, N, Q, S T, V, W, and Y
<220> FEATURE:
<221> NAME/KEY: MOD_RES
<222> LOCATION: (5)..(5)
<223> OTHER INFORMATION: D, E, F, G, I, M, R, S, T, and V
<220> FEATURE:
<221> NAME/KEY: MOD_RES
<222> LOCATION: (6)..(6)
<223> OTHER INFORMATION: F, W, and Y
<220> FEATURE:
<221> NAME/KEY: MOD_RES
<222> LOCATION: (7)..(7)
<223> OTHER INFORMATION: D, E, L, N, Q, and S
<220> FEATURE:
<221> NAME/KEY: MOD_RES
<222> LOCATION: (9)..(9)
<223> OTHER INFORMATION: I, M, and V
<220> FEATURE:
<221> NAME/KEY: MOD_RES
<222> LOCATION: (10)..(10)
<223> OTHER INFORMATION: D, E, N, Q, and R
<220> FEATURE:
<221> NAME/KEY: MOD_RES
<222> LOCATION: (11)..(11)
<223> OTHER INFORMATION: F, I, and L
<220> FEATURE:
<221> NAME/KEY: MOD_RES
<222> LOCATION: (13)..(13)
<223> OTHER INFORMATION: I, L, R, T, W, and Y
<220> FEATURE:
<221> NAME/KEY: MOD_RES
<222> LOCATION: (14)..(14)
<223> OTHER INFORMATION: A, F, H, I, L, N, P, Q, S, T, and W

<400> SEQUENCE: 1074

Xaa Xaa Cys Xaa Xaa Xaa Xaa Gly Xaa Xaa Xaa Cys Xaa Xaa
1               5                   10

<210> SEQ ID NO 1075
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: an amino acid comprising an acidic side chain
      or large hydrophobic side chain
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: an amino acid comprising a large hydrophobic
      side chain
<220> FEATURE:
<221> NAME/KEY: MOD_RES
<222> LOCATION: (6)..(6)
<223> OTHER INFORMATION: an amino acid comprising a small hydrophobic
```

```
    side chain or a large hydrophobic side chain
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: an amino acid comprising a large hydrophobic
    side chain
<220> FEATURE:
<221> NAME/KEY: MOD_RES
<222> LOCATION: (9)..(9)
<223> OTHER INFORMATION: an amino acid comprising a large hydrophobic
    side chain

<400> SEQUENCE: 1075

Xaa Xaa Xaa Xaa Xaa Xaa Xaa Xaa Xaa
1               5

<210> SEQ ID NO 1076
<211> LENGTH: 13
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<221> NAME/KEY: MOD_RES
<222> LOCATION: (1)..(1)
<223> OTHER INFORMATION: an amino acid comprising an acidic side chain
    or cysteine
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: an amino acid comprising an acidic side chain
    or large hydrophobic side chain
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: an amino acid comprising a large hydrophobic
    side chain
<220> FEATURE:
<221> NAME/KEY: MOD_RES
<222> LOCATION: (8)..(8)
<223> OTHER INFORMATION: an amino acid comprising a small hydrophobic
    side chain or a large hydrophobic side chain
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (10)..(10)
<223> OTHER INFORMATION: an amino acid comprising a large hydrophobic
    side chain
<220> FEATURE:
<221> NAME/KEY: MOD_RES
<222> LOCATION: (11)..(11)
<223> OTHER INFORMATION: an amino acid comprising a large hydrophobic
    side chain
```

```
<220> FEATURE:
<221> NAME/KEY: MOD_RES
<222> LOCATION: (12)..(12)
<223> OTHER INFORMATION: an amino acid comprising a small hydrophobic
      side chain or an acidic side chain or cysteine
<220> FEATURE:
<221> NAME/KEY: MOD_RES
<222> LOCATION: (13)..(13)
<223> OTHER INFORMATION: an amino acid comprising an acidic side chain
      or a hydroxyl-containing side chain or cysteine

<400> SEQUENCE: 1076

Xaa Xaa Xaa Xaa Xaa Xaa Xaa Xaa Xaa Xaa Xaa Xaa Xaa
1               5                   10

<210> SEQ ID NO 1077
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: an amino acid comprising an acidic side chain
      or a hydroxyl-containing side chain
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: an amino acid comprising a large hydrophobic
      side chain
<220> FEATURE:
<221> NAME/KEY: MOD_RES
<222> LOCATION: (6)..(6)
<223> OTHER INFORMATION: an amino acid comprising a large hydrophobic
      side chain

<400> SEQUENCE: 1077

Xaa Xaa Cys Xaa Xaa Xaa
1               5

<210> SEQ ID NO 1078
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: an amino acid comprising a large hydrophobic
      side chain or an acidic side chain
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: an amino acid comprising an acidic side chain
      or a hydroxyl-containing side chain
```

```
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: an amino acid comprising a large hydrophobic
      side chain
<220> FEATURE:
<221> NAME/KEY: MOD_RES
<222> LOCATION: (9)..(9)
<223> OTHER INFORMATION: an amino acid comprising a large hydrophobic
      side chain
<220> FEATURE:
<221> NAME/KEY: MOD_RES
<222> LOCATION: (10)..(10)
<223> OTHER INFORMATION: an amino acid comprising a large hydrophobic
      side chain
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (12)..(12)
<223> OTHER INFORMATION: Any amino acid

<400> SEQUENCE: 1078

Xaa Xaa Xaa Xaa Xaa Cys Xaa Xaa Xaa Xaa Xaa Xaa
1               5                   10

<210> SEQ ID NO 1079
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D, E, S, T, and Y
<220> FEATURE:
<221> NAME/KEY: MOD_RES
<222> LOCATION: (2)..(2)
<223> OTHER INFORMATION: E, L, P, and Q
<220> FEATURE:
<221> NAME/KEY: MOD_RES
<222> LOCATION: (4)..(4)
<223> OTHER INFORMATION: D, E, L, S, and T
<220> FEATURE:
<221> NAME/KEY: MOD_RES
<222> LOCATION: (5)..(5)
<223> OTHER INFORMATION: F, S, and W
<220> FEATURE:
<221> NAME/KEY: MOD_RES
<222> LOCATION: (6)..(6)
<223> OTHER INFORMATION: F, N, W, and Y

<400> SEQUENCE: 1079

Xaa Xaa Cys Xaa Xaa Xaa
1               5

<210> SEQ ID NO 1080
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: D, G, I, and Q
<220> FEATURE:
<221> NAME/KEY: MOD_RES
<222> LOCATION: (2)..(2)
<223> OTHER INFORMATION: D, I, and L
<220> FEATURE:
<221> NAME/KEY: MOD_RES
<222> LOCATION: (3)..(3)
<223> OTHER INFORMATION: G, L, M, R, S, and Y
<220> FEATURE:
<221> NAME/KEY: MOD_RES
<222> LOCATION: (4)..(4)
<223> OTHER INFORMATION: D, E, S, T, and Y
<220> FEATURE:
<221> NAME/KEY: MOD_RES
<222> LOCATION: (5)..(5)
<223> OTHER INFORMATION: E, L, P, and Q
<220> FEATURE:
<221> NAME/KEY: MOD_RES
<222> LOCATION: (7)..(7)
<223> OTHER INFORMATION: D, E, L, S, and T
<220> FEATURE:
<221> NAME/KEY: MOD_RES
<222> LOCATION: (8)..(8)
<223> OTHER INFORMATION: F, S, and W
<220> FEATURE:
<221> NAME/KEY: MOD_RES
<222> LOCATION: (9)..(9)
<223> OTHER INFORMATION: F, N, W, and Y
<220> FEATURE:
<221> NAME/KEY: MOD_RES
<222> LOCATION: (10)..(10)
<223> OTHER INFORMATION: F, I, L, and R
<220> FEATURE:
<221> NAME/KEY: MOD_RES
<222> LOCATION: (11)..(11)
<223> OTHER INFORMATION: A, E, L, and S
<220> FEATURE:
<221> NAME/KEY: MOD_RES
<222> LOCATION: (12)..(12)
<223> OTHER INFORMATION: K, N, Q, and V

<400> SEQUENCE: 1080

Xaa Xaa Xaa Xaa Xaa Cys Xaa Xaa Xaa Xaa Xaa Xaa
1               5                   10

<210> SEQ ID NO 1081
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D, E, G, L, S, T, and Y
<220> FEATURE:
<221> NAME/KEY: MOD_RES
<222> LOCATION: (2)..(2)
<223> OTHER INFORMATION: E, L, P, and Q
<220> FEATURE:
<221> NAME/KEY: MOD_RES
<222> LOCATION: (4)..(4)
<223> OTHER INFORMATION: D, E, K, L, S, and T
<220> FEATURE:
<221> NAME/KEY: MOD_RES
<222> LOCATION: (5)..(5)
<223> OTHER INFORMATION: D, F, S, and W
<220> FEATURE:
<221> NAME/KEY: MOD_RES
<222> LOCATION: (6)..(6)
<223> OTHER INFORMATION: F, N, W, and Y
```

```
<400> SEQUENCE: 1081

Xaa Xaa Cys Xaa Xaa Xaa
1               5

<210> SEQ ID NO 1082
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D, G, I, and Q
<220> FEATURE:
<221> NAME/KEY: MOD_RES
<222> LOCATION: (2)..(2)
<223> OTHER INFORMATION: D, I, and L
<220> FEATURE:
<221> NAME/KEY: MOD_RES
<222> LOCATION: (3)..(3)
<223> OTHER INFORMATION: G, L, M, Q, R, S, and Y
<220> FEATURE:
<221> NAME/KEY: MOD_RES
<222> LOCATION: (4)..(4)
<223> OTHER INFORMATION: D, E, G, L, S, T, and Y
<220> FEATURE:
<221> NAME/KEY: MOD_RES
<222> LOCATION: (5)..(5)
<223> OTHER INFORMATION: E, L, P, and Q
<220> FEATURE:
<221> NAME/KEY: MOD_RES
<222> LOCATION: (7)..(7)
<223> OTHER INFORMATION: D, E, K, L, S, and T
<220> FEATURE:
<221> NAME/KEY: MOD_RES
<222> LOCATION: (8)..(8)
<223> OTHER INFORMATION: D, F, S, and W
<220> FEATURE:
<221> NAME/KEY: MOD_RES
<222> LOCATION: (9)..(9)
<223> OTHER INFORMATION: F, N, W, and Y
<220> FEATURE:
<221> NAME/KEY: MOD_RES
<222> LOCATION: (10)..(10)
<223> OTHER INFORMATION: F, I, L, R and W
<220> FEATURE:
<221> NAME/KEY: MOD_RES
<222> LOCATION: (11)..(11)
<223> OTHER INFORMATION: A, E, L, and S
<220> FEATURE:
<221> NAME/KEY: MOD_RES
<222> LOCATION: (12)..(12)
<223> OTHER INFORMATION: H, L, K, N, Q, and V

<400> SEQUENCE: 1082

Xaa Xaa Xaa Xaa Xaa Cys Xaa Xaa Xaa Xaa Xaa Xaa
1               5                   10

<210> SEQ ID NO 1083
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: an amino acid comprising a large hydrophobic
      side chain
<220> FEATURE:
<221> NAME/KEY: MOD_RES
<222> LOCATION: (3)..(3)
```

```
<223> OTHER INFORMATION: an amino acid comprising a large hydrophobic
      side chain
<220> FEATURE:
<221> NAME/KEY: MOD_RES
<222> LOCATION: (4)..(4)
<223> OTHER INFORMATION: an amino acid comprising a large hydrophobic
      side chain
<220> FEATURE:
<221> NAME/KEY: MOD_RES
<222> LOCATION: (5)..(5)
<223> OTHER INFORMATION: an amino acid comprising a large hydrophobic
      side chain
<220> FEATURE:
<221> NAME/KEY: MOD_RES
<222> LOCATION: (6)..(6)
<223> OTHER INFORMATION: an amino acid comprising a basic side chain and
      an acidic or polar neutral side chain
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: an amino acid comprising a small hydrophobic
      side chain
<220> FEATURE:
<221> NAME/KEY: MOD_RES
<222> LOCATION: (9)..(9)
<223> OTHER INFORMATION: an amino acid comprising an acidic or a polar
      neutral side chain
<220> FEATURE:
<221> NAME/KEY: MOD_RES
<222> LOCATION: (10)..(10)
<223> OTHER INFORMATION: an amino acid comprising a large hydrophobic
      side chain
<220> FEATURE:
<221> NAME/KEY: MOD_RES
<222> LOCATION: (11)..(11)
<223> OTHER INFORMATION: an amino acid comprising a small hydrophobic
      side chain or a hydroxyl-containing side chain
<220> FEATURE:
<221> NAME/KEY: MOD_RES
<222> LOCATION: (12)..(12)
<223> OTHER INFORMATION: an amino acid comprising a large hydrophobic
      side chain
<220> FEATURE:
<221> NAME/KEY: MOD_RES
<222> LOCATION: (13)..(13)
<223> OTHER INFORMATION: an amino acid comprising a large hydrophobic
      side chain

<400> SEQUENCE: 1083

Cys Xaa Xaa Xaa Xaa Xaa Xaa Xaa Xaa Xaa Xaa Xaa Xaa Cys
1               5                   10

<210> SEQ ID NO 1084
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1084

Cys Gly Met Ala Ile Gly Asp Leu Cys Met Trp Thr
1               5                   10

<210> SEQ ID NO 1085
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 1085

Gly Gly Gly Ser
1

<210> SEQ ID NO 1086
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1086

Gly Gly Gly Gly Ser
1               5

<210> SEQ ID NO 1087
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1087

Gly Gly Gly Gly Ser Gly Gly Gly Gly Ser Gly Gly Gly Gly Ser
1               5                   10                  15

<210> SEQ ID NO 1088
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1088

Gly Gly Gly Gly Gly Gly Gly Gly
1               5

<210> SEQ ID NO 1089
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1089

Gly Gly Gly Gly Gly Gly
1               5

<210> SEQ ID NO 1090
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(15)
<223> OTHER INFORMATION: This sequence may encompass 1-3 "Glu Ala Ala
      Ala Lys" repeating units

<400> SEQUENCE: 1090

Glu Ala Ala Ala Lys Glu Ala Ala Ala Lys Glu Ala Ala Ala Lys
```

-continued

```
1               5                   10                  15

<210> SEQ ID NO 1091
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1091

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Lys Glu Ala
                20                  25                  30

Ala Ala Lys Glu Ala Ala Ala Lys Glu Ala Ala Ala Lys Ala
        35                  40                  45

<210> SEQ ID NO 1092
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1092

Pro Ala Pro Ala Pro
1               5

<210> SEQ ID NO 1093
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1093

Ala Glu Ala Ala Ala Lys Glu Ala Ala Ala Lys Ala
1               5                   10

<210> SEQ ID NO 1094
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(34)
<223> OTHER INFORMATION: This sequence may encompass 5-17 "Ala Pro"
      repeating units

<400> SEQUENCE: 1094

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
                20                  25                  30

Ala Pro

<210> SEQ ID NO 1095
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 1095

Val Ser Gln Thr Ser Lys Leu Thr Arg Ala Glu Thr Val Phe Pro Asp
1               5                   10                  15

Val

<210> SEQ ID NO 1096
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1096

Pro Leu Gly Leu Trp Ala
1               5

<210> SEQ ID NO 1097
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1097

Gly Phe Leu Gly
1

<210> SEQ ID NO 1098
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1098

Arg Val Gln Asp Val Ile Glu Arg Phe Trp Asp Phe Ile Asp Gln Leu
1               5                   10                  15

Ser Gly Ser Gly Ser Gly Lys
            20

<210> SEQ ID NO 1099
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1099

Val Asp Ala Asp Gly Pro Leu Ala Arg Leu Lys Lys Ala Ile Phe Ser
1               5                   10                  15

Pro Gly Ser Gly Ser Gly Lys
            20

<210> SEQ ID NO 1100
<211> LENGTH: 40
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-20 "Pro Ala"
      repeating units

<400> SEQUENCE: 1100

Pro Ala Pro Ala Pro Ala Pro Ala Pro Ala Pro Ala Pro Ala Pro Ala
1               5                   10                  15

Pro Ala Pro Ala Pro Ala Pro Ala Pro Ala Pro Ala Pro Ala
            20                  25                  30

Pro Ala Pro Ala Pro Ala Pro Ala
        35                  40

<210> SEQ ID NO 1101
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1101

Pro Ala Pro Ala Pro Ala Pro Ala Pro Ala Pro Ala Pro Ala Pro Ala
1               5                   10                  15

Pro Ala Pro Ala
            20

<210> SEQ ID NO 1102
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-20 "Gly Ser"
      repeating units

<400> SEQUENCE: 1102

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser
            20                  25                  30

Gly Ser Gly Ser Gly Ser Gly Ser
        35                  40

<210> SEQ ID NO 1103
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1103

Gly Ser Gly Ser Gly Ser Gly Ser Gly Ser Gly Ser Gly Ser Gly Ser
1               5                   10                  15

Gly Ser Gly Ser
            20
```

IL-2RBETA BINDING COMPOUNDS

This application is a continuation of U.S. application Ser. No. 16/531,954, mailed on Aug. 5, 2019, now allowed, which claims benefit under 35 U.S.C. § 119(e) to U.S. Provisional Application No. 62/785,754 filed on Dec. 28, 2018, and U.S. Provisional Application No. 62/715,097 filed on Aug. 6, 2018, each of which is incorporated by reference in its entirety.

FIELD

The present disclosure relates to IL-2Rβ ligands, to IL-2Rγc ligands and to compounds having an IL-2Rβ ligand and/or an IL-2Rγc ligand. Compounds such as synthetic heterodimers and recombinant fusion proteins comprising an IL-2Rβ ligand and/or an IL-2Rγc ligand can be IL-2 receptor agonists.

SEQUENCE LISTING

The instant application contains a Sequence Listing which has been submitted electronically in ASCII format and is hereby incorporated by reference in its entirety. The ASCII copy, created on Sep. 10, 2021, is named 62AJ-000520US-303563_SL.txt and is 363,046 bytes in size.

BACKGROUND

Recombinant human Interleukin-2 (IL-2) was one of the first immuno-oncology agents studied in the clinic and was approved by the FDA for use against some particularly challenging cancers, melanoma and renal carcinoma in the 1990s. IL-2 is effective, producing durable responses in up to 10% of patients with these tumors, but its utility is limited by very serious, dose-limiting toxicities. In addition, the efficacy of IL-2 in directing T-cell-mediated anti-tumor response is compromised by concurrent IL-2-driven upregulation of T-cell suppressive systems. There has been a continuing search for strategies to reduce the toxicity of IL-2 therapy, and to avoid the immunosuppressive limitations on anti-tumor activity. To date, modestly effective strategies have been developed to control systemic exposure, and thus toxicity, of this potent biologic. Elucidation of the complicated biology of IL-2 has led to modifications of the natural IL-2 molecule to alter the balance of tumor toxicity and suppression. However, these approaches are limited by the use of natural IL-2 as a template, thus retaining elements of the undesirable, structure-driven bioactivities of the parent molecule.

Crucial to its anti-tumor properties, IL-2 exerts potent stimulatory effects on NK and cytotoxic CD8+ T-cells. However, the anti-tumor effects are paradoxically suppressed by IL-2-directed stimulation of T-regulatory cells (Tregs), which effectively blunts the anti-tumor immune response. This dual effect of IL-2 is largely controlled by the nature of the IL-2 receptor (IL-2R) subunits expressed on the various cells responsible for immune homeostasis. IL-2 is recognized by combinations of three receptor subunits, which are differentially and conditionally expressed on many types of immune cells. The two signaling subunits, known as IL-2Rβ (β) and IL-2Rγ-common (γc), initiate signaling when brought into correctly-oriented apposition by binding to IL-2. IL-2 binds to IL-2Rβγc with an affinity of about 1 nM to form an active ternary complex. Most immune cells express, at various levels, the IL-2Rβ and IL-2Rγc subunits. There is also a third, non-signaling IL-2R subunit, IL-2Rα (also known as CD25), which is expressed on a subset of immune cells, notably Tregs. The complex of IL-2Rαβγc has a very high affinity for IL-2 (about 10 pM), and cells expressing all three subunits are therefore much more sensitive to IL-2. A popular and well-supported strategy for improving the efficacy of IL-2 receptor agonists against tumors involves engineering IL-2R selectivity to reduce the binding of IL-2 to the IL-2Rα subunit while maintaining IL-2Rβγc binding and signaling to favor infiltration and stimulation of cytotoxic effector T-cells (Teff cells) over Tregs at tumor sites.

The cause of IL-2 toxicity in the clinical setting is less well understood; but is thought to be the result of exaggerated peripheral immuno-stimulation of IL-2Rβγc-expressing T-cells accompanied by excessive release of inflammatory cytokines. Toxicity is induced by the frequent administration of high doses of IL-2 required to sustain adequate tumor exposure because of the short half-life of the natural cytokine.

Strategies to address the limitations of IL-2 as a useful immuno-oncology therapy utilize mutants, fusion proteins, or chemically-modified IL-2 to alter the complex biology of the immune regulator. An example is a modified form of IL-2, decorated with 6 large cleavable polyethylene glycol (PEG) moieties that serve the dual purposes of altering receptor subunit binding specificity and prolonging the circulating half-life of a reversibly inactive prodrug of IL-2. As the prodrug systemically circulates, a cascade of PEG removal imparts a complicated pharmacokinetic (PK) profile of variously-active and inactive forms of the cytokine, producing low sustained peripheral exposure to active IL-2 agonism, and thereby avoids the $C_{max}$-driven severe side effects of high dose IL-2. The last two PEGs to be cleaved are located near the IL-2Rα binding site, interfering with IL-2Rα binding, but allowing for IL-2Rβγc signaling, consequently favoring cytotoxic T-cell activity over the suppressive Treg activity. This yields a promising therapeutic molecule that addresses two principal deficiencies of IL-2 as an anti-cancer therapeutic: (a) avoiding activation of IL-2Rαβγc on Tregs, and (b) half-life extension of the IL-2Rβγc-activating compound. However, these effects are necessarily intertwined and are difficult to optimize separately, as is often required during pre-clinical and clinical development. This limits the use of a bioactive IL-2 protein as a starting point for imparting multiple new properties.

SUMMARY

According to the present invention, an IL-2Rβ ligand exhibits a binding affinity (IC50) to the human IL-2Rβ subunit of less than 100 μM.

According to the present invention, an IL-2Rβ ligand comprises an amino acid sequence selected from any one of SEQ ID NO: 1 to SEQ ID NO: 193, SEQ ID NO: 578 to SEQ ID NO: 903, SEQ ID NO: 1028 to SEQ ID NO: 1050, and SEQ ID NOS 1052-1064, and 1084.

According to the present invention, an IL-2Rγc ligand exhibits a binding affinity (IC50) to the human IL-2Rγc subunit of less than 100 μM.

According to the present invention, an IL-2Rγc ligand comprises an amino acid sequence selected from any one of SEQ ID NO: 194 to SEQ ID NO: 267, SEQ ID NO: 904 to SEQ ID NO: 1027, and SEQ ID NOS 1065-1083.

According to the present invention, a compound comprises at least one IL-2Rβ ligand according to the present invention and/or an IL-2Rγc ligand according to the present invention.

According to the present invention, a pharmaceutical composition comprises an IL-2Rβ ligand according to the present invention and/or an IL-2Rγc ligand according to the present invention; a compound according to the present invention; or a combination thereof.

According to the present invention, methods of treating cancer in a patient comprise administering to a patient in need of such treatment, a therapeutically effective amount of a pharmaceutical composition according to the present invention.

According to the present invention, methods of treating an autoimmune disease in a patient comprise administering to a patient in need of such treatment, a therapeutically effective amount of a pharmaceutical composition according to the present invention.

According to the present invention, methods include: methods of screening compounds for IL-2Rβ and/or IL-2Rγc activity; methods of activating the human IL-2 receptor; methods of treating a disease in a patient wherein the IL-2 receptor signaling pathway is associated with the etiology of the disease; methods of treating a disease in a patient wherein activation of the IL-2 receptor is effective in treating the disease; methods of treating a disease in a patient wherein inhibition of the IL-2 receptor is effective in treating the disease; methods of treating a disease in a patient, wherein cells expressing the IL-2Rβ and/or IL-2Rγc subunit are associated with the etiology of the disease; methods of treating a disease in a patient, wherein cells expressing the IL-2Rγc subunit and/or the L-2Rγc subunit are associated with the etiology of the disease; methods of treating a disease in a patient wherein reducing the sensitivity of Treg cells to IL-2 is effective in treating the disease; methods of imaging cells expressing the IL-2Rβ subunit and/or the IL-2Rγc subunit; methods of diagnosing a disease in a patient wherein the disease is associated with cells expressing the IL-2Rβ subunit and/or the IL-2Rγc subunit; methods of targeting a compound to cells expressing the IL-2Rβ subunit and/or the IL-2Rγc subunit; and methods of delivering a cytotoxic compound to cells expressing the the IL-2Rβ subunit and/or IL-2Rγc subunit.

According to the present invention, a binding site of the IL-2Rβ subunit, wherein the group of IL-2Rβ ligands having amino acid sequences of SEQ ID NOS: 1-163, 164-182, 578-808, 1028-1042, 1052-1060, and 1084, competitively bind to the binding site with each of the other IL-2Rβ ligands within the group; an IL-2Rβ ligand having amino acid sequence of SEQ ID NO: 1041 does not compete for binding to the binding site with the group of IL-2Rβ ligands; and IL-2 does not compete for binding to the binding site with the group of IL-2Rβ ligands.

According to the present invention, a binding site of the IL-2Rγc subunit, wherein the group of IL-2Rγc ligands having amino acid sequences of SEQ ID NOS: 194-210, 904-913, 211-233, 914-920, 234-245, 246-254, 921-922, 265-267, 932-940, and 1065-1082, competitively bind to the binding site with each of the other IL-2Rγc ligands within the group; an IL-2Rγc ligand having amino acid sequence of SEQ ID NO: 948 does not compete for binding to the binding site with the group of IL-2Rγc ligands; and IL-2 does not compete for binding to the binding site with the group of IL-2Rγc ligands.

Reference is now made to certain compounds and methods. The disclosed embodiments are not intended to be limiting of the claims. To the contrary, the claims are intended to cover all alternatives, modifications, and equivalents.

BRIEF DESCRIPTION OF THE DRAWINGS

The drawings described herein are for illustration purposes only. The drawings are not intended to limit the scope of the present disclosure.

DETAILED DESCRIPTION

Figure 1:
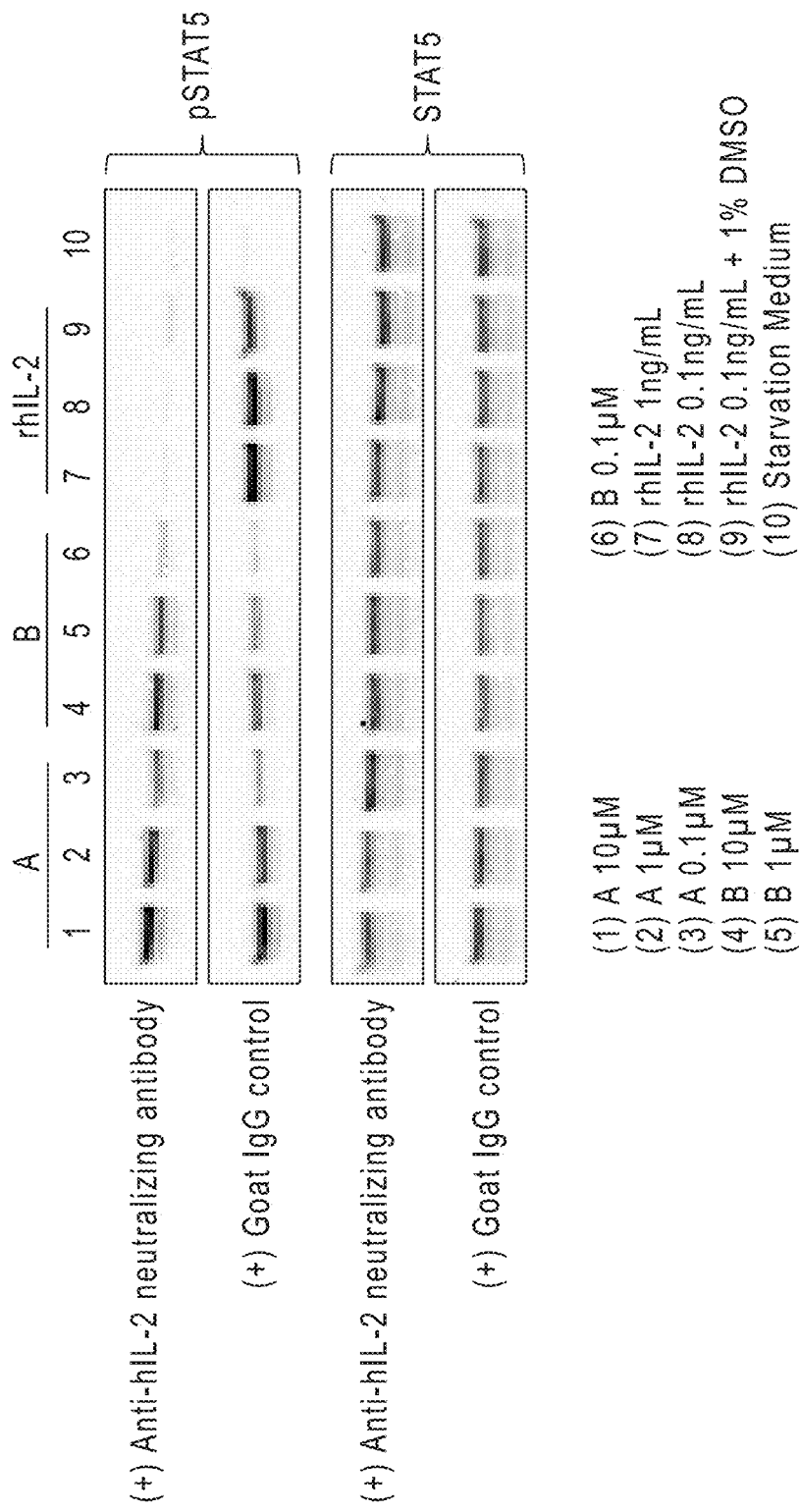
FIG. 1 shows STAT5 phosphorylation in NK-92 cells by IL-2Rβγc agonists according to the present disclosure by Western Blot analysis.

A dash ("-") that is not between two letters or symbols is used to indicate a point of attachment for a moiety or substituent. For example, —$CONH_2$ is attached through the carbon atom and —$X^1$—$X^2$— denotes amino acids $X^1$ and $X^2$ covalently bonded through a single bond.

"Alkyl" refers to a saturated or unsaturated, branched, or straight-chain, monovalent hydrocarbon radical derived by the removal of one hydrogen atom from a single carbon atom of a parent alkane, alkene, or alkyne. Examples of alkyl groups include methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like. The term "alkyl" is specifically intended to include groups having any degree or level of saturation, i.e., groups having exclusively carbon-carbon single bonds, groups having one or more carbon-carbon double bonds, groups having one or more carbon-carbon triple bonds, and groups having combinations of carbon-carbon single, double, and triple bonds. Where a specific level of saturation is intended, the terms alkanyl, alkenyl, and alkynyl are used. In certain embodiments, an alkyl group is $C_{1-6}$ alkyl, $C_{1-5}$ alkyl, $C_{1-4}$ alkyl, $C_{1-3}$ alkyl, and in certain embodiments, ethyl or methyl.

"Cycloalkyl" refers to a saturated or partially unsaturated cyclic alkyl radical. In certain embodiments, a cycloalkyl group is $C_{3-4}$ cycloalkyl, $C_{3-5}$ cycloalkyl, $C_{5-6}$ cycloalkyl, cyclopropyl, cyclopentyl, and in certain embodiments, cyclohexyl. In certain embodiments, cycloalkyl is selected from cyclopropyl, cyclobutyl, cyclopentyl, and cyclohexyl.

"Heterocycloalkyl" by itself or as part of another substituent refers to a saturated or unsaturated cyclic alkyl radical in which one or more carbon atoms (and certain associated hydrogen atoms) are independently replaced with the same or different heteroatom; or to a parent aromatic ring system in which one or more carbon atoms (and certain associated hydrogen atoms) are independently replaced with the same or different heteroatom such that the ring system violates the Hückel-rule. Examples of heteroatoms to replace the carbon atom(s) include N, P, O, S, and Si. Examples of heterocycloalkyl groups include groups derived from epoxides, azirines, thiiranes, imidazolidine, morpholine, piperazine, piperidine, pyrazolidine, pyrrolidine, quinuclidine, and the like. In certain embodiments, heterocycloalkyl is $C_5$ heterocycloalkyl and is selected from pyrrolidinyl, tetrahydrofuranyl, tetrahydrothiophenyl, imidazolidinyl, oxazolidinyl, thiazolidinyl, doxolanyl, and dithiolanyl. In certain embodiments, heterocycloalkyl is $C_6$ heterocycloalkyl and is selected from piperidinyl, tetrahydropyranyl, piperizinyl, oxazinyl, dithianyl, and dioxanyl. In certain embodiments a heterocycloalkyl group is $C_{3-6}$ heterocycloalkyl, $C_{3-5}$ heterocycloalkyl, $C_{5-6}$ heterocycloalkyl, and in certain embodiments, $C_5$ heterocycloalkyl or $C_6$ heterocycloalkyl. In certain embodiments of heterocycloalkyl, the heteroatomic group is selected from —O—, —S—, —NH—, —N(—CH$_3$)—, —SO—, and —SO$_2$—, in certain embodiments, the heteroatomic group is selected from —O— and —NH—, and in certain embodiments the heteroatomic group is —O— or —NH—.

"Agonist" refers to a biologically active ligand which binds to its complementary biologically active receptor or subunit(s) and activates the receptor to cause a biological response mediated by the receptor, or to enhance a preexisting biological activity mediated by the receptor.

"Affinity" refers to the strength of the binding interaction between a single biomolecule to its ligand/binding partner. Affinity is expressed as the $IC_{50}$.

"Antagonist" refers to a biologically active ligand or compound that binds to its complementary receptor or subunit(s) and blocks or reduces a biological response of the receptor.

Amino acid residues are abbreviated as follows: alanine is Ala or A; arginine is Arg is R; asparagine is Asn or N; aspartic acid is Asp or D; cysteine is Cys or C; glutamic acid is Glu or E; glutamine is Gln or Q; glycine is Gly or G; histidine is His or H; isoleucine is Ile or I; leucine is Leu or L; lysine is Lys or K; methionine is Met or M; phenylalanine is Phe or F; proline is Pro or P; serine is Ser or S; threonine is Thr or T; tryptophan is Trp or W; tyrosine is Tyr or Y; and valine is Val or V.

"Non-natural amino acids" include, for example, β-amino acids, homo-amino acids, proline and pyruvic acid derivatives, histidine derivatives with alkyl or heteroatom moieties attached to the imidazole ring, amino acids with pyridine-containing side chains, 3-substituted alanine derivatives, glycine derivatives, ring-substituted phenylalanine and tyrosine derivatives, and N-methyl amino acids.

Amino acids having a large hydrophobic side chain include isoleucine (I), leucine (L), methionine (M), valine (V), phenylalanine (F), tyrosine (Y), and tryptophan (W).

Amino acids having a small hydrophobic side chain include alanine (A), glycine (G), proline (P), serine (S), and threonine (T).

Amino acids having a basic side chain include arginine (R), lysine (K), and histidine (H).

Amino acids having an acidic side chain include aspartate (D) and glutamate (E).

Amino acids having a polar/neutral side chain include histidine (H), asparagine (N), glutamine (Q), serine (S), threonine (T), and tyrosine (Y).

Amino acids having an aromatic side chain include phenylalanine (F), histidine (H), tryptophan (W), and tyrosine (Y).

Amino acids having a hydroxyl side chain include serine (S), threonine (T), and tyrosine (Y).

"Conservative amino acid substitution" means that amino acids within each of the following groups can be substituted with another amino acid within the group: amino acids having a small hydrophobic side chain comprising alanine (A), glycine (G), proline (P), serine (S), and threonine (T); amino acids having a hydroxyl-containing side chain comprising serine (S), threonine (T), and tyrosine (Y); amino acids having an acidic side chain comprising aspartate (D) and glutamate (E); amino acids comprising a polar-neutral side chain comprising histidine (H), asparagine (N), glutamine (Q), serine (S), threonine (T), and tyrosine (Y); amino acids having a basic side chain comprising arginine (R), lysine (K), and histidine (H); amino acids having a large hydrophobic side chain comprising isoleucine (I), leucine (L), methionine (M), valine (V), phenylalanine (F), tyrosine (Y), and tryptophan (W)); and amino acids having an aromatic side chain comprising phenylalanine (F), histidine (H), tryptophan (W), and tyrosine (Y).

"PEG," "polyethylene glycol" and "poly(ethylene glycol)" refer to any nonpeptidic water-soluble poly(ethylene oxide). PEGs can comprise a structure —(OCH$_2$CH$_2$)$_n$— where n is, for example, an integer from 1 to 4,000. A PEG can also include moieties such as —CH$_2$CH$_2$—O(CH$_2$CH$_2$O)$_n$—CH$_2$CH$_2$— and/or —(OCH$_2$CH$_2$)$_n$O— moieties, depending upon whether or not the terminal oxygens have been displaced, e.g., during a synthetic transformation. A PEG can be capped with a suitable end group. At least 50% of the repeating subunits of a PEG can have the structure —CH$_2$CH$_2$—. A PEG can have any suitable molecular weight, structure, and/or geometry such as branched, linear, forked, or multifunctional.

Molecular weight in the context of a polymer refers to the number average molecular weight as determined by gel permeation chromatography using a polystyrene standard. A polymer can have a polydispersity index (i.e., number average molecular weight and weight average molecular weight of the polymers are not equal), for example, less than 1.2, less than 1.15, less than 1.10, less than 1.05, or less than 1.03.

A linker refers to a moiety that binds at least one IL-2R ligand such as an IL-2Rα ligand, an IL-2Rβ ligand, and/or an IL-2Rγc ligand. A linker can bind to another IL-2R ligand which can be the same IL-2R ligand or a different IL-2R ligand. A linker can also bind to one or more additional moieties that provide a desired physiological function. A linker can be divalent or multivalent. A linker can be hydrolytically stable or may include a physiologically hydrolyzable or enzymatically degradable linkage. A linker can bind IL-2R ligands to form dimers, trimers, or higher order multi-ligand peptides (heteromers) and compounds.

A "physiologically cleavable" or "hydrolyzable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Suitable hydrolytically unstable or weak linkages include but are not limited to carboxylate ester, phosphate ester, anhydrides, acetals, ketals, acyloxyalkyl ether, imines, orthoesters, peptides and oligonucleotides.

An "enzymatically degradable linkage" means a linkage that can be degraded or cleaved by one or more enzymes.

A "hydrolytically stable" linkage or bond refers to a chemical bond, such as a covalent bond, that is substantially stable in water such that the chemical bond does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethanes, and the like. Generally, a hydrolytically stable linkage is one that exhibits a rate of hydrolysis of less than about 1% to 2% per day under physiological conditions.

An "IL-2Rα ligand" refers to a peptide capable of binding to the IL-2Rα subunit of a mammalian IL-2 receptor with an affinity ($IC_{50}$) less than 100 μM.

An "IL-2Rβ ligand" refers to a peptide capable of binding to the IL-2Rβ subunit of a mammalian IL-2 receptor with an affinity ($IC_{50}$) less than 100 μM.

An "IL-2Rγc ligand" refers to a peptide capable of binding to the IL-2Rγc subunit of a mammalian IL-2 receptor with an affinity ($IC_{50}$) less than 100 μM.

A "human IL-2Rα ligand" comprises refers to a peptide capable of binding to the IL-2Rα subunit of the human IL-2 receptor with an affinity ($IC_{50}$) less than 100 μM.

A "human IL-2Rβ ligand" refers to a peptide capable of binding to the IL-2Rβ subunit of the human IL-2 receptor with an affinity ($IC_{50}$) less than 100 μM.

A "human IL-2Rγc ligand" refers to a peptide capable of binding to the IL-2Rγc subunit of a mammalian IL-2 receptor with an affinity ($IC_{50}$) less than 100 μM.

A "human IL-2Rα ligand" comprises refers to a peptide capable of binding to the IL-2Rα subunit of the human IL-2 receptor with an affinity ($IC_{50}$) less than 100 μM.

The "IL-2Rβ subunit" refers to the human (*Homo sapiens*) interleukin-2 receptor subunit β precursor NCBI Reference Sequence NP_000689.1.

The "IL-2Rγc subunit" refers to the human (*Homo sapiens*) interleukin-2 receptor subunit γ precursor NCBI Reference Sequence NP_000197.1.

An "IL-2R ligand fusion protein" refers to a protein made by recombinant DNA technology in which the translational reading frame of a ligand of a mammalian IL-2 receptor is fused to that of another protein, i. e., IL-2 receptor fusion partner, to produce a single recombinant polypeptide. An IL-2R ligand fusion protein can comprise an IL-2Rβ ligand, an IL-2Rγc ligand, or both an IL-2Rβ ligand and an IL-2Rγc ligand. An IL-2R ligand fusion protein can be produced as a disulfide-linked dimer, joined together by disulfide bonds located in the hinge region. An IL-2R ligand fusion protein can include a peptide linker such as an amino acid sequence located between two proteins comprising a fusion protein, such that the linker peptide sequence is not derived from either partner protein. Peptide linkers can be incorporated into fusion proteins as spacers to promote proper protein folding and stability of the component protein moieties, to improve protein expression, and/or to enable better bioactivity of the two fusion partners. Peptide linkers can be divided into the categories of unstructured flexible peptides or rigid structured peptides.

Bioisosteres are atoms or molecules that fit the broadest definition for isosteres. The concept of bioisosterism is based on the concept that single atom, groups, moieties, or whole molecules, which have chemical and physical similarities produce similar biological effects. A bioisostere of a parent compound can still be recognized and accepted by its appropriate target, but its functions will be altered as compared to the parent molecule. Parameters affected with bioisosteric replacements include, for example, size, conformation, inductive and mesomeric effects, polarizability, capacity for electrostatic interactions, charge distribution, H-bond formation capacity, pKa (acidity), solubility, hydrophobicity, lipophilicity, hydrophilicity, polarity, potency, selectivity, reactivity, or chemical and metabolic stability, ADME (absorption, distribution, metabolism, and excretion). Although common in pharmaceuticals, carboxyl groups or carboxylic acid functional groups ($-CO_2H$) in a parent molecule may be replaced with a suitable surrogate or (bio)isostere to overcome chemical or biological shortcomings while retaining the desired attributes of the parent molecule bearing one or more carboxyl groups or carboxylic acid functional groups ($-CO_2H$).

"Isostere" or "isostere replacement" refers to any amino acid or other analog moiety having physiochemical and/or structural properties similar to a specified amino acid. An "isostere" or "suitable isostere" of an amino acid is another amino acid of the same class, wherein amino acids belong to the following classes based on the propensity of the side chain to be in contact with polar solvent like water: hydrophobic (low propensity to be in contact with water), polar or charged (energetically favorable contact with water). Examples of charged amino acid residues include lysine (+), arginine (+), aspartate (−) and glutamate (−). Examples of polar amino acids include serine, threonine, asparagine, glutamine, histidine and tyrosine. Illustrative hydrophobic amino acids include alanine, valine, leucine, isoleucine, proline, phenylalanine, tryptophan, cysteine and methionine. The amino acid glycine does not have a side chain and is difficult to assign to one of the above classes. However, glycine is often found at the surface of proteins, often within loops, providing high flexibility to these regions, and an isostere may have a similar feature. Proline has the opposite effect, providing rigidity to the protein structure by imposing certain torsion angles on the segment of the polypeptide chain. An isostere can be a derivative of an amino acid, e.g., a derivative having one or more modified side chains as compared to the reference amino acid.

"Cyclized" refers to a reaction in which one part of a peptide or polypeptide molecule becomes linked to another part of the peptide or polypeptide molecule to form a closed ring, such as by forming a disulfide bridge or other similar bond, e.g., a lactam bond. In particular embodiments, peptide monomer compounds or monomer subunits of peptide dimer compounds described herein are cyclized via an intramolecular bond between two amino acid residues present in the peptide monomer or monomer subunit.

"Patient" refers to a mammal, for example, a human.

"Peptide" refers to a polymer in which the monomers are α-amino acids joined together through amide bonds. A peptide can comprise, for example, less than 100 amino acids, less than 50 amino acids, less than 40 amino acids, less than 30 amino acids, or less than 20 amino acids. A peptide can comprise naturally-occurring α-amino acids, non-naturally occurring amino acids, or a combination thereof.

In addition to peptides consisting only of naturally-occurring amino acids, peptidomimetics or peptide analogs are also provided. Peptide mimetics that are structurally similar to therapeutically useful peptides may be used to produce an equivalent or enhanced therapeutic or prophylactic effect. Generally, peptidomimetics are structurally similar to a paradigm peptide, for example, a peptide that has a biological or pharmacological activity, such as a naturally-occurring receptor-binding peptide, but have one or more peptide linkages optionally replaced by a linkage such as —$CH_2$—NH—, —$CH_2$—S—, —$CH_2$—$CH_2$—, —CH=CH— (cis and trans), —$COCH_2$—, —CH(OH)$CH_2$—, and —$CH_2$SO—, by methods known in the art.

Systematic substitution of one or more amino acids of a consensus sequence with a D-amino acid of the same type, such as D-lysine in place of L-lysine, may be used to generate more stable peptides. In addition, constrained peptides comprising a consensus sequence or a substantially identical consensus sequence variation may be generated by methods known in the art; for example, by adding internal cysteine residues capable of forming intramolecular disulfide bridges which cyclize the peptide.

Synthetic or non-naturally occurring amino acids refer to amino acids which do not naturally occur in vivo but which, nevertheless, can be incorporated into the peptide ligands provided by the present disclosure. Suitable examples of synthetic amino acids include the D-α-amino acids of naturally occurring L-α-amino acid as well as non-naturally occurring D- and L-α-amino acids represented by the formula $H_2NCHR^5COOH$ where $R^5$ is $C_{1-6}$ alkyl, $C_{3-8}$ cycloalkyl, $C_{3-8}$ heterocycloalkyl; an aromatic residue of from 6 to 10 carbon atoms optionally having from 1 to 3 substituents on the aromatic nucleus selected from the group consisting of hydroxyl, lower alkoxy, amino, and carboxyl; -alkylene-Y where alkylene is an alkylene group of from 1 to 7 carbon atoms and Y is selected from a hydroxyl, amino, cycloalkyl, and cycloalkenyl having from 3 to 7 carbon atoms; aryl of from 6 to 10 carbon atoms, such as from 1 to 3 substituents on the aromatic nucleus selected from the group consisting of hydroxyl, lower alkoxy, amino and carboxyl; heterocyclic of from 3 to 7 carbon atoms and 1 to 2 heteroatoms selected from the group consisting of oxygen, sulfur, and nitrogen; —C(O)$R^2$ where $R^2$ is selected from the group consisting of hydrogen, hydroxy, lower alkyl, lower alkoxy, and —$NR^3R^4$ where $R^3$ and $R^4$ are independently selected from the group consisting of hydrogen and lower alkyl; —S(O)$_n R^6$ where n is 1 or 2 and $R^2$ is $C_{1-4}$ alkyl and with the proviso that $R^5$ does not define a side chain of a naturally occurring amino acid.

Examples of other synthetic amino acids include amino acids wherein the amino group is separated from the carboxyl group by more than one carbon atom such as b-alanine, g-aminobutyric acid, and the like.

Examples of suitable synthetic amino acids include the D-amino acids of naturally occurring L-amino acids, L-1-naphthyl-alanine, L-2-naphthylalanine, L-cyclohexylalanine, L-2-amino isobutyric acid, the sulfoxide and sulfone derivatives of methionine, i.e., HOOC—($H_2$NCH)$CH_2CH_2$—S(O)$_n R^6$, where n and R are as defined above as well as the lower alkoxy derivative of methionine, i.e., HOOC—($H_2$NCH)$CH_2CH_2OR^6$ where $R^6$ is as defined above.

"Polypeptide" refers to a polymer in which the monomers are α-amino acids joined together through amide bonds and comprising greater than 100 amino acids.

"N-terminus" refers to the end of a peptide or polypeptide, such as an N-terminus of an IL-2Rβ ligand or an IL-2Rγc ligand, that bears an amino group in contrast to the carboxyl end bearing a carboxyl acid group.

"C-terminus" refers to the end of a peptide or polypeptide, such as a C-terminus of an IL-2Rβ ligand or an IL-2Rγc ligand, that bears a carboxylic acid group in contrast to the amino terminus bearing an amino group.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids and one or more protonable functional groups such as primary, secondary, or tertiary amines within the parent compound. Examples of inorganic acids include hydrochloric acid, hydrobromic acid, sulfuric acid, nitric acid, phosphoric acid, and the like. In certain embodiments the salts are formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. In certain embodiments, a salt is formed when one or more acidic protons present in the parent compound are replaced by a metal ion, e.g., an alkali metal ion, an alkaline earth ion, or an aluminum ion, or combinations thereof; or coordinates with an organic base such as ethanolamine, diethanolamine, triethanolamine, N-methylglucamine, and the like. In certain embodiments, a pharmaceutically acceptable salt is the hydrochloride salt. In certain embodiments, a pharmaceutically acceptable salt is the sodium salt. In certain embodiments where a compound has two or more ionizable groups, a pharmaceutically acceptable salt comprises one or more counterions, such as a bi-salt, for example, a dihydrochloride salt.

The term "pharmaceutically acceptable salt" includes hydrates and other solvates, as well as salts in crystalline or non-crystalline form. Where a particular pharmaceutically acceptable salt is disclosed, it is understood that the particular salt (e.g., a hydrochloride salt) is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art. See also: Stahl and Wermuth, C. G. (Editors), Handbook of Pharmaceutical Salts, Wiley-VCH, Weinheim, Germany, 2008.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Solvate" refers to a molecular complex of a compound with one or more solvent molecules in a stoichiometric or non-stoichiometric amount. Such solvent molecules are those commonly used in the pharmaceutical arts, which are known to be innocuous to a patient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water.

"Pharmaceutical composition" refers to an IL-2R binding compound provided by the present disclosure or a pharmaceutically acceptable salt thereof and at least one pharmaceutically acceptable vehicle with which the compound or a pharmaceutically acceptable salt thereof is administered to a patient. Pharmaceutically acceptable vehicles are known in the art.

"Disease" refers to a disease, disorder, condition, or symptom of any of the foregoing.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by taking the compound in a preventative fashion. The application of a therapeutic for preventing or prevention of a disease of disorder is known as 'prophylaxis.'

"Prodrug" refers to a derivative of a therapeutic compound that requires a transformation within the body to release the active therapeutic compound. Prodrugs are frequently, although not necessarily, pharmacologically inactive until converted to the parent drug.

"Promoiety" refers to a group bonded to a therapeutic compound, typically to a functional group of the therapeutic compound, via bond(s) that are cleavable under specified conditions of use. The bond(s) between the drug and promoiety may be cleaved by enzymatic or non-enzymatic means. Under the conditions of use, for example following administration to a patient, the bond(s) between the therapeutic compound and the promoiety may be cleaved to release the parent therapeutic compound. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation of a patient to which the prodrug is administered or the acidic conditions of the stomach or the agent may be supplied exogenously.

"Substantially" means, for example, greater than 90%, greater than 95%, greater than 98%, or greater than 99%.

"Therapeutically effective amount" refers to the amount of a compound that, when administered to a subject for treating a disease, or at least one of the clinical symptoms of a disease, is sufficient to treat the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Treating" or "treatment" of a disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter or manifestation that may or may not be discernible to the patient. In certain embodiments, "treating" or "treatment" refers to delaying the onset of the disease or at least one or more symptoms thereof in a patient who may be exposed to or predisposed to a disease or disorder even though that patient does not yet experience or display symptoms of the disease.

"Tregs" or "Treg cells" refer to regulatory T cells. Regulatory T cells are a class of T cells that suppress the activity of other immune cells and are defined using flow cytometry by the cell marker phenotypes CD4+/CD25+/FOXP3+, CD4+CD25+CD127lo, or CD4+/CD25+/FOXP3+/CD127lo. Because FOXP3 is an intracellular protein and requires cell fixation and permeablization for staining, the cell surface phenotype CD4+CD25+CD127lo− can be used for defining live Tregs. Tregs also include various Treg subclasses, such as tTregs (thymus-derived) and pTregs (peripherally-derived, differentiated from naive T cells in the periphery). All Tregs express the IL-2Rαβγ receptor, do not produce IL-2 and are dependent on IL-2 for growth. A person skilled in the art will recognize that Tregs will be more potently activated by an IL-2Rαβγc-biased agonist.

"CD4+T cells" are a type of lymphocyte that functions to coordinate the immune response by stimulating other immune cells such as macrophages, B lymphocytes (B cells), CD8 lymphocytes (CD8 cells) to fight infection. CD4+T cells recognize peptides presented on MHC Class II molecules, which are found on antigen presenting cells.

"CD8+ (cytotoxic) T cells" are generated in the thymus and express the T-cell receptor. Cytotoxic T cells express a dimeric co-receptor, CD8, which typically comprises one CD8a and one CD80 chain. CD8+T cells recognize peptides presented by MHC Class 1 molecules found on all nucleated cells. The CD8 heterodimer binds to a conservative portion of MHC Class 1 during T cell/antigen presenting cell interactions. CD8+T-cells (cytotoxic T lymphocytes, or CTLs) are important for immune defense against intracellular pathogens including viruses and bacteria, and for tumor surveillance.

"NK (natural killer) cells" are lymphocytes in the same family as T and B cells and, as cells of the innate immune system, are classified as group I innate lymphocytes (ILCs). NK cells respond to a wide variety of pathological challenges including killing virally infected cells and detecting and controlling early signs of cancer.

"Functional activation of T cells" is defined as an IL-2-mediated response in T cells. Assays for functional activation of T cells include stimulation of pSTAT5, Treg cell proliferation or markers of proliferation (such as Ki67), change in immune cell type ratios, and stimulation of the levels of T-cell effector proteins.

Reference is now made in detail to certain embodiments of compounds, compositions, and methods. The disclosed embodiments are not intended to be limiting of the claims. To the contrary, the claims are intended to cover all alternatives, modifications, and equivalents.

Interleukin-2 (IL-2) plays a crucial role in regulating immune responses and maintaining peripheral self-tolerance by having both immuno-stimulatory and immuno-regulatory functions. IL-2 acts primarily as a T cell growth factor, essential for the proliferation and survival of T cells as well as for the generation of effector and memory T cells. IL-2 is a four α-helical bundle cytokine that belongs to a family of structurally related cytokines that includes IL-4, IL-7, IL-9, IL-15, and IL-21. IL-2 is produced by activated CD4+ T cells in response to antigen stimulation and can also be produced by CD8+ T cells and innate immune cells such as activated dendritic cells (DCs) and natural killer (NK) cells.

IL-2 binds to various forms of the IL-2 receptor (IL-2R), notably the monomeric, dimeric, and trimeric forms. Monomeric IL-2R consists of the membrane-associated IL-2Rα (CD25) chain, which also exists in a soluble form; however, it is not capable of inducing signaling events. The trimeric IL-2R consists of IL-2Rα, IL2Rβ (CD122), and IL-2Rγc, also known as the common γ-chain (γc) or CD132 and is shared by all members of the IL-2 cytokine family. Dimeric IL-2R comprises the IL-2Rγc and IL-2Rβ subunits. In contrast to monomeric IL-2R, both the dimeric and trimeric IL-2 receptors lead to a downstream signaling cascade upon IL-2 binding IL-2 binds with high affinity to the trimeric IL-2R but with low-moderate affinity to the dimeric IL-2R, varying the sensitivity of the cell to IL-2 Additionally. IL-2 can bind to IL-2Rα expressed on the surface of activated dendritic cells for trans presentation to neighboring cells including antigen-specific naïve T cells and NK cells that express both IL-2Rβ and IL-2Rγc subunits. This trans presentation of IL-2 has been shown to facilitate initial high affinity IL-2 signaling, required early in the immune response to prime naïve T-cells to produce IL-2.

IL-2 is first captured by IL2Rα, bringing about a conformational change to IL-2, increasing its affinity for IL-2Rβ. Association of IL-2 with the IL-2Rβγc induces the dimerization of the signaling motifs in the cytoplasmic tails of IL-2R p and IL-2Rγc leading to the phosphorylation/activation of the Janus kinases, JAK1 and JAK3, which in turn exert kinase activity on key tyrosine residues in the tail of the IL-2Rβ subunit.

Downstream signaling occurs via three major pathways, the JAK-STAT pathway, the phosphoinositide 3-kinase (PI3K)-AKT pathway, and the mitogen-activated protein kinase (MAPK) pathway. These pathways ultimately result in the transcription of target genes that contribute to IL-2-dependent biological actions, through the recruitment of the adaptor protein She and the transcription factor STAT5. Target genes of IL-2 signaling include cyclin D2, bcl-2, fasL, cd25 (encoding IL-2Rα), socs1-2, and the IL-2 silencing gene prdm1, which encodes for the transcription factor, BLIMP1. The production of the negative regulator of IL-2 BLIMP1 is essential for maintaining the balance between effector T cells and Treg cells, which is crucial for immune homeostasis.

IL-2 plays a dual role in T cell activation by stimulating the proliferation and differentiation of T cells as well as by maintaining and expanding the population of immuno-suppressive Treg cells. The conventional naïve CD4+ and CD8+ T cells express the dimeric IL-2R, and therefore require a high concentration of IL-2 to induce their initial proliferation. Once activated, these T cells express the high-affinity trimeric IL-2R, driving the differentiation of the T cells into either effector (Teff) or memory cells. This differentiation depends on the strength and duration of the IL-2 signal.

During the primary expansion of CD8+ T cells in the presence of low-moderate levels of IL-2, a subset of CD8+ T cells will differentiate into memory T cells. The cells do this by downregulating CD25 and upregulating CD127 (IL-7R) and CD62 (L-selectin), which are crucial receptors for secondary responses upon re-infection. During an acute infection, sustained high levels of IL-2 leads to a rapid up-regulation of CD25 and the differentiation of CD8+ cells into cytotoxic effector cells. The up-regulation induces an IL-2-driven expression of the death receptor fas and fasL, causing activation-induced cell death (AICD) upon pathogen clearance. For CD4+ T cells, the activation of STAT5 signaling by IL-2 influences their differentiation into multiple helper T cell populations, including Th1, Th2, and Th17 by regulating the expression of the appropriate receptors for each response.

Homeostatic or background levels of IL-2 are essential for the survival and function of Treg cells by maintaining the expression of FOXP3 and CD25. Treg cells naturally occur in the thymus and upon contact with self-peptides become activated. Additionally, Treg cells can be generated by stimulation of conventional CD4+ T cells upon interaction with antigens in peripheral lymphoid organs. Because Treg cells do not produce IL-2, they are dependent on IL-2-producing cells such as conventional T cells. Additionally, due to their high expression of IL-2Rα (CD25), Tregs are able to consume and limit the systemic concentration of IL-2, ensuring the regulation of the immune balance. In the absence of IL-2, the number of Treg cells decreases and the number of effector T cells increases, leading to an enhanced susceptibility to autoimmune and inflammatory disorders. Therefore, the unique activation of Treg cells at low levels of IL-2, which does not activate CD4+ or CD8+ T cells, has allowed for the development of IL-2 as a promising therapeutic in autoimmune and inflammatory diseases.

The production of IL-2 from both arms of the immune system highlights the importance of this cytokine in the early stages of infection, as well as in the secondary adaptive response. Furthermore, the dual functions of IL-2 in both protective immunity and immune tolerance allows IL-2 to be a potential therapeutic in seemingly contrasting therapies, as both an immune stimulant and an immune suppressor, for cancer and autoimmune disease, respectively.

The present disclosure in directed to IL-2Rβ ligands, IL-2Rγc ligands, and compounds comprising IL-2Rβ ligands and/or IL-2Rγc ligands. Compounds comprising IL-2Rβ ligands and IL-2Rγc ligands can be IL-2R agonists including selective IL-2R agonists.

IL-2Rβ ligands and IL-2Rγc ligands provided by the present disclosure comprise peptide domains amenable to strategies to simultaneously mask peripheral bioactivity, target delivery to a tumor, selectively activate cytotoxic anti-tumor cells, and direct IL-2 receptor activation at tumor sites. IL-2Rβ ligands and IL-2Rγc ligands and compounds comprising IL-2Rβ ligands and/or IL-2Rγc ligands provided by the present disclosure can also be used to treat autoimmune diseases.

IL-2Rα ligands and compounds comprising IL-2Rα ligands are disclosed in U.S. Provisional Application No. 62/856,305 filed on Jun. 3, 2019, which is incorporated by reference in its entirety.

The IL-2R agonists and compounds comprising IL-2Rβ ligands and/or IL-2Rγc ligands can be designed to selectively activate a specific form of the IL-2 receptor. The small peptide IL-2R ligands, having an amino acid sequence that is unrelated to that of the natural cytokine, and can selectively bind to and activate the IL-2Rβ and/or IL-2Rγc subunits to produce therapeutic IL-2 activity, while avoiding the effects that have limited clinical success of IL-2-based compounds in cancer therapy. Because the IL-2R peptide ligands are small, i.e. from 5 to 30 amino acids, with very low immunogenic potential, the small peptide IL-2R ligands can be incorporated into compounds to enhance therapeutic efficacy. For example, this allows the affinity of the IL-2R peptide ligands for each of the three IL-2R subunits to be tuned to direct the responsiveness of a particular immune cell population and thereby affords flexibility to chemically target tumor sites.

Peptide ligands for the IL-2Rβ and IL-2Rγc subunits can be identified from highly complex peptide diversity libraries such as phage display libraries, optimized by peptide synthesis, and can be assembled into monomers, homooligomers, heterodimers, or into other compounds and can be designed to bring the IL-2R and IL-2Rγc binding subunits into a competent signaling conformation.

Small agonists of IL-2R provided by the present disclosure can activate cells that do not express the IL-2Rα subunit with a similar potency as cells that do express the IL-2Rα subunit thereby avoiding preferential activation of cells expressing the IL-2Rα such as Tregs. These IL-2R agonists are referred to as selective IL-2Rβγc agonists. Because the selective IL-2R agonists provided by the present disclosure can be chemically-synthesized, the IL-2R agonists can be modified using natural and/or non-natural amino acids to independently tailor binding affinity to each receptor subunit to optimize potency and efficacy, and to improve metabolic stability. The small agonists also allow such modifications to be made with a low likelihood of inducing immunogenicity. Also, due to their chemical malleability, peptides can be "caged" to construct a reversibly inactive prodrug using tumor-specific environmental triggers such as proteases, or complexes sensitive to low pH. For example, the pH-dependent binding properties of peptides can be optimized by use of non-natural amino acids having side-chain ionizable groups with pKa's in the range of pH 5.0 to pH 8.0. As with proteins, pharmacokinetic-enhancing moieties, such as PEG, can be appended to peptides, either as part of, or independent of, the "caging" strategy. Finally, sites on a peptide can be reserved for attaching a variety of tumor targeting moieties, such as tumor-specific antibodies. These features of IL-2Rβγc agonists can be exploited in the design of optimal therapeutic candidates based on the IL-2Rβγc agonists provided by the present disclosure.

Certain compounds provided by the present disclosure comprise ligands that selectively activate a specific form of the IL-2 receptor. These agonists can stimulate cytotoxic tumor-targeted cell populations without inducing immunosuppressive activity of Tregs at tumor sites. The cellular selectivity of the agonists can enhance the efficacy of IL-2 for anti-tumor therapy.

Peptides having a binding affinity to the IL-2Rβγc subunits can be identified by random peptide diversity generating systems in conjunction with an affinity enrichment process, for example, using peptides on plasmids or peptides on phage systems. Synthetic peptide library technologies such as DNA-encoded peptide libraries can also be used.

Using such systems, random peptides are generally designed to have a defined number of amino acid residues in length, such as from 6 to 20 amino acids. To generate a collection of oligonucleotides encoding the random peptides, the codon motif $(NNK)_x$, where N is nucleotide A, C, G, or T (equimolar; depending on the methodology employed, other nucleotides can be employed), K is G or T (equimolar), and x is an integer corresponding to the number of amino acids in the peptide, such as from 6 to 20, can be used to specify any one of the 32 possible codons resulting from the NNX motif: 1 for each of 12 amino acids, 2 for each of 5 amino acids, 3 for each of 3 amino acids, and only one of the three stop codons. Thus, the NNK motif encodes all of the amino acids, encodes only one stop codon, and reduces codon bias.

In the systems employed, the random peptides can be presented either on the surface of a phage particle, as part of a fusion protein comprising either the pIII or the pVIII coat protein of a phage fd derivative (peptides on phage) or as a fusion protein with the LacI peptide fusion protein bound to a plasmid (peptides on plasmids). The phage or plasmids, including the DNA encoding the peptides, can be identified and isolated by an affinity enrichment process using immobilized IL-2Rβ and/or IL-2Rγc subunits. The affinity enrichment process, sometimes referred to as "panning," involves multiple rounds of incubating the phage or plasmids with the immobilized receptor, collecting the phage or plasmids that bind to the receptor (along with the accompanying DNA), and producing more of the phage or plasmids (along with the accompanying LacI-peptide fusion protein) collected. The extracellular domain (ECD) of the IL-2Rβ and/or IL-2Rγc subunits can be used during panning. An engineered form of the IL-2Rβ and IL-2Rγc can be expressed in host cells, such as CHO cells. Following receptor harvesting, the receptor can be tested for binding to IL-2Rβ or IL-2Rγc specific phage clones. Peptides can also be identified by panning IL-2R subunits fused to an Fc domain. The IL-2 receptor, as well as its extracellular domain, can be produced in recombinant host cells.

After several rounds of affinity enrichment, the phage or plasmids and accompanying peptides can be examined by ELISA to determine if the peptides bind specifically to the IL-2Rβ and/or IL-2Rγc subunits. The assay can be performed using methods similar to those described for the affinity enrichment process, except that after removing unbound phage, the wells can be treated with an antibody such as a rabbit anti-phage antibody, then with alkaline phosphatase (AP)-conjugated goat anti-rabbit antibody. The amount of alkaline phosphatase in each well can be determined by standard methods.

By comparing test wells with control wells without the IL-2 receptor, one can determine whether the fusion proteins bind to the receptor specifically. The phage pools found to bind to the IL-2R and/or IL-2Rγc subunits can be screened in a colony lift probing format using radiolabeled monovalent receptor. This probe can be produced using protein kinase A to phosphorylate a peptide sequence fused to the C-terminus of the soluble receptor. The receptor can then be labeled to high specific activity with $^{33}P$ for use as a monovalent probe to identify high affinity ligands using colony lifts.

Peptides found to bind specifically to the IL-2Rβ subunits or IL-2Rγc subunits can then synthesized as the free peptide (e.g., no phage) and tested in a blocking assay. The blocking assay can be carried out in similar manner to the ELISA, except that IL-2Rβ or IL-2Rγc binding peptides or a reference peptide can be added to the wells before a tracer compound for which receptor binding can be detected. Examples of tracer compounds include a specific phage clone bearing a receptor-binding peptide, a radiolabeled or biotinylated peptide known to bind to the receptor, or a labeled variant of IL-2. Peptides that blocked tracer binding to IL-2Rβ or IL-2Rγc are preferred compounds of the invention.

When using random peptide generation systems that allow for multivalent ligand-receptor interaction, the density of the immobilized receptor can be an important factor in determining the affinity of the ligands that can bind to the immobilized receptor. At higher receptor densities, such as, when each anti-receptor antibody-coated well is treated with 0.25 mg to 0.5 mg of receptor, multivalent binding is more likely to occur than at lower receptor densities (e.g., each anti-receptor antibody-coated well treated with 0.5 to 1 ng of the receptor). If multivalent binding is occurring, then one will be more likely to isolate ligands with relatively lower affinity, unless one uses high densities of immobilized receptor to identify lead compounds and uses lower receptor densities to isolate higher affinity derivative compounds.

Screening methods that can be used to identify peptides that bind IL-2R can involve first identifying lead peptides which bind to the extracellular domain of the receptor and then synthesizing other peptides which resemble the lead peptides. For example, using peptides on phage system, a random library can be screened to discover a phage that presents a peptide that binds to the IL-2Rβ and/or IL-2Rγc subunits. The phage DNAs can be sequenced to determine the sequences of the peptides displayed on the surface of the phages.

For example, clones capable of specific binding to IL-2R can be identified from a random linear library. The sequences of these peptides can serve as the basis for the construction of other peptide libraries designed to contain a high frequency of derivatives of the initially identified peptides. These libraries can be synthesized so as to favor the production of peptides that differ from the binding peptide in only a few residues. This approach involves the synthesis of an oligonucleotide with the binding peptide coding sequence, except that rather than using pure preparations of each of the four nucleoside triphosphates in the synthesis, mixtures of the four nucleoside triphosphates (i.e., 55% of the "correct" nucleotide, and 15% each of the other three nucleotides is one preferred mixture for this purpose and 70% of the "correct" nucleotide and 10% of each of the other three nucleotides is another preferred mixture for this purpose) can be used so as to generate derivatives of the binding peptide coding sequence.

A variety of strategies can be used to derivatize the lead peptides by making "mutagenesis on a theme" libraries, based on a consensus sequence and mutagenized at 70:10:10:10 frequency with 5 NNK codons on each terminus (probing with radiolabeled monovalent receptor and with or without peptide elution).

The "peptides on plasmids" method can also be used for peptide screening and mutagenesis studies. According to this approach, random peptides can be fused at the C-terminus of LacI through expression from a plasmid vector carrying the fusion gene. Linkage of the LacI-peptide fusion to its encoding DNA occurs via the lacO sequences on the plasmid, forming a stable peptide-LacI-plasmid complex that can be screened by affinity purification (panning) on an immobilized receptor. The plasmids thus isolated can then be reintroduced into *E. coli* by electroporation to amplify the selected population for additional rounds of screening, or for the examination of individual clones.

In addition, random peptide screening and mutagenesis studies can be performed using a modified C-terminal Lac-I display system in which display valency can be reduced. The libraries can be screened, and the resulting DNA inserts can be cloned as a pool into a maltose binding protein (MBP) vector allowing their expression as a C-terminal fusion protein. Crude cell lysates from randomly picked individual MBP fusion clones can then assayed for IL-2R binding in an ELISA format.

A variety of methods can be used to evaluate $IC_{50}$ binding affinity values. For example, a competitive binding ELISA assay, an IL-2 tracer, an IL-2Rβ ligand tracer, or an IL-2Rγc ligand tracer, can be used to determine whether the peptides inhibit the binding of the tracer to the extracellular domain of the IL-2 receptor. The $IC_{50}$ value can be determined using the free peptide, which optionally can be C-terminally amidated, or can be prepared as an ester or other carboxy amide. To recreate the exact sequence displayed by a phage, the N-terminal and C-terminal amino acids of the synthetic peptides can be preceded by one or two glycine residues. These glycines are not believed to be necessary for binding or activity.

In general, peptides and peptidomimetics having an $IC_{50}$ of greater than about 100 μM lack sufficient binding affinity ($IC_{50}$) to be useful in imaging, targeting, diagnostic, and therapeutic applications. For imaging, targeting, and diagnostic purposes, the peptides and peptidomimetics can have an $IC_{50}$, for example, of about 1 μM or less and, for pharmaceutical purposes, the peptides and peptidomimetics can have an $IC_{50}$, for example, less than 100 μM, or less than 100 nM.

Robust and quantitative bioassays can be used to characterize the biological activity of a compound exhibiting IL-2Rβγc agonist activity. The assays can measure the activation of the IL-2 receptor, measure the downstream functional consequences of IL-2R activation and/or measure therapeutically-relevant outcomes and functions of the activated IL-2 receptor. The assays can be used to measure the therapeutic activity and potency of an IL-2R selective agonist and compounds comprising an IL-2Rβ and/or IL-2Rγc ligand and can also be used to measure the pharmacodynamics of an IL-2 selective agonist in animals or in humans.

Activation of the IL-2Rβγc subunits can be determined using a suitable assay. An example is an assay that can measure the phosphorylation of the signal transduction protein STAT5, measured flow cytometry with an antibody specific for the phosphorylated protein (pSTAT5). Phosphorylation of STAT5 is an essential step in the IL-2 signal transduction pathway. Therefore, measurement of phosphorylated STAT5 (pSTAT5) in cells will be recognized as reflective of IL-2 activation in these cells and will be predictive of other biological outcomes of IL-2 treatment given appropriate exposure time and conditions.

Another assay for assessing functional activation is to use an assay that measures IL-2-stimulated proliferation of cells. Cell proliferation can be determined, for example, by measuring the incorporation of tritiated thymidine into a purified T-cell population, by measuring an increase in cell numbers of a particular T-cell type in a mixed population of cells using flow cytometry, or by measuring the cell divisionassociated dilution of a vital fluorescent dye such as carboxyfluorescein succinimidyl ester (CFSE) by flow cytometry.

An IL-2Rβ ligand provided by the present disclosure can exhibit a binding affinity (IC$_{50}$) to the human IL-2Rβ subunit of less than 100 M, less than 10 μM, less than 1 μM, less than 0.1 μM, or less than 0.01 μM.

An IL-2Rβ ligand can exhibit a binding affinity (IC$_{50}$) to the human IL-2Rβ subunit from 1 μM to 100 M, from 10 μM to 10 M, from 100 μM to 1 μM, from 0.001 μM to 1 μM, or from 0.01 μM to 1 μM.

An IL-2Rβ ligand provided by the present disclosure can exhibit a binding affinity (IC$_{50}$) to a mammalian IL-2Rβ subunit of less than 100 M, less than 10 M, less than 1 M, less than 0.1 μM, or less than 0.01 μM.

An IL-2Rβ ligand can exhibit a binding affinity (IC$_{50}$) to a mammalian IL-2Rβ subunit from 1 μM to 100 M, from 10 μM to 10 μM, from 100 μM to 1 μM, from 0.001 μM to 1 μM, or from 0.01 μM to 1 μM.

An IL-2Rβ ligand provided by the present disclosure can exhibit a binding affinity (IC$_{50}$) to each of the human IL-2Rβ subunit and to the human IL-2Rγc subunit of less than 100 μM, less than 10 M, less than 1 μM, less than 0.1 μM, or less than 0.01 μM.

An IL-2Rβ ligand can exhibit a binding affinity (IC$_{50}$) to each of the human IL-2Rβ subunit and to the human IL-2Rγc subunit from 1 μM to 100 μM, from 10 μM to 10 μM, from 100 μM to 1 M, from, 0.001 μM to 1 M, or from 0.01 μM to 1 μM.

An IL-2Rβ ligand can exhibit a binding affinity (IC$_{50}$) to the human IL-2Rα (CD25) subunit of greater than 100 M, greater than 1 mM, greater than 10 mM, or greater than 100 mM.

An IL-2Rβ ligand can exhibit a binding affinity (IC$_{50}$) to the human IL-2Rβ subunit that is at least 10 times greater than the binding affinity (IC$_{50}$) of the IL-2Rβ ligand to the human IL-2Rα subunit, at least 50 times greater, at least 100 times greater, at least 500 times greater, or at least 1,000 times greater.

An IL-2Rβ ligand can comprise an amino acid sequence selected from SEQ ID NO: 1 to SEQ ID NO: 193, from SEQ ID NO: 578 to SEQ ID NO: 903, and SEQ ID NO: 1028 to SEQ ID NO: 1050, and from SEQ ID NOS 1052-1064 and 1084.

An IL-2Rβ ligand can comprise an amino acid sequence selected from SEQ ID NO: 1 to SEQ ID NO: 193 from SEQ ID NO: 578 to SEQ ID NO: 903, and SEQ ID NO: 1028 to SEQ ID NO: 1050, and from SEQ ID NOS 1052-1064 and 1084 can independently comprise one or more of the following conservative substitutions: amino acids having a small hydrophobic side chain comprising alanine (A), glycine (G), proline (P), serine (S) or threonine (T), or tyrosine (Y); amino acids having a hydroxyl-containing side chain comprising serine (S), threonine (T); amino acids having an acidic side chain comprising aspartate (D) or glutamate (E); amino acids having a polar neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

An IL-2Rβ ligand can have the amino acid sequence of Formula (1) (SEQ ID NO: 1), the amino acid sequence of Formula (1a) (SEQ ID NO: 2), or the amino acid sequence of Formula (1b) (SEQ ID NO: 3):

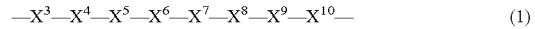

$$—X^3—X^4—X^5—X^6—X^7—X^8—X^9—X^{10}— \quad (1)$$

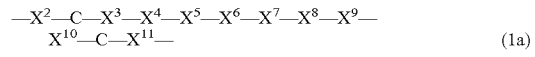

$$—X^2—C—X^3—X^4—X^5—X^6—X^7—X^8—X^9—X^{10}—C—X^{11}— \quad (1a)$$

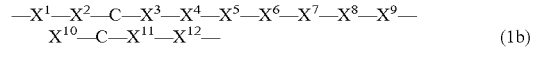

$$—X^1—X^2—C—X^3—X^4—X^5—X^6—X^7—X^8—X^9—X^{10}—C—X^{11}—X^{12}— \quad (1b)$$

wherein, $X^1$ is selected from A, D, E, F, G, I, K, L, M, N, P, Q, S, T, V, W, and Y; $X^2$ is selected from A, C, D, E, F, G, H, K, L, N, P, R, S, T, W, and Y; $X^3$ is selected from A, D, E, F, G, H, M, N, Q, R, S, T, W, and Y; $X^4$ is selected from A, D, E, F, G, I, K, L, M, N, Q, R, S, T, V, and Y; $X^5$ is selected from A, G, I, Q, S, T, V, and W; $X^6$ is selected from A, D, E, G, H, K, L, M, N, P, Q, R, S, T, and V; $X^7$ is selected from F, I, K, L, Q, and V; $X^8$ is selected from D, F, G, H, M, N, W, and Y; $X^9$ is selected from A, D, E, M, P, Q, S, T, V, and W; $X^{10}$ is selected from D, F, I, L, M, S, T, V, and Y; $X^{11}$ is selected from D, E, F, H, I, L, M, Q, S, T, V, W, and Y; and $X^{12}$ is selected from F, I, L, M, N, S, V, W, and Y.

In IL-2Rβ ligands of Formula (1)-(1b), $X^1$ can be selected from F, I, L, M, and V.

In IL-2Rβ ligands of Formula (1)-(1b), $X^2$ can be selected from D, E, F, G, H, L, N, P, R, S, T, W, and Y.

In IL-2Rβ ligands of Formula (1)-(1b), $X^5$ can be A.

In IL-2Rβ ligands of Formula (1)-(1b), $X^6$ can be selected from D, E, and Q.

In IL-2Rβ ligands of Formula (1)-(1b), $X^7$ can be selected from F, I, L, and V.

In IL-2Rβ ligands of Formula (1)-(1b), $X^8$ can be G.

In IL-2Rβ ligands of Formula (1)-(1b), $X^9$ can be selected from D, E, and Q.

In IL-2Rβ ligands of Formula (1)-(1b), $X^{10}$ can be selected from F, I, L, M, V, and Y.

In IL-2Rβ ligands of Formula (1)-(1b), $X^{11}$ can be selected from D and E.

In IL-2Rβ ligands of Formula (1)-(1b), $X^{12}$ can be selected from F, I, L, M, and V.

In IL-2Rβ ligands of Formula (1)-(1b), $X^1$ can be selected from F, I, L, M, and V; $X^2$ can be selected from D, E, F, G, H, L, N, P, R, S, T, W, and Y; $X^3$ can be selected from A, D, E, F, G, H, M, M, N, Q, R, S, T, W, and Y; $X^4$ can be selected from A, D, E, F, G, I, K, L, M, N, Q, R, S, T, V, and Y; $X^5$ can be A; $X^6$ can be selected from D, E, and Q; X can be selected from F, I, L, and V; $X^8$ can be G; $X^9$ can be selected from D, E, and Q; $X^{10}$ can be selected from F, I, L, M, V, and Y; $X^{11}$ can be selected from D and E; and $X^{12}$ can be selected from F, I, L, M, and V.

An IL-2Rβ ligand can comprise the amino acid sequence of Formula (1) (SEQ ID NO: 1052), the amino acid sequence of Formula (1a) (SEQ ID NO: 1053), or the amino acid sequence of Formula (1b) (SEQ ID NO: 1054):

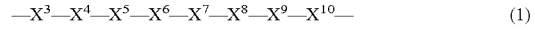

$$—X^3—X^4—X^5—X^6—X^7—X^8—X^9—X^{10}— \quad (1)$$

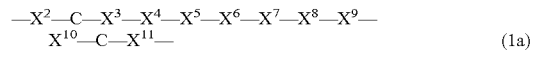

$$—X^2—C—X^3—X^4—X^5—X^6—X^7—X^8—X^9—X^{10}—C—X^{11}— \quad (1a)$$

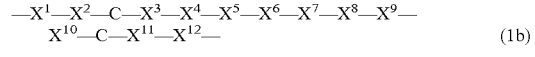

$$—X^1—X^2—C—X^3—X^4—X^5—X^6—X^7—X^8—X^9—X^{10}—C—X^{11}—X^{12}— \quad (1b)$$

wherein, $X^1$ can be selected from an amino acid $X^2$ can be selected from an amino acid; $X^3$ can be selected from an amino acid; $X^4$ can be selected from an amino acid; $X^5$ can be selected from an amino acid comprising a small hydrophobic side chain; $X^6$ can be selected from an amino acid; $X^7$ can be selected from an amino acid comprising a large hydrophobic side chain; $X^8$ can be selected from an amino acid comprising a small hydrophobic side chain; $X^9$ can be selected from an amino acid comprising a polar-neutral or an acidic side chain; $X^{10}$ can be selected from an amino acid comprising a large hydrophobic side chain; $X^{11}$ can be selected from an amino acid; and $X^{12}$ can be selected from an amino acid comprising a large hydrophobic side chain.

In IL-2Rβ ligands of Formula (1)-(1b), $X^1$ can be selected from an amino acid comprising a large hydrophobic side chain; $X^2$ can be selected from an amino acid; $X^3$ can be selected from an amino acid; $X^4$ can be selected from an amino acid; $X^5$ can be selected from an amino acid comprising a small hydrophobic side chain; $X^6$ can be selected from an amino acid comprising a polar-neutral or an acidic side chain; $X^7$ can be selected from an amino acid comprising a large hydrophobic side chain; $X^8$ can be selected from an amino acid comprising a small hydrophobic side chain; $X^9$ can be selected from an amino acid comprising a polar-neutral or an acidic side chain; $X^{10}$ can be selected from an amino acid comprising a large hydrophobic side chain; $X^{11}$ can be selected from an amino acid comprising a polar-neutral or an acidic side chain; and $X^{12}$ can be selected from an amino acid comprising a large hydrophobic side chain.

In IL-2Rβ ligands of Formula (1)-(1b), $X^1$ can be selected from I, L, M, V, F, W, and Y; $X^2$ can be selected from an amino acid; $X^3$ can be selected from an amino acid; $X^4$ can be selected from an amino acid; $X^5$ can be selected from A, G, P, S, and T; $X^6$ can be selected from H, N, Q, S, T, Y, D, and E; $X^7$ can be selected from I, L, M, V, F, W, and Y; $X^8$ can be selected from A, G, P, S, and T; $X^9$ can be selected from H, N, Q, S, T, Y, D, and E; $X^{10}$ can be selected from I, L, M, V, F, W, and Y; $X^{11}$ can be selected from H, N, Q, S, T, Y, D, and E; and $X^1$ can be selected from I, L, M, V, F, W, and Y.

In IL-2Rβ ligands of Formula (1)-(1b), $X^1$ can be selected from I, L, M, V, F, W, and Y; $X^2$ can be selected from an amino acid; $X^3$ can be selected from an amino acid; $X^4$ can be selected from an amino acid; X can be A; $X^6$ can be selected from H, N, Q, S, T, Y, D, and E; $X^7$ can be selected from I, L, M, V, F, W, and Y; $X^8$ can be G; $X^9$ can be selected from H, N, Q, S, T, Y, D, and E; $X^{10}$ can be selected from I, L, M, V, F, W, and Y; $X^{11}$ can be selected from H, N, Q, S, T, Y, D, and E; and $X^{12}$ can be selected from I, L, M, V, F, W, and Y.

In IL-2Rβ ligands of Formula (1)-(1b), $X^1$ can be selected from I, L, M, and V.

In IL-2Rβ ligands of Formula (1)-(1b), $X^2$ can be selected from D and E.

In IL-2Rβ ligands of Formula (1)-(1b), $X^6$ can be selected from Q, E, and D.

In IL-2Rβ ligands of Formula (1)-(1b), $X^7$ can be selected from V, L, and I.

In IL-2Rβ ligands of Formula (1)-(1b), $X^9$ can be selected from E, D, and Q.

In IL-2Rβ ligands of Formula (1)-(1b), $X^{10}$ can be selected from L, V, I, and Y.

In IL-2Rβ ligands of Formula (1)-(1b), $X^{11}$ can be selected from D and E.

In IL-2Rβ ligands of Formula (1)-(1b), $X^{12}$ can be selected from L, I, and F.

In IL-2Rβ ligands of Formula (1)-(1b), $X^1$ can be selected from L, I, F, and V; $X^2$ can be selected from D and E; $X^6$ can be selected from Q, E, and D; $X^7$ can be selected from V, L, and I; $X^8$ can be G; $X^9$ can be selected from E, D, and Q; $X^{10}$ can be selected from L, V, I, and Y; $X^{11}$ can be selected from D and E; and $X^{12}$ can be selected from L, I, and F.

In IL-2Rβ ligands of Formula (1)-(1b), $X^1$ can be selected from F, I, M, and Y; $X^2$ can be selected from E, D, and R; $X^3$ can be selected from and amino acid; $X^4$ can be selected from an amino acid; $X^5$ can be A; $X^6$ can be selected from A, P, and Q; $X^7$ can be selected from I and V; $X^8$ can be G; $X^9$ can be selected from E and Q; $X^{10}$ can be selected from I, L, and V; $X^{11}$ can be selected from E, D, and Q; and $X^{12}$ can be selected from I and L.

An IL-2Rβ ligand can comprise an amino acid sequence selected from any one of SEQ ID NO: 4 to SEQ ID NO: 163:

```
                              SEQ ID NO: 4
Q D C S S A S V G T I C Y L

SEQ ID NO: 5
Q E C G V W D L W P D C W I

SEQ ID NO: 6
A F C D E A R V G E L C V M

SEQ ID NO: 7
D D C S T A Q V G E L C V M

SEQ ID NO: 8
D T C A I A Q L Y D L C D L

SEQ ID NO: 9
D Y C R N S N V G D V C Y L

SEQ ID NO: 10
E D C R Y A E V G V L C Q M

SEQ ID NO: 11
F D C Q T A E L G D L C I V

SEQ ID NO: 12
F F C Y L I G Q D E F C E F

SEQ ID NO: 13
F P C Q I A M I G E Y C D W

SEQ ID NO: 14
F R C W E A P V G E I C E L

SEQ ID NO: 15
F S C D Q A T L G Q I C V I

SEQ ID NO: 16
G D C Y F S Q I G E L C M L

SEQ ID NO: 17
G P C Q Q A K L G E L C D L

SEQ ID NO: 18
I D C A Q A T V G Q Y C T L

SEQ ID NO: 19
I D C S D A A V G A L C T Q

SEQ ID NO: 20
I D C T R A S L G D I C V W

SEQ ID NO: 21
I E C E R A Q I G E V C Q I

SEQ ID NO: 22
I F C G D A Q L G E V C S L

SEQ ID NO: 23
I F C Q F A R L G Q T C Q L

SEQ ID NO: 24
I P C S I A Q L F S L C D V

SEQ ID NO: 25
I P C Y L A E L G Q V C S L
```

SEQ ID NO: 26
K N C E V A R L G D Y C E I

SEQ ID NO: 27
L A C S Q A P L G T L C E I

SEQ ID NO: 28
L D C G I A L Q G Q L C D Y

SEQ ID NO: 29
L D C S L S S L G D Y C Y M

SEQ ID NO: 30
L G C F E A Q I G M I C D L

SEQ ID NO: 31
L H C Y L A V L G Q L C D V

SEQ ID NO: 32
L L C Q V A S L G D Y C T I

SEQ ID NO: 33
L P C D M A D L F T L C D Y

SEQ ID NO: 34
L S C G I A Q I G Q V C D M

SEQ ID NO: 35
L W C Q D A Q I G D V C W L

SEQ ID NO: 36
M E C F L A A V G Q I C E L

SEQ ID NO: 37
M F C Q T A E V G Q M C L L

SEQ ID NO: 38
M L C W E A P V G D V C T I

SEQ ID NO: 39
N F C S G A G L G E L C V I

SEQ ID NO: 40
N L C E Y S K V G E V C V F

SEQ ID NO: 41
N Y C Y Q A L L D T Y C I L

SEQ ID NO: 42
P D C W Y A G L G Q I C E F

SEQ ID NO: 43
P S C W M A Q V G D L C F I

SEQ ID NO: 44
P T C D T A A V G D L C E F

SEQ ID NO: 45
Q D C F Q A P I G S L C Y L

SEQ ID NO: 46
Q W C Y M T D V G D L C E L

SEQ ID NO: 47
S D C H L A Q V G E F C F L

SEQ ID NO: 48
S D C Y L S Q V G S L C D F

SEQ ID NO: 49
S P C S E A S L F Q L C D L

SEQ ID NO: 50
S W C Q V G D F W D V C T S

SEQ ID NO: 51
T E C W L Q A L G E L C D F

SEQ ID NO: 52
V A C S S V Q V G E L C D F

SEQ ID NO: 53
V E C M M S S L G D L C S F

SEQ ID NO: 54
V N C W E A Q V G W L C D W

SEQ ID NO: 55
V T C D K A T V G Q M C S I

SEQ ID NO: 56
W S C D V A S V G S Y C M L

SEQ ID NO: 57
X D C S E A L L G Q I C T Y

SEQ ID NO: 58
Y D C R I A Q V G E L C D L

SEQ ID NO: 59
Y E C F Q A Q V G Q L C D V

SEQ ID NO: 60
V D C S R A V V G E L C V N

SEQ ID NO: 61
Q A C E V A K V G E L C D L

SEQ ID NO: 62
I R C E D A L L G D F C I F

SEQ ID NO: 63
L F C H Q A Q I G E L C S V

SEQ ID NO: 64
P D C S V A L L G E S C S V

SEQ ID NO: 65
T G C N L A Q I G D L C D L

SEQ ID NO: 66
I G C S L A R L G E Y C V I

SEQ ID NO: 67
L E C W Q A Q K G D L C D L

SEQ ID NO: 68
M D C S D A H V G Q I C S I

SEQ ID NO: 69
A L C Q A A Q V G Q L C D L

SEQ ID NO: 70
L W C G D A S L G Q L C W L

SEQ ID NO: 71
D H C S E A Q I G Q L D H L

SEQ ID NO: 72
L D C F Y A T L G Q V C S L

SEQ ID NO: 73
P D C S E A L L G Q I C T Y

SEQ ID NO: 74
T G C W Q A P V G S L C E L

SEQ ID NO: 75
S G C E Y A T L G S L C D L

SEQ ID NO: 76
S L C S L A P L G S L C D L

SEQ ID NO: 77
S L C S M V G L G Q L C D L

SEQ ID NO: 78
I P C S V A R V G W L C D L

SEQ ID NO: 79
D P C Y A A V L N S L C D I

DSCQNAPLGSYCVL  SEQ ID NO: 80

LPCSLAKLHELCDI  SEQ ID NO: 81

LSCSDAQLMQLCEI  SEQ ID NO: 82

CCYQAMVGDLCDFC  SEQ ID NO: 83

SSASVGTI  SEQ ID NO: 84

GVWDLWPD  SEQ ID NO: 85

DEARVGEL  SEQ ID NO: 86

STAQVGEL  SEQ ID NO: 87

AIAQLYDL  SEQ ID NO: 88

RNSNVGDV  SEQ ID NO: 89

RYAEVGVL  SEQ ID NO: 90

QTAELGDL  SEQ ID NO: 91

YLIGQDEF  SEQ ID NO: 92

QIAMIGEY  SEQ ID NO: 93

WEAPVGEI  SEQ ID NO: 94

DQATLGQI  SEQ ID NO: 95

YFSQIGEL  SEQ ID NO: 96

QQAKLGEL  SEQ ID NO: 97

AQATVGQY  SEQ ID NO: 98

SDAAVGAL  SEQ ID NO: 99

TRASLGDI  SEQ ID NO: 100

ERAQIGEV  SEQ ID NO: 101

GDAQLGEV  SEQ ID NO: 102

QFARLGQT  SEQ ID NO: 103

SIAQLFSL  SEQ ID NO: 104

YLAELGQV  SEQ ID NO: 105

EVARLGDY  SEQ ID NO: 106

SQAPLGTL  SEQ ID NO: 107

GIALQGQL  SEQ ID NO: 108

SLSSLGDY  SEQ ID NO: 109

FEAQIGMI  SEQ ID NO: 110

YLAVLGQL  SEQ ID NO: 111

QVASLGDY  SEQ ID NO: 112

DMADLFTL  SEQ ID NO: 113

GIAQIGQV  SEQ ID NO: 114

QDAQIGDV  SEQ ID NO: 115

FLAAVGQI  SEQ ID NO: 116

QTAEVGQM  SEQ ID NO: 117

WEAPVGDV  SEQ ID NO: 118

SGAGLGEL  SEQ ID NO: 119

EYSKVGEV  SEQ ID NO: 120

YQALLDTY  SEQ ID NO: 121

WYAGLGQI  SEQ ID NO: 122

WMAQVGDL  SEQ ID NO: 123

DTAAVGDL  SEQ ID NO: 124

FQAPIGSL  SEQ ID NO: 125

YMTDVGDL  SEQ ID NO: 126

HLAQVGEF  SEQ ID NO: 127

YLSQVGSL  SEQ ID NO: 128

SEASLFQL  SEQ ID NO: 129

QVGDFWDV  SEQ ID NO: 130

WLQALGEL  SEQ ID NO: 131

SSVQVGEL  SEQ ID NO: 132

MMSSLGDL  SEQ ID NO: 133

| | |
|---|---|
| WEAQVGWL | SEQ ID NO: 134 |
| DKATVGQM | SEQ ID NO: 135 |
| DVASVGSY | SEQ ID NO: 136 |
| SEALLGQI | SEQ ID NO: 137 |
| RIAQVGEL | SEQ ID NO: 138 |
| FQAQVGQL | SEQ ID NO: 139 |
| SRAVVGEL | SEQ ID NO: 140 |
| EVAKVGEL | SEQ ID NO: 141 |
| EDALLGDF | SEQ ID NO: 142 |
| HQAQIGEL | SEQ ID NO: 143 |
| SVALLGES | SEQ ID NO: 144 |
| NLAQIGDL | SEQ ID NO: 145 |
| SLARLGEY | SEQ ID NO: 146 |
| WQAQKGDL | SEQ ID NO: 147 |
| SDAHVGQI | SEQ ID NO: 148 |
| QAAQVGQL | SEQ ID NO: 149 |
| GDASLGQL | SEQ ID NO: 150 |
| SEAQIGQL | SEQ ID NO: 151 |
| FYATLGQV | SEQ ID NO: 152 |
| SEALLGQI | SEQ ID NO: 153 |
| WQAPVGSL | SEQ ID NO: 154 |
| EYATLGSL | SEQ ID NO: 155 |
| SLAPLGSL | SEQ ID NO: 156 |
| SMVGLGQL | SEQ ID NO: 157 |
| SVARVGWL | SEQ ID NO: 158 |
| YAAVLNSL | SEQ ID NO: 159 |
| QNAPLGSY | SEQ ID NO: 160 |
| SLAKLHEL | SEQ ID NO: 161 |
| SDAQLMQL | SEQ ID NO: 162 |
| YQAMVGDL | SEQ ID NO: 163 |

An IL-2Rβ ligand can comprise an amino acid sequence selected from any one of SEQ ID NO: 1 to SEQ ID NO: 163 and SEQ ID NOS 1052-1057, wherein the amino acid sequence can be terminated with amino acids -G-G- on the N-terminus, on the C-terminus, or on both the N- and C-termini.

An IL-2Rβ ligand can comprise an amino acid sequence selected from any one of SEQ ID NO: 1 to SEQ ID NO: 163 and SEQ ID NOS 1052-1057, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

IL-2Rβ ligands of SEQ ID NO: 1 to SEQ ID NO: 163 and SEQ ID NOS 1052-1057 exhibit an affinity to the IL-2Rβ subunit of less than 100 µM.

An IL-2Rβ ligand can comprise the amino acid sequence of Formula (2) (SEQ ID NO: 164), the amino acid sequence of Formula (2a) (SEQ ID NO: 165), or the amino acid sequence of Formula (2b) (SEQ ID NO: 166):

$$—X^{15}—X^{16}—X^{17}—X^{18}—X^{19}—X^{20}—X^{21}—X^{22}— \tag{2}$$

$$—X^{14}—C—X^{15}—X^{16}—X^{17}—X^{18}—X^{19}—X^{20}—X^{21}—X^{22}—C—X^{23}— \tag{2a}$$

$$—X^{13}—X^{14}—C—X^{15}—X^{16}—X^{17}—X^{18}—X^{19}—X^{20}—X^{21}—X^{22}—C—X^{23}—X^{24}— \tag{2b}$$

wherein, selected from V, W, and Y; $X^{20}$ can be W; $X^{21}$ can be P; $X^{22}$ can be selected from D and S; $X^{23}$ can be selected from L and Q; and $X^{24}$ can be selected from I, L, and V.

An IL-2Rβ ligand can comprise an amino acids sequence selected from any one of SEQ ID NO: 167 to SEQ ID NO: 182:

```
                                              SEQ ID NO: 167
E I C N V G Q V W P D C L L

SEQ ID NO: 168
G Q C L P G D F W P A C Y E

SEQ ID NO: 169
N M C L V G D Y W P S C Q I

SEQ ID NO: 170
Q I C D V G Q W W P D C Q V

SEQ ID NO: 171
V L C D Y M N S D Y Q C I T

SEQ ID NO: 172
A E C G V G A I W P S C L W

SEQ ID NO: 173
R L C D L F A I W P D C L F

SEQ ID NO: 174
D F C L V G D L W P S C W L

SEQ ID NO: 175
N V G Q V W P D

SEQ ID NO: 176
L P G D F W P A

SEQ ID NO: 177
L V G D Y W P S

SEQ ID NO: 178
D V G Q W W P D

SEQ ID NO: 179
D Y M N S D Y Q

SEQ ID NO: 180
G V G A I W P S

SEQ ID NO: 181
D L F A I W P D

SEQ ID NO: 182
L V G D L W P S
```

An IL-2Rβ ligand can comprise an amino acid sequence selected from any one of SEQ ID NO: 164 to SEQ ID NO: 182 and SEQ ID NOS 1058-1060, wherein the amino acid sequence can be terminated with amino acids -G-G- on the N-terminus, on the C-terminus, or on both the N- and C-termini.

An IL-2Rβ ligand can comprise an amino acid sequence selected from any one of SEQ ID NO: 164 to SEQ ID NO: 182 and SEQ ID NOS 1058-1060, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

IL-2Rβ ligands of SEQ ID NO: 164 to SEQ ID NO: 182 and SEQ ID NOS 1058-1060 exhibit an affinity to the IL-2Rβ subunit of less than 100 μM.

An IL-2Rβ ligand can comprise the amino acid sequence of Formula (2) (SEQ ID NO: 1058), the amino acid sequence of Formula (2a) (SEQ ID NO: 1059), or the amino acid sequence of Formula (2b) (SEQ ID NO: 1060):

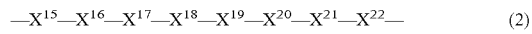

$$-X^{15}-X^{16}-X^{17}-X^{18}-X^{19}-X^{20}-X^{21}-X^{22}- \quad (2)$$

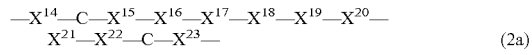

$$-X^{14}-C-X^{15}-X^{16}-X^{17}-X^{18}-X^{19}-X^{20}-X^{21}-X^{22}-C-X^{23}- \quad (2a)$$

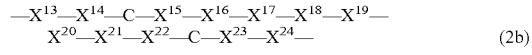

$$-X^{13}-X^{14}-C-X^{15}-X^{16}-X^{17}-X^{18}-X^{19}-X^{20}-X^{21}-X^{22}-C-X^{23}-X^{24}- \quad (2b)$$

wherein, $X^{13}$ can be selected from an amino acid; $X^{14}$ can be selected from an amino acid comprising a large hydrophobic side chain; $X^{15}$ can be selected from an amino acid; $X^{16}$ can be selected from an amino acid comprising a large hydrophobic side chain; $X^{17}$ can be selected from an amino acid comprising a small hydrophobic side chain; $X^{18}$ can be selected from an amino acid; $X^{19}$ can be selected from an amino acid; $X^{20}$ can be selected from an amino acid comprising a large hydrophobic side chain; $X^{21}$ can be selected from an amino acid comprising a small hydrophobic side chain; $X^{22}$ can be selected from an amino acid; $X^{23}$ can be selected from an amino acid; and $X^{24}$ can be selected from an amino acid comprising a large hydrophobic side chain.

In IL-2Rβ ligands of Formula (2)-(2b), $X^{13}$ can be selected from an amino acid; $X^{14}$ can be selected from an amino acid comprising a large hydrophobic side chain; $X^{15}$ can be selected from an amino acid; $X^{16}$ can be selected from an amino acid comprising a large hydrophobic side chain; $X^{17}$ can be selected from an amino acid comprising a small hydrophobic side chain; $X^{18}$ can be selected from an amino acid comprising a polar-neutral or an acidic side chain; $X^{19}$ can be selected from an amino acid comprising large hydrophobic or neutral side chain; $X^{20}$ can be selected from an amino acid comprising a large hydrophobic side chain; $X^{21}$ can be selected from an amino acid comprising a small hydrophobic side chain; $X^{22}$ can be selected from an amino acid; $X^{23}$ can be selected from an amino acid; and $X^{24}$ can be selected from an amino acid comprising a large hydrophobic side chain.

In IL-2Rβ ligands of Formula (2)-(2b), $X^{13}$ can be selected from an amino acid; $X^{14}$ can be selected from I, L, M, V, F, W, and Y; $X^{15}$ can be selected from D, E, I, L, M, V, F, Y, and W; $X^{16}$ can be selected from I, L, M, N, V, F, Y, and W; $X^{17}$ can be selected from A, G, P, S, and T; $X^{18}$ can be selected from H, N, Q, S, T, Y, D, and E; $X^{19}$ can be selected from I, L, M, V, F, W, and Y; $X^{20}$ can be selected from I, L, M, N, V, F, Y, and W; $X^{21}$ can be selected from A, G, P, S, and T; $X^{22}$ can be selected from an amino acid; $X^{23}$ can be selected from an amino acid; and $X^{24}$ can be selected from I, L, M, V, F, W, and Y.

In IL-2Rβ ligands of Formula (2)-(2b), $X^{14}$ can be selected from I and M.

In IL-2Rβ ligands of Formula (2)-(2b), $X^{16}$ can be V.

In IL-2Rβ ligands of Formula (2)-(2b), $X^{17}$ can be G.

In IL-2Rβ ligands of Formula (2)-(2b), $X^{18}$ can be selected from D and Q.

In IL-2Rβ ligands of Formula (2)-(2b), $X^{20}$ can be W.

In IL-2Rβ ligands of Formula (2)-(2b), $X^{21}$ can be P.

In IL-2Rβ ligands of Formula (2)-(2b), $X^{23}$ can be selected from F, I, L, and V.

In IL-2Rβ ligands of Formula (2)-(2b), $X^{13}$ can be selected from an amino acid; $X^{14}$ can be selected from I and M; $X^{15}$ can be selected from an amino acid; $X^{16}$ can be V; $X^{17}$ can be G; $X^{18}$ can be selected from D and Q; $X^{19}$ can be selected from I, L, M, V, F, W, and Y; $X^{20}$ can be W; $X^{21}$ can be P; $X^{22}$ can be selected from an amino acid; $X^{23}$ can be selected from an amino acid; and $X^{24}$ can be selected from F, I, L, and V.

An IL-2Rβ ligand can comprise the amino acid sequence of Formula (3) (SEQ ID NO: 183) or the amino acid sequence of Formula (3a) (SEQ ID NO: 184):

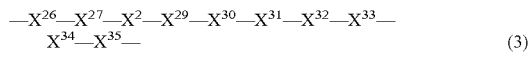

(3)

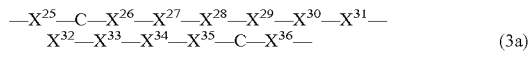

(3a)

wherein, $X^{25}$ can be selected from an amino acid; $X^{26}$ can be selected from an amino acid; $X^{27}$ can be selected from I and V; $X^{28}$ can be G; $X^{29}$ can be selected from D, E, and N; $X^{30}$ can be selected from F, L, and Y; $X^{31}$ can be selected from F, I, and V; $X^{32}$ can be selected from D and Q; $X^{33}$ can be selected from an amino acid; $X^{34}$ can be selected from an amino acid; $X^{35}$ can be selected from an amino acid; and $X^{36}$ can be selected from an amino acid.

In IL-2Rβ ligands of Formula (3)-(3a), $X^{25}$ can be selected from L, S, T, and Y; $X^{26}$ can be selected from H and Q; $X^{27}$ can be selected from I and V; $X^{28}$ can be G; $X^{29}$ can be selected from D, E, and N; $X^{30}$ can be selected from F, L, and Y; $X^{31}$ can be selected from F, I, and V; $X^{32}$ can be selected from D and Q; $X^{33}$ can be selected from D, L, and W; $X^{34}$ can be selected from G, L, and T; $X^{35}$ can be selected from D, I, and S; and $X^{36}$ can be selected from A and M.

An IL-2Rβ ligand can comprise the amino acid sequence of Formula (3) (SEQ ID NO: 1061) or the amino acid sequence of Formula (3a) (SEQ ID NO: 1062):

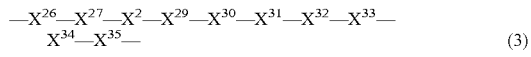

(3)

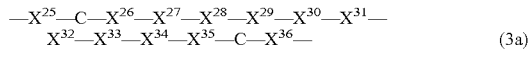

(3a)

wherein, $X^{25}$ can be selected from an amino acid; $X^{26}$ can be selected from an amino acid; $X^{27}$ can be selected from an amino acid comprising a large hydrophobic side chain; $X^{28}$ can be selected from an amino acid comprising a small hydrophobic side chain; $X^{29}$ can be selected from an amino acid comprising an acidic side chain or a polar neutral side chain; $X^{30}$ can be selected from an amino acid; $X^{31}$ can be selected from an amino acid; $X^{32}$ can be selected from an amino acid comprising a polar-neutral side chain or an acidic side chain; $X^{33}$ can be selected from an amino acid; $X^{34}$ can be selected from an amino acid; $X^{35}$ can be selected from an amino acid; and $X^{36}$ can be selected from an amino acid.

In IL-2Rβ ligands of Formula (3)-(3a), $X^{25}$ can be selected from an amino acid; $X^{26}$ can be selected from an amino acid; $X^{27}$ can be selected from an amino acid comprising a large hydrophobic side chain; $X^{28}$ can be selected from an amino acid comprising a small hydrophobic side chain; $X^{29}$ can be selected from an amino acid comprising an acidic side chain or a polar neutral side chain; $X^{30}$ can be selected from an amino acid comprising a large hydrophobic side chain; $X^{31}$ can be selected from an amino acid comprising a large hydrophobic side chain; $X^{32}$ can be selected from an amino acid comprising a polar-neutral side chain or an acidic side chain; $X^{33}$ can be selected from an amino acid; $X^{34}$ can be selected from an amino acid; $X^{35}$ can be selected from an amino acid; and $X^{36}$ can be selected from an amino acid.

An IL-2Rβ ligand can comprise the amino acid sequence of Formula (3) (SEQ ID NO: 1063) or the amino acid sequence of Formula (3a) (SEQ ID NO: 1064):

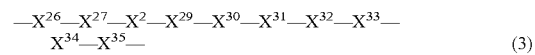

(3)

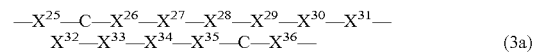

(3a)

wherein, $X^{25}$ can be selected from an amino acid; $X^{26}$ can be selected from an amino acid; $X^{27}$ can be selected from I, L, M, V, F, Y, and W; $X^{28}$ can be selected from A, G, P, S, and T; $X^{29}$ can be selected from D, E, H, N, Q, S, T, and Y; $X^{30}$ can be selected from I, L, M, V, F, Y, and W; $X^{31}$ can be selected from I, L, M, V, F, Y, and W; $X^{32}$ can be selected from D, E, H, N, Q, T, and Y; $X^{33}$ can be selected from an amino acid; $X^{34}$ can be selected from an amino acid; $X^{35}$ can be selected from an amino acid; and $X^{36}$ can be selected from an amino acid.

In IL-2Rβ ligands of Formula (3)-(3a), $X^{27}$ can be selected from V and I.

In IL-2Rβ ligands of Formula (3)-(3a), $X^{28}$ can be G.

In IL-2Rβ ligands of Formula (3)-(3a), $X^{29}$ can be selected from D and E.

In IL-2Rβ ligands of Formula (3)-(3a), $X^{30}$ can be selected from V, L, F, and Y.

In IL-2Rβ ligands of Formula (3)-(3a), $X^{31}$ can be selected from I, V, and F.

In IL-2Rβ ligands of Formula (3)-(3a), $X^{32}$ can be selected from Q and D.

In IL-2Rβ ligands of Formula (3)-(3a), $X^{25}$ can be selected from an amino acid; $X^{26}$ can be selected from an amino acid; $X^{27}$ can be selected from V and I; $X^{28}$ can be G; $X^{29}$ can be selected from D and E; $X^{30}$ can be selected from V, L, F, and Y; $X^{31}$ can be selected from I, V, and F; $X^{32}$ can be selected from Q and D; $X^{33}$ can be selected from an amino acid; $X^{34}$ can be selected from an amino acid; $X^{35}$ can be selected from an amino acid; and $X^{36}$ can be selected from an amino acid.

An IL-2Rβ ligand can comprise an amino acid sequence selected from any one of SEQ ID NO: 185 to SEQ ID NO: 193:

```
                                         SEQ ID NO: 185
     L C H V G D Y I Q D G I C M

SEQ ID NO: 186
     S C Q I G E L V D L T D C A

SEQ ID NO: 187
     T C Q V G D F F D W L S C A

SEQ ID NO: 188
     Y A C A E N V I D W L C T

SEQ ID NO: 189
     L C H V G D Y I Q D G I C M
```

```
                                    SEQ ID NO: 190
        S C Q I G E L V D L T D C A

SEQ ID NO: 191
        T C Q V G D F F D W L S C A

SEQ ID NO: 192
        Y A C A E N V I D W L C T

SEQ ID NO: 193
        C V L L E H S S V G D I I C
```

An IL-2Rβ ligand can comprise an amino acid sequence selected from any one of SEQ ID NO: 183 to SEQ ID NO: 193 and SEQ ID NOS 1061-1064, wherein the amino acid sequence can be terminated with amino acids -G-G- on the N-terminus, on the C-terminus, or on both the N- and C-termini.

An IL-2Rβ ligand can comprise an amino acid sequence selected from any one of SEQ ID NO: 183 to SEQ ID NO: 193 and SEQ ID NOS 1061-1064, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

IL-2Rβ ligands of SEQ ID NO: 183 to SEQ ID NO: 193 and SEQ ID NOS 1061-1064 exhibit an affinity to the IL-2Rβ subunit of less than 100 μM.

An IL-2Rβ ligand can comprise the amino acid sequence of Formula (13) (SEQ ID NO: 1028):

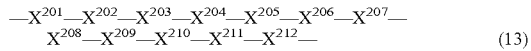

$$-X^{201}-X^{202}-X^{203}-X^{204}-X^{205}-X^{206}-X^{207}-X^{208}-X^{209}-X^{210}-X^{211}-X^{212}-$$ (13)

wherein, $X^{201}$ can be selected from an amino acid; $X^{202}$ can be selected from an amino acid; $X^{203}$ can be selected from an amino acid comprising an acidic side chain; $X^{204}$ can be selected from an amino acid comprising a large hydrophobic side chain; $X^{205}$ can be selected from an amino acid comprising a small hydrophobic side chain; $X^{206}$ can be selected from an amino acid comprising an acidic side chain; $X^{207}$ can be selected from an amino acid comprising a large hydrophobic side chain; $X^{208}$ can be selected from an amino acid; $X^{209}$ can be selected from an amino acid comprising an acidic side chain; $X^{210}$ can be selected from an amino acid; $X^{211}$ can be selected from an amino acid; and $X^{212}$ can be selected from an amino acid comprising a large hydrophobic side chain.

In IL-2Rβ ligands of Formula (13), $X^{201}$ can be selected from an amino acid; $X^{202}$ can be selected from an amino acid; $X^{203}$ can be selected from D and E; $X^{204}$ can be selected from I, L, M, V, F, Y, and W; $X^{205}$ can be selected from A, G, P, S, and T; $X^{206}$ can be selected from D and E; $X^{207}$ can be selected from I, L, M, V, F, Y, and W; $X^{208}$ can be selected from an amino acid; $X^{209}$ can be selected from D and E; $X^{210}$ can be selected from an amino acid; $X^{211}$ can be selected from an amino acid; and $X^{212}$ can be selected from I, L, M, V, F, Y, and W.

In IL-2Rβ ligands of Formula (13), $X^{201}$ can be selected from C, F, L, S, and W; $X^{202}$ can be selected from C, D, F, G, L, M, Q, S, V, W, and Y; $X^{203}$ can be selected from A, C, D, E, L, M, N, S, W, and Y; $X^{204}$ can be selected from A, D, I, M, V, and W; $X^{205}$ can be selected from D, E, G, and I; $X^{206}$ can be selected from C, D, G, H, L, Q, S, and T; $X^{207}$ can be selected from C, D, I, L, V, W, and Y; $X^{208}$ can be selected from C, D, L, V, and W; $X^{209}$ can be selected from C, D, G, I, M, N, P, Q, and W; $X^{210}$ can be selected from D, F, L, M, P, S, T, and Y; $X^{211}$ can be selected from C, F, L, V, and W; and $X^{212}$ can be selected from L, N, S, T, and V.

In IL-2Rβ ligands of Formula (13), $X^{201}$ can be selected from C, F, L, S, and W.

In IL-2Rβ ligands of Formula (13), $X^{202}$ can be selected from C, D, F, G, L, M, Q, S, V, W, and Y.

In IL-2Rβ ligands of Formula (13), $X^{203}$ can be selected from D and E.

In IL-2Rβ ligands of Formula (13), $X^{204}$ can be V.

In IL-2Rβ ligands of Formula (13), $X^{205}$ can be G.

In IL-2Rβ ligands of Formula (13), $X^{206}$ can be D.

In IL-2Rβ ligands of Formula (13), $X^{207}$ can be selected from I, W, and Y.

In IL-2Rβ ligands of Formula (13), $X^{208}$ can be selected from C, D, L, V, and W.

In IL-2Rβ ligands of Formula (13), $X^{209}$ can be D.

In IL-2Rβ ligands of Formula (13), $X^{210}$ can be selected from D, F, L, M, P, S, T, and Y.

In IL-2Rβ ligands of Formula (13), $X^{211}$ can be selected from C, F, L, V, and W.

In IL-2Rβ ligands of Formula (13), $X^{212}$ can be selected from L and V.

In IL-2Rβ ligands of Formula (13), $X^{201}$ can be selected from an amino acid; $X^{202}$ can be selected from an amino acid; $X^{203}$ can be selected from D and E; $X^{204}$ can be V; $X^{205}$ can be G; $X^{205}$ can be D; $X^{207}$ can be selected from I, Y, and W; $X^{208}$ can be selected from an amino acid; $X^{209}$ can be D; $X^{210}$ can be selected from an amino acid; $X^{211}$ can be selected from an amino acid; and $X^{212}$ can be selected from I, L, M, V, F, Y, and W.

An IL-2Rβ ligand can comprise an amino acid sequence selected from any one of SEQ ID NO: 1029 to SEQ ID NO: 1043 and SEQ ID NO: 1084:

```
                                    SEQ ID NO: 1029
        C Q S V G D W C D M

SEQ ID NO: 1030
        C D A V G S W C D F C

SEQ ID NO: 1031
        C F T V G D Y C G Y

SEQ ID NO: 1032
        W C S D I G Q Y C D Y

SEQ ID NO: 1033
        C Y E V G D Y C Q S

SEQ ID NO: 1034
        C G M A I G D L C M

SEQ ID NO: 1035
        C L E V G C I W D M F V

SEQ ID NO: 1036
        F C D M G T V W P D L S
```

```
                                  SEQ ID NO: 1037
D C M L Y E L C D I D V L

SEQ ID NO: 1038
S C C V G D I W D T F

SEQ ID NO: 1039
R W G D V G D L L M P F L

SEQ ID NO: 1040
F L V C D D H Y C W L W T

SEQ ID NO: 1041
W E S W N V G D L V N L V N W

SEQ ID NO: 1042
C Y E V G D Y C Q S P L

SEQ ID NO: 1043
R W G D V G D L L M P L
```

An IL-2Rβ ligand can comprise an amino acid sequence selected from any one of SEQ ID NO: 1028 to SEQ ID NO: 1043 and SEQ ID NO: 1084, wherein the amino acid sequence can be terminated with amino acids -G-G- on the N-terminus, on the C-terminus, or on both the N- and C-termini.

An IL-2Rβ ligand can comprise an amino acid sequence selected from any one of SEQ ID NO: 1028 to SEQ ID NO: 1043 and SEQ ID NO: 1084, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

An IL-2β ligand can comprise an amino acid sequence selected from any one of SEQ ID NO: 1044 to SEQ ID NO: 1050:

```
                                  SEQ ID NO: 1044
R S C Y Y K R P R L W C S E

SEQ ID NO: 1045
I C Y Y S P S D N T T V C E

SEQ ID NO: 1046
A S C X W L V S F G R S V C L

SEQ ID NO: 1047
C L S I G F R D I C F Y R V

SEQ ID NO: 1048
D C M L Y E L C D I D V L

SEQ ID NO: 1049
F L V C D D H Y C W L W T

SEQ ID NO: 1050
I C Y Y S P S D N T T V C E
```

An IL-2Rβ ligand can comprise an amino acid sequence selected from any one of SEQ ID NO: 1044 to SEQ ID NO: 1050, wherein the amino acid sequence can be terminated with amino acids -G-G- on the N-terminus, on the C-terminus, or on both the N- and C-termini.

An IL-2Rβ ligand can comprise an amino acid sequence selected from any one of SEQ ID NO: 1044 to SEQ ID NO: 1050, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

IL-2Rβ ligands of SEQ ID NO: 144 to SEQ ID NO: 150 exhibit an affinity to the IL-2Rβ subunit of less than 100 μM.

An IL-2β ligand can comprise the amino acid sequence of Formula (10) (SEQ ID NO: 578):

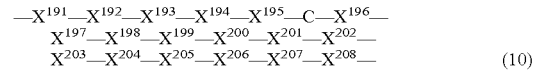

$$—X^{191}—X^{192}—X^{193}—X^{194}—X^{195}—C—X^{196}— \\ X^{197}—X^{198}—X^{199}—X^{200}—X^{201}—X^{202}— \\ X^{203}—X^{204}—X^{205}—X^{206}—X^{207}—X^{208}— \quad (10)$$

wherein, $X^{191}$ can be selected from an amino acid comprising a large hydrophobic side chain or an aromatic side chain; $X^{192}$ can be selected from an amino acid; $X^{193}$ can be selected from an amino acid comprising a large hydrophobic side chain or an aromatic side chain; $X^{194}$ can be selected from an amino acid comprising a large hydrophobic side chain or a basic side chain; $X^{195}$ can be selected from an amino acid comprising an acidic side chain or a small hydrophobic side chain; $X^{196}$ can be selected from an amino acid comprising a large hydrophobic side chain or a basic side chain; $X^{197}$ can be selected from an amino acid comprising a large hydrophobic side chain; $X^{198}$ can be selected from an amino acid comprising a small hydrophobic side chain; $X^{199}$ can be selected from an amino acid comprising a polar/neutral side chain or a basic side chain; $X^{200}$ can be selected from an amino acid comprising a large hydrophobic side chain; $X^{201}$ can be selected from an amino acid comprising a small hydrophobic side chain; $X^{202}$ can be selected from an amino acid comprising an acidic side chain or a polar/neutral side chain; $X^{203}$ can be selected from an amino acid comprising a large hydrophobic side chain; $X^{204}$ can be selected from an amino acid comprising an acidic side chain; $X^{205}$ can be selected from an amino acid comprising a large hydrophobic side chain; $X^{206}$ can be selected from an amino acid comprising an acidic side chain or an aromatic side chain; $X^{207}$ can be selected from an amino acid comprising an amino acid; and $X^{208}$ can be selected from an amino acid comprising an acidic side chain.

In IL-2Rβ ligands of Formula (10), $X^{191}$ can be selected from F, H, I, L, M, V, W, and Y; $X^{192}$ can be selected from an amino acid; $X^{193}$ can be selected from F, H, I, L, M, V, W, and Y; $X^{194}$ can be selected from F, I, L, M, V, W, Y, H, K, and R; $X^{195}$ can be selected from D, E, A, G, P, S, and T; $X^{196}$ can be selected from F, I, L, M, V, W, Y, H, K, and R; $X^{197}$ can be selected from F, I, L, M, V, W, and Y; $X^{198}$ can be selected from A, G, P, S, and T; $X^{199}$ can be selected from H, N, Q, S, T, Y, H, K, and R; $X^{200}$ can be selected from F, I, L, M, V, W, and Y; $X^{201}$ can be selected from A, G, P, S, and T; $X^{202}$ can be selected from D, E, H, N, Q, S, T, and Y; $X^{203}$ can be selected from F, I, L, M, V, W, and Y; $X^{204}$ can be selected from D and E; $X^{205}$ can be selected from F, I, L, M, V, W, and Y; $X^{206}$ can be selected from D, E, F, H, I, L, M, V, W, and Y; $X^{207}$ can be selected from an amino acid; and $X^{208}$ can be selected from D and E.

In IL-2Rβ ligands of Formula (10), $X^{191}$ can be selected from F, H, W, and Y.

In IL-2Rβ ligands of Formula (10), $X^{191}$ can be W.

In IL-2Rβ ligands of Formula (10), $X^{192}$ can be selected from an amino acid.

In IL-2Rβ ligands of Formula (10), $X^{193}$ can be selected from F, H, W, and Y.

In IL-2Rβ ligands of Formula (10), $X^{193}$ can be selected from F, W, and Y.

In IL-2Rβ ligands of Formula (10), $X^{194}$ can be selected from H, L, and Y.

In IL-2Rβ ligands of Formula (10), $X^{194}$ can be L.

In IL-2Rβ ligands of Formula (10), $X^{194}$ can be Y.

In IL-2Rβ ligands of Formula (10), $X^{195}$ can be selected from D and P.

In IL-2Rβ ligands of Formula (10), $X^{195}$ can be D.

In IL-2Rβ ligands of Formula (10), $X^{195}$ can be P.

In IL-2Rβ ligands of Formula (10), $X^{196}$ can be selected from H and W.

In IL-2Rβ ligands of Formula (10), $X^{196}$ can be H.

In IL-2Rβ ligands of Formula (10), $X^{196}$ can be W.

In IL-2Rβ ligands of Formula (10), $X^{197}$ can be M.

In IL-2Rβ ligands of Formula (10), $X^{198}$ can be A.

In IL-2Rβ ligands of Formula (10), $X^{199}$ can be selected from H, K, R, and Q.

In IL-2Rβ ligands of Formula (10), $X^{199}$ can be Q.

In IL-2Rβ ligands of Formula (10), $X^{199}$ can be selected from H, K, and R.

In IL-2Rβ ligands of Formula (10), $X^{200}$ can be selected from L and V.

In IL-2Rβ ligands of Formula (10), $X^{200}$ can be L.

In IL-2Rβ ligands of Formula (10), $X^{201}$ can be G.

In IL-2Rβ ligands of Formula (10), $X^{202}$ can be selected from D, E, and Q.

In IL-2Rβ ligands of Formula (10), $X^{202}$ can be E.

In IL-2Rβ ligands of Formula (10), $X^{203}$ can be L.

In IL-2Rβ ligands of Formula (10), $X^{204}$ can be selected from D and E.

In IL-2Rβ ligands of Formula (10), $X^{204}$ can be D.

In IL-2Rβ ligands of Formula (10), $X^{205}$ can be L.

In IL-2Rβ ligands of Formula (10), $X^{206}$ can be selected from D and E.

In IL-2Rβ ligands of Formula (10), $X^{207}$ can be selected from an amino acid.

In IL-2Rβ ligands of Formula (10), $X^{208}$ can be selected from D and E.

In IL-2Rβ ligands of Formula (10), $X^{191}$ can be selected from F, H, W, and Y; $X^{191}$ can be selected from an amino acid; $X^{193}$ can be selected from F, H, W, and Y; $X^{191}$ can be selected from H, L, and Y; $X^{195}$ can be selected from D and P; $X^{196}$ can be selected from H, R, and W; $X^{197}$ can be M; $X^{198}$ can be A; $X^{199}$ can be selected from H, K, R, and Q; $X^{200}$ can be selected from L and V; $X^{201}$ can be G; $X^{202}$ can be selected from D, E, and Q; $X^{203}$ can be L; $X^{204}$ can be selected from D and E; $X^{205}$ can be L; $X^{206}$ can be selected from D, E, H, F, W, and Y; $X^{207}$ can be selected from an amino acid; and $X^{208}$ can be selected from D and E.

In IL-2Rβ ligands of Formula (10), $X^{191}$ can be selected from F, H, W, and Y; $X^{192}$ can be selected from an amino acid; $X^{193}$ can be Y; $X^{194}$ can be selected from H, L, and Y; $X^{195}$ can be D; $X^{196}$ can be W; $X^{197}$ can be M; $X^{198}$ can be A; $X^{199}$ can be Q; $X^{200}$ can be selected from L and V; $X^{201}$ can be G; $X^{202}$ can be selected from D, E, and Q; $X^{203}$ can be L; $X^{204}$ can be selected from D and E; $X^{205}$ can be L; $X^{206}$ can be selected from D and E; $X^{207}$ can be selected from an amino acid; and $X^{208}$ can be selected from D and E.

In IL-2Rβ ligands of Formula (10), $X^{191}$ can be selected from F, H, W, and Y; $X^{192}$ can be selected from an amino acid; $X^{193}$ can be Y; $X^{194}$ can be selected from H, L, and Y; $X^{195}$ can be D; $X^{196}$ can be H; $X^{197}$ can be M; $X^{198}$ can be A; $X^{199}$ can be Q; $X^{200}$ can be selected from L and V; $X^{201}$ can be G; $X^{202}$ can be selected from D, E, and Q; $X^{203}$ can be L; $X^{204}$ can be selected from D and E; $X^{205}$ can be L; $X^{206}$ can be selected from D and E; $X^{207}$ can be selected from an amino acid; and $X^{208}$ can be selected from D and E.

In IL-2Rβ ligands of Formula (10), $X^{191}$ can be selected from F, H, W, and Y; $X^{192}$ can be selected from an amino acid; $X^{193}$ can be Y; $X^{194}$ can be selected from H, L, and Y; $X^{195}$ can be D; $X^{196}$ can be R; $X^{197}$ can be M; $X^{198}$ can be A; $X^{199}$ can be Q; $X^{200}$ can be selected from L and V; $X^{201}$ can be G; $X^{202}$ can be selected from D, E, and Q; $X^{203}$ can be L; $X^{204}$ can be selected from D and E; $X^{205}$ can be L; $X^{206}$ can be selected from D and E; $X^{207}$ can be selected from an amino acid; and $X^{208}$ can be selected from D and E.

In IL-2Rβ ligands of Formula (10), $X^{191}$ can be selected from F, H, W, and Y; $X^{192}$ can be selected from an amino acid; $X^{193}$ can be Y; $X^{194}$ can be selected from H, L, and Y; $X^{195}$ can be P; $X^{196}$ can be W; $X^{197}$ can be M; $X^{198}$ can be A; $X^{199}$ can be Q; $X^{200}$ can be selected from L and V; $X^{201}$ can be G; $X^{202}$ can be selected from D, E, and Q; $X^{203}$ can be L; $X^{204}$ can be selected from D and E; $X^{205}$ can be L; $X^{206}$ can be selected from D and E; $X^{207}$ can be selected from an amino acid; and $X^{208}$ can be selected from D and E.

In IL-2Rβ ligands of Formula (10), $X^{191}$ can be selected from F, H, W, and Y; $X^{192}$ can be selected from an amino acid; $X^{193}$ can be Y; $X^{194}$ can be selected from H, L, and Y; $X^{195}$ can be D; $X^{196}$ can be W; $X^{197}$ can be M; $X^{198}$ can be A; $X^{199}$ can be selected from H, K, and R; $X^{200}$ can be selected from L and V; $X^{201}$ can be G; $X^{202}$ can be selected from D, E, and Q; $X^{203}$ can be L; $X^{204}$ can be selected from D and E; $X^{205}$ can be L; $X^{206}$ can be selected from D and E; $X^{207}$ can be selected from an amino acid; and $X^{208}$ can be selected from D and E.

In IL-2Rβ ligands of Formula (10), $X^{191}$ can be selected from F, H, W, and Y; $X^{192}$ can be selected from an amino acid; $X^{193}$ can be Y; $X^{194}$ can be selected from H, L, and Y; $X^{195}$ can be D; $X^{196}$ can be W; $X^{197}$ can be M; $X^{198}$ can be A; $X^{199}$ can be Q; $X^{200}$ can be selected from L and V; $X^{201}$ can be G; $X^{202}$ can be selected from D, E, and Q; $X^{203}$ can be L; $X^{204}$ can be selected from D and E; $X^{205}$ can be L; $X^{206}$ can be selected from F, H, W, and Y; $X^{207}$ can be selected from an amino acid; and $X^{208}$ can be selected from D and E.

In IL-2Rβ ligands of Formula (10), $X^{191}$ can be selected from A, D, E, F, G, H, I, K, L, N, M, P, Q, R, S, T, V, W, and Y; $X^{192}$ can be selected from A, D, E, F, G, H, I, K, L, M, N, P, Q, R, S, T, V, W, and Y; $X^{193}$ can be selected from A, C, D, F, G, H, I, L, M, N P, R, S, T, V, W, and Y; $X^{194}$ can be selected from F, H, I, K, L, N, P, Q, R, S, T, V, W, and Y; $X^{195}$ can be selected from A, D, E, F, G, H, K, L, M, N, P, Q, S, W, and Y; $X^{196}$ can be selected from A, E, F, G, H, Q, R, S, W, and Y; $X^{197}$ can be selected from A, D, E, F, I, K, L, M, N, Q, R, S, T, V, W, and Y; $X^{198}$ can be A; $X^{199}$ can be selected from A, D, H, K, L, N, P, Q, R, S, and Y; $X^{200}$ can be selected from I, L, M, P, and V; $X^{201}$ can be selected from G, H, and W; $X^{202}$ can be selected from D, E, and Q; $X^{203}$ can be L; $X^{204}$ can be selected from A, D, E, H, I, L, T, V, and Y; $X^{205}$ can be selected from F, I, L, M, V, W, and Y; $X^{206}$ can be selected from A, D, E, F, G, H, I, K, L, M, N, P, Q, R, S, T, V, W, and Y; $X^{207}$ can be selected from A, C, D, E, F, G, H, I, L, M, N, P, Q, R, S, T, V, W, and Y; and $X^{208}$ can be selected from A, D, E, F, G, H, K, L, M, N, P, Q, R, S, T, V, W, and Y.

In IL-2Rβ ligands of Formula (10), $X^{191}$ can be selected from F, H, W, and Y; $X^{192}$ can be selected from A, D, E, F, G, H, I, K, L, M, N, P, Q, R, S, T, V, W, and Y; $X^{193}$ can be selected from F, H, W, and Y; $X^{194}$ can be selected from F, H, I, L, V W, and Y; $X^{195}$ can be selected from D, E, and P; $X^{196}$ can be selected from F, H, R, S, W, and Y; $X^{197}$ can be selected from F, I, L, M, and V; $X^{198}$ can be A; $X^{199}$ can be selected from H, K, N, Q, and R; $X^{200}$ can be selected from I, L, and V; $X^{201}$ can be G; $X^{202}$ can be selected from D, E, and Q; $X^{203}$ can be selected from F, I, L, M, V, and Y; $X^{204}$ can be selected from D and E; $X^{205}$ can be L; $X^{206}$ can be selected from D, E, N, and Q; $X^{207}$ can be selected from A, D, E, F, G, H, I, L, M, N, P, Q, R, S, T, V, W, and Y; and $X^{208}$ can be selected from D and E.

In IL-2Rβ ligands of Formula (10), $X^{191}$ can be W; $X^{192}$ can be selected from A, D, E, F, G, H, I, K, L, M, N, P, Q, R, S, T, V, W, and Y; $X^{193}$ can be selected from F, H, W, and Y; $X^{194}$ can be Y; $X^{195}$ can be selected from D, E, and P; $X^{196}$ can be selected from H, R, and W; $X^{197}$ can be selected from I and M; $X^{198}$ can be A; $X^{199}$ can be selected from K, Q, and R; $X^{200}$ can be selected from I, L, and V; $X^{201}$ can be G; $X^{202}$ can be E; $X^{203}$ can be L; $X^{204}$ can be D; $X^{205}$ can be L; $X^{206}$ can be selected from D and E; $X^{207}$ can be selected from A, D, E, F, G, H, I, L, M, N, P, Q, R, S, T, V, W, and Y; and $X^{208}$ can be selected from D and E.

In IL-2Rβ ligands of Formula (10), $X^{191}$ can be selected from A, D, E, F, G, H, I, K, L, N, M, P, Q, R, S, T, V, W, and Y; $X^{192}$ can be selected from A, D, E, F, G, H, I, K, L, M, N, P, Q, R, S, T, V, W, and Y; $X^{193}$ can be selected from F, H, W, and Y; $X^{194}$ can be selected from F, H, L, W, and Y; $X^{195}$ can be selected from D, E, and P; $X^{196}$ can be selected from F, H, R, S, W, and Y; $X^{197}$ can be selected from F, I, L, M, and V; $X^{198}$ can be A; $X^{199}$ can be selected from H, K, Q, N, and R; $X^{200}$ can be selected from I, L, and V; $X^{201}$ can be G; $X^{202}$ can be selected from D, E, and Q; $X^{203}$ can be L; $X^{204}$ can be selected from D and E; $X^{205}$ can be selected from F, I, L, M, V, and W; $X^{206}$ can be selected from D, E, F, I, L, M, V, W, and Y; $X^{207}$ can be selected from A, D, E, F, G, H, I, L, M, N, P, Q, R, S, T, V, W, and Y; and $X^{208}$ can be selected from D and E.

In IL-2Rβ ligands of Formula (10), $X^{191}$ can be selected from A, D, E, F, G, H, I, K, L, N, M, P, Q, R, S, T, V, W, and Y.

In IL-2Rβ ligands of Formula (10), $X^{191}$ can be selected from A, G, P, S, and T.

In IL-2Rβ ligands of Formula (10), $X^{191}$ can be selected from F, H, I, L, M, V, W, and Y.

In IL-2Rβ ligands of Formula (10), $X^{191}$ can be selected from F, H, W, and Y.

In IL-2Rβ ligands of Formula (10), $X^{192}$ can be selected from A, D, E, F, G, H, I, K, L, M, N, P, Q, R, S, T, V, W, and Y.

In IL-2Rβ ligands of Formula (10), $X^{192}$ can be selected from A, G, P, S, and T.

In IL-2Rβ ligands of Formula (10), $X^{192}$ can be selected from F, H, I, L, M, V, W, and Y.

In IL-2Rβ ligands of Formula (10), $X^{193}$ can be selected from F, H, W, and Y.

In IL-2Rβ ligands of Formula (10), $X^{193}$ can be W.

In IL-2Rβ ligands of Formula (10), $X^{194}$ can be selected from F, H, L, W, and Y.

In IL-2Rβ ligands of Formula (10), $X^{194}$ can be selected from H, L, and Y.

In IL-2Rβ ligands of Formula (10), $X^{195}$ can be Y.

In IL-2Rβ ligands of Formula (10), $X^{195}$ can be selected from D, E, and P.

In IL-2Rβ ligands of Formula (10), $X^{195}$ can be D.

In IL-2Rβ ligands of Formula (10), $X^{195}$ can be P.

In IL-2Rβ ligands of Formula (10), $X^{196}$ can be selected from F, H, R, S, W, and Y.

In IL-2Rβ ligands of Formula (10), $X^{196}$ can be selected from H, R, and W.

In IL-2Rβ ligands of Formula (10), $X^{196}$ can be W.

In IL-2Rβ ligands of Formula (10), $X^{197}$ can be selected from F, I, L, M, and V.

In IL-2Rβ ligands of Formula (10), $X^{197}$ can be selected from I and M.

In IL-2Rβ ligands of Formula (10), $X^{197}$ can be M.

In IL-2Rβ ligands of Formula (10), $X^{198}$ can be A.

In IL-2Rβ ligands of Formula (10), $X^{199}$ can be selected from H, K, Q, N, and R.

In IL-2Rβ ligands of Formula (10), $X^{199}$ can be selected from H, K, and R.

In IL-2Rβ ligands of Formula (10), $X^{199}$ can be Q.

In IL-2Rβ ligands of Formula (10), $X^{200}$ can be selected from I, L, and V.

In IL-2Rβ ligands of Formula (10), $X^{200}$ can be selected from L and V.

In IL-2Rβ ligands of Formula (10), $X^{201}$ can be G.

In IL-2Rβ ligands of Formula (10), $X^{202}$ can be selected from D, E, and Q.

In IL-2Rβ ligands of Formula (10), $X^{202}$ can be E.

In IL-2Rβ ligands of Formula (10), $X^{203}$ can be L.

In IL-2Rβ ligands of Formula (10), $X^{204}$ can be selected from D and E.

In IL-2Rβ ligands of Formula (10), $X^{204}$ can be D.

In IL-2Rβ ligands of Formula (10), $X^{205}$ can be selected from F, I, L, M, V, and W.

In IL-2Rβ ligands of Formula (10), $X^{205}$ can be L.

In IL-2Rβ ligands of Formula (10), $X^{206}$ can be selected from D and E.

In IL-2Rβ ligands of Formula (10), $X^{206}$ can be D.

In IL-2Rβ ligands of Formula (10), $X^{206}$ can be selected from F, I, L, M, V, W, and Y.

In IL-2Rβ ligands of Formula (10), $X^{207}$ can be selected from A, D, E, F, G, H, I, L, M, N, P, Q, R, S, T, V, W, and Y.

In IL-2Rβ ligands of Formula (10), $X^{207}$ can be selected from A, G, P, S, and T.

In IL-2Rβ ligands of Formula (10), $X^{207}$ can be selected from F, I, L, M, V, W, and Y.

In IL-2Rβ ligands of Formula (10), $X^{208}$ can be selected from D and E.

In IL-2Rβ ligands of Formula (10), $X^{191}$ can be selected from F, I, L, M, V, W, and Y; $X^{192}$ can be selected from A, D, E, F, G, H, I, K, L, M, N, P, Q, R, S, T, V, W, and Y; $X^{193}$ can be selected from F, H, W, and Y; $X^{194}$ can be selected from H, L, and Y; $X^{195}$ can be selected from D and P; $X^{196}$ can be selected from H, R, and W; $X^{197}$ can be selected from I and M; $X^{198}$ can be A; $X^{199}$ can be selected from H, K, Q, and R; $X^{200}$ can be selected from L and V; $X^{201}$ can be G; $X^{202}$ can be selected from D, E, and Q; $X^{203}$ can be L; $X^{204}$ can be selected from D and E; $X^{205}$ can be L; $X^{206}$ can be selected from D, E, F, I, L, M, V, W, and Y; $X^{207}$ can be selected from A, D, E, F, G, H, I, L, M, N, P, Q, R, S, T, V, W, and Y; and $X^{208}$ can be selected from D and E.

In IL-2Rβ ligands of Formula (10), $X^{191}$ can be selected from F, I, L, M, V, W, and Y; $X^{192}$ can be selected from A, D, E, F, G, H, I, K, L, M, N, P, Q, R, S, T, V, W, and Y; $X^{193}$ can be W; $X^{194}$ can be Y; $X^{195}$ can be selected from D and P; $X^{196}$ can be W; $X^{197}$ can be M; $X^{198}$ can be A; $X^{199}$ can be Q; $X^{199}$ can be selected from H, K, and R; $X^{200}$ can be selected from L and V; $X^{201}$ can be G; $X^{202}$ can be E; $X^{203}$ can be L; $X^{204}$ can be selected from D and E; $X^{205}$ can be L; $X^{206}$ can be D; $X^{207}$ can be selected from A, D, E, F, G, H, I, L, M, N, P, Q, R, S, T, V, W, and Y; and $X^{208}$ can be selected from D and E.

In IL-2Rβ ligands of Formula (10), $X^{191}$ can be selected from F, I, L, M, V, W, and Y; $X^{193}$ can be W; $X^{194}$ can be Y; $X^{195}$ can be selected from D and P; $X^{196}$ can be selected from H, R, and W; $X^{197}$ can be M; $X^{198}$ can be A; $X^{199}$ can be selected from H, K, Q, and R; $X^{200}$ can be selected from L and V; $X^{201}$ can be G; $X^{202}$ can be E; $X^{203}$ can be L; $X^{204}$ can be D; $X^{205}$ can be L; $X^{206}$ can be D; $X^{207}$ can be selected from A, D, E, F, G, H, I, L, M, N, P, Q, R, S, T, V, W, and Y; and $X^2$ can be selected from D and E.

An IL-2Rβ ligand can comprise an amino acid sequence selected from any one of SEQ ID NO: 579 to SEQ ID NO: 808:

```
                                       SEQ ID NO: 579
I Y C G F A P L G E L C I L

SEQ ID NO: 580
L P C W I A Q V G E L C D L

SEQ ID NO: 581
L P C H M A Q L G E L C D L

SEQ ID NO: 582
H P C W M A K V G E L C D L

SEQ ID NO: 583
Y P C H M A N V G E L C D L

SEQ ID NO: 584
S G S N D V P H C S M A D L G D L C H L

SEQ ID NO: 585
W H Q W L R K D C R F A K L G E L C D L

SEQ ID NO: 586
G R G V E Y K E C W M A S L G E L C T L

SEQ ID NO: 587
G R A D Q V L P C W M A Q L G E L C E L

SEQ ID NO: 588
I N Q S V L W P C H L A A V G D L C D L

SEQ ID NO: 589
L V G W N H Y D C S V A R V G E L C D L

SEQ ID NO: 590
Y P C W M A Q I G E L C D L

SEQ ID NO: 591
Y P C H I A L L G E L C D L

SEQ ID NO: 592
L Y C W Q A Q L G Q L C D L

SEQ ID NO: 593
Y D C R F A Q L G E L C D L

SEQ ID NO: 594
L M C W N A Q L G D L C D L

SEQ ID NO: 595
T M A S N W Y D C H M A Q V G E L C D L

SEQ ID NO: 596
L E Y D W N Q A C S K A H L G E L C V L

SEQ ID NO: 597
R I L Y E Y P D C W M A Q L G E L C E L

SEQ ID NO: 598
A Q A R F W H D C S I A H V G E L C D L

SEQ ID NO: 599
T A A E Y W Y P C W M A Q V G E L C D L

SEQ ID NO: 600
G P S M T Y K A C W M A Q L G E L C E L

SEQ ID NO: 601
Y F C H I A K L G E L C D L

SEQ ID NO: 602
L A C R F A K L G E L C D L

SEQ ID NO: 603
L P C W M A Q L G D L C D L

SEQ ID NO: 604
L Y R P N Y S D C S M A Q L G E L C E M

SEQ ID NO: 605
K L G K G W H D C S V A Q V G E L C D L

SEQ ID NO: 606
D V F K N W Y D C R I A K L G E L C D L

SEQ ID NO: 607
E Y V L K W P D C S S A Q L G E L C E L

SEQ ID NO: 608
R A L R K F H D C S T A R L G E L C D L

SEQ ID NO: 609
Q V E G S Y Y D C R W A H L G E L C D L

SEQ ID NO: 610
Y P C R M A K L G E L C D L

SEQ ID NO: 611
Y P C W L A H V G E L C D L

SEQ ID NO: 612
Y P C W M A Q L G E L C D L

SEQ ID NO: 613
Y D C S I A Q L G E L C D L

SEQ ID NO: 614
L Y C W A A Q L G E L C D L

SEQ ID NO: 615
L A C W M A H L G D L C D L

SEQ ID NO: 616
S S Y D M D Q D C R W A Q L G Q L C A I

SEQ ID NO: 617
M E N K Y W Y D C S V A L V G E L C D L

SEQ ID NO: 618
K V K L S W Y D C S V A Q V G E L C D L

SEQ ID NO: 619
G F L L E W Y D C R I A Q V G E L C D L

SEQ ID NO: 620
Y D S R S Y L P C H M A Q L G D L C D L

SEQ ID NO: 621
E S M G L G Y P C W R A Q L G E L C D L
```

SEQ ID NO: 622
Y P C W M A L V G E L C D L

SEQ ID NO: 623
Y D C R F A L L G E L C D L

SEQ ID NO: 624
Y W C W M A Q L G E L C D L

SEQ ID NO: 625
K W C W L A H L G E L C D L

SEQ ID NO: 626
L P C W L A K V G D L C D L

SEQ ID NO: 627
D H L Q R W W P C R L A R L G E L C D L

SEQ ID NO: 628
K S G Q R Y Y D C S M A Q L G E L C D L

SEQ ID NO: 629
E L V K T W Y P C W K A H V G E L C D L

SEQ ID NO: 630
R S L F L W H D C S T A Q L G E L C D L

SEQ ID NO: 631
L P R S G W Y D C S I A H V G E L C D L

SEQ ID NO: 632
L S V N K W Y P C W I A D V G E L C D W

SEQ ID NO: 633
Y P C W I A Q V G E L C D L

SEQ ID NO: 634
L K C W M A Q L G E L C D L

SEQ ID NO: 635
L D C R F A Q V G D L C D I

SEQ ID NO: 636
L W C W M A Q L G E L C D L

SEQ ID NO: 637
Y P C W V A K L G E L C D F

SEQ ID NO: 638
W S S K V V K P C H I A R L G E L C E L

SEQ ID NO: 639
L D E T Y W Y D C H V A Q V G E L C D L

SEQ ID NO: 640
T S L D S Y Y D C G M A K V G E L C D L

SEQ ID NO: 641
E S G H Y I K H C S I A L L G E L C H L

SEQ ID NO: 642
R T Y D P G Q D C R L A Q L G E L C E L

SEQ ID NO: 643
L M C W L A Q L G E L C E L

SEQ ID NO: 644
Y P C W I A K V G E L C D L

SEQ ID NO: 645
Y W C W M A Q V G E L C D L

SEQ ID NO: 646
Y E C H L A K L G E L C D L

SEQ ID NO: 647
R G R W E W Y D C S I A Q V G E L C D V

SEQ ID NO: 648
R S F E N W Y D C R I A Q L G E L C D L

SEQ ID NO: 649
P S S R G Y K P C W S A Q V G E L C E L

SEQ ID NO: 650
V D V S G W K P C Y M A H L G E L C D L

SEQ ID NO: 651
V E T T A W Y P C E L A Q L G E L C D L

SEQ ID NO: 652
L H C H N A Q V G D L C D L

SEQ ID NO: 653
L W C H M A N L G D L C D L

SEQ ID NO: 654
Y P C H I A Q V G E L C D L

SEQ ID NO: 655
Y P C H V A Q L G E L C D L

SEQ ID NO: 656
Y D C S M A Q L G E L C D L

SEQ ID NO: 657
Q W C W M A R L G E L C D L

SEQ ID NO: 658
L M V W D R R D C S T A Q L G E L C D L

SEQ ID NO: 659
T R N E F V Y P C W L A Q V G E L C D L

SEQ ID NO: 660
A V R N V W Y D C S F A R L H E L C D V

SEQ ID NO: 661
E V N W L Y Y D C R F A H L G E L C D L

SEQ ID NO: 662
R K T W I W K D C S I A R V G E L C D L

SEQ ID NO: 663
Y D C R I A Q V G E L C D L

SEQ ID NO: 664
Y P C H M A Q L G E L C D L W S W G D I

SEQ ID NO: 665
F D C R F A Q V G D L C D L W S P E H I

SEQ ID NO: 666
L P C W L A N V G E L C D L P G K F E R

SEQ ID NO: 667
Y D C R N A H V G E L C D L I D V P W E

SEQ ID NO: 668
L K C W M A Q V G E L C D L G V D D G Q

SEQ ID NO: 669
Y E C W M A K L G E L C D M Y L E G E I

SEQ ID NO: 670
G D V Y F C W N A K L G E L C D L F E M

SEQ ID NO: 671
V Q Y K K C W M A Q L G D L C E L D P S

SEQ ID NO: 672
P L C Y S C Q M A R V G E L C D L G C D

SEQ ID NO: 673
I G Y H A C W M A Q L G D L C D L H D N

SEQ ID NO: 674
M S W Y D C W M A Q V G E L C D L H V L

SEQ ID NO: 675
Y L C R F A Q L G E L C D L H V H W E D

SEQ ID NO: 676
Y Y C G I A N V G E L C D L E M G G N I

SEQ ID NO: 677
Y H C R F A Q V G E L C D L E P Q I T W

SEQ ID NO: 678
L G C W L A H V G E L C D L M F P G D E

SEQ ID NO: 679
G W H H W C H M A Q V G E L C D L Q V T

SEQ ID NO: 680
E T V S D C R M A Q V G E L C E Y H S A

SEQ ID NO: 681
W S W Y D C R I A Q I G E L C D L I T M

SEQ ID NO: 682
W L F Y D C R W A Q V G E L C D L S G D

SEQ ID NO: 683
Y P C W I A Q I G E L C D M D P R A N M

SEQ ID NO: 684
Y D C R F A Q L G E L C D L Y E T D G R

SEQ ID NO: 685
Y W C R F A Q V G E L C D V Q M Y A S Q

SEQ ID NO: 686
L P C W M A Q V G Q L C Y L D T E R H S

SEQ ID NO: 687
Y A C Y I A K L G E L C D L E M T D H G

SEQ ID NO: 688
P E W Y D C S T A Q V G E L C D L F D D

SEQ ID NO: 689
S S Y Y S C S M A Q L G E L C D L K L S

SEQ ID NO: 690
D R F N P C H M A Q L G E L C D L A R D

SEQ ID NO: 691
W L Y P E C R F A Q V G Q L C E F R N Q

SEQ ID NO: 692
A G W H P C H L A Q V G E L C D L D A L

SEQ ID NO: 693
Y A C W L A K V G E L C D M D E D F T I

SEQ ID NO: 694
Y S C G I A K V G E L C D L V D Q E P D

SEQ ID NO: 695
H P C H M A R L G E L C D L H S G V Y D

SEQ ID NO: 696
L Y C G F A Q V G D L C D L D V E V T Y

SEQ ID NO: 697
L P C W K A Y V G E L C D L N M P R L D

SEQ ID NO: 698
A E V K P C H M A Q V G D L C D L T G G

SEQ ID NO: 699
T P H Y P C W M A H M G E L C D L E W K

SEQ ID NO: 700
P I Y Q P C H M A A L G E L C D L G T A

SEQ ID NO: 701
S K F Y D C R I A K L G E L C D L R S G

SEQ ID NO: 702
L D W H A C W E A Q V G E L C D L R R S

SEQ ID NO: 703
L W C H M A N V G E L C D I D W T N G S

SEQ ID NO: 704
L A C H V A Q L G E L C D L W P D G V N

SEQ ID NO: 705
K P C Y M A Q V G E L C D L P A E S L S

SEQ ID NO: 706
Y D C S I A Q L G E L C D V E P W E S M

SEQ ID NO: 707
Y W C R W A Q V G E L C D L E V E N K D

SEQ ID NO: 708
L H C Y D A Q V G E L C D L E N W L H Q

SEQ ID NO: 709
I K M S P C H L A Q V G E L C D L Q W E

SEQ ID NO: 710
R H F L D C R I A Q I G D L C D L I G F

SEQ ID NO: 711
P A Y Y D C S I A K V G E L C D L S M M

SEQ ID NO: 712
V R F H D C S I A L V G D L C D L H M Y

SEQ ID NO: 713
V T P Y Y C W N A K L G E L C D M M W N

SEQ ID NO: 714
E Y S L D C R I A Q L G Q L C D L M R W

SEQ ID NO: 715
Y D C R M A K V G E L C D L W D T L Y

SEQ ID NO: 716
Y D C H M A K L G E L C D L M L G D V T

SEQ ID NO: 717
Y P C H L A H V G E L C D L E G G T E F

SEQ ID NO: 718
Y D C S I A R V G E L C D L L Q D W W P

SEQ ID NO: 719
L P C W L A Q V G E L C D L Q E E T G S

SEQ ID NO: 720
D G H Y E C W K A Q L G E L C D L A G A

SEQ ID NO: 721
S F V Q D C S L A Q L W D L C E I W T D

SEQ ID NO: 722
E P F Y H C S I A Q L G E L C D L V R A

SEQ ID NO: 723
W P W Q D C S T A Q L G D L C D L M S Y

SEQ ID NO: 724
G L T L P C W M A Q L G E L C D L N N A

SEQ ID NO: 725
N L H Y D C R I A Q V G E L C D L T Y E

SEQ ID NO: 726
Y H C F L A Q V G D L C D L W D S M T T

SEQ ID NO: 727
R W C H M A Q L G D L C E L Y I F D K H

SEQ ID NO: 728
L P C H L A Q V G E L C D L P S S M L T

SEQ ID NO: 729
W A W L D C H N A Q V G E L C D L L R D

SEQ ID NO: 730
T S F H D C R I A N V G E L C D L S I L

SEQ ID NO: 731
V S W Y P C H M A Q V G E L C D L G F S

SEQ ID NO: 732
G N F K Q C H M A A V G E L C E M E N E

SEQ ID NO: 733
A V W Y D C R I A Q V G E L C D L V H P

SEQ ID NO: 734
Y D C F F A H V G E L C D L M G N S G T

SEQ ID NO: 735
K A C H M A Q L G E L C D L Y Q G G I N

SEQ ID NO: 736
Y P C W L A L P G E L C D L M E S T V N

SEQ ID NO: 737
Y D C S L A Q L G E L C D L T G P S Y G

SEQ ID NO: 738
Y P C H V A Q V G E L C D L S P G L H G

SEQ ID NO: 739
H M F Y P C W R A Q V G E L C D L A N Y

SEQ ID NO: 740
S G W Y P C R I A R L G E L C D L W E G

SEQ ID NO: 741
Q V H Y D C S M A Q L G E L C D L Y D E

SEQ ID NO: 742
L W F Y D C R F A H V G E L C D L E Q T

SEQ ID NO: 743
V G R Q M R K A C H M A L L G E L C D L

SEQ ID NO: 744
H W C W M A R L G E L C D L

SEQ ID NO: 745
S V L L S Y P L C R F A Q L G E L C D L

SEQ ID NO: 746
Y F C W M A K L G E L C D L

SEQ ID NO: 747
L H I L K N Y P C Y L A Q V G E L C D L

SEQ ID NO: 748
H I M R T W Y D C S I A Q I G E L C D L

SEQ ID NO: 749
P E R G G W Y D C R F A K L G E L C D L

SEQ ID NO: 750
G G M A K Y N P C H I A K L G E L C D L

SEQ ID NO: 751
Y F C W M A Q L G E L C D L

SEQ ID NO: 752
I S G L G I Y P C W M A H L G E L C D L

SEQ ID NO: 753
G V T Y Q W Y D C S I A L V G E L C D I

SEQ ID NO: 754
Y P C H L A L L G E L C D L

SEQ ID NO: 755
R P W R Q W Y D C S I A R L G E L C D I

SEQ ID NO: 756
Y P C W M A Q V G E L C D L

SEQ ID NO: 757
Y D C S I A K L G E L C D L

SEQ ID NO: 758
V S V W K D C S I A Q L G E L C D L

SEQ ID NO: 759
N E Q M I P W P C H L A Q L G D L C D L

SEQ ID NO: 760
F P C W L A K L G D L C D L

SEQ ID NO: 761
Y W C H I A Q L G E L C D L

SEQ ID NO: 762
D S N A P W Y D C S K A L L G E L C D L

SEQ ID NO: 763
W S I A N F Y D C R F A H L G E L C D L

SEQ ID NO: 764
L P C H M A L L G Q L C D L

SEQ ID NO: 765
L M C W F A Q L G D L C D L

SEQ ID NO: 766
Y P C W I A K L G E L C D F

SEQ ID NO: 767
A Y R A M P Y Y C W M A Q L G E L C D L

SEQ ID NO: 768
G S S V E T K P C W M A Y L G E L C H L

SEQ ID NO: 769
Y P C W L A R V G E L C D L D S G D V H

SEQ ID NO: 770
Y D C S M A L L G E L C D L W M P A I K

SEQ ID NO: 771
Y P C W M A H V G E L C D L E G W F G V

SEQ ID NO: 772
G V F Y D C R I A Q L G E L C D L W A S

SEQ ID NO: 773
Y K F L P C W R A R V G E L C D L D T A

SEQ ID NO: 774
A N F Y D C R Y A Q L G E L C D L M N V

SEQ ID NO: 775
R R A S W C H L A Q V G E L C D L L W E

SEQ ID NO: 776
H P C H M A Q V G E L C D L N F P Y V E

SEQ ID NO: 777
T P C Y M A K L G E L C D L E E W A L E

SEQ ID NO: 778
L W C W M A Q V G E L C D L E E R S F M

SEQ ID NO: 779
Y P C H M A Q L G E L C D L W S W G D I

SEQ ID NO: 780
L P C W K A N L G E L C D L Y D M G H S

SEQ ID NO: 781
W A F Y D C F T A Q V G E L C D L S I G

SEQ ID NO: 782
K T W Y D C R F A Q L G E L C D L N M N

SEQ ID NO: 783
L P C W L A R L G E L C D L Q Y E Y N D

-continued

SEQ ID NO: 784
F S F Q H C H M A Q L G E L C D L G Y E

SEQ ID NO: 785
Y P C R I A K L G E L C D L S E W Q Q L

SEQ ID NO: 786
Y A C W F A Q V G E L C D L E E D M V T

SEQ ID NO: 787
G F S H F C W E A Q V G E L C D L I Y G

SEQ ID NO: 788
L Y C W M A Q L G E L C D L E H V D W N

SEQ ID NO: 789
L W C G I A Q L G E L C D L E L G I H D

SEQ ID NO: 790
L L C W M A Q L G E L C D L E G E V M K

SEQ ID NO: 791
K V W Y P C R I A Q V G E L C D L D Q F

SEQ ID NO: 792
G E W Y D C R I A Q V G E L C D L W P V

SEQ ID NO: 793
Y P C W F A K L G E L C D L G L T D T K

SEQ ID NO: 794
V S W V D C H M A Q V G E L C D L R D S

SEQ ID NO: 795
Q F W L G C W M A Q V G E L C D L D Q P

SEQ ID NO: 796
Y T W L D C S V A Q L G Q L C D L W S M

SEQ ID NO: 797
A L S W L W Q D C A L A Q L G E L C D L

SEQ ID NO: 798
G D L V M F Y D C R F A R V G E L C D L

SEQ ID NO: 799
R L F D P D Q N C R F A L L G E L C L L

SEQ ID NO: 800
G S V W E F Y D C F I A R V G E L C D L

SEQ ID NO: 801
S D L M V W K P C W T A Q L G E L C D L

SEQ ID NO: 802
K Y C G F A Q L G E L C V L

SEQ ID NO: 803
Y P C W M A Q V G E L C D L F L E S V P

SEQ ID NO: 804
M G F Y P C W T A Q L G E L C D L S V D

SEQ ID NO: 805
P L N Y P C W I A Q L G E L C D L D L R

SEQ ID NO: 806
W K F Q D C R T A Q V G E L C D L W P Y

SEQ ID NO: 807
L Y C G M A H V G Q L C I L E D W R G A

SEQ ID NO: 808
W Y P C W M A Q L G E L C D L D

An IL-2Rβ ligand can comprise an amino acid sequence selected from any one of SEQ ID NO: 578 to SEQ ID NO: 808, wherein the amino acid sequence can be terminated with amino acids -G-G- on the N-terminus, on the C-terminus, or on both the N- and C-termini.

An IL-2Rβ ligand can comprise an amino acid sequence selected from any one of SEQ ID NO: 578 to SEQ ID NO: 808, wherein each amino acid independently comprises one or more of the following conservative substitutions: amino acids having a small hydrophobic side chain comprising alanine (A), glycine (G), proline (P), serine (5), or threonine (7); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

IL-2Rβ ligands of SEQ ID NO: 578 to SEQ ID NO: 808 exhibit an affinity to the IL-2Rβ subunit of less than 100 μM.

An IL-2Rβ ligand can comprise the amino acid sequence of Formula (11) (SEQ ID NO: 809):

$$-X^{211}-X^{212}-X^{213}-X^{214}-C-X^{215}-X^{216}-X^{217}-X^{218}-X^{219}-X^{220}-X^{221}-X^{222}-C-X^{223}-X^{224}-X^{225}- \quad (11)$$

wherein, $X^{211}$ can be selected from an amino acid; $X^{212}$ can be selected from an amino acid comprising an aromatic side chain; $X^{213}$ can be selected from an amino acid comprising a large hydrophobic side chain or an aromatic side chain; $X^{214}$ can be P; $X^{215}$ can be selected from an amino acid comprising an aromatic side chain; $X^{216}$ can be selected from an amino acid comprising a large hydrophobic side chain; $X^{217}$ can be A; $X^{218}$ can be selected from an amino acid comprising a basic side chain or a polar/neutral side chain; $X^{219}$ can be selected from an amino acid comprising a large hydrophobic side chain; $X^{220}$ can be G; $X^{221}$ can be selected from an amino acid comprising an acidic side chain or a polar/neutral side chain; $X^{222}$ can be L; $X^{223}$ can be D; $X^{224}$ can be selected from an amino acid comprising a large hydrophobic side chain; and $X^{225}$ can be selected from an amino acid comprising an acidic side chain.

In IL-2Rβ ligands of Formula (11), $X^{211}$ can be selected from an amino acid; $X^{212}$ can be selected from F, H, W, and Y; $X^{213}$ can be selected from F, H, I, L, M, V, W, and Y; $X^{214}$ can be P; $X^{215}$ can be selected from F, H, W, and Y; $X^{216}$ can be selected from F, I, L, M, V, W, and Y; $X^{217}$ can be A; $X^{218}$ can be selected from K, R, H, N, Q, S, T, and Y; $X^{219}$ can be selected from F, I, L, M, V, W, and Y; $X^{220}$ can be G; $X^{221}$ can be selected from D, E, H, N, Q, S, T, and Y; $X^{222}$ can be L; $X^{223}$ can be D; $X^{224}$ can be selected from F, I, L, M, V, W, and Y; and $X^{225}$ can be selected from D and E.

In IL-2Rβ ligands of Formula (11), $X^{211}$ can be selected from an amino acid.

In IL-2Rβ ligands of Formula (11), $X^{211}$ can be selected from H, K, and R.

In IL-2Rβ ligands of Formula (11), $X^{211}$ can be selected from H and R.

In IL-2Rβ ligands of Formula (11), $X^{212}$ can be selected from F, H, W, and Y.

In IL-2Rβ ligands of Formula (11), $X^{212}$ can be W.

In IL-2Rβ ligands of Formula (11), $X^{213}$ can be selected from F, H, I, L, M, V, W, and Y.

In IL-2Rβ ligands of Formula (11), $X^{213}$ can be L.

In IL-2Rβ ligands of Formula (11), $X^{213}$ can be Y.
In IL-2Rβ ligands of Formula (11), $X^{214}$ can be P.
In IL-2Rβ ligands of Formula (11), $X^{211}$ can be selected from F, H, W, and Y.
In IL-2Rβ ligands of Formula (11), $X^{215}$ can be W.
In IL-2Rβ ligands of Formula (11), $X^{216}$ can be selected from F, I, L, M, V, W, and Y.
In IL-2Rβ ligands of Formula (11), $X^{216}$ can be M.
In IL-2Rβ ligands of Formula (11), $X^{217}$ can be A.
In IL-2Rβ ligands of Formula (11), $X^{218}$ can be selected from K, R, H, N, Q, S, T, and Y.
In IL-2Rβ ligands of Formula (11), $X^{218}$ can be selected from K and R.
In IL-2Rβ ligands of Formula (11), $X^{218}$ can be Q.
In IL-2Rβ ligands of Formula (11), $X^{219}$ can be selected from F, I, L, M, V, W, and Y.
In IL-2Rβ ligands of Formula (11), $X^{219}$ can be L.
In IL-2Rβ ligands of Formula (11), $X^{220}$ can be G.
In IL-2Rβ ligands of Formula (11), $X^{221}$ can be selected from D, E, H, N, Q, S, T, and Y.
In IL-2Rβ ligands of Formula (11), $X^{221}$ can be E.
In IL-2Rβ ligands of Formula (11), $X^{222}$ can be L.
In IL-2Rβ ligands of Formula (11), $X^{223}$ can be D.
In IL-2Rβ ligands of Formula (11), $X^{224}$ can be selected from F, I, L, M, V, W, and Y.
In IL-2Rβ ligands of Formula (11), $X^{224}$ can be L.
In IL-2Rβ ligands of Formula (11), $X^{225}$ can be selected from D and E.
In IL-2Rβ ligands of Formula (11), $X^{211}$ can be selected from H, K, and R; $X^{212}$ can be W; $X^{213}$ can be Y; $X^{214}$ can be P; $X^{215}$ can be W; $X^{216}$ can be M; $X^{217}$ can be A; $X^{218}$ can be selected N and Q; $X^{219}$ can be selected from L and V; $X^{220}$ can be G; $X^{221}$ can be selected from E, D, and Q; $X^{222}$ can be L; $X^{223}$ can be D; $X^{224}$ can be selected from L and M; and $X^{225}$ can be selected from D and E.
In IL-2Rβ ligands of Formula (11), $X^{211}$ can be selected from A, D, E, G, H, L, M, N, Q, R, S, T, and V; $X^{212}$ can be selected from C, F, W, and Y; $X^{213}$ can be selected from F, H, K, L, N, Q, R, S, W, and Y; $X^{214}$ can be P; $X^{215}$ can be selected from W and Y; $X^{216}$ can be selected from F, I, K, L, M, R, S, T, and V; $X^{217}$ can be A; $X^{218}$ can be selected from D, E, G, H, K, L, N, Q, R, S, and Y; $X^{219}$ can be selected from L, P, and V; $X^{220}$ can be selected from G, H, and W; $X^{221}$ can be selected from D, E, and Q; $X^{222}$ can be selected from L and M; $X^{223}$ can be D; $X^{224}$ can be selected from L, M, Q, and V; and $X^{225}$ can be selected from A, D, E, F, G, H, L, N, Q, T, and V.
In IL-2Rβ ligands of Formula (11), $X^{211}$ can be selected from H an R; $X^{212}$ can be selected from F and W; $X^{213}$ can be selected from F, L, W, and Y; $X^{214}$ can be P; $X^{215}$ can be selected from W and Y; $X^{216}$ can be selected from F, I, L, M, and V; $X^{217}$ can be A; $X^{218}$ can be selected D, E, H, K, N, Q, and R; $X^{219}$ can be selected from L and V; $X^{200}$ can be G; $X^{221}$ can be selected from D, E, and Q; $X^{222}$ can be selected from L and M; $X^{223}$ can be D; $X^{224}$ can be selected L, M, and V; and $X^{225}$ can be selected from D and E.
In IL-2Rβ ligands of Formula (11), $X^{211}$ can be selected from H and R; $X^{212}$ can be W; $X^{213}$ can be Y; $X^{214}$ can be P; $X^{215}$ can be W; $X^{216}$ can be M; $X^{217}$ can be A; $X^{218}$ can be Q; $X^{219}$ can be L; $X^{220}$ can be G; $X^{221}$ can be Q; $X^{222}$ can be L; $X^{223}$ can be D; $X^{224}$ can be L; and $X^{225}$ can be selected from D and E.
In IL-2Rβ ligands of Formula (11), $X^{211}$ can be selected from H and R; $X^{212}$ can be W; $X^{213}$ can be L; $X^{214}$ can be P; $X^{215}$ can be W; $X^{216}$ can be M; $X^{217}$ can be A; $X^{218}$ can be Q; $X^{219}$ can be L; $X^{220}$ can be G; $X^{221}$ can be Q; $X^{222}$ can be L; $X^{223}$ can be D; $X^{224}$ can be L; and $X^{225}$ can be selected from D and E.
In IL-2Rβ ligands of Formula (11), $X^{211}$ can be selected from H and R; $X^{212}$ can be W; $X^{213}$ can be Y; $X^{214}$ can be P; $X^{211}$ can be W; $X^{216}$ can be M; $X^{217}$ can be A; $X^{218}$ can be selected from K and R; $X^{219}$ can be L; $X^{220}$ can be G; $X^{221}$ can be Q; $X^{222}$ can be L; $X^{223}$ can be D; $X^{224}$ can be L; and $X^{225}$ can be selected from D and E.

An IL-2Rβ ligand can comprise an amino acid sequence selected from any one of SEQ ID NO: 810 to SEQ ID NO: 903:

```
                                    SEQ ID NO: 810
Q P C W L A Q V G D L C D L L W P G P L

SEQ ID NO: 811
W L P C W I A R L G D L C D L E

SEQ ID NO: 812
W Y P C W M A L L G E L C D Q E

SEQ ID NO: 813
W Y P C Y R A R L G E L C D L D

SEQ ID NO: 814
W Q R E W R W F P C W M A K L G D M C D L D

SEQ ID NO: 815
Q D E A V E W F P C W M A R L G E L C D L E

SEQ ID NO: 816
Y Y P C W M A R L G E L C D L D

SEQ ID NO: 817
S V V V N N W L P C W M A Q L G E L C D L D

SEQ ID NO: 818
W Y P C W L A Q L G D L C D L D

SEQ ID NO: 819
V M S P T R W L P C W I A K L G E L C D L E

SEQ ID NO: 820
W F P C W M A Q L G Q L C D L E

SEQ ID NO: 821
W R P C W R A Y L G E L C D L E A M P R A T

SEQ ID NO: 822
I R S C S P C W S A D V G E L C D L E C E W

SEQ ID NO: 823
S G H W Y P C W M A R L G E L C D M E E R A

SEQ ID NO: 824
W Y P C W M A Q L G E L C D L Q T M G Y S H

SEQ ID NO: 825
A G D W L P C W M A E L G E L C D L E G P T

SEQ ID NO: 826
W L P C W I A S L G E L C D L D T G K R Q G

SEQ ID NO: 827
W L P C W M A H L G Q L C D L D L P G K S M

SEQ ID NO: 828
E G V F F P C W I A R L G E L C D L D H G L

SEQ ID NO: 829
T G R W K P C W M A G L H E L C D L E G F R

SEQ ID NO: 830
R K H F Y P C W M A Q L G E L C D L E G M P

SEQ ID NO: 831
D I G Y Y P C W M A Q V G D L C D L D D E K
```

DSDWWPCWMAQLGELCDLEDAR  SEQ ID NO: 832

GERWKPCWIAQLGELCDLDFNW  SEQ ID NO: 833

WWPCWMAQLGEMCDLEYPYVPG  SEQ ID NO: 834

QTKLEGWYPCWMAQLGELCDLD  SEQ ID NO: 835

WGRKEQWLPCWKAQLGELCDLE  SEQ ID NO: 836

VPRANAWHPCWMAQLGELCDLE  SEQ ID NO: 837

GRQQKGWYPCWLAQLGELCDME  SEQ ID NO: 838

WLNRHLFNPCWMARLGELCDLE  SEQ ID NO: 839

AQVRREWYPCWMAQLGELCDLT  SEQ ID NO: 840

ETEQMSWYPCWVAQLWELCDLD  SEQ ID NO: 841

WLPCWLAKLGELCDLEWLPCW  SEQ ID NO: 842

ERRPDTWFPCWRALVGELCDLE  SEQ ID NO: 843

WGRNRSWYPCWMAQLGELCDLE  SEQ ID NO: 844

QDRRSPWYPCWMAKLGELCDLA  SEQ ID NO: 845

TRRWYPCYLAKLGELCDLFEGGTR  SEQ ID NO: 846

SEQWWPCWIARLGELCDLDRELSE  SEQ ID NO: 847

WYPCWVAQLGEICDLEMTGPDSWYP  SEQ ID NO: 848

QDGWLPCWMAQLGELCDLEYKR  SEQ ID NO: 849

NRRWYPCWMAQLGELCDLDSRP  SEQ ID NO: 850

FYPCWMAHLGELCDLDGDTDSM  SEQ ID NO: 851

KSNFFPCWIAQLGQLCDLEPET  SEQ ID NO: 852

FYPCWMANLGELCDLDFLRELN  SEQ ID NO: 853

HASWLPCWLAQLGELCDLEPNP  SEQ ID NO: 854

NGAWYPCWMAQVGELCDLEERW  SEQ ID NO: 855

WRRWYPCWVAQVGELCDLEIEA  SEQ ID NO: 856

RQAWYPCWMAQLGELCDLEAEL  SEQ ID NO: 857

RQRWYPCWMARLGELCDLDEPT  SEQ ID NO: 858

NNSREGWFPCWLAKLGDLCDLD  SEQ ID NO: 859

YYPCWMAQLGELCDLE  SEQ ID NO: 860

WYPCWLAQLGELCDLD  SEQ ID NO: 861

SWHAETWYPCWLAQVGELCDLD  SEQ ID NO: 862

KMHKAVWLPCWMAQVGELCDLE  SEQ ID NO: 863

DVLGDRWYPCWIAKLGELCDLD  SEQ ID NO: 864

WYPCWMAQLGELCDLD  SEQ ID NO: 865

KLQSWRWYPCWMAQLGELCDLD  SEQ ID NO: 866

NEPEGGFYPCWLAQLGELCDLH  SEQ ID NO: 867

WYPCWMARLGELCDLE  SEQ ID NO: 868

FYPCWTALLGELCDLEPGPPAM  SEQ ID NO: 869

WGTTWRWYPCWMAQLGELCDLE  SEQ ID NO: 870

AKGWDTWKPCWLANLGELCDLE  SEQ ID NO: 871

RDESAGYYPCWIAQLGELCDLE  SEQ ID NO: 872

WYPCWIAKLGELCDLE  SEQ ID NO: 873

WYPCWIAQLGELCDLD  SEQ ID NO: 874

WYPCWLAKLGELCDLD  SEQ ID NO: 875

QGPVRLWYPCWMAQLGELCDLD  SEQ ID NO: 876

WYPCWMAQPGELCDVD  SEQ ID NO: 877

WHPCWIAQLGELCDLE  SEQ ID NO: 878

WYPCWIAQLGELCDLE  SEQ ID NO: 879

VRPMGVWYPCWIAQLGELCDLV  SEQ ID NO: 880

VPRWYPCWIAQLGELCDLDSDD  SEQ ID NO: 881

YRGWLPCWRAKLGDLCDLGQPM  SEQ ID NO: 882

GEAWYPCWLARLGELCDMDPRV  SEQ ID NO: 883

WYPCWMAQLGELCDLDESTRLT  SEQ ID NO: 884

IGSWWPCWMAQLGELCDLEPEL  SEQ ID NO: 885

-continued

SEQ ID NO: 886
G T T W Y P C W L A Q L G E L C D L D V L E

SEQ ID NO: 887
W W P C W M A Q L G D L C D L E E T S G G T

SEQ ID NO: 888
W Y P C W M A Q L G E L C D L G P T E S N L

SEQ ID NO: 889
W Y P C W M A N L G E L C D L E Y P S W A Q

SEQ ID NO: 890
R G M C Y P C W F A R L G E L C D L E C D Q

SEQ ID NO: 891
W Y P C W M A Q L G E L C D L D A G A R H L

SEQ ID NO: 892
K S G W Y P C W M A K L G E L C D L E A Q P

SEQ ID NO: 893
G P R F Y P C W I A Q L G E L C D L E D M G

SEQ ID NO: 894
R V T W Y P C W M A Q L G E L C D L E E S V

SEQ ID NO: 895
W L P C W M A Q L G D L C D L E Q Y V P L P

SEQ ID NO: 896
Y L P C W M A H L G E L C D L D S P L K A R

SEQ ID NO: 897
W Y P C W M A Q L G E L C D L D D H W P A M

SEQ ID NO: 898
W Y P C W R A Q L G E L C D L D P P I A V E

SEQ ID NO: 899
W Y P C W M A N L G E L C D L E A E R S P V

SEQ ID NO: 900
R D Q Y Y P C W M A Q L G E L C D L D E V F

SEQ ID NO: 901
W Y P C W M A Q L G D L C D L E K P V T E R

SEQ ID NO: 902
W Y P C W I A R L G E L C D L E T S G G F P

SEQ ID NO: 903
S G H C Y P C W L A G L G E L C D L N C G

An IL-2Rβ ligand can comprise an amino acid sequence selected from any one of SEQ ID NO: 809 to SEQ ID NO: 903, wherein the amino acid sequence can be terminated with amino acids -G-G- on the N-terminus, on the C-terminus, or on both the N- and C-termini.

An IL-2Rβ ligand can comprise an amino acid sequence selected from any one of SEQ ID NO: 809 to SEQ ID NO: 903, wherein each amino acid independently comprises one or more of the following conservative substitutions: amino acids having a small hydrophobic side chain comprising alanine (A), glycine (G), proline (P), serine (5), or threonine (7); amino acids having a hydroxyl-containing side chain comprising serine (5), threonine (T), or tyrosine (Y); amino acids having an acidic side chain comprising aspartate (D) or glutamate (E); amino acids having a polar-neutral side chain comprising histidine (H), asparagine (N), glutamine (Q), serine (5), threonine (7), or tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

IL-2Rβ ligands of SEQ ID NO: 809 to SEQ ID NO: 903 can exhibit a binding affinity ($IC_{50}$) to the IL-2Rβ subunit of less than 100 µM.

An IL-2Rβ ligand can comprise, for example, from 5 to 50 amino acids, from 5 to 40 amino acids, from 5 to 30 amino acids, from 5 to 30 amino acids, from 6 to 25 amino acids, or from 7 to 20 amino acids.

An IL-2Rβ ligand can exhibit a binding affinity ($IC_{50}$) to the human IL-2Rβ subunit, to a mammalian IL-2Rβ subunit, or to both the human IL-2Rβ subunit and a mammalian IL-2Rβ subunit from 1 µM to 100 µM, from 10 µM to 10 µM, from 100 µM to 1 µM, from, 0.001 µM to 1 µM, or from 0.01 µM to 1 µM.

An IL-2Rβ ligand provided by the present disclosure can exhibit, for example, a binding affinity ($IC_{50}$) to the human IL-2Rβ subunit from 0.1 µM to 50 µM.

An IL-2Rβ ligand can exhibit a binding affinity ($IC_{50}$) to the human IL-2Rβ subunit, to a mammalian IL-2Rβ subunit, or to both the human IL-2Rβ subunit and a mammalian IL-2Rβ subunit of less than 100 µM, less than 10 µM, less than 1 µM, less than 0.1 M, or less than 0.01 µM.

An IL-2Rβ ligand can exhibit a binding affinity ($IC_{50}$) to each of the human IL-2Rβ subunit and to the human IL-2Rγc subunit of less than 100 µM, less than 10 µM, less than 1 µM, less than 0.1 M, or less than 0.01 µM.

An IL-2Rβ ligand can exhibit a binding affinity ($IC_{50}$) to each of the human IL-2Rβ subunit and to the human IL-2Rγc subunit from 1 µM to 100 µM, from 10 µM to 10 µM, from 100 µM to 1 M, from, 0.001 µM to 1 M, or from 0.01 µM to 1 µM.

An IL-2Rβ ligand provided by the present disclosure can exhibit a binding affinity ($IC_{50}$) to the human IL-2Rα (CD25) subunit of greater than 100 M, greater than 1 mM, greater than 10 mM, or greater than 100 mM.

An IL-2Rβ ligand can exhibit a binding affinity ($IC_{50}$) to the human IL-2Rβ subunit that can be at least 10 times greater, at least 50 times greater, at least 100 time greater, at least 500 times greater, or at least 1,000 times greater than the binding affinity of the IL-2Rβ ligand to the human IL-2Rα subunit.

An IL-2Rγc ligand provided by the present disclosure can exhibit a binding affinity ($IC_{50}$) to the human IL-2Rγc subunit of less than 100 µM, less than 10 µM, less than 1 M, less than 0.1 M, or less than 0.01 µM.

An IL-2Rγc ligand provided by the present disclosure can exhibit a binding affinity ($IC_{50}$) to the human IL-2Rγc subunit from 1 µM to 100 µM, from 10 µM to 10 M, from 100 µM to 1 µM, from, 0.001 pM to 1 µM, or from 0.01 µM to 1 µM.

An IL-2Rγc ligand provided by the present disclosure can exhibit a binding affinity ($IC_{50}$) to a mammalian IL-2Rγc subunit, for example, of less than 100 µM, less than 10 M, less than 1 M, less than 0.1 M, or less than 0.01 µM.

An IL-2Rγc ligand provided by the present disclosure can exhibit a binding affinity ($IC_{50}$) to a mammalian IL-2Rγc subunit, for example, from 1 µM to 100 µM, from 10 µM to 10 µM, from 100 µM to 1 M, from, 0.001 µM to 1 µM, or from 0.01 µM to 1 µM.

An IL-2Rγc ligand provided by the present disclosure can comprise an amino acid sequence selected from any one of SEQ ID NO: 194 to SEQ ID NO: 267 and SEQ ID NO: 904 to SEQ ID NO: 1027 and SEQ ID NOS 1065-1082.

An IL-2Rγc ligand provided by the present disclosure can comprise an amino acid sequence of any one of SEQ ID NO: 194 to SEQ ID NO: 267 and SEQ ID NO: 904 to SEQ ID NO: 1027 and SEQ ID NOS 1065-1082 independently comprising one or more of the following conservative substitutions: amino acids having a small hydrophobic side chain comprising alanine (A) or glycine (G); amino acids having a hydroxyl-containing side chain comprising serine (S), threonine (T), or tyrosine (Y); amino acids having a acidic and polar-neutral side chain comprising aspartic acid (I) or glutamic acid (E); asparagine (N) or glutamine (Q); amino acids having aromatic side chains comprise phenylalanine (F), tryptophan (W), tyrosine (Y), or histidine (H); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W) and amino acids having an aromatic side chain comprising phenylalanine (F), histidine (H), tryptophan (W), or tyrosine (Y).

An IL-2Rγc ligand can comprise the amino acid sequence of Formula (4) (SEQ ID NO: 194) or the amino acid sequence of Formula (4a) (SEQ ID NO: 195):

$$-X^{53}-X^{54}-X^{55}-X^{56}-X^{57}-X^{58}-X^{59}-X^{60}- \quad (4)$$

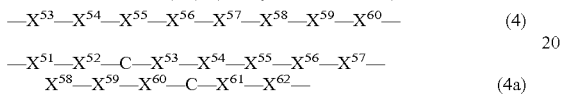

wherein, $X^{51}$ can be selected from G, I, K, L, Q, R, T, Y, and V; $X^{52}$ can be selected from A, D, E, H, I, L, M, R, S, T, V, and W; $X^{53}$ can be selected from D, E, F, N, Q, S, and T; $X^{54}$ can be selected from A, D, E, G, I, M, N, Q, R, S, and T; $X^{55}$ can be selected from D, E, F, Q, S, T, W, and Y $X^{56}$ can be selected from D, E, F, G, L, M, N, Q, and Y; $X^{57}$ can be selected from E, G, N, S and Q; $X^{58}$ can be selected from I, K, M, P, T, and V; $X^{59}$ can be selected from I, L, M, S, T, and V; $X^{60}$ can be selected from F, I, and L; $X^{61}$ can be selected from F, T, and W; and $X^{62}$ can be selected from A, E, F, G, I, K, L, M, N, P, Q, S, T, V, W, and Y.

In IL-2Rγc ligands of Formula (4) and (4a), $X^{51}$ can be selected from I, L, and V.

In IL-2Rγc ligands of Formula (4) and (4a), $X^{52}$ can be selected from S and T.

In IL-2Rγc ligands of Formula (4) and (4a), $X^{53}$ can be selected from D, E, N, and Q.

In IL-2Rγc ligands of Formula (4) and (4a), $X^{54}$ can be selected from D, E, N, and Q.

In IL-2Rγc ligands of Formula (4) and (4a), $X^{55}$ can be selected from F, W, and Y.

In IL-2Rγc ligands of Formula (4) and (4a), $X^{56}$ can be selected from D, E, N, and Q.

In IL-2Rγc ligands of Formula (4) and (4a), $X^{57}$ can be G.

In IL-2Rγc ligands of Formula (4) and (4a), $X^{58}$ can be selected from I and V.

In IL-2Rγc ligands of Formula (4) and (4a), $X^{59}$ can be selected from I, L, M, and V.

In IL-2Rγc ligands of Formula (4) and (4a), $X^{60}$ can be selected from F, I, and L.

In IL-2Rγc ligands of Formula (4) and (4a), $X^{61}$ can be W.

In IL-2Rγc ligands of Formula (4) and (4a), $X^{62}$ can be selected from N and Q.

In IL-2Rγc ligands of Formula (4) and (4a), $X^{51}$ can be selected from I, L, and V; $X^{52}$ can be selected from S and T; $X^{53}$ can be selected from D, E, N, and Q; $X^{54}$ can be selected from D and N; $X^{55}$ can be selected from F, W, and Y; $X^{56}$ can be selected from D, E, N, and Q; $X^{57}$ can be G; $X^{58}$ can be selected from I and V; $X^{59}$ can be selected from I, L, M, and V; $X^{60}$ can be selected from F, I, and L; $X^{61}$ can be W; and $X^{62}$ can be selected from N and Q.

An IL-2Rγc ligand can comprise an amino acid sequence selected from any one of SEQ ID NO: 196 to SEQ ID NO: 210 and SEQ ID NO: 904 to SEQ ID NO: 913:

| | |
|---|---|
| Q L C Q I W Q E V L L C W P | SEQ ID NO: 196 |
| I E C N R D E C P M I C W A | SEQ ID NO: 197 |
| K V C E M W G G V L L C W N | SEQ ID NO: 198 |
| L E C N N S Y G V L L C W S | SEQ ID NO: 199 |
| R I C Q D F Q G V I L C W L | SEQ ID NO: 200 |
| R R C Q D Y L G I L L C W E | SEQ ID NO: 201 |
| R T C T E W E N V V L C W V | SEQ ID NO: 202 |
| T S C F N F D G V L L C W Q | SEQ ID NO: 203 |
| V S C E S W Q G T L F C W Q | SEQ ID NO: 204 |
| V T C Q D W N G V L L C F P | SEQ ID NO: 205 |
| G T C Q E Y N G V M I C W G | SEQ ID NO: 206 |
| I A C S Q E M G I L L C W V | SEQ ID NO: 207 |
| K W C Q D W F G V L L C T V | SEQ ID NO: 208 |
| L T C Q N W Q G V S L C W N | SEQ ID NO: 209 |
| L V C D D T L G V T L C W W | SEQ ID NO: 210 |
| I H C N S Q M G I L I C W Y | SEQ ID NO: 904 |
| I M C D S S S G V S I C W T | SEQ ID NO: 905 |
| I T C Q T F N G V P L C W K | SEQ ID NO: 906 |
| L E C D A S M S V M I C W F | SEQ ID NO: 907 |
| R V C Q D W L G V K L C W N | SEQ ID NO: 908 |
| V S C D G S S G V L L C W M | SEQ ID NO: 909 |
| Y L C D E S M G V K L C W F | SEQ ID NO: 910 |
| V T C Q T W N Q V L L C W S | SEQ ID NO: 911 |
| L D C D T S M G V P L C W F | SEQ ID NO: 912 |
| V M C E D W G G V P I C W I | SEQ ID NO: 913 |

An IL-2Rγc ligand can comprise an amino acid sequence selected from any one of SEQ ID NO: 194 to SEQ ID NO: 210 and SEQ ID NO: 904 to SEQ ID NO: 913 and SEQ ID NOS 1065-1070, wherein the amino acid sequence can be terminated with amino acids -G-G- on the N-terminus, on the C-terminus, or on both the N- and C-termini.

An IL-2Rγc ligand can comprise an amino acid sequence selected from any one of SEQ ID NO: 194 to SEQ ID NO: 210 and SEQ ID NO: 904 to SEQ ID NO: 913 and SEQ ID NOS 1065-1070, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

IL-2Rγc ligands of SEQ ID NO: 194 to SEQ ID NO: 210 and SEQ ID NO: 904 to SEQ ID NO: 913 and SEQ ID NOS 1065-1070 exhibit a binding affinity ($IC_{50}$) to the IL-2Rγc subunit of less than 100 pM.

An IL-2Rγc ligand can comprise the amino acid sequence of Formula (4) (SEQ ID NO: 1065) or the amino acid sequence of Formula (4a) (SEQ ID NO: 1066):

$$-X^{53}-X^{54}-X^{55}-X^{56}-X^{57}-X^{58}-X^{59}-X^{60}- \quad (4)$$

$$-X^{51}-X^{52}-C-X^{53}-X^{54}-X^{55}-X^{56}-X^{57}- \\ X^{58}-X^{59}-X^{60}-C-X^{61}-X^{62}- \quad (4a)$$

wherein, $X^{51}$ can be selected from an amino acid; $X^{52}$ can be selected from an amino acid; $X^{53}$ can be selected from an amino acid comprising a polar-neutral side chain or an acidic side chain; $X^{54}$ can be selected from an amino acid comprising a polar-neutral side chain or an acidic side chain; $X^{55}$ can be selected from an amino acid; $X^{56}$ can be selected from an amino acid; $X^{57}$ can be selected from an amino acid comprising a small hydrophobic side chain; $X^{58}$ can be selected from an amino acid comprising a large hydrophobic side chain; $X^{59}$ can be selected from an amino acid comprising a large hydrophobic side chain; $X^{60}$ can be selected from an amino acid comprising a large hydrophobic side chain; $X^{61}$ can be selected from an amino acid comprising a large hydrophobic side chain; and $X^{62}$ can be selected from an amino acid.

In IL-2Rγc ligands of Formula (4) and (4a), $X^{51}$ can be selected from an amino acid comprising a large hydrophobic side chain and a basic side chain; $X^{52}$ can be selected from an amino acid comprising a hydroxyl-containing side chain and a large hydrophobic side chain; $X^{53}$ can be selected from an amino acid comprising a polar-neutral side chain or an acidic side chain; $X^{54}$ can be selected from an amino acid comprising a polar-neutral side chain or an acidic side chain; $X^{55}$ can be selected from an amino acid comprising a large hydrophobic side chain; $X^{56}$ can be selected from an amino acid comprising a polar-neutral side chain or an acidic side chain; $X^{57}$ can be selected from an amino acid comprising a small hydrophobic side chain; $X^{58}$ can be selected from an amino acid comprising a large hydrophobic side chain; $X^{59}$ can be selected from an amino acid comprising a large hydrophobic side chain; $X^{60}$ can be selected from an amino acid comprising a large hydrophobic side chain; $X^{61}$ can be selected from an amino acid comprising a large hydrophobic side chain; and $X^{62}$ can be selected from an amino acid comprising a polar-neutral side chain.

In IL-2Rγc ligands of Formula (4) and (4a), $X^{51}$ can be selected from R, K, H, F, I, L, M, V, Y, and W; $X^{52}$ can be selected from S, T, F, I, L, M, V, Y, and W; $X^{53}$ can be selected from D, E, H, N, Q, S, T, and Y; $X^{54}$ can be selected from D, E, H, N, Q, S, T, and Y; $X^{55}$ can be selected from F, I, L, M, V, Y, and W; $X^{56}$ can be selected from D, E, H, N, Q, S, T, and Y; $X^{57}$ can be selected from A, G, P, S, and T; $X^{58}$ can be selected from F, I, L, M, V, Y, and W; $X^{59}$ can be selected from F, I, L, M, V, Y, and W; $X^{60}$ can be selected from F, I, L, M, V, Y, and W; $X^{61}$ can be selected from F, I, L, M, V, Y, and W; and $X^{62}$ can be selected from H, N, Q, S, T, and Y.

In IL-2Rγc ligands of Formula (4) and (4a), $X^{51}$ can be selected from I, L, and V.

In IL-2Rγc ligands of Formula (4) and (4a), $X^{52}$ can be selected from S and T.

In IL-2Rγc ligands of Formula (4) and (4a), $X^{53}$ can be selected from D, E, and Q.

In IL-2Rγc ligands of Formula (4) and (4a), $X^{54}$ can be selected from D, E, and N.

In IL-2Rγc ligands of Formula (4) and (4a), $X^{55}$ can be selected from F, Y, and W.

In IL-2Rγc ligands of Formula (4) and (4a), $X^{56}$ can be selected from D, E, N, and Q.

In IL-2Rγc ligands of Formula (4) and (4a), $X^{57}$ can be G.

In IL-2Rγc ligands of Formula (4) and (4a), $X^{58}$ can be selected from I and V.

In IL-2Rγc ligands of Formula (4) and (4a), $X^{59}$ can be selected from I, L, M, and V.

In IL-2Rγc ligands of Formula (4) and (4a), $X^{60}$ can be selected from F, I, and L.

In IL-2Rγc ligands of Formula (4) and (4a), $X^{61}$ can be W.

In IL-2Rγc ligands of Formula (4) and (4a), $X^{62}$ can be selected from N and Q.

In IL-2Rγc ligands of Formula (4) and (4a), $X^{51}$ can be selected from I, L, and V; $X^{52}$ can be selected from S and T; $X^{53}$ can be selected from D, E, and Q; $X^{54}$ can be selected from D, E, and N; $X^{55}$ can be selected from F, Y, and W; $X^{56}$ can be selected from D, E, N, and Q; $X^{57}$ can be G; $X^{58}$ can be selected from I and V; $X^{59}$ can be selected from I, L, M, and V; $X^{60}$ can be selected from F, I, and L; $X^{61}$ can be W; and $X^{62}$ can be selected from N and Q.

In IL-2Rγc ligands of Formula (4) and (4a), $X^{51}$ can be selected from G, I, K, L, Q, R, and V; $X^{52}$ can be selected from A, D, E, H, I, L, M, R, S, T, V, and W; $X^{53}$ can be selected from D, E, F, N, Q, S, and T; $X^{54}$ can be selected from A, D, E, G, I, M, N, R, S, and T; $X^{55}$ can be selected from D, E, F, Q, S, T, W, and Y; $X^{56}$ can be selected from D, E, F, G, L, M, N, Q, S, and Y; $X^{57}$ can be selected from C, E, G, N, Q, and S; $X^{58}$ can be selected from I, P, T, and V; $X^{59}$ can be selected from I, K, L, M, P, S, T, and V; $X^{60}$ can be selected from F, I, and L; $X^{61}$ can be selected from F, T, and W; and $X^{62}$ can be selected from A, E, F, G, I, K, L, M, N, P, Q, S, T, V, W, and Y.

In IL-2Rγc ligands of Formula (4) and (4a), $X^{51}$ can be selected from I, L, and V; $X^{52}$ can be selected from S and T; $X^{53}$ can be selected from D, E, N, and Q; $X^{54}$ can be selected from D, E, N, S, and T; $X^{55}$ can be selected from F, S, T, W, and Y; $X^{56}$ can be selected from D, E, N, and Q; $X^{57}$ can be selected from G and N; $X^{58}$ can be selected from I and V; $X^{59}$ can be selected from I, L, M, and V; $X^{60}$ can be selected from F, I, and L; $X^{61}$ can be W; and $X^{62}$ can be selected from N and Q.

In IL-2Rγc ligands of Formula (4) and (4a), $X^{51}$ can be selected from I, L, and V; $X^{52}$ can be selected from S and T; $X^{53}$ can be Q; $X^{54}$ can be selected from D, E, N, S, and T; $X^{55}$ can be selected from S, T, and W; $X^{56}$ can be selected from D, E, N, and Q; $X^{57}$ can be G; $X^{58}$ can be V; $X^{59}$ can be L; $X^{60}$ can be L; $X^{61}$ can be W; and $X^{62}$ can be selected from N and Q.

An IL-2Rγc ligand can comprise the amino acid sequence of Formula (5) (SEQ ID NO: 211) or Formula (5a) (SEQ ID NO: 212):

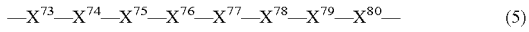  (5)

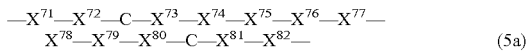  (5a)

wherein, $X^{71}$ can be selected from F, G, I, L, P, Q, R, T, and V; $X^{72}$ can be selected from A, D, E, I, M, R, S, T, and V; $X^{73}$ can be selected from D, E, F, M, N, Q, S T, V, W, and Y; $X^{74}$ can be selected from D, E, F, G, I, L, M, P, R, S, T, and V; $X^{75}$ can be selected from F, H, L, W, and Y; $X^{76}$ can be selected from D, E, H, L, N, Q, S, and T; $X^{77}$ can be selected from G, T, Q, and E; $X^{78}$ can be selected from I, L, M, Q, and V; $X^{79}$ can be selected from D, E, N, Q, and R; $X^{80}$ can be selected from D, F, I, and L; $X^{81}$ can be selected from F, I, L, R, T, W, and Y; and $X^{82}$ can be selected from A, F, G, H, I, L, N, P, Q, S, T, and W.

In IL-2Rγc ligands of Formula (5) and (5a), $X^{71}$ can be selected from I, L, and V.

In IL-2Rγc ligands of Formula (5) and (5a), $X^{72}$ can be selected from A, D, E, I, M, and V.

In IL-2Rγc ligands of Formula (5) and (5a), $X^{73}$ can be selected from E, Q, and N.

In IL-2Rγc ligands of Formula (5) and (5a), $X^{74}$ can be selected from D and E.

In IL-2Rγc ligands of Formula (5) and (5a), $X^{75}$ can be selected from F, W, and Y.

In IL-2Rγc ligands of Formula (5) and (5a), $X^{76}$ can be selected from D, E, L, N, and Q.

In IL-2Rγc ligands of Formula (5) and (5a), $X^{77}$ can be G.

In IL-2Rγc ligands of Formula (5) and (5a), $X^{78}$ can be selected from I, M, and V.

In IL-2Rγc ligands of Formula (5) and (5a), $X^{79}$ can be selected from D, E, Q, and R.

In IL-2Rγc ligands of Formula (5) and (5a), $X^{80}$ can be selected from F, I, and L.

In IL-2Rγc ligands of Formula (5) and (5a), $X^{81}$ can be W.

In IL-2Rγc ligands of Formula (5) and (5a), $X^{82}$ can be selected from N and Q.

In IL-2Rγc ligands of Formula (5) and (5a), $X^{71}$ can be selected from I, L, and V; $X^{72}$ can be selected from A, D, E, I, M, and V; $X^{73}$ can be selected from E, Q, and N; $X^{74}$ can be selected from D and E; $X^{75}$ can be selected from F, W, and Y; $X^{76}$ can be selected from D, E, L, N, and Q; $X^{77}$ can be G; $X^{78}$ can be selected from I, M, and V; $X^{79}$ can be selected from D, E, Q, and R; $X^{80}$ can be selected from F, I, and L; $X^{81}$ can be W; and $X^{82}$ can be selected from N and Q.

An IL-2Rγc ligand can comprise the amino acid sequence of Formula (5) (SEQ ID NO: 1071) or Formula (5a) (SEQ ID NO: 1072):

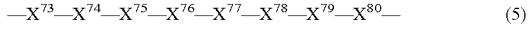  (5)

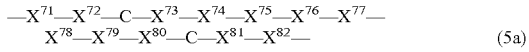  (5a)

wherein, $X^{71}$ can be selected from an amino acid; $X^{72}$ can be selected from an amino acid; $X^{73}$ can be selected from an amino acid; $X^{74}$ can be selected from an amino acid; $X^{75}$ can be selected from an amino acid comprising a large hydrophobic side chain; $X^{76}$ can be selected from an amino acid; $X^{77}$ can be selected from a small hydrophobic side chain; $X^{78}$ can be selected from an amino acid comprising a large hydrophobic side chain; $X^{79}$ can be selected from an amino acid comprising a basic side chain, an acidic side chain, or a polar-neutral side chain; $X^{80}$ can be selected from an amino acid comprising a large hydrophobic side chain; $X^{81}$ can be selected from an amino acid comprising a large hydrophobic side chain; and $X^{82}$ can be selected from an amino acid.

In IL-2Rγc ligands of Formula (5) and (5a), $X^{71}$ can be selected from an amino acid comprising a large hydrophobic side chain; $X^{72}$ can be selected from an amino acid comprising an acidic side chain or a large hydrophobic side chain; $X^{73}$ can be selected from an amino acid comprising an acidic side chain, a hydroxyl-containing side chain, or a polar neutral side chain; $X^{74}$ can be selected from an amino acid comprising an acidic side chain, a hydroxyl-containing side chain, or a large hydrophobic side chain; $X^{75}$ can be selected from an amino acid comprising a large hydrophobic side chain; $X^{76}$ can be selected from an amino acid comprising an acidic side chain, a hydroxyl-containing side chain, or a polar neutral side chain; $X^{77}$ can be selected from a small hydrophobic side chain; $X^{78}$ can be selected from an amino acid comprising a large hydrophobic side chain; $X^{79}$ can be selected from an amino acid comprising a basic side chain, an acidic side chain, or a polar-neutral side chain; $X^{80}$ can be selected from an amino acid comprising a large hydrophobic side chain; $X^{81}$ can be selected from an amino acid comprising a large hydrophobic side chain; and $X^{82}$ can be selected from an amino acid comprising a polar neutral side chain.

In IL-2Rγc ligands of Formula (5) and (5a), $X^{71}$ can be selected from F, I, L, M, V, Y, and W; $X^{72}$ can be selected from D, E, F, I, L, M, V, Y, and W; $X^{73}$ can be selected from D, E, S, T, H, N, Q, S, T, and Y; $X^{74}$ can be selected from D, E, S, T, F, I, L, M, V, Y, and W; $X^{75}$ can be selected from F, I, L, M, V, Y, and W; $X^{76}$ can be selected from D, E, S, T, H, N, Q, S, T, and Y; $X^{77}$ can be selected from A, G, P, S, and T; $X^{78}$ can be selected from F, I, L, M, V, Y, and W; $X^{79}$ can be selected from R, K, H, D, E, H, N, Q, S, T, and Y; $X^{80}$ can be selected from F, I, L, M, V, Y, and W; $X^{81}$ can be selected from F, I, L, M, V, Y, and W; and $X^{82}$ can be selected from H, N, Q, S, T, and Y.

In IL-2Rγc ligands of Formula (5) and (5a), $X^{71}$ can be selected from I, L, and V.

In IL-2Rγc ligands of Formula (5) and (5a), $X^{72}$ can be selected from D, E, I, M, and V.

In IL-2Rγc ligands of Formula (5) and (5a), $X^{73}$ can be selected from E, N, and Q.

In IL-2Rγc ligands of Formula (5) and (5a), $X^{74}$ can be selected from D and E.

In IL-2Rγc ligands of Formula (5) and (5a), $X^{75}$ can be selected from F, W, and Y.

In IL-2Rγc ligands of Formula (5) and (5a), $X^{76}$ can be selected from D, E, and N.

In IL-2Rγc ligands of Formula (5) and (5a), $X^{77}$ can be G.

In IL-2Rγc ligands of Formula (5) and (5a), $X^{78}$ can be selected from I, M, and V.

In IL-2Rγc ligands of Formula (5) and (5a), $X^{79}$ can be selected from D, E, N, Q, and R.

In IL-2Rγc ligands of Formula (5) and (5a), $X^{80}$ can be selected from F, I, and L.

In IL-2Rγc ligands of Formula (5) and (5a), $X^{81}$ can be W.

In IL-2Rγc ligands of Formula (5) and (5a), $X^{82}$ can be selected from N and Q.

In IL-2Rγc ligands of Formula (5) and (5a), $X^{71}$ can be selected from I, L, and V; $X^{72}$ can be selected from D, E, I, M, and V; $X^{73}$ can be selected from E, N, and Q; $X^{74}$ can be selected from D and E; $X^{75}$ can be selected from F, W, and Y; $X^{76}$ can be selected from D, E, and N; $X^{77}$ can be G; $X^{78}$ can be selected from I, M, and V; $X^{79}$ can be selected from D, E, N, Q, and R; $X^{80}$ can be selected from F, I, and L; $X^{81}$ can be W; and $X^{82}$ can be selected from N and Q.

In IL-2Rγc ligands of Formula (5) and (5a), $X^{71}$ can be selected from F, G, I, L, P, Q, R, T, and V; $X^{72}$ can be selected from A, D, E, I, M, L, M, R, S, T, and V; $X^{73}$ can be selected from D, E, F, M, N, Q, S, T, V, W, and Y; $X^{74}$ can be selected from D, E, F, G, I, L, M, P, R, S, T, and V; $X^{75}$ can be selected from F, H, L, W, and Y; $X^{76}$ can be selected from D, E, H, L, N, Q, S, and T; $X^{77}$ can be selected from E, G, Q, and T; $X^{78}$ can be selected from I, L, M, Q, and V; $X^{79}$ can be selected from D, E, N, Q, and R; $X^{80}$ can be selected from D, F, I, and L; $X^{81}$ can be selected from C, F, I, L, Q, R, T, W, and Y; and $X^{82}$ can be selected from A, F, G, H, I, L, N, P, Q, S, T, and W.

In IL-2Rγc ligands of Formula (5) and (5a), $X^{71}$ can be selected from F, I, L, and V; $X^{72}$ can be selected from D, E, I, S, T, and V; $X^{73}$ can be selected from D, E, N, and Q; $X^{74}$ can be selected from D, E, F, I, L, M, and V; $X^{75}$ can be selected from F, W, and Y; $X^{76}$ can be selected from D, E, N, and Q; $X^{77}$ can be G; $X^{78}$ can be selected from I, L, M, and V; $X^{79}$ can be selected from D, E, N, Q, and R; $X^{80}$ can be selected from D, F, I, and L; $X^{81}$ can be selected from F, I, L, and W; and $X^{82}$ can be selected from F, I, L, N, Q, and W.

In IL-2Rγc ligands of Formula (5) and (5a), $X^{71}$ can be selected from F, I, L, and V; $X^{72}$ can be selected from D, E, I, S, T, and V; $X^{73}$ can be selected from D, E, N, and Q; $X^{74}$ can be selected from D, E, F, I, L, M, and V; $X^{75}$ can be W; $X^{76}$ can be selected from D, E, N, and Q; $X^{77}$ an be G; $X^{78}$ can be V; $X^{79}$ can be selected from D, E, N, Q, and R; $X^{80}$ can be L; $X^{81}$ can be W; and $X^{82}$ can be selected from F, I, L, N, Q, and W.

An IL-2Rγc ligand can comprise an amino acid sequence selected from any one of SEQ ID NO: 213 to SEQ ID NO: 233 and SEQ ID NO: 914 to SEQ ID NO: 920:

```
                                        SEQ ID NO: 213
I E C E F W D G M Q L C W Q

SEQ ID NO: 214
Q I C Q E W S G V N L C W H

SEQ ID NO: 215
I L C Q D W S G I E I C W S

SEQ ID NO: 216
L I C Y T Y E G V E L C W Q

SEQ ID NO: 217
L V C S M F N G V D L C W Q

SEQ ID NO: 218
P R C E I W L G V E L C R I

SEQ ID NO: 219
T E C Q V W N G V E L C Y I

SEQ ID NO: 220
V D C V I W E G V Q L C T W

SEQ ID NO: 221
V V C T D Y L G V Q L C W T

SEQ ID NO: 222
V M C E R W Q G V E L C W L

SEQ ID NO: 223
V V C Q G W S G V D I C W Q

SEQ ID NO: 224
D C S M W E G V E L C W

SEQ ID NO: 225
I V C E E W S G V R F C W N

SEQ ID NO: 226
Q T C W D Y E G M E L C L I

SEQ ID NO: 227
P A C Q D W N G V E L C I L

SEQ ID NO: 228
Q E C T D W Q G V E L C L L

SEQ ID NO: 229
R I C N D W N G V Q L C W P

SEQ ID NO: 230
V I C Q S Y D G V E F C W F

SEQ ID NO: 231
V V C E M Y S G V Q I C W A

SEQ ID NO: 232
L D C M D Y N G V R L C W N

SEQ ID NO: 233
F T C W D Y N G V D L C Q I

SEQ ID NO: 914
F S C F I L E T L E L A C W P

SEQ ID NO: 915
G A C N P H T Q Q E D C F G

SEQ ID NO: 916
I E C Q V F H G L E L C W I

SEQ ID NO: 917
V M C E L F D E V E L C W F

SEQ ID NO: 918
F V C E L W D G I E L C I P

SEQ ID NO: 919
L T C V T Y E G V D L C W Q

SEQ ID NO: 920
V E C D V Y H G V E I C W A
```

An IL-2Rγc ligand can comprise an amino acid sequence selected from any one of SEQ ID NO: 211 to SEQ ID NO: 233 and SEQ ID NO: 914 to SEQ ID NO: 920 and SEQ ID NOS 1071-1074, wherein the amino acid sequence can be terminated with amino acids -G-G- on the N-terminus, on the C-terminus, or on both the N- and C-termini.

An IL-2Rγc ligand can comprise an amino acid sequence selected from any one of SEQ ID NO: 211 to SEQ ID NO: 233 and SEQ ID NO: 914 to SEQ ID NO: 920 and SEQ ID NOS 1071-1074, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

IL-2Rγc ligands of SEQ ID NO: 211 to SEQ ID NO: 233 and SEQ ID NO: 914 to SEQ ID NO: 920 and SEQ ID NOS 1071-1074, exhibit a binding affinity (IC$_{50}$) to the IL-2Rγc subunit of less than 100 μM.

An IL-2Rγc ligand can comprise the amino acid sequence of Formula (6) (SEQ ID NO: 234) or Formula (6a) (SEQ ID NO: 235):

$$-X^{93}-X^{94}-X^{95}-X^{96}-X^{97}-X^{98}-X^{99}-X^{100}-X^{101}- \quad (6)$$

$$-X^{91}-X^{92}-X^{93}-X^{94}-X^{95}-X^{96}-X^{97}-X^{98}-X^{99}-X^{100}-X^{101}-X^{102}-X^{103}- \quad (6a)$$

wherein, $X^{91}$ can be selected from C, D, E, and L; $X^{92}$ can be selected from C, L, M, R, S, V, and W; $X^{93}$ can be selected from C, D, F, P, and R; $X^{94}$ can be selected from A, D, L, Q, S, and W; $X^{95}$ can be selected from D, E, F, L, and V; $X^{96}$ can be selected from A, D, E, F, G, K, Q, and S; $X^{97}$ can be selected from E, L, M, and W; $X^{98}$ can be selected from G, I, L, W, and Y; $X^{99}$ can be selected from E, I, R, T, and V; $X^{100}$ can be W; $X^{101}$ can be selected from C, A, I, L, P, and V; $X^{102}$ can be selected from C, D, G, H; and $X^{103}$ can be selected from C, D, E, H, S, and T.

In IL-2Rγc ligands of Formula (6) and (6a), $X^{91}$ can be selected from D and E.

In IL-2Rγc ligands of Formula (6) and (6a), $X^{92}$ can be selected from L, M, R, S, V, and W.

In IL-2Rγc ligands of Formula (6) and (6a), $X^{93}$ can be selected from D and F.

In IL-2Rγc ligands of Formula (6) and (6a), $X^{94}$ can be S.

In IL-2Rγc ligands of Formula (6) and (6a), $X^{95}$ can be selected from D and E.

In IL-2Rγc ligands of Formula (6) and (6a), $X^{96}$ can be selected from D and E.

In IL-2Rγc ligands of Formula (6) and (6a), $X^{97}$ can be selected from L, M, and W.

In IL-2Rγc ligands of Formula (6) and (6a), $X^{98}$ can be G.

In IL-2Rγc ligands of Formula (6) and (6a), $X^{99}$ can be E.

In IL-2Rγc ligands of Formula (6) and (6a), $X^{100}$ can be W.

In IL-2Rγc ligands of Formula (6) and (6a), $X^{101}$ can be selected from I, L, and V.

In IL-2Rγc ligands of Formula (6) and (6a), $X^{102}$ can be selected from D and G.

In IL-2Rγc ligands of Formula (6) and (6a), $X^{103}$ can be selected from S and T.

In IL-2Rγc ligands of Formula (6) and (6a), $X^{91}$ can be selected from D and E; $X^{92}$ can be selected from L, M, R, S, V, and W; $X^{93}$ can be selected from D and F; $X^{94}$ can be S; $X^{95}$ can be selected from D and E; $X^{96}$ can be selected from D and E; $X^{97}$ can be selected from L, M, and W; $X^{98}$ can be G; $X^{99}$ can be E; $X^{100}$ can be W; $X^{101}$ can be selected from I, L, and V; $X^{102}$ can be selected from D and G; and $X^{103}$ can be selected from S and T.

An IL-2Rγc ligand can comprise an amino acid sequence selected from any one of SEQ ID NO: 236 to SEQ ID NO: 245:

```
                                    SEQ ID NO: 236
M C W L E W G E W V G S C L

SEQ ID NO: 237
L C F S E F L G E W V D C N

SEQ ID NO: 238
V C S F D E A W G E W I C E

SEQ ID NO: 239
D C P Q V S W Y E W L D C Y

SEQ ID NO: 240
Y C L F D E Q M G E W L C H

SEQ ID NO: 241
C E S F S E A L G T W I D C

SEQ ID NO: 242
C V F L E D W W I W A G D C

SEQ ID NO: 243
E C D A F G W I I W P H C L

SEQ ID NO: 244
F C W D S D K M L R W V C S

SEQ ID NO: 245
Q C R R S D F E Y V W L C T
```

An IL-2Rγc ligand can comprise an amino acid sequence selected from any one of SEQ ID NO: 234 to SEQ ID NO: 245 and SEQ ID NOS 1075-1076, wherein the amino acid sequence can be terminated with amino acids -G-G- on the N-terminus, on the C-terminus, or on both the N- and C-termini.

An IL-2Rγc ligand can comprise an amino acid sequence selected from any one of SEQ ID NO: 234 to SEQ ID NO: 245 and SEQ ID NOS 1075-1076, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

IL-2Rγc ligands of SEQ ID NO: 234 to SEQ ID NO: 245 and SEQ ID NOS 1075-1076 exhibit a binding affinity (IC$_{50}$) to the IL-2Rγc subunit of less than 100 μM.

An IL-2Rγc ligand can comprise the amino acid sequence of Formula (6) (SEQ ID NO: 1075) or Formula (6a) (SEQ ID NO: 1076):

$$-X^{93}-X^{94}-X^{95}-X^{96}-X^{97}-X^{98}-X^{99}-X^{100}-X^{101}- \quad (6)$$

$$-X^{91}-X^{92}-X^{93}-X^{94}-X^{95}-X^{96}-X^{97}-X^{98}-X^{99}-X^{100}-X^{101}-X^{102}-X^{103}- \quad (6a)$$

wherein, $X^{91}$ can be selected from an amino acid comprising an acidic side chain or cysteine; $X^{92}$ can be selected from an amino acid; $X^{93}$ can be selected from an amino acid comprising an acidic side chain or large hydrophobic side chain; $X^{94}$ can be selected from an amino acid; $X^{95}$ can be selected from an amino acid; $X^{96}$ can be selected from an amino acid; $X^{97}$ can be selected from an amino acid comprising a large hydrophobic side chain; $X^{98}$ can be selected from an amino acid comprising a small hydrophobic side chain or a large hydrophobic side chain; $X^{99}$ can be selected from an amino acid; $X^{100}$ can be selected from an amino acid comprising a large hydrophobic side chain; $X^{101}$ can be selected from an amino acid comprising a large hydrophobic side chain; $X^{102}$ can be selected from an amino acid comprising a small hydrophobic side chain or an acidic side chain or cysteine; and $X^{103}$ can be selected from an amino acid comprising an acidic side chain or a hydroxyl-containing side chain or cysteine.

In IL-2Rγc ligands of Formula (6) and (6a), $X^{91}$ can be selected from an amino acid comprising an acidic side chain; $X^{92}$ can be selected from an amino acid; $X^{93}$ can be selected from an amino acid comprising an acidic side chain or large hydrophobic side chain; $X^{94}$ can be selected from an amino acid comprising an acidic side chain or a hydroxyl-containing side chain; $X^{95}$ can be selected from an amino acid comprising an acidic side chain; $X^{96}$ can be selected from an amino acid; $X^{97}$ can be selected from an amino acid comprising a large hydrophobic side chain; $X^{98}$ can be selected from an amino acid comprising a small hydrophobic side chain or a large hydrophobic side chain; $X^{99}$ can be selected from an amino acid comprising an acidic side chain or large hydrophobic side chain; $X^{100}$ can be selected from an amino acid comprising a large hydrophobic side chain; $X^{101}$ can be selected from an amino acid comprising a large hydrophobic side chain; $X^{102}$ can be selected from an amino acid comprising a small hydrophobic side chain or an acidic side chain; and $X^{103}$ can be selected from an amino acid comprising an acidic side chain or a hydroxyl-containing side chain.

In IL-2Rγc ligands of Formula (6) and (6a), $X^{91}$ can be selected from D and E; $X^{92}$ can be selected from an amino acid; $X^{93}$ can be selected from D, E, F, I, L, M, V, Y, and W; $X^{94}$ can be selected from D, E, S, and T; $X^{95}$ can be selected from D and E; $X^{96}$ can be selected from an amino acid; $X^{97}$ can be selected from F, I, L, M, V, Y, and W; $X^{98}$ can be selected from A, G, P, S, T, F, I, L, M, V, Y, and W; $X^{99}$ can be selected from D, E, F, I, L, M, V, Y, and W; $X^{100}$ can be selected from F, I, L, M, V, Y, and W; $X^{101}$ can be selected from F, I, L, M, V, Y, and W; $X^{102}$ can be selected from D, E, A, G, P, S, and T; and $X^{103}$ can be selected from D, E, S, and T.

In IL-2Rγc ligands of Formula (6)-(6a), $X^{91}$ can be selected from D and E.

In IL-2Rγc ligands of Formula (6)-(6a), $X^{92}$ can be selected from an amino acid.

In IL-2Rγc ligands of Formula (6) and (6a), $X^{93}$ can be selected from D and F.

In IL-2Rγc ligands of Formula (6) and (6a), $X^{94}$ can be S.

In IL-2Rγc ligands of Formula (6) and (6a), $X^{95}$ can be selected from D and E.

In IL-2Rγc ligands of Formula (6) and (6a), $X^{96}$ can be selected from an amino acid.

In IL-2Rγc ligands of Formula (6) and (6a), $X^{97}$ can be selected from L, M, and W.

In IL-2Rγc ligands of Formula (6) and (6a), $X^{98}$ can be G.

In IL-2Rγc ligands of Formula (6) and (6a), $X^{99}$ can be E.

In IL-2Rγc ligands of Formula (6) and (6a), $X^{100}$ can be W.

In IL-2Rγc ligands of Formula (6) and (6a), $X^{101}$ can be selected from I, L, and V.

In IL-2Rγc ligands of Formula (6) and (6a), $X^{102}$ can be selected from D and G.

In IL-2Rγc ligands of Formula (6) and (6a), $X^{103}$ can be selected from S and T.

In IL-2Rγc ligands of Formula (6) and (6a), $X^{91}$ can be selected from D and E; $X^{92}$ can be selected from an amino acid; $X^{93}$ can be selected from D and F; $X^{94}$ can be S; $X^{95}$ can be selected from D and E; $X^{96}$ can be selected from an amino acid; $X^{97}$ can be selected from L, M, and W; $X^{98}$ can be G; $X^{99}$ can be E; $X^{100}$ can be W; $X^{101}$ can be selected from I, L, and V; $X^{102}$ can be selected from D and G; and $X^{103}$ can be selected from S and T.

An IL-2Rγc ligand can comprise the amino acid sequence of Formula (7) (SEQ ID NO: 246) or Formula (7a) (SEQ ID NO: 247):

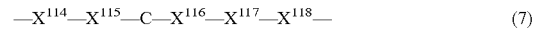

(7)

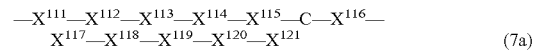

(7a)

wherein, $X^{111}$ can be selected from D, G, I, and Q; $X^{112}$ can be selected from D, I, and L; $X^{113}$ can be selected from G, L, M, Q, R, S, and Y; $X^{114}$ can be selected from D, E, G, L, S, T, and Y; $X^{115}$ can be selected from E, L, P, and Q; $X^{116}$ can be selected from D, E, K, L, S, and T; $X^{117}$ can be selected from D, F, S, and W; $X^{118}$ can be selected from F, N, W, and Y; $X^{119}$ can be selected from F, I, L, R, and W; $X^{120}$ can be selected from A, E, L, and S; and $X^{121}$ can be selected from H, I, K, N, Q, and V.

In IL-2Rγc ligands of Formula (7) and (7a), $X^{111}$ can be selected from D and Q.

In IL-2Rγc ligands of Formula (7) and (7a), $X^{112}$ can be selected from I and L.

In IL-2Rγc ligands of Formula (7) and (7a), $X^{113}$ can be selected from G, L, M, R, S, and Y.

In IL-2Rγc ligands of Formula (7) and (7a), $X^{114}$ can be L.

In IL-2Rγc ligands of Formula (7) and (7a), $X^{115}$ can be selected from E and Q.

In IL-2Rγc ligands of Formula (7) and (7a), $X^{116}$ can be selected from D and E.

In IL-2Rγc ligands of Formula (7) and (7a), $X^{117}$ can be selected from F and W.

In IL-2Rγc ligands of Formula (7) and (7a), $X^{118}$ can be selected from F, W, and Y.

In IL-2Rγc ligands of Formula (7) and (7a), $X^{119}$ can be selected from F, I, and L.

In IL-2Rγc ligands of Formula (7) and (7a), $X^{120}$ can be S.

In IL-2Rγc ligands of Formula (7) and (7a), $X^{121}$ can be selected from N and Q.

In IL-2Rγc ligands of Formula (7) and (7a), $X^{111}$ can be selected from D and Q; $X^{112}$ can be selected from I and L; $X^{113}$ can be selected from G, L, M, R, S, and Y; $X^{114}$ can be L; $X^{115}$ can be selected from E and Q; $X^{116}$ can be selected from D and E; $X^{117}$ can be selected from F and W; $X^{118}$ can be selected from F, W, and Y; $X^{119}$ can be selected from F, I, and L; $X^{120}$ can be S; and $X^{121}$ can be selected from N and Q.

In IL-2Rγc ligands of Formula (7) and (7a), $X^{111}$ can be selected from D, G, I, Q, and W; $X^{112}$ can be selected from C, D, I, and L; $X^{113}$ can be selected from G, L, M, Q, R, S, and Y; $X^{114}$ can be selected from D, E, G, L, Q, S, T, and Y; $X^{115}$ can be selected from E, G, L, P, and Q; $X^{116}$ can be selected from D, E, K, L, S, and T; $X^{117}$ can be selected from D, F, S, and W; $X^{118}$ can be selected from F, N, W, and Y; $X^{119}$ can be selected from F, I, L, R, and W; $X^{120}$ can be selected from A, C, E, L, and S; and $X^{121}$ can be selected from H, I, K, N, Q, and V.

In IL-2Rγc ligands of Formula (7) and (7a), $X^{111}$ can be selected from D and Q; $X^{112}$ can be selected from I and L; $X^{113}$ can be selected from G, L, M, Q, R, S, and Y; $X^{114}$ can be selected from D and S; $X^{115}$ can be L; $X^{116}$ can be selected from D and E; $X^{117}$ can be selected from F and W;

$X^{118}$ can be selected from F, W, and Y; $X^{119}$ can be selected from F, I, L, and W; $X^{120}$ can be selected from L and S; and $X^{121}$ can be selected from N and Q.

An IL-2Rγc ligand can comprise an amino acid sequence selected from any one of SEQ ID NO: 248 to SEQ ID NO: 254 and SEQ ID NO: 921 to SEQ ID NO: 922 and SEQ ID NO: 1051:

```
                                    SEQ ID NO: 248
D L S D L C T F W L S Q

SEQ ID NO: 249
G L Q E L C S F Y I A Q

SEQ ID NO: 250
Q I R Q L C E F W L S Q

SEQ ID NO: 251
Q L G T L C D F F R E N

SEQ ID NO: 252
W C L S Q E E F N F L V

SEQ ID NO: 253
Y S E E L S W I C K Q L

SEQ ID NO: 254
I D M Y P Q E W W F C N

SEQ ID NO: 921
L S L G Q K D W W L I L

SEQ ID NO: 922
Q L Q G L C D F F W A H
```

An IL-2Rγc ligand can comprise an amino acid sequence selected from any one of SEQ ID NO: 246 to SEQ ID NO: 254 and SEQ ID NO: 921 to SEQ ID NO: 922 and SEQ ID NOS 1051 and 1077-1082, wherein the amino acid sequence can be terminated with amino acids -G-G- on the N-terminus, on the C-terminus, or on both the N- and C-termini.

An IL-2Rγc ligand can comprise an amino acid sequence selected from any one of SEQ ID NO: 246 to SEQ ID NO: 254 and SEQ ID NO: 921 to SEQ ID NO: 922 and SEQ ID NOS 1051 and 1077-1082, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

IL-2Rγc ligands of SEQ ID NO: 246 to SEQ ID NO: 254 and and SEQ ID NO: 921 to SEQ ID NO: 922 and SEQ ID NOS 1051 and 1077-1082 exhibit a binding affinity ($IC_{50}$) to the IL-2Rγc subunit of less than 100 μM.

An IL-2Rγc ligand can comprise the amino acid sequence of Formula (7) (SEQ ID NO: 1077) or Formula (7a) (SEQ ID NO: 1078):

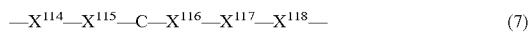

(7)

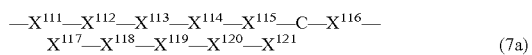

(7a)

wherein, $X^{111}$ can be selected from an amino acid; $X^{112}$ can be selected from an amino acid comprising a large hydrophobic side chain or an acidic side chain; $X^{113}$ can be selected from an amino acid; $X^{114}$ can be selected from an amino acid comprising an acidic side chain or a hydroxyl-containing side chain; $X^{115}$ can be selected from an amino acid; $X^{116}$ can be selected from an amino acid; $X^{117}$ can be selected from an amino acid comprising a large hydrophobic side chain; $X^{118}$ can be selected from an amino acid comprising a large hydrophobic side chain; $X^{119}$ can be selected from an amino acid comprising a large hydrophobic side chain; $X^{120}$ can be selected from an amino acid; and $X^{121}$ can be selected from an amino acid.

In IL-2Rγc ligands of Formula (7) and (7a), $X^{111}$ can be selected from an amino acid; $X^{112}$ can be selected from an amino acid comprising a large hydrophobic side chain or an acidic side chain; $X^{113}$ can be selected from an amino acid; $X^{114}$ can be selected from an amino acid comprising an acidic side chain or a hydroxyl-containing side chain; $X^{115}$ can be selected from an amino acid comprising a large hydrophobic side chain; $X^{116}$ can be selected from an amino acid comprising an acidic side chain; $X^{117}$ can be selected from an amino acid comprising a large hydrophobic side chain; $X^{118}$ can be selected from an amino acid comprising a large hydrophobic side chain; $X^{119}$ can be selected from an amino acid comprising a large hydrophobic side chain; $X^{120}$ can be selected from an amino acid; and $X^{121}$ can be selected from an amino acid comprising a polar-neutral side chain.

In IL-2Rγc ligands of Formula (7) and (7a), $X^{111}$ can be selected from an amino acid; $X^{112}$ can be selected from D, E, F, I, L, M, V, Y, and W; $X^{113}$ can be selected from an amino acid; $X^{114}$ can be selected from D, E, S, and T; $X^{115}$ can be selected from F, I, L, M, V, Y, and W; $X^{116}$ can be selected from D and E; $X^{117}$ can be selected from F, I, L, M, V, Y, and W; $X^{118}$ can be selected from F, I, L, M, V, Y, and W; $X^{119}$ can be selected from F, I, L, M, V, Y, and W; $X^{120}$ can be selected from an amino acid; and $X^{121}$ can be selected from H, N, Q, S, T, and Y.

In IL-2Rγc ligands of Formula (7) and (7a), $X^{111}$ can be selected from an amino acid.

In IL-2Rγc ligands of Formula (7) and (7a), $X^{112}$ can be selected from I and L.

In IL-2Rγc ligands of Formula (7) and (7a), $X^{113}$ can be selected from an amino acid.

In IL-2Rγc ligands of Formula (7) and (7a), $X^{114}$ can be selected from D, E, and S.

In IL-2Rγc ligands of Formula (7) and (7a), $X^{115}$ can be L.

In IL-2Rγc ligands of Formula (7) and (7a), $X^{116}$ can be selected from D and E.

In IL-2Rγc ligands of Formula (7) and (7a), $X^{117}$ can be selected from F and W.

In IL-2Rγc ligands of Formula (7) and (7a), $X^{118}$ can be selected from F, W and Y.

In IL-2Rγc ligands of Formula (7) and (7a), $X^{119}$ can be selected from F, I, and L.

In IL-2Rγc ligands of Formula (7) and (7a), $X^{120}$ can be selected from an amino acid.

In IL-2Rγc ligands of Formula (7) and (7a), $X^{121}$ can be selected from Q and N.

In IL-2Rγc ligands of Formula (7) and (7a), $X^{111}$ can be selected from an amino acid; $X^{112}$ can be selected from I and L; $X^{113}$ can be selected from an amino acid; $X^{114}$ can be selected from D, E, and S; $X^{115}$ can be L; $X^{116}$ can be selected from D and E; $X^{117}$ can be selected from F and W; $X^{118}$ can be selected from F, W and Y; $X^{119}$ can be selected from F, I, and L; $X^{120}$ can be selected from an amino acid; and $X^{121}$ can be selected from Q and N.

An IL-2Rγc ligand can comprise an amino acid sequence selected from any one of SEQ ID NO: 255 to SEQ ID NO: 264 and SEQ ID NO: 923 to SEQ ID NO: 930:

```
                              SEQ ID NO: 255
C P L S L M G S E R I F V C

SEQ ID NO: 256
C T Y F G P D A F R M L F C

SEQ ID NO: 257
C Y F N S I F L G E S P F C

SEQ ID NO: 258
C Y L I Y K N N Q L A L Q C

SEQ ID NO: 259
C Y V V Y N Y Q E F R Y L C

SEQ ID NO: 260
L Y C R D N D G T Q Y C E T

SEQ ID NO: 261
Y Y C Y L N I W T M K C E D

SEQ ID NO: 262
Y Y C Y L N I W P V K C E D

SEQ ID NO: 263
L E C A T S E E P Y Y C Y L

SEQ ID NO: 264
C D C Q H H R C R T G G L V

SEQ ID NO: 923
L F N F C Q G D K T C M Q W H

SEQ ID NO: 924
E C G G A W A M L L W P H C T

SEQ ID NO: 925
I C T R L H D V V P I W S C P

SEQ ID NO: 926
Q C Y R P S R D I P L Y L C S

SEQ ID NO: 927
L F N F C Q G D K T C M Q W H

SEQ ID NO: 928
V C W L T H N R Q S Y Y C D

SEQ ID NO: 929
C D L W P L T A Q N F Y G C

SEQ ID NO: 930
C P G E L R G P E R A W V C
```

An IL-2Rγc ligand can comprise an amino acid sequence selected from any one of SEQ ID NO: 255 to SEQ ID NO: 264 and SEQ ID NO: 923 to SEQ ID NO: 930, wherein the amino acid sequence can be terminated with amino acids -G-G- on the N-terminus, on the C-terminus, or on both the N- and C-termini.

An IL-2Rγc ligand can comprise an amino acid sequence selected from any one of SEQ ID NO: 255 to SEQ ID NO: 264 and SEQ ID NO: 923 to SEQ ID NO: 930, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

IL-2Rγc ligands of SEQ ID NO: 255 to SEQ ID NO: 264 and SEQ ID NO: 923 to SEQ ID NO: 930 exhibit a binding affinity ($IC_{50}$) to the IL-2Rγc subunit of less than 100 μM.

An IL-2Rγc ligand can comprise the amino acid sequence of Formula (8) (SEQ ID NO: 931):

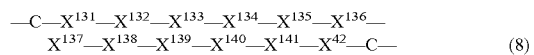

(8)

wherein, $X^{131}$ can be selected from an amino acid comprising a large hydrophobic side chain; $X^{132}$ can be selected from an amino acid comprising a large hydrophobic side chain; $X^{133}$ can be selected from an amino acid comprising a large hydrophobic side chain; $X^{134}$ can be selected from an amino acid comprising a large hydrophobic side chain or an aromatic side chain; $X^{135}$ can be selected from an amino acid comprising a basic side chain and an acidic or polar neutral side chain; $X^{136}$ can be selected from an amino acid; $X^{137}$ can be selected from an amino acid comprising a small hydrophobic side chain; $X^{138}$ can be selected from an amino acid comprising an acidic or a polar neutral side chain; $X^{139}$ can be selected from an amino acid comprising a large hydrophobic side chain or an aromatic side chain; $X^{140}$ can be selected from an amino acid comprising a small hydrophobic side chain or a hydroxyl-containing side chain; $X^{141}$ can be selected from an amino acid comprising a large hydrophobic side chain or an aromatic side chain; and $X^{142}$ can be selected from an amino acid comprising a large hydrophobic side chain.

In IL-2Rγc ligands of Formula (8), $X^{131}$ can be selected from F, I, L, M, V, Y, and W; $X^{132}$ can be selected from F, I, L, M, V, Y, and W; $X^{133}$ can be selected from F, I, L, M, V, Y, and W; $X^{134}$ can be selected from F, H, I, L, M, V, Y, and W; $X^{135}$ can be selected from R, K, H, D, E, N, and Q; $X^{136}$ can be selected from an amino acid; $X^{137}$ can be selected from A, G, P, S, and T; $X^{138}$ can be selected from D, E, N, and Q; $X^{139}$ can be selected from F, H, I, L, M, V, Y, and W; $X^{140}$ can be selected from A, G, P, S, T, and Y; $X^{141}$ can be selected from F, H, I, L, M, V, Y, and W; and $X^{142}$ can be selected from F, I, L, M, V, Y, and W.

In IL-2Rγc ligands of Formula (8), $X^{131}$ can be selected from F and Y; $X^{132}$ can be I; $X^{133}$ can be selected from F, I, L, M, V, Y, and W; $X^{134}$ can be Y; $X^{135}$ can be R; $X^{136}$ can be selected from an amino acid; $X^{137}$ can be G; $X^{138}$ can be E; $X^{139}$ can be F; $X^{140}$ can be selected from S, T, and Y; $X^{141}$ can be Y; and $X^{142}$ can be selected from F, I, L, M, V, Y, and W.

In IL-2Rγc ligands of Formula (8), $X^{131}$ can be selected from F and Y.

In IL-2Rγc ligands of Formula (8), $X^{132}$ can be selected from I, V, and L.

In IL-2Rγc ligands of Formula (8), $X^{132}$ can be I.

In IL-2Rγc ligands of Formula (8), $X^{133}$ can be selected from M, L, Y, and I.

In IL-2Rγc ligands of Formula (8), $X^{134}$ can be selected from F, H, and Y.

In IL-2Rγc ligands of Formula (8), $X^{134}$ can be Y.

In IL-2Rγc ligands of Formula (8), $X^{135}$ can be selected from R, K, D, and E.

In IL-2Rγc ligands of Formula (8), $X^{135}$ can be R.

In IL-2Rγc ligands of Formula (8), $X^{136}$ can be selected from an amino acid.

In IL-2Rγc ligands of Formula (8), $X^{137}$ can be G.

In IL-2Rγc ligands of Formula (8), $X^{138}$ can be selected from D and E.

In IL-2Rγc ligands of Formula (8), $X^{138}$ can be E.

In IL-2Rγc ligands of Formula (8), $X^{139}$ can be selected from F, Y, and W.

In IL-2Rγc ligands of Formula (8)), $X^{139}$ can be F.

In IL-2Rγc ligands of Formula (8), $X^{140}$ can be selected from S and T.

In IL-2Rγc ligands of Formula (8), $X^{141}$ can be selected from F, I, L, M, V, Y, and W.

In IL-2Rγc ligands of Formula (8), $X^{141}$ can be Y.

In IL-2Rγc ligands of Formula (8), $X^{142}$ can be selected from I, L, M, V, and Y.

In IL-2Rγc ligands of Formula (8), $X^{131}$ can be selected from F and Y; $X^{132}$ can be I; $X^{13}$ can be selected from M, L, Y, and I; $X^{134}$ can be Y; $X^{135}$ can be R; $X^{136}$ can be selected from an amino acid; $X^{137}$ can be G; $X^{138}$ can be E; $X^{139}$ can be F; $X^{140}$ can be selected from S and T; $X^{141}$ can be Y; and $X^{142}$ can be selected from F, I, L, M, V, Y, and W.

In IL-2Rγc ligands of Formula (8), $X^{131}$ can be selected A, C, D, E, F, G, L, P, and Y; $X^{132}$ can be selected from C, I, L, N, S, and V; $X^{133}$ can be selected from A, I, L, M, Q, R, and Y; $X^{134}$ can be selected from F, H, K, L, T, and Y; $X^{135}$ can be selected from D, E, G, H, I, K, L, P, Q, R, S, and Y; $X^{136}$ can be selected from E, F, G, H, I, L, N, Q, R, S, and T; $X^{137}$ can be selected from C, D, E, G, K, N, P, Q, and T $X^{138}$ can be selected from D, E, F, K, P, R, and T; $X^{139}$ can be selected from A, F, L, R, T, V, W, and Y; $X^{140}$ can be selected from D, E, G, L, N, S, T, W, and Y; $X^{141}$ can be selected from A, C, F, G, I, L, M, and Y; and $X^{142}$ can be selected from C, E, I, L, M, V, and Y.

In IL-2Rγc ligands of Formula (8), $X^{131}$ can be selected F and Y; $X^{132}$ can be selected from I, L, and V; $X^{133}$ can be selected from I, M, R, and Y; $X^{134}$ can be selected from F, H, and Y; $X^{135}$ can be selected from D, E, K, and R; $X^{136}$ can be selected from E, F, G, H, I, L, N, Q, R, S, and T; $X^{137}$ can be G; $X^{138}$ can be selected from D and E; $X^{139}$ can be selected from F, W, and Y; $X^{140}$ can be selected from S and T; $X^{141}$ can be selected from F, I, L, M, and Y; and $X^{142}$ can be selected from I, L, M, V and Y.

In IL-2Rγc ligands of Formula (8), $X^{131}$ can be F; $X^{132}$ can be I; $X^{133}$ can be selected from I, M, R, and Y; $X^{134}$ can be Y; $X^{135}$ can be selected from D, E, K, and R; $X^{136}$ can be selected from E, F, G, H, I, L, N, Q, R, S, and T; $X^{137}$ can be G; $X^{138}$ can be E; $X^{139}$ can be F; $X^{140}$ can be selected from S and T; $X^{141}$ can be Y; and $X^{142}$ can be selected from I, L, M, V and Y.

In IL-2Rγc ligands of Formula (8), $X^{131}$ can be F, $X^{132}$ can be I, $X^{134}$ can be Y, $X^{125}$ can be R, $X^{137}$ can be G, $X^{138}$ can be E, $X^{139}$ can be F, and $X^{141}$ can be Y.

An IL-2Rγc ligand can comprise an amino acid sequence selected from any one of SEQ ID NO: 265 to SEQ ID NO: 267 and SEQ ID NO: 932 to SEQ ID NO: 940:

```
                                       SEQ ID NO: 265
       C G I A Y R S G E F T M I C

SEQ ID NO: 266
       C P S M L Q G P E R T W V C

SEQ ID NO: 267
       W C I Y Y P F T D V E A C T

SEQ ID NO: 932
       C A N L H D T Q E W W Y Y C

SEQ ID NO: 933
       C E L L T G I P E Y N F L C

SEQ ID NO: 934
       C F I R F Y Q D K Y D Y V C

SEQ ID NO: 935
       C F I R Y L R G E F S F V C

SEQ ID NO: 936
       C F L R F I H G E L D Y Y C

SEQ ID NO: 937
       C F V M Y K N N E F S L I C

SEQ ID NO: 938
       C G I A Y R S G E F T M I C

SEQ ID NO: 939
       C L I Y K E Q K F A L I E C

SEQ ID NO: 940
       C Y I I Y R L G T F S Y M C
```

An IL-2Rγc ligand can comprise an amino acid sequence selected from any one of SEQ ID NO: 265 to SEQ ID NO: 267 and SEQ ID NO: 931 to SEQ ID NO: 940, and SEQ ID NO: 1083, wherein the amino acid sequence can be terminated with amino acids -G-G- on the N-terminus, on the C-terminus, or on both the N- and C-termini.

An IL-2Rγc ligand can comprise an amino acid sequence selected from any one of SEQ ID NO: 265 to SEQ ID NO: 267 and SEQ ID NO: 931 to SEQ ID NO: 940, and SEQ ID NO: 1083, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

IL-2Rγc ligands of SEQ ID NO: 265 to SEQ ID NO: 267 and SEQ ID NO: 931 to SEQ ID NO: 940, and SEQ ID NO: 1083 exhibit a binding affinity ($IC_{50}$) to the IL-2Rγc subunit of less than 100 μM.

An IL-2Rγc ligand can comprise the amino acid sequence of Formula (9) (SEQ ID NO: 941) or the amino acid sequence of Formula 9a) (SEQ ID NO: 942):

$$-X^{155}-X^{156}-X^{157}-X^{158}-X^{159}- \qquad (9)$$

$$\begin{aligned}-X^{151}-X^{152}-X^{153}-X^{154}-C-X^{155}-X^{156}-\\X^{157}-X^{158}-X^{159}-C-X^{160}-X^{161}-X^{162}-\\X^{163}-\end{aligned} \qquad (9a)$$

wherein, $X^{151}$ can be selected from an amino acid comprising a small hydrophobic side chain or a hydroxyl-containing side chain; $X^{152}$ can be selected from an amino acid comprising a large hydrophobic side chain; $X^{153}$ can be selected from an amino acid comprising an acidic or polar neutral side chain; $X^{154}$ can be selected from an amino acid comprising a basic side chain; $X^{155}$ can be selected from an amino acid comprising a large hydrophobic side chain; $X^{156}$ can be selected from an amino acid comprising a small hydrophobic side chain or a hydroxyl-containing side chain; $X^{157}$ can be selected from an amino acid comprising a small hydrophobic side chain; $X^{158}$ can be selected from an amino acid comprising a small hydrophobic side chain or a hydroxyl-containing side chain; $X^{159}$ can be selected from an amino acid comprising a small hydrophobic side chain or a hydroxyl-containing side chain; $X^{160}$ can be selected from an amino acid comprising a small hydrophobic side chain or a hydroxyl-containing side chain; $X^{161}$ can be selected from an amino acid; $X^{162}$ can be selected from an amino acid comprising a large hydrophobic side chain or a basic side chain; and $X^{163}$ can be selected from an amino acid comprising a large hydrophobic side chain.

In IL-2Rγc ligands of Formula (9) and Formula (9a), $X^{131}$ can be selected from A, G, P, S, and T; $X^{152}$ can be selected from F, I, L, M, V, Y, and W; $X^{153}$ can be selected from D, E, N, and Q; $X^{154}$ can be selected from H, K, and R; $X^{155}$ can be selected from F, I, L, M, V, Y, and W; $X^{156}$ can be selected from A, G, P, S, and T; $X^{157}$ can be selected from A, G, P, S, and T; $X^{158}$ can be selected from A, G, P, S, and T; $X^{159}$ can be selected from A, G, P, S, and T; $X^{160}$ can be selected from A, G, P, S, and T; $X^{161}$ can be selected from an amino acid; $X^{162}$ can be selected from F, I, L, M, V, Y, W, R, K, and H; and $X^{163}$ can be selected from F, I, L, M, V, Y, and W.

In IL-2Rγc ligands of Formula (9) and Formula (9a). $X^{151}$ can be selected from K, M, N, and K; $X^{152}$ can be selected from M, L, and Y; $X^{153}$ can be selected from N, Y, and L; $X^{154}$ can be K; $X^{155}$ can be selected from A, W, R, Y, and N; $X^{156}$ can be selected from T, N, and S; $X^{157}$ can be selected from P and A; $X^{158}$ can be selected from S, R, F, and L; $X^{159}$ can be selected from Q, S, E, and T; $X^{160}$ can be selected from S, Q, and A; $X^{161}$ can be selected from V, S, G, L, and N; $X^{162}$ can be selected from I, K, R, and V; and $X^{163}$ can be selected from F and L.

In IL-2Rγc ligands of Formula (9) and Formula (9a), $X^{151}$ can be selected from S and T.

In IL-2Rγc ligands of Formula (9) and Formula (9a), $X^{152}$ can be selected from L and M.

In IL-2Rγc ligands of Formula (9) and Formula (9a), $X^{152}$ can be L.

In IL-2Rγc ligands of Formula (9) and Formula (9a), $X^{153}$ can be N.

In IL-2Rγc ligands of Formula (9) and Formula (9a), $X^{154}$ can be K.

In IL-2Rγc ligands of Formula (9) and Formula (9a), $X^{155}$ can be selected from W and Y.

In IL-2Rγc ligands of Formula (9) and Formula (9a), $X^{156}$ can be selected from S and T.

In IL-2Rγc ligands of Formula (9) and Formula (9a), $X^{156}$ can be S.

In IL-2Rγc ligands of Formula (9) and Formula (9a), $X^{157}$ can be P.

In IL-2Rγc ligands of Formula (9) and Formula (9a), $X^{158}$ can be S.

In IL-2Rγc ligands of Formula (9) and Formula (9a), $X^{159}$ can be selected from S and T.

In IL-2Rγc ligands of Formula (9) and Formula (9a), $X^{159}$ can be S.

In IL-2Rγc ligands of Formula (9) and Formula (9a), $X^{160}$ can be S.

In IL-2Rγc ligands of Formula (9) and Formula (9a), $X^{161}$ can be selected from an amino acid.

In IL-2Rγc ligands of Formula (9) and Formula (9a), $X^{162}$ can be selected from I, V, R, and K.

In IL-2Rγc ligands of Formula (9) and Formula (9a), $X^{162}$ can be selected from I and V.

In IL-2Rγc ligands of Formula (9) and Formula (9a), $X^{162}$ can be selected from R and K.

In IL-2Rγc ligands of Formula (9) and Formula (9a), $X^{163}$ can be selected from F and L.

In IL-2Rγc ligands of Formula (9) and Formula (9a), $X^{163}$ can be L.

In IL-2Rγc ligands of Formula (9) and Formula (9a), $X^{151}$ can be selected from S and T; $X^{152}$ can be L; $X^{153}$ can be N; $X^{154}$ can be K; $X^{155}$ can be selected from W and Y; $X^{156}$ can be S; $X^{157}$ can be P; $X^{158}$ can be S; $X^{159}$ can be S; $X^{160}$ can be S T; $X^{161}$ can be selected from an amino acid; $X^{162}$ can be I; and $X^{163}$ can be F.

In IL-2Rγc ligands of Formula (9) and Formula (9a), $X^{152}$ can be L, $X^{153}$ can be N, $X^{154}$ can be K, $X^{156}$ can be S, $X^{157}$ can be P, $X^{158}$ can be S, $X^{159}$ can be S, $X^{160}$ can be S, $X^{162}$ can be I, and $X^{163}$ can be F.

An IL-2Rγc ligand can comprise an amino acid sequence selected from any one of SEQ ID NO: 943 to SEQ ID NO: 948:

```
                                         SEQ ID NO: 943
      K M N K C A T P S Q C S V I F

SEQ ID NO: 944
      N L N K C W N P R S C S S K F

SEQ ID NO: 945
      T Y N K C R S P F E C S G I F

SEQ ID NO: 946
      Y L N K C Y S P S S C Q L R L

SEQ ID NO: 947
      S L Y K C N S P L S C S N I F

SEQ ID NO: 948
      S L L K C Y N A S T C A S V F
```

An IL-2Rγc ligand can comprise an amino acid sequence selected from any one of SEQ ID NO: 941 to SEQ ID NO: 948, wherein the amino acid sequence can be terminated with amino acids -G-G- on the N-terminus, on the C-terminus, or on both the N- and C-termini.

An IL-2Rγc ligand can comprise an amino acid sequence selected from any one of SEQ ID NO: 941 to SEQ ID NO: 948, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

IL-2Rγc ligands of SEQ ID NO: 941 to SEQ ID NO: 948 exhibit a binding affinity ($IC_{50}$) to the IL-2Rγc subunit of less than 100 μM.

An IL-2Rγc ligand can comprise the amino acid sequence of Formula (12) (SEQ ID NO: 949):

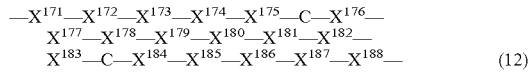

(12)

wherein, $X^{171}$ can be selected from an amino acid comprising a basic side chain; $X^{172}$ can be selected from an amino acid comprising a hydroxyl-containing side chain; $X^{173}$ can be selected from an amino acid comprising an acidic side chain or a large hydrophobic side chain; $X^{174}$ can be selected from an amino acid comprising a large hydrophobic side chain; $X^{175}$ can be selected from an amino acid comprising an acidic side chain or a large hydrophobic side chain; $X^{176}$ can be selected from an amino acid comprising an acidic side chain or a polar/neutral side chain; $X^{177}$ can be selected from an amino acid comprising an acidic side chain; $X^{178}$ can be selected from an amino acid comprising a large hydrophobic side chain or an aromatic side chain; $X^{179}$ can be selected from an amino acid comprising an acidic side chain or a polar/neutral side chain; $X^{180}$ can be G; $X^{181}$ can be V; $X^{182}$ can be E; $X^{183}$ can be L; $X^{184}$ can be W; $X^{185}$ can be selected from an amino acid comprising a large hydrophobic side chain; $X^{186}$ can be E; $X^{187}$ can be selected from an amino acid; and $X^{188}$ can be selected from an amino acid comprising an acidic side chain.

In IL-2Rγc ligands of Formula (12), $X^{171}$ can be selected from H, K, and R; $X^{172}$ can be selected from S, T, and Y; $X^{173}$ can be selected from D, E, F, I, L, M, V, W, and Y; $X^{174}$ can be selected from F, I, L, M, V, W, and Y; $X^{175}$ can be selected from D, E, F, I, L, M, V, W, and Y; $X^{176}$ can be selected from D, E, H, N, Q, S, T, and Y; $X^{177}$ can be selected from D and E; $X^{178}$ can be selected from F, H, I, L, M, V, W, and Y; $X^{179}$ can be selected from D, E, H, N, Q, S, T, and Y; $X^{180}$ can be G; $X^{181}$ can be V; $X^{182}$ can be E; $X^{183}$ can be L; $X^{184}$ can be W; $X^{185}$ can be selected from F, I, L, M, V, W, and Y; $X^{186}$ can be E; $X^{187}$ can be selected from an amino acid; and $X^{188}$ can be selected from D and E.

In IL-2Rγc ligands of Formula (12), $X^{171}$ can be selected from D, E, G, H, K, M, N, P, Q, R, S, and T; $X^{172}$ can be selected from A, D, E, G, I, K, L, P, Q, R, S, T, V, W, and Y; $X^{173}$ can be selected from A, D, E, F, G, I, Q, S, T, V, W, and Y; $X^{174}$ can be selected from A, I, E, I, L, M, N, Q, R, S, T, and V; $X^{175}$ can be selected from A, E, I, L, M, N, Q, R, S, T, and V; $X^{176}$ can be selected from D, E, H, L, Q, R, and V; $X^{177}$ can be selected from D, E, N, T, and V; $X^{178}$ can be selected from F, S, W, and Y; $X^{179}$ can be selected from A, D, E, G, H, K, N, Q, R, and Y; $X^{180}$ can be selected from G and R; $X^{181}$ can be V; $X^{182}$ can be selected from D, E, and Y; $X^{183}$ can be selected from F, I, and L; $X^{184}$ can be W; $X^{185}$ can be selected from C, H, I, L, P, Q, T, V, and Y; $X^{186}$ can be selected from A, D, E, G, M, R, S, T, and V; $X^{187}$ can be selected from A, D, E, F, G, I, M, N, P, Q, R, S, T, V, W, and Y; and $X^{188}$ can be selected from A, C, D, E, F, G, I, K, L, N, P, Q, R, S, and V.

In IL-2Rγc ligands of Formula (12), $X^{171}$ can be selected from H, K, and R; $X^{172}$ can be selected from S, T, and Y; $X^{173}$ can be selected from D, E, F, I, and V; $X^{174}$ can be selected from I and V; $X^{175}$ can be selected from E, I, L, M, and V; $X^{176}$ can be selected from D, E, and Q; $X^{177}$ can be selected from D and E; $X^{178}$ can be selected from F and W; $X^{179}$ can be selected from D, E, N, and Q; $X^{180}$ can be G; $X^{181}$ can be V; $X^{182}$ can be selected from D and E; $X^{183}$ can be L; $X^{184}$ can be W; $X^{185}$ can be selected from I, L, Q, and V; $X^{186}$ can be selected from D and E; $X^{187}$ can be selected from A, D, E, F, G, I, M, N, P, Q, R, S, T, V, W, and Y; and $X^{188}$ can be selected from D, E, N, and Q.

In IL-2Rγc ligands of Formula (12), $X^{171}$ can be selected from K and R; $X^{172}$ can be selected from S, T, and Y; $X^{173}$ can be selected from D, E, F, I, and V; $X^{174}$ can be V; $X^{175}$ can be selected from E, L, M, and V; $X^{176}$ can be Q; $X^{177}$ can be selected from D and E; $X^{178}$ can be W; $X^{179}$ can be selected from D, E, N, and Q; $X^{180}$ can be G; $X^{181}$ can be V; $X^{182}$ can be E; $X^{183}$ can be L; $X^{184}$ can be W; $X^{185}$ can be selected from I, L, Q, and V; $X^{186}$ can be selected from D and E; $X^{187}$ can be selected from A, D, E, F, G, I, M, N, P, Q, R, S, T, V, W, and Y; and $X^{188}$ can be selected from D, E, N, and Q.

In IL-2Rγc ligands of Formula (12), $X^{171}$ can be selected from H, K, and R.

In IL-2Rγc ligands of Formula (12), $X^{172}$ can be selected from S, T, and Y.

In IL-2Rγc ligands of Formula (12), $X^{173}$ can be selected from D, E, F, I, L, M, V, W, and Y.

In IL-2Rγc ligands of Formula (12), $X^{173}$ can be selected from D and E.

In IL-2Rγc ligands of Formula (12), $X^{173}$ can be selected from F, I, L, M, V, W, and Y.

In IL-2Rγc ligands of Formula (12), $X^{174}$ can be selected from F, I, L, M, V, W, and Y.

In IL-2Rγc ligands of Formula (12), $X^{174}$ can be V.

In IL-2Rγc ligands of Formula (12), $X^{175}$ can be selected from D, E, F, I, L, M, V, W, and Y.

In IL-2Rγc ligands of Formula (12), $X^{175}$ can be selected from D and E.

In IL-2Rγc ligands of Formula (12), $X^{175}$ can be selected from F, I, L, M, V, W, and Y.

In IL-2Rγc ligands of Formula (12), $X^{176}$ can be selected from D, E, H, N, Q, S, T, and Y.

In IL-2Rγc ligands of Formula (12), $X^{176}$ can be selected from E and Q.

In IL-2Rγc ligands of Formula (12), $X^{177}$ can be selected from D and E.

In IL-2Rγc ligands of Formula (12), $X^{178}$ can be selected from F, H, I, L, M, V, W, and Y.

In IL-2Rγc ligands of Formula (12), $X^{178}$ can be selected from F, H, W, and Y.

In IL-2Rγc ligands of Formula (12), $X^{178}$ can be W.

In IL-2Rγc ligands of Formula (12), $X^{179}$ can be selected from D, E, H, N, Q, S, T, and Y.

In IL-2Rγc ligands of Formula (12), $X^{179}$ can be selected from D, E, and Q.

In IL-2Rγc ligands of Formula (12), $X^{180}$ can be G.

In IL-2Rγc ligands of Formula (12), $X^{181}$ can be V.

In IL-2Rγc ligands of Formula (12), $X^{182}$ can be E.

In IL-2Rγc ligands of Formula (12), $X^{183}$ can be L.

In IL-2Rγc ligands of Formula (12), $X^{184}$ can be W.

In IL-2Rγc ligands of Formula (12), $X^{185}$ can be selected from F, I, L, M, V, W, and Y.

In IL-2Rγc ligands of Formula (12), $X^{185}$ can be L.

In IL-2Rγc ligands of Formula (12), $X^{186}$ can be E.

In IL-2Rγc ligands of Formula (12), $X^{187}$ can be selected from an amino acid.

In IL-2Rγc ligands of Formula (12), $X^{188}$ can be selected from D and E.

In IL-2Rγc ligands of Formula (12), $X^{171}$ can be selected from H, K, and R; $X^{172}$ can be selected from S, T, and Y; $X^{173}$ can be selected from D, E, F, I, L, M, V, W, and Y; $X^{174}$ can be selected from F, I, L, M, V, W, and Y; $X^{175}$ can be selected from D, E, F, I, L, M, V, W, and Y; $X^{176}$ can be selected from D, E, H, N, Q, S, T, and Y; $X^{177}$ can be selected from D and E; $X^{178}$ can be selected from F, H, I, L, M, V, W, and Y; $X^{179}$ can be selected from D, E, H, N, Q, S, T, and Y; $X^{180}$ can be G; $X^{181}$ can be V; $X^{182}$ can be E; $X^{183}$ can be L; $X^{184}$ can be selected from W; $X^{185}$ can be selected from F, I, L, M, V, W, and Y; $X^{186}$ can be E; $X^{187}$ can be selected from an amino acid; and $X^{188}$ can be selected from D and E.

In IL-2Rγc ligands of Formula (12), $X^{171}$ can be selected from H, K, and R; $X^{172}$ can be selected from S, T, and Y; $X^{173}$ can be selected from D and E; $X^{174}$ can be V; $X^{175}$ can be selected from D and E; $X^{176}$ can be selected from E and Q; $X^{177}$ can be selected from D and E; $X^{178}$ can be selected from F, H, W, and Y; $X^{179}$ can be selected from D, E, and Q; $X^{180}$ can be G; $X^{181}$ can be V; $X^{182}$ can be E; $X^{183}$ can be L; $X^{184}$ can be W; $X^{185}$ can be selected from F, I, L, M, V, W, and Y; $X^{186}$ can be E; $X^{187}$ can be selected from an amino acid; and $X^{188}$ can be selected from D and E.

In IL-2Rγc ligands of Formula (12), $X^{171}$ can be selected from H, K, and R; $X^{172}$ can be selected from S, T, and Y; $X^{173}$ can be selected from F, I, L, M, V, W, and Y; $X^{174}$ can be V; $X^{175}$ can be selected from F, I, L, M, V, W, and Y; $X^{176}$ can be selected from E and Q; $X^{177}$ can be selected from D and E; $X^{178}$ can be selected from F, H, W, and Y; $X^{179}$ can be selected from D, E, and Q; $X^{180}$ can be G; $X^{181}$ can be V; $X^{182}$ can be E; $X^{183}$ can be L; $X^{184}$ can be W; $X^{185}$ can be selected from F, I, L, M, V, W, and Y; $X^{186}$ can be E; $X^{187}$ can be selected from an amino acid; and $X^{186}$ can be selected from D and E.

In IL-2Rγc ligands of Formula (12), $X^{171}$ can be selected from H, K, and R; $X^{172}$ can be selected from S, T, and Y; $X^{173}$ can be selected from D, E, F, I, L, M, V, W, and Y; $X^{174}$ can be V; $X^{175}$ can be selected from D, E, F, I, L, M, V, W, and Y; $X^{176}$ can be selected from D, E, H, N, Q, S, T, and Y; $X^{176}$ can be selected from E and Q; $X^{177}$ can be selected from D and E; $X^{178}$ can be W; $X^{179}$ can be selected from D, E, and Q; $X^{180}$ can be G; $X^{181}$ can be V; $X^{182}$ can be E; $X^{183}$ can be L; $X^{184}$ can be W; $X^{185}$ can be selected from F, I, L, M, V, W, and Y; $X^{186}$ can be E; $X^{187}$ can be selected from an amino acid; and $X^{188}$ can be selected from D and E.

An IL-2Rγc ligand can comprise an amino acid sequence selected from any one of SEQ ID NO: 950 to SEQ ID NO: 1027:

I E C D T S Y G V Y I C W Q  SEQ ID NO: 950

I E C E E W R G V E L C W Q  SEQ ID NO: 951

P E G R E V V V C R D W Y G V E L C W Q  SEQ ID NO: 952

I W G R T V V E C Q D W E G V E L C W Q  SEQ ID NO: 953

L A L R K E V V C Q E Y Y G V E L C W I  SEQ ID NO: 954

H E A R E V V V C Q D W Y G V E L C W Q  SEQ ID NO: 955

M V N R E V V V C E D W Y G V E L C W Q  SEQ ID NO: 956

T A N Q T V V E C Q V W G G V E L C W Q  SEQ ID NO: 957

V E C Q E W G G V E L C W C  SEQ ID NO: 958

D V E C V D W G G V E L C W H  SEQ ID NO: 959

I V C E E W R G V E L C W L  SEQ ID NO: 960

D F E R S Y V V C Q D W D G V E L C W I  SEQ ID NO: 961

A H S R Q E V V C E E W Y G V E L C W I  SEQ ID NO: 962

S A P E R W V E C E D W Q G V E L C W V  SEQ ID NO: 963

Y S R E L Y V Q C E D W E G V E L C W I  SEQ ID NO: 964

V V C Q D W E G V E L C W Q  SEQ ID NO: 965

D V V C Q N W E G V D L C W H  SEQ ID NO: 966

S A G R Q E V V C Q D W N G V E L C W I  SEQ ID NO: 967

G Q G R E V V V C H D W Y G V E L C W Q  SEQ ID NO: 968

D W R R S V V E C Q D W Y G V E L C W Q  SEQ ID NO: 969

D V V C Q N W D G V D L C W H  SEQ ID NO: 970

T L G R T V V E C Q D W G G V E L C W Q  SEQ ID NO: 971

R L L N S V V E C L D W E G V E L C W Q  SEQ ID NO: 972

I V C E D W R G V E L C W I  SEQ ID NO: 973

V V C Q E W E G V E L C W C  SEQ ID NO: 974

G D R P K E V V C E D W K G V E L C W I  SEQ ID NO: 975

E R P R S F I E C Q E W E G V E L C W L  SEQ ID NO: 976

E G S T T T I E C E E W A G V E L C W L  SEQ ID NO: 977

A N Q N T V V E C Q D W H G V E L C W Q  SEQ ID NO: 978

R S D D E V V V C Q E W E G V E L C W Q  SEQ ID NO: 979

I E C E E W A G V E L C W L  SEQ ID NO: 980

T W N M S E L E C Q D W N G V E I C W H  SEQ ID NO: 981

G N D D S Y I V C E E W K G V E L C W I  SEQ ID NO: 982

F A H H G V V E C Q E W Y G V E L C W Q  SEQ ID NO: 983

L N R S V W I E C E E Y E G V E L C W L  SEQ ID NO: 984

SEQ ID NO: 985
W S K K A E V V C E E W G G V E F C W I

SEQ ID NO: 986
R S N Q T V V E C Q D W E G V E L C W Q

SEQ ID NO: 987
V V C Q E W E G V E L C W Y A G E C M Q

SEQ ID NO: 988
I L C Q E F E G V E L C W L E E S L A E

SEQ ID NO: 989
K S Q V E C Q D W E G V E L C W V V S E

SEQ ID NO: 990
K I T V E C Q D W D G V E L C W P T W I

SEQ ID NO: 991
R P Q I E C Q E W Q G V E L C W T R E E

SEQ ID NO: 992
V S C Q E W D G V E L C W V D G D L A A

SEQ ID NO: 993
I M C Q E W D G V E L C W L E R D K A N

SEQ ID NO: 994
G L E I A C E D W Y G V E L C W L R R A

SEQ ID NO: 995
G Y G V L C Q E W Q G V E L C W P V Q R E A G V

SEQ ID NO: 996
P Y G V V C Q D W A G V E L C W V E N R

SEQ ID NO: 997
K L T V E C Q D W D G V E L C W V G V E

SEQ ID NO: 998
I N C Q T W N G V E L C W V D E G L Y Q

SEQ ID NO: 999
V V C Q E W E G V E L C W V E P P L L P

SEQ ID NO: 1000
R V Q V E C E D W N G V E L C W P V R V

SEQ ID NO: 1001
D R Q V V C E E W D G V E L C W I E E S

SEQ ID NO: 1002
K T T V A C Q D W G G V E L C W V E R V

SEQ ID NO: 1003
R P E V V C Q E W E G V E L C W I S P L

SEQ ID NO: 1004
R L G V E C Q E W E G V D L C W I S A F

SEQ ID NO: 1005
K P V V V C E E W Q G V E L C W L E I Q

SEQ ID NO: 1006
V V C E V F Q G V E L C W C E N E E F T

SEQ ID NO: 1007
T D E V S C Q E W E G V E L C W I E R Q

SEQ ID NO: 1008
P V E V R C Q E W E G V E L C W V V G I

SEQ ID NO: 1009
G P E V V C E E F N R V E L C W V E Y N

SEQ ID NO: 1010
K Y I V E C Q E W G G V E L C W P E M V

SEQ ID NO: 1011
V T C Q E Y E G V E L C W T V G C A Y S

SEQ ID NO: 1012
V V C Q E W E G V E L C W Q T G P A H A

SEQ ID NO: 1013
I V C E E Y N G V E L C W V E T S V K P

SEQ ID NO: 1014
E Q Q V V C Q E W N G V E L C W I E A G

SEQ ID NO: 1015
Q L G V E C Q N W R G V E L C W V S E I

SEQ ID NO: 1016
T A E V V C Q E W D G V E L C W I E V L

SEQ ID NO: 1017
S P S I V C E E W A G V E L C W V D Y S

SEQ ID NO: 1018
A V C Q D W Y G V E L C W C M Q D I L D

SEQ ID NO: 1019
V E C E E W G G V E L C W L A D E V M W

SEQ ID NO: 1020
H S T V I C Q D W D G V E L C W I E N D

SEQ ID NO: 1021
K K I V V C Q D W G G V E L C W T E D D

SEQ ID NO: 1022
S V E V V C E E W H G V E L C W P V F I

SEQ ID NO: 1023
R W A V S C Q D W Q G I E L C W P E W D

SEQ ID NO: 1024
R T G V E C Q D W H G V E L C W P V W E

SEQ ID NO: 1025
G Y G V V C E D F R G V E L C W L E R K

SEQ ID NO: 1026
R T E V E C E D W E G V E L C W L

SEQ ID NO: 1027
I L C E E W Q G V E L C W L E G G G S

An IL-2Rγc ligand can comprise an amino acid sequence selected from any one of SEQ ID NO: 949 to SEQ ID NO: 1027, wherein the amino acid sequence can be terminated with amino acids -G-G-on the N-terminus, on the C-terminus, or on both the N- and C-termini.

An IL-2Rγc ligand can comprise an amino acid sequence selected from any one of SEQ ID NO: 949 to SEQ ID NO: 1027, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

IL-2Rγc ligands of SEQ ID NO: 949 to SEQ ID NO: 1027 exhibit a binding affinity ($IC_{50}$) to the IL-2Rγc subunit of less than 100 μM.

An IL-2Rγc ligand can comprise, for example, from 5 to 50 amino acids, from 5 to 40 amino acids, from 5 to 30 amino acids, from 5 to 30 amino acids, from 6 to 25 amino acids, or from 7 to 20 amino acids.

An IL-2Rγc ligand can exhibit a binding affinity ($IC_{50}$) to the human IL-2Rγc subunit, to a mammalian IL-2Rγc subunit, or to both the human IL-2Rγc subunit and a mammalian IL-2Rγc subunit from 1 μM to 100 μM, from 10 μM to 10 μM, from 100 μM to 1 μM, from, 0.001 μM to 1 M, or from 0.01 μM to 1 μM.

An IL-2Rγc ligand provided by the present disclosure can exhibit, for example, a binding affinity ($IC_{50}$) to the human IL-2Rγc subunit from 0.1 μM to 50 μM.

An IL-2Rγc ligand can exhibit a binding affinity ($IC_{50}$) to the human IL-2Rγc subunit, to a mammalian IL-2Rγc subunit, or to both the human IL-2Rγc subunit and a mammalian IL-2Rγc subunit of less than 100 μM, less than 10 μM, less than 1 μM, less than 0.1 M, or less than 0.01 μM.

An IL-2Rγc ligand can exhibit a binding affinity ($IC_{50}$) to each of the human IL-2Rγc subunit and to the human IL-2Rγc subunit of less than 100 μM, less than 10 μM, less than 1 μM, less than 0.1 M, or less than 0.01 μM.

An IL-2Rγc ligand can exhibit a binding affinity ($IC_{50}$) to each of the human IL-2Rγc subunit and to the human IL-2Rγc subunit from 1 μM to 100 μM, from 10 μM to 10 μM, from 100 μM to 1 M, from, 0.001 μM to 1 M, or from 0.01 μM to 1 μM.

An IL-2Rγc ligand provided by the present disclosure can exhibit a binding affinity ($IC_{50}$) to the human IL-2Rα (CD25) subunit of greater than 100 M, greater than 1 mM, greater than 10 mM, or greater than 100 mM.

An IL-2Rγc ligand can exhibit a binding affinity ($IC_{50}$) to the human IL-2Rγc subunit that is at least 10 times greater, at least 50 times greater, at least 100 time greater, at least 500 times greater, or at least 1,000 times greater than the binding affinity ($IC_{50}$) of the IL-2Rγc ligand to the human IL-2Rα subunit.

Amino acid sequences having SEQ ID NO: 268 to SEQ ID NO: 376 are excluded from the scope of the amino acid sequences according to the present invention. In a genus or sub-genus of amino acid sequences that otherwise encompasses any one of SEQ ID NO: 268 to SEQ ID NO: 376, the amino acid sequence of SEQ ID NO: 268 to SEQ ID NO: 376 are not included within the scope of the genus or sub-genus.

```
I S A G R W G D V G D L I P        SEQ ID NO: 268

G V Q S R W G D V G D L I P W      SEQ ID NO: 269

F P V P R W G D W G D L I E L      SEQ ID NO: 270

R W G D V G D L I G                SEQ ID NO: 271

R W G D V G D L I W                SEQ ID NO: 272

R W G D V G D L I G                SEQ ID NO: 273

R W G D V G D L I V                SEQ ID NO: 274

R W G D V G D L V S                SEQ ID NO: 275

R W G D V G D L V M                SEQ ID NO: 276

R W G D V G D M V E                SEQ ID NO: 277

R Y G E V G D L L P                SEQ ID NO: 278

R W G D W G D L L P                SEQ ID NO: 279

R W G D W G D L I P                SEQ ID NO: 280

R W G D W G D L V A                SEQ ID NO: 281

R W G D W G D L V E                SEQ ID NO: 282

R W G D W G D L V W                SEQ ID NO: 283

R W G D W G D L V G                SEQ ID NO: 284

R W G D V G D L V P                SEQ ID NO: 285

R W G D W G D M V V                SEQ ID NO: 286

W S G P G I L G E Y M              SEQ ID NO: 287

W D G P G L G E F F                SEQ ID NO: 288

W S G P G I L G E F M              SEQ ID NO: 289

W Y G P G I L G E Y M              SEQ ID NO: 290

W E G P G L G E Y M                SEQ ID NO: 291

W E G P G I L G E Y                SEQ ID NO: 292

I D C G V A T V G E L C            SEQ ID NO: 293

I S C S E A G L G E L C            SEQ ID NO: 294

I D C S Q A M L G E L C            SEQ ID NO: 295

I D C S E A W L G E L C            SEQ ID NO: 296

I D C S E A A L G T L C            SEQ ID NO: 297

L D C S I A A L G E L C            SEQ ID NO: 298

L D C S E A I L G Q L C            SEQ ID NO: 299

L D C G E A I L G E L C            SEQ ID NO: 300

L D C R D A V L G E L C            SEQ ID NO: 301

M D C S E R A L G E L C            SEQ ID NO: 302
```

-continued

MDCSQAGLGELC SEQ ID NO: 303

MDCREAALGELC SEQ ID NO: 304

MDCWEAALGELC SEQ ID NO: 305

MDCSEALLGELC SEQ ID NO: 306

MDCYDARLGDLC SEQ ID NO: 307

MDSSQAALGELC SEQ ID NO: 308

VDCSEAVLGQLC SEQ ID NO: 309

LDCSRASLGELC SEQ ID NO: 310

MDCSQAGLGELC SEQ ID NO: 311

IDCSEAGLGELC SEQ ID NO: 312

IDCSEAALGELC SEQ ID NO: 313

INCSEAVIGQLC SEQ ID NO: 314

IDCSNAVVGQLC SEQ ID NO: 315

IDCSAAGLGELC SEQ ID NO: 316

LDCSNAGWGDLC SEQ ID NO: 317

LDCSEAVLGELC SEQ ID NO: 318

LDCHLAVLGELC SEQ ID NO: 319

LDCSVAVLGELC SEQ ID NO: 320

LDCSEAWLGHLC SEQ ID NO: 321

MDCSQAALGDLC SEQ ID NO: 322

MDCSWAWLGDLC SEQ ID NO: 323

MDCSDAVLGDLC SEQ ID NO: 324

MDCHEAALGHLC SEQ ID NO: 325

MDCSQAVLGELC SEQ ID NO: 326

MDCSIRALGELC SEQ ID NO: 327

TECSEAGLWELC SEQ ID NO: 328

TECSEAGLWELC SEQ ID NO: 329

MDCRWAALGELC SEQ ID NO: 330

MDCSKAALGELC SEQ ID NO: 331

MDCSEAVLGELC SEQ ID NO: 332

MDCSIRALGELC SEQ ID NO: 333

VDCSEAVLGQLC SEQ ID NO: 334

MDCSERALGELC SEQ ID NO: 335

IDCGVATVGELC SEQ ID NO: 336

IDCSEAALGELC SEQ ID NO: 337

INCSEAVIGDLC SEQ ID NO: 338

IDCSQAMLGELC SEQ ID NO: 339

IDCSEAVLGELC SEQ ID NO: 340

IDCSAAGLGELC SEQ ID NO: 341

IDCSEAALGTLC SEQ ID NO: 342

LDCSNAGVGDLC SEQ ID NO: 343

LDCSIAALGELC SEQ ID NO: 344

LDCSEAILGQLC SEQ ID NO: 345

LDCHLAVLGELC SEQ ID NO: 346

LDCSVAVLGELC SEQ ID NO: 347

LDCRDAVLGELC SEQ ID NO: 348

MDCSERALGELC SEQ ID NO: 349

MDCSQAALGDLC SEQ ID NO: 350

MDCSVAVLGDLC SEQ ID NO: 351

MDCREAALGELC SEQ ID NO: 352

MDCWEAALGELC SEQ ID NO: 353

MDCHEAALGHLC SEQ ID NO: 354

MDCSQAVLGELC SEQ ID NO: 355

MDCYDARLGDLC SEQ ID NO: 356

-continued

| Sequence | SEQ ID NO: |
|---|---|
| M D S S Q A A L G E L C | 357 |
| T E C S E A G L W E L C | 358 |
| M D C S E A V L G E L C | 359 |
| I S C S E A G L G E L C | 360 |
| M D C S Q A A L G D L C | 361 |
| M D C S Q A G L G E L C | 362 |
| I S C S E A G L G E L C | 363 |
| I D C S N A V V G Q L C | 364 |
| L D C S E A V L G E L C | 365 |
| L D C G E A I L G E L C | 366 |
| L D C S E A V L G H L C | 367 |
| M D C S Q A G L C E L C | 368 |
| M D C S D A V L G D L C | 369 |
| M D C S E A L L G E L C | 370 |
| H C L D M G C T F P V W | 371 |
| A R S D Y G L G A I W P | 372 |
| R A C R V M P C L P D L | 373 |
| S G C G R E L G W C | 374 |
| T Q E V Y Y S L L | 375 |
| G T Q E A C F G L L | 376 |

Solid tumors exhibit metabolic differences from normal tissues. The greater reliance of solid tumors on glycolytic metabolism, produces a more acidic tumor microenvironment. For example, the solid tumor microenvironment can have a pH that is from 1 pH to 2 pH less than that of most normal tissues. This pH differential can be exploited to enhance the activity of therapeutic agents in solid tumors relative to activity in normal peripheral tissue.

Using suitable pH-selective screening methods, peptides can be identified that have a greater binding affinity to IL-2 at lower pH and a weaker binding affinity at a neutral pH. IL-2 agonists and antagonists can be constructed based on the identified pH-selective peptides. These pH-selective agonists and antagonists can exhibit an enhanced therapeutic index reflecting increased cytoxicity targeting solid tumors and with reduced toxicity to normal tissue.

Acidic-biased affinity selection has been used to identify receptor ligands having increased affinity at pH <6.5 commensurate with a solid tumor microenvironement and having decreased affinity at neutral pH >7.0 commensurate with that of normal tissue. These peptide ligands can serve as components to construct pH-targeted and pH-selective antagonists and agonists.

An IL-2Rβ ligand provided by the present disclosure can comprise a pH-selective IL-2Rβ ligand.

A pH-selective IL-2Rβ ligand can comprise the amino acid sequence of Formula (1) (SEQ ID NO: 1055), the amino acid sequence of Formula (1a) (SEQ ID NO: 1056), or the amino acid sequence of Formula (1b) (SEQ ID NO: 1057):

$$-X^3-X^4-X^5-X^6-X^7-X^8-X^9-X^{10}- \quad (1)$$

$$-X^2-C-X^3-X^4-X^5-X^6-X^7-X^8-X^9-X^{10}-C-X^{11}- \quad (1a)$$

$$-X^1-X^2-C-X^3-X^4-X^5-X^6-X^7-X^8-X^9-X^{10}-C-X^{11}-X^{12}- \quad (1b)$$

wherein, $X^1$ can be selected from an amino acid comprising a large hydrophobic side chain; $X^2$ can be selected from an amino acid; $X^3$ can be selected from an amino acid; $X^4$ can be selected from an amino acid; $X^5$ can be selected from an amino acid; $X^6$ can be selected from an amino acid; $X^7$ can be selected from an amino acid; $X^8$ can be selected from an amino acid comprising a polar-neutral or an acidic side chain; $X^9$ can be selected from an amino acid comprising a polar-neutral or an acidic side chain; $X^{10}$ can be selected from an amino acid; $X^{11}$ can be selected from an amino acid; and $X^2$ can be selected from an amino acid.

In pH-selective IL-2Rβ ligands of Formula (1)-(1b), $X^1$ can be selected from an amino acid comprising a large hydrophobic side chain; $X^2$ can be selected from an amino acid comprising an acidic side chain; $X^3$ can be selected from an amino acid; $X^4$ can be selected from an amino acid; $X^5$ can be selected from an amino acid comprising small hydrophobic side chain; $X^6$ can be selected from an amino acid comprising a polar-neutral or an acidic side chain; $X^7$ can be selected from an amino acid comprising a polar-neutral or a large hydrophobic side chain; $X^8$ can be selected from an amino acid comprising a small hydrophobic side chain; $X^9$ can be selected from an amino acid comprising a polar-neutral or an acidic side chain; $X^{10}$ can be selected from an amino acid comprising a large hydrophobic side chain; $X^{11}$ can be selected from an amino acid comprising an acidic side chain; and $X^{12}$ can be selected from an amino acid comprising a large hydrophobic side chain.

In pH-selective IL-2Rβ ligands of Formula (1)-(1b), $X^1$ can be selected from I, L, M, V, F, W, and Y; $X^2$ can be selected from D and E; $X^3$ can be selected from an amino acid; $X^4$ can be selected from an amino acid; $X^5$ can be selected from A, G, P, S, and T; $X^6$ can be selected from H, N, Q, S, T, Y, D, and E; $X^7$ can be selected from H, N, Q, S, T, Y, I, L, M, V, F, W, and Y; $X^8$ can be selected from A, G, P, S, and T; $X^9$ can be selected from H, N, Q, S, T, Y, D, and E; $X^{10}$ can be selected from I, L, M, V, F, W, and Y; $X^{11}$ can be selected from D and E; and $X^{12}$ can be selected from I, L, M, V, F, W, and Y.

In pH-selective IL-2Rβ ligands of Formula (1)-(1b), $X^1$ can be selected from I, L, M, V, F, W, and Y; $X^2$ can be selected from D and E; $X^3$ can be selected from an amino acid; $X^4$ can be selected from an amino acid; $X^5$ can be A; $X^6$ can be selected from H, N, Q, S, T, Y, D, and E; $X^7$ can be selected from H, N, Q, S, T, Y, I, L, M, V, F, W, and Y; $X^8$ can be G; $X^9$ can be selected from H, N, Q, S, T, Y, D, and E; $X^{10}$ can be selected from I, L, M, V, F, W, and Y; $X^{11}$ can be selected from D and E; and $X^{12}$ can be selected from I, L, M, V, F, W, and Y.

In pH-selective IL-2Rβ ligands of Formula (1)-(1b), $X^1$ can be selected from L, I, F and V.

In pH-selective IL-2Rβ ligands of Formula (1)-(1b), $X^2$ can be selected from D and E.

In pH-selective IL-2Rβ ligands of Formula (1)-(1b), $X^6$ can be selected from Q, E, and D;

In pH-selective IL-2Rβ ligands of Formula (1)-(1b), $X^7$ can be selected from V, L, and I.

In pH-selective IL-2Rβ ligands of Formula (1)-(1b), $X^9$ can be selected from E, D, and Q.

In pH-selective IL-2Rβ ligands of Formula (1)-(1b), $X^{10}$ can be selected from L, V, I, and Y.

In pH-selective IL-2Rβ ligands of Formula (1)-(1b), $X^{11}$ can be selected from D and E.

In pH-selective IL-2Rβ ligands of Formula (1)-(1b), $X^{12}$ can be selected from L, I, and F.

In pH-selective IL-2Rβ ligands of Formula (1)-(1b), $X^1$ can be selected from L, I, F, and V; $X^2$ can be selected from D and E; $X^6$ can be selected from Q, E, and D; $X^7$ can be selected from V, L, and I; $X^9$ can be selected from E, D, and Q; $X^{10}$ can be selected from L, V, I, and Y; $X^{11}$ can be selected from D and E; and $X^{12}$ can be selected from L, I, and F.

In pH-selective IL-2Rβ ligands of Formula (1)-(1b), $X^1$ can be selected from F, I, M, and Y; $X^2$ can be selected from E, D, and R; $X^3$ can be selected from and amino acid; $X^4$ can be selected from an amino acid; $X^5$ can be A; $X^6$ can be selected from A, P, and Q; $X^7$ can be selected from I and V; X can be G; $X^9$ can be selected from E and Q; $X^{10}$ can be selected from I, L, and V; $X^{11}$ can be selected from E, D, and Q; and $X^2$ can be selected from I and L.

A pH-selective IL-2Rβ ligand can comprise an amino acid sequence selected from any one of SEQ ID NO: 400 to SEQ ID NO: 577:

```
                                    SEQ ID NO: 400
D H K T W S A D C R I A Q V G E L C Q L

SEQ ID NO: 401
R R I A Q C S K A Q V G E L C E L

SEQ ID NO: 402
G V K D G W E D C G I A Q V G E L C V L

SEQ ID NO: 403
E D C W M A Q V G Q L C D L

SEQ ID NO: 404
R T L E H V E P C R I A G L G E L C D L

SEQ ID NO: 405
E Y C Q M A Q L G D L C D L

SEQ ID NO: 406
H G T F A C S L A Q V G D L C E L F G N

SEQ ID NO: 407
F D C R F A Q L G G L C D L

SEQ ID NO: 408
A K F F D C S F A P V G Y L C D L I V I

SEQ ID NO: 409
F E C R I A K V G E L C D L

SEQ ID NO: 410
F E C R T A P V G E L C D L W P W E L D

SEQ ID NO: 411
F E C W I A Q V G E L C D L

SEQ ID NO: 412
F E C W R A Q V G E L C D L

SEQ ID NO: 413
G D C R F A H L G D L C D L S G T S G A

SEQ ID NO: 414
F V V N E L G D C R F A Q L G E L C D L

SEQ ID NO: 415
G D C R I A E V G E L C D L

SEQ ID NO: 416
H D C W F A K L G E L C D L R Q M S F V

SEQ ID NO: 417
H D C Y S A H V G E L C D L N E P D G K

SEQ ID NO: 418
H E C R F A Q V G E L C D L

SEQ ID NO: 419
H Q C R F A H V G E L C D L F V F E S Y

SEQ ID NO: 420
I D C R F A R L G Y L C D L Q T N E H M

SEQ ID NO: 421
K A C S I A Q V G D L C E I Y G F D D A

SEQ ID NO: 422
R Q S R M W K A C S L A H L G E L C D L

SEQ ID NO: 423
K D C R L A Y V G E L C D L N R S D T I

SEQ ID NO: 424
A T F K D C R S S D V G E L C D M T N M

SEQ ID NO: 425
K D C R T A L I G D L C D L T L H L G G

SEQ ID NO: 426
K D C S I A Q V G E L C E F S R S G R T

SEQ ID NO: 427
Q D G A K L K E C R V A Q V G E L C E F

SEQ ID NO: 428
Q V L K N C R L A H I G E L C Y L S E R

SEQ ID NO: 429
R T M K Q C S I A Q V G E L C D L A V T

SEQ ID NO: 430
K S C A R A Q V G E L C Y I E G A E D A

SEQ ID NO: 431
M N Q K Y C K L A Q V G E L C D L S M D

SEQ ID NO: 432
L A C R A A Q V G Q L C D L

SEQ ID NO: 433
L A C R M A Q V G E L C D L

SEQ ID NO: 434
L A C W M A H V G Q L C E L E A H K V V

SEQ ID NO: 435
L D C R F A L L G Q L C D L F F G Q R P

SEQ ID NO: 436
L D C R I A P L G E L C D M F I S A F N

SEQ ID NO: 437
L D C R M A Q V G D L C D L
```

SEQ ID NO: 438
S D V L D C R V A Q V G S L C E L Y E

SEQ ID NO: 439
L D C S K A D V G E L C D P W W S R L K

SEQ ID NO: 440
A W N P L V L D C S T S Q V G D L C E L

SEQ ID NO: 441
F S G P D W L E C R F A Q L G Q M C D L

SEQ ID NO: 442
L E C R L A H L G E L C D L

SEQ ID NO: 443
L E C R L A R L G D L C Y L

SEQ ID NO: 444
L I M L E C R M A K L G E Y C Y F D A E

SEQ ID NO: 445
L E C R M A L V G D L C D L

SEQ ID NO: 446
L E C R S A Q M G D L C D L

SEQ ID NO: 447
L K C R M A R L G D L C D L D I G R N M

SEQ ID NO: 448
L L C R M A H L G E L C D L

SEQ ID NO: 449
L L C R N A Q V G Q I C D L M P F M L S

SEQ ID NO: 450
L L C S M A H V G E L C Y L L Q G T Q E

SEQ ID NO: 451
K E F L N C R I A Q V G E L C E M H Y E

SEQ ID NO: 452
A K S K G E L N C R Y A H V G E L C E L

SEQ ID NO: 453
L Q C R L A Q L G E L C V F

SEQ ID NO: 454
L R C R M A Q V G D L C D L D R A W D W

SEQ ID NO: 455
L S C R M A L V G Q L C E L

SEQ ID NO: 456
L S C S I A Q V G E L C D L

SEQ ID NO: 457
L S C W V A H L G D L C D L E R D V K E

SEQ ID NO: 458
N D C R F A H L G E L C D L D L E R A R

SEQ ID NO: 459
A S G N D C R M A Q V G Q L C D L E W M

SEQ ID NO: 460
S W V N N C R M A Q V G E L C D L P N W

SEQ ID NO: 461
T Y A K L V N Y C W T A Q L G E L C Y L

SEQ ID NO: 462
P D C S V A V L G E L C D L

SEQ ID NO: 463
G L N P M I P G C Q M A Q V G E L C E L

SEQ ID NO: 464
P Q C R T A L L G E L C E L

SEQ ID NO: 465
P Q C R T A Q V G E L C D L

SEQ ID NO: 466
K A G Q A C R I A H V G E L C D L N E T

SEQ ID NO: 467
Q A C R M A Q V G E L C D F Y G T P E S

SEQ ID NO: 468
L E F M W I Q D C G M A E V G E L C E L

SEQ ID NO: 469
Q D C K F A Q L W D L C D L

SEQ ID NO: 470
D E M Q D C Q I A Q V G E L C D L G L E

SEQ ID NO: 471
E Y F S H D Q D C Q T A Q L G E L C K M

SEQ ID NO: 472
Q D C R F A Q L G D L C D L

SEQ ID NO: 473
Q D C R F A H L G E L C D L T E G Q W W

SEQ ID NO: 474
Q D C R F A H V G D I C D L

SEQ ID NO: 475
G I P Q D C R I A L V G E L C D L D I A

SEQ ID NO: 476
Q D C R K A N V G E L C Y L D W D S P T

SEQ ID NO: 477
Q D C R L A H L G D L C D L W S P R Q N

SEQ ID NO: 478
R V F Q D C R L A L V G E L C E L V G P

SEQ ID NO: 479
S R S I R V Q D C R L A R V G D L C E L

SEQ ID NO: 480
Q D C R M A H L G E L C T L

SEQ ID NO: 481
Q D C R M A Q V G H L C D L

SEQ ID NO: 482
Q D C R M A Q V G E L C E L R G G D S S

SEQ ID NO: 483
S Y L Q D C R M A Q V G Q L C D L N D S

SEQ ID NO: 484
N Q F Q D C R R A L V G Q L C D M Y S K

SEQ ID NO: 485
A V K R F Q D C R T A P V G T L C D L

SEQ ID NO: 486
Q D C R T A P V G D L C D I M G E D V L

SEQ ID NO: 487
W T W Q D C S L A Q V G D L C D I G K K

SEQ ID NO: 488
Q D C W M A Q L G E L C D L F S D H K V

SEQ ID NO: 489
P G V Q D C X I A H X G E L C E F V W N

SEQ ID NO: 490
S W G E L L Q E C R F A H L G E L C S L

SEQ ID NO: 491
W G R Q E C R F A N V G D L C D V S N Y

SEQ ID NO: 492
A V N Q E C R F A R L G E L C V L K N I

SEQ ID NO: 493
N Q V Q E C R I A Q L G D L C E M Y Q S

SEQ ID NO: 494
V L E V L R Q E C R M A Q V G E L C D L

SEQ ID NO: 495
S V W Q E C S M A Q V G D L C E L H I G

SEQ ID NO: 496
K I R R D S Q G C E I A Q V G E L C E L

SEQ ID NO: 497
Q G C W M A Q L G E L C D L S V Q E Y L

SEQ ID NO: 498
Q I C Q T A L V G E L C D L I A D V V T

SEQ ID NO: 499
W P M S Q F Q K C A T A Q V G E L C E L

SEQ ID NO: 500
F I A Q K C R L A K V G E L C D L G Y S

SEQ ID NO: 501
N L R Q N C R D A P V G E L C D L E W I

SEQ ID NO: 502
Q N C R F A Q L G Q L C D L

SEQ ID NO: 503
Q N C S T A K V G E L C D L L M E G T E

SEQ ID NO: 504
Q P C R M A H L F E L C D L

SEQ ID NO: 505
Q P C R N A H L G Q L C D L Q T W T N S

SEQ ID NO: 506
G Y E P I M R A C R N A Q V G D L C D L

SEQ ID NO: 507
V T G W T Y R D C R I A N V G D L C E L

SEQ ID NO: 508
Y Q K G Y S R E C S T A Q L G E L C D L

SEQ ID NO: 509
G A K G R L R E C Y M A Q V G E L C D L

SEQ ID NO: 510
R G C E T A Q V G E L C D E D M W H D R

SEQ ID NO: 511
S D C R I A R V G E L C D L L S D E G K

SEQ ID NO: 512
S D C R L A Q V G Q L C D R R R F R G V

SEQ ID NO: 513
L Y V V R N S D C R M A N V G E L C D L

SEQ ID NO: 514
E K S S D C R N A Q V G E L C D L

SEQ ID NO: 515
S D C S V A N V G D L C N L

SEQ ID NO: 516
N R L S F S S E C R L A Q V G E L C D L

SEQ ID NO: 517
S G C R F A H L G E L C D L

SEQ ID NO: 518
T D C R M A Q V G E L C Y L

SEQ ID NO: 519
T N C R L A H V G D L C D L

SEQ ID NO: 520
W Q R G Q G T Q C R F A L V G E L C D L

SEQ ID NO: 521
L K K Y R H V A C R M A V V G E L C D L

SEQ ID NO: 522
P M G M D P V A C R T A Q V G Q L C D L

SEQ ID NO: 523
V D C R Q A Q V G D L C E L S D E E I S

SEQ ID NO: 524
V D C W I A Q L G E L C E L E D G R R Q

SEQ ID NO: 525
M W I G H A V E C R F A H V G D L C D L

SEQ ID NO: 526
V L C R I A Q V G Q L C E L

SEQ ID NO: 527
V M C R T A Q V G E L C D I

SEQ ID NO: 528
V N C R Q A Q V G D L C D F E G I M S D

SEQ ID NO: 529
V N C S I A K L G E L C Y V

SEQ ID NO: 530
W E C R W A Q V G D L C D L

SEQ ID NO: 531
W Q C R W A Q V G E L C D L S S E N D N

SEQ ID NO: 532
W Y C W M A Q I G E L C D L

SEQ ID NO: 533
Y Q C S I A R L G E L C D L

SEQ ID NO: 534
Y A C R F A H V G D L C D L

SEQ ID NO: 535
E Q T R S G Y A C R T A Q V G E L C D L

SEQ ID NO: 536
Y D C Q K A Q L G E L C D L R Y S V R D

SEQ ID NO: 537
Y D C E M A Q V G E L C D L

SEQ ID NO: 538
D S Q Y K Y Y D C G R A Q L G E L C E L

SEQ ID NO: 539
Y D C R F A H L G D L C D L

SEQ ID NO: 540
Y D C R F A H L G D L C D L

SEQ ID NO: 541
Y D C R F A H L G D L C D L

SEQ ID NO: 542
Y D C R F A Q V G Q L C D I

SEQ ID NO: 543
Y D C R I A Q V G Q L C D L

SEQ ID NO: 544
Y D C R I A Q V G E L C D L

SEQ ID NO: 545
Y D C R I A Q V G D L C D L I S N S N R

SEQ ID NO: 546
MNDYDCRIARMGELCDLLLD

SEQ ID NO: 547
YDCRLARLGDLCDLRVLGVE

SEQ ID NO: 548
YDCRMAKVGDLCDLWSVWGR

SEQ ID NO: 549
ISQHRNYDCRMAQLGELCDL

SEQ ID NO: 550
YDCRSAPVGELCDLVPKDWA

SEQ ID NO: 551
TWAYDCRTAEVGELCDLPVQ

SEQ ID NO: 552
IIIYDCRTAQLGELCEINYD

SEQ ID NO: 553
YDCRVAHVGELCDLPFVGRA

SEQ ID NO: 554
LSVYDCSKARLGELCDLVLE

SEQ ID NO: 555
DGYDYWYDCTMAYVGELCDF

SEQ ID NO: 556
TGKYDCWKAMVGELCDLRVM

SEQ ID NO: 557
MKYYECRFAPLGELCELGVI

SEQ ID NO: 558
YECRIAQVGELCDL

SEQ ID NO: 559
NHWYECRIAQVGEVCDL

SEQ ID NO: 560
YECRLAHVGDLCDL

SEQ ID NO: 561
YECRMANVGELCDI

SEQ ID NO: 562
YECRNAQVGDLCDLGSYVGN

SEQ ID NO: 563
VEEYFCRIAHLGELCDLGLK

SEQ ID NO: 564
TSSYFCRMAELFHLCDLEES

SEQ ID NO: 565
KGGYGCRFARLGELCDLDST

SEQ ID NO: 566
YLCQVAGVGELCDLEESGRN

SEQ ID NO: 567
FEEYNCRFARLGELCDMGSQ

SEQ ID NO: 568
GRFYPCNMAQVGELCELMEY

SEQ ID NO: 569
YPCRMADVGELCDL

SEQ ID NO: 570
LLSYPCRMAQVGELCDIAMK

SEQ ID NO: 571
YQCRFALVGQLCDL

SEQ ID NO: 572
YQCRLAHLGELCDL

SEQ ID NO: 573
YQCRMAQVGELCDL

SEQ ID NO: 574
GIDEDWYSCWIAEVGELCDL

SEQ ID NO: 575
YWCRMAPVGELCDLPGTVL

SEQ ID NO: 576
YWCSVAKVGELCDL

SEQ ID NO: 577
HGLYYCRTAHLGELCDLQSI pH-selective IL-2Rβ ligands that exhibit a greater than 15% decrease in binding to the IL-2Rβ receptor at pH 7.5 compared to pH 6.0 include SEQ ID NOS: 400, 402-405, 407, 409, 410, 411, 413, 415, 416, 418, 419, 420, 421, 423, 425-432, 436, 438-440, 442-446, 448, 450, 452, 453-456, 459-461, 463-468, 470, 471, 473-477, 479, 481-486, 489, 491, 493-496, 498-507, 510-519, 521-524, 526-531, 534-537, 543, 545-548, 550, 551, 558-564, 566, 568-573, and 575, where the pH-selective binding is determined as described in Examples 9-12.

pH-selective IL-2Rβ ligands that exhibit a greater than 50% decrease in binding to the IL-2Rβ receptor at pH 7.5 compared to pH 6.0 include SEQ ID NOS: 400, 404-405, 407, 409, 410, 413, 415, 420, 426, 431, 432, 438-440, 442, 444-446, 450, 452, 453, 455, 459, 464-467, 473-475, 479, 480, 482-484, 486, 489, 493, 496, 498, 502, 504, 510-514, 516-519, 521-523, 527-530, 537, 543, 545-547, 550, 558-564, 571-573, and 575, where the pH-selective binding is determined as described in Examples 9-12.

A pH-selective pH-selective IL-2Rβ ligand can exhibit a greater than 99% decrease in binding to the IL-2Rβ receptor at pH 7.5 compared to pH 6.0, a greater than 90%, a greater than 80%, a greater than 70%, a greater than 60%, a greater than 50%, a greater than 40%, a greater than 30%, a greater than 20%, or a greater than 10% decrease in binding to the IL-2Rβ receptor at pH 7.5 compared to pH 6.0, where the pH-selective binding is determined as described in Examples 9-12.

A pH-selective pH-selective IL-2Rβ ligand can comprise from 5 to 30 amino acids.

A pH-selective pH-selective IL-2Rβ ligand can exhibit a binding affinity to the human IL-2Rβ subunit at pH 6.0 from 1 μM to 100 μM.

A pH-selective pH-selective IL-2Rβ ligand can exhibit a binding affinity to the human IL-2Rβ subunit at pH 6.0 from 0.1 μM to 50 μM.

A pH-selective pH-selective IL-2Rβ ligand can exhibit a binding affinity to the human IL-2Rβ subunit at pH 6.0 of less than 100 μM.

A pH-selective pH-selective IL-2Rβ ligand can exhibit a binding affinity to a mammalian IL-2Rβ subunit at pH 6.0 of less than 100 μM.

A pH-selective pH-selective IL-2Rβ ligand can exhibit a binding affinity to each of the human IL-2Rβ subunit and to the human IL-2Rγc subunit of less than 100 μM.

A pH-selective pH-selective IL-2Rβ ligand can exhibit a binding affinity to the human IL-2Rα (CD25) subunit of greater than 100 μM.

A pH-selective pH-selective IL-2Rβ ligand can exhibit a binding affinity to the human IL-2Rβ subunit that is at least 10 times greater than the binding affinity of the IL-2Rβ ligand to the human IL-2Rα subunit.

Using suitable pH-selective screening methods, peptides can be identified that have a greater binding affinity to IL-2 at lower pH and a weaker binding affinity at a neutral pH. IL-2 agonists and antagonists can be constructed based on the identified pH-selective peptides. These pH-selective agonists and antagonists can exhibit an enhanced therapeutic index reflecting increased cytotoxicity targeting solid tumors and with reduced toxicity to normal tissue.

Acidic-biased affinity selection has been used to identify receptor ligands having increased affinity at pH <6.5 commensurate with a solid tumor microenvironment and having decreased affinity at neutral pH >7.0 commensurate with that of normal tissue. These peptide ligands can serve as components to construct pH-targeted and pH-selective antagonists and agonists.

Certain IL-2Rβ ligands provided by the present disclosure exhibit a binding affinity to the IL-2Rβ subunit of less than 10 µM, and a binding affinity ($IC_{50}$) to the IL-2Rγc subunit of greater than 100 µM.

Certain families of IL-2Rβ ligands bind to the IL-2Rβ subunit competitively with certain other families of IL-2Rβ ligands and non-competitively with other families of IL-2Rβ ligands and also non-competitively with IL-2, and withnd no detectable binding to the the IL-2Rγc subunit.

A specific binding site of the IL-2Rβ subunit can be defined as a binding site in which certain IL-2Rβ ligands of the group of IL-2Rβ ligands having amino acid sequences of SEQ ID NOS: 1-163, 164-182, 578-808, 1028-1043, 1052-1060, and 1084, competitively bind to the binding site with each of the other IL-2Rβ ligands within the group of IL-2Rβ ligands; an IL-2Rβ ligand having amino acid sequence of SEQ ID NO: 1044 does not compete for binding to the binding site with the group of IL-2Rβ ligands; and IL-2 does not compete for binding to the binding site with the group of IL-2Rβ ligands.

Certain IL-2Rβ ligands of the group of IL-2Rβ ligands (SEQ ID NOS: 1-163, 164-182, 578-808, 1028-1043, 1052-1060, and 1084) have a binding affinity ($IC_{50}$) to the IL-2Rβ subunit of less than 100 pM and a binding affinity ($IC_{50}$) to the IL-2Rγc no detectable binding.

An IL-2Rγc ligand having the amino acid sequence of SEQ ID NO: 224 does not compete for binding to the binding site with the group of IL-2Rβ ligands.

The group of IL-2Rβ ligands (SEQ ID NOS: 1-163, 164-182, 578-808, 1028-1043, 1052-1060, and 1084) can comprise the group of IL-2Rβ ligands having the amino acid sequence of SEQ ID NOS: 58, 83, 142, 169, 170, 1033, and 663.

This IL-2R binding site for IL-2Rβ ligands can be characterized using competitive binding assays as described, for example, in Example 20.

Certain IL-2Rγc ligands provided by the present disclosure exhibit a binding affinity to the IL-2Rγc subunit of less than 100 µM, and a binding affinity ($IC_{50}$) to the IL-2Rβ subunit of greater than 100 µM.

Certain families of IL-2Rγc ligands bind to the IL-2Rγc subunit competitively with certain other families of IL-2Rγc ligands and non-competitively with other families of IL-2Rγc ligands.

A specific binding site of the IL-2Rγc subunit can be defined as a binding site in which the group of IL-2Rγc ligands having amino acid sequences of SEQ ID NOS: 194-210, 904-913, 211-233, 914-920, 234-245, 246-254, 921-922, 265-267, 932-940, 1051, and 1065-1082, competitively bind to the binding site with each of the other IL-2Rγc ligands within the group of IL-2Rγc ligands; an IL-2Rγc ligand having amino acid sequence of SEQ ID NO: 948 does not compete for binding to the binding site with the group of IL-2Rγc ligands.

Certain IL-2Rγc ligands of the group of IL-2Rγc ligands (SEQ ID NOS: 194-210, 904-913, 211-233, 914-920, 234-245, 246-254, 921-922, 265-267, 932-940, 1051, and 1065-1082) have a binding affinity ($IC_{50}$) to the IL-2Rγc subunit of less than 100 µM and a binding affinity ($IC_{50}$) to the IL-2Rβ subunit of greater than 100 µM.

An IL-2Rβ ligand having the amino acid sequence of SEQ ID NO: 58 does not compete for binding to the binding site with the group of IL-2Rγc ligands.

The group of IL-2Rγc ligands can comprise the group of IL-2Rγc ligands having the amino acid sequence of SEQ ID NOS: 198, 202, 224, 236, 248, 1051, and 266.

This IL-2R binding site for these IL-2Rγc ligands can be characterized using competitive binding assays as described, for example, in Example 20.

Compounds provided by the present disclosure comprising an IL-2Rβ ligand having an amino acid sequence of SEQ ID NOS: 1-163, 164-182, 578-808, 1028-1043, 1052-1060 or 1084 can bind to the specific binding site on the IL-2Rβ subunit; and Compounds provided by the present disclosure comprising an IL-2Rγc ligand having an amino acid sequence of SEQ ID NOS: 194-210, 904-913, 211-233, 914-920, 234-245, 246-254, 921-922, 265-267, 932-940, 1051, or 1065-1082, can bind to the specific binding site on the IL-2Rγc subunit.

Methods of treating a disease in a patient provided by the present disclosure can comprise administering to a patient a therapeutically effective amount of a compound comprising an IL-2Rβ ligand having an amino acid sequence of SEQ ID NOS: 1-163, 164-182, 578-808, 1028-1043, 1052-1060 or 1084 and/or an IL-2Rγc ligand having an amino acid sequence of SEQ ID NOS: 194-210, 904-913, 211-233, 914-920, 234-245, 246-254, 921-922, 265-267, 932-940, 1051, or 1065-1082.

Methods of treating a disease in a patient provided by the present disclosure can comprise administering to a patient a therapeutically effective amount of a compound that binds to the specific binding site of the IL-2Rβ and/or the specific binding site of the IL-2Rγc subunit.

Methods provided by the present disclosure include methods of modulating the activity of IL-2R by providing a ligand or compound that interacts with the specific binding site of the IL-2Rβ and/or the specific binding site of the IL-2Rγc subunit.

Methods of diagnosing a disease in a patient provided by the present disclosure comprise administering to a patient an effective amount of a ligand or a compound that binds to the specific binding site of the IL-2Rβ and/or the specific binding site of the IL-2Rγc subunit.

Peptides provided by the present disclosure can be synthesized by methods known in the art, for example, by using standard solid phase techniques. The standard methods include exclusive solid phase synthesis, partial solid phase synthesis methods, fragment condensation, classical solution synthesis, and even by recombinant DNA technology. On solid phase, the synthesis can commence from the C-terminal end of the peptide using an α-amino protected resin. A suitable starting material can be prepared, for example, by attaching the required α-amino acid to a chloromethylated resin, a hydroxymethyl resin, or a benzhydrylamine resin. Peptides provided by the present disclosure can be prepared by coupling an α-amino-protected amino acid to the chloromethylated resin with the aid of, for example, a cesium bicarbonate catalyst. After the initial coupling, the α-amino protecting group can be removed by a choice of reagents including trifluoroacetic acid (TFA) or hydrochloric acid (HCl) solutions in organic solvents at room temperature.

The α-amino protecting groups are those known to be useful in the art of stepwise synthesis of peptides. Included are acyl type protecting groups such as formyl, trifluoroacetyl, and acetyl, aromatic urethane type protecting groups such as benzyloxycarboyl (Cbz) and substituted Cbz, aliphatic urethane protecting groups such as tert-butyloxycarbonyl (Boc), isopropyloxycarbonyl, and cyclohexyloxycarbonyl and alkyl type protecting groups such as benzyl and triphenylmethyl. Boc and Fmoc are preferred protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

Suitable side chain protecting groups for Tyr include tetrahydropyranyl, tert-butyl, trityl, benzyl, Cbz, Z—Br—Cbz, and 2,5-dichlorobenzyl. Suitable side chain protecting groups for Asp include benzyl, 2,6-dichlorobenzyl, methyl, ethyl, and cyclohexyl. Suitable side chain protecting groups for Thr and Ser include acetyl, benzoyl, trityl, tetrahydropyranyl, benzyl, 2,6-dichlorobenzyl, and Cbz. The side chain protecting group for Thr and Ser is benzyl. Suitable side chain protecting groups for Arg include nitro, tosyl (Tos), Cbz, adamantyloxycarbonyl mesitoylsulfonyl (Mts), or Boc. Suitable side chain protecting groups for Lys include Cbz, 2-chlorobenzyloxycarbonyl (2-ClCbz), 2-bromobenzyloxycarbonyl (2-BrCbz), Tos, or Boc.

After removal of the α-amino protecting group, the remaining protected amino acids can be coupled stepwise in a desired order. An excess of each protected amino acid is generally used with an appropriate carboxyl group activator such as dicyclohexylcarbodiimide (DCC) in solution, for example, in methylene chloride ($CH_2Cl_2$), dimethyl formamide (DMF) mixtures.

After the desired amino acid sequence has been completed, the desired peptide can be decoupled from the resin support by treatment with a reagent such as trifluoroacetic acid or hydrogen fluoride (HF), which not only cleaves the peptide from the resin, but also cleaves all remaining side chain protecting groups. When the chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides. These solid phase peptide synthesis procedures are well known in the art and can be used to not only determine the minimum size of a peptide with such activity, one can also make all of the peptides that form the group of peptides that differ from the preferred motif (or the minimum size of that motif) in one, two, or more residues. Individual peptides can then be screened for ability to bind to the IL-2Rβ subunit and/or to the IL-2Rγc subunit. Peptide synthesis methods can also be used to synthesize truncation analogs and deletion analogs and combination of truncation and deletion analogs of all of the peptide compounds provided by the present disclosure.

These procedures can also be used to synthesize peptides in which amino acids other than the 20 naturally occurring, genetically encoded, amino acids are substituted at one, two, or more positions of any of the compounds of the invention. For example, naphthylalanine can be substituted for tryptophan, facilitating synthesis. Other synthetic amino acids that can be substituted into the peptides of the present invention include L-hydroxypropyl, L-3, 4-dihydroxyphenylalanyl, d amino acids such as L-d-hydroxylysyl and D-d-methylalanyl, L-a-methylalanyl, b amino acids, and isoquinolyl. D-amino acids and non-naturally occurring synthetic amino acids can also be incorporated into peptides provided by the present disclosure.

A naturally occurring side chains of the 20 genetically encoded amino acids (or D amino acids) can be replaced with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic. For example, proline analogs in which the ring size of the proline residue is changed from 5 members to 4, 6, or 7 members can be employed. Cyclic groups can be saturated or unsaturated, and if unsaturated, can be aromatic or non-aromatic.

Cyclic groups can be saturated or unsaturated, and if unsaturated, can be aromatic or non-aromatic. Heterocyclic groups can contain, for example, one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, and piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

A peptide provided by the present disclosure can be modified, for example, by phosphorylation, and by other methods known in the art. Thus, the peptides of the disclosure can also serve as a basis to prepare peptide mimetics with similar biological activity.

A variety of techniques are available for constructing peptide mimetics with the same or similar desired biological activity as a corresponding peptide but with more favorable activity than the peptide with respect to solubility, stability, and susceptibility to hydrolysis and proteolysis. The following describes methods for preparing peptide mimetics modified at the N-terminal amino group, the C-terminal carboxyl group, and/or changing one or more of the amido linkages in the peptide to a non-amido linkage. Two or more such modifications can be coupled in one peptide mimetic structure (e.g., modification at the C-terminal carboxyl group and inclusion of a —$CH_2$-carbamate linkage between two amino acids in the peptide).

Peptides can be synthesized as the free or can be prepared as the corresponding amide or ester. The amino and/or carboxy terminus of the peptide can also be modified. Amino terminus modifications include methylating (i.e., —$NHCH_3$ or —$NH(CH_3)_2$), acetylating, adding a carbobenzoyl group, or blocking the amino terminus with any blocking group containing a carboxylate functionality defined by RCOO—, where R can be selected from the group consisting of naphthyl, acridinyl, steroidyl, and similar groups. Carboxy terminus modifications include replacing the free acid with a carboxamide group or forming a cyclic lactam at the carboxy terminus to introduce structural constraints. Amino terminus modifications also include, for example, alkylating, acetylating, adding a carbobenzoyl group, and forming a succinimide group.

In preparing peptide mimetics in which the C-terminal carboxyl group is replaced by an ester such as —C(O)OR, the resins used to prepare the peptide acids are employed, and the side chain protected peptide is cleaved with base and the appropriate alcohol, such as methanol. Side chain protecting groups can then be removed in the usual fashion by treatment with hydrogen fluoride to obtain the desired ester.

In preparing peptide mimetics in which the C-terminal carboxyl group is replaced by the amide —C(O)NR$^3$R$^4$, a benzhydrylamine resin is used as the solid support for peptide synthesis. Upon completion of the synthesis, hydrogen fluoride treatment to release the peptide from the support results directly in the free peptide amide (i.e., the C-terminus is —C(O)NH$_2$). Alternatively, use of the chloromethylated resin during peptide synthesis coupled with reaction with ammonia to cleave the side chain protected peptide from the support yields the free peptide amide and reaction with an alkylamine or a dialkylamine yields a side chain protected alkylamide or dialkylamide (i.e., the C-terminus is —C(O)NRR$^1$ where R and R$^1$ are as defined above). Side chain protection can then be removed in the usual fashion by treatment with hydrogen fluoride to give the free amides, alkylamides, or dialkylamides.

The C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride (CH$_2$Cl$_2$), dimethyl formamide (DMF) mixtures. The cyclic peptide can then be formed by internal displacement of the activated ester with the N-terminal amine.

Peptides can be cyclized or can incorporate a desamino or descarboxy residue at the termini of the peptide, so that there is no terminal amino or carboxyl group, to decrease susceptibility to proteases or to restrict the conformation of the peptide. C-terminal functional groups of the peptides include, for example, amide, amide lower alkyl, amide di(lower alkyl), lower alkoxy, hydroxy, and carboxy, and the lower ester derivatives thereof, and pharmaceutically acceptable salts thereof.

Peptide compounds provided by the present disclosure can also serve as structural models for non-peptidic compounds with similar biological activity. Those of skill in the art recognize that a variety of techniques are available for constructing compounds with the same or similar desired biological activity as a particular peptide compound but with more favorable activity than the peptide compound with respect to, for example, solubility, stability, and susceptibility to hydrolysis and proteolysis. These techniques include replacing the peptide backbone with a backbone composed of phosphonates, amidates, carbamates, sulfonamides, secondary amines, and N-methylamino acids.

Peptide mimetics with one or more of the peptidyl linkages —C(O)NH— can be replaced by linkages as a —CH$_2$-carbamate linkage, a phosphonate linkage, a —CH$_2$-sulfonamide linkage, a urea linkage, a secondary amine (—CH$_2$NH—) linkage, or an alkylated peptidyl linkage —C(O)NR$^6$— where R$^6$ is C$_{1-6}$ alkyl can be prepared during conventional peptide synthesis by substituting a suitably protected amino acid analogue for the amino acid reagent at the appropriate point during synthesis.

Suitable reagents include, for example, amino acid analogs in which the carboxyl group of the amino acid has been replaced with a moiety suitable for forming one of the above linkages. For example, if a —C(O)NR— in the peptide can be replaced with a —CH$_2$-carbamate linkage (—CH$_2$OC(O) NR—), then the carboxyl (—COOH) group of a suitably protected amino acid is first reduced to the —CH$_2$OH group which is then converted by conventional methods to a —OC(O)Cl functionality or a para-nitrocarbonate —OC(O) O—C$_6$H$_4$-p-NO$_2$ functionality. Reaction of either of such functional groups with the free amine or an alkylated amine on the N-terminus of the partially fabricated peptide found on the solid support leads to the formation of a —CH$_2$OC (O)NR— linkage. Similarly, an amido linkage in a peptide can be replaced with a phosphonate linkage.

Replacing an amido linkage in the peptide with a —CH$_2$-sulfonamide linkage can be achieved by reducing the carboxyl (—COOH) group of a suitably protected amino acid to the —CH$_2$OH group and the hydroxyl group is then converted to a suitable leaving group such as a tosyl group by conventional methods. Reaction of the tosylated derivative with, for example, thioacetic acid followed by hydrolysis and oxidative chlorination will provide for the —CH$_2$—S(O)$_2$Cl functional group which replaces the carboxyl group of the otherwise suitably protected amino acid. Use of this suitably protected amino acid analogs in peptide synthesis provides for inclusion of an —CH$_2$S(O)$_2$NR— linkage, which replaces the amido linkage in the peptide thereby providing a peptide mimetic. Replacing an amido linkage in the peptide with a urea linkage can be achieved using similar methods.

Secondary amine linkages in which a —CH$_2$NH— linkage replaces the amido linkage in the peptide can be prepared by employing, for example, a suitably protected dipeptide analogue in which the carbonyl bond of the amido linkage has been reduced to a CH$_2$ group by conventional methods. For example, in the case of diglycine, reduction of the amide to the amine will yield after deprotection H$_2$NCH$_2$CH$_2$NHCH$_2$COOH which is then used in N-protected form in the next coupling reaction. The preparation of such analogs by reduction of the carbonyl group of the amido linkage in the dipeptide is known in the art.

Suitably protected amino acid analogs can be employed in a conventional peptide synthesis in the same manner as would the corresponding amino acid. For example, typically about 3 equivalents of the protected amino acid analog can be employed in this reaction. An inert organic diluent such as methylene chloride or DMF is employed and, when an acid is generated as a reaction by-product, the reaction solvent will typically contain an excess amount of a tertiary amine to scavenge the acid generated during the reaction. One particularly preferred tertiary amine is diisopropylethylamine which is typically employed in about 10-fold excess. The reaction results in incorporation into the peptide mimetic of an amino acid analogue having a non-peptidyl linkage. Such substitution can be repeated as desired such that from zero to all of the amido bonds in the peptide have been replaced by non-amido bonds.

Peptides provided by the present disclosure can be cyclized or a desamino or descarboxy residue can be incorporated at the termini of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

Peptides provided by the present disclosure can exist in a cyclized form with an intramolecular disulfide bond between the thiol groups of the cysteines. Alternatively, an intermolecular disulfide bond between the thiol groups of the cysteines can be produced to yield a dimeric (or higher oligomeric) compound. One or more of the cysteine residues may also be substituted with a homocysteine. One of the sulfurs can be replaced by a $CH_2$ group or other isostere for sulfur. These analogs can be made via an intramolecular or intermolecular displacement. One of skill in the art will readily appreciate that this displacement can also occur using other homologs of the a-amino-g-butyric acid derivative shown above and homocysteine.

Alternatively, the amino-terminus of the peptide can be capped with an α-substituted acetic acid, wherein the α-substituent is a leaving group, such as an α-haloacetic acid, for example, α-chloroacetic acid, α-bromoacetic acid, or α-iodoacetic acid. Peptides provided by the present disclosure can be cyclized or dimerized via displacement of the leaving group by the sulfur of the cysteine or homocysteine residue.

An IL-2R agonist and a compound comprising an IL-2Rβ ligand and/or an IL-2Rγc ligand can be, for example, a synthetic peptide, a conjugate of a peptide to another peptide or protein, a recombinant fusion protein, or a single chain peptide.

An IL-2R agonist compound can comprise an IL-2Rβ ligand provided by the present disclosure, an IL-2Rγc ligand provided by the present disclosure, or both an IL-2Rβ ligand provided by the present disclosure and an IL-2Rγc ligand provided by the present disclosure.

An IL-2R agonist compound can comprise an IL-2Rβ ligand provided by the present disclosure such as an IL-2Rβ ligand of SEQ ID NOS: 1-193, 578-903, 1028-1050, 1052-1064, or 1084, an IL-2Rγc ligand provided by the present disclosure such as an IL-2Rγc ligand of SEQ ID. NO: 194-267, 904-1027, or 1065-1083, or both an IL-2Rβ ligand provided by the present disclosure and an IL-2Rγc ligand provided by the present disclosure.

A peptide provided by the present disclosure can comprise an IL-2Rβ ligand or an IL-2Rγc ligand and additional amino acids.

The additional amino acids can be bonded to the C-terminus of the IL-2Rβ ligand or the IL-2Rγc ligand, to the N-terminus of the IL-2Rβ ligand or the IL-2Rγc ligand, or to both the C-terminus and the N-terminus of the IL-2Rβ ligand or the IL-2Rγc ligand.

A peptide comprising an IL-2Rβ ligand and/or an IL-2Rγc ligand can comprise, for example, from 10 to 50 amino acids, from 10 to 40 amino acids, from 10 to 30 amino acids, or from 15 to 25 amino acids.

A peptide comprising an IL-2Rβ ligand and/or an IL-2Rγc ligand can comprise, for example, from 5 to 300 amino acids, from 10 to 200 amino acids, or from 10 to 100 amino acids.

A peptide comprising an IL-2Rβ ligand and an IL-2Rγc ligand can have at least substantially the same binding affinity ($IC_{50}$) for the respective human IL-2 subunit as that of the respective IL-2R ligand alone.

A compound comprising an IL-2Rβ ligand and/or an IL-2Rγc ligand can be a conjugate.

A conjugate can comprise one or more IL-2Rβ ligands, one or more IL-2Rγc ligands, or a combination thereof.

A conjugate can be a homodimer comprising two IL-2Rβ ligands or two IL-2Rγc ligands.

A conjugate can be a heterodimer comprising at least one IL-2Rβ ligand and at least one IL-2Rγc ligand.

A conjugate can be a heterodimer comprising at least one IL-2Rβ ligand and at least one IL-2Rγc ligand covalently coupled to a protein.

A conjugate can comprise a linker, wherein the linker is configured to attach an IL-2Rβ ligand and/or an IL-2Rγc ligand to one or more other IL-2Rβ ligands and/or IL-2Rγc ligands. The linker can be attached to an IL-2Rβ ligand and/or an IL-2Rγc ligand and any additional moiety by a covalent bond, or by non-covalent bonding such as by ionic bonding.

Each IL-2Rβ ligand and/or an IL-2Rγc ligand can independently be attached to a linker through the C-terminus, the N-terminus, or both the C-terminus and N-terminus.

For example, in a homodimer, the C-terminus of a first IL-2Rβ ligand and the C-terminus of a second IL-2Rβ ligand can be attached to the linker; the N-terminus of a first IL-2Rβ ligand and the N-terminus of a second IL-2Rβ ligand can be attached to the linker; or the C-terminus of a first IL-2Rβ ligand and the N-terminus of a second IL-2Rβ ligand can be attached to the linker.

For example, in a homodimer, the C-terminus of a first IL-2Rγc ligand and the C-terminus of a second IL-2Rγc ligand can be attached to the linker; the N-terminus of a first IL-2Rγc ligand and the N-terminus of a second IL-2Rγc ligand can be attached to the linker; or the C-terminus of a first IL-2Rγc ligand and the N-terminus of a second IL-2Rγc ligand can be attached to the linker.

For example, in a heterodimer, the C-terminus of an IL-2Rβ ligand and the C-terminus of an IL-2Rγc ligand can be attached to the linker; the N-terminus of an IL-2Rβ ligand and the N-terminus of an IL-2Rγc ligand can be attached to the linker; the C-terminus of an IL-2Rβ ligand and the N-terminus of an IL-2Rγc ligand can be attached to the linker, or the N-terminus of an IL-2Rβ ligand and the C-terminus of an IL-2Rγc ligand can be attached to the linker.

A heterodimeric compound comprising an IL-2Rβ ligand and an IL-2Rγc ligand can be configured to activate the IL-2 receptor.

A heterodimeric compound comprising an IL-2Rβ ligand and an IL-2Rγc ligand can be configured to activate the IL-2 receptor without activating cells expressing the IL-2Rα ligand.

For example, when incubated with a heterodimeric compound comprising an IL-2Rβ ligand and an IL-2Rγc ligand, primary human peripheral blood mononuclear cells (PBMC) expressing the IL-2Rβγc subunits phosphorylate transcription 5 (STAT5); and primary human peripheral blood mononuclear cells (PBMC) expressing the IL-2Rα (CD25) subunit, do not phosphorylate transcription 5 (STAT5).

A heterodimer can comprise an IL-2Rβ ligand, an IL-2Rγc ligand, and a linker, wherein the linker is configured such that the heterodimer is an agonist for the IL-2 receptor.

A linker can comprise a length that facilitates binding of an IL-2Rβ ligand and/or an IL-2Rγc ligand to the IL-2 receptor. For example, a linker can have a length, for example, from 20 Å to 100 Å, from 30 Å to 80 Å, or from 40 Å to 60 Å.

A linker can comprise a chemical structure that facilitates binding of an IL-2Rβ ligand and/or an IL-2Rγc ligand to the IL-2 receptor. For example, a linker can comprise a peptide, or a hydrocarbon.

A peptide linker can comprise, for example, from 5 to 100 amino acids, from 5 to 80 amino acids, from 5 to 60 amino acids, from 5 to 40 amino acids, from 5 to 20 amino acids, or from 5 to 10 amino acids. A peptide linker can comprise, for example, from 2 to 100 amino acids, from 2 to 80 amino acids, from 2 to 60 amino acids, from 2 to 40 amino acids, from 2 to 20 amino acids, from 5 to 10 amino acids, or from 2 to 5 amino acids.

A hydrocarbon linker can be a polyethylene oxide. A polyethylene oxide can have the structure of the formula —(O—(CH$_2$)$_2$-)$_n$—(CH$_2$)$_2$—, where n is an integer from 1 to 30.

A hydrocarbon linker can be derived from a polyethylene oxide having the structure of the formula H$_2$N—(O—(CH$_2$)$_2$-)$_n$—(CH$_2$)$_2$—COOH, where n is an integer from 1 to 30.

Peptide dimer compounds can comprise two monomer subunits, wherein the peptide dimer compounds comprise IL-2Rβ ligands and/or IL-2Rγc ligands. Monomer subunits present in a peptide dimer compound can be linked at either their C- or N-terminus or via internal amino acid residues such as by a linker moiety. Both monomer subunits can be linked via their respective N-termini, both monomer subunits can be linked via their respective C-termini, or both monomer subunits can be linked via internal amino acid residues. One monomer subunit can be linked via any of its N-terminus, C-terminus, or by an internal amino acid to another monomer subunit via any of its N-terminus, C-terminus or an internal amino acid, and linkages may occur via the same or different amino acid residues on two monomer subunits of a peptide dimer compound. Monomer subunits of peptide dimer compounds can be linked via both their N-terminus and their C-terminus. The two N-termini of the monomer subunits can be linked; the two C-termini of the monomer subunits can be linked; the N-terminus of the first monomer subunit can be linked to the C-terminus of the second monomer subunit of a peptide dimer compound, and the C-terminus of the first monomer subunit can be linked to the N-terminus of the second monomer subunit of the peptide dimer compound.

A linker can comprise a peptide or a non-peptide. A linker moiety can include any suitable structure, length, and/or size. A linker moiety can include, for example, DIG, PEG13, PEG25, PEG1K, PEG2K, PEG3.4K, PEG4K, PEG5K, IDA, IDA-Palm, IDA-Boc, IDA-Ac, IDA-isovaleric acid, ADA triazine, triazine-Boc, isophthalic acid, 1,3-phenylenediacetic acid, Glu, Asp, D-Glu, D-Asp, 1,4-phenylenediacetic acid, biphenyl diacetic acid, cyclopropylacetic acid, succinic acid, glutaric acid, dodecanedioic acid, suitable aliphatic diacids, suitable aromatic diacids, heteroaromatics, and polyethylene glycols having a molecular weight, for example, from 400 Da to 40,000 Da. When a linker is IDA, ADA or any linker with free amine it can be acylated with acylating organic compound such as 2-me-trifluorobutyl, trifluoropentyl, acetyl, octonyl, butyl, pentyl, hexyl, palmityl, lauryl, oleoyl, lauryl, trifluoromethyl butyric, cyclopentane carboxylic, cyclopropylacetic, 4-fluorobenzoic, 4-fluorophenyl acetic, 3-phenylpropionic, tetrahedro-2H-pyran-4-carboxylic, succinic acid, and glutaric acid, straight chain aliphatic acids with 10 to 20 carbon units, cholic acid and other bile acids. A small PEG (PEG4-PEG13), Glu, IsoGlu or Asp can be used as spacer before acylations.

A linker can connect two monomer subunits by connecting two sulfur containing C- or N-terminal amino acids. The two sulfur-containing amino acids can be connected by a linker comprising a di-halide, an aliphatic chain, or a PEG. A linker can connect two monomeric subunits by connecting sulfur containing C-terminal amino acids at the C-terminus of each monomer subunit. A linker can connect two monomeric subunits by connecting sulfur containing N-terminal amino acids at the N-terminus of each monomer subunit. A linker can connect two monomeric subunits by connecting a sulfur-containing C-terminal amino acid of one monomer subunit to a sulfur-containing N-terminal amino acid of the other monomer subunit. The two sulfur-containing amino acids can be connected by a linker comprising homobifunctional maleimide crosslinkers, di-halide, 1,2-bis(bromomomethyl)benzene, 1,2-bis(chloromomethyl)benzene, 1,3-bis(bromomomethyl)benzene, 1,3-bis(chloromomethyl)benzene, 1,4-bis(bromomomethyl)benzene, 1,4-bis(chloromomethyl)benzene, 3,3'-bis-bromomethyl-biphenyl, or 2,2'-bis-bromomethyl-biphenyl. Examples of haloacetyl crosslinkers contain an iodoacetyl or a bromoacetyl group. These homo bifunctional linkers may contain spacers comprising PEG or an aliphatic chain. A linker can be a bifunctional linker (e.g., di-acid, di-amine, dihalide, N-hydroxy succinamine (NHS)-activated diesters, bis-maleimides, which may be capable of linking two monomer subunits through amine, ester, thioether, di-thio, or ether bonds.

Examples of suitable linkers include DIG, PEG4, PEG4-biotin, PEG13, PEG25, PEG1K, PEG2K, PEG3.4K, PEG4K, PEG5K, IDA, ADA, Boc-IDA, glutaric acid, isophthalic acid, 1,3-phenylenediacetic acid, 1,4-phenylenediacetic acid, 1,2-phenylenediacetic acid, triazine, Boc-triazine, IDA-biotin, PEG4-Biotin, AADA, aliphatics, aromatics, heteroaromatics, and polyethylene glycol-based linkers having a molecular weight from 400 Da to 40,000 Da. Examples of suitable bifunctional linkers include di-acid, di-amine, dihalide, N-hydroxy succinamine (NHS)-activated diesters, bis-maleimides, which may be capable of linking two monomer subunits through amine, ester, thioether, di-thio, or ether bonds.

Peptide monomers and compounds can form cyclized structures through a disulfide bond, lactam bond, olefin bond, triazole bond, selenoether bond or a diselenide bond. A cyclized structure of each peptide ligand can, in some circumstances, increase potency and selectivity of the ligands and compounds comprising the ligands.

For example, a heterodimer can comprise an IL-2Rβ ligand provided by the present disclosure such as an IL-2Rβ ligand of SEQ ID NOS: 1-193, 578-903, 1028-1050, 1052-1064, or 1084, an IL-2Rγc ligand provided by the present disclosure such as an IL-2Rγc ligand of SEQ ID NOS: 194-267, 904-1027, and 1065-1083 and a linker such as a polyethylene glycol-based linker having a length from 10 Å to 60 Å.

The individual IL-2Rβ and IL-2Rγc ligands can be linked in various ways to produce heterodimers, that can be evaluated for IL-2R agonist activity, antagonist activity or other relevant activity. Agonist activity can depend on heterodimers binding simultaneously to both IL-2R and IL-2Rγc subunits to induce proximity and orientation compatible with signaling. Several compound characteristics can influence the activity of heterodimers such as, for example, the linker structure, the linker length, the peptide ligand orientation, and the ECD binding site-specificity of the monomeric peptides.

Because signaling of the IL-2 receptor may be compatible with a range of induced subunit orientations a linker can facilitate binding outside the IL-2R binding site(s). The dimensions of the quaternary complex of IL-2 with the IL-2Rα, IL-2R and IL-2Rγc subunits suggest that linkers with a length up to about 50 Å may be useful to connect IL-2Rβ and IL-2Rγc ligands to induce productive subunit alignment and agonist activity.

For example, a heterodimer comprising an IL-2Rβ ligand and an IL-2Rγc ligand can be attached through a PEG linker. At the terminus of the PEG-linker distal to the peptide, an alkyne functionality can be attached. The other peptide monomer can be functionalized with a terminal azide. The monomers can be coupled utilizing click chemistry, for example, using a 1,3 dipolar Huisgen cycloaddition reaction between the azide and alkyne to form a triazole linkage, under conditions compatible with maintenance of disulfide bridges that are present in certain peptide ligands. Alkyne and azide groups can be incorporated into each monomer using commercially-available amino acid building blocks. The spacing between the two peptide ligands can be selected using PEG-linkers of various lengths. Using commercially available Fmoc-PEG amino acids, total linker lengths from 10 Å, or less to 50 Å, or more can be synthesized, providing for a wide range heterodimer linker length diversity.

Induced receptor subunit orientation and the potential for proper intra-cellular alignment and signaling can be, in part, a function of the orientations in which the peptide ligands link to form the heterodimer. To determine suitable induced subunit orientations, peptide ligands can be linked in any of four (4) possible orientations such that the C-termini of both subunit binding ligands are coupled through a linker, the N-termini of both subunit binding ligands are coupled through a linker, or the N-terminus of one binding subunit can be bound through the C-terminus of the other binding subunit (2 scenarios possible) through a suitable linker. Heterodimers can also be linked through amino acid side chains. Heterodimers can also be linked through amino acid side chains. Heterodimer linkage orientation can be engineered, for example, by synthesizing ligand monomers with the click functionality, i.e., azide or alkyne, and PEG-linker on either the N- or on the C-terminus.

Peptides provided by the present disclosure can include at least one IL-2Rβ ligand and/or at least one IL-2Rγc ligand. A peptide can include, for example, less than 50 amino acids, which can include the amino acids constituting at least one IL-2Rβ ligand and/or at least one IL-2Rγc ligand.

A peptide comprising an IL-2Rβ ligand and/or an IL-2Rγc ligand can comprise, for example, from 5 to 100 amino acids, from 5 to 80 amino acids, from 5 to 50 amino acids, from 10 to 40 amino acids, from 10 to 30 amino acids, or from 15 to 25 amino acids.

In addition to an IL-2Rβ ligand and/or an IL-2Rγc ligand, a peptide can include additional amino acids, for example, for establishing the conformation of an IL-2Rβ ligand and/or an IL-2Rγc ligand and/or for coupling the IL-2Rβ ligand and/or the IL-2Rγc ligand to other compounds. The additional amino acids can be bonded to the N-terminus and/or to the C-terminus of the IL-2Rβ ligand and/or the IL-2Rγc ligand.

Conjugates provided by the present disclosure include at least one IL-2Rβ ligand and/or at least one IL-2Rγc ligand.

A conjugate can comprise a polypeptide.

A polypeptide can be a single chain peptide having two more IL-2Rβ ligands and/or two or more IL-2Rγc ligands. The IL-2Rβ ligands and/or the IL-2Rγc ligands can be bonded through amino acid linkers.

An amino acid linker can comprise, for example, more than one amino acid, greater than 5 amino acids, greater than 10 amino acids, greater than 50 amino acids, or greater than 100 amino acids. A peptide linker can comprise, for example, from 1 to 100 amino acids from 3 amino acids to 75 amino acids, from 5 amino acids to 50 amino acids, or from 10 amino acids to 25 amino acids.

For example, in a homodimer, the C-terminus of a first IL-2Rβ ligand and/or IL-2Rγc ligand and the C-terminus of a second IL-2Rβ ligand and/or IL-2Rγc ligand can be attached to the linker; the N-terminus of a first IL-2Rβ ligand and/or IL-2Rγc ligand and the N-terminus of a second IL-2Rβ ligand and/or IL-2Rγc ligand can be attached to the linker; or the C-terminus of a first IL-2Rβ ligand and/or IL-2Rγc ligand and the N-terminus of a second IL-2Rβ ligand and/or IL-2Rγc ligand can be attached to the linker.

A polypeptide comprising an IL-2Rβ ligand and/or IL-2Rγc ligand provided by the present disclosure can comprise, for example, from 5 amino acids to 4,000 amino acids, from 5 amino acids to 3,000 amino acids, from 5 amino acids to 2,500 amino acids, or from 5 amino acids to 2,000 amino acids.

A polypeptide can be a synthetic peptide or a recombinant polypeptide.

A single chain peptide can be a heteromer having at least one IL-2Rβ ligand and/or IL-2Rγc ligand in combination with one or more IL-2Rα ligands, one or more IL-2Rβ ligands, and/or one or more IL-2Rγc ligands. For example, a single chain peptide can comprise an IL-2Rα ligand, an IL-2Rβ ligand, and/or an IL-2Rγc ligand with amino acid linkers coupling adjacent ligands. A single chain peptide can further include additional amino acids at the N-terminus and/or C-terminus of the polypeptide.

An IL-2Rα ligand, an IL-2Rβ ligand and/or IL-2Rγc ligand can be arranged in any order.

Each of the adjacent ligands can independently be coupled through the N-terminus of each ligand, through the C-terminus of each ligand, through the N-terminus and C-terminus of the adjacent ligands, or through the side chains of the ligands and/or linkers.

For example, in a heteromer, the C-terminus of an IL-2Rα ligand can be attached to the linker and the N-terminus of an IL-2Rβ ligand or the N-terminus of an IL-2Rγc ligand can be attached to the linker; the C-terminus of an IL-2Rβ ligand or the N-terminus of an IL-2Rγc ligand can be attached to the linker, or the N-terminus of an IL-2Rα ligand can be attached to the linker.

The individual IL-2Rβ ligands and/or IL-2Rγc ligands can be linked in various ways to produce homodimers or homomers, heteromers, that can be evaluated for IL-2R agonist and/or IL-2R antagonist activity. For example, homodimers of IL-2Rα ligands or heteromers of an IL-2Rα ligand with an IL-2Rβ ligands and/or IL-2Rγc can function as an IL-2R antagonist. Agonist activity can depend on heteromers binding simultaneously to both IL-2R and IL-2Rγc subunits to induce proximity and orientation compatible with signaling or inhibition. Several compound characteristics can influence the activity of homodimers or heteromers such as, for example, the linker structure, the linker length, the peptide ligand orientation, the ECD binding site-specificity of the monomeric peptides, and the affinities of each ligand for the respective receptor subunits. IL-2R agonist and IL-2R antagonist activity can depend, for example, on increasing the affinity of the IL-2Rα ligand to the IL-2Rα subunit, the IL-2Rβ ligand to the IL-2Rβ subunit, and/or the IL-2Rγc ligand to the IL-2Rγc subunit. Induced receptor subunit orientation and the potential for proper intra-cellular alignment and signaling can be, in part, a function of the orientations in which the peptide ligands link to form the heteromer. To determine suitable induced subunit orientations, adjacent IL-2R ligands can be linked in any of four (4) possible orientations such that the C-termini of both subunit binding ligands are coupled through a linker, the N-termini of both subunit binding ligands are coupled through a linker, or the N-terminus of one binding subunit can be bound through the C-terminus of the other binding subunit through a suitable linker. Homomers and heteromers can also be linked through amino acid side chains. Heteromer linkage orientation can be engineered, for example, by synthesizing ligand monomers with the click functionality, i.e., azide or alkyne, and PEG-linker on either the N-terminus or on the C-terminus.

A polypeptide can be a synthetically modified polypeptide comprising one or more IL-2Rβ ligands and/or one or more IL-2Rγc ligands. The modifications can influence, for example, the activity of the polypeptide or the pharmacokinetics of the polypeptide. Examples include polypeptides incorporating polyethylene glycol moieties or albumin binding moieties.

Compounds comprising an IL-2Rβ ligand, an IL-2Rγc ligand, or both an IL-2Rβ ligand and an IL-2Rγc ligand include fusion proteins.

An IL-2Rβ ligand and/or an IL-2Rγc ligand can be fused to another protein that imparts a desired functionality to the construct. For example, the protein can impart a desired pharmacokinetic profile or can be designed to target specific antigens.

Examples of suitable fusion partners include Fc fusion proteins, IgG fusion proteins, human serum albumin (HSA) fusion proteins, other human proteins and mutants and/or variants thereof; and hydrophilic, biodegradable protein polymers. A fusion protein partner can be a naturally occurring protein, a modified-naturally occurring protein, or a synthetic protein.

For example, an IL-2Rβ ligand and/or an IL-2Rγc ligand provided by the present disclosure can be fused to a protein that increases the circulating half-life of the compound. Fusion of therapeutic proteins with the IgG or IgG Fc domain accomplishes this by increasing the hydrodynamic radius of the protein, thus reducing renal clearance, and through Neonatal Fc Receptor (FcRn)-mediated recycling of the fusion protein, thus prolonging the circulating half-life. Other fusion proteins can be designed to modify properties such as the pharmacokinetics, biodistribution, pharmacodynamics, pharmacology, cytotoxicity, and/or targeting.

A fusion protein provided by the present disclosure can comprise a peptide, or multiple tandem peptides provided by the present disclosure linked to one or more fusion protein partners. A fusion protein partner can be linked to the N-terminus and/or the C-terminus of tandem peptides. One or more fusion protein partners can be linked to the N-terminus and/or the C-terminus of tandem peptides. An IL-2Rβ ligand and/or an IL-2Rγc ligand can be linked to one or more fusion protein partners, where each of the fusion protein partners can be the same or some of the fusion protein partners can be different than other of the fusion protein partners linked to a peptide.

The amino acid sequence at the junction between an IL-2Rβ ligand and/or IL-2Rγc ligand and a fusion partner protein can be either a direct fusion of the two protein sequences or a fusion with an intervening linker peptide. Linker peptides can be included as spacers between the two protein moieties. Linker peptides can promote proper protein folding and stability of the component protein moieties, improve protein expression, and enhance bioactivity of the component protein moieties. Peptide linkers used in fusion proteins can be designed to be unstructured flexible peptides. Peptide linkers can be, for example, rich in glycine and serine, such as repeats of a sequence such as, for example, GS, GGS, GGGS (SEQ ID NO: 1085), GGGGS (SEQ ID NO: 1086), (GGGGs)3 (SEQ ID NO: 1087), (Gly)8 (SEQ ID NO: 1088), (Gly)6 (SEQ ID NO: 1089), (EAAAK)1-3 (SEQ ID NO: 1090), A(EAAAK)4ALEA(EAAAK)4A (SEQ ID NO: 1091), PAPAP (SEQ ID NO: 1092), AEAAAKEAAAKA (SEQ ID NO: 1093), (Ala-Pro)a (10-34 aa) (SEQ ID NO: 1094), disulfide, VSQTSKLTR AETVFPDV (SEQ ID NO: 1095), PLG LWA (SEQ ID NO: 1096), and GFLG (SEQ ID NO: 1097), RVQDVIERFWD-FIDQLSGSGSGK (SEQ ID NO: 1098), and VDADG-PLARLKKAIFSPGSGSGK (SEQ ID NO: 1099), (PA)n where n is an integer 1 to 20 (SEQ ID NO: 1100) such as (PA)10 (SEQ ID NO: 1101), and (GS)n where n is an integer from 1 to 20 (SEQ ID NO: 1102) such as (GS)10 (SEQ ID NO: 1103). A flexible linker peptide with a fully extended β-strand conformation can have an end-to-end length of approximately 3.5 Å per residue. Thus, a linker peptide of 5, 10, 15, or 10 residues will have a maximum fully extended length of 17.5 Å, 35 Å, 52.5 Å, 70 Å, 140 Å, or more than 140 Å, respectively.

A linker peptide can facilitate obtaining an appropriate conformation and orientation of individual fusion protein moieties to facilitate the engagement of the IL-2Rβ ligand and/or IL-2Rγc ligand with the IL-2Rβ subunit and/or IL-2Rγc subunit, facilitate binding of the IL-2Rβ ligand and/or IL-2Rγc ligand to the IL-2 receptor, enable fusion protein recycling, and prolong the circulating half-life of the active moiety. Because the factors influencing these interactions are difficult to predict, the requirement for and the proper length of a linker peptide must be empirically tested and determined.

There are multiple options for the design and construction of a fusion protein comprising an IL-2Rβ and/or an IL-2Rγc ligand and which can be selected to obtain a molecule having the desired biological activity and pharmaceutical characteristics. Design options include, for example, the nature of the IL-2 selective agonist, the choice of the partner protein moiety, the configuration of fusion partners in the fusion protein, and the amino acid sequence at the junction between the IL-2R ligand and the fusion partner protein.

In general, preparation of the fusion proteins provided by the present disclosure can be accomplished by recognized recombinant DNA techniques involving, for example, polymerase chain amplification reactions (PCR), preparation of plasmid DNA, cleavage of DNA with restriction enzymes, preparation of oligonucleotides, ligation of DNA, isolation of mRNA, introduction of the DNA into a suitable cell, transformation or transfection of a host, and culturing of the host. Additionally, fusion proteins can be isolated and purified using chaotropic agents and well known electrophoretic, centrifugation, and chromatographic methods.

Genes encoding fusion proteins provided by the present disclosure can involve restriction enzyme digestion and ligation as the basic steps employed to yield DNA encoding the desired fusions. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The expression construct can be assembled in stages employing rounds of restriction, ligation, and transformation of E. coli. Numerous cloning vectors suitable for construction of the expression construct are known in the art. The selection of a cloning vector can be influenced by the gene transfer system selected for introduction of the expression construct into the host cell. At the end of each stage, the resulting construct may be analyzed by restriction, DNA sequence, hybridization and PCR analyses.

Site-directed mutagenesis can be used to introduce specific mutations into the genes encoding the fusion proteins provided by the present disclosure by methods known in the art. Any suitable site-directed mutagenesis procedure can be used in the present invention. There are many commercial kits available that can be used to prepare the variants of this invention.

Various promoters (transcriptional initiation regulatory region) may be used according to the invention. The selection of the appropriate promoter can depend on the proposed expression host. Promoters from heterologous sources may be used as long as they are functional in the chosen host.

Various signal sequences may be used to facilitate expression of the proteins described herein. Signal sequence are selected or designed for efficient secretion and processing in the expression host may also be used. A signal sequence which is homologous to the human IL-2 coding sequence may be used for mammalian cells. Other suitable signal sequence/host cell pairs include the B. subtilis sacB signal sequence for secretion in B. subtilis, and the Saccharontyces cerevisiae α-mating factor or P. pastoris acid phosphatase phoI signal sequences for P. pastoris secretion. The signal sequence may be joined directly through the sequence encoding the signal peptidase cleavage site to the protein coding sequence, or through a short nucleotide bridge.

Elements for enhancing transcription and translation have been identified for eukaryotic protein expression systems. For example, positioning the cauliflower mosaic virus (CaMV) promoter 1000 bp on either side of a heterologous promoter may elevate transcriptional levels by 10- to 400-fold in plant cells. The expression construct should also include the appropriate translational initiation sequences. Modification of the expression construct to include a Kozak consensus sequence for proper translational initiation may increase the level of translation by 10-fold.

The expression cassettes are joined to appropriate vectors compatible with the host that is being employed. The vector must be able to accommodate the DNA sequence coding for the fusion proteins to be expressed. Suitable host cells include eukaryotic and prokaryotic cells, such as those cells that can be easily transformed and exhibit rapid growth in culture medium. Examples of suitable host cells include prokaryotes such as E. coli, Bacillus subtillus, etc. and eukaryotes such as animal cells and yeast strains, e.g., S. cerevisiae. Suitable mammalian cells include HEK, J558, NSO, SP2-O or CHO. Other suitable hosts include, e.g., insect cells such as Sf9. Conventional culturing conditions can be employed. Stable transformed or transfected cell lines can then be selected. In vitro transcription-translation systems can also be employed as an expression system.

Nucleic acids encoding a desired fusion protein can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration.

Alternatively, one can use synthetic gene construction for all or part of the construction of the fusion proteins described herein. This can entail in vitro synthesis of a designed polynucleotide molecule to encode a polypeptide molecule of interest. Gene synthesis can be performed utilizing a number of techniques, such as the multiplex microchip-based technology and similar technologies wherein oligonucleotides are synthesized and assembled upon photo-programmable microfluidic chips.

Fusion proteins provided by the present disclosure can be isolated from harvested host cells or from the culture medium. Standard protein purification techniques are used to isolate the proteins of interest from the medium or from the harvested cells. For example, the purification techniques can be used to express and purify a desired fusion protein on a large-scale (i.e., in at least milligram quantities) from a variety of approaches including roller bottles, spinner flasks, tissue culture plates, bioreactor, or a fermenter.

Compounds provided by the present disclosure comprise at least one IL-2Rβ ligand and/or at least one IL-2Rγc ligand. Compounds can comprise, for example, from 1 to 10 IL-2Rβ ligands and/or IL-2Rγc ligands, from 1 to 6 IL-2Rβ ligands and/or IL-2Rγc ligands, or from 1 to 3 IL-2Rβ ligands and/or IL-2Rγc ligands. Examples of compounds comprising an IL-2Rβ ligand and/or IL-2Rγc ligand include peptides and conjugates. Examples of conjugates include one or more IL-2Rβ ligands, and/or one or more IL-2Rγc ligands bound to a polypeptide, a macromolecule such as a polyethylene glycol, a fusion protein, or a biological molecule such as an antibody.

Functionally, compounds comprising at least one IL-2Rβ ligand and/or at least one IL-2Rγc ligand can be IL-2Rβγc agonists, IL-2Rαβγc agonists, IL-2Rβγc antagonists, IL-2Rαβγc antagonists, diagnostic reagents, imaging reagents, targeting compounds, cytotoxic compounds, and compounds exhibiting dual pharmacology.

Compounds comprising an IL-2Rβ ligand and/or an IL-2Rγc ligand provided by the present disclosure can have a molecular weight, for example, from 1,000 to 400,000 Da, from 1,000 to 200,000 Da, from 1,000 to 100,000 Da, from 1,000 Da to 20,000 Da, from 1,500 Da to 15,000 Da, from 2,000 Da to 10,000 Da, or from 5,000 Da to 10,000 Da.

Compounds comprising an IL-2Rβ ligand and/or an IL-2Rγc ligand provided by the present disclosure can be attached to one or more moieties that impart a property to the compound that enhances therapeutic efficacy. Examples of properties include potency, aqueous solubility, polarity, lipophilicity, pharmacokinetics, targeting, bioavailability, pH-dependent binding, bioactivity, pharmacodynamics, cellular activity, metabolism, efficacy, reversible incapacitation (caging), selectivity, or a combination of any of the foregoing.

Compounds comprising an IL-2Rβ ligand and/or an IL-2Rγc ligand can comprise one or more moieties that are cleavable in vivo. The moiety can be cleavable in a target specific environment such as, for example, by a target specific or target enriched enzyme, or pH. The moiety can be cleavable upon exposure to electromagnetic energy such as visible light or infrared radiation and/or by exposure to thermal energy.

Compounds comprising an IL-2Rβ ligand and/or an IL-2Rγc ligand can include a polymer, a peptide, or an antibody.

Compounds comprising an IL-2Rβ ligand and/or IL-2Rγc an ligand can include a tumor-targeting moiety such as, for example, a tumor-specific antibody, a tumor-specific antibody fragment, a tumor-specific protein, a tumor-specific peptide, a non-peptidyl tumor cell ligand, or a combination of any of the foregoing.

Compounds comprising an IL-2Rβ ligand and/or an IL-2Rγc ligand can include an immune cell-targeting moiety such as, for example, an immune cell-specific antibody, an immune cell-specific antibody fragment, an immune cell-specific protein, an immune cell-specific peptide, a non-peptidyl immune cell-ligand, or a combination of any of the foregoing.

Compounds comprising an IL-2Rβ ligand and/or an IL-2Rγc ligand can comprise a caged molecule or molecules. A caged molecule can in effect encapsulate the compound and can serve to prevent bioactivity in certain tissues, for example, to protect peripheral tissues from the toxicity of IL-2Rαβγc activation.

Compounds comprising an IL-2Rβ ligand and/or an IL-2Rγc ligand can comprise a moiety, wherein the moiety comprises a small molecule, a peptide, a polymer, or an antibody. The small molecule can be a non-peptidyl molecule. The moiety can exhibit a pharmacological effect. The pharmacological effect can manifest when the moiety is bound to the IL-2Rβ ligand and/or the IL-2Rγc ligand and/or after the moiety is cleaved from the compound comprising an IL-2Rβ ligand and/or the IL-2Rγc ligand.

Compounds comprising an IL-2Rβ ligand and/or an IL-2Rγc ligand can comprise a moiety configured to sustain a circulating reservoir of the compound comprising an IL-2Rβ ligand and/or an IL-2Rγc ligand.

Compounds comprising an IL-2Rβ ligand and/or an IL-2Rγc ligand can comprise a moiety configured to target the IL-2R-directed immuno-stimulation of the effector immune cells in a tumor.

Compounds comprising an IL-2Rβ ligand and/or an IL-2Rγc ligand can comprise a moiety configured to target specific immune cells such as Treg cells.

The moiety can comprise a compound that is toxic to a cell targeted by the compound comprising an IL-2Rβ ligand and/or an IL-2Rγc ligand. The toxic moiety can be cleavable or otherwise activated such as by exposure to electromagnetic radiation. The toxic moiety can be activated, for example, by exposure to electromagnetic radiation such as visible radiation or ultraviolet radiation. Compounds comprising an IL-2Rβ ligand and/or an IL-2Rγc ligand provided by the present disclosure can activate the IL-2 receptor. Compounds comprising an IL-2Rβ ligand and/or IL-2Rγc ligand provided by the present disclosure can inhibit the IL-2 receptor. Certain compounds comprising an IL-2Rβ ligand and/or an IL-2Rγc ligand provided by the present disclosure can bind to the IL-2Rβ subunit and/or to the IL-2Rγc subunit and prevent other compounds from binding to the IL-2Rβ subunit and/or the IL-2Rγc subunit. Compounds comprising an IL-2Rβ ligand and/or an IL-2Rγc ligand can reduce the potency of or interfere with the binding of IL-2R agonists to cells that highly express the IL-2Rβ subunit and/or the IL-2Rγc subunit. Compounds comprising an IL-2Rβ ligand and/or an IL-2Rγc ligand can reduce the sensitivity of cells to IL-2.

Compounds comprising an IL-2Rβ ligand and/or IL-2Rγc ligand provided by the present disclosure can include compounds that act as IL-2Rβγc agonists or IL-2Rαβγc agonists.

An IL-2Rβγc agonist or an IL-2Rαβγc agonist provided by the present disclosure can comprise synthetic peptides or recombinant peptides linked in tandem to create a single chain peptide comprising an IL-2Rβ ligand, an IL-2Rγc ligand and, in the case of an IL-2Rαβγc agonist, an IL-2Rα ligand. The ligands can be in any order and can be separated by amino acid linkers. The synthetic peptides can comprise natural amino acids or peptides with natural amino acids and suitable substitutions with unnatural amino acids. IL-2Rβγc agonists and IL-2Rαβγc agonists provided by the present disclosure can be a recombinant fusion protein comprising an IL-2Rγc ligand and an IL-2Rβ ligand, and in the case of an IL-2Rαβγc agonist, an IL-2Rα ligand, and a fusion partner such as an Fc protein, an IgG protein, human serum albumin or other natural or designed protein, or a hydrophilic, biodegradable protein polymer. An IL-2Rβγc agonist or an IL-2Rαβγc agonist can comprise one or more IL-2Rβ ligands and/or one or more IL-2Rγc ligands and, in the case of an IL-2Rαβγc agonist, one or more IL-2Rα ligands. An IL-2Rβγc agonist or an IL-2Rαβγc agonist can comprise an IL-2Rβ ligand and an IL-2Rγc ligand and, in the case of an IL-2Rαβγc agonist, an IL-2Rα ligand, and can further include one or more moieties selected to modify the pharmacokinetics of the IL-2R agonist such as PEG or an albumin binding moiety.

An IL-2Rβγc agonist can bind to IL-2Rβ subunit and IL-2Rγc subunit and can activate the IL-2 receptor. The binding affinity ($IC_{50}$) of the IL-2Rβγc agonist to the IL-2Rβ subunit and IL-2Rγc subunit can independently be, for example, less than 100 μM, less than 10 M, less than 1 M, less than 100 nM, less than 10 nM, or less than 1 nM. An IL-2Rβγc agonist can bind to IL-2Rβ and IL-2Rγc either competitively or non-competitively with IL-2.

An IL-2Rαβγc agonist can bind to IL-2Rα, IL-2Rβ, and IL-2Rγc and activate the IL-2 receptor. The binding affinity ($IC_{50}$) of the IL-2Rαβγc agonist to IL-2Rα, IL-2Rβ, and IL-2Rγc can be, for example, less than 100 μM, less than 10 μM, less than 1 μM, less than 100 nM, less than 10 nM, or less than 1 nM. An IL-2Rαβγc agonist can bind to IL-2Rα, IL-2Rβ, and IL-2Rγc either competitively or non-competitively with IL-2.

An IL-2Rβγc agonist or an IL-2Rαβγc agonist comprising an IL-2Rβ ligand and an IL-2Rγc ligand and, in the case of an IL-2Rαβγc agonist, an IL-2Rα ligand, can be configured to more potently activate cells expressing the IL-2Rβ subunit and the IL-2Rγc subunit, thereby facilitating the ability to differentially activate IL-2R expressed on the surface of different cell types by controlling dose of the agonist. For example, when incubated with a heteromeric compound comprising an IL-2Rβ ligand and IL-2Rγc ligand, primary human peripheral blood mononuclear cells (PBMC) expressing the IL-2Rαβγc subunit phosphorylate transcription 5 (STAT5). A heteromer can comprise an IL-2Rβ ligand, an IL-2Rγc ligand, and a linker, where the linker is configured such that the heteromer is an agonist for the IL-2 receptor. A linker can comprise a length that facilitates binding of an IL-2Rβ ligand and an IL-2Rγc ligand to the IL-2 receptor. For example, a linker can have a length from 10 Å to 400 Å, from 10 Å to 300 Å, from 10 Å to 200 Å, 20 Å to 100 Å, from 30 Å to 80 Å, or from 40 Å to 60 Å. A linker can comprise a chemical structure that facilitates simultaneous binding of an IL-2Rβ ligand and an IL-2Rγc ligand to the respective IL-2 receptor subunits. For example, a linker can comprise a peptide or a hydrocarbon.

An IL-2Rβγc agonist or an IL-2Rαβγc agonist can partially activate the IL-2 receptor. Partial activation refers to a level of activation, that is, for example, less than 75% of maximum activation, less than 50%, less than 25%, less than 10%, or less than 1% of the maximum activation. Maximum activation ($E_{max}$) is the amplitude of cellular signal (activation) achievable at high agonist concentration such as a high concentration of IL-2. Partial IL-2R agonists can be effective in modulating the levels of response of IL-2R to activation of the IL-2Rβ and IL-2Rγc subunits among different cell types expressing IL-2R. For example, different cell types are known to vary in expression levels of each of the IL-2R subunits, IL-2Rα, IL-2Rβ, and IL-2Rγc, and to exhibit different sensitivities to IL-2R agonists.

An IL-2R agonist comprising one or more IL-2Rα ligands, one or more IL-2Rβ ligands, and one or more IL-2Rγc ligands can exhibit increased binding and potency on cells expressing the IL-2Rα subunit (such as Tregs).

An IL-2Rαβγc agonist can comprise an IL-2Rα ligand and modified IL-2Rβ ligands and/or IL-2Rγc ligands. Modified IL-2Rβ and IL-2Rγc ligands can be selected or designed to bind and activate IL-2R, but with low or modest affinity and potency to IL-2R. Such IL-2Rαβγc agonists can have greater differential sensitivity for IL-2R activation between cells that highly express IL-2Rα and cells having a low level of IL-2Rα expression; for example, between Tregs that have a high expression of IL-2Rα and Teff cells that have a low expression level of IL-2Rα.

An IL-2Rβγc agonist or an IL-2Rαβγc agonist can comprise one or more IL-2Rβ ligands and/or one or more IL-2Rγc ligands and in the case of an IL-2Rαβγc agonist, one or more IL-2Rα ligands. The presence of multiple IL-2Rα ligands, IL-2Rβ ligands and/or IL-2Rγc ligands can preferentially increase the potency of the IL-2R agonists on cells that highly express IL-2Rα, IL-2Rβ and/or IL-2Rγc compared to cells having low expression levels of IL-2Rα, IL-2Rβ, and/or IL-2Rγc.

An IL-2R agonist can comprise a moiety having an additional pharmacological activity other than that mediated by activation of the IL-2 receptor. The pharmacological activity can be an activity that has a therapeutic efficacy that is synergistic with that of the IL-2R agonist or the pharmacological activity can be an activity that has a therapeutic efficacy that is not synergistic with that of the IL-2R agonist. For example, a moiety or molecule having a useful pharmacological activity can comprise a checkpoint inhibitor.

Compounds provided by the present disclosure include IL-2Rβ antagonists and IL-2Rγc antagonists. An IL-2R antagonist is a compound comprising an IL-2Rβ ligand or an IL-2Rγc ligand that inhibits binding of IL-2 and mutants and modified forms thereof, to the IL-2Rβ subunit or to the IL-2Rγc subunit and/or diminishes IL-2 activation of the IL-2 receptor.

IL-2Rβ antagonists and IL-2Rγc antagonists can attenuate the sensitivity of cells expressing the IL-2Rβ subunit and/or the IL-2Rγc subunit to activation by IL-2 or mutants and modified forms thereof.

IL-2Rβ antagonists and IL-2Rγc antagonists can include compounds having more than one IL-2Rβ ligand or more than one IL-2Rγc ligand and can bind competitively or non-competitively with IL-2 to the IL-2 receptor.

IL-2Rβ antagonists and IL-2Rγc antagonists can comprise one or more IL-2Rβ ligands or one or more IL-2Rγc ligands and a moiety having a useful pharmacological activity. The moiety can exhibit a pharmacological activity that is synergistic with IL-2R inhibition or is not synergistic with inhibition of IL-2R.

IL-2Rβ antagonists and IL-2Rγc antagonists can further include recombinant fusion proteins.

Compounds provided by the present disclosure include IL-2R antagonists.

An IL-2R antagonist can comprise an IL-2Rα ligand and an IL-2Rβ ligand; an IL-2Rα ligand and an IL-2Rγc ligand; or an IL-2Rβ ligand and an IL-2Rγc ligand.

IL-2R antagonists include compounds that bind to either the IL-2Rβ or IL-2Rγc subunit and inhibit activation of the IL-2 receptor.

IL-2R antagonists include compounds that bind to the IL-2Rβ and the IL-2Rγc subunits and inhibit activation of the IL-2 receptor, where the IL-2Rβ and IL-2Rγc ligands are configured to not activate the IL-2 receptor. Such compounds are high affinity antagonists for IL-2R activation and the presence of both IL-2R and IL-2Rγc ligands enhances the potency of the IL-2R antagonists.

IL-2R antagonists include compounds comprising an IL-2Rβ ligand, and an IL-2Rγc ligand, which are configured to exhibit partial activation of the IL-2 receptor. These compounds are examples of partial IL-2R antagonists. Such compounds are useful for modulating the level of response of cells to IL-2R agonists among cells having different expression levels of IL-2R subunits. Use of the partial IL-2R agonists/antagonists can modulate the response of cells to IL-2R agonists among cells having different expression levels of the IL-2Rβ, and/or IL-2Rγc subunits.

An IL-2R antagonist can comprise one or more IL-2Rβ and/or IL-2Rγc ligands. An IL-2R antagonist can be a peptide or a polypeptide, which can be synthetic or recombinant. The IL-2R ligands can be coupled in any order, in any orientation, and can be coupled with linkers. The linkers can comprise natural and/or unnatural amino acids and/or non-peptidyl structures.

An IL-2R antagonist can be chemically modified to include, for example, moieties that affect the pharmacokinetics of the IL-2R antagonist such as PEG and albumin-binding moieties.

IL-2R antagonists can further include recombinant fusion proteins.

Compounds comprising an IL-2Rβ ligand and/or IL-2Rγc ligand include diagnostic reagents. As a diagnostic agent, a compound comprising an IL-2Rβ ligand and/or IL-2Rγc ligand can be used to detect and/or to measure cells expressing the IL-2Rβ subunit and/or IL-2Rγc subunit. The compounds can be used to determine the level of IL-2Rβ and/or IL-2Rγc expression of a cell, or population of cells, or of a tissue. The compounds can be used to assess the binding affinity of the IL-2Rβ subunit and/or IL-2Rγc subunit to a cell or population of cells. The compounds may be used to determine the particular type of cell, for example, based on IL-2Rβ and/or IL-2Rγc expression levels.

The compounds can be useful for in vitro and in vivo diagnostics.

A diagnostic compound comprising an IL-2Rβ ligand and/or IL-2Rγc ligand can comprise a detectable marker. The detectable marker can be cleavable or non-cleavable.

A detectable marker can comprise, for example, a radiolabel, a fluorescent label, an enzymatic label.

A diagnostic compound comprising an IL-2Rβ ligand and/or IL-2Rγc ligand can be used to measure cells expressing the IL-2Rβ subunit and/or IL-2Rγc subunit and/or the level of expression of cells expressing the IL-2Rβ subunit and/or IL-2Rγc subunit in a biological sample such as a sample of blood of a patient. Measurements can be made, for example, using flow cytometry. The number of cells expressing the IL-2Rβ subunit and/or IL-2Rγc subunit and/or the expression level of the IL-2Rβ subunit and/or IL-2Rγc subunit, when correlated with a disease in a patient or a pharmacologically significant parameter of the disease in a patient can be used to inform treatment of the disease. For example, if a level of expression of the IL-2Rβ subunit and/or IL-2Rγc subunit is above or below a therapeutically meaningful threshold for a particular disease, a compound comprising an IL-2Rβ ligand and/or IL-2Rγc ligand provided by the present disclosure can be administered to the patient to treat the disease.

Compounds comprising an IL-2Rβ ligand and/or IL-2Rγc ligand can be attached to a solid support. Based on the ability of the compounds to bind to the IL-2Rβ subunit and/or IL-2Rγc subunit, the compounds can be used as reagents for detecting IL-2Rβ subunits and/or IL-2Rγc subunits, for example, on living cells, fixed cells, in biological fluids, in tissue homogenates, in purified, and natural in biological materials. In addition, based on their ability to bind the IL-2Rβ subunit and/or IL-2Rγc subunit, the peptides of the present invention can be used, for example, in in situ staining, FACS (fluorescence-activated cell sorting), Western Blotting, and ELISA. In addition, compounds provided by the present disclosure can be used in receptor purification, or to purify cells expressing the IL-2Rβ subunit and/or IL-2Rγc subunit on the cell surface.

Compounds comprising an IL-2Rβ ligand and/or IL-2Rγc ligand provided by the present disclosure can also be used as reagents for various medical research and diagnostic uses. Such uses include, for example, use as a calibration standard for quantitating the activities of candidate IL-2R agonists or IL-2R antagonists in functional assays; use to maintain the proliferation and growth of IL-2-dependent cell lines; (3) use in structural analysis of the IL-2 receptor through co-crystallization; use to investigate the mechanism of IL-2 signal transduction/receptor activation; and other research and diagnostic applications wherein the IL-2 receptor is implicated.

Assessing single patient response to therapy and qualifying a patient for optimal therapy are among the greatest challenges of modern healthcare and relate to trends in personalized medicine. A compound comprising an IL-2Rβ ligand and/or IL-2Rγc ligand can have target selectivity for diseases in which cells associated with the etiology of the disease express the IL-2Rβ subunit and/or IL-2Rγc subunit. For example, a compound comprising an IL-2Rβ ligand and/or IL-2Rγc ligand radiolabeled for positron emission tomography (PET) or single photon emission computed tomography (SPECT) can be used to predict the targeting of the treatment based on a single-study, case-by-case patient analysis thus excluding subjects that are expected not to benefit from treatment with a therapeutic compound affecting the activity of the IL-2Rβ subunit and/or IL-2Rγc subunit. PET/SPECT scans using radiolabeled a compound comprising an IL-2Rβ ligand and/or IL-2Rγc ligand, once correlated to the concentration of a compound comprising an IL-2Rβ ligand and/or IL-2Rγc ligand can provide a three-dimensional distribution map, which can then be used for macroscopic dose calculations.

Compounds comprising an IL-2Rβ ligand and/or IL-2Rγc ligand can comprise one or more imaging agents. The IL-2Rβ ligand and/or IL-2Rγc ligand can direct and localize the compound to cells, populations of cells, and tissue expressing the IL-2Rβ subunit and/or IL-2Rγc subunit. The imaging compounds can comprise one or more imaging agents such as radiolabels, fluorescent labels, enzymatic labels, or PET imaging agents.

The imaging agents can be used to determine the number of cells expressing the IL-2Rβ subunit and/or IL-2Rγc subunit, the expression level of cells expressing the IL-2Rβ subunit and/or IL-2Rγc subunit, or properties of the IL-2Rβ subunit and/or IL-2Rγc subunit such as the affinity of the IL-2Rβ subunit and/or IL-2Rγc subunit to a particular IL-2Rβ ligand and/or IL-2Rγc ligand and/or compound comprising an IL-2Rβ ligand and/or an IL-2Rγc ligand. The imaging agents can be used, for example, to evaluate cancer cells expressing the IL-2Rβ subunit and/or the IL-2Rγc subunit, or to evaluate Treg and/or Teff cells.

The label can be detected to determine a biodistribution of the compound in a patient or to assess the potential for therapeutic efficacy. For example, tumors expressing high levels of the IL-2R receptor and/or the IL-2Rβ subunit and/or IL-2Rγc subunit may be attractive targets for therapeutic compounds comprising an IL-2Rβ ligand and/or IL-2Rγc ligand provided by the present disclosure.

The imaging agents can be used to evaluate cells expressing the IL-2Rβ subunit and/or the IL-2Rγc subunit before therapy, during therapy, and/or following therapy.

Imaging agents comprising an IL-2Rβ ligand and/or an IL-2Rγc ligand can further comprise a moiety capable of binding to a cell surface and in particular to a protein expressed on the cell surface. The protein can be indicative of a certain cell type and is referred to as a cell surface marker. Imaging agents comprising both an IL-2Rβ ligand and/or an IL-2Rγc ligand and a cell surface marker can be used to assess cells, a population of cells, and/or a tissue expressing both the IL-2Rβ subunit and/or IL-2Rγc subunit and the cell surface marker. Assessment can include determining the number of cells expressing both the IL-2Rβ subunit and/or the IL-2Rγc subunit and the cell surface marker, the expression levels of the IL-2Rβ subunit and/or the IL-2Rγc subunit and the cell surface marker, and/or the affinity of the imaging agent to the IL-2Rβ subunit and/or the IL-2Rγc subunit and/or the cell surface marker.

The imaging agents can be used to evaluate cells expressing the IL-2Rβ subunit and/or the IL-2Rγc subunit and the cell surface marker before therapy, during therapy, and/or following therapy.

As a practical example, T-cell infiltration of tumor lesions is a known prognostic factor in several tumor types and is used as a treatment mechanism in some of these tumor types. For example, in metastatic melanoma, treatment with immune checkpoint inhibitors induces clinical benefit in about 30-50% of the patients. Tumor-infiltrating T-cells express the IL-2 receptor on their surface. Therefore, these T-cells can be visualized by molecular imaging with a compound comprising an IL-2Rβ ligand and/or an IL-2Rγc ligand and a radiolabel such as a PET tracer.

As another example, IL-2 is synthesized and secreted by activated T lymphocytes, especially CD8+ CTL and CD4+ Th1 lymphocytes. T lymphocyte activation is observed in many types of inflammatory diseases, such as inflammatory degenerative diseases, graft rejection, tumor inflammation, organ-specific autoimmune diseases, and adipose inflammatory insulin resistance. IL-2 binds with high affinity to the cell membrane IL-2 receptor, which is mainly expressed on the cell surface of activated T lymphocytes. PET imaging of activated T lymphocytes by radiolabeled IL-2Rβ ligand and/or IL-2Rγc ligand therefore provides an in vivo, dynamic approach in studying the immune-cell infiltration in these inflammatory diseases.

Compounds provided by the present disclosure can be labeled. Labeled compounds can be useful in diagnostics.

Compounds comprising an IL-2Rβ ligand and/or an IL-2Rγc ligand and selective IL-2Rβγc agonists provided by the present disclosure can be labeled with a detectable marker. The label can be used to determine a biodistribution of the compound in a patient or to assess the potential for therapeutic efficacy. For example, tumors expressing high levels of the IL-2R receptor may be attractive targets for selective IL-2Rβγc agonists and compounds comprising an IL-2Rβ ligand and/or an IL-2Rγc ligand provided by the present disclosure.

Thus, compounds provided by the present disclosure include labeled compounds. A labeled compound can be a detectable marker, for example, a radiolabeled amino acid or an attachment of biotinyl moieties to a polypeptide, wherein said attached biotinyl moieties can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, for example, a radioisotope such as, $^3$H, $^4$C, $^{35}$S, $^{125}$I, and $^{131}$I, a fluorescent labels such as FITC, rhodamine, and lanthanide phosphors, an enzymatic label such as horseradish peroxidase, β-galactosidase, luciferase, and alkaline phosphatase, biotinyl groups, predetermined polypeptide epitopes recognized by a secondary reporter such as leucine zipper pair sequences, binding sites for secondary antibodies, metal ligands, and epitope tags. A label can be attached by spacer arms of various lengths to reduce potential steric hindrance.

Compounds comprising an IL-2Rβ ligand and/or an IL-2Rγc ligand can comprise a cell-specific targeting moiety or molecule.

A cell-specific targeting moiety can comprise a moiety that has an affinity for a component on the surface of a cell such as a receptor, a protein, or an epitope. A moiety can comprise, for example, a ligand or an antibody having an affinity to a cell surface component.

The targeting moiety can direct and concentrate compounds comprising an IL-2Rβ ligand and/or an IL-2Rγc ligand at the cells, population of cells, or tissue targeted by the targeting moiety.

The targeting moiety can enhance the potency of IL-2R agonism or IL-2R antagonism for the cells or population of cells being targeted.

The targeting moiety can provide a differential response to IL-2R agonism or to IL-2R antagonism between the cells being targeted and the cells not being targeted by the targeting moiety.

The targeting moiety can provide a differential response to IL-2R agonism or IL-2R antagonism between cells having a high expression level of the targeted component and cells having a lower expression level of the targeted component.

Compounds comprising an IL-2Rβ ligand and/or an IL-2Rγc ligand can further comprise a bioactive moiety or a bioactive molecule. A compound comprising an IL-2Rβ ligand and/or an IL-2Rγc ligand can be used to deliver the bioactive moiety or bioactive molecule to cells, to a population of cells, or to a tissue expressing the IL-2Rβ subunit and/or the IL-2Rγc subunit.

The bioactive moiety or molecule can be non-cleavable and capable of exerting a biological activity when bound to the compound comprising an IL-2Rβ ligand and/or an IL-2Rγc ligand.

The bioactive moiety or molecule can be cleavable. The moiety can be cleavable by any suitable mechanism such as by pH, enzymatic, thermal, and/or electromagnetic mechanisms. Electromagnetic mechanisms include, for example, exposing the compounds to infrared, visible, or ultraviolet radiation, where the bioactive moiety is attached to the compounds comprising an IL-2Rβ ligand and/or an IL-2Rγc ligand through a photolabile moiety capable of being cleaved by the radiation.

The bioactive molecule can be non-cleavable but otherwise activatable, such as for example, activatable by exposure to electromagnetic radiation.

IL-2Rβ ligands and/or IL-2Rγc ligands can be selected to have enhanced binding to the IL-2Rβ subunit and/or to the IL-2Rγc subunit at a certain pH. For example, a pH-selective IL-2Rβ ligand and/or IL-2Rγc ligand can have a greater affinity to the IL-2Rβ subunit and/or IL-2Rγc subunit, respectively, at low pH commensurate with that of a solid tumor microenvironment. Compounds comprising low-pH selective IL-2Rβ ligands and/or IL-2Rγc ligands can be used to preferentially activate cells in low pH environments expressing the IL-2Rβ subunit and/or the IL-2Rγc subunit compared to cells in normal pH environments associated with healthy tissue.

Thus, compounds comprising selective IL-2Rβ ligands and/or IL-2Rγc ligands such as pH-selective IL-2Rβ ligands and/or pH-selective IL-2Rγc ligands can be used with other pH-selective bioactive moieties and molecules.

A bioactive moiety or bioactive molecule can itself be selective for a particular cell population. For example, a bioactive moiety or bioactive molecule can exhibit a greater or lesser affinity, potency, and/or activity at the cell being targeted by a selective IL-2Rβ ligand and/or IL-2Rγc ligand. For example, the bioactive moiety or molecule can exhibit greater bioactivity in a low pH tumor microenvironment when targeted by a pH-selective an IL-2Rβ ligand and/or IL-2Rγc ligand. In this example, the bioactive moiety is directed to cells located in the low-pH tumor microenvironment that express the IL-2Rβ subunit and/or IL-2Rγc subunit by the pH-selective IL-2Rβ ligand and/or IL-2Rγc ligand. Thus, the activity of the pH-selective bioactive moiety is enhanced in the low-pH tumor microenvironment.

Compounds comprising an IL-2Rβ ligand and/or IL-2Rγc ligand can further comprise a cytotoxic moiety or cytotoxic molecule. Such compounds can be used to deliver a cytotoxic moiety or compound to a cell expressing the IL-2Rβ subunit and/or IL-2Rγc subunit such as T-cells. The cytotoxic moiety or molecule can exert cytotoxicity when bound to the compound or can be cleavable and the moiety or molecule can be cytotoxic when released from the compound; or the cytotoxic moiety can be activated by electromagnetic radiation.

The cytotoxic moiety or molecule can be used to deplete cells expressing the IL-2Rβ subunit and/or the IL-2Rγc subunit being targeted.

IL-2Rβ ligand- and/or IL-2Rγc ligand-containing cytotoxic compounds can have more than one IL-2Rβ ligand and/or more than one IL-2Rγc ligand and thereby can exhibit a higher affinity and/or selectivity to cells, populations of cells, and tissue that highly express the IL-2Rβ subunit and/or the IL-2Rγc subunit compared to cells having a lower expression level of the IL-2Rβ subunit and/or the IL-2Rγc subunit.

IL-2Rβ ligand- and/or IL-2Rγc ligand-containing cytotoxic compounds can further include a cell surface targeting component. Such cytotoxic compounds can exhibit enhanced efficacy to cells, populations of cells, and tissue expressing the IL-2Rβ subunit and/or IL-2Rγc subunit and the surface target component.

Examples of suitable cytotoxic molecules include anti-microtubule agents, alkylating agents, and DNA minor groove binding agents.

Compounds comprising an IL-2Rβ ligand and/or IL-2Rγc ligand can further comprise a moiety having a useful pharmacological activity unrelated to IL-2 activity.

The pharmacological moiety can function synergistically with IL-2R agonist activity or synergistically with IL-2R antagonist activity or the pharmacology moiety may not exhibit synergism with activity of the IL-2Rβ subunit and/or the IL-2Rγc subunit.

Examples of suitable pharmacological moieties include antibodies and antibody fragments that are inhibitors of checkpoint molecules, pro-apoptotic and anti-apoptotic molecules, cytotoxic molecules, agonists of chemokine, antagonists of chemokine, cytokine, growth factor and other cell surface receptors, and ligands and inhibitors of cell surface adhesion molecules such as integrins.

Peptides provided by the present disclosure can be synthesized by methods known in the art, for example, by using standard solid phase techniques.

A peptide comprising an IL-2Rβ ligand and/or IL-2Rγc ligand provided by the present disclosure can be modified, for example, by phosphorylation, and by other methods known in the art. Thus, the peptides provided by the disclosure can also serve as a basis to prepare peptide mimetics with similar biological activity.

A variety of techniques are available for constructing peptide mimetics with the same or similar desired biological activity as a corresponding peptide but with more favorable activity than the peptide with respect to solubility, stability, and susceptibility to hydrolysis and proteolysis.

Selective IL-2Rβγc agonists and compounds comprising IL-2Rβ ligands and/or IL-2Rγc ligands provided by the present disclosure may be incorporated into pharmaceutical compositions to be administered to a patient by any appropriate route of administration including intradermal, intramuscular, intraperitoneal, intravenous, subcutaneous, intranasal, epidural, oral, peroral, sublingual, intracerebral, intravaginal, transdermal, rectal, inhalation, or topical. In certain embodiments, pharmaceutical compositions provided by the present disclosure are injectable formulations. Pharmaceutical compositions provided by the present disclosure can be injectable intravenous formulations. Pharmaceutical compositions provided by the present disclosure can be oral formulations. Oral formulations may be oral dosage forms. A pharmaceutical composition may be formulated for intravenous administration or for subcutaneous administration.

Pharmaceutical compositions provided by the present disclosure may comprise a therapeutically-effective amount of a selective IL-2Rβγc agonist, a compound comprising an IL-2Rβ ligand and/or an IL-2Rγc ligand, or a pharmaceutically acceptable salt of any of the foregoing together with a suitable amount of one or more pharmaceutically acceptable vehicles so as to provide a composition for proper administration to a patient. Suitable pharmaceutical vehicles and methods of preparing pharmaceutical compositions are described in the art.

A selective IL-2Rβγc agonist or a compound comprising an IL-2Rβ ligand and/or an IL-2Rγc ligand may be administered by intravenous injection. Suitable forms for injection include sterile aqueous solutions or dispersions of a selective IL-2Rβγc agonist or compound comprising an IL-2Rβ ligand and/or IL-2Rγc ligand. A selective IL-2Rβγc agonist or a compound comprising an IL-2Rβ ligand and/or IL-2Rγc ligand may be formulated in a physiological buffer solution. Prior to administration, a selective IL-2Rβγc agonist, a compound comprising an IL-2Rβ ligand and/or IL-2Rγc ligand, or a pharmaceutically acceptable salt of any of the foregoing may be sterilized by any art recognized technique, including addition of antibacterial or antifungal agents, for example, paraben, chlorobutanol, phenol, sorbic acid, thimersol, and the like. A selective IL-2Rβγc agonist, a compound comprising an IL-2Rβ ligand and/or IL-2Rγc ligand, or a pharmaceutically acceptable salt of any of the foregoing may be sterilized by filtration before administration to a subject thereby minimizing or eliminating the need for additional sterilization agents. An injectable dosage of a selective IL-2Rβγc agonist or a compound comprising an IL-2Rβ ligand and/or IL-2Rγc ligand may include from about 0.01 mL to about 10 mL, from about 0.1 mL to about 10 mL, from about 0.1 mL to about 5 mL, and in certain embodiments, from about 1 mL to about 5 mL.

Pharmaceutical compositions may comprise a therapeutically effective amount of one or more selective IL-2Rβγc agonists or compounds comprising an IL-2Rβ ligand and/or IL-2Rγc ligand, preferably in purified form, together with a suitable amount of a pharmaceutically acceptable vehicle, so as to provide a form for proper administration to a patient. When administered to a patient, the compounds and pharmaceutically acceptable vehicles are preferably sterile. Water is a preferred vehicle when the compound is administered intravenously. Saline solutions and aqueous dextrose and glycerol solutions may also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Pharmaceutical compositions may also contain minor amounts of wetting or emulsifying agents, or pH buffering agents. In addition, auxiliary, stabilizing, thickening, lubricating and coloring agents may be used.

Pharmaceutical compositions comprising a compound may be manufactured by means of conventional mixing, dissolving, granulating, levitating, emulsifying, encapsulating, entrapping or lyophilizing processes. Pharmaceutical compositions may be formulated in a conventional manner using one or more physiologically acceptable carriers, diluents; excipients or auxiliaries, which facilitate processing of compounds into preparations which can be used pharmaceutically. Proper formulation is dependent upon the route of administration chosen. Pharmaceutical compositions provided by the present disclosure may take the form of solutions, suspensions, emulsion, or any other form suitable for use. Examples of suitable pharmaceutical vehicles are described in the art.

For parenteral administration, selective IL-2Rβγc agonists and compounds comprising an IL-2Rβ ligand and/or an IL-2Rγc ligand may be incorporated into a solution or suspension. Parenteral administration refers to the administration by injection, for instance by intravenous, intracapsular, intrathecal, intrapleural, intratumoral, subcutaneously, or intraperitoneal injection or intravesically. A selective IL-2Rβγc agonist or compound comprising an IL-2Rβ ligand and/or an IL-2Rγc ligand can be administered intravenously.

A solution or suspension may also comprise at least one of the following adjuvants: sterile diluents such as water for injection, saline, fixed oils, polyethylene glycols, glycerol, propylene glycol or other synthetic solvents, antioxidants such as ascorbic acid or sodium bisulfite, buffers such as acetates, citrates or phosphates, and agents for adjustment of the tonicity such as sodium chloride or dextrose. A parenteral preparation may be enclosed into ampoules, disposable syringes or multiple dosage vessels made of glass or plastic.

Assessing single patient response to therapy and qualifying a patient for optimal therapy are among the greatest challenges of modern healthcare and relate to trends in personalized medicine. The selective IL-2Rβγc agonist or compound comprising an IL-2Rβ ligand and/or IL-2Rγc ligand can have target selectivity for certain cancers. Selective IL-2Rβγc agonists and compounds comprising an IL-2Rβ ligand and/or an IL-2Rγc ligand, radiolabeled for positron emission tomography (PET) or Single Photon Emission Computed Tomography (SPECT) may be used to predict the targeting of the treatment based on a single-study, case-by-case patient analysis thus excluding subjects that are expected not to benefit from treatment. PET/SPECT scans using radiolabeled selective IL-2Rβγc agonists or compounds comprising an IL-2Rβ ligand and/or IL-2Rγc ligand, once correlated to the concentration selective IL-2Rβγc agonist or compound comprising an IL-2Rβ ligand and/or IL-2Rγc ligand can provide a three-dimensional distribution map, which can then be used for macroscopic dose calculations.

Accordingly, it is within the capability of those of skill in the art to assay and use the selective IL-2Rβγc agonist, a compound comprising an IL-2Rβ ligand and/or an IL-2Rγc ligand, and/or pharmaceutical compositions thereof for therapy.

A selective IL-2Rβγc agonist, a compound comprising an IL-2Rβ ligand and/or IL-2Rγc ligand, and/or pharmaceutical composition thereof can generally be used in an amount effective to achieve the intended purpose. For use to treat a disease such as cancer, a selective IL-2Rβγc agonist, a compound comprising an IL-2Rβ ligand and/or an IL-2Rγc ligand, and/or pharmaceutical compositions thereof, may be administered or applied in a therapeutically effective amount.

The amount of a selective IL-2Rβγc agonist, a compound comprising an IL-2Rβ ligand and/or IL-2Rγc ligand, and/or pharmaceutical composition of any of the foregoing that will be effective in the treatment of a particular disorder or condition disclosed herein will depend in part on the nature of the disorder or condition, and can be determined by standard clinical techniques known in the art. In addition, in vitro or in vivo assays may optionally be employed to help identify optimal dosage ranges. The amount of selective IL-2Rβγc agonist, a compound comprising an IL-2Rβ ligand and/or an IL-2Rγc ligand, and/or pharmaceutical composition of any of the foregoing administered will depend on, among other factors, the subject being treated, the weight of the subject, the severity of the affliction, the manner of administration and the judgment of the prescribing physician.

A selective IL-2Rβγc agonist or a compound comprising an IL-2Rβ ligand and/or an IL-2Rγc ligand may be assayed in vitro and in vivo, for the desired therapeutic activity, prior to use in humans. For example, in vitro assays may be used to determine whether administration of a specific compound or a combination of compounds is preferred. The compounds may also be demonstrated to be effective and safe using animal model systems.

In certain embodiments, a therapeutically effective dose of a selective IL-2Rβγc agonist, a compound comprising an IL-2Rβ ligand and/or an IL-2Rγc ligand, and/or pharmaceutical composition of any of the foregoing will provide therapeutic benefit without causing substantial toxicity. Toxicity of a selective IL-2Rβγc agonist, a compound comprising an IL-2Rβ ligand and/or an IL-2Rγc ligand, and/or pharmaceutical compositions of any of the foregoing may be determined using standard pharmaceutical procedures and may be readily ascertained by the skilled artisan. The dose ratio between toxic and therapeutic effect is the therapeutic index. In certain embodiments, a selective IL-2Rβγc agonist, a compound comprising an IL-2Rβ ligand and/or an IL-2Rγc ligand, and/or pharmaceutical composition of any of the foregoing exhibits a particularly high therapeutic index in treating disease and disorders. A dose of a selective IL-2Rβγc agonist a compound comprising an IL-2Rβ ligand and/or an IL-2Rγc ligand, and/or pharmaceutical composition of any of the foregoing will be within a range of circulating concentrations that include an effective dose with minimal toxicity.

A compound comprising an IL-2Rβ and/or an IL-2Rγc ligand provided by the present disclosure or a pharmaceutical composition thereof may be included in a kit that may be used to administer the compound to a patient for therapeutic purposes. A kit may include a pharmaceutical composition comprising a selective IL-2Rβγc agonist or a compound comprising an IL-2Rβ ligand and/or an IL-2Rγc ligand provided by the present disclosure suitable for administration to a patient and instructions for administering the pharmaceutical composition to the patient. The kit can be a kit for treating cancer. A kit for use in treating cancer in a patient can comprise a selective IL-2Rβγc agonist or a compound comprising an IL-2Rβ ligand and/or an IL-2Rγc ligand provided by the present disclosure, a pharmaceutically acceptable vehicle for administering the compound, and instructions for administering the compound to a patient.

The pharmaceutical compositions can be included in a container, pack, or dispenser together with instructions for administration.

Instructions supplied with a kit may be printed and/or supplied, for example, as an electronic-readable medium, a video cassette, an audiotape, a flash memory device, or may be published on an internet web site or distributed to a patient and/or health care provider as an electronic communication.

Selective IL-2Rβγc agonists and compounds comprising an IL-2Rβ ligand and/or an IL-2Rγc ligand provided by the present disclosure may be used for treating cancer in a patient. The cancer can be, for example, a solid tumor or a metastasis.

Selective IL-2Rβγc agonists and compounds comprising an IL-2Rβ ligand and/or an IL-2Rγc ligand provided by the present disclosure or a pharmaceutical composition thereof may be administered to treat a cancer known to be treated by activation or inhibition of the IL-2 receptor. Selective IL-2Rβγc agonists and compounds comprising an IL-2Rβ ligand and/or IL-2Rγc ligand provided by the present disclosure or a pharmaceutical composition thereof may be administered to treat a cancer known to be treated by activation or inhibition of the IL-2Rβγc subunits and where simultaneous activation of the IL-2Rα subunit compromises therapeutic efficacy and/or minimizes unwanted side effects.

Selective IL-2Rβγc agonists and compounds comprising an IL-2Rβ ligand and/or an IL-2Rγc ligand provided by the present disclosure or a pharmaceutical composition thereof can be used to treat, for example, one or more of the following cancers: acute lymphoblastic leukemia, acute myeloid leukemia, adrenocortical carcinoma, appendix cancer, astrocytoma, atypical teratoid/rhabdoid tumor, basal cell carcinoma (nonmelanoma), B-cell lymphoma, bladder cancer, bone cancer, brain and spinal cord tumors, brain stem cancer, brain tumor, breast cancer, bronchial tumors, Burkitt lymphoma, carcinoid tumor, carcinoma of head and neck, central nervous system embryonal tumors, cerebellar astrocytoma, cerebral astrocytoma/malignant glioma, cervical cancer, chordoma, chronic lymphocytic leukemia, chronic myelogenous leukemia, colorectal cancer, craniopharyngioma, cutaneous T-cell lymphoma, desmoplastic small round cell tumor, ductal carcinoma, dye cancer, endocrine pancreas tumors (islet cell tumors), endometrial cancer, ependymoblastoma, esophageal cancer, esthesioneuroblastoma, Ewing family of tumors, extracranial germ cell tumor, extrahepatic bile duct cancer, gallbladder cancer, gastric cancer, gastrointestinal carcinoid tumor, gastrointestinal stromal tumor, gestational trophoblastic tumor, glioblastoma, glioma, hairy cell leukemia, head and neck cancer, heart cancer, hematopoetic tumors of the lymphoid lineage, hepatocellular cancer, Hodgkin lymphoma, hypopharyngeal cancer, hypothalamic and visual pathway glioma, IDs-related lymphoma, intraocular melanoma, islet cell tumors, Kaposi sarcoma, kidney cancer, Langerhans cell histiocytosis, laryngeal cancer, leukemia, lip and oral cavity cancer, male breast cancer, malignant fibrous histiocytoma, malignant germ cell tumors, malignant mesothelioma, medulloblastoma, melanoma, Merkel cell carcinoma, mesothelioma, mouth cancer, multiple endocrine neoplasia syndrome, multiple myeloma, mycosis fungoides, myelodysplastic, myeloproliferative neoplasms, nasal cavity and paranasal sinus cancer, nasopharyngeal cancer, neuroblastoma, non-Hodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pineal parenchymal tumors, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, primary liver cancer, primary metastatic squamous neck cancer with occult, prostate cancer, rectal cancer, renal cell cancer, renal pelvis and ureter, respiratory tract carcinoma, retinoblastoma, rhabdomyosarcoma, salivary gland cancer, sarcoma, Sézary syndrome, skin cancer, skin cancer, small intestine cancer, soft tissue sarcoma, squamous cell carcinoma (non-melanoma), stomach cancer, supratentorial primitive neuroectodermal tumors, T-cell lymphoma, testicular cancer, throat cancer, thymoma and thymic carcinoma, thyroid cancer, transitional cell cancer, urethral cancer, uterine sarcoma, vaginal cancer, visual pathway and hypothalamic glioma, vulvar cancer, Waldenström macroglobulinemia, Wilms tumor, and systemic and central metastases of any of the foregoing.

Selective IL-2Rβγc agonists and compounds comprising an IL-2Rβ ligand and/or an IL-2Rγc ligand provided by the present disclosure, or a pharmaceutical composition of any of the foregoing can be used to treat solid tumors.

Selective IL-2Rβγc agonists, compounds comprising an IL-2Rβ ligand and/or an IL-2Rγc ligand provided by the present disclosure or a pharmaceutical composition of any of the foregoing can be used to treat, for example, one or more of the following cancers wherein the cancer is selected from any of the primary adult and childhood brain and CNS cancers including glioblastoma (GBM) and astrocytoma, skin cancers including melanoma, lung cancers including small cell lung cancers, non-small cell lung cancers (NSCLC), and large cell lung cancers, breasts cancers including triple negative breast cancer (TNBC), blood cancers including myelodysplastic syndrome (MDS), multiple myeloma (MM), and acute myeloid leukemia (AML), prostate cancer including castrate resistant prostate cancer (CRPC), liver cancers including hepatocellular carcinoma (HCC), esophageal and gastric cancers, and any systemic and central metastases of any of the foregoing.

The amount of a selective IL-2Rβγc agonists, compounds comprising an IL-2Rβ ligand and/or an IL-2Rγc ligand provided by the present disclosure, or pharmaceutical composition of any of the foregoing that will be effective in the treatment of a cancer will depend, at least in part, on the nature of the disease, and may be determined by standard clinical techniques known in the art. In addition, in vitro or in vivo assays may be employed to help identify optimal dosing ranges. Dosing regimens and dosing intervals may also be determined by methods known to those skilled in the art. The amount of a selective IL-2Rβγc agonist or compound comprising an IL-2Rβ ligand and/or an IL-2Rγc ligand provided by the present disclosure administered may depend on, among other factors, the subject being treated, the weight of the subject, the severity of the disease, the route of administration, and the judgment of the prescribing physician.

For systemic administration, a therapeutically effective dose may be estimated initially from in vitro assays. Initial doses may also be estimated from in vivo data, e.g., animal models, using techniques that are known in the art. Such information may be used to more accurately determine useful doses in humans. One having ordinary skill in the art may optimize administration to humans based on animal data.

A dose of a selective IL-2Rβγc agonist or compound comprising an IL-2Rβ ligand and/or an IL-2Rγc ligand provided by the present disclosure and appropriate dosing intervals may be selected to maintain a sustained therapeutically effective concentration of the selective IL-2Rβγc agonist or compound comprising an IL-2Rβ ligand and/or an IL-2Rγc ligand provided by the present disclosure in the blood of a patient, and in certain embodiments, without exceeding a minimum adverse concentration.

In certain embodiments, pharmaceutical compositions comprising a selective IL-2Rβγc agonist or compound comprising an IL-2Rβ ligand and/or an IL-2Rγc ligand provided by the present disclosure may be administered, for example once per week, every 2 weeks, every 3 weeks, every 4 weeks, every 5 weeks, or every 6 weeks. Dosing may be provided alone or in combination with other drugs and may continue as long as required for effective treatment of the disease. Dosing may also be undertaken using continuous or semi-continuous administration over a period of time. Dosing includes administering a pharmaceutical composition to a mammal, such as a human, in a fed or fasted state.

A pharmaceutical composition may be administered in a single dosage form or in multiple dosage forms or as a continuous or an accumulated dose over a period of time. When multiple dosage forms are used the amount of a selective IL-2Rβγc agonist or compound comprising an IL-2Rβ ligand and/or IL-2Rγc ligand provided by the present disclosure contained within each of the multiple dosage forms may be the same or different.

Suitable daily dosage ranges for administration may range from about 2 µg to about 200 mg of a selective IL-2Rβγc agonist or compound comprising an IL-2Rβ ligand and/or an IL-2Rγc ligand provided by the present disclosure per kilogram body weight.

Suitable daily dosage ranges for administration may range from about 1 µg to about 50 mg of a selective IL-2Rβγc agonist or compound comprising an IL-2Rβ ligand and/or an IL-2Rγc ligand provided by the present disclosure per square meter ($m^2$) of body surface.

A selective IL-2Rβγc agonist or compound comprising an IL-2Rβ ligand and/or an IL-2Rγc ligand provided by the present disclosure may be administered to treat cancer in a subject in an amount, for example, from 0.001 mg/day to 100 mg/day, or in any other appropriate daily dose. A dose can be for example, from 0.01 pg/kg body weight/week to 100 pg/kg body weight/week or any other suitable dose.

A pharmaceutical composition comprising a selective IL-2Rβγc agonist or compound comprising an IL-2Rβ ligand and/or an IL-2Rγc ligand provided by the present disclosure may be administered to treat cancer in a subject so as to provide a therapeutically effective concentration of a selective IL-2Rβγc agonist or compound comprising an IL-2Rβ ligand and/or an IL-2Rγc ligand provided by the present disclosure in the blood or plasma of the subject. A therapeutically effective concentration of a compound of a selective IL-2Rβγc agonist or compound comprising an IL-2Rβ ligand and/or an IL-2Rγc ligand provided by the present disclosure in the blood of a subject can be, for example, from 0.01 µg/L to 1,000 µg/L, from 0.1 µg/L to 500 µg/L, from 1 µg/L to 250 µg/L, or from about 10 µg/L to about 100 µg/L. A therapeutically effective concentration of a selective IL-2Rβγc agonist or compound comprising an IL-2Rβ ligand and/or an IL-2Rγc ligand provided by the present disclosure in the blood of a subject can be, for example, at least 0.01 µg/L, at least 0.1 µg/L, at least 1 µg/L, at least about 10 µg/L, or at least 100 µg/L. A therapeutically effective concentration of a selective IL-2Rβγc agonist or compound comprising an IL-2Rβ ligand and/or an IL-2Rγc ligand in the blood of a subject can be, for example, less than an amount that causes unacceptable adverse effects including adverse effects to homeostasis. A therapeutically effective concentration of a selective IL-2Rβγc agonist or compound comprising an IL-2Rβ ligand and/or an IL-2Rγc ligand in the blood of a subject can be an amount sufficient to restore and/or maintain homeostasis in the subject.

Pharmaceutical compositions comprising a selective IL-2Rβγc agonist or compound comprising an IL-2Rβ ligand and/or IL-2Rγc ligand may be administered to treat a disease in a subject so as to provide a therapeutically effective concentration of the selective IL-2Rβγc agonist or compound comprising an IL-2Rβ ligand and/or an IL-2Rγc ligand in the blood of a subject for an extended period of time such as, for example, for at least about 4 hours, for at least about 6 hours, for at least about 12 hours, for at least 1 day, for at least 2 days, for at least 3 days, or at least 1 week.

The amount of a selective IL-2Rβγc agonist or compound comprising an IL-2Rβ ligand and/or an IL-2Rγc ligand administered may vary during a treatment regimen.

Pharmaceutical compositions provided by the present disclosure may further comprise one or more pharmaceutically active compounds in addition to a selective IL-2Rβγc agonist or compound comprising an IL-2Rβ ligand and/or an IL-2Rγc ligand provided by the present disclosure. Such compounds may be provided, for example, to treat the cancer being treated with the a selective IL-2Rβγc agonist a compound comprising an IL-2Rβ ligand and/or an IL-2Rγc ligand or to treat a disease, disorder, or condition other than the cancer being treated with the selective IL-2Rβγc agonist or compound comprising an IL-2Rβ ligand and/or an IL-2Rγc ligand, to treat a side-effect caused by administering the selective IL-2Rβγc agonist or compound comprising an IL-2Rβ ligand and/or an IL-2Rγc ligand, to augment the efficacy of the a selective IL-2Rβγc agonist or compound comprising an IL-2Rβ ligand and/or an IL-2Rγc ligand, and/or to modulate the activity of the selective IL-2Rβγc agonist or compound comprising an IL-2Rβ ligand and/or an IL-2Rγc ligand.

A selective IL-2Rβγc agonist or compound comprising an IL-2Rβ ligand and/or an IL-2Rγc ligand provided by the present disclosure may be used in combination with at least one other therapeutic agent. A selective IL-2Rβγc agonist or compound comprising an IL-2Rβ ligand and/or an IL-2Rγc ligand may be administered to a patient together with another compound for treating cancer in the subject. In certain embodiments, the at least one other therapeutic agent may be a different selective IL-2Rβγc agonist or compound comprising an IL-2Rβ ligand and/or an IL-2Rγc ligand. A selective IL-2Rβγc agonist or compound comprising an IL-2Rβ ligand and/or an IL-2Rγc ligand and the at least one other therapeutic agent may act additively or, and in certain embodiments, synergistically. The at least one additional therapeutic agent may be included in the same pharmaceutical composition or vehicle comprising the selective IL-2Rβγc agonist or compound comprising an IL-2Rβ ligand and/or an IL-2Rγc ligand or may be in a separate pharmaceutical composition or vehicle. Accordingly, methods provided by the present disclosure further include, in addition to administering a selective IL-2Rβγc agonist or compound comprising an IL-2Rβ ligand and/or an IL-2Rγc ligand, administering one or more therapeutic agents effective for treating cancer or a different disease, disorder or condition than cancer. Methods provided by the present disclosure include administration of a selective IL-2Rβγc agonist or compound comprising an IL-2Rβ ligand and/or an IL-2Rγc ligand and one or more other therapeutic agents provided that the combined administration does not inhibit the therapeutic efficacy of a selective IL-2Rβγc agonist or compound comprising an IL-2Rβ ligand and/or an IL-2Rγc ligand and/or does not produce adverse combination effects.

A pharmaceutical composition comprising a selective IL-2Rβγc agonist or a compound comprising an IL-2Rβ ligand and/or an IL-2Rγc ligand may be administered concurrently with the administration of another therapeutic agent, which may be part of the same pharmaceutical composition as, or in a different pharmaceutical composition than that comprising a selective IL-2Rβγc agonist and/or a compound comprising an IL-2Rβ ligand and/or an IL-2Rγc ligand. A selective IL-2Rβγc agonist and/or a compound comprising an IL-2Rβ ligand and/or an IL-2Rγc ligand may be administered prior or subsequent to administration of another therapeutic agent. In certain embodiments of combination therapy, the combination therapy may comprise alternating between administering a selective IL-2Rβγc agonist or a compound comprising an IL-2Rβ ligand and/or an IL-2Rγc ligand and a composition comprising another therapeutic agent, e.g., to minimize adverse drug effects associated with a particular drug. When a selective IL-2Rβγc agonist or a compound comprising an IL-2Rβ ligand and/or an IL-2Rγc ligand is administered concurrently with another therapeutic agent that potentially may produce an adverse drug effect including, for example, toxicity, the other therapeutic agent may be administered at a dose that falls below the threshold at which the adverse drug reaction is elicited.

A pharmaceutical composition comprising a selective IL-2Rβγc agonist or a compound comprising an IL-2Rβ ligand and/or an IL-2Rγc ligand provided by the present disclosure may be administered with one or more substances, for example, to enhance, modulate and/or control release, bioavailability, therapeutic efficacy, therapeutic potency, and/or stability, of the selective IL-2Rβγc agonist or compound comprising an IL-2Rβ ligand and/or an IL-2Rγc ligand. For example, a pharmaceutical composition comprising a selective IL-2Rβγc agonist or compound comprising an IL-2Rβ ligand and/or an IL-2Rγc ligand can be co-administered with an active agent having pharmacological effects that enhance the therapeutic efficacy of the selective IL-2Rβγc agonist or compound comprising an IL-2Rβ ligand and/or an IL-2Rγc ligand.

A selective IL-2Rβγc agonist, a compound comprising an IL-2Rβ ligand and/or an IL-2Rγc ligand, or a pharmaceutical composition comprising any of the foregoing may be administered in conjunction with an agent known or believed to be effective in treating cancer in a patient, such as the same cancer being treated with the selective IL-2Rβγc agonist or compound comprising an IL-2Rβ ligand and/or an IL-2Rγc ligand.

A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interfere with proliferation.

In certain embodiments, a selective IL-2Rβγc agonist, a compound comprising an IL-2Rβ ligand and/or an IL-2Rγc ligand, or a pharmaceutical composition comprising any of the foregoing may be administered in conjunction with an agent known or believed to interfere with metabolism. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interfere with mitochondrial metabolism. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to be an anti-metabolite. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interfere RNA transcription. A selective IL-2Rβγc agonist, a compound comprising an IL-2Rβ ligand and/or an IL-2Rγc ligand, or a pharmaceutical composition comprising a selective IL-2Rβγc agonist may be administered in conjunction with an agent known or believed to interfere with RNA translation. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interfere with protein synthesis. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interfere with synthesis of precursors for DNA synthesis and replication. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interfere with purine synthesis. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interfere with nucleoside synthesis. A selective IL-2Rβγc agonist, a compound comprising an IL-2Rβ ligand and/or an IL-2Rγc ligand, or a pharmaceutical composition of any of the foregoing may be administered in conjunction with an agent known or believed to interact with mTOR. A selective IL-2Rβγc agonist, a compound comprising an IL-2Rβ ligand and/or an IL-2Rγc ligand, or a pharmaceutical composition of any of the foregoing may be administered in conjunction with an agent known or believed to interact be an mTOR inhibitor. A selective IL-2Rγγc agonist, a compound comprising an IL-2Rβ ligand and/or an IL-2Rγc ligand, or a pharmaceutical composition of any of the foregoing may be administered in conjunction with an agent known or believed to interfere with cell cycle checkpoints.

An IL-2Rβγc agonist, a compound comprising an IL-2Rβ ligand and/or an IL-2Rγc ligand, or a pharmaceutical composition of any of the foregoing may be administered in conjunction with a checkpoint inhibitor including CTLA-4 inhibitors such as ipilimumab, PD1 inhibitors such as pembrolizumab and nivolumab, and PD-LI inhibitors such as atezolizumab, avelumab, and durvalumab. An IL-2Rβγc agonist, a compound comprising an IL-2Rβ ligand and/or an IL-2Rγc ligand, or a pharmaceutical composition of any of the foregoing may be administered in conjunction with an immunomodulator such as CD137/4-1BB, CD27, GIYR, and/or OC40.

A selective IL-2Rβγc agonist, a compound comprising an IL-2Rβ ligand and/or an IL-2Rγc ligand, or a pharmaceutical composition of any of the foregoing may be administered in conjunction with an agent known or believed to be cytotoxic. A selective IL-2Rβγc agonist, a compound comprising an IL-2Rβ ligand and/or an IL-2Rγc ligand, or a pharmaceutical composition of any of the foregoing may be administered in conjunction with an agent known or believed to be cytostatic. A selective IL-2Rβγc agonist, a compound comprising an IL-2Rβ ligand and/or an IL-2Rγc ligand, or a pharmaceutical composition of any of the foregoing may be administered in conjunction with an agent known or believed to cause DNA damage. A selective IL-2Rβγc agonist, a compound comprising an IL-2Rβ ligand and/or an IL-2Rγc ligand, or a pharmaceutical composition of any of the foregoing may be administered in conjunction with an agent known or believed to cause cell cycle arrest. A selective IL-2Rβγc agonist, a compound comprising an IL-2Rβ ligand and/or an IL-2Rγc ligand, or a pharmaceutical composition comprising of any of the foregoing may be administered in conjunction with an agent known or believed to cause mitotic catastrophe.

A selective IL-2Rβγc agonist, a compound comprising an IL-2Rβ ligand and/or an IL-2Rγc ligand, or a pharmaceutical composition of any of the foregoing may be administered in conjunction with an agent known or believed to modulate drug resistance. A selective IL-2Rβγc agonist, a compound comprising an IL-2Rβ ligand and/or an IL-2Rγc ligand, or a pharmaceutical composition of any of the foregoing may be administered in conjunction with an agent known or believed to reduce multi-drug resistance. A selective IL-2Rβγc agonist, a compound comprising an IL-2Rβ ligand and/or an IL-2Rγc ligand, or a pharmaceutical composition of any of the foregoing may be administered in conjunction with an agent known or believed to interact with membrane proteins. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interact with plasma membrane proteins. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interact with nuclear membrane proteins. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interact with a major vault protein or proteins. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interact with gen products of the MVP (major vault protein) gene.

A selective IL-2Rβγc agonist, a compound comprising an IL-2Rβ ligand and/or an IL-2Rγc ligand, or a pharmaceutical composition of any of the foregoing, may be administered in conjunction with an agent known or believed to modulate glutathione concentration. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to modulate glutathione concentration within cells. A selective IL-2Rβγc agonist, a compound comprising an IL-2Rβ ligand and/or an IL-2Rγc ligand, or a pharmaceutical composition comprising a selective IL-2Rβγc agonist or a compound comprising an IL-2Rβ ligand and/or an IL-2Rγc ligand may be administered in conjunction with an agent known or believed to decrease glutathione concentration within cells. A selective IL-2Rβγc agonist, a compound comprising an IL-2Rβ ligand and/or an IL-2Rγc ligand, or a pharmaceutical composition comprising a selective IL-2Rβγc agonist or a compound comprising an IL-2Rβ ligand and/or IL-2Rγc ligand may be administered in conjunction with an agent known or believed to reduce glutathione uptake into cells. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to reduce glutathione synthesis. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to reduce glutathione synthesis within cells.

A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interfere with neovascularization. A selective IL-2Rβγc agonist, a compound comprising an IL-2Rβ ligand and/or IL-2Rγc ligand, or a pharmaceutical composition comprising any of the foregoing may be administered in conjunction with an agent known or believed to reduce neovascularization. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to promote neovascularization.

A selective IL-2Rβγc agonist, a compound comprising an IL-2Rβ ligand and/or an IL-2Rγc ligand, or a pharmaceutical composition of any of the foregoing may be administered in conjunction with an agent known or believed to interfere with hormone homeostasis. In certain embodiments, a selective IL-2Rβγc agonist, a compound comprising an IL-2Rβ ligand and/or an IL-2Rγc ligand, or a pharmaceutical composition comprising any of the foregoing may be administered in conjunction with an agent known or believed to interfere with hormone synthesis. A selective IL-2Rβγc agonist, a compound comprising an IL-2Rβ ligand and/or IL-2Rβ ligand and/or an IL-2Rγc ligand or a pharmaceutical composition comprising any of the foregoing may be administered in conjunction with an agent known or believed to interfere with hormone receptor binding. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interfere with hormone signal transduction.

A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interfere with growth factor homeostasis. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interfere with growth factor synthesis. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interfere with growth factor receptor expression. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interfere with growth factor binding to growth factor receptors. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interfere with growth factors binding to growth factor receptors. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to interfere with growth factor receptor signal transduction. A selective IL-2Rβγc agonist, a compound comprising an IL-2Rβ ligand and/or IL-2Rγc ligand, or a pharmaceutical composition comprising any of the foregoing may be administered in conjunction with an agent known or believed to interfere with the Hedgehog (Hh) signaling. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to inhibit the Hedgehog pathway signaling. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to inhibit ALK (anaplastic lymphoma kinase) pathway signaling. A selective IL-2Rβγc agonist, a compound comprising an IL-2Rβ ligand and/or an IL-2Rγc ligand, or a pharmaceutical composition comprising any of the foregoing may be administered in conjunction with an agent known or believed to inhibit non-homologous end joining (NHEJ) is a pathway.

A selective IL-2Rβγc agonist, a compound comprising an IL-2Rβ ligand and/or an IL-2Rγc ligand, or a pharmaceutical composition of any of the foregoing may be administered in conjunction with one or more agents known or believed to be a VEGFR (vascular endothelial growth factor receptor) inhibitor, a RTK (receptor tyrosine kinase) inhibitor, a sodium channel current blocker, aFAK (focal adhesion kinase) inhibitor, a GLI (glioma-associated oncogene) inhibitor, a GLI1 inhibitor, a GLI2 inhibitor, a GLI3 inhibitor, a MAPK (mitogen-activated protein kinase) inhibitor, a MAPK/ERK pathway (also known as Ras-Raf-MEK-ERK pathways) inhibitor, a MEK1 inhibitor, a MEK2 inhibitor, a MEK5 inhibitor, a MEK5/ERK5 inhibitor, aRTA (renal tubular acidosis) inhibitor, a ALK (anaplastic lymphoma kinase) inhibitor, Aa LK kinase inhibitor, a nuclear translocation inhibitor, a PORCN (porcupine) inhibitor, a 5-ARI (5α-reductase inhibitor), topoisomerase inhibitor, a Ras (rat sarcoma) inhibitor, a K-ras inhibitor, a CERK (ceramide kinase) inhibitor, a PKB (protein kinase B, also known as AKT) inhibitor, a AKT1 inhibitor, EZH2 (enhacer of zeste homolog 2) inhibitor, a BET (bromodomain and extraterminal domain motif) inhibitor, a SYK (apleen tyrosine kinase) inhibitor, JAK (janus kinase) inhibitors, a SYK/JAK inhibitor, a IDO (indoleamine-pyrrole 2,3-dioxygenase) inhibitor, a IDO1 inhibitor, a RXR (retinoic X receptors) activating agent, a selectively RXR activating agent, a p-glycoprotein inhibitor, a ERK inhibitor, a PI3K (phosphatidylinositol-4, 5-bisphosphate 3-kinase) inhibitor, a BRD (bromodomain-containing protein) inhibitor, a BRD2 inhibitor, a BRD3 inhibitor, a BRD4 inhibitor, a BRDT (bromodomain testis-specific protein) inhibitor, a reverse transcriptase inhibitor, a NRT (nucleoside analog reverse-transcriptase) inhibitor, a PIM (proviral integrations of moloney virus) inhibitor, a EGFR (epidermal growth factor receptor) inhibitor, a photosensitizer, a radiosensitizer, a ROS (proto-oncogene, receptor tyrosine kinase) inhibitor, a ROS1 (proto-oncogene 1) inhibitor, a CK (caseine kinase) inhibitor, a CK2 inhibitor, a Bcr-Abl (breakpoint cluster region-Abelson proto-oncogene) tyrosine-kinase inhibitor such as dasatinib, a microtubule stabilizing agent, a microtubule depolymerization/disassembly inhibitor, a DNA intercalator, an androgen receptor antagonist, a chemoprotective agents, a HDAC (histone deacetylase) inhibitor, a DPP (dipeptidyl pepdidase) inhibitor, a DPP-4 inhibitor, BTK (Bruton's tyrosine kinase) inhibitor, a kinase inhibitor such as imatinib, a tyrosine kinase inhibitor such as nilotinib, a ARP (poly (ADP-ribose) polymerase) inhibitor, a CDK (cyclin-dependent kinase) inhibitor, a CDK4 inhibitor, a CDK6 inhibitor, a CDK4/6 inhibitor, a HIF1α (hypoxia-inducible factor 1-α) inhibitor, a DNA ligase inhibitor, a DNA ligase IV inhibitor, a NHEJ (non-homologous end joining) inhibitor, a DNA ligase IV, a NHEJ inhibitor and a RAF inhibitor, a TKI and a RAF inhibitor, a TKI and RAF inhibitor such as sorafenib, a PDT (photodynamic therapy) sensitizer, an ATR (ataxia telangiectasia- and Rad3-related protein kinase) inhibitor, or a combination of any of the foregoing.

A selective IL-2Rβγc agonist, a compound comprising an IL-2Rβ ligand and/or an IL-2Rγc ligand or a pharmaceutical composition of any of any of the foregoing may be administered in conjunction with one or more chemotherapeutic agents, such as, for example, a VEGFR inhibitor such as fruquintinib, motesanib/AMG-706, vatalanib; a RTK inhibitor such as ponatinib; a sodium channel blocker such as GS967; a FAK inhibitor such as TAE226; a GLI1 and GLI2 inhibitor such as GANT61, a MEK inhibitor such as binimetinib; a RTA inhibitor such as linifanib; an ALK inhibitor such as brigstinib; bromopyruvic acid; a DNA alkylating agent such as thiotepa; nuclear translocations factors such as JSH-23; a PORCn inhibitor such as Wnt-C59; a 5α-reductase inhibitor such as dutasteride; a topoisomerase inhibitor such as carubicin; a RAS inhibitor such as Kobe0065; a CerK inhibitor such as NVP-231; an AKT inhibitor such as uprosertib; a EZH2 inhibitor such as GSK-503; a BET bromodomain inhibitor such as OTXO15; a MEK5/ERK5 inhibitor such as BIX02189; a Syl/JAK inhibitor such as cerdulatinib; an IDO1 inhibitor such as NLG919; a retinoic X receptor activating agent such as bexsrotene; a PGP inhibitor such as acotiamide or actotiamide HCl; an Erk inhibitor such SCH772984; a PI3K inhibitor such as gedatolisib; a JAK inhibitor such as ruxolitinib; an AKT inhibitor such as afuresertib or afuresertib HCl; an ALK1 inhibitor such as ceritinib; an HDAC inhibitor such as abexinostat; a DPP inhibitor such as oamarigliptin; an EGFR inhibitor such as gefittinib; an EZH2 inhibitor such as GSK126; a BTK inhibitor such as ibrutinib; a kinase inhibitor such as imatinin HCl; an IDO inhibitor such as INCB024360; a DNA crosslinker such as mitomycin C; a tyrosine kinase inhibitor such as nilotinib, a PARP inhibitor such as olaparib; a tubilin stabilization promoter such as paclitaxel; a CDK4/6 inhibitor such as palbociclib; a RTK inhibitor such as sunitinib; a PDT sensitizer such as tslsporfin; a p-glycoprotein inhibitor such as tariquidar; an ATR inhibitor such as VE-822; an HDAC inhibitor such as PCI-24781; a DPP inhibitor such as omarigliptin; an EGFR inhibitor such as gefinib; an EZH2 inhibitor such as GSK126; a BTK inhibitor such as irbrutinib; an IDO inhibitor such as INCB024360; or a combination of any of the foregoing.

For example, a selective IL-2Rβγc agonist, a compound comprising an IL-2Rβ ligand and/or an IL-2Rγc ligand, or a of any of the foregoing may be administered in conjunction with another chemotherapeutic agents, such as, for example, N-acetyl cysteine (NAC), adriamycin, alemtuzumab, amifostine, arsenic trioxide, ascorbic acid, bendamustine, bevacizumab, bortezomib, busulfan, buthionine sulfoxime, carfilzomib, carmustine, clofarabine, cyclophosphamide, cyclosporine, cytarabine, dasatinib, datinomycin, defibrotide, dexamethasone, docetaxel, doxorubicin, etoposide, filgrastim, floxuridine, fludarabine, gemcitabine, interferon α, ipilimumab, lenalidomide, leucovorin, melphalan, mycofenolate mofetil, paclitaxel, palifermin, panobinostat, pegfilrastim, prednisolone, prednisone, revlimid, rituximab, sirolimus, sodium 2-mercaptoethane sulfonate (MESNA), sodium thiosulfate, tacrolimus, temozolomide, thalidomide, thioguanine, thiotepa, topotecan, velcade, or a combination of any of the foregoing. In certain embodiments, a selective IL-2Rβγc agonist and/or pharmaceutical compositions thereof can be used in combination therapy with other chemotherapeutic agents including one or more antimetabolites such as folic acid analogs; pyrimidine analogs such as fluorouracil, floxuridine, and cytosine arabinoside; purine analogs such as mercaptopurine, thiogunaine, and pentostatin; natural products such as vinblastine, vincristine, etoposide, tertiposide, dactinomycin, daunorubicin, doxurubicin, bleomycin, mithamycin, mitomycin C, L-asparaginase, and interferon α; platinum coordination complexes such as cisplatinum, and carboplatin; mitoxantrone; hydroxyurea; procarbazine; hormones and antagonists such as prednisone, hydroxyprogesterone caproate, medroxyprogesterone acetate, megestrol acetate, diethylstilbestrol, ethinyl estradiol, tamoxifen, testosterone propionate, fluoxymesterone, flutamide, and leuprolide, anti-angiogenesis agents or inhibitors such as angiostatin, retinoic acids, paclitaxel, estradiol derivatives, and thiazolopyrimidine derivatives; apoptosis prevention agents; triptolide; colchicine; luliconazole; and radiation therapy.

A selective IL-2Rβγc agonist or a compound comprising an IL-2Rβ ligand and/or an IL-2Rγc ligand may be co-administered with a compound that inhibits DNA repair such as, for example, O6-benzylguanine (O6-BG).

A selective IL-2Rβγc agonist, a compound comprising an IL-2Rβ ligand and/or an IL-2Rγc ligand, or a pharmaceutical composition comprising any of the foregoing may be administered in conjunction with one or more chemotherapeutic agents, such as, for example, abarelix, abiraterone, abiraterone acetate, n-acetyl cysteine, aclanibicin hydrochloride, adriamycin, adenine, afatinib, afatinib dimaleate, alemtuzumab, alendronate sodium, alitretinoin, allopurinol sodium, altretamine, amifostine, aminoglutethimide, aminolevulinic acid, amrubicin, amsacrine, anastrozole, angiostatin, apremilast, aprepitant, arsenic trioxide, ascorbic acid, l-asparaginase, azacitidine, azathioprine sodium, bazedoxifene (serm), belinostat, bendamustine hcl, o6-benzylguanine (o6-bg), bevacizumab, bexarotene, bicalutamide, biricodar, bleomycin sulfate, bortezomib, bosutinib, brivudine, buserelin, busulfan, buthionine sulfoxime, cabazitaxel, cabozantinib, capecitabine, carboplatin, carboquone, carfilzomib, carmofur, carmustine, ceritinib, chlorambucil, cisplatin, cladribine, clodronate disodium, clofarabine, crizotinib, cyclophosphamide, cyclosporine, cytarabine, cytosine arabinoside, dabrafenib, dacarbazine, dactinomycin, dasatinib, datinomycin, daunorubicin, decitabine, defibrotide, degarelix acetate, dexamethasone, dexrazoxane hydrochloride, diaziquone, diethyl stilbestrol, docetaxel, doxifluridine, doxorubicin hydrochloride, doxorubicin free base, dromostanolone propionate, dutasteride, eltrombopag, enzalutamide, epirubicin hydrochloride, eribulin mesylate, erlotinib hydrochloride, estramustine phosphate sodium, ethinyl estradiol, etoposide phosphate, etoposide, everolimus, exemestane, fentanyl, filgrastim, fingolimod, floxuridine, fludarabine phosphate, fluorouracil, fluoxymesterone, flutamide, formestane, formylmelphalan, fosaprepitant, fotemustine, fulvestrant, gefitinib, gemcitabine hydrochloride, gemcitabine free base, glutathione, glyciphosphoramide, glyfosfin, goserelin acetate, granisetron hydrochloride, heptaplatin, hexyl 5-aminolevulinate, histrelin acetate, hydroxyprogesterone caproate, hydroxyurea, ibandronate sodium, ibrutinib, icotinib, idanibicin HCl, idelalisib, idoxuridine, ifosfamide, interferon α, imatinib mesylate, imiquimod, ingenol mebutate, ipilimumab, irinotecan hydrochloride, ixabepilone, lanreotide acetate, lapatinib free base, lapatinib ditosylate, lasofoxifene, lenalidomide, letrozole, leucovorin calcium, leuprolide acetate, levamisole hydrochloride, levoleucovorin calcium, iobenguane, lobaplatin, lomustine, maropitant, masoprocol, mechlorethamine hydrochloride, megestrol acetate, medroxyprogesterone acetate, melphalan hydrochloride, mercaptopurine, mercaptoethane sulfonate sodium, methotrexate, methoxsalen, methyl aminolevulinate, methylene blue, methylisoindigotin, mifamurtide, miltefosine, miriplatin, mithamycin, mitobronitol, mitomycin C, mitotane, mitoxantrone hydrochloride, mycophenolate mofetil, nabiximols, nafarelin, nandrolone, nedaplatin, nelarabine, netupitant, nilotinib, nilutamide, nimustine, nintedanib, nocodazole, octreotide, olaparib, omacetaxine mepesuccinate, ondansetron hydrochloride, oxaliplatin, paclitaxel, palbociclib, palifermin, palonosetron hydrochloride, pamidronate disodium, panobinostat, pasireotide, pazopanib hydrochloride, pegfilrastim, pemetrexed disodium, pentostatin, peplomycin, pipobroman, pirarubicin, plerixafor, plicamycin, pomalidomide, ponatinib, porfimer sodium, porfiromycin, pralatrexate, prednimustine, prednisolone, prednisone, procarbazine hydrochloride, quinagolide hydrochloride, raloxifene, raltitrexed, radotinib, ranimustine, retinoic acids, revlimide, rituxinab, romidepsin, ruxolitinib, ruxolitinib phosphate, semustine, sirolimus, sodium thiosulfate, sorafenib free base, sorafenib tosylate, streptozocin, sufentanil, sunitinib, tacrolimus, talaporfin sodium, tamibarotene, tamoxifen citrate, tapentadol, temoporfin, temozolomide, temsirolimus, teniposide, teriflunomide, tertiposide, testolactone, testosterone propionate, thalidomide, thioguanine, thiotepa, thymalfasin, toceranib phosphate, topotecan hydrochloride, toremifene citrate, trabectedin, trametinib, tretinoin, trilostane, triptorelin, tropisetron, uramustine, valrubicin, vandetanib, vedotin, vemurafenib, verteporfin, vinblastine, vincristine sulfate, vincristine free base, vindesine, vinorelbine tartrate, vorinostat, and zoledronic acid.

A selective IL-2Rβγc agonist, a compound comprising an IL-2Rβ ligand and/or an IL-2Rγc ligand, or a pharmaceutical composition comprising any of the foregoing may be administered in conjunction with one or more chemotherapeutic agents, including abemaciclib, abiraterone acetate, ABVD, ABVE, ABVE-PC, AC, acalabrutinib, AC-T, ADE, ado-trastuzumab emtansine, afatinib dimaleate, aldesleukin, alectinib, alemtuzumab, alpelisib, amifostine, aminolevulinic acid hydrochloride, anastrozole, apalutamide, aprepitant, arsenic trioxide, asparaginase *Erwinia chrysanthemi*, atezolizumab, avelumab, axicabtagene ciloleucel, axitinib, azacitidine, BEACOPP, belinostat, bendamustine hydrochloride, BEP, bevacizumab, bexarotene, bicalutamide, binimetinib, bleomycin sulfate, blinatumomab, bortezomib, bosutinib, brentuximab vedotin, brigatinib, BuMel, busulfan, cabazitaxel, cabozantinib-s-malate, CAF, calaspargase pegol-mknl, capecitabine, caplacizumab-yhdp, CAPOX, carboplatin, carboplatin-taxol, carfilzomib, carmustine, carmustine implant, CEM, cemiplimab-rwlc, ceritinib, cetuximab, CEV, chlorambucil, chlorambucil-prednisone, CHOP, cisplatin, cladribine, clofarabine, CMF, cobimetinib, copanlisib hydrochloride, COPDAC, COPP, COPP-ABV, crizotinib, CVP, cyclophosphamide, cytarabine, cytarabine liposome, dabrafenib mesylate, dacarbazine, dacomitinib, dactinomycin, daratumumab, darbepoetin a, dasatinib, daunorubicin hydrochloride, daunorubicin hydrochloride and cytarabine liposome, decitabine, defibrotide sodium, degarelix, denileukin diftitox, denosumab, dexamethasone, dexrazoxane hydrochloride, dinutuximab, docetaxel, doxorubicin hydrochloride, doxorubicin hydrochloride liposome, durvalumab, duvelisib, elotuzumab, eltrombopag olamine, emapalumab-lzsg, enasidenib mesylate, encorafenib, enzalutamide, epirubicin Hydrochloride, EPOCH, epoetin alfa, erdafitinib, eribulin mesylate, erlotinib hydrochloride, etoposide, etoposide phosphate, everolimus, exemestane, fec, filgrastim, fludarabine phosphate, fluorouracil injection, fluorouracil-topical, flutamide, folfiri, folfiri-bevacizumab, folfiri-cetuximab, folfirinox, folfox, fostamatinib disodium, FU-LV, fulvestrant, gefitinib, gemcitabine hydrochloride, gemcitabine-cisplatin, gemcitabine-oxaliplatin, gemtuzumab ozogamicin, gilteritinib fumarate, glasdegib maleate, glucarpidase, goserelin acetate, granisetron, HPV bivalent vaccine, HPV bivalent vaccine, recombinant HPV nonavalent vaccine, HPV nonavalent vaccine, recombinant, HPV quadrivalent vaccine, HPV uadrivalent vaccine recombinant, hydroxyurea, hyper-CVAD, ibritumomab tiuxetan, ibrutinib, ICE, idarubicin hydrochloride, idelalisib, ifosfamide, imatinib mesylate, imiquimod, inotuzumab ozogamicin, Interferon α-2b Recombinant, iobenguane I$^{131}$, ipilimumab, irinotecan hydrochloride, irinotecan hydrochloride liposome, ivosidenib, ixabepilone, ixazomib citrate, JEB, lanreotide acetate, lapatinib ditosylate, larotrectinib sulfate, lenalidomide, lenvatinib mesylate, letrozole, leucovorin calcium, leuprolide acetate, lomustine, lorlatinib, lutetium Lu 177-dotatate, mechlorethamine hydrochloride, megestrol acetate, melphalan, melphalan hydrochloride, mercaptopurine, mesna, methotrexate, methylnaltrexone bromide, midostaurin, mitomycin c, mitoxantrone hydrochloride, mogamulizumab-kpkc, moxetumomab pasudotox-tdfk, MVAC, necitumumab, nelarabine, neratinib maleate, netupitant and palonosetron hydrochloride, nilotinib, nilutamide, niraparib tosylate monohydrate, nivolumab, obinutuzumab, OEPA, ofatumumab, OFF, olaparib, olaratumab, omacetaxine mepesuccinate, ondansetron hydrochloride, OPPA, osimertinib mesylate, oxaliplatin, paclitaxel, paclitaxel albumin-stabilized nanoparticle formulation, PAD, palbociclib, palifermin, palonosetron hydrochloride, palonosetron hydrochloride and netupitant, pamidronate disodium, panitumumab, panobinostat, pazopanib hydrochloride, PCV, PEB, pegaspargase, pegfilgrastim, peginterferon α-2b, pembrolizumab, pemetrexed disodium, pertuzumab, plerixafor, polatuzumab vedotin-piiq, pomalidomide, ponatinib hydrochloride, pralatrexate, prednisone, procarbazine hydrochloride, propranolol hydrochloride, radium 223 dichloride, raloxifene hydrochloride, ramucirumab, rasburicase, ravulizumab-cwvz, R-CHOP, R-CVP, recombinant HPV bivalent vaccine, recombinant HPV nonavalent vaccine, recombinant HPV quadrivalent vaccine, recombinant interferon α-2b, regorafenib, R-EPOCH, ribociclib, R-ICE, rituximab, rituximab and hyaluronidase human, rolapitant hydrochloride, romidepsin, romiplostim, rucaparib camsylate, ruxolitinib phosphate, siltuximab, sipuleucel-t, sonidegib, sorafenib tosylate, STANFORD V, sunitinib malate, TAC, tagraxofusp-erzs, talazoparib tosylate, talc, talimogene laherparepvec, tamoxifen citrate, temozolomide, temsirolimus, thalidomide, thioguanine, thiotepa, tisagenlecleucel, tocilizumab, topotecan hydrochloride, toremifene, TPF, trabectedin, trametinib, trastuzumab, trastuzumab and hyaluronidase-oysk, trifluridine and tipiracil hydrochloride, uridine triacetate, VAC, Valrubicin, VAMP, vandetanib, VeIP, vemurafenib, venetoclax, vinblastine sulfate, vincristine sulfate liposome, vinorelbine tartrate, vip, vismodegib, vorinostat, XELIRI, XELOX, Ziv-aflibercept, zoledronic acid, and compbinations of any of the foregoing.

The efficacy of administering a selective IL-2Rβγc agonist or a compound comprising an IL-2Rβ ligand and/or an IL-2Rγc ligand provided by the present disclosure for treating cancer may be assessed using in vitro and animal studies and in clinical trials.

The suitability of a selective IL-2Rβγc agonist, a compound comprising an IL-2Rβ ligand and/or an IL-2Rγc ligand provided by the present disclosure and/or pharmaceutical compositions of any of the foregoing in treating cancers listed above may be determined by methods described in the art. For example, screens developed to demonstrate the anti-tumor activity of oncolytic agents are known (Miller, et al., *J Med Chem*, 1977, 20(3), 409-413; Sweeney, et al., *Cancer Res*, 1978, 38(9), 2886-2891; and Weiss and Von Hoff, *Semin Oncol*, 1985, 12(3 Suppl 4), 69-74). Accordingly, it is well with the capability of those of skill in the art to assay and use the compounds and/or pharmaceutical compositions thereof to treat the above diseases or disorders.

Compounds provided by the present disclosure can be useful in treating autoimmune diseases. Autoimmune diseases are defined as human diseases in which the immune system attacks its own proteins, cells, and tissues. A comprehensive listing and review of autoimmune diseases can be found in *The Autoimmune Diseases* (Rose and Mackay, 2014, Academic Press).

IL-2Rβγc agonists, compounds comprising an IL-2Rβ ligand and/or an IL-2Rγc ligand provided by the present disclosure and pharmaceutical compositions of any of the foregoing may be administered to a patient to treat an inflammatory disease or an autoimmune disease.

Examples of inflammatory diseases include allergy, Alzheimer's disease, anemia, ankylosing spondylitis, arthritis, atherosclerosis, asthma, autism, arthritis, carpal tunnel syndrome, celiac disease, colitis, Crohn's disease, congestive heart failure, dermatitis, diabetes, diverticulitis, eczema, fibromyalgia, fibrosis, gall bladder disease gastroesophageal reflux disease, Hashimoto's thyroiditis, heart attack, hepatitis, irritable bowel syndrome, kidney failure, lupus, multiple sclerosis, nephritis, neuropathy, pancreatitis, Parkinson's disease, psoriasis, polymyalgia rheumatica, rheumatoid arthritis, scleroderma, stroke, surgical complications, and ulcerative colitis.

Examples of autoimmune diseases include Addison's disease, agammaglobulinemia, alopecia areata, amyloidosis, anklylosing spondylitis, anti-GBM/anti-TBN nephritis, antiphospholipid syndrome, autoimmune angioedema, autoimmune dysautonomia, autoimmune encephalomyelitis, autoimmune hepatitis, autoimmune inner ear disease, autoimmune myocarditis, autoimmune pancreatitis, autoimmune retinopathy, autoimmune urticaria, axonal and neuronal neuropathy, Balo disease, Behcet's disease, benign mucosal pemphigoid, bullous pemphigoid, Castleman disease, celiac disease, Chagas disease, chronic inflammatory demyelinating polyneuropathy, chronic recurrent multifocal osteomyelitis, Churg-Strauss, cicatricial pemphigoid, Cogan' syndrome, cold agglutinin disease, congenital heart block, Coxcackie myocarditits, CREST syndrome, Crohn's disease, dermatitis herpetiformis, dermatomyositis, Devic's disease, discoid lupus, Dressler's syndrome, endometriosis, eosinophilic esophagitis, eosinophilic fasciitis, erythema nodosum, essential mixed cryoglobulinemia, Evans syndrome, fibromyalgia, fibrosing alveolitis, giant cell arteritis, giant cell myocarditis, glomerulonephritis, Goodpasture's syndrome, granulomatosis with polyangiitis, Graves' disease, Gullain-Barre syndrome, Hashimoto' thyroiditis, hemolytic anemia, Henoch-Schonlein purpura, herpes gestationis or pemphigoid gestationis, hypogammaglobulinemia, IgA nephropahy, IgG4-related sclerosing disease, immune thrombocytopenic purpura, inclusion body myositis, interstitial cystitis, juvenile arthritis, juvenile diabetes, juvenile myositis, Kawasaki disease, Lambert-Eaton syndrome, leukocytoclastic vasculitis, lichen planus, lichen sclerosus, ligneous conjunctivitis, linear IgA disease, lupus, Lyme disease chronic, Meniere's diseases, microscopic polyangiitis, mixed connective tissue disease, Mooren's ulcer, Mucha-Habermann disease, multiple sclerosis, myasthenia gravis, myositis, narcolepsy, neuromyelitis, optica, neutropenia, ocular cicatricial pemphigoid, optic neuritis, palindromic rheumatism, PANDAS, paraneoplastic cerebellar degeneration, paroxysmal nocturnal hemoglobinuria, Parry Romberg syndrome, pars planitis, Parsonnage-Turner syndrome, pemphigus, peripheral neuropathy, perivenous encephalomyelitis, pernicious anemia, POEMS syndrome, polyarteritis nodosa, polyglandular syndromes, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia, pyoderma gangrenosum, Raynaud's phenomenon, reactive arthritis, reflex sympathetic dystrophy, relapsing polychondritis, restless legs syndrome, retroperitoneal fibrosis, rheumatic fever, rheumatoid arthritis, sarcodosis, Schmidt syndrome, scleritis, scleroderma, Sjogren's syndrome, sperm and testicular autoimmunity, stiff person syndrome, subacute bacterial endocarditis, Susac's syndrome, sympathetic ophthalmia, Takayasu's arteritis, temporal arteritis, thrombocytopenic purpura, Tolosa-Hunt syndrome, transverse myelitis, type 1 diabetes, ulcerative colitis, undifferentiated connective tissue disease, uveitis, vaculitis, vitiligo, and Wegener's granulomatosis.

A selective IL-2Rαβγc agonist, a compound comprising an IL-2Rβ ligand and/or an IL-2Rγc ligand, or a pharmaceutical composition comprising any of the foregoing may be administered in conjunction with one or more immunosuppresants including, for example, corticosteroids such as prednisone, budesonide, and prednisolone; Janus kinase inhibitors such as tofacitinib; calcineurin inhibitors such as cyclosporine and tacrolimus; mTOR inhibitors such as sirolimus and everolimus; IMDH inhibitors such as azathioprine, leflunomide, and mycophenolate; biologics such as abatacept adalimumab, anakinra, certolizumab, etanercept, golimumab, infliximab, ixekizumab, natalizumab, rituximab, secukinumab, tocilizumab, ustekinumab, and vedolizumab; and monoclonal antibodies such as basiliximab and daclizumab.

IL-2Rβγc agonists, compounds comprising an IL-2Rβ and/or an IL-2Rγc ligand provided by the present disclosure and pharmaceutical compositions of any of the foregoing may be administered to a patient to treat a disease associated with the activation, proliferation, metabolism, and/or differentiation of T-cells.

IL-2Rβγc agonists, a compound comprising an IL-2Rβ and/or an IL-2Rγc ligand provided by the present disclosure and pharmaceutical compositions of any of the foregoing may be administered to a patient to treat an organ transplant.

IL-2Rβγc agonists, compounds comprising an IL-2Rβ and/or an IL-2Rγc ligand provided by the present disclosure and pharmaceutical compositions of any of the foregoing may be administered to a patient together with another compound for treating an inflammatory disease or an autoimmune disease in the subject. The at least one other therapeutic agent may be a different IL-2Rβγc agonist or compound comprising an IL-2Rβ and/or an IL-2Rγc ligand provided by the present disclosure. An IL-2Rβγc agonist or a compound comprising an IL-2Rβ and/or an IL-2Rγc ligand and the at least one other therapeutic agent may act additively or synergistically. The at least one additional therapeutic agent may be included in the same pharmaceutical composition or vehicle comprising the IL-2Rβγc agonist or a compound comprising an IL-2Rβ and/or an IL-2Rγc ligand or may be in a separate pharmaceutical composition or vehicle. Accordingly, methods provided by the present disclosure further include, in addition to administering an IL-2Rβγc agonist or a compound comprising an IL-2Rβ and/or an IL-2Rγc ligand, administering one or more therapeutic agents effective for treating an inflammatory disease or an autoimmune disease or a different disease, disorder or condition than an inflammatory disease or an autoimmune disease. Methods provided by the present disclosure include administration of an IL-2Rβγc agonist or a compound comprising an IL-2Rβ and/or an IL-2Rγc ligand and one or more other therapeutic agents provided that the combined administration does not inhibit the therapeutic efficacy of an IL-2Rβγc agonist or a compound comprising an IL-2Rβ and/or an IL-2Rγc ligand and/or does not produce adverse combination effects.

Pharmaceutical compositions comprising an IL-2Rβγc agonist may or a compound comprising an IL-2Rβ and/or an IL-2Rγc ligand be administered concurrently with the administration of another therapeutic agent, which may be part of the same pharmaceutical composition as, or in a different pharmaceutical composition than that comprising an IL-2Rβγc agonist or a compound comprising an IL-2Rβ and/or an IL-2Rγc ligand. An IL-2Rβγc agonist or a compound comprising an IL-2Rβ and/or an IL-2Rγc ligand may be administered prior or subsequent to administration of another therapeutic agent. In combination therapy, the combination therapy may comprise alternating between administering an IL-2Rβγc agonist or a compound comprising an IL-2Rβ and/or an IL-2Rγc ligand and a composition comprising another therapeutic agent, e.g., to minimize adverse drug effects associated with a particular drug. When an IL-2Rβγc agonist or a compound comprising an IL-2Rβ and/or an IL-2Rγc ligand is administered concurrently with another therapeutic agent that potentially may produce an adverse drug effect including, for example, toxicity, the other therapeutic agent may be administered at a dose that falls below the threshold at which the adverse drug reaction is elicited.

Pharmaceutical compositions comprising an IL-2Rβγc agonist or a compound comprising an IL-2Rβ and/or an IL-2Rγc ligand may be administered with one or more substances to enhance, modulate and/or control release, bioavailability, therapeutic efficacy, therapeutic potency, stability, and the like of a compound of an IL-2Rβγc agonist or a compound comprising an IL-2Rβ and/or an IL-2Rγc and/or an IL-2Rβ and/or an IL-2Rγc ligand. For example, to enhance the therapeutic efficacy of an IL-2Rβγc agonist or a compound comprising an IL-2Rβ and/or an IL-2Rγc ligand, an IL-2Rβγc agonist or a compound comprising an IL-2Rβ and/or an IL-2Rγc ligand or a pharmaceutical composition of any of the foregoing may be co-administered with one or more active agents to increase the absorption or diffusion of the IL-2Rβγc agonist or the compound comprising an IL-2Rβ and/or an IL-2Rβ and/or an IL-2Rγc ligand from the gastrointestinal tract to the systemic circulation, or to inhibit degradation of the IL-2Rβγc agonist or a compound comprising an IL-2Rβ and/or an IL-2Rγc ligand in the blood of a subject. A pharmaceutical composition comprising an IL-2Rβγc agonist or a compound comprising an IL-2Rβ and/or an IL-2Rγc ligand may be co-administered with an active agent having pharmacological effects that enhance the therapeutic efficacy of the IL-2Rβγc agonist or a compound comprising an IL-2Rβ and/or an IL-2Rγc ligand.

An IL-2Rβγc agonist, a compound comprising an IL-2Rβ and/or an IL-2Rγc ligand, or a pharmaceutical composition comprising any of the foregoing may be administered in conjunction with an agent known or believed to be effective in treating an inflammatory disease or an autoimmune disease in a patient.

An IL-2Rβγc agonist, a compound comprising an IL-2Rβ and/or an IL-2Rγc ligand, or a pharmaceutical composition comprising any of the foregoing may be administered in conjunction with an agent known or believed to interfere with proliferation. An IL-2Rβγc agonist, a compound comprising an IL-2Rβ and/or an IL-2Rγc ligand, or a pharmaceutical composition comprising any of the foregoing may be administered in conjunction with an agent known or believed to interfere with mitosis. An IL-2Rβγc agonist, a compound comprising an IL-2Rβ and/or an IL-2Rγc ligand, or a pharmaceutical composition comprising any of the foregoing may be administered in conjunction with an agent known or believed to interfere with DNA replication. An IL-2Rβγc agonist, a compound comprising an IL-2Rβ and/or an IL-2Rβ and/or an IL-2Rγc ligand, or a pharmaceutical composition comprising an IL-2Rβγc agonist may be administered in conjunction with an agent known or believed to interfere with DNA repair.

Compounds provided by the present disclosure can be useful in vitro as tools for understanding the biological role of IL-2, including the evaluation of the many factors thought to influence, and be influenced by, the production of IL-2 and the receptor binding process. The present compounds are also useful in the development of other compounds that bind to and activate the IL-2R, because the present compounds provide useful information concerning the relationship between structure and activity that should facilitate such development.

The compounds are also useful as competitive binders in assays to screen for new IL-2 receptor antagonists. In such assay embodiments, the compounds of the invention can be used without modification or can be modified in a variety of ways; for example, by labeling, such as covalently or non-covalently joining a moiety which directly or indirectly provides a detectable signal. In any of these assays, the materials thereto can be labeled either directly or indirectly. Possibilities for direct labeling include label groups such as: radiolabels such as $^{125}$I, enzymes such as peroxidase and alkaline phosphatase, and fluorescent labels capable of monitoring the change in fluorescence intensity, wavelength shift, or fluorescence polarization. Possibilities for indirect labeling include biotinylation of one constituent followed by binding to avidin coupled to one of the above label groups. The compounds may also include spacers or linkers in cases where the compounds are to be attached to a solid support.

Based on their ability to bind to the IL-2 receptor, the peptides provided by the present disclosure can be used as reagents for detecting IL-2 receptors, for example, on living cells, fixed cells, in biological fluids, in tissue homogenates, in purified, and natural biological materials. For example, by labelling such peptides, one can identify cells having IL-2 receptor on their surfaces. In addition, based on their ability to bind the IL-2 receptor, the peptides of the present invention can be used, for example, in in situ staining, FACS (fluorescence-activated cell sorting), Western Blotting, and ELISA. In addition, based on their ability to bind to the IL-2 receptor, peptides provided by the present disclosure can be used in receptor purification, or in purifying cells expressing IL-2 receptors on the cell surface (or inside permeabilized cells).

The compounds provided by the present disclosure can also be utilized as commercial reagents for various medical research and diagnostic uses. Such uses include, for example, (1) use as a calibration standard for quantitating the activities of candidate IL-2 agonists in a variety of functional assays; (2) use to maintain the proliferation and growth of IL-2-dependent cell lines; (3) use in structural analysis of the IL-2 receptor through co-crystallization; (4) use to investigate the mechanism of IL-2 signal transduction/receptor activation; and (5) other research and diagnostic applications wherein the IL-2 receptor is preferably activated or such activation is conveniently calibrated against a known quantity of an IL-2R agonist.

EXAMPLES

The following examples describe in detail methods used for determining the activity of peptides with the IL-2Rβ and IL-2Rγc subunits. It will be apparent to those skilled in the art that many modifications, both to materials and methods, may be practiced without departing from the scope of the disclosure. In the examples, the IL-2Rβ subunit refers to human IL-2Rβ (CD122 protein, Fc Tag) (27-239), Accession No. NP_000869.1 and was obtained from ACRObiosystems, Inc., product number ILB-H5253. The IL-2Rγc subunit" refers to human IL-2Rγc (CD132 protein, Fc Tag) (23-254), Accession No. AAH14972 and was obtained from ACRObiosystems, Inc., product number ILG-H5256.

Example 1

Phage Display pIII Library Panning Against Fc-Receptor Fusions on Magnetic Beads (Acid Elution) Library Panning Procedure Fifty (50) μL of Protein G Dynabead® (Invitrogen) was used for each library sample. After resuspending the stock bottle, the desired volume of beads was transferred to a sterile microfuge tube and applied to the magnet.

With the beads on a magnet, the supernatant was removed, and the beads were washed with 1 mL of PT buffer (1×PBS, 0.05% Tween®20).

The supernatant was removed and 1 mL of PBS+1% BSA+0.05% Tween®20 was added and mixed at 25° C. for at least 1 hour to block the beads.

A tube was applied to the magnet and the blocking solution was removed. For each library to be tested, 5 pg of a Fc-fused receptor of interest was added to each library sample for each round to bring the total volume to at least 400 μL. The samples were mixed at 25° C. for at least 1 h. The sample was applied to the magnet and the supernatant was removed.

Two-hundred 200 μL of PT buffer was added for each 50 μL of bead. The sample was thoroughly mixed and 200 μL aliquots were transferred into tubes that were pre-labeled for each library to be screened. An additional 500 μL of PT was added to each tube, the samples mixed, and then applied to the magnet. A total of 700 μL/tube was used for the wash.

One (1) mL aliquots of the libraries removed from the −20° C. freezer. One-hundred (1000 μL of 10×BT buffer (5% BSA, 0.5% Tween® 20 in 1×PBS) was added to each tube and vortexed. The library samples were transferred to pre-labeled tubes containing beads. The samples were then incubated at 4° C. on the rotator for at least 2 h. For the additional rounds of screening, 1 mL aliquots of the amplification from the previous round from each library was used. The beads were recovered with the magnet and the phage solution removed. The beads were washed 2× with 1 mL of PT buffer. Five-hundred (500) μL of PT buffer was added and the suspension was transferred to a clean tube. The beads were recovered on the magnet and the final wash removed.

Four-hundred seventy-five (475) μL of phage elution buffer was added to each well (0.2 M glycine-HCL, pH 2.2, 1 mg/mL BSA). The samples were incubated at 25° C. for 10 min on the rotator. The beads were recovered on the magnet and the eluted phage transferred to a clean tube.

Twenty-five (25) μL of neutralization buffer (2 M Tris Base) was added to the 475 μL of elution. The neutralized samples were maintained at 4° C. until the TG1 cells were ready amplification. The samples were stored at −20° C. after screening. Fifty (50) μL (about 10% of the total volume) was transferred to a 1.5 mL microfuge tube and store at −20° C. for use in deep sequencing.

Example 2

TG1 Culture and Library Amplification

A fresh TG1 (or OmniMax) culture was grown for about 1 to 1.5 h after adding the libraries to the beads. 2X-YT medium (10 mL) was placed into a 50 mL Falcon® tube. Two-hundred (200) μL of the TG1 overnight was added to the falcon tube. 2X-YT medium (600 μL) was placed in a cuvette for OD600 blank. The culture was grown at 250 rpm and 37° C., taking the first OD measurement after 60 min. The TG1 cells should be in log phase at the time of use with an OD600 of 0.5-0.7.

Eluted phage (400 μL to 450 μL) was added to 1 mL of the TG1 cells at an OD600 of 0.5-0.7 in a 50 mL Falcon® tube. The phage and TG1 cells were incubated at 37° C. for 30 min without shaking. About 50 to 100 μL was set aside for titering and characterization.

2YT medium (10.5 mL) was added to 12 μL of carbenicillin (carb) (100 mg/mL to make 100 pg/mL) and 24 μL of 50% glucose (to make 0.1% glucose) and the cells incubated while shaking at 37° C. at 250 rpm for 1 h.

M13K07 helper phage ($5 \times 10^{10}$ pfu, 24 μL of the stock, $2 \times 10^{12}$ pfu/mL) was then added and swirled to mix. The phage and cells were incubated at 37° C. for 30 min without shaking.

Kanamycin was diluted to 3 mg/mL and arabinose to 2.4% in 2YT medium/Carbenicillin-100/0 .1% glucose and 100 μL was added to each amplification. The mixture was incubated overnight at 37° C. and 250 rpm.

The culture was transferred to a 50 mL high-speed VWR centrifuge tube and centrifuged at 8,000 g for 15 min at 4° C. in a JSP-F50C centrifuge to pellet the cells.

The supernatant was transferred to a 50 mL high-speed VWR centrifuge tube and 0.2 volumes of PEG/NaCl (multiply the volume by 0.25 mL to 3 mL PEG/NaCl for 12 mL amplification) was added, mixed, and incubated on ice for 30 minutes.

The cells were then centrifuge at 10,500 g for 15 min at 4° C. in a JSP-F50C centrifuge. The supernatant was removed, and the phage pellet was resuspended in a total of 1 mL of PBT (1×PBS, 0.05% Tween® 20, 0.5% BSA) by pipetting.

The sample was transferred to an Eppendorf tube, vortexed, and centrifuged at 12,000 rpm for 30 sec. The supernatant was transferred to a clean Eppendorf tube and stored at 4° C. This amplified phage sample (250-500 μL) was used for the next round of screening.

Example 3

Preparation of Cultures from Individual Colonies

Ninety-six (96) wells of a deep well plate were filled with 1 mL of 2YT broth/Ampicillin-50/0 .1% glucose. Ninety-six (96) colonies were placed into the wells using P20 tips. The tips were left in the wells to mark the position. The tips were removed using a multi-channel pipette after the entire plate was completed. The plate was covered with a breathable film.

The inoculated plate(s) were incubated in a shaker at 37° C. until the cultures became turbid, typically within 4 h at 250 rpm.

The plate(s) was removed from the incubator and 50 μL of the culture from each well was removed to another deep well block designated as the "Archive Block" containing 1 mL of 2YT broth/Ampicillin-50/0.1% glucose. The plate(s) were covered with a breathable film and incubated overnight at 37° C. and 250 rpm.

After incubating overnight, M13K07 helper phage was added to $2 \times 10^{10}$ pfu/mL in 2YT broth/Ampicillin-50/0.1% glucose (make 6.0 mL per block). Fifty (50) μL of the diluted M13K07 was added to each culture well in the deep well block. The deep well block was covered with breathable film and incubated for 30 min at 37° C. and 250 rpm.

Kanamycin was diluted to 0.5 mg/ml and arabinose to 0.4% in 2YT broth/Ampicillin-50/0.1% glucose (make 6.0 ml per block) and 50 μL was added to each well. The plate was covered with a breathable film and incubated overnight at 37° C. and 250 rpm.

The "Archive Block" culture was removed from the incubator and 50 μL was transferred to a 96-well plate containing 50 μL of 50% glycerol. The plate was sealed with foil and stored at −80° C. The remaining culture in the block was covered with a foil seal and stored at 4° C.

The block was centrifuged and inoculated with M13K07 at 4000 rpm for 15 min. While avoiding the bacterial pellet, 850 μL of the phage supernatant was transferred to a fresh deep well plate, covered with a foil seal, and stored at 4° C.

Example 4

ELISA Protocol for Fc-Receptor Fusions

For each block to be assayed, a 1×96 well ELISA plate was coated with Fc-receptor fusion (1 μg/mL in PBS) at 50 μL/well. The wells were incubated at 25° C. for at least 1 h.

The Fc-receptor fusion was removed from each well. Three-hundred (300) μL of blocking buffer (1×PBS, 1% BSA) was added to each well of a receptor-coated plate. Plates were covered with film and left at 37° C. for 1 h or overnight at 4° C.

The plate was washed 4 times with PT (1×PBS, 0.05% Tween® 20) buffer.

Fifty (50) μL of PBT was added to each well. Fifty (50) μL of the phage supernatant from the block was added to each well and incubated at 4° C. for 1 h.

The plates were washed 4 times with cold PT.

To each well 100 μL of anti-M13-HRP antibody diluted 1:5000 in cold PBT was added. The wells were incubated for 1 h at 4° C.

The plates were then washed 4 times with cold PT.

Fifty (50) μL of TMB was then added to each well, and the wells were incubated for 1-10 min at 25° C. Fifty (50) μL of a "stop" solution was added and the plate read at 450 nm.

Example 5

Evaluation of Peptide Heterodimer Ability to Dimerize IL-2Rβγc and to Activate IL-2 Responsive Cells Following the identification of ligands that exhibit IL-2R and IL-2Rγc binding activity, compounds were identified that exhibit IL-2R agonist activity. This involved assessing the ability of the peptide to dimerize the IL-2Rβγc subunits and to signal in cell-based assays. Dimerization is a necessary, but not sufficient, step in the activation of receptor signaling. To assess agonist activity in cell-based assays, IL-2 responsive cell lines were tested for an indicator of IL-2 signaling, phosphorylation of STAT5. Compounds that exhibited IL-2Rβγc agonist activity in these cell lines were then be tested in primary human peripheral blood mononuclear cells (PBMC) for IL-2R agonism, and for the desired selectivity favoring activation of cell types expressing IL-2Rβγc subunits, but with low or no IL-2Rα (CD25) subunit expression.

Dimerization potential was assessed using a β-Gal complementation system in which a portion of the intracellular domains of each respective IL-2 receptor subunit was replaced with functionally complementary fragments of β-Gal, which regain catalytic activity when brought into sufficiently proximity. Cells expressing these constructs generate β-Gal activity, with an IC$_{50}$ of about 26 nM, when treated with IL-2 (see DiscoverX product specifications). All synthetic, potentially agonist, peptides were tested using this assay.

Candidate compounds were scored for induction of STAT5 phosphorylation in two cell lines: (1) NK-92 cells, a human cell line that expresses all three IL-2 receptor subunits, and which were responsive to IL-2Rβγc-biased variants as well as wild type IL-2; and (2) TF-1β cells, derived from the human erythroleukemia line TF-1, which naturally expresses only IL-2Rγc, and was engineered to be IL-2 responsive by transfection of IL-2Rβ. TF-1β was constructed and IL-2R subunit expression levels in both cell lines were verified by QPCR and FACS analysis.

Compounds were tested in both cell lines. Dose response assays were conducted to determine the IC$_{50}$ of the test compounds and to compare the test compounds with IL-2 as an indicator of IL-2Rβγc receptor bias.

The conferring of IL-2 responsiveness on TF-1 cells by transfection and expression of the IL-2Rβ subunit demonstrates that peptide agonist activity is dependent on the presence of the IL-2Rβ subunit. To determine that compound activity was not due to contamination with cytokines, or to an indirect action of the peptide inducing production of IL-2 or IL-15, neutralizing antibodies (R&D Systems) against IL-2 and IL-15 were included in the activity assay and shown to inhibit the activity of IL-2 and IL-15 but had no effect on the agonist activity of the test peptides.

Compounds exhibiting IL-2R agonist activity in the cell lines were tested on human primary immune cells, PBMCs, collected from individual donors (commercially available from Lonza), and in some cases on purified CD4+ cells (Lonza). A substantial fraction of PBMCs from normal donors were responsive to IL-2. To assess IL-2 agonist activity of the test compounds, cells were exposed to the compounds or IL-2 and scored for STAT5 phosphorylation by Western Blot analysis. Those compounds exhibiting STAT5 activation of PBMCs were subjected to a follow-on assay designed to assess subunit bias of the compounds compared to IL-2. This assay involved determining a dose response of the test compounds and IL-2 (1 to 1000 IU) over 30 min, scored by a FACS-based protocol allowing detection of both intracellular pSTAT5 as an indicator of IL-2R activation, and cell surface CD25, the IL-2Rα subunit. Cells expressing the three IL-2R subunits, IL-2Rαβγc, bind IL-2 with very high affinity (about 10 μM) and are therefore sensitive to low concentrations of IL-2; whereas cells expressing only IL-2Rβγc (about 1 nM affinity) require exposure to substantially higher IL-2 levels for activation. Because compounds provided by the present disclosure were selected for binding to the IL-2Rβ and IL-2Rγc subunits, but not to the IL-2Rα subunit, the potency of the compounds is expected to be uncorrelated with the level of expression of IL-2Rα on cells; and comparison of response profiles of cells treated with compounds provided by the present disclosure or treated with IL-2 should reveal any bias.

Example 6

Identified Peptides

Four stochastic libraries with each library containing approximately 10$^{10}$ independent recombinants, with each clone potentially displaying a unique peptide sequence have been screened for binding to individual human IL-2Rβ and IL-2Rγc subunits. In screening these four initial libraries against the Rβ subunit extracellular domain (ECD), 98 unique peptide clones were identified and confirmed as ligands of IL-2Rβ. These IL-2Rβ ligands can be grouped into at least two sequence families: family 1 and family 2.

In screening the four initial libraries against the γc subunit, 15 unique peptide sequences have been identified, which on first analysis of this limited number of clones, suggests that these may represent more than one distinct sequence family. At the current level of resolution these peptide sequences appear to have no sequence similarity to human IL-2. Most of the peptides so far recovered have been tested for binding to the IL-2Rβ and/or IL-2Rγc subunits, and all peptides tested were found to bind only to the subunit against which they were selected (by phage ELISA; capable of detecting affinities as weak as 10-50 μM).

An analysis of a sample of the identified peptides was performed to determine human and mouse receptor specificity. Initially selected on human IL-2 receptors, none of the IL-2Rβ ligands and IL-2Rγc ligands bound only to the corresponding human subunit.

Peptides having SEQ ID NO: 377 to SEQ ID NO: 399 have been synthesized and have been evaluated for IL-2Rβ and IL-2Rγc activity. Peptides having SEQ ID NO: 377 to SEQ ID NO: 385 include an IL-2Rβ ligand and peptides having SEQ ID NO: 386 to SEQ ID NO: 399 include an IL-2Rγc ligand.

```
                                         SEQ ID NO: 377
    G G F R C W E A P V G E I C E L G G NH2

SEQ ID NO: 378
    G G I E C E R A Q I G E V C Q I G G NH2

SEQ ID NO: 379
    G G M E C F L A A V G Q I C E L G G NH2

SEQ ID NO: 380
    G G Y D C R I A Q V G E L C D L G G NH2

SEQ ID NO: 381
    G G E I C N V G Q V W P D C L L G G NH2

SEQ ID NO: 382
    G G N M C L V G D Y W P S C Q I G G NH2

SEQ ID NO: 383
    G G Q I C D V G Q W W P D C Q V G G NH2

SEQ ID NO: 384
    C Y E V G D Y C Q S F L G G NH2

SEQ ID NO: 385
    R W G D V G D L L M P L G G NH2

SEQ ID NO: 386
    D L S D L C T F W L S Q G G NH2

SEQ ID NO: 387
    D L S D L S T F W L S Q G G NH2

SEQ ID NO: 388
    D C S M W E G V E L C W G G NH2

SEQ ID NO: 389
    G G L C F S E F L G E W V D C N G G NH2

SEQ ID NO: 390
    G G V C S F D E A W G E W I C E G G NH2

SEQ ID NO: 391
    G G K V C E M W G G V L L C W N G G R NH2

SEQ ID NO: 392
    G G R T C T E W E N V V L C W V G G NH2
```

-continued

SEQ ID NO: 393
G G I L C Q D W S G I E I C W S G G R NH$_2$

SEQ ID NO: 394
G G L I C Y T Y E G V E L C W Q G G R NH$_2$

SEQ ID NO: 395
G G V M C E R W Q G V E L C W L G G NH$_2$

SEQ ID NO: 396
G G M C W L E W G E W V G S C L G G R NH$_2$

SEQ ID NO: 397
G G C Y V V Y N Y Q E F R Y L C G G R NH$_2$

SEQ ID NO: 398
G G L Y C R D N D G T Q Y C E T G G NH$_2$

SEQ ID NO: 399
G G V V C Q D W E G V E L C W Q G G R NH$_2$

Example 7

Preparation of NK-92 Cells for Testing STAT5 Activation

NK-92 cells were seeded in a 24-well plate at 4×10$^5$ cells, in 1 mL starvation medium (SM), and incubated overnight at 37° C., 5% CO$_2$. The starvation medium contained RPMI 1640+20% FBS+2 mM L-glutamine+1 mM NaPyr+10 mM HEPES+0.1 mM BME (no rhIL-2 supplement).

Treatment mixtures were of 1 pg/mL Anti-hIL-2 neutralizing antibody (0.2 mg/mL stock) or goat IgG control (1 mg/mL stock) were prepared.

The treatment mixtures and the antibody mix were added to the cells for 30 min at 37° C., 5% CO$_2$. Each sample was then transferred to a 1.5 mL microfuge tube and spun down at 1,500 RPM for 5 minutes. The cells were washed in 1 mL PBS and centrifuged again.

A phosphatase and protease inhibitor cocktail (Thermo #78442) were added to mPER buffer at a 1:100 dilution. After the cells were pelleted, 50 μL of mPER buffer was added to each sample and pipetted repeatedly to homogenize.

The lysates were centrifuged at 14,000 RPM for 5 min at RT. The supernatants were transferred to clean tubes and stored frozen at −80° C.

The human IL-2 Antibody (goat IgG) was obtained from R&D Systems No. AF-202-NA; the normal goat IgG Control was obtained from R&D Systems No. AB-108-C; the Anti-STAT5 Antibody (rabbit), the Cell Signaling No. 94205S, the Anti-pSTAT5 Antibody (rabbit), the Cell Signaling No. 4322S, and the Goat anti-rabbit IgG-HRP was obtained from Jackson Immunoresearch No. 111-035-144.

The antibodies, treatment and working stock prep for each of the samples is provided in Table 1. Compounds A and B are IL-2Rβγc agonists provided by the present disclosure.

TABLE 1

STAT5 activation samples in NK-92 cells.

| No. | Antibody | Vol (μL) | Treatment | Vol (μL) | Working stock prep |
|---|---|---|---|---|---|
| 1 | Anti-hIL-2 IgG | 5 | A 10 μM | 100 | 100 μM (1:100 of 10 mM stock in SM) |
| 2 | Anti-hIL-2 IgG | 5 | A 1 μM | 10 | 100 μM (1:100 of 10 mM stock in SM) |
| 3 | Anti-hIL-2 IgG | 5 | A 0.1 μM | 1 | 100 μM (1:100 of 10 mM stock in SM) |
| 4 | Anti-hIL-2 IgG | 5 | B 10 μM | 100 | 100 μM (1:100 of 10 mM stock in SM) |
| 5 | Anti-hIL-2 IgG | 5 | B 1 μM | 10 | 100 μM (1:100 of 10 mM stock in SM) |
| 6 | Anti-hIL-2 IgG | 5 | B 0.1 μM | 1 | 100 μM (1:100 of 10 mM stock in SM) |
| 7 | Anti-hIL-2 IgG | 5 | rh-IL2 1 ng/mL | 10 | 100 ng/mL (1:1000 of 100 μg/mL stock in SM) |
| 8 | Anti-hIL-2 IgG | 5 | rhIL-2 0.1 ng/mL | 1 | 100 ng/mL (1:1000 of 100 μg/mL stock in SM) |
| 9 | Anti-hIL-2 IgG | 5 | rhIL-2 0.1 ng/mL + 1% DMSO | 1 | 100 ng/mL (1:1000 of 100 μg/mL stock in SM) + 10 μL DMSO |
| 10 | Anti-hIL-2 IgG | 5 | Starvation Medium (SM) | N/A | N/A |
| 11 | Goat IgG control | 1 | A 10 μM | 100 | 100 μM (1:100 of 10 mM stock in SM) |
| 12 | Goat IgG control | 1 | A 1 μM | 10 | 100 μM (1:100 of 10 mM stock in SM) |
| 13 | Goat IgG control | 1 | A 0.1 μM | 1 | 100 μM (1:100 of 10 mM stock in SM) |
| 14 | Goat IgG control | 1 | B 10 μM | 100 | 100 μM (1:100 of 10 mM stock in SM) |
| 15 | Goat IgG control | 1 | B 1 μM | 10 | 100 μM (1:100 of 10 mM stock in SM) |
| 16 | Goat IgG control | 1 | B 0.1 μM | 1 | 100 μM (1:100 of 10 mM stock in SM) |
| 17 | Goat IgG control | 1 | rh-IL2 1 ng/mL | 10 | 100 ng/mL (1:1000 of 100 μg/mL stock in SM) |
| 18 | Goat IgG control | 1 | rhIL-2 0.1 ng/mL | 1 | 100 ng/mL (1:1000 of 100 μg/mL stock in SM) |
| 19 | Goat IgG control | 1 | rhIL-2 0.1 ng/mL + 1% DMSO | 1 | 100 ng/mL (1:1000 of 100 μg/mL stock in SM) + 10 μL DMSO |
| 20 | Goat IgG control | 1 | Starvation Medium (SM) | N/A | N/A |

The samples were applied to a Western Blot and the result are shown in FIG. 1. In the Western Blot shown in FIG. 1, sample numbers 1-10 were probed with an anti-pSTAT5 antibody, sample numbers 1-10 were probed with an anti-STAT5 antibody, sample numbers 11-20 were probed with an anti-pSTAT5 antibody, and sample numbers 11-20 were probed with anti-STAT5 antibody. The treatment reagents included Anti-STAT5 Antibody (rabbit), Cell Signaling No. 94205S; Anti-pSTAT5 Antibody (rabbit), Cell Signaling No. 4322S; and Goat anti-rabbit IgG-HRP, Jackson Immunoresearch No. 111-035-144.

Compounds A and B induced (in a dose-responsive manner) STAT5 phosphorylation (pSTAT5). As shown in FIG. 1, the first 2 sets of three lanes include the two test compounds, and the next three lanes are the IL-2 positive controls. The final lanes (10) are 'starved" cells showing no background of pSTAT5 in the starting cell population. Compound A refers to a heterodimer of SEQ. ID. NO: 58 and SEQ ID. NO. 224. Compound B refers to a heterodimer of SEQ. ID. NO: 58 and SEQ ID. NO. 237.

In the top row of lanes, are the results of a control experiment which was designed to rule out the possibility that the test samples were contaminated with IL-2. To evaluate for contamination, the same manipulations as in the lanes described above were performed, except that an IL-2 neutralizing antibody was added to all samples. As is shown in lanes 7-9, the IL-2 controls were suppressed by this treatment, but the test compound lanes (1-6) show about the same results as the minus Ab lanes, demonstrating that the activity in the compound lanes is not due to contaminating IL-2. In addition, the lane 9 control has a high amount of added DMSO (1%), the diluent for the peptide compound. Addition of DMSO causes no STAT5 phosphorylation.

Figure 3:
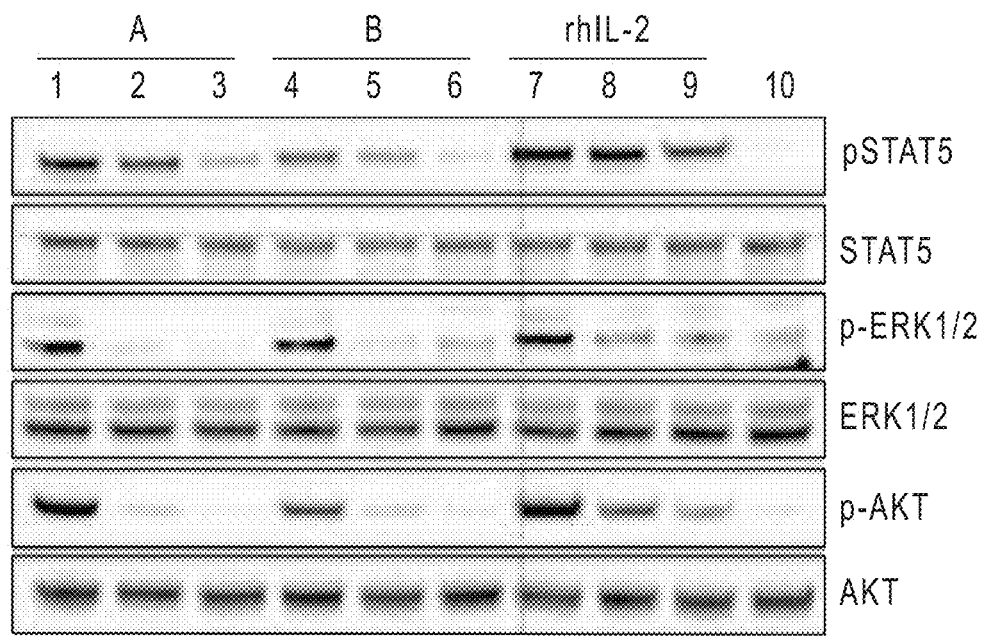
FIG. 3 shows activation of STAT5, ERK1/2 and AKT in NK-92 cells by IL-2Rβγc agonists according to the present disclosure by Western Blot analysis.
Figure 4A:
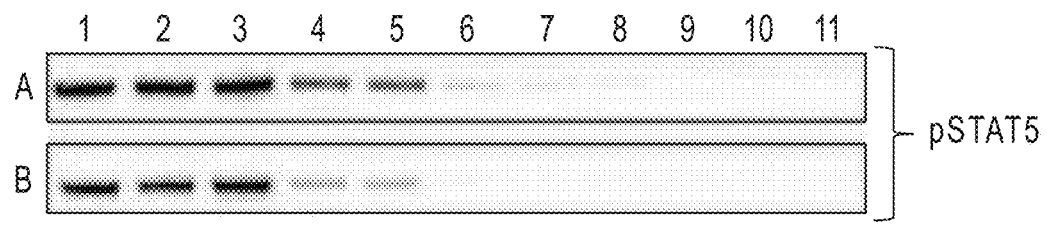
FIG. 4A shows STAT5 phosphorylation in NK-92 cells by IL-2Rβγc agonists according to the present disclosure by Western Blot analysis.
Figure 4B:
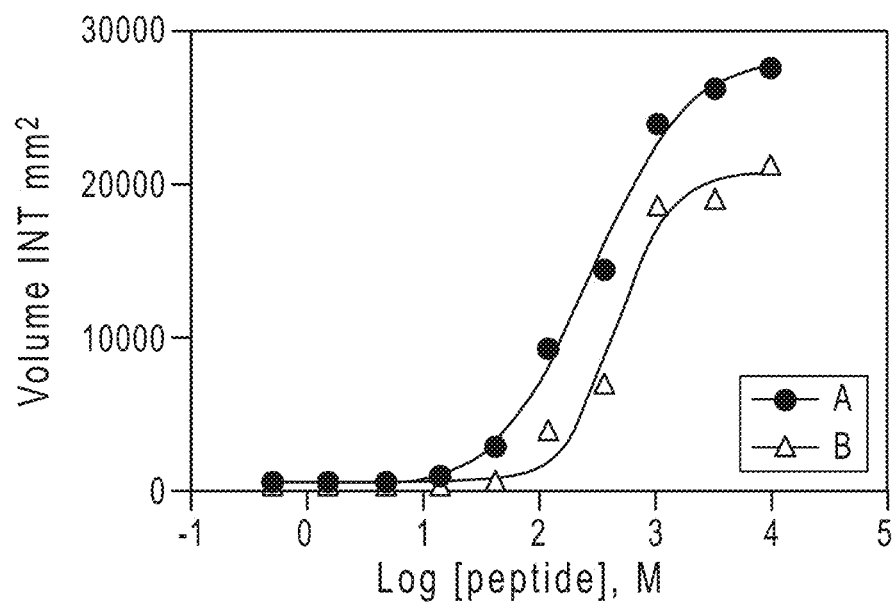
FIG. 4B shows pSTAT5 dose response curves in NK-92 cells by the IL-2Rβγc agonists evaluated in FIG. 4A.

The activation of STAT5, ERK1/2 and AKT in NK-92 cells by IL-2Rβγc agonists A and B provided by the present disclosure is shown in FIG. 3. IL-2Rβγc agonist A refers to a heterodimer of SEQ. ID. NO: 58 and SEQ ID. NO. 224. IL-2Rβγc agonist B refers to a heterodimer of SEQ. ID. NO: 58 and SEQ ID. NO. 237.

pSTAT5 dose response curves for L-2Rβγc agonists A and B in NK-92 cells are shown in FIGS. 4A and 4B.

Figure 5A:
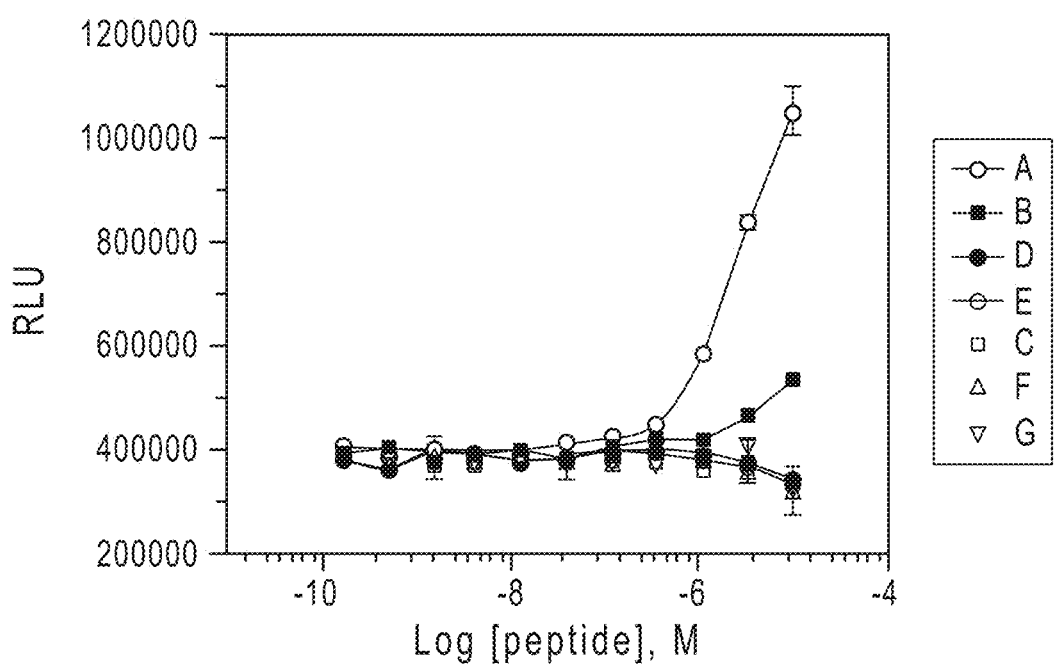
FIGS. 5A-5C show the results of an NK-92 proliferation assay using IL-2Rβγc agonists according to the present disclosure (FIG. 5A), by rhIL-2 (FIG. 5B), and as an overlay comparison (FIG. 5C).
Figure 5B:
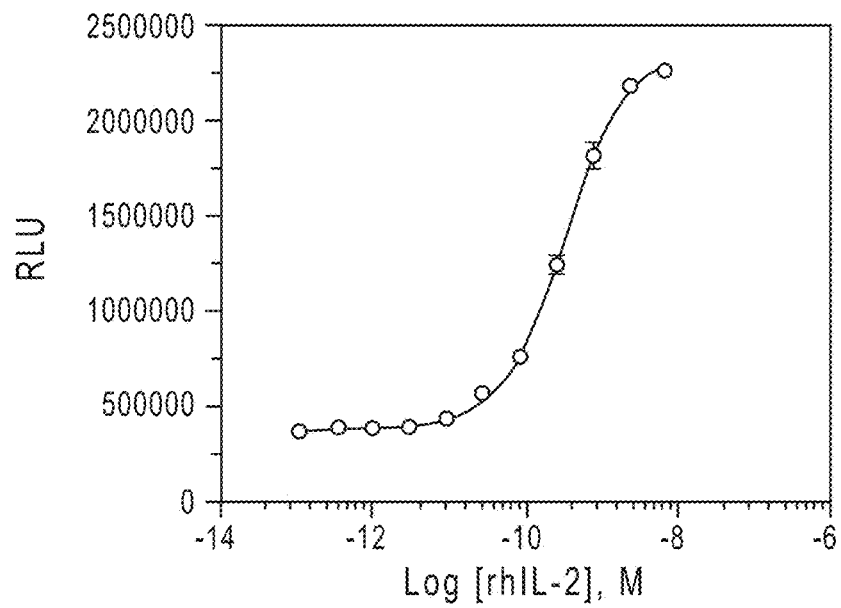
Figure 5C:
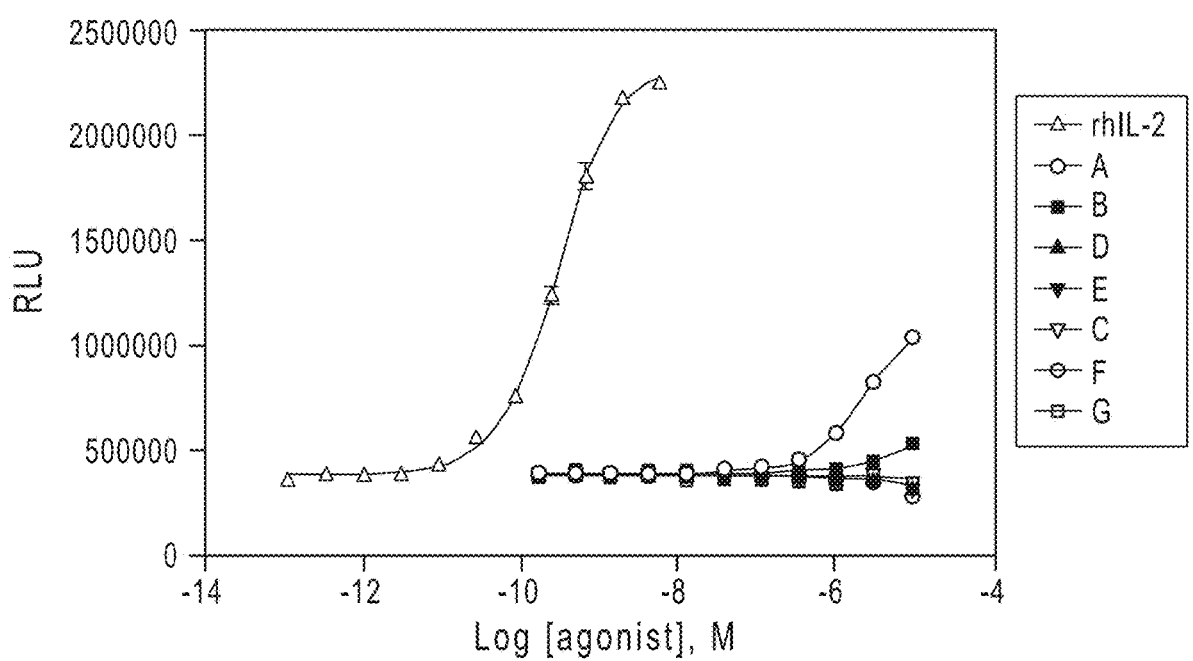

The results of a NK-92 cell proliferation assay using IL-2Rβγc agonists A and B, rhIL-2 and other peptides C-G is shown in FIGS. 5A-5C. Compounds A-G are defined as in Table 2:

TABLE 2

Composition of peptides A-G.

| Peptide | Composition |
|---|---|
| A | Heterodimer of E and F |
| B | Heterodimer of E and G |
| C | IL-27R/gp130 heterodimer |
| D | gp130 homodimer |
| E | IL-2Rβ ligand; SEQ ID. NO. 58 |
| F | IL-2Rγc ligand; SEQ ID. NO. 224 |
| G | IL-2Rγc ligand; SEQ ID. NO. 237 |

To perform the assay, NK-92 cells were plated in starvation medium at 20,000 cells/well in a 96-well plate. Treatment was added to each well in 3-fold serial dilutions with the peptides having maximum concentration of 10 μM and rhL-2 having a maximum concentration of 6.67 nM. The cells were then incubated at 37° C. for 48 h. CellTiter-Glo® reagent was added and the cells incubated for 10 min at 25° C. before luminescence reading. FIG. 5A shows the RLU for the peptide samples, FIG. 5B for the rhIL-2 sample, and FIG. 5C shows an overlay of FIGS. 5A and 5B.

Example 8

Preparation of TF-1β and TF-1 Cells for Testing STAT5 Activation

TF-1β and TF-1 parental cells were counted. The cells were collected and $2.5 \times 10^6$ cells pelleted at 200×g for 5 minutes. The pelleted cells were washed with 25 mL RPMI with no additives.

The TF-1β and TF-1 parental cells were seeded at $5 \times 10^5$ cells in a T25 flask, in 5 mL starvation medium (SM), and incubated overnight with the flask upright at 37° C. under 5% $CO_2$.

The TF-1β and TF-1 parental cells were counted, and the viability was determined. If necessary, the cells were diluted to $5 \times 10^5$ cells/mL in SM and then 1 mL of the suspension was added to 6 wells/cell line of a 24-well dish and incubate at 37° C. under 5% $CO_2$.

The treatments (see Example 7) were added to the cells for 30 min at 37° C. under 5% $CO_2$. The treated cells were transferred to a 1.5 mL microfuge tube and spun down at 1,500 RPM for 5 min. The cells were washed in 1 mL PBS, centrifuged again, and the supernatant aspirated. The treatment reagents included Anti-STAT5 Antibody (rabbit), Cell Signaling No. 94205S; Anti-pSTAT5 Antibody (rabbit), Cell Signaling No. 4322S; and Goat anti-rabbit IgG-HRP, Jackson Immunoresearch No. 111-035-144.

A phosphatase and protease inhibitor cocktail (Thermo No. 78442) were added to mPER buffer at 1:100 dilution. After the cells were pelleted, add 50 μL of mPER buffer was added to each sample and the mixture repeatedly pipetted to homogenize.

The lysates were centrifuged at 14,000 RPM for 5 min at 25° C. The supernatants were transferred to clean tubes and stored frozen at −80° C.

The antibodies, treatment and working stock prep for each of the samples is provided in Table 3. Compounds A and B are IL-2Rβγc agonists provided by the present disclosure.

TABLE 3

STAT5 activation samples in TF-1β and TF-1 cells.

| # | Cell line | Treatment | Vol (μL) | Working stock prep |
|---|---|---|---|---|
| 1 | TF-1β | A 10 μM | 100 | 100 μM (1:100 of 10 mM stock in SM) |
| 2 | TF-1β | B 10 μM | 100 | 100 μM (1:100 of 10 mM stock in SM) |
| 3 | TF-1β | C 10 μM | 100 | 100 μM (1:100 of 10 mM stock in SM) |
| 4 | TF-1β | rhIL-2 1 ng/mL | 10 | 100 ng/mL (1:1000 of 100 μg/mL stock in SM) |
| 5 | TF-1β | Starvation Medium[1] (SM) | 100 | N/A |
| 6 | TF-1 | A 10 μM | 100 | 100 μM (1:100 of 10 mM stock in SM) |
| 7 | TF-1 | B 10 μM | 100 | 100 μM (1:100 of 10 mM stock in SM) |
| 8 | TF-1 | C 10 μM | 100 | 100 μM (1:100 of 10 mM stock in SM) |
| 9 | TF-1 | rhIL-2 1 ng/mL | 10 | 100 ng/mL (1:1000 of 100 μg/mL stock in SM) |
| 10 | TF-1 | Starvation Medium[1] (SM) | 100 | N/A |

[1]Starvation medium: RPMI 1640, 2.5 g/L glucose (4.5 g/L total), 5% FBS, 2 mM L-glutamine, 1 mM NaPyr, and 10 mM HEPES (no GM-CSF supplement).

Figure 2A:
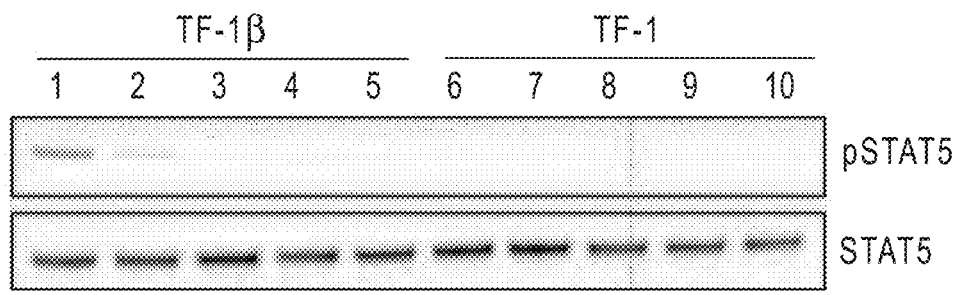
FIG. 2A shows STAT5 phosphorylation in TF-1 cells by IL-2Rβγc agonists according to the present disclosure by Western Blot analysis.

The samples were applied to a Western Blot and the results are shown in FIG. 2A.

Figure 2B:
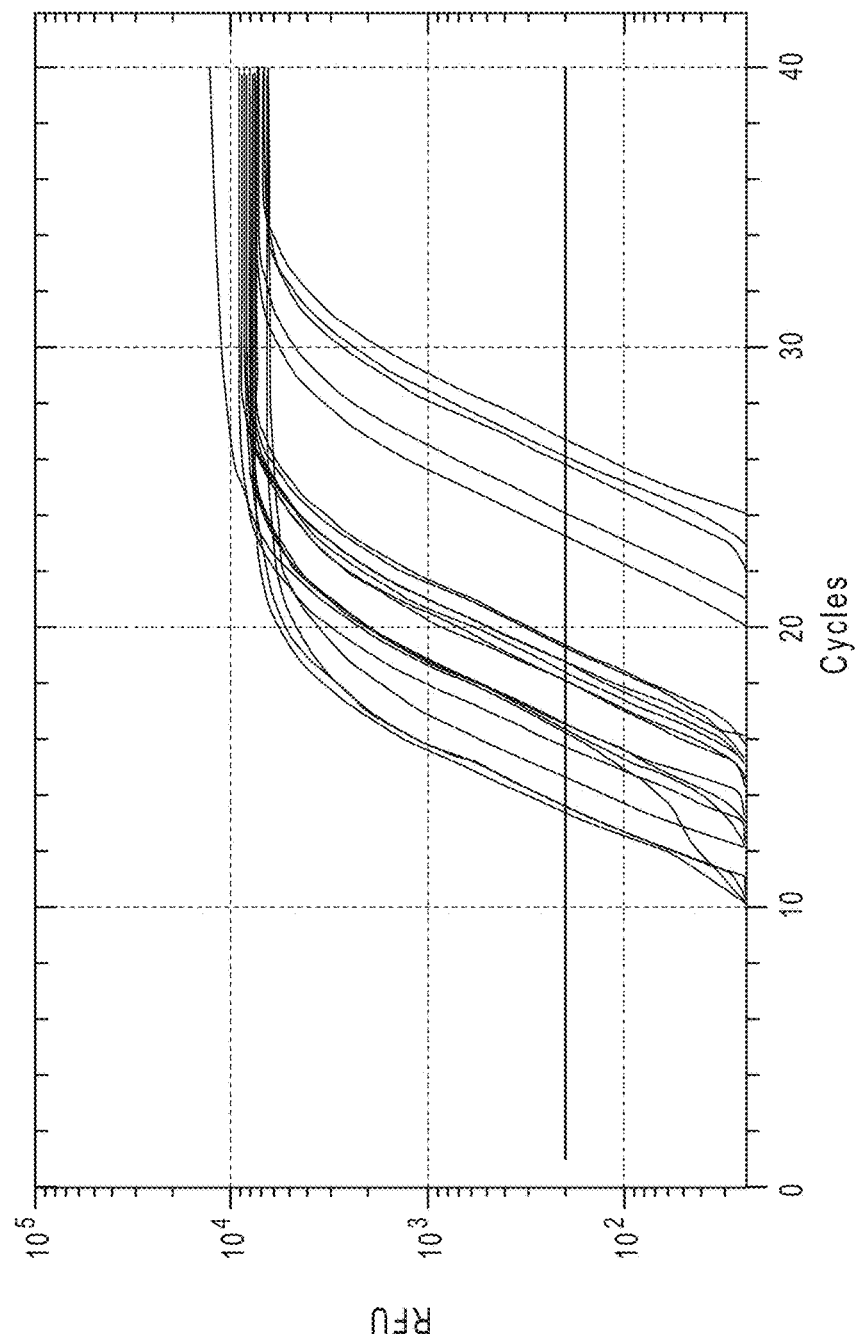
FIG. 2B shows RT-qPCR gene expression profiling comparing several transfected TF-1 cell populations.

RT-qPCR gene expression profiling comparing several TF-1β cells cell populations (G418 concentration varied) transfected with full length IL-2Rβ used in the peptide simulation pSTAT5 evaluation is shown in Table 4, and in FIG. 2B. In FIG. 2B, the relative expression level was normalized to GAPDH=1×10$^6$ copies (REL=1×10$^6$× 2$^{(Ctgraph-Cttarget)}$).

TABLE 4

RT-qPCR gene expression profiles of TF-1 and TF-1β cells transfected with IL-2Rβ.

| Target | TF-1 (ATCC) | TF-1 Control | TF-1β 2A | TF-1β 2B | TF-1β 3A | TF-1β 3B |
|---|---|---|---|---|---|---|
| IL-2Rα | 224 | 209 | 202 | 200 | 170 | 139 |
| IL-2Rβ | 1,329 | 1,177 | 44,029 | 39,122 | 36,941 | 28,685 |
| IL-2Rγ | 35,258 | 18,886 | 28,492 | 23,508 | 27,253 | 24,511 |

Example 9 pH Selective Screening

The IL-2Rβ subunit was screened with two peptide libraries to identify peptides exhibiting pH-dependent affinity for the receptor subunit. The screening approach utilized cycles of binding and elution under various acidic and neutral pH conditions.

Example 10

Phage Screening ELISA Protocol for pH-Dependence

Figure 6:
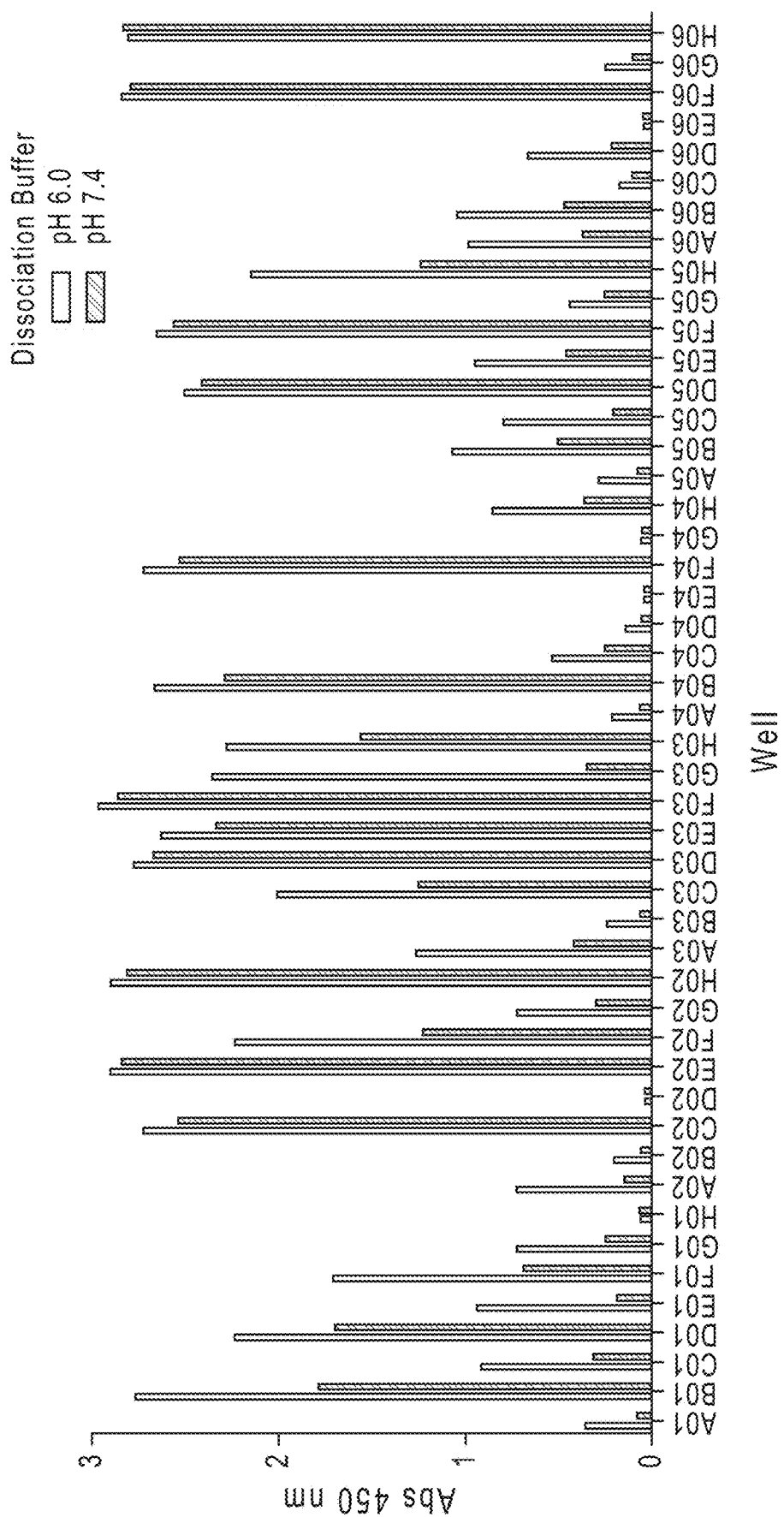
FIG. 6 shows the ELISA signal for various phage binding at pH 6.0 and pH 7.5.

The binding of phage to IL-2Rβ-GPI was determined using phage ELISA at the two target pH values and the percent change in binding at pH 7.4 relative to binding at pH 6.0 was calculated. Results for several peptides are shown in FIG. 6. Well G03 is an example of a phage displaying pH-dependent binding to IL-2Rβ.

Figure 7:
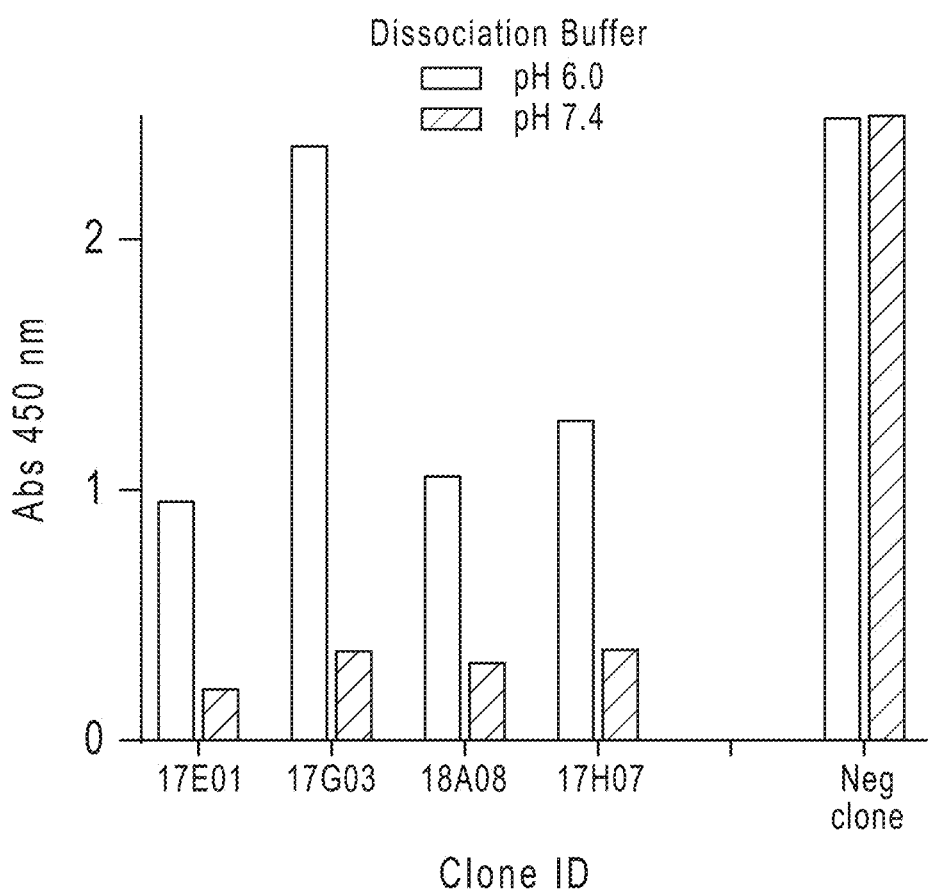
FIG. 7 show the ELISA signal for a phage exhibiting pH-dependent binding compared to a non-pH-dependent clone that exhibited a similar binding affinity at pH 6.0 and pH 7.5.

FIG. 7 shows an example of phage clones exhibiting pH-dependent binding (17E01, 17G03, 18A08, 17H07) compared to a non-pH dependent clone that exhibited similar binding affinity at both pH 6.0 and pH 7.4 (negative clone).

Example 11

ELISA Protocol for pH-Dependent Phage Titration

The ELISA screening protocol described in Example 10 was used with the following differences: (1) all 96-well ELISA plates contained IL-2Rβ-GPI target; and (2) the titration of the phage supernatants was prepared in 2 different PBT pH buffers; pH 6.0 and pH 7.4.

Phage titration was performed in a 96-well polypropylene plate using the following procedure. A 3-times dilution of phage in PBT pH 6 buffer and pH 7.4 buffer was prepared. One-hundred (100) μL of the diluted phage were transferred to the target-coated assay plate and incubated at 4° C. for 1 h.

The pH 6.0 wells were washed 3 times with cold PT pH 6.0 and the pH 7.4 wells were washed 2 times with cold PT pH 7.4.

The bound phage were detected with anti-M13-HRP.

Figure 8A:
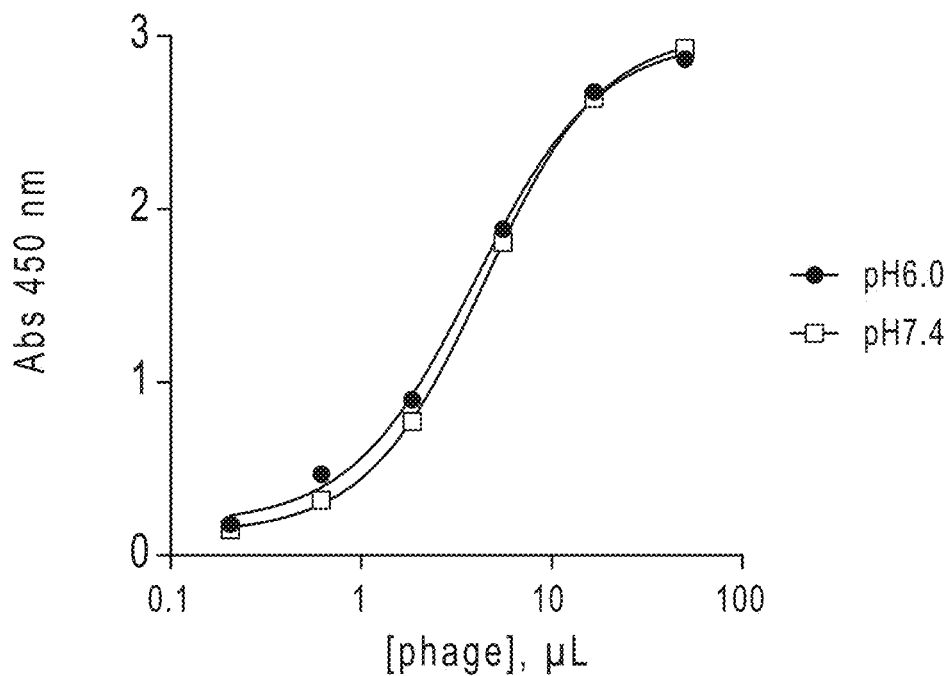
FIGS. 8A-8B show phage binding $IC_{50}$ curves for a non-pH-independent clone (FIG. 8A) and a pH-dependent phage (FIG. 8B) at pH 6.0 and pH 7.5.
Figure 8B:
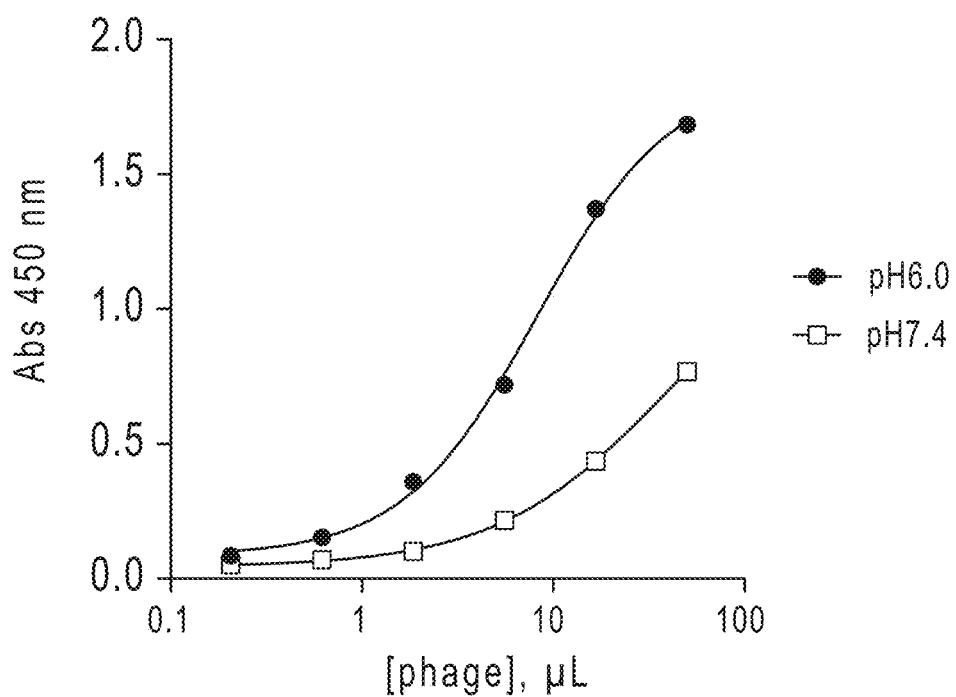

Binding curves for a pH-independent peptide that exhibited similar binding at pH 6.0 and pH 7.4 are shown in FIG. 8A and binding curves for a pH-dependent clone are show FIG. 8B.

Example 12

ELISA Protocol for Biotinylated Peptide pH-Dependent Binding (IL-2Rβ/Fc-Receptor Binding/Multivalent)

For each peptide to be assayed, 16 ELISA plate wells were coated with neutravidin (10 μg/mL in PBS pH7.2) at 50 μL/well. The coated wells were incubated at 25° C. for at least 1 h.

The neutravidin was removed from each well. Three-hundred (300) μL of blocking buffer (1×PBS pH 7.2, 1% BSA) was added to each well of the neutravidin-coated plates. All plates were covered and maintained at 25° C. for 1 h or overnight at 4° C.

The incubated plates were washed 4 times with PT (1×PBS pH 7.2, 0.05% Tween® 20) buffer.

The biotinylated peptides were diluted to 1 μM in PBT pH 7.2 buffer and 50 uL was added to the appropriate 16 wells (8 for each binding pH). The plates were incubated at 25° C. for at least 1 h.

Two (2) titrations of IL-2Rβ-Fc protein were prepared in a polypropylene plate starting at 2 pg/mL using PBT pH 6.0 and pH 7.4 and diluting 3-fold.

The plates were washed 4-times with PT (1×PBS pH 7.2, 0.05% Tween® 20) buffer.

Fifty (50) μL of the IL-2Rβ-Fc protein dilutions were added to the assay plates buffered at pH 6.0 or pH 7.4) and incubated for 1 h at 4° C.

The incubated plates were washed 3-times with the corresponding pH buffer PT (50 mM PBS pH 6.0, 0.05% Tween® 20 or 50 mM PBS pH 7.4, 0.05% Tween® 20).

Fifty (50) μL of goat anti-huIgG-HRP diluted 1:2500 in cold PBT pH 6.0 was added to each well. The plates were then Incubated for 1 h at 4° C.

The plates were then washed 4 times with cold PT pH 6.0.

Fifty (50) μL of TMB was then added to each well, and the wells were incubated for 1-10 min at 25° C. Fifty (50) μL of a "stop" solution was added to each well, and the plates were read at 450 nm.

Figure 9A:
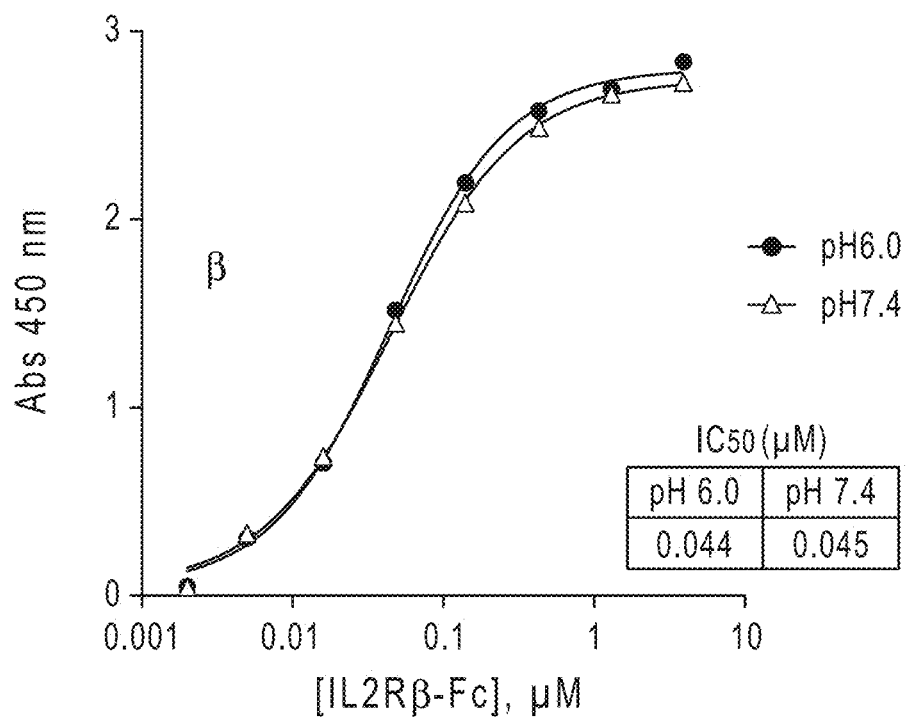
FIGS. 9A-9B shows $IC_{50}$ curves for peptide binding to IL-2Rβ-Fc for a non-pH-independent clone (FIG. 9A) and for a peptide from screening that exhibited pH-dependent binding (FIG. 9B).
Figure 9B:
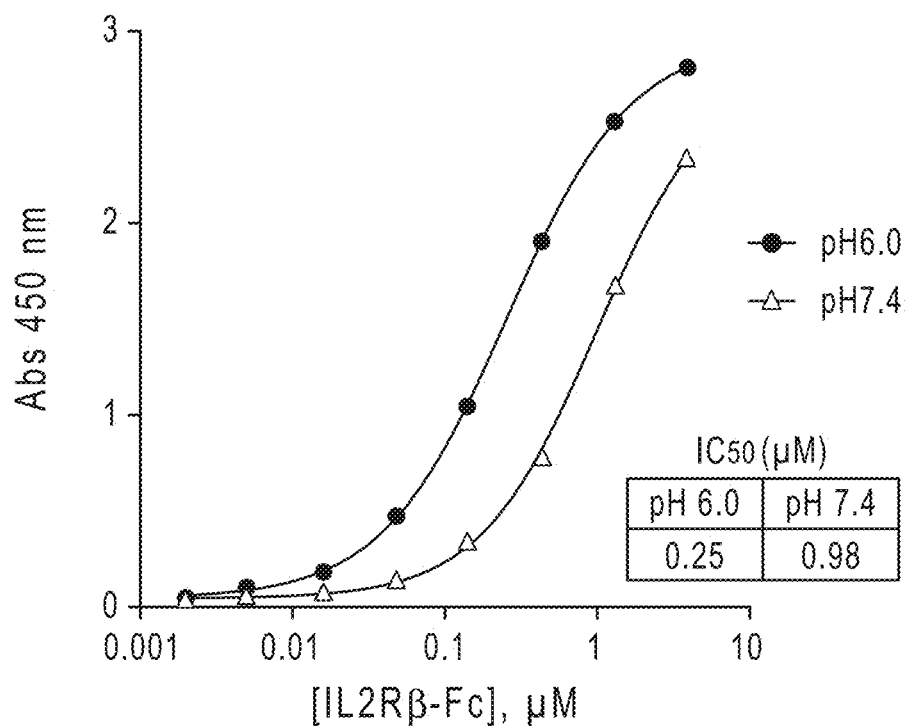

IL-2Rβ-Fc binding curves comparing a peptide exhibiting pH-independent binding at pH 6.0 and pH 7.4 and a pH-dependent peptide is shown in FIGS. 9A and 9B, respectively. Fc binding is a multivalent interaction and therefore an over estimate of monovalent binding.

Example 13

Specific Heterodimeric IL-2Rβγc Agonist

A heterodimer was constructed by linking the C-terminus of IL-2Rγc ligand having SEQ ID NO: 58 to the C-terminus of IL-2Rβ ligand having SEQ ID NO. 224 with a linker comprising 4 amino acids and having a length of about 34 Å using standard click chemistry methods.

Figure 10:
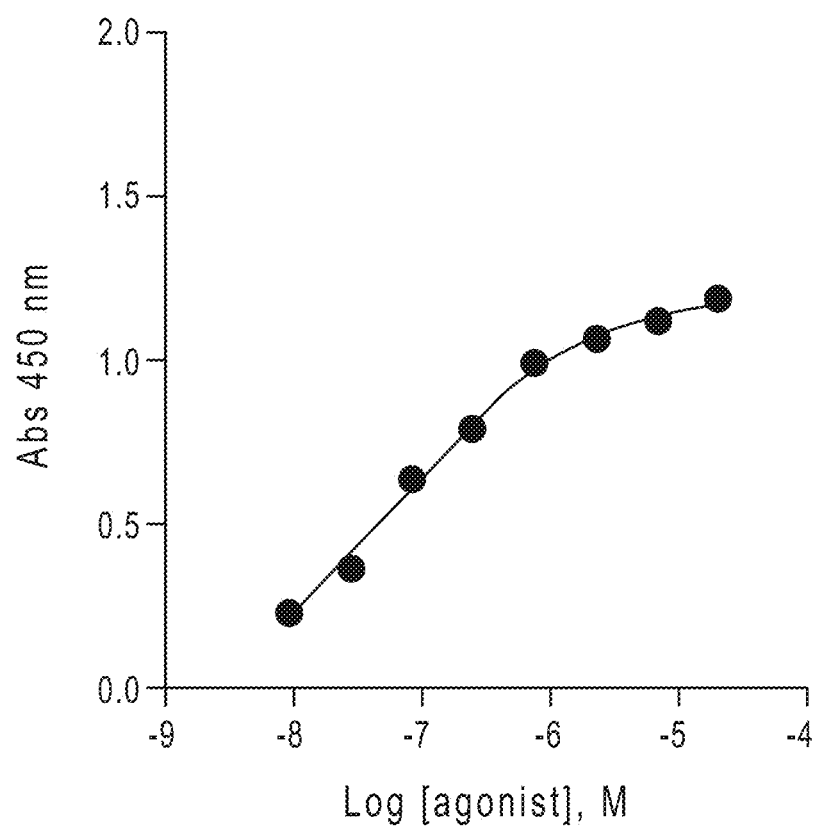
FIG. 10 shows STAT5 phosphorylation in NK-92 cells by a heterodimeric IL-2Rβγc agonist provided by the present disclosure.

The heterodimer was incubated with NK92 cells and the STAT5 phosphorylation measured as a function of concentration using the methods described in Examples 7 and 8. The results are presented in FIG. 10.

Example 14

Specific Heterodimer

A heterodimer was constructed by linking an IL-2Rβ ligand provided by the present disclosure to an IL-2Rγc ligand provided by the present disclosure with a linker comprising from 3 to 6 amino acids using standard click chemistry methods.

Example 15 pSTAT5 Activation in NK92 and TF1-β Cells

The expression levels of the IL-2R subunits in NK92 and TF-1β cells was determined using RT-qPCR gene expression profiling. The results are presented in Table 5.

The heterodimer of Example 14 was incubated with NK92 cells and TF-1β cells and the STAT5 phosphorylation measured as a function of concentration using the methods described in Examples 7 and 8. The results are presented in Table 5.

TABLE 5

IL-2Rαβγc subunit expression levels and STAT5 phosphorylation.

| | NK92 Cells | TF-1β Cells |
|---|---|---|
| IL-2Rα[1] | 111,181 | 194 |
| IL-2Rβ[1] | 303,457 | 227,488 |
| IL-2Rγc[1] | 609,073 | 43,169 |
| $EC_{50}$ (M) | $<10^{-8}$ | $<10^{-8}$ |

[1]Relative expression level: normalized to GAPDH = 1 × 10⁶ copies; REL = 1E⁶ × $2^{(Ct\ gapdh - Ct\ target)}$.

Example 15

Proliferation of NK-92 Cells

The proliferation of NK-92 cells was determined using the procedure described in Example 7.

The $EC_{50}$ for NK-92 cell proliferation for the heterodimer of Example 14 was $<10^{-8}$ M.

Example 16 pSTAT5 Activation in Human T-Cells pSTAT5 activation of resting CD8 T-cells, resting CD4 T-cells, and resting Treg (CD25hi CD127lo) cells by the heterodimer of Example 14 was determined using the method described in Example 17.

The incubation time was 30 min and pSTAT5 was measured by flow cytometry.

The heterodimer of Example 14 exhibited a similar potency in the different human T-cell populations tested. In comparison, IL-2 has a potency bias for Treg and CD4 T-cells.

Example 17

STAT5 Phospholylation in Resting and Activated Human CD-8 T-Cells

CD8 T-cells were isolated using the entire PBMC pool with an EasySep™ Human CD8+ T Cell Isolation Kit commercially available from STEMCELL™ Technologies Inc.

Treg cells were isolated using the entire PBMC pool with an EasySep™ Human CD4+CD127 lowCD25+ Regulatory T-Cell Isolation Kit commercially available from STEMCELL™ Technologies Inc.

For the resting group, the pSTAT5 assay was preformed and the lysates frozen at −180° C. until ELISA measurement.

For the activation group, cells were resuspended at 10⁶ cells/mL in CTS OpTmizer™ medium and prepared for CD28/CD3 activation.

For CD8 cells, a solution of 1 μg/μL aCD28 antibody was added to the cell suspension and plated at 2-3 mL/well in a 6-well plate pre-coated with 1 μg/mL a CD3 antibody.

For Treg cells, a solution of 10 μg/mL a CD28 antibody was added to the cell suspension and plated at 2-3 mL/well in a 6-well plate pre-coated with 10 μg/mL a CD3 antibody.

The cells were incubated for three (3) days.

Following incubation, the cells were resuspended in fresh CTS™ OpTmizer™ medium (ThermoFisher Scientific) at 5×10³ cells/mL and plated at 2-3 mL/well in a 6-well plate. The re-plated cells were incubated for two (2) days.

Control and test compounds were added at various concentrations to the cells and incubated at 37° C. for 30 minutes.

The cells were harvested counted, lysed and assayed for pSTAT5 activation.

For the resting CD8 T-cells, the $EC_{50}$ for STAT5 phosphorylation was $<10^{-8}$ M.

For activated CD8 T-cells, the $EC_{50}$ for STAT5 phosphorylation was $<10^{-8}$ M.

Example 18

STAT5 Phosphorylation in Resting and Activated Human Treg Cells

The same procedure as described in Example 17 was used to measure STAT5 phosphorylation.

For the resting Treg-cells, the $EC_{50}$ for STAT5 phosphorylation was $<10^{-8}$ M.

For activated Treg-cells, the $EC_{50}$ for STAT5 phosphorylation was $<10^{-8}$ M.

Example 19

IL-2Rα and IL-2Rβ Binding

The expression levels of the IL-2R subunits in TF-1 parental and TF-1β cells was determined using RT-qPCR gene expression profiling. The results are presented in Table 6.

TF-1 parental cells and TF-1β cells were incubated with the heterodimer of Example 14 and the STAT5 activation measured as a function of concentration. The results are presented in Table 6.

TABLE 6

IL-2Rαβγc subunit expression levels and STAT5 activation.

| | TF-1 Parental Cells | TF-1β Cells |
|---|---|---|
| IL-2Rα[1] | 209 | 139 |
| IL-2Rβ[1] | 1,177 | 28,685 |
| IL-2Rγc[1] | 18,886 | 24,511 |
| EC$_{50}$ (M) | ND[2] | <10$^{-8}$ |

[1]Relative expression level: normalized to GAPDH = 1 × 10$^6$ copies; REL = 1E$^6$ × 2$^{(Ct\ gapdh - Ct\ target)}$
[2]Not determined.

For the TF-1 parental cells, STAT5 was not activated.

For activated Treg-cells, the EC$_{50}$ for STAT5 phosphorylation was <10$^{-8}$ M.

These results demonstrate that the activity of the heterodimer of Example 14 requires the presence of the IL-2Rβ subunit. Also, in separate experiments it was determined that the activity of the heterodimer of Example 14 was not blocked by IL-2 and IL-15 antibodies.

Example 20

Competitive Binding

Competitive binding assays were performed to characterize the IL-2R binding sites for certain IL-2Rβ and to IL-2Rγc ligands.

Representative phage clones displaying peptides from IL-2Rβ ligand families were bound to the extracellular domain (ECD) of IL-2Rβ immobilized in microtiter wells. Phage binding was conducted in the presence and absence of synthetic test peptides to determine if phage peptides and test peptides competed for binding to the same sites on IL-2Rβ. Synthetic test peptides were selected to represent peptides from IL-2Rβ ligand families, as well positive and negative control peptides. IL-2Rβ ligand family sequences and the specific IL-2Rβ ligands evaluated are provided in Table 7.

TABLE 7

IL-2Rβ ligand families and ligands.

| IL-2Rβ Ligand Family | Family SEQ ID NOS: | Specific IL-2Rβ SEQ ID NO: | Peptide Sequence |
|---|---|---|---|
| 1 | 1-163 1052-1057 | 58 | Y D C R I A Q V G E L C D L |
| 2A | 164-182 1058-1060 | 169 | N M C L V G D Y W P S C Q I |
| 2A | 164-182 1058-1060 | 170 | Q I C D V G Q W W P D C Q V |
| 2B | 1-163 1052-1057 | 83 | C C Y Q A M V G D L C D F C |
| 2C | 1028-1043 1084 | 1084[1] | C G M A I G D L C M W T |
| 2C | 1028-1043 1084 | 1043 | R W G D V G D L L M P L |
| 4 | 1044 | 1044 | R S C Y Y K R P R L W C S E |
| IL-2Rγc Ligand | 211-233 914-920 1071-1074 1083 | 224 | D C S M W E G V E L C W |

[1]Modified peptide having SEQ ID NO: 1034 with amino acids -W-T-.

The IL-2Rβ ligands had a binding affinity (IC$_{50}$) to the IL-2Rβ subunit of less than 10 μM and a binding affinity (IC$_{50}$) to the IL-2Rγc subunit of greater than 100 μM.

Phage binding to the immobilized IL-2Rβ ECD was detected by staining with antibody against phage coat proteins (anti-phage Ab), staining with labeled secondary antibody against the anti-phage Ab, and scored by reading OD in the microtiter plate optical reader.

The ELISA signal for each phage binding in the presence and absence of the test peptides was compared to determine which synthetic peptides competed with which phage peptides for binding to the IL-2Rβ subunit. Those peptide pairs which exhibited competitive binding (i.e., cross inhibition) were considered to bind at the same functional site on the IL-2 receptor. The results are presented in Table 8.

TABLE 8

Binding of IL-2Rβ ligands to IL-2R.

| | Phage Clone Peptide SEQ ID NO: | | | | |
|---|---|---|---|---|---|
| Peptide SEQ ID NO: | IL-2β Family | 58<br>1 | 170<br>2A | 83<br>2B | 1034 or 1084<br>2C | 1044<br>4 |
| 58 | 1 | +[1] | + | + | + | − |
| 169 | 2A | + | + | + | + | − |
| 1042 | 2C | + | + | + | + | − |
| 1044 | 4 | −[2] | − | − | − | + |
| 224 | IL-2Rγc Ligand | − | − | − | − | − |

[1]Peptide competes with phage binding.
[2]Peptide does not compete with phage binding.

The IL-2Rβ ligands did not bind competitively to the binding site of the IL-2Rβ subunit with IL-2.

A similar study was performed to evaluate the binding of IL-2Rγc ligands. IL-2Rγc ligand family sequences and the specific IL-2Rγc ligands evaluated are provided in Table 9.

TABLE 9

IL-2Rγc ligand families and ligands.

| IL-2Rγc Ligand Family | Family SEQ ID NOS: | Specific IL-2Rγc SEQ ID NO: | Peptide Sequence |
|---|---|---|---|
| 1A | 194-210 904-913 1065-1070 | 198 | K V C E M W G G V L L C W N |
| 1A | 194-210 904-913 1065-1070 | 202 | R T C T E W E N V V L C W V |
| 1B | 211-233 914-920 1071-1074 | 224 | D C S M W E G V E L C W |
| 2 | 234-245 1075-1076 | 236 | M C W L E W G E W V G S C L |
| 3 | 246-254 921-922 1077-1082 | 1051[1] | D L S D L S T F W L S Q |

TABLE 9-continued

IL-2Rγc ligand families and ligands.

| IL-2Rγc Ligand Family | Family SEQ ID NOS: | Specific IL-2Rγc SEQ ID NO: | Peptide Sequence |
|---|---|---|---|
| 4 | 265-267 932-940 | 266 | C P S M L Q G P E R T W V C |
| 5 | 941-948 | 948 | S L L K C Y N A S T C A S V F |
| IL-2Rβ Ligand | 1-163 1052-1057 | 58 | Y D C R I A Q V G E L C D L |

[1]Modified ligand having amino acid SEQ ID NO: 248.

The IL-2Rγc ligands had a binding affinity ($IC_{50}$) to the IL-2Rγc subunit of less than 10 μM and a binding affinity ($IC_{50}$) to the IL-2β subunit of greater than 100 μM.

The results are presented in Table 10.

TABLE 10

Binding of IL-2Rγc ligands to IL-2R.

| Peptide SEQ ID NO: | IL-2Rγc Family | Phage Clone Peptide SEQ ID NO: | | | | | |
|---|---|---|---|---|---|---|---|
| | | 198 1A | 224 1B | 236 2 | 248 or 1051 3 | 266 4 | 948 5 |
| 202 | 1A | +[1] | + | + | + | + | − |
| 224 | 1B | + | + | + | + | + | − |
| 236 | 2 | + | + | + | + | + | − |
| 248 or 1051 | 3 | + | + | + | + | + | − |
| 948 | 5 | −[2] | − | − | − | − | + |
| 58 | IL-2Rβ Ligand | − | − | − | − | − | − |

[1]Peptide competes with phage binding.
[2]Peptide does not compete with phage binding.

ASPECTS OF THE INVENTION

The invention is further defined by the following aspects.

Aspect 1. An IL-2Rβ ligand, wherein the IL-2Rβ ligand exhibits a binding affinity to the human IL-2Rβ subunit of less than 100 μM.

Aspect 2. The IL-2Rβ ligand of aspect 1, wherein the IL-2Rβ ligand comprises from 5 to 30 amino acids.

Aspect 3. The IL-2Rβ ligand of any one of aspects 1 to 2, wherein the IL-2Rβ ligand exhibits a binding affinity to the human IL-2Rβ subunit from 1 μM to 100 μM.

Aspect 4. The IL-2Rβ ligand of any one of aspects 1 to 2, wherein the IL-2Rβ ligand exhibits a binding affinity to the human IL-2Rβ subunit from 0.1 μM to 50 μM.

Aspect 5. The IL-2Rβ ligand of any one of aspects 1 to 2, wherein the IL-2Rβ ligand exhibits a binding affinity to the human IL-2Rβ subunit of less than 100 μM.

Aspect 6. The IL-2Rβ ligand of any one of aspects 1 to 5, wherein the IL-2Rβ ligand exhibits a binding affinity to a mammalian IL-2Rβ subunit of less than 100 μM.

Aspect 7. The IL-2Rβ ligand of any one of aspects 1 to 6, wherein the IL-2Rβ ligand exhibits a binding affinity to each of the human IL-2Rβ subunit and to the human IL-2Rγc subunit of less than 100 μM.

Aspect 8. The IL-2Rβ ligand of any one of aspects 1 to 7, wherein the IL-2Rβ ligand exhibits a binding affinity to the human IL-2Rα (CD25) subunit of greater than 100 μM.

Aspect 9. The IL-2Rβ ligand of any one of aspects 1 to 8, wherein the IL-2Rβ ligand exhibits a binding affinity to the human IL-2Rβ subunit that is at least 10 times greater than the binding affinity of the IL-2Rβ ligand to the human IL-2Rα subunit.

Aspect 10. The IL-2Rβ ligand of any one of aspects 1 to 9, wherein the IL-2Rβ ligand comprises the amino acid sequence of Formula (1) (SEQ ID NO: 1), the amino acid sequence of Formula (1a) (SEQ ID NO: 2), or the amino acid sequence of Formula (1b) (SEQ ID NO: 3):

$$-X^3-X^4-X^5-X^6-X^7-X^8-X^9-X^{10}- \qquad (1)$$

$$-X^2-C-X^3-X^4-X^5-X^6-X^7-X^8-X^9-X^{10}-C-X^{11}- \qquad (1a)$$

$$-X^1-X^2-C-X^3-X^4-X^5-X^6-X^7-X^8-X^9-X^{10}-C-X^{11}-X^{12}- \qquad (1b)$$

wherein, $X^1$ is selected from A, D, E, F, G, I, K, L, M, N, P, Q, S, T, V, W, and Y; $X^2$ is selected from A, C, D, E, F, G, H, K, L, N, P, R, S, T, W, and Y; $X^3$ is selected from A, D, E, F, G, H, M, N, Q, R, S, T, W, and Y; $X^4$ is selected from A, D, E, F, G, I, K, L, M, N, Q, R, S, T, V, and Y; $X^5$ is selected from A, G, I, Q, S, T, V, and W; $X^6$ is selected from A, D, E, G, H, K, L, M, N, P, Q, R, S, T, and V; $X^7$ is selected from F, I, K, L, Q, and V; $X^8$ is selected from D, F, G, H, M, N, W, and Y; $X^9$ is selected from A, D, E, M, P, Q, S, T, V, and W; $X^{10}$ is selected from D, F, I, L, M, S, T, V, and Y; $X^{11}$ is selected from D, E, F, H, I, L, M, Q, S, T, V, W, and Y; and $X^{12}$ is selected from F, I, L, M, N, S, V, W, and Y.

Aspect 11. The IL-2Rβ ligand of aspect 10, wherein $X^1$ is selected from F, I, L, M, and V.

Aspect 12. The IL-2Rβ ligand of any one of aspects 1 to 11, wherein $X^2$ is selected from D, E, F, G, H, L, N, P, R, S, T, W, and Y.

Aspect 13. The IL-2Rβ ligand of any one of aspects 1 to 12, wherein $X^5$ is A.

Aspect 14. The IL-2Rβ ligand of any one of aspects 1 to 13, wherein $X^6$ is selected from D, E, and Q.

Aspect 15. The IL-2Rβ ligand of any one of aspects 1 to 14, wherein $X^7$ is selected from F, I, L, and V.

Aspect 16. The IL-2Rβ ligand of any one of aspects 1 to 15, wherein $X^8$ is G.

Aspect 17. The IL-2Rβ ligand of any one of aspects 1 to 16, wherein $X^9$ is selected from D, E, and Q.

Aspect 18. The IL-2Rβ ligand of any one of aspects 1 to 17, wherein $X^{10}$ is selected from F, I, L, M, V, and Y.

Aspect 19. The IL-2Rβ ligand of any one of aspects 1 to 18, wherein $X^{11}$ is selected from D and E.

Aspect 20. The IL-2Rβ ligand of any one of aspects 1 to 19, wherein $X^{12}$ is selected from F, I, L, M, and V.

Aspect 21. The IL-2Rβ ligand of aspect 10, wherein, $X^1$ is selected from F, I, L, M, and V; $X^2$ is selected from D, E, F, G, H, L, N, P, R, S, T, W, and Y; $X^3$ is selected from A, D, E, F, G, H, M, N, Q, R, S, T, W, and Y; $X^4$ is selected from A, D, E, F, G, I, K, L, M, N, Q, R, S, T, V, and Y; $X^5$ is A; $X^6$ is selected from D, E, and Q; $X^7$ is selected from F, I, L, and V; $X^8$ is G; $X^9$ is selected from D, E, and Q; $X^{10}$ is selected from F, I, L, M, V, and Y; $X^{11}$ is selected from D and E; and $X^{12}$ is selected from F, I, L, M, and V.

Aspect 22. The IL-2Rβ ligand of any one of aspects 1 to 9, wherein the IL-2Rβ ligand comprises the amino acid sequence of Formula (1) (SEQ ID NO: 1052), the amino acid sequence of Formula (1a) (SEQ ID NO: 1053), or the amino acid sequence of Formula (1b) (SEQ ID NO: 1054):

$$-X^3-X^4-X^5-X^6-X^7-X^8-X^9-X^{10}- \qquad (1)$$

$$-X^2-C-X^3-X^4-X^5-X^6-X^7-X^8-X^9-X^{10}-C-X^{11}- \qquad (1a)$$

$$-X^1-X^2-C-X^3-X^4-X^5-X^6-X^7-X^8-X^9-X^{10}-C-X^{11}-X^{12}- \qquad (1b)$$

wherein, $X^1$ is selected from an amino acid $X^2$ is selected from an amino acid; $X^3$ is selected from an amino acid; $X^5$ is selected from an amino acid; $X^6$ is selected from an amino acid comprising a small hydrophobic side chain; $X^6$ is selected from an amino acid; $X^7$ is selected from an amino acid comprising a large hydrophobic side chain; $X^8$ is selected from an amino acid comprising a small hydrophobic side chain; $X^9$ is selected from an amino acid comprising a polar-neutral or an acidic side chain; $X^{10}$ is selected from an amino acid comprising a large hydrophobic side chain; $X^{11}$ is selected from an amino acid; and $X^{12}$ is selected from an amino acid comprising a large hydrophobic side chain.

Aspect 23. The IL-2Rβ ligand of aspect 22, wherein, $X^1$ is selected from an amino acid comprising a large hydrophobic side chain; $X^2$ is selected from an amino acid; $X^3$ is selected from an amino acid; $X^4$ is selected from an amino acid; $X^5$ is selected from an amino acid comprising a small hydrophobic side chain; $X^6$ is selected from an amino acid comprising a polar-neutral or an acidic side chain; $X^7$ is selected from an amino acid comprising a large hydrophobic side chain; $X^8$ is selected from an amino acid comprising a small hydrophobic side chain; $X^9$ is selected from an amino acid comprising a polar-neutral or an acidic side chain; $X^{10}$ is selected from an amino acid comprising a large hydrophobic side chain; $X^{11}$ is selected from an amino acid comprising a polar-neutral or an acidic side chain; and $X^{12}$ is selected from an amino acid comprising a large hydrophobic side chain.

Aspect 24. The IL-2Rβ ligand of aspect 22, wherein, $X^1$ is selected from I, L, M, V, F, W, and Y; $X^2$ is selected from an amino acid; $X^3$ is selected from an amino acid; $X^4$ is selected from an amino acid; $X^5$ is selected from A, G, P, S, and T; $X^6$ is selected from H, N, Q, S, T, Y, D, and E; $X^7$ is selected from I, L, M, V, F, W, and Y; $X^8$ is selected from A, G, P, S, and T; $X^9$ is selected from H, N, Q, S, T, Y, D, and E; $X^{10}$ is selected from I, L, M, V, F, W, and Y; $X^{11}$ is selected from H, N, Q, S, T, Y, D, and E; and $X^{12}$ is selected from I, L, M, V, F, W, and Y.

Aspect 25. The IL-2Rβ ligand of aspect 22, wherein $X^1$ is selected from I, L, M, V, F, W, and Y; $X^2$ is selected from an amino acid; $X^3$ is selected from an amino acid; $X^4$ is selected from an amino acid; $X^5$ is A; $X^6$ is selected from H, N, Q, S, T, Y, D, and E; $X^7$ is selected from I, L, M, V, F, W, and Y; $X^8$ is G; $X^9$ is selected from H, N, Q, S, T, Y, D, and E; $X^{10}$ is selected from I, L, M, V, F, W, and Y; $X^{11}$ is selected from H, N, Q, S, T, Y, D, and E; and $X^{12}$ is selected from I, L, M, V, F, W, and Y.

Aspect 26. The IL-2Rβ ligand of aspect 25, wherein $X^1$ is selected from I, L, M, and V.

Aspect 27. The IL-2Rβ ligand of any one of aspects 25 to 26, wherein $X^2$ is selected from D and E.

Aspect 28. The IL-2Rβ ligand of any one of aspects 25 to 27, wherein $X^6$ is selected from Q, E, and D.

Aspect 29. The IL-2Rβ ligand of any one of aspects 25 to 28, wherein $X^7$ is selected from V, L, and I.

Aspect 30. The IL-2Rβ ligand of any one of aspects 25 to 29, wherein $X^9$ is selected from E, D, and Q.

Aspect 31. The IL-2Rβ ligand of any one of aspects 25 to 30, wherein $X^{10}$ is selected from L, V, I, and Y.

Aspect 32. The IL-2Rβ ligand of any one of aspects 25 to 31, wherein $X^{11}$ is selected from D and E.

Aspect 33. The IL-2Rβ ligand of any one of aspects 25 to 32, wherein $X^{12}$ is selected from L, I, and F.

Aspect 34. The IL-2Rβ ligand of aspect 25, wherein, $X^1$ is selected from L, I, F, and V; $X^2$ is selected from D and E; $X^6$ is selected from Q, E, and D; $X^7$ is selected from V, L, and I; $X^9$ is selected from E, D, and Q; $X^{10}$ is selected from L, V, I, and Y; $X^{11}$ is selected from D and E; and $X^{12}$ is selected from L, I, and F.

Aspect 35. The IL-2Rβ ligand of aspect 25, wherein, $X^1$ is selected from F, I, M, and Y; $X^2$ is selected from E, D, and R; $X^3$ is selected from and amino acid; $X^4$ is selected from an amino acid; $X^5$ is A; $X^6$ is selected from A, P, and Q; $X^7$ is selected from I and V; $X^8$ is G; $X^9$ is selected from E and Q; $X^{10}$ is selected from I, L, and V; $X^{11}$ is selected from E, D, and Q; and $X^{12}$ is selected from I and L.

Aspect 36. The IL-2Rβ ligand of any one of aspects 1 to 9, wherein the IL-2Rβ ligand comprises an amino acid sequence selected from any one of SEQ ID NO: 4 to SEQ ID NO: 163:

Aspect 37. The IL-2Rβ ligand of aspect 36, wherein the IL-2Rβ ligand comprises an amino acid sequence selected from any one of SEQ ID NO: 4 to SEQ ID NO: 163, wherein the amino acid sequence is terminated with amino acids -G-G on the N-terminus, on the C-terminus, or on both the N- and C-termini.

Aspect 38. The IL-2Rβ ligand of any one of aspects 36 to 37, wherein the IL-2Rβ ligand comprises an amino acid sequence selected from any one of SEQ ID NO: 4 to SEQ ID NO: 163, wherein each amino acid independently comprises one or more of the following conservative substitutions: amino acids having a small hydrophobic side chain comprising alanine (A), glycine (G), proline (P), serine (S), and threonine (T); amino acids having a hydroxyl-containing side chain comprising serine (S) or threonine (T); amino acids having an acidic side chain comprising aspartate (D) and glutamate (E); amino acids having a polar-neutral side chain comprising histidine (H), asparagine (N), glutamine (Q), serine (S), threonine (T), and tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W).

Aspect 39. The IL-2Rβ ligand of any one of aspects 1 to 9, wherein the IL-2Rβ ligand comprises the amino acid sequence of Formula (2) (SEQ ID NO: 164), the amino acid sequence of Formula (2a) (SEQ ID NO: 165), or the amino acid sequence of Formula (2b) (SEQ ID NO: 166):

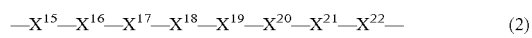

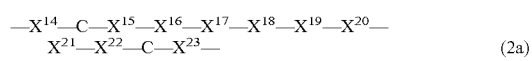

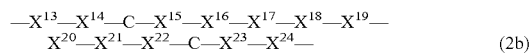

wherein, $X^{13}$ is selected from A, D, E, G, N, Q, R, and V; $X^{14}$ is selected from E, F, I, L, M, and Q; $X^{15}$ is selected from D, G, L, and N; $X^{16}$ is selected from L, P, V, and Y; $X^{17}$ is selected from F, G, and M; $X^{18}$ is selected from A, D, N, and Q; $X^{19}$ is selected from F, I, L, S, V, W, and Y; $X^{20}$ is selected from D and W; $X^{21}$ is selected from P and Y; $X^{22}$ is selected from A, D, Q, and S; $X^{23}$ is selected from I, L, Q, W, and Y; and $X^{24}$ is selected from E, F, I, L, T, V, and W.

Aspect 40. The IL-2Rβ ligand of aspect 39, wherein $X^{16}$ is V.

Aspect 41. The IL-2Rβ ligand of any one of aspects 39 to 40, wherein $X^{17}$ is G.

Aspect 42. The IL-2Rβ ligand of any one of aspects 39 to 41, wherein $X^{20}$ is W.

Aspect 43. The IL-2Rβ ligand of any one of aspects 39 to 42, wherein $X^{21}$ is P.

Aspect 44. The IL-2Rβ ligand of aspect 39, wherein, $X^{13}$ is selected from E, N, and Q; $X^{14}$ is selected from I and M; $X^{15}$ is selected from D, L, and N; $X^{16}$ is V; $X^{17}$ is G; $X^{18}$ is selected from D and Q; $X^{19}$ is selected from V, W, and Y; $X^{20}$ is W; $X^{21}$ is P; $X^{22}$ is selected from D and S; $X^{23}$ is selected from L and Q; and $X^{24}$ is selected from I, L, and V.

Aspect 45. The IL-2Rβ ligand of any one of aspects 1 to 9, wherein the IL-2Rβ ligand comprises an amino acid sequence selected from any one of SEQ ID NO: 167 to SEQ ID NO: 182.

Aspect 46. The IL-2Rβ ligand of aspect 45, wherein the IL-2Rβ ligand comprises an amino acid sequence selected from any one of SEQ ID NO: 167 to SEQ ID NO: 182, wherein the amino acid sequence is terminated with amino acids -G-G on the N-terminus, on the C-terminus, or on both the N- and C-termini.

Aspect 47. The IL-2Rβ ligand of any one of aspects 45 to 46, wherein the IL-2Rβ ligand comprises an amino acid sequence selected from any one of SEQ ID NO: 167 to SEQ ID NO: 182, wherein each amino acid independently comprises one or more of the following conservative substitutions: amino acids having a small hydrophobic side chain comprising alanine (A), glycine (G), proline (P), serine (S) and threonine (T); amino acids having a hydroxyl-containing side chain comprising serine (S) or threonine (T); amino acids having an acidic side chain comprising aspartate (D) and glutamate (E); amino acids having a polar-neutral side chain comprising histidine (H), asparagine (N), glutamine (Q), serine (S), threonine (T), and tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W).

Aspect 48. The IL-2Rβ ligand of any one of aspects 1 to 9, wherein the IL-2Rβ ligand comprises the amino acid sequence of Formula (2) (SEQ ID NO: 1058), the amino acid sequence of Formula (2a) (SEQ ID NO: 1059), or the amino acid sequence of Formula (2b) (SEQ ID NO: 1060):

$$-X^{15}-X^{16}-X^{17}-X^{18}-X^{19}-X^{20}-X^{21}-X^{22}- \quad (2)$$

$$-X^{14}-C-X^{15}-X^{16}-X^{17}-X^{18}-X^{19}-X^{20}-X^{21}-X^{22}-C-X^{23}- \quad (2a)$$

$$-X^{13}-X^{14}-C-X^{15}-X^{16}-X^{17}-X^{18}-X^{19}-X^{20}-X^{21}-X^{22}-C-X^{23}-X^{24}- \quad (2b)$$

wherein, $X^{13}$ is selected from an amino acid; $X^{14}$ is selected from an amino acid comprising a large hydrophobic side chain; $X^{15}$ is selected from an amino acid; $X^{16}$ is selected from an amino acid comprising a large hydrophobic side chain; $X^{17}$ is selected from an amino acid comprising a small hydrophobic side chain; $X^{18}$ is selected from an amino acid; $X^{19}$ is selected from an amino acid; $X^{20}$ is selected from an amino acid comprising a large hydrophobic side chain; $X^{21}$ is selected from an amino acid comprising a small hydrophobic side chain; $X^{22}$ is selected from an amino acid; $X^{23}$ is selected from an amino acid; and $X^{24}$ is selected from an amino acid comprising a large hydrophobic side chain.

Aspect 49. The IL-2Rβ ligand of aspect 48, wherein, $X^{13}$ is selected from an amino acid; $X^{14}$ is selected from an amino acid comprising a large hydrophobic side chain; $X^{15}$ is selected from an amino acid; $X^{16}$ is selected from an amino acid comprising a large hydrophobic side chain; $X^{17}$ is selected from an amino acid comprising a small hydrophobic side chain; $X^{18}$ is selected from an amino acid comprising a polar-neutral or an acidic side chain; $X^{19}$ is selected from an amino acid comprising large hydrophobic or neutral side chain; $X^{20}$ is selected from an amino acid comprising a large hydrophobic side chain; $X^{21}$ is selected from an amino acid comprising a small hydrophobic side chain; $X^{22}$ is selected from an amino acid; $X^{23}$ is selected from an amino acid; and $X^{24}$ is selected from an amino acid comprising a large hydrophobic side chain.

Aspect 50. The IL-2Rβ ligand of aspect 48, wherein, $X^{13}$ is selected from an amino acid; $X^{14}$ is selected from I, L, M, V, F, W, and Y; $X^{15}$ is selected from D, E, I, L, M, V, F, Y, and W; $X^{16}$ is selected from I, L, M, N, V, F, Y, and W; $X^{17}$ is selected from A, G, P, S, and T; $X^{18}$ is selected from H, N, Q, S, T, Y, D, and E; $X^{19}$ is selected from I, L, M, V, F, W, and Y; $X^{20}$ is selected from I, L, M, N, V, F, Y, and W; $X^{21}$ is selected from A, G, P, S, and T; $X^{22}$ is selected from an amino acid; $X^{23}$ is selected from an amino acid; and $X^{24}$ is selected from I, L, M, V, F, W, and Y.

Aspect 51. The IL-2Rβ ligand of aspect 50, wherein $X^{14}$ is selected from I and M.

Aspect 52. The IL-2Rβ ligand of any one of aspects 50 to 51, wherein $X^{16}$ is V.

Aspect 53. The IL-2Rβ ligand of any one of aspects 50 to 52, wherein $X^{17}$ is G.

Aspect 54. The IL-2Rβ ligand of any one of aspects 50 to 53, wherein $X^{18}$ is selected from D and Q.

Aspect 55. The IL-2Rβ ligand of any one of aspects 50 to 54, wherein $X^{20}$ is W.

Aspect 56. The IL-2Rβ ligand of any one of aspects 50 to 55, wherein $X^{21}$ is P.

Aspect 57. The IL-2Rβ ligand of any one of aspects 50 to 56, wherein $X^{23}$ is selected from F, I, L, and V.

Aspect 58. The IL-2Rβ ligand of aspect 50, wherein, $X^{13}$ is selected from an amino acid; $X^{14}$ is selected from I and M; $X^{15}$ is selected from an amino acid; $X^{16}$ is V; $X^{17}$ is G; $X^{18}$ is selected from D and Q; $X^{19}$ is selected from I, L, M, V, F, W, and Y; $X^{20}$ is W; $X^{21}$ is P; $X^{22}$ is selected from an amino acid; $X^{23}$ is selected from an amino acid; and $X^{24}$ is selected from F, I, L, and V.

Aspect 59. The IL-2Rβ ligand of any one of aspects 1 to 9, wherein the IL-2Rβ ligand comprises the amino acid sequence of Formula (3) (SEQ ID NO: 183) or the amino acid sequence of Formula (3a) (SEQ ID NO: 184):

$$-X^{26}-X^{27}-X^{2}-X^{29}-X^{30}-X^{31}-X^{32}-X^{33}-X^{34}-X^{35}- \quad (3)$$

$$-X^{25}-C-X^{26}-X^{27}-X^{28}-X^{29}-X^{30}-X^{31}-X^{32}-X^{33}-X^{34}-X^{35}-C-X^{36}- \quad (3a)$$

wherein, $X^{25}$ is selected from an amino acid; $X^{26}$ is selected from an amino acid; $X^{27}$ is selected from I and V; $X^{28}$ is G; $X^{29}$ is selected from D, E, and N; $X^{30}$ is selected from F, L, and Y; $X^{31}$ is selected from F, I, and V; $X^{32}$ is selected from D and Q; $X^{33}$ is selected from an amino acid; $X^{34}$ is selected from an amino acid; $X^{35}$ is selected from an amino acid; and $X^{36}$ is selected from an amino acid.

Aspect 60. The IL-2Rβ ligand of aspect 59, wherein, $X^{25}$ is selected from L, S, T, and Y; $X^{26}$ is selected from H and Q; $X^{27}$ is selected from I and V; $X^{28}$ is G; $X^{29}$ is selected from D, E, and N; $X^{30}$ is selected from F, L, and Y; $X^{31}$ is selected from F, I, and V; $X^{32}$ is selected from D and Q; $X^{33}$ is selected from D, L, and W; $X^{34}$ is selected from G, L, and T; $X^{35}$ is selected from D, I, and S; and $X^{36}$ is selected from A and M.

Aspect 61. The IL-2Rβ ligand of any one of aspects 1 to 9, wherein the IL-2Rβ ligand comprises the amino acid sequence of Formula (3) (SEQ ID NO: 1061) or the amino acid sequence of Formula (3a) (SEQ ID NO: 1062):

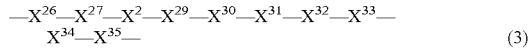

(3)

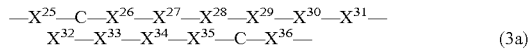

(3a)

wherein, $X^{25}$ is selected from an amino acid; $X^{26}$ is selected from an amino acid; $X^{27}$ is selected from an amino acid comprising a large hydrophobic side chain; $X^{28}$ is selected from an amino acid comprising a small hydrophobic side chain; $X^{29}$ is selected from an amino acid comprising an acidic side chain or a polar neutral side chain; $X^{30}$ is selected from an amino acid; $X^{31}$ is selected from an amino acid; $X^{32}$ is selected from an amino acid comprising a polar-neutral side chain or an acidic side chain; $X^{33}$ is selected from an amino acid; $X^{34}$ is selected from an amino acid; $X^{35}$ is selected from an amino acid; and $X^{36}$ is selected from an amino acid.

Aspect 62. The IL-2Rβ ligand of aspect 61, wherein, $X^{25}$ is selected from an amino acid; $X^{26}$ is selected from an amino acid; $X^{27}$ is selected from an amino acid comprising a large hydrophobic side chain; $X^{28}$ is selected from an amino acid comprising a small hydrophobic side chain; $X^{29}$ is selected from an amino acid comprising an acidic side chain or a polar neutral side chain; $X^{30}$ is selected from an amino acid comprising a large hydrophobic side chain; $X^{31}$ is selected from an amino acid comprising a large hydrophobic side chain; $X^{32}$ is selected from an amino acid comprising a polar-neutral side chain or an acidic side chain; and $X^{33}$ is selected from an amino acid; $X^{34}$ is selected from an amino acid; $X^{35}$ is selected from an amino acid; and $X^{36}$ is selected from an amino acid.

Aspect 63. The IL-2Rβ ligand of any one of aspects 1 to 9, wherein the IL-2Rβ ligand comprises the amino acid sequence of Formula (3) (SEQ ID NO: 1063) or the amino acid sequence of Formula (3a) (SEQ ID NO: 1064):

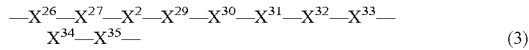

(3)

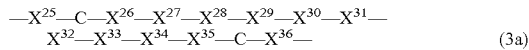

(3a)

wherein, $X^{25}$ is selected from an amino acid; $X^{26}$ is selected from an amino acid; $X^{27}$ is selected from I, L, M, V, F, Y, and W; $X^{28}$ is selected from A, G, P, S, and T; $X^{29}$ is selected from D, E, H, N, Q, S, T, and Y; $X^{30}$ is selected from I, L, M, V, F, Y, and W; $X^{31}$ is selected from I, L, M, V, F, Y, and W; $X^{32}$ is selected from D, E, H, N, Q, T, and Y; $X^{33}$ is selected from an amino acid; $X^{34}$ is selected from an amino acid; $X^{35}$ is selected from an amino acid; and $X^{36}$ is selected from an amino acid.

Aspect 64. The IL-2Rβ ligand of aspect 63, wherein $X^{27}$ is selected from V and I.

Aspect 65. The IL-2Rβ ligand of any one of aspects 63 to 64, wherein $X^{28}$ is G.

Aspect 67. The IL-2Rβ ligand of any one of aspects 63 to 65, wherein $X^{29}$ is selected from D and E.

Aspect 68. The IL-2Rβ ligand of any one of aspects 63 to 66, wherein $X^{30}$ is selected from V, L, F, and Y.

Aspect 69. The IL-2Rβ ligand of any one of aspects 63 to 67, wherein $X^{31}$ is selected from I, V, and F.

Aspect 69a. The IL-2Rβ ligand of any one of aspects 63 to 68, wherein $X^{32}$ is selected from Q and D.

Aspect 70. The IL-2Rβ ligand of aspect 63, wherein, $X^{25}$ is selected from an amino acid; $X^{26}$ is selected from an amino acid; $X^{11}$ is selected from V and I; $X^{28}$ is G; $X^{29}$ is selected from D and E; $X^{30}$ is selected from V, L, F, and Y; $X^{31}$ is selected from I, V, and F; $X^{32}$ is selected from Q and D; $X^{33}$ is selected from an amino acid; $X^{34}$ is selected from an amino acid; $X^{35}$ is selected from an amino acid; and $X^{36}$ is selected from an amino acid.

Aspect 71. The IL-2Rβ ligand of any one of aspects 1 to 9, wherein the IL-2Rβ ligand comprises an amino acid sequence selected from any one of SEQ ID NO: 185 to SEQ ID NO: 193.

Aspect 72. The IL-2Rβ ligand of aspect 71, wherein the IL-2Rβ ligand comprises an amino acid sequence selected from any one of SEQ ID NO: 185 to SEQ ID NO: 193, wherein the amino acid sequence is terminated with amino acids -G-G on the N-terminus, on the C-terminus, or on both the N- and C-termini.

Aspect 73. The IL-2Rβ ligand of any one of aspects 71 to 72, wherein the IL-2Rβ ligand comprises an amino acid sequence selected from any one of SEQ ID NO: 185 to SEQ ID NO: 193, wherein each amino acid independently comprises one or more of the following conservative substitutions: amino acids having a small hydrophobic side chain comprising alanine (A), glycine (G), proline (P), serine (S) and threonine (T); amino acids having a hydroxyl-containing side chain comprising serine (S) or threonine (T); amino acids having an acidic side chain comprising aspartate (D) and glutamate (E); amino acids having a polar-neutral side chain comprising histidine (H), asparagine (N), glutamine (Q), serine (S), threonine (T), and tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W).

Aspect 74. An IL-2Rγc ligand, wherein the IL-2Rγc ligand exhibits a binding affinity to the human IL-2Rγc subunit of less than 100 µM.

Aspect 75. The IL-2Rγc ligand of aspect 74, wherein the IL-2Rγc ligand comprises from 5 to 30 amino acids.

Aspect 76. The IL-2Rγc ligand of any one of aspects 74 to 75, wherein the IL-2Rγc ligand exhibits a binding affinity to the human IL-2Rγc subunit in a range from 1 µM to 100 µM.

Aspect 77. The IL-2Rγc ligand of any one of aspects 74 to 75, wherein the IL-2Rγc ligand exhibits a binding affinity to the human IL-2Rγc subunit in a range from 0.1 µM to 50 µM.

Aspect 78. The IL-2Rγc ligand of any one of aspects 74 to 75, wherein the IL-2Rγc ligand exhibits a binding affinity to the human IL-2Rγc subunit of less than 100 µM.

Aspect 79. The IL-2Rγc ligand of any one of aspects 74 to 78, wherein the IL-2Rγc ligand exhibits a binding affinity to each of the human IL-2Rβ subunit and to the human IL-2Rγc subunit of less than 100 µM.

Aspect 80. The IL-2Rγc ligand of any one of aspects 74 to 79, wherein the IL-2Rγc ligand exhibits a binding affinity to the human IL-2Rα (CD25) subunit.

Aspect 81. The IL-2Rγc ligand of any one of aspects 74 to 80, wherein the IL-2Rγc ligand exhibits a binding affinity to the human IL-2Rγc subunit that is at least 10 times greater than the binding affinity of the IL-2Rγc ligand to the human IL-2Rα subunit.

Aspect 82. The IL-2Rγc ligand of any one of aspects 74 to 81, wherein the IL-2Rγc ligand comprises the amino acid sequence of Formula (4) (SEQ ID NO: 1067) or the amino acid sequence of Formula (4a) (SEQ ID NO: 1068):

$$—X^{53}—X^{54}—X^{55}—X^{56}—X^{57}—X^{58}—X^{59}—X^{60}— \quad (4)$$

$$—X^{51}—X^{52}—C—X^{53}—X^{54}—X^{55}—X^{56}—X^{57}—$$
$$X^{58}—X^{59}—X^{60}—C—X^{61}—X^{62}— \quad (4a)$$

wherein, $X^{51}$ is selected from G, I, K, L, Q, R, T, and V; $X^{52}$ is selected from A, E, I, L, R, S, T, V, and W; $X^{53}$ is selected from D, E, F, N, Q, S, and T; $X^{54}$ is selected from D, E, I, M, N, Q, R, and S; $X^{55}$ is selected from D, E, F, S, T, W, and Y; $X^{56}$ is selected from D, E, F, G, L, M, N, Q, and Y; $X^{57}$ is selected from E, G, and N; $X^{58}$ is selected from I, P, T, and V; $X^{59}$ is selected from I, L, M, S, T, and V; $X^{60}$ is selected from F, I, and L; $X^{61}$ is selected from F, T, and W; and $X^{62}$ is selected from A, E, G, M, L, N, P, Q, S, V, and W.

Aspect 83. The IL-2Rγc ligand of aspect 82, wherein $X^{51}$ is selected from I, L, and V.

Aspect 84. The IL-2Rγc ligand of any one of aspects 82 to 83, wherein $X^{52}$ is selected from S and T.

Aspect 85. The IL-2Rγc ligand of any one of aspects 82 to 84, wherein $X^{53}$ is selected from D, E, N, and Q.

Aspect 86. The IL-2Rγc ligand of any one of aspects 82 to 85, wherein $X^{54}$ is selected from D, E, N, and Q.

Aspect 87. The IL-2Rγc ligand of any one of aspects 82 to 86, wherein $X^{55}$ is selected from F, W, and Y.

Aspect 88. The IL-2Rγc ligand of any one of aspects 82 to 87, wherein $X^{56}$ is selected from D, E, N, and Q.

Aspect 89. The IL-2Rγc ligand of any one of aspects 82 to 88, wherein $X^{57}$ is G.

Aspect 90. The IL-2Rγc ligand of any one of aspects 82 to 89, wherein $X^{58}$ is selected from I and V.

Aspect 91. The IL-2Rγc ligand of any one of aspects 82 to 90, wherein $X^{59}$ is selected from I, L, M, and V.

Aspect 92. The IL-2Rγc ligand of any one of aspects 82 to 91, wherein $X^{60}$ is selected from F, I, and L.

Aspect 93. The IL-2Rγc ligand of any one of aspects 82 to 92, wherein $X^{61}$ is W.

Aspect 94. The IL-2Rγc ligand of any one of aspects 82 to 93, wherein $X^{62}$ is selected from N and Q.

Aspect 95. The IL-2Rγc ligand of aspect 82, wherein, $X^{51}$ is selected from I, L, and V; $X^{52}$ is selected from S and T; $X^{53}$ is selected from D, E, N, and Q; $X^{54}$ is selected from D and N; $X^{55}$ is selected from F, W, and Y; $X^{56}$ is selected from D, E, N, and Q; $X^{57}$ is G; $X^{58}$ is selected from I and V; $X^{59}$ is selected from I, L, M, and V; XV is selected from F, I, and L; $X^{61}$ is W; and $X^{62}$ is selected from N and Q.

Aspect 96. The IL-2Rγc ligand of any one of aspects 74 to 81, wherein the IL-2Rγc ligand comprises an amino acid sequence selected from any one of SEQ ID NO: 196 to SEQ ID NO: 210.

Aspect 97. The IL-2Rγc ligand of aspect 96, wherein the IL-2Rγc ligand comprises an amino acid sequence selected from any one of SEQ ID NO: 196 to SEQ ID NO: 210, wherein the amino acid sequence is terminated with amino acids -G-G on the N-terminus, on the C-terminus, or on both the N- and C-termini.

Aspect 98. The IL-2Rβ ligand of any one of aspects 96 to 97, wherein the IL-2Rβ ligand comprises an amino acid sequence selected from any one of SEQ ID NO: 196 to SEQ ID NO: 210, wherein each amino acid independently comprises one or more of the following conservative substitutions: amino acids having a small hydrophobic side chain comprising alanine (A), glycine (G), proline (P), serine (S) and threonine (T); amino acids having a hydroxyl-containing side chain comprising serine (S) or threonine (T); amino acids having an acidic side chain comprising aspartate (D) and glutamate (E); amino acids having a polar-neutral side chain comprising histidine (H), asparagine (N), glutamine (Q), serine (S), threonine (T), and tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W).

Aspect 99. The IL-2Rγc ligand of any one of aspects 74 to 81, wherein the IL-2Rγc ligand comprises the amino acid sequence of Formula (4) (SEQ ID NO: 1065) or the amino acid sequence of Formula (4a) (SEQ ID NO: 1066):

$$—X^{53}—X^{54}—X^{55}—X^{56}—X^{57}—X^{58}—X^{59}—X^{60}— \quad (4)$$

$$—X^{51}—X^{52}—C—X^{53}—X^{54}—X^{55}—X^{56}—X^{57}—$$
$$X^{58}—X^{59}—X^{60}—C—X^{61}—X^{62}— \quad (4a)$$

wherein, $X^{51}$ is selected from an amino acid; $X^{52}$ is selected from an amino acid; $X^{53}$ is selected from an amino acid comprising a polar-neutral side chain or an acidic side chain; $X^{54}$ is selected from an amino acid comprising a polar-neutral side chain or an acidic side chain; $X^{55}$ is selected from an amino acid; $X^{56}$ is selected from an amino acid; $X^{57}$ is selected from an amino acid comprising a small hydrophobic side chain; $X^{58}$ is selected from an amino acid comprising a large hydrophobic side chain; $X^{59}$ is selected from an amino acid comprising a large hydrophobic side chain; $X^{60}$ is selected from an amino acid comprising a large hydrophobic side chain; $X^{61}$ is selected from an amino acid comprising a large hydrophobic side chain; and $X^{62}$ is selected from an amino acid.

Aspect 100. The IL-2Rγc ligand of aspect 99, wherein, $X^{51}$ is selected from an amino acid comprising a large hydrophobic side chain and a basic side chain; $X^{52}$ is selected from an amino acid comprising a hydroxyl-containing side chain and a large hydrophobic side chain; $X^{53}$ is selected from an amino acid comprising a polar-neutral side chain or an acidic side chain; $X^{54}$ is selected from an amino acid comprising a polar-neutral side chain or an acidic side chain; $X^{55}$ is selected from an amino acid comprising a large hydrophobic side chain; $X^{56}$ is selected from an amino acid comprising a polar-neutral side chain or an acidic side chain; $X^{57}$ is selected from an amino acid comprising a small hydrophobic side chain; $X^{58}$ is selected from an amino acid comprising a large hydrophobic side chain; $X^{59}$ is selected from an amino acid comprising a large hydrophobic side chain; $X^{60}$ is selected from an amino acid comprising a large hydrophobic side chain; $X^{61}$ is selected from an amino acid comprising a large hydrophobic side chain; and $X^{62}$ is selected from an amino acid comprising a polar-neutral side chain.

Aspect 101. The IL-2Rγc ligand of aspect 99, wherein, $X^{51}$ is selected from R, K, H, F, I, L, M, V, Y, and W; $X^{52}$ is selected from S, T, F, I, L, M, V, Y, and W; $X^{53}$ is selected from D, E, H, N, Q, S, T, and Y; $X^{54}$ is selected from D, E, H, N, Q, S, T, and Y; $X^{55}$ is selected from F, I, L, M, V, Y, and W; $X^{56}$ is selected from D, E, H, N, Q, S, T, and Y; $X^{57}$ is selected from A, G, P, S, and T; $X^{58}$ is selected from F, I, L, M, V, Y, and W; $X^{59}$ is selected from F, I, L, M, V, Y, and W; $X^{60}$ is selected from F, I, L, M, V, Y, and W; $X^{61}$ is selected from F, I, L, M, V, Y, and W; and $X^{62}$ is selected from H, N, Q, S, T, and Y.

Aspect 102. The IL-2Rγc ligand of aspect 101, wherein $X^{51}$ is selected from I, L, and V.

Aspect 103. The IL-2Rγc ligand of any one of aspects 101 to 102, wherein $X^{52}$ is selected from S and T.

Aspect 104. The IL-2Rγc ligand of any one of aspects 101 to 103, wherein $X^{53}$ is selected from D, E, and Q.

Aspect 105. The IL-2Rγc ligand of any one of aspects 101 to 104, wherein $X^{54}$ is selected from D, E, and N.

Aspect 106. The IL-2Rγc ligand of any one of aspects 101 to 105, wherein $X^{55}$ is selected from F, Y, and W.

Aspect 107. The IL-2Rγc ligand of any one of aspects 101 to 106, wherein $X^{56}$ is selected from D, E, N, and Q.

Aspect 108. The IL-2Rγc ligand of any one of aspects 101 to 107, wherein $X^{57}$ is G.

Aspect 109. The IL-2Rγc ligand of any one of aspects 101 to 108, wherein $X^{58}$ is selected from I and V.

Aspect 110. The IL-2Rγc ligand of any one of aspects 101 to 109, wherein $X^{59}$ is selected from I, L, M, and V.

Aspect 111. The IL-2Rγc ligand of any one of aspects 101 to 110, wherein $X^{60}$ is selected from F, I, and L.

Aspect 112. The IL-2Rγc ligand of any one of aspects 101 to 111, wherein $X^{61}$ is W.

Aspect 113. The IL-2Rγc ligand of any one of aspects 101 to 112, wherein $X^{62}$ is selected from N and Q.

Aspect 114. The IL-2Rγc ligand of aspect 101, wherein, $X^{51}$ is selected from I, L, and V; $X^{52}$ is selected from S and T; $X^{53}$ is selected from D, E, and Q; $X^{54}$ is selected from D, E, and N; $X^{55}$ is selected from F, Y, and W; $X^{56}$ is selected from D, E, N, and Q; $X^{57}$ is G; $X^{58}$ is selected from I and V; $X^{59}$ is selected from I, L, M, and V; $X^{60}$ is selected from F, I, and L; $X^{61}$ is W; and $X^{62}$ is selected from N and Q.

Aspect 115. The IL-2Rγc ligand of any one of aspects 74 to 81, wherein the IL-2Rγc ligand comprises the amino acid sequence of Formula (5) (SEQ ID NO: 1073) or Formula (5a) (SEQ ID NO: 1074):

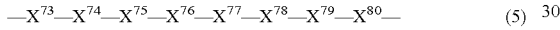  (5)

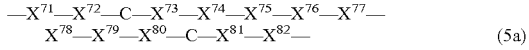  (5a)

wherein, $X^{71}$ is selected from I, L, P, Q, R, T, and V; $X^{72}$ is selected from A, D, E, I, M, R, T, and V; $X^{73}$ is selected from E, M, N, Q, S T, V, W, and Y; $X^{74}$ is selected from D, E, F, G, I, M, R, S, T, and V; $X^{75}$ is selected from F, W, and Y; $X^{76}$ is selected from D, E, L, N, Q, and S; $X^{77}$ is selected from G; $X^{78}$ is selected from I, M, and V; $X^{79}$ is selected from D, E, N, Q, and R; $X^{80}$ is selected from F, I, and L; $X^{81}$ is selected from I, L, R, T, W, and Y; and $X^{82}$ is selected from A, F, H, I, L, N, P, Q, S, T, and W.

Aspect 116. The IL-2Rγc ligand of aspect 115, wherein $X^{71}$ is selected from I, L, and V.

Aspect 117. The IL-2Rγc ligand of any one of aspects 115 to 116, wherein $X^{72}$ is selected from A, D, E, I, M, and V.

Aspect 118. The IL-2Rγc ligand of any one of aspects 115 to 117, wherein $X^{73}$ is selected from E, Q, and N.

Aspect 119. The IL-2Rγc ligand of any one of aspects 115 to 118, wherein $X^{74}$ is selected from D and E.

Aspect 120. The IL-2Rγc ligand of any one of aspects 115 to 119, wherein $X^{75}$ is selected from F, W, and Y.

Aspect 121. The IL-2Rγc ligand of any one of aspects 115 to 120, wherein $X^{76}$ is selected from D, E, L, N, and Q.

Aspect 122. The IL-2Rγc ligand of any one of aspects 115 to 121, wherein $X^{77}$ is G.

Aspect 123. The IL-2Rγc ligand of any one of aspects 115 to 122, wherein $X^{78}$ is selected from I, M, and V.

Aspect 124. The IL-2Rγc ligand of any one of aspects 115 to 123, wherein $X^{79}$ is selected from D, E, Q, and R.

Aspect 125. The IL-2Rγc ligand of any one of aspects 115 to 124, wherein $X^{80}$ is selected from F, I, and L.

Aspect 126. The IL-2Rγc ligand of any one of aspects 115 to 125, wherein $X^{81}$ is W.

Aspect 127. The IL-2Rγc ligand of any one of aspects 115 to 126, wherein $X^{82}$ is selected from N and Q.

Aspect 128. The IL-2Rγc ligand of aspect 115, wherein, $X^{71}$ is selected from I, L, and V; $X^{72}$ is selected from A, D, E, I, M, and V; $X^{73}$ is selected from E, Q, and N; $X^{74}$ is selected from D and E; $X^{75}$ is selected from F, W, and Y; $X^{76}$ is selected from D, E, L, N, and Q; $X^{77}$ is G; $X^{78}$ is selected from I, M, and V; $X^{79}$ is selected from D, E, Q, and R; $X^{80}$ is selected from F, I, and L; $X^{81}$ is W; and $X^{82}$ is selected from N and Q.

Aspect 129. The IL-2Rγc ligand of any one of aspects 74 to 81, wherein the IL-2Rγc ligand comprises the amino acid sequence of Formula (5) (SEQ ID NO: 1071) or Formula (5a) (SEQ ID NO: 1072):

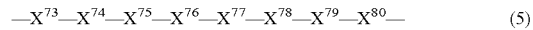  (5)

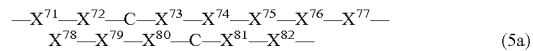  (5a)

wherein, $X^{71}$ is selected from an amino acid; $X^{72}$ is selected from an amino acid; $X^{73}$ is selected from an amino acid; $X^{74}$ is selected from an amino acid; $X^{75}$ is selected from an amino acid comprising a large hydrophobic side chain; $X^{76}$ is selected from an amino acid; $X^{77}$ is selected from a small hydrophobic side chain; $X^{78}$ is selected from an amino acid comprising a large hydrophobic side chain; $X^{79}$ is selected from an amino acid comprising a basic side chain, an acidic side chain, or a polar-neutral side chain; $X^{80}$ is selected from an amino acid comprising a large hydrophobic side chain; $X^{81}$ is selected from an amino acid comprising a large hydrophobic side chain; and $X^{82}$ is selected from an amino acid.

Aspect 130. The IL-2Rγc ligand of aspect 129, wherein, $X^{71}$ is selected from an amino acid comprising a large hydrophobic side chain; $X^{72}$ is selected from an amino acid comprising an acidic side chain or a large hydrophobic side chain; $X^{73}$ is selected from an amino acid comprising an acidic side chain, a hydroxyl-containing side chain, or a polar neutral side chain; $X^{74}$ is selected from an amino acid comprising an acidic side chain, a hydroxyl-containing side chain, or a large hydrophobic side chain; $X^{75}$ is selected from an amino acid comprising a large hydrophobic side chain; $X^{76}$ is selected from an amino acid comprising an acidic side chain, a hydroxyl-containing side chain, or a polar neutral side chain; $X^{77}$ is selected from a small hydrophobic side chain; $X^{78}$ is selected from an amino acid comprising a large hydrophobic side chain; $X^{79}$ is selected from an amino acid comprising a basic side chain, an acidic side chain, or a polar-neutral side chain; $X^{80}$ is selected from an amino acid comprising a large hydrophobic side chain; $X^{81}$ is selected from an amino acid comprising a large hydrophobic side chain; and $X^{82}$ is selected from an amino acid comprising a polar neutral side chain.

Aspect 131. The IL-2Rγc ligand of aspect 129, wherein, $X^{71}$ is selected from F, I, L, M, V, Y, and W; $X^{72}$ is selected from D, E, F, I, L, M, V, Y, and W; $X^{73}$ is selected from D, E, S, T, H, N, Q, S, T, and Y; $X^{74}$ is selected from D, E, S, T, F, I, L, M, V, Y, and W; $X^{75}$ is selected from F, I, L, M, V, Y, and W; $X^{76}$ is selected from D, E, S, T, H, N, Q, S, T, and Y; $X^{77}$ is selected from A, G, P, S, and T; $X^{78}$ is selected from F, I, L, M, V, Y, and W; $X^{79}$ is selected from R, K, H, D, E, H, N, Q, S, T, and Y; $X^{80}$ is selected from F, I, L, M, V, Y, and W; $X^{81}$ is selected from F, I, L, M, V, Y, and W; and $X^{82}$ is selected from H, N, Q, S, T, and Y.

Aspect 132. The IL-2Rγc ligand of aspect 131, wherein $X^{71}$ is selected from I, L, and V.

Aspect 133. The IL-2Rγc ligand of any one of aspects 131 to 132, wherein $X^{72}$ is selected from D, E, I, M, and V.

Aspect 134. The IL-2Rγc ligand of any one of aspects 131 to 133, wherein $X^{73}$ is selected from E, N, and Q.

Aspect 135. The IL-2Rγc ligand of any one of aspects 131 to 134, wherein $X^{74}$ is selected from D and E.

Aspect 136. The IL-2Rγc ligand of any one of aspects 131 to 135, wherein $X^{75}$ is selected from F, W, and Y.

Aspect 137. The IL-2Rγc ligand of any one of aspects 131 to 136, wherein $X^{76}$ is selected from D, E, and N.

Aspect 138. The IL-2Rγc ligand of any one of aspects 131 to 137, wherein $X^{77}$ is selected from G.

Aspect 139. The IL-2Rγc ligand of any one of aspects 131 to 138, wherein $X^{78}$ is selected from I, M, and V.

Aspect 140. The IL-2Rγc ligand of any one of aspects 131 to 139, wherein $X^{79}$ is selected from D, E, N, Q, and R.

Aspect 141. The IL-2Rγc ligand of any one of aspects 131 to 140, wherein $X^{80}$ is selected from F, I, and L.

Aspect 142. The IL-2Rγc ligand of any one of aspects 131 to 141, wherein $X^{81}$ is W.

Aspect 143. The IL-2Rγc ligand of any one of aspects 131 to 142, wherein $X^{82}$ is selected from N and Q.

Aspect 144. The IL-2Rγc ligand of aspect 131, wherein, $X^{71}$ is selected from I, L, and V; $X^{72}$ is selected from D, E, I, M, and V; $X^{73}$ is selected from E, N, and Q; $X^{74}$ is selected from D and E; $X^{75}$ is selected from F, W, and Y; $X^{76}$ is selected from D, E, and N; $X^{77}$ is selected from G; $X^{78}$ is selected from I, M, and V; $X^{79}$ is selected from D, E, N, Q, and R; $X^{80}$ is selected from F, I, and L; $X^{81}$ is W; and $X^{82}$ is selected from N and Q.

Aspect 145. The IL-2Rγc ligand of any one of aspects 74 to 81, wherein the IL-2Rγc ligand comprises an amino acid sequence selected from any one of SEQ ID NO: 213 to SEQ ID NO: 233:

Aspect 146. The IL-2Rγc ligand of aspect 145, wherein the IL-2Rγc ligand comprises an amino acid sequence selected from any one of SEQ ID NO: 213 to SEQ ID NO: 233, wherein the amino acid sequence is terminated with amino acids -G-G on the N-terminus, on the C-terminus, or on both the N- and C-termini.

Aspect 147. The IL-2Rβ ligand of any one of aspects 145 to 146, wherein the IL-2Rβ ligand comprises an amino acid sequence selected from any one of SEQ ID NO: 213 to SEQ ID NO: 233, wherein each amino acid independently comprises one or more of the following conservative substitutions: amino acids having a small hydrophobic side chain comprising alanine (A), glycine (G), proline (P), serine (S) and threonine (T); amino acids having a hydroxyl-containing side chain comprising serine (S) or threonine (T); amino acids having an acidic side chain comprising aspartate (D) and glutamate (E); amino acids having a polar-neutral side chain comprising histidine (H), asparagine (N), glutamine (Q), serine (S), threonine (T), and tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W).

Aspect 148. The IL-2Rγc ligand of any one of aspects 74 to 81, wherein the IL-2Rγc ligand comprises the amino acid sequence of Formula (6) (SEQ ID NO: 234) or Formula (6a) (SEQ ID NO: 235):

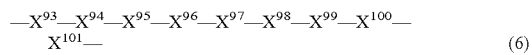
(6)

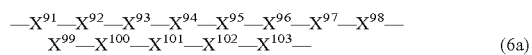
(6a)

wherein, $X^{91}$ is selected from C, D, E, and L; $X^{92}$ is selected from C, L, M, R, S, V, and W; $X^{93}$ is selected from C, D, F, P, and R; $X^{94}$ is selected from A, D, L, Q, S, and W; $X^{95}$ is selected from D, E, F, L, and V; $X^{96}$ is selected from A, D, E, F, G, K, Q, and S; $X^{97}$ is selected from E, L, M, and W; $X^{98}$ is selected from G, I, L, W, and Y; $X^{99}$ is selected from E, I, R, T, and V; $X^{100}$ is W; $X^{101}$ is selected from C, A, I, L, P, and V; $X^{102}$ is selected from C, D, G, H; and $X^{103}$ is selected from C, D, E, H, S, and T.

Aspect 149. The IL-2Rγc ligand of aspect 148, wherein $X^{91}$ is selected from D and E.

Aspect 150. The IL-2Rγc ligand of any one of aspects 148 to 149, wherein $X^{92}$ is selected from L, M, R, S, V, and W.

Aspect 151. The IL-2Rγc ligand of any one of aspects 148 to 150, wherein $X^{93}$ is selected from D and F.

Aspect 152. The IL-2Rγc ligand of any one of aspects 148 to 151, wherein $X^{94}$ is S.

Aspect 153. The IL-2Rγc ligand of any one of aspects 148 to 152, wherein $X^{95}$ is selected from D and E.

Aspect 154. The IL-2Rγc ligand of any one of aspects 148 to 153, wherein $X^{96}$ is selected from D and E.

Aspect 155. The IL-2Rγc ligand of any one of aspects 148 to 154, wherein $X^{97}$ is selected from L, M, and W.

Aspect 156. The IL-2Rγc ligand of any one of aspects 148 to 155, wherein $X^{98}$ is G.

Aspect 157. The IL-2Rγc ligand of any one of aspects 148 to 156, wherein $X^{99}$ is E.

Aspect 158. The IL-2Rγc ligand of any one of aspects 148 to 157, wherein $X^{100}$ is W.

Aspect 159. The IL-2Rγc ligand of any one of aspects 148 to 158, wherein $X^{101}$ is selected from I, L, and V.

Aspect 160. The IL-2Rγc ligand of any one of aspects 148 to 159, wherein $X^{102}$ is selected from D and G.

Aspect 161. The IL-2Rγc ligand of any one of aspects 148 to 160, wherein $X^{103}$ is selected from S and T.

Aspect 162. The IL-2Rγc ligand of aspect 148, wherein, $X^{91}$ is selected from D and E; $X^{92}$ is selected from L, M, R, S, V, and W; $X^{93}$ is selected from D and F; $X^{94}$ is S; $X^{95}$ is selected from D and E; $X^{96}$ is selected from D and E; $X^{97}$ is selected from L, M, and W; $X^{98}$ is G; $X^{99}$ is E; $X^{100}$ is W; $X^{101}$ is selected from I, L, and V; $X^{102}$ is selected from D and G; and $X^{103}$ is selected from S and T.

Aspect 163. The IL-2Rγc ligand of any one of aspects 74 to 81, wherein the IL-2Rγc ligand comprises an amino acid sequence selected from any one of SEQ ID NO: 236 to SEQ ID NO: 245.

Aspect 164. The IL-2Rγc ligand of aspect 163, wherein the IL-2Rγc ligand comprises an amino acid sequence selected from any one of SEQ ID NO: 236 to SEQ ID NO: 245, wherein the amino acid sequence is terminated with amino acids -G-G on the N-terminus, on the C-terminus, or on both the N- and C-termini.

Aspect 165. The IL-2Rβ ligand of any one of aspects 163 to 164, wherein the IL-2Rβ ligand comprises an amino acid sequence selected from any one of SEQ ID NO: 236 to SEQ ID NO: 245, wherein each amino acid independently comprises one or more of the following conservative substitutions: amino acids having a small hydrophobic side chain comprising alanine (A), glycine (G), proline (P), serine (S) and threonine (T); amino acids having a hydroxyl-containing side chain comprising serine (S) or threonine (T); amino acids having an acidic side chain comprising aspartate (D) and glutamate (E); amino acids having a polar-neutral side chain comprising histidine (H), asparagine (N), glutamine (Q), serine (S), threonine (T), and tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W).

Aspect 166. The IL-2Rγc ligand of any one of aspects 74 to 81, wherein the IL-2Rγc ligand comprises the amino acid sequence of Formula (6) (SEQ ID NO: 1075) or Formula (6a) (SEQ ID NO: 1076):

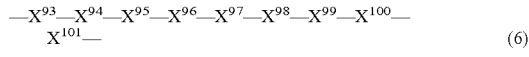

$$-X^{93}-X^{94}-X^{95}-X^{96}-X^{97}-X^{98}-X^{99}-X^{100}-X^{101}- \quad (6)$$

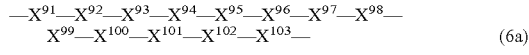

$$-X^{91}-X^{92}-X^{93}-X^{94}-X^{95}-X^{96}-X^{97}-X^{98}-X^{99}-X^{100}-X^{101}-X^{102}-X^{103}- \quad (6a)$$

wherein, $X^{91}$ is selected from an amino acid comprising an acidic side chain or cysteine; $X^{92}$ is selected from an amino acid; $X^{93}$ is selected from an amino acid comprising an acidic side chain or large hydrophobic side chain; $X^{94}$ is selected from an amino acid; $X^{95}$ is selected from an amino acid; $X^{96}$ is selected from an amino acid; $X^{97}$ is selected from an amino acid comprising a large hydrophobic side chain; $X^{98}$ is selected from an amino acid comprising a small hydrophobic side chain or a large hydrophobic side chain; $X^{99}$ is selected from an amino acid; $X^{100}$ is selected from an amino acid comprising a large hydrophobic side chain; $X^{101}$ is selected from an amino acid comprising a large hydrophobic side chain; $X^{102}$ is selected from an amino acid comprising a small hydrophobic side chain or an acidic side chain or cysteine; and $X^{103}$ is selected from an amino acid comprising an acidic side chain or a hydroxyl-containing side chain or cysteine.

Aspect 167. The IL-2Rγc ligand of aspect 166, wherein, $X^{91}$ is selected from an amino acid comprising an acidic side chain; $X^{92}$ is selected from an amino acid; $X^{93}$ is selected from an amino acid comprising an acidic side chain or large hydrophobic side chain; $X^{94}$ is selected from an amino acid comprising an acidic side chain or a hydroxyl-containing side chain; $X^{95}$ is selected from an amino acid comprising an acidic side chain; $X^{96}$ is selected from an amino acid; $X^{97}$ is selected from an amino acid comprising a large hydrophobic side chain; $X^{98}$ is selected from an amino acid comprising a small hydrophobic side chain or a large hydrophobic side chain; $X^{99}$ is selected from an amino acid comprising an acidic side chain or large hydrophobic side chain; $X^{100}$ is selected from an amino acid comprising a large hydrophobic side chain; $X^{101}$ is selected from an amino acid comprising a large hydrophobic side chain; $X^{102}$ is selected from an amino acid comprising a small hydrophobic side chain or an acidic side chain; and $X^{103}$ is selected from an amino acid comprising an acidic side chain or a hydroxyl-containing side chain.

Aspect 168. The IL-2Rγc ligand of aspect 166, wherein, $X^{91}$ is selected from D and E; $X^{92}$ is selected from an amino acid; $X^{93}$ is selected from D, E, F, I, L, M, V, Y, and W; $X^{94}$ is selected from D, E, S, and T; $X^{95}$ is selected from D and E; $X^{96}$ is selected from an amino acid; $X^{97}$ is selected from F, I, L, M, V, Y, and W; $X^{98}$ is selected from A, G, P, S, T, F, I, L, M, V, Y, and W; $X^{99}$ is selected from D, E, F, I, L, M, V, Y, and W; $X^{100}$ is selected from F, I, L, M, V, Y, and W; $X^{101}$ is selected from F, I, L, M, V, Y, and W; $X^{102}$ is selected from D, E, A, G, P, S, and T; and $X^{103}$ is selected from D, E, S, and T.

Aspect 169. The IL-2Rγc ligand of aspect 168, wherein $X^{91}$ is selected from D and E.

Aspect 170. The IL-2Rγc ligand of any one of aspects 168 to 169, wherein $X^{92}$ is selected from an amino acid.

Aspect 171. The IL-2Rγc ligand of any one of aspects 168 to 170, wherein $X^{93}$ is selected from D and F.

Aspect 172. The IL-2Rγc ligand of any one of aspects 168 to 171, wherein $X^{94}$ is S.

Aspect 173. The IL-2Rγc ligand of any one of aspects 168 to 172, wherein $X^{95}$ is selected from D and E.

Aspect 174. The IL-2Rγc ligand of any one of aspects 168 to 173, wherein $X^{96}$ is selected from an amino acid.

Aspect 175. The IL-2Rγc ligand of any one of aspects 168 to 174, wherein $X^{97}$ is selected from L, M, and W.

Aspect 176. The IL-2Rγc ligand of any one of aspects 168 to 175, wherein $X^{98}$ is G.

Aspect 177. The IL-2Rγc ligand of any one of aspects 168 to 176, wherein $X^{99}$ is E.

Aspect 178. The IL-2Rγc ligand of any one of aspects 168 to 177, wherein $X^{100}$ is W.

Aspect 179. The IL-2Rγc ligand of any one of aspects 168 to 178, wherein $X^{101}$ is selected from I, L, and V.

Aspect 180. The IL-2Rγc ligand of any one of aspects 168 to 179, wherein $X^{102}$ is selected from D and G.

Aspect 181. The IL-2Rγc ligand of any one of aspects 168 to 180, wherein $X^{103}$ is selected from S and T.

Aspect 182. The IL-2Rγc ligand of aspect 168, wherein, $X^{91}$ is selected from D and E; $X^{92}$ is selected from an amino acid; $X^{93}$ is selected from D and F; $X^{94}$ is S; $X^{95}$ is selected from D and E $X^{96}$ is selected from an amino acid; $X^{97}$ is selected from L, M, and W; $X^{98}$ is G; $X^{99}$ is E; $X^{100}$ is W; $X^{101}$ is selected from I, L, and V; $X^{102}$ is selected from D and G; and $X^{103}$ is selected from S and T.

Aspect 183. The IL-2Rγc ligand of any one of aspects 74 to 81, wherein the IL-2Rγc ligand comprises the amino acid sequence of Formula (7) (SEQ ID NO: 1079) or Formula (7a) (SEQ ID NO: 1080):

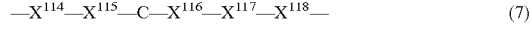

$$-X^{114}-X^{115}-C-X^{116}-X^{117}-X^{118}- \quad (7)$$

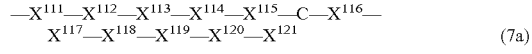

$$-X^{111}-X^{112}-X^{113}-X^{114}-X^{115}-C-X^{116}-X^{117}-X^{118}-X^{119}-X^{120}-X^{121} \quad (7a)$$

wherein, $X^{111}$ is selected from D, G, I, and Q; $X^{112}$ is selected from D, I, and L; $X^{113}$ is selected from G, L, M, R, S, and Y; $X^{114}$ is selected from D, E, S, T, and Y; $X^{115}$ is selected from E, L, P, and Q; $X^{116}$ is selected from D, E, L, S, and T $X^{117}$ is selected from F, S, and W; $X^{118}$ is selected from F, N, W, and Y; $X^{119}$ is selected from F, I, L, and R; $X^{120}$ is selected from A, E, L, and S; and $X^{121}$ is selected from K, N, Q, and V.

Aspect 184. The IL-2Rγc ligand of aspect 183, wherein $X^{111}$ is selected from D and Q.

Aspect 185. The IL-2Rγc ligand of any one of aspects 183 to 184, wherein $X^{112}$ is selected from I and L.

Aspect 186. The IL-2Rγc ligand of any one of aspects 183 to 185, wherein $X^{113}$ is selected from G, L, M, R, S, and Y.

Aspect 187. The IL-2Rγc ligand of any one of aspects 183 to 186, wherein $X^{114}$ is L.

Aspect 188. The IL-2Rγc ligand of any one of aspects 183 to 187, wherein $X^{115}$ is selected from E and Q.

Aspect 189. The IL-2Rγc ligand of any one of aspects 183 to 188, wherein $X^{116}$ is selected from D and E.

Aspect 190. The IL-2Rγc ligand of any one of aspects 183 to 189, wherein $X^{117}$ is selected from F and W.

Aspect 191. The IL-2Rγc ligand of any one of aspects 183 to 190, wherein $X^{118}$ is selected from F, W, and Y.

Aspect 192. The IL-2Rγc ligand of any one of aspects 183 to 191, wherein $X^{119}$ is selected from F, I, and L.

Aspect 193. The IL-2Rγc ligand of any one of aspects 183 to 192, wherein $X^{120}$ is S.

Aspect 194. The IL-2Rγc ligand of any one of aspects 183 to 193, wherein $X^{121}$ is selected from N and Q.

Aspect 195. The IL-2Rγc ligand of aspect 183, wherein, $X^{111}$ is selected from D and Q; $X^{112}$ is selected from I and L; $X^{113}$ is selected from G, L, M, R, S, and Y; $X^{114}$ is L; $X^{115}$ is selected from E and Q; $X^{116}$ is selected from D and E $X^{117}$ is selected from F and W; $X^{118}$ is selected from F, W, and Y; $X^{119}$ is selected from F, I, and L; $X^{120}$ is S; and $X^{121}$ is selected from N and Q.

Aspect 196. The IL-2Rγc ligand of any one of aspects 74 to 81, wherein the IL-2Rγc ligand comprises an amino acid sequence selected from any one of SEQ ID NO: 248 to SEQ ID NO: 254 and SEQ ID NO: 1051:

Aspect 197. The IL-2Rγc ligand of aspect 196, wherein the IL-2Rγc ligand comprises an amino acid sequence selected from any one of SEQ ID NO: 248 to SEQ ID NO: 254 and SEQ ID NO: 1051, wherein the amino acid sequence is terminated with amino acids -G-G on the N-terminus, on the C-terminus, or on both the N- and C-termini.

Aspect 198. The IL-2Rβ ligand of any one of aspects 196 to 197, wherein the IL-2Rβ ligand comprises an amino acid sequence selected from any one of SEQ ID NO: 248 to SEQ ID NO: 254 and SEQ ID NO: 1051, wherein each amino acid independently comprises one or more of the following conservative substitutions: amino acids having a small hydrophobic side chain comprising alanine (A), glycine (G), proline (P), serine (S) and threonine (T); amino acids having a hydroxyl-containing side chain comprising serine (S) or threonine (T); amino acids having an acidic side chain comprising aspartate (D) and glutamate (E); amino acids having a polar-neutral side chain comprising histidine (H), asparagine (N), glutamine (Q), serine (S), threonine (T), and tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W).

Aspect 199. The IL-2Rγc ligand of of any one of aspects 74 to 81, wherein the IL-2Rγc ligand comprises the amino acid sequence of Formula (7) (SEQ ID NO: 1077) or Formula (7a) (SEQ ID NO: 1078):

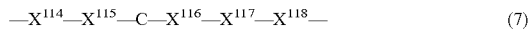

$$-X^{114}-X^{115}-C-X^{116}-X^{117}-X^{118}- \quad (7)$$

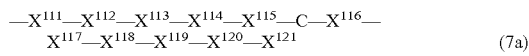

$$-X^{111}-X^{112}-X^{113}-X^{114}-X^{115}-C-X^{116}-X^{117}-X^{118}-X^{119}-X^{120}-X^{121} \quad (7a)$$

wherein, $X^{111}$ is selected from an amino acid; $X^{112}$ is selected from an amino acid comprising a large hydrophobic side chain or an acidic side chain; $X^{113}$ is selected from an amino acid; $X^{114}$ is selected from an amino acid comprising an acidic side chain or a hydroxyl-containing side chain; $X^{115}$ is selected from an amino acid; $X^{116}$ is selected from an amino acid; $X^{117}$ is selected from an amino acid comprising a large hydrophobic side chain; $X^{118}$ is selected from an amino acid comprising a large hydrophobic side chain; $X^{119}$ is selected from an amino acid comprising a large hydrophobic side chain; $X^{120}$ is selected from an amino acid; and $X^{121}$ is selected from an amino acid.

Aspect 200. The IL-2Rγc ligand of aspect 199, wherein, $X^{111}$ is selected from an amino acid; $X^{112}$ is selected from an amino acid comprising a large hydrophobic side chain or an acidic side chain; $X^{113}$ is selected from an amino acid; $X^{114}$ is selected from an amino acid comprising an acidic side chain or a hydroxyl-containing side chain; $X^{115}$ is selected from an amino acid comprising a large hydrophobic side chain; $X^{116}$ is selected from an amino acid comprising an acidic side chain; $X^{117}$ is selected from an amino acid comprising a large hydrophobic side chain; $X^{118}$ is selected from an amino acid comprising a large hydrophobic side chain; $X^{119}$ is selected from an amino acid comprising a large hydrophobic side chain; $X^{120}$ is selected from an amino acid; and $X^{121}$ is selected from an amino acid comprising a polar-neutral side chain.

Aspect 201. The IL-2Rγc ligand of aspect 199, wherein, $X^{111}$ is selected from an amino acid; $X^{112}$ is selected from D, E, F, I, L, M, V, Y, and W; $X^{113}$ is selected from an amino acid; $X^{114}$ is selected from D, E, S, and T; $X^{115}$ is selected from F, I, L, M, V, Y, and W; $X^{116}$ is selected from D and E; $X^{117}$ is selected from F, I, L, M, V, Y, and W; $X^{118}$ is selected from F, I, L, M, V, Y, and W; $X^{119}$ is selected from F, I, L, M, V, Y, and W; $X^{120}$ is selected from an amino acid; and $X^{121}$ is selected from H, N, Q, S, T, and Y.

Aspect 202. The IL-2Rγc ligand of aspect 201, wherein $X^{111}$ is selected from an amino acid.

Aspect 203. The IL-2Rγc ligand of any one of aspects 201 to 202, wherein $X^{112}$ is selected from I and L.

Aspect 204. The IL-2Rγc ligand of any one of aspects 201 to 203, wherein $X^{113}$ is selected from an amino acid.

Aspect 205. The IL-2Rγc ligand of any one of aspects 201 to 204, wherein $X^{114}$ is selected from D, E, and S.

Aspect 206. The IL-2Rγc ligand of any one of aspects 201 to 205, wherein $X^{115}$ is L.

Aspect 207. The IL-2Rγc ligand of any one of aspects 201 to 206, wherein $X^{116}$ is selected from D and E.

Aspect 208. The IL-2Rγc ligand of any one of aspects 201 to 207, wherein $X^{117}$ is selected from F and W.

Aspect 209. The IL-2Rγc ligand of any one of aspects 201 to 208, wherein $X^{118}$ is selected from F, W and Y.

Aspect 210. The IL-2Rγc ligand of any one of aspects 201 to 209, wherein $X^{119}$ is selected from F, I, and L.

Aspect 211. The IL-2Rγc ligand of any one of aspects 201 to 210, wherein $X^{120}$ is selected from an amino acid.

Aspect 212. The IL-2Rγc ligand of any one of aspects 201 to 211, wherein $X^{121}$ is selected from Q and N.

Aspect 213. The IL-2Rγc ligand of aspect 201, wherein, $X^{111}$ is selected from an amino acid; $X^{112}$ is selected from I and L; $X^{113}$ is selected from an amino acid; $X^{114}$ is selected from D, E, and S; $X^{115}$ is L; $X^{116}$ is selected from D and E; $X^{117}$ is selected from F and W; $X^{118}$ is selected from F, W and Y; $X^{119}$ is selected from F, I, and L; $X^{120}$ is selected from an amino acid; and $X^{121}$ is selected from Q and N.

Aspect 214. The IL-2Rγc ligand of any one of aspects 74 to 81, wherein the IL-2Rγc ligand comprises an amino acid sequence selected from any one of SEQ ID NO: 255 to SEQ ID NO: 267:

Aspect 215. The IL-2Rγc ligand of aspect 214, wherein the IL-2Rγc ligand comprises an amino acid sequence selected from any one of SEQ ID NO: 255 to SEQ ID NO: 267, wherein the amino acid sequence is terminated with amino acids -G-G on the N-terminus, on the C-terminus, or on both the N- and C-termini.

Aspect 216. The IL-2Rβ ligand of any one of aspects 214 to 215, wherein the IL-2Rβ ligand comprises an amino acid sequence selected from any one of SEQ ID NO: 255 to SEQ ID NO: 267, wherein each amino acid independently comprises one or more of the following conservative substitutions: amino acids having a small hydrophobic side chain comprising alanine (A), glycine (G), proline (P), serine (S) and threonine (T); amino acids having a hydroxyl-containing side chain comprising serine (S) or threonine (T); amino acids having an acidic side chain comprising aspartate (D) and glutamate (E); amino acids having a polar-neutral side chain comprising histidine (H), asparagine (N), glutamine (Q), serine (S), threonine (T), and tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W).

Aspect 217. A pH-selective IL-2Rβ ligand comprising an amino acid sequence selected from a ligand having SEQ ID NO: 400 to SEQ ID NO: 577.

Aspect 218. The pH-selective IL-2Rβ ligand of aspect 217, wherein the pH-selective IL-2Rβ ligand exhibits a greater than 15% decrease in binding to the IL-2Rβ receptor at pH 7.5 compared to pH 6.0.

Aspect 219. The pH-selective IL-2Rβ ligand of aspect 518, wherein the ligand comprises an amino acid sequence selected from a ligand having SEQ ID: NOS: 400, 402-405, 407, 409, 410, 411, 413, 415, 416, 418, 419, 420, 421, 423, 425-432, 436, 438-440, 442-446, 448, 450, 452, 453-456, 459-461, 463-468, 470, 471, 473-477, 479, 481-486, 489, 491, 493-496, 498-507, 510-519, 521-524, 526-531, 534-537, 543, 545-548, 550, 551, 558-564, 566, 568-573, and 575, wherein the pH-selective binding is determined as described in Examples 9-12.

Aspect 220. The pH-selective IL-2Rβ ligand of aspect 217, wherein the pH-selective IL-2Rβ ligand exhibits a greater than 50% decrease in binding to the IL-2Rβ receptor at pH 7.5 compared to pH 6.0.

Aspect 221. The pH-selective IL-2Rβ ligand of aspect 520, wherein the ligand comprises an amino acid sequence selected from a ligand having SEQ ID: NOS: 400, 404-405, 407, 409, 410, 413, 415, 420, 426, 431, 432, 438-440, 442, 444-446, 450, 452, 453, 455, 459, 464-467, 473-475, 479, 480, 482-484, 486, 489, 493, 496, 498, 502, 504, 510-514, 516-519, 521-523, 527-530, 537, 543, 545-547, 550, 558-564, 571-573, and 575, where the pH-selective binding is determined as described in Examples 9-12.

Aspect 222. The pH-selective IL-2Rβ ligand of any one of aspects 217 to 221, wherein the pH-selective IL-2Rβ ligand comprises an amino acid sequence selected from any one of SEQ ID NO: 400 to SEQ ID NO: 577, wherein the amino acid sequence is terminated with amino acids -G-G on the N-terminus, on the C-terminus, or on both the N- and C-termini.

Aspect 223. The pH-selective IL-2Rβ ligand of any one of aspects 217 to 222, wherein the pH-selective IL-2Rβ ligand an amino acid sequence selected from any one of SEQ ID NO: 400 to SEQ ID NO: 577, wherein each amino acid independently comprises one or more of the following conservative substitutions: amino acids having a small hydrophobic side chain comprising alanine (A), glycine (G), proline (P), serine (S) and threonine (T); amino acids having a hydroxyl-containing side chain comprising serine (S) or threonine (T); amino acids having an acidic side chain comprising aspartate (D) and glutamate (E); amino acids having a polar-neutral side chain comprising histidine (H), asparagine (N), glutamine (Q), serine (S), threonine (T), and tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W).

Aspect 224. The pH-selective IL-2Rβ ligand of any one of aspects 217 to 223, wherein the pH-selective IL-2Rβ ligand comprises from 5 to 30 amino acids.

Aspect 225. The pH-selective IL-2Rβ ligand of any one of aspects 217 to 224, wherein the pH-selective IL-2Rβ ligand exhibits a binding affinity ($IC_{50}$) to the human IL-2Rβ subunit at pH 6.0 from 1 μM to 100 μM.

Aspect 226. The pH-selective IL-2Rβ ligand of any one of aspects 217 to 224, wherein the pH-selective IL-2Rβ ligand exhibits a binding affinity ($IC_{50}$) to the human IL-2Rβ subunit at pH 6.0 from 0.1 μM to 50 μM.

Aspect 227. The pH-selective IL-2Rβ ligand of any one of aspects 217 to 224, wherein the pH-selective IL-2Rβ ligand exhibits a binding affinity ($IC_{50}$) to the human IL-2Rβ subunit at pH 6.0 of less than 100 μM.

Aspect 228. The pH-selective IL-2Rβ ligand of any one of aspects 217 to 224, wherein the pH-selective IL-2Rβ ligand exhibits a binding affinity ($IC_{50}$) to a mammalian IL-2Rβ subunit at pH 6.0 of less than 100 μM.

Aspect 229. The pH-selective IL-2Rβ ligand of any one of aspects 217 to 228, wherein the pH-selective IL-2Rβ ligand exhibits a binding affinity ($IC_{50}$) to each of the human IL-2Rβ subunit and to the human IL-2Rγc subunit of less than 100 μM.

Aspect 230. The pH-selective IL-2Rβ ligand of any one of aspects 217 to 229, wherein the pH-selective IL-2Rβ ligand exhibits a binding affinity ($IC_{50}$) to the human IL-2Rα (CD25) subunit of greater than 100 μM.

Aspect 231. The pH-selective IL-2Rβ ligand of any one of aspects 217 to 230, wherein the pH-selective IL-2Rβ ligand exhibits a binding affinity ($IC_{50}$) to the human IL-2Rβ subunit that is at least 10 times greater than the binding affinity ($IC_{50}$) of the IL-2Rβ ligand to the human IL-2Rα subunit.

Aspect 232. A compound comprising: an IL-2Rβ ligand of any one of aspects 1 to 73 and 217 t0 231; an IL-2Rγc ligand of any one of aspects 74 to 216; or an IL-2Rβ ligand of any one of aspects 1 to 73 and an IL-2Rγc ligand of any one of aspects 74 to 216.

Aspect 233. The compound of aspect 232, wherein the compound is selected from a peptide, a conjugate, a fusion protein, and a single chain peptide.

Aspect 234. The compound of aspect 233, wherein the compound is a peptide.

Aspect 235. The compound of aspect 234, wherein the peptide has a molecular weight within a range from 500 Daltons to 15,000 Daltons.

Aspect 236. The compound of any one of aspects 234 to 235, wherein the peptide comprises from 5 to 5,000 amino acids.

Aspect 237. The compound of aspect 233, wherein the compound comprises a conjugate.

Aspect 238. The compound of aspect 237, wherein the conjugate comprises at least one IL-2Rβ ligand.

Aspect 239. The compound of aspect 237, wherein the conjugate comprises: at least two IL-2Rβ ligands; and at least one linker attached to each of the at least two IL-2Rβ ligands.

Aspect 240. The compound of any one of aspects 237 to 239, wherein the conjugate comprises a least one IL-2Rγc ligand.

Aspect 241. The compound of aspect 237, wherein the conjugate comprises: at least two IL-2Rγc ligands; and at least one linker attached to each of the at least two IL-2Rγc ligands.

Aspect 242. The compound of aspect 237, wherein the conjugate comprises: at least one IL-2Rβ ligand; at least one IL-2Rγc ligand; and at least one linker attached to the at least one IL-2Rβ ligand and to the at least one IL-2Rγc ligand.

Aspect 243. The compound of any one of aspects 237 to 228, wherein the conjugate comprises at least one moiety, amino acid, or polypeptide configured to modify a property of the conjugate.

Aspect 244. The compound of aspect 243, wherein the property is selected from aqueous solubility, polarity, lipophilicity, pharmacokinetic profile, targeting, bioavailability, pH-dependent binding, and caging (reversible incapacitation).

Aspect 245. The compound of any one of aspects 243 to 244, wherein the at least one moiety is cleavable in vivo.

Aspect 246. The compound of any one of aspects 243 to 245, wherein the at least one moiety comprises an irreversibly cleavable promoiety.

Aspect 247. The compound of aspect 246, wherein the promoiety is configured to be releasable in a target-specific environment.

Aspect 248. The compound of aspect 247, wherein the target-specific environment comprises an enzyme, pH, or a combination thereof.

Aspect 249. The compound of aspect 248, wherein the moiety comprises a polymer, a peptide, an antibody, or a combination of any of the foregoing Aspect 250. The compound of aspect 243, comprising a pharmacokinetic moiety.

Aspect 251. The compound of aspect 250, wherein the pharmacokinetic moiety comprises a polyethylene glycol.

Aspect 252. The compound of aspect 243, comprising a tumor-targeting moiety.

Aspect 253. The compound of aspect 252, wherein the tumor-targeting moiety comprises a tumor-specific antibody, a tumor-specific antibody fragment, a tumor-specific protein, a tumor-specific peptide, or a combination of any of the foregoing.

Aspect 254. The compound of aspect 232, comprising a linker covalently bound to the IL-2Rβ ligand, an IL-2Rγc ligand, or a combination thereof.

Aspect 255. The compound of aspect 254, wherein the linker is a peptide having from 5 to 50 amino acids.

Aspect 256. The compound of aspect 254, wherein the linker comprises a polyethylene glycol.

Aspect 257. The compound of aspect 232, wherein the compound comprises a heterodimer, wherein the heterodimer comprises: an IL-2Rβ ligand; an IL-2Rγc ligand; and a linker; wherein each of the IL-2Rβ ligand and the IL-2Rγc ligand comprise an amino-terminus (N-terminus), a carboxy terminus (C-terminus), and an amino acid side chain; wherein the IL-2Rβ ligand is attached to the linker through the amino-terminus (N-terminus), the carboxy terminus (C-terminus), an amino acid side chain, or a combination of any of the foregoing; and wherein the IL-2Rγc ligand is attached to the linker through the amino-terminus (N-terminus), the carboxy terminus (C-terminus), an amino acid side chain, or a combination of any of the foregoing.

Aspect 258. The compound of aspect 232, wherein the conjugate comprises a heterodimer, wherein the heterodimer comprises: an IL-2Rβ ligand; an IL-2Rγc ligand; and a linker; wherein each of the IL-2Rβ ligand and the IL-2Rγc ligand comprise an amino-terminus (N-terminus) and a carboxy terminus (C-terminus); and wherein each of the IL-2Rβ ligand and the IL-2Rγc ligand is covalently bound to the linker.

Aspect 259. The compound of aspect 258, wherein each of the IL-2Rβ ligand and the IL-2Rγc ligand is covalently bound to the linker through the respective C-termini.

Aspect 260. The compound of aspect 258, wherein, the N-terminus of the IL-2Rβ ligand is covalently bound to the linker; and the C-terminus of the IL-2Rγc ligand is covalently bound to the linker.

Aspect 261. The compound of aspect 258, wherein, the C-terminus of the IL-2Rβ ligand is covalently bound to the linker; and the N-terminus of the IL-2Rγc ligand is covalently bound to the linker.

Aspect 262. The compound of aspect 258, wherein, the IL-2Rβ ligand is covalently bound to the linker through an amino acid side chain; and the IL-2Rγc ligand is covalently bound to the linker through an amino acid side chain.

Aspect 263. The compound of aspect 258, wherein, the IL-2Rβ ligand is covalently bound to the linker through an amino acid side chain, through the C-terminus, or through the N-terminus; and the IL-2Rγc ligand is covalently bound to the linker through an amino acid side chain, through the C-terminus, or through the N-terminus.

Aspect 264. The compound of aspect 258, wherein the heterodimer is configured to activate the IL-2 receptor.

Aspect 265. The compound of aspect 258, wherein the linker is configured such that the heterodimer activates the IL-2 receptor.

Aspect 266. The compound of any one of aspects 258 to 265, wherein, when incubated with the heterodimer, primary human peripheral blood mononuclear cells (PBMC) expressing the human IL-2Rβγc subunit, phosphorylate transcription 5 (STAT5).

Aspect 267. The compound of any one of aspects 258 to 266, wherein, when incubated with the heterodimer, primary human peripheral blood mononuclear cells (PBMC) expressing the human IL-2Rα [CD25] subunit, do not phosphorylate transcription 5 (STAT5).

Aspect 268. The compound of any one of aspects 258 to 267, wherein the heterodimer comprises a conformation configured to activate human IL-2Rβγc signaling pathways.

Aspect 269. The compound of aspect 232, wherein the compound comprises a single chain peptide.

Aspect 270. The compound of aspect 269, wherein the single chain peptide comprises at least one IL-2Rβ ligand.

Aspect 271. The compound of aspect 269, wherein the single chain peptide comprises: at least two IL-2Rβ ligands; and at least one linker attached to the at least two IL-2Rβ ligands.

Aspect 272. The compound of aspect 269, wherein the single chain peptide comprises a least one IL-2Rγc ligand.

Aspect 273. The compound of aspect 269, wherein the single chain peptide comprises: at least two IL-2Rγc ligands; and at least one linker attached to the at least two IL-2Rγc ligands.

Aspect 274. The compound of aspect 269, wherein the single chain peptide comprises: at least one IL-2Rβ ligand; at least one IL-2Rγc ligand; and at least one linker attached to the at least one IL-2Rβ ligand and to the at least one IL-2Rγc ligand.

Aspect 275. The compound of aspect 232, wherein the compound is a fusion protein.

Aspect 276. The compound of aspect 275, wherein the fusion protein comprises: an IL-2Rβ ligand; an IL-2Rγc ligand; and a peptide linker domain, wherein the peptide linker domain is bound to the IL-2Rβ ligand and to the IL-2Rγc ligand.

Aspect 277. The compound of aspect 275, wherein, each domain has an amino-terminus (N-terminus) and a carboxy terminus (C-terminus); and wherein the fusion protein is configured so that the C-terminus and the human IL-2 variant protein domain is fused through a peptide bond to the N-terminus of the peptide linker domain, and the N-terminus of the peptide linker domain, and the N-terminus of the IgG Fc protein domain is fused through a peptide bond to the C-terminus of the peptide linker domain.

Aspect 278. A nucleic acid encoding the fusion protein of aspect 275.

Aspect 279. The compound of aspect 232, wherein the compound comprises a label.

Aspect 280. The compound of aspect 279, wherein the label is selected from a radioisotope, a fluorophore, or a combination thereof.

Aspect 281. The compound of aspect 232, wherein the compound comprises a cage to protect peripheral tissues for the toxicity of IL-2R activation.

Aspect 282. The compound of aspect 232, wherein the compound comprises a prodrug.

Aspect 283. The compound of aspect 282, wherein the compound comprises a moiety configured to sustain a circulating reservoir of the prodrug.

Aspect 284. The compound of aspect 232, wherein the compound comprises a moiety configured to target the IL-2R-directed immuno-stimulation of the effector immune cells in the tumor.

Aspect 285. A pharmaceutical composition comprising; the IL-2Rβ ligand of any one of aspects 1 to 73 and 217 to 231; the IL-2Rγc ligand of any one of aspects 74 to 216; the compound of any one of aspects 232 to 284; or a combination of any of the foregoing.

Aspect 286. A method of treating cancer in a patient, comprising administering to a patient in need of such treatment, a therapeutically effective amount of the pharmaceutical composition of aspect 270.

Aspect 287. A method of treating cancer in a patient, comprising administering to a patient in need of such treatment, a therapeutically effective amount of; the IL-2Rβ ligand of any one of aspects 1 to 73 and 217 to 231; the IL-2Rγc ligand of any one of aspects 74 to 216; the compound of any one of aspects 232 to 284; or a combination of any of the foregoing.

Aspect 288. The method of aspect 287, wherein the cancer comprises a solid tumor.

Aspect 289. A method of treating an autoimmune disease in a patient, comprising administering to a patient in need of such treatment, a therapeutically effective amount of the pharmaceutical composition of aspect 285.

Aspect 290. A method of treating an autoimmune disease in a patient, comprising administering to a patient in need of such treatment, a therapeutically effective amount of; the IL-2Rβ ligand of any one of aspects 1 to 73 and 217 to 231; the IL-2Rγc ligand of any one of aspects 74 to 216; the compound of any one of aspects 232 to 284; or a combination of any of the foregoing.

Aspect 291. A method of screening compounds for IL-2 receptor activity, comprising: contacting a cell with, the IL-2Rβ ligand of any one of aspects 1 to 73 and 217 to 231; the IL-2Rγc ligand of any one of aspects 74 to 216; the compound of any one of aspects 232 to 284; or a combination of any of the foregoing; wherein the cell expresses the IL-2 receptor; and contacting the cell with a test compound; and determining the activity of the test compound.

Aspect 292. A method of activating the human IL-2Rβ subunit, the human IL-2Rγc subunit, or both the human IL-2Rβ subunit and the human IL-2Rγc subunit, comprising contacting a cell expressing the IL-2 receptor in vivo with: the IL-2Rβ ligand of any one of aspects 1 to 73 and 217 to 231; the IL-2Rγc ligand of any one of aspects 74 to 216; the compound of any one of aspects 232 to 284; or a combination of any of the foregoing.

Aspect 293. A method of activating the human IL-2Rβ subunit and the human IL-2Rγc subunit in a patient, comprising administering to a patient an effective amount of: the IL-2Rβ ligand of any one of aspects 1 to 73 and 217 to 231; the IL-2Rγc ligand of any one of aspects 74 to 216; the compound of any one of aspects 232 to 284; or a combination of any of the foregoing.

Aspect 294. A method of treating a disease in a patient, wherein the IL-2 receptor signaling pathway is associated with the etiology of the disease, comprising administering to a patient in need of such treatment a therapeutically effective amount of: the IL-2Rβ ligand of any one of aspects 1 to 73 and 217 to 231; the IL-2Rγc ligand of any one of aspects 74 to 216; the compound of any one of aspects 232 to 284; or a combination of any of the foregoing.

Aspect 295. A method of treating a disease in a patient, wherein activation of the IL-2 receptor is effective in treating the disease, comprising administering to a patient in need of such treatment a therapeutically effective amount of: the IL-2Rβ ligand of any one of aspects 1 to 73 and 217 to 231; the IL-2Rγc ligand of any one of aspects 74 to 216; the compound of any one of aspects 232 to 284; or a combination of any of the foregoing.

Aspect 1A. An IL-2Rβ ligand, wherein the IL-2Rβ ligand exhibits a binding affinity ($IC_{50}$) to the human IL-2Rβ subunit of less than 100 μM.

Aspect 2A. The IL-2Rβ ligand of aspect 1A, wherein the IL-2Rβ ligand comprises from 5 to 30 amino acids.

Aspect 3A. The IL-2Rβ ligand of any one of aspects 1A to 2A, wherein the IL-2Rβ ligand exhibits a binding affinity ($IC_{50}$) to the human IL-2Rβ subunit from 1 μM to 100 μM.

Aspect 4A. The IL-2Rβ ligand of any one of aspects 1A to 2A, wherein the IL-2Rβ ligand exhibits a binding affinity ($IC_{50}$) to the human IL-2Rβ subunit from 0.1 μM to 50 μM.

Aspect 5A. The IL-2Rβ ligand of any one of aspects 1A to 2A, wherein the IL-2Rβ ligand exhibits a binding affinity ($IC_{50}$) to the human IL-2Rβ subunit of less than 100 μM.

Aspect 6A. The IL-2Rβ ligand of any one of aspects 1A to 2A, wherein the IL-2Rβ ligand exhibits a binding affinity ($IC_{50}$) to a mammalian IL-2Rβ subunit of less than 100 μM.

Aspect 7A. The IL-2Rβ ligand of any one of aspects 1A to 6A, wherein the IL-2Rβ ligand exhibits a binding affinity ($IC_{50}$) to each of the human IL-2Rβ subunit and to the human IL-2Rγc subunit of less than 100 μM.

Aspect 8A. The IL-2Rβ ligand of any one of aspects 1A to 7A, wherein the IL-2Rβ ligand exhibits a binding affinity ($IC_{50}$) to the human IL-2Rα (CD25) subunit of greater than 100 μM.

Aspect 9A. The IL-2Rβ ligand of any one of aspects 1A to 7A, wherein the IL-2Rβ ligand exhibits a binding affinity ($IC_{50}$) to the human IL-2Rβ subunit that is at least 10 times greater than the binding affinity ($IC_{50}$) of the IL-2Rβ ligand to the human IL-2Rα subunit.

Aspect 10A. The IL-2Rβ ligand of any one of aspects 1A to 9A, wherein the IL-2Rβ ligand comprises the amino acid sequence of Formula (1) (SEQ ID NO: 1), the amino acid sequence of Formula (1a) (SEQ ID NO: 2), or the amino acid sequence of Formula (1b) (SEQ ID NO: 3):

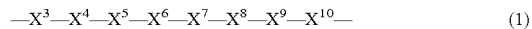

$$—X^3—X^4—X^5—X^6—X^7—X^8—X^9—X^{10}— \quad (1)$$

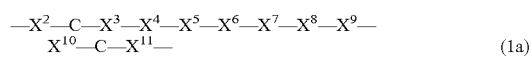

$$—X^2—C—X^3—X^4—X^5—X^6—X^7—X^8—X^9—X^{10}—C—X^{11}— \quad (1a)$$

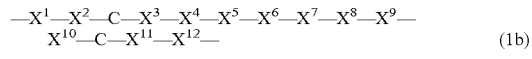

$$—X^1—X^2—C—X^3—X^4—X^5—X^6—X^7—X^8—X^9—X^{10}—C—X^{11}—X^{12}— \quad (1b)$$

wherein, $X^1$ is selected from A, D, E, F, G, I, K, L, M, N, P, Q, S, T, V, W, and Y; $X^2$ is selected from A, C, D, E, F, G, H, K, L, N, P, R, S, T, W, and Y; $X^3$ is selected from A, D, E, F, G, H, M, N, Q, R, S, T, W, and Y; $X^4$ is selected from A, D, E, F, G, I, K, L, M, N, Q, R, S, T, V, and Y; $X^5$ is selected from A, G, I, Q, S, T, V, and W; $X^6$ is selected from A, D, E, G, H, K, L, M, N, P, Q, R, S, T, and V; $X^7$ is selected from F, I, K, L, Q, and V; $X^8$ is selected from D, F, G, H, M, N, W, and Y; $X^9$ is selected from A, D, E, M, P, Q, S, T, V, and W; $X^{10}$ is selected from D, F, I, L, M, S, T, V, and Y; $X^{11}$ is selected from D, E, F, H, I, L, M, Q, S, T, V, W, and Y; and $X^{12}$ is selected from F, I, L, M, N, S, V, W, and Y.

Aspect 11A. The IL-2Rβ ligand of aspect 10A, wherein $X^1$ is selected from F, I, L, M, and V.

Aspect 12A. The IL-2Rβ ligand of any one of aspects 10A to 11A, wherein $X^2$ is selected from D, E, F, G, H, L, N, P, R, S, T, W, and Y.

Aspect 13A. The IL-2Rβ ligand of any one of aspects 10A to 12A, wherein $X^5$ is A.

Aspect 14A. The IL-2Rβ ligand of any one of aspects 10A to 13A, wherein $X^6$ is selected from D, E, and Q.

Aspect 15A. The IL-2Rβ ligand of any one of aspects 10A to 14A, wherein $X^7$ is selected from F, I, L, and V.

Aspect 16A. The IL-2Rβ ligand of any one of aspects 10A to 15A, wherein $X^8$ is G.

Aspect 17A. The IL-2Rβ ligand of any one of aspects 10A to 16A, wherein $X^9$ is selected from D, E, and Q.

Aspect 18A. The IL-2Rβ ligand of any one of aspects 10A to 17A, wherein $X^{10}$ is selected from F, I, L, M, V, and Y.

Aspect 19A. The IL-2Rβ ligand of any one of aspects 10A to 18A, wherein $X^{11}$ is selected from D and E.

Aspect 20 Å. The IL-2Rβ ligand of any one of aspects 10A to 19A, wherein $X^{12}$ is selected from F, I, L, M, and V.

Aspect 21A. The IL-2Rβ ligand of aspect 10A, wherein, $X^1$ is selected from F, I, L, M, and V; $X^2$ is selected from D, E, F, G, H, L, N, P, R, S, T, W, and Y; $X^3$ is selected from A, D, E, F, G, H, M, N, Q, R, S, T, W, and Y; $X^4$ is selected from A, D, E, F, G, I, K, L, M, N, Q, R, S, T, V, and Y; $X^5$ is A; $X^6$ is selected from D, E, and Q; $X^7$ is selected from F, I, L, and V; $X^8$ is G; $X^9$ is selected from D, E, and Q; $X^{10}$ is selected from F, I, L, M, V, and Y; $X^{11}$ is selected from D and E; and $X^{12}$ is selected from F, I, L, M, and V.

Aspect 22A. The IL-2Rβ ligand of any one of aspects 1A to 9A, wherein the IL-2Rβ ligand comprises the amino acid sequence of Formula (1) (SEQ ID NO: 1052), the amino acid sequence of Formula (1a) (SEQ ID NO: 1053), or the amino acid sequence of Formula (1b) (SEQ ID NO: 1054):

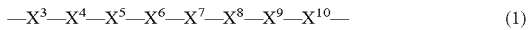

(1)

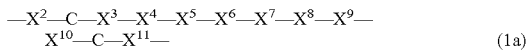

(1a)

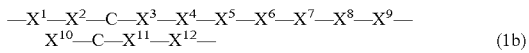

(1b)

wherein, $X^1$ is selected from an amino acid; $X^2$ is selected from an amino acid; $X^3$ is selected from an amino acid; $X^4$ is selected from an amino acid; $X^5$ is selected from an amino acid comprising a small hydrophobic side chain; $X^6$ is selected from an amino acid; $X^7$ is selected from an amino acid comprising a large hydrophobic side chain; $X^8$ is selected from an amino acid comprising a small hydrophobic side chain; $X^9$ is selected from an amino acid comprising a polar-neutral or an acidic side chain; $X^{10}$ is selected from an amino acid comprising a large hydrophobic side chain; $X^{11}$ is selected from an amino acid; and $X^{12}$ is selected from an amino acid comprising a large hydrophobic side chain.

Aspect 23A. The IL-2Rβ ligand of aspect 22A, wherein, $X^1$ is selected from an amino acid comprising a large hydrophobic side chain; $X^2$ is selected from an amino acid; $X^3$ is selected from an amino acid; $X^4$ is selected from an amino acid; $X^5$ is selected from an amino acid comprising a small hydrophobic side chain; $X^6$ is selected from an amino acid comprising a polar-neutral or an acidic side chain; $X^7$ is selected from an amino acid comprising a large hydrophobic side chain; $X^8$ is selected from an amino acid comprising a small hydrophobic side chain; $X^9$ is selected from an amino acid comprising a polar-neutral or an acidic side chain; $X^{10}$ is selected from an amino acid comprising a large hydrophobic side chain; $X^{11}$ is selected from an amino acid comprising a polar-neutral or an acidic side chain; and $X^{12}$ is selected from an amino acid comprising a large hydrophobic side chain.

Aspect 24A. The IL-2Rβ ligand of any one of aspects 22A to 23A, wherein, $X^1$ is selected from I, L, M, V, F, W, and Y; $X^2$ is selected from an amino acid; $X^3$ is selected from an amino acid; $X^4$ is selected from an amino acid; $X^5$ is selected from A, G, P, S, and T; $X^6$ is selected from H, N, Q, S, T, Y, D, and E; $X^7$ is selected from I, L, M, V, F, W, and Y; $X^8$ is selected from A, G, P, S, and T; $X^9$ is selected from H, N, Q, S, T, Y, D, and E; $X^{10}$ is selected from I, L, M, V, F, W, and Y; $X^{11}$ is selected from H, N, Q, S, T, Y, D, and E; and $X^{12}$ is selected from I, L, M, V, F, W, and Y.

Aspect 25A. The IL-2Rβ ligand of any one of aspects 22A to 23A, wherein, $X^1$ is selected from I, L, M, V, F, W, and Y; $X^2$ is selected from an amino acid; $X^3$ is selected from an amino acid; $X^4$ is selected from an amino acid; $X^5$ is A; $X^6$ is selected from H, N, Q, S, T, Y, D, and E; $X^7$ is selected from I, L, M, V, F, W, and Y; $X^8$ is G; $X^9$ is selected from H, N, Q, S, T, Y, D, and E; $X^{10}$ is selected from I, L, M, V, F, W, and Y; $X^{11}$ is selected from H, N, Q, S, T, Y, D, and E; and $X^{12}$ is selected from I, L, M, V, F, W, and Y.

Aspect 26A. The IL-2Rβ ligand of aspect 25A, wherein $X^1$ is selected from I, L, M, and V.

Aspect 27A. The IL-2Rβ ligand of any one of aspects 25A to 26A, wherein $X^2$ is selected from D and E.

Aspect 28A. The IL-2Rβ ligand of any one of aspects 25A to 27A, wherein $X^6$ is selected from Q, E, and D.

Aspect 29A. The IL-2Rβ ligand of any one of aspects 25A to 28A, wherein $X^7$ is selected from V, L, and I.

Aspect 30A. The IL-2Rβ ligand of any one of aspects 25A to 29A, wherein $X^9$ is selected from E, D, and Q.

Aspect 31A. The IL-2Rβ ligand of any one of aspects 25A to 30A, wherein $X^{10}$ is selected from L, V, I, and Y.

Aspect 32A. The IL-2Rβ ligand of any one of aspects 25A to 31A, wherein $X^{11}$ is selected from D and E.

Aspect 33A. The IL-2Rβ ligand of any one of aspects 25A to 32A, wherein $X^{12}$ is selected from L, I, and F.

Aspect 34A. The IL-2Rβ ligand of aspect 25A, wherein, $X^1$ is selected from L, I, F, and V; $X^2$ is selected from D and E; $X^6$ is selected from Q, E, and D; $X^7$ is selected from V, L, and I; $X^9$ is selected from E, D, and Q; $X^{10}$ is selected from L, V, I, and Y; $X^{11}$ is selected from D and E; and $X^{12}$ is selected from L, I, and F.

Aspect 35A. The IL-2Rβ ligand of aspect 25A, wherein, $X^1$ is selected from F, I, M, and Y; $X^2$ is selected from E, D, and R; $X^3$ is selected from and amino acid; $X^4$ is selected from an amino acid; $X^5$ is A; $X^6$ is selected from A, P, and Q; $X^7$ is selected from I and V; $X^8$ is G; $X^9$ is selected from E and Q; $X^{10}$ is selected from I, L, and V; $X^{11}$ is selected from E, D, and Q; and $X^{12}$ is selected from I and L.

Aspect 36A. The IL-2Rβ ligand of aspect 22A, wherein the IL-2Rβ ligand comprises an amino acid sequence selected from any one of SEQ ID NO: 4 to SEQ ID NO: 163:

Aspect 37A. The IL-2Rβ ligand of aspect 36A, wherein the IL-2Rβ ligand comprises an amino acid sequence selected from any one of SEQ ID NO: 4 to SEQ ID NO: 163, wherein the amino acid sequence is terminated with amino acids -G-G- on the N-terminus, on the C-terminus, or on both the N- and C-termini.

Aspect 38A. The IL-2Rβ ligand of any one of aspects 36A to 37A, wherein the IL-2Rβ ligand comprises an amino acid sequence selected from any one of SEQ ID NO: 4 to SEQ ID NO: 163, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

Aspect 39A. The IL-2Rβ ligand of any one of aspects 1A to 9A, wherein the IL-2Rβ ligand comprises the amino acid sequence of Formula (2) (SEQ ID NO: 164), the amino acid sequence of Formula (2a) (SEQ ID NO: 165), or the amino acid sequence of Formula (2b) (SEQ ID NO: 166):

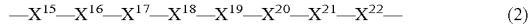

(2)

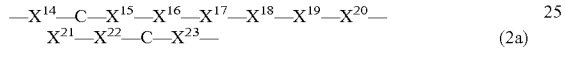

(2a)

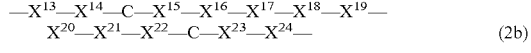

(2b)

wherein, $X^3$ is selected from A, D, E, G, N, Q, R, and V; $X^4$ is selected from E, F, I, L, M, and Q; $X^5$ is selected from D, G, L, and N; $X^{16}$ is selected from L, P, V, and Y; $X^{17}$ is selected from F, G, and M; $X^{18}$ is selected from A, D, N, and Q; $X^{19}$ is selected from F, I, L, S, V, W, and Y; $X^{20}$ is selected from D and W; $X^{21}$ is selected from P and Y; $X^{22}$ is selected from A, D, Q, and S; $X^{23}$ is selected from I, L, Q, W, and Y; and $X^{24}$ is selected from E, F, I, L, T, V, and W.

Aspect 40A. The IL-2Rβ ligand of aspect 39A, wherein $X^{16}$ is V.

Aspect 41A. The IL-2Rβ ligand of any one of aspects 39A to 40A, wherein $X^{17}$ is G.

Aspect 42A. The IL-2Rβ ligand of any one of aspects 39A to 41A, wherein $X^{20}$ is W.

Aspect 43A. The IL-2Rβ ligand of any one of aspects 39A to 42A, wherein $X^{21}$ is P.

Aspect 44A. The IL-2Rβ ligand of aspect 39A, wherein, $X^{13}$ is selected from E, N, and Q; $X^{14}$ is selected from I and M; $X^{15}$ is selected from D, L, and N; $X^{16}$ is V; $X^{17}$ is G; $X^{18}$ is selected from D and Q; $X^{19}$ is selected from V, W, and Y; $X^{20}$ is W; $X^{21}$ is P; $X^{22}$ is selected from D and S; $X^{23}$ is selected from L and Q; and $X^{24}$ is selected from I, L, and V.

Aspect 45A. The IL-2Rβ ligand of aspect 39A, wherein the IL-2Rβ ligand comprises an amino acid sequence selected from any one of SEQ ID NO: 167 to SEQ ID NO: 182.

Aspect 46A. The IL-2Rβ ligand of aspect 45A, wherein the IL-2Rβ ligand comprises an amino acid sequence selected from any one of SEQ ID NO: 167 to SEQ ID NO: 182, wherein the amino acid sequence is terminated with amino acids -G-G- on the N-terminus, on the C-terminus, or on both the N- and C-termini.

Aspect 47A. The IL-2Rβ ligand of any one of aspects 45A to 46A, wherein the IL-2Rβ ligand comprises an amino acid sequence selected from any one of SEQ ID NO: 167 to SEQ ID NO: 182, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

Aspect 48A. The IL-2Rβ ligand of any one of aspects 1A to 9A, wherein the IL-2Rβ ligand comprises the amino acid sequence of Formula (2) (SEQ ID NO: 1058), the amino acid sequence of Formula (2a) (SEQ ID NO: 1059), or the amino acid sequence of Formula (2b) (SEQ ID NO: 1060):

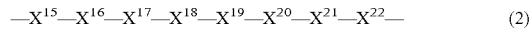

(2)

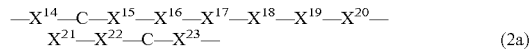

(2a)

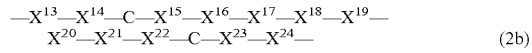

(2b)

wherein, $X^{13}$ is selected from an amino acid; $X^{14}$ is selected from an amino acid comprising a large hydrophobic side chain; $X^{15}$ is selected from an amino acid; $X^{16}$ is selected from an amino acid comprising a large hydrophobic side chain; $X^{17}$ is selected from an amino acid comprising a small hydrophobic side chain; $X^{18}$ is selected from an amino acid; $X^{19}$ is selected from an amino acid; $X^{20}$ is selected from an amino acid comprising a large hydrophobic side chain; $X^{21}$ is elected from an amino acid comprising a small hydrophobic side chain; $X^{22}$ is selected from an amino acid; $X^{23}$ is selected from an amino acid; and $X^{24}$ is selected from an amino acid comprising a large hydrophobic side chain.

Aspect 49A. The IL-2Rβ ligand of aspect 48A, wherein, $X^{13}$ is selected from an amino acid; $X^{14}$ is selected from an amino acid comprising a large hydrophobic side chain; $X^{15}$ is selected from an amino acid; $X^{16}$ is selected from an amino acid comprising a large hydrophobic side chain; $X^{17}$ is selected from an amino acid comprising a small hydrophobic side chain; $X^{18}$ is selected from an amino acid comprising a polar-neutral or an acidic side chain; $X^{19}$ is selected from an amino acid comprising large hydrophobic or neutral side chain; $X^{20}$ is selected from an amino acid comprising a large hydrophobic side chain; $X^{21}$ is selected from an amino acid comprising a small hydrophobic side chain; $X^{22}$ is selected from an amino acid; $X^{23}$ is selected from an amino acid; and $X^{24}$ is selected from an amino acid comprising a large hydrophobic side chain.

Aspect 50A. The IL-2Rβ ligand of any one of aspects 48A to 49A, wherein, $X^{13}$ is selected from an amino acid; $X^{14}$ is selected from I, L, M, V, F, W, and Y; $X^{15}$ is selected from D, E, I, L, M, V, F, Y, and W; $X^{16}$ is selected from I, L, M, N, V, F, Y, and W; $X^{17}$ is selected from A, G, P, S, and T; $X^{18}$ is selected from H, N, Q, S, T, Y, D, and E; $X^{19}$ is selected from I, L, M, V, F, W, and Y; $X^{20}$ is selected from I, L, M, N, V, F, Y, and W; $X^{21}$ is selected from A, G, P, S, and T; $X^{22}$ is selected from an amino acid; $X^{23}$ is selected from an amino acid; and $X^{24}$ is selected from I, L, M, V, F, W, and Y.

Aspect 51A. The IL-2Rβ ligand of aspect 50A, wherein $X^{14}$ is selected from I and M.

Aspect 52A. The IL-2Rβ ligand of any one of aspects 50A to 51A, wherein $X^{16}$ is V.

Aspect 53A. The IL-2Rβ ligand of any one of aspects 50A to 52A, wherein $X^{17}$ is G.

Aspect 54A. The IL-2Rβ ligand of any one of aspects 50A to 53A, wherein $X^{18}$ is selected from D and Q.

Aspect 55A. The IL-2Rβ ligand of any one of aspects 50A to 54A, wherein $X^{20}$ is W.

Aspect 56A. The IL-2Rβ ligand of any one of aspects 50A to 55A, wherein $X^{21}$ is P.

Aspect 57A. The IL-2Rβ ligand of any one of aspects 50A to 56A, wherein $X^{23}$ is selected from F, I, L, and V.

Aspect 58A. The IL-2Rβ ligand of aspect 50A, wherein, $X^{13}$ is selected from an amino acid; $X^{14}$ is selected from I and M; $X^{15}$ is selected from an amino acid; $X^{16}$ is V; $X^{17}$ is G; $X^{18}$ is selected from D and Q; $X^{19}$ is selected from I, L, M, V, F, W, and Y; $X^{20}$ is W; $X^{21}$ is P; $X^{22}$ is selected from an amino acid; $X^2$ is selected from an amino acid; and $X^{24}$ is selected from F, I, L, and V.

Aspect 59A. The IL-2Rβ ligand of any one of aspects 1A to 9A, wherein the IL-2Rβ ligand comprises the amino acid sequence of Formula (3) (SEQ ID NO: 183) or the amino acid sequence of Formula (3a) (SEQ ID NO: 184):

$$-X^{26}-X^{27}-X^2-X^{29}-X^{30}-X^{31}-X^{32}-X^{33}-X^{34}-X^{35}- \quad (3)$$

$$-X^{25}-C-X^{26}-X^{27}-X^{28}-X^{29}-X^{30}-X^{31}-X^{32}-X^{33}-X^{34}-X^{35}-C-X^{36}- \quad (3a)$$

wherein, $X^{25}$ is selected from an amino acid; $X^{26}$ is selected from an amino acid; $X^{27}$ is selected from I and V; $X^{28}$ is G; $X^{29}$ is selected from D, E, and N; $X^{30}$ is selected from F, L, and Y; $X^{31}$ is selected from F, I, and V; $X^{32}$ is selected from D and Q; $X^{33}$ is selected from an amino acid; $X^{34}$ is selected from an amino acid; $X^{35}$ is selected from an amino acid; and $X^{36}$ is selected from an amino acid.

Aspect 60A. The IL-2Rβ ligand of aspect 59A, wherein, $X^{25}$ is selected from L, S, T, and Y; $X^{26}$ is selected from H and Q; $X^{27}$ is selected from I and V; $X^{28}$ is G; $X^{29}$ is selected from D, E, and N; $X^{30}$ is selected from F, L, and Y; $X^{31}$ is selected from F, I, and V; $X^{32}$ is selected from D and Q; $X^{33}$ is selected from D, L, and W; $X^{34}$ is selected from G, L, and T; $X^{35}$ is selected from D, I, and S; and $X^{36}$ is selected from A and M.

Aspect 61A. The IL-2Rβ ligand of any one of aspects 1A to 9A, wherein the IL-2Rβ ligand comprises the amino acid sequence of Formula (3) (SEQ ID NO: 1061) or the amino acid sequence of Formula (3a) (SEQ ID NO: 1062):

$$-X^{26}-X^{27}-X^2-X^{29}-X^{30}-X^{31}-X^{32}-X^{33}-X^{34}-X^{35}- \quad (3)$$

$$-X^{25}-C-X^{26}-X^{27}-X^{28}-X^{29}-X^{30}-X^{31}-X^{32}-X^{33}-X^{34}-X^{35}-C-X^{36}- \quad (3a)$$

wherein, $X^{25}$ is selected from an amino acid; $X^{26}$ is selected from an amino acid; $X^{27}$ is selected from an amino acid comprising a large hydrophobic side chain; $X^{28}$ is selected from an amino acid comprising a small hydrophobic side chain; $X^{29}$ is selected from an amino acid comprising an acidic side chain or a polar neutral side chain; $X^{30}$ is selected from an amino acid; $X^{31}$ is selected from an amino acid; $X^{32}$ is selected from an amino acid comprising a polar-neutral side chain or an acidic side chain; $X^{33}$ is selected from an amino acid; $X^{34}$ is selected from an amino acid; $X^{35}$ is selected from an amino acid; and $X^{36}$ is selected from an amino acid.

Aspect 62A. The IL-2Rβ ligand of aspect 61A, wherein $X^{25}$ is selected from an amino acid; $X^{26}$ is selected from an amino acid; $X^{27}$ is selected from an amino acid comprising a large hydrophobic side chain; $X^{28}$ is selected from an amino acid comprising a small hydrophobic side chain; $X^{29}$ is selected from an amino acid comprising an acidic side chain or a polar neutral side chain; $X^{30}$ is selected from an amino acid comprising a large hydrophobic side chain; $X^{31}$ is selected from an amino acid comprising a large hydrophobic side chain; $X^{32}$ is selected from an amino acid comprising a polar-neutral side chain or an acidic side chain; and $X^{33}$ is selected from an amino acid; $X^{34}$ is selected from an amino acid; $X^{35}$ is selected from an amino acid; and $X^{36}$ is selected from an amino acid.

Aspect 63A. The IL-2Rβ ligand of any one of aspects 1A to 9A, wherein the IL-2Rβ ligand comprises the amino acid sequence of Formula (3) (SEQ ID NO: 1063) or the amino acid sequence of Formula (3a) (SEQ ID NO: 1064):

$$-X^{26}-X^{27}-X^2-X^{29}-X^{30}-X^{31}-X^{32}-X^{33}-X^{34}-X^{35}- \quad (3)$$

$$-X^{25}-C-X^{26}-X^{27}-X^{28}-X^{29}-X^{30}-X^{31}-X^{32}-X^{33}-X^{34}-X^{35}-C-X^{36}- \quad (3a)$$

wherein, $X^{25}$ is selected from an amino acid; $X^{26}$ is selected from an amino acid; $X^{27}$ is selected from I, L, M, V, F, Y, and W; $X^{28}$ is selected from A, G, P, S, and T; $X^{29}$ is selected from D, E, H, N, Q, S, T, and Y; $X^{30}$ is selected from I, L, M, V, F, Y, and W; $X^{31}$ is selected from I, L, M, V, F, Y, and W; $X^{32}$ is selected from D, E, H, N, Q, T, and Y; $X^{33}$ is selected from an amino acid; $X^{34}$ is selected from an amino acid; $X^{35}$ is selected from an amino acid; and $X^{36}$ is selected from an amino acid.

Aspect 64A. The IL-2Rβ ligand of aspect 63A, wherein $X^{27}$ is selected from V and I.

Aspect 65A. The IL-2Rβ ligand of any one of aspects 63A to 64A, wherein $X^{28}$ is G.

Aspect 66A. The IL-2Rβ ligand of any one of aspects 63A to 65A, wherein $X^{29}$ is selected from D and E.

Aspect 67A. The IL-2Rβ ligand of any one of aspects 63A to 66A, wherein $X^{30}$ is selected from V, L, F, and Y.

Aspect 68A. The IL-2Rβ ligand of any one of aspects 63A to 67A, wherein $X^{31}$ is selected from I, V, and F.

Aspect 69A. The IL-2Rβ ligand of any one of aspects 63A to 68A, wherein $X^{32}$ is selected from Q and D.

Aspect 70A. The IL-2Rβ ligand of aspect 63A, wherein, $X^{25}$ is selected from an amino acid; $X^{26}$ is selected from an amino acid; $X^{27}$ is selected from V and I; $X^{28}$ is G; $X^{29}$ is selected from D and E; $X^{30}$ is selected from V, L, F, and Y; $X^{31}$ is selected from I, V, and F; $X^{32}$ is selected from Q and D; $X^{33}$ is selected from an amino acid; $X^{34}$ is selected from an amino acid; $X^{35}$ is selected from an amino acid; and $X^{36}$ is selected from an amino acid.

Aspect 71A. The IL-2Rβ ligand of aspect 63A, wherein the IL-2Rβ ligand comprises an amino acid sequence selected from any one of SEQ ID NO: 185 to SEQ ID NO: 193:

Aspect 72A. The IL-2Rβ ligand of aspect 71A, wherein the IL-2Rβ ligand comprises an amino acid sequence selected from any one of SEQ ID NO: 185 to SEQ ID NO: 193, wherein the amino acid sequence is terminated with amino acids -G-G- on the N-terminus, on the C-terminus, or on both the N- and C-termini.

Aspect 73A. The IL-2Rβ ligand of any one of aspects 71A to 72A, wherein the IL-2Rβ ligand comprises an amino acid sequence selected from any one of SEQ ID NO: 185 to SEQ ID NO: 193, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

Aspect 74A. The IL-2Rβ ligand of any one of aspects 1A to 9A, wherein the IL-2Rβ ligand comprises the amino acid sequence of Formula (13) (SEQ ID NO: 1028):

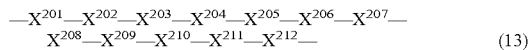

$$—X^{201}—X^{202}—X^{203}—X^{204}—X^{205}—X^{206}—X^{207}—X^{208}—X^{209}—X^{210}—X^{211}—X^{212}— \quad (13)$$

wherein, $X^{201}$ is selected from an amino acid; $X^{202}$ is selected from an amino acid; $X^{203}$ is selected from an amino acid comprising an acidic side chain; $X^{204}$ is selected from an amino acid comprising a large hydrophobic side chain; $X^{205}$ is selected from an amino acid comprising a small hydrophobic side chain; $X^{206}$ is selected from an amino acid comprising an acidic side chain; $X^{207}$ is selected from an amino acid comprising a large hydrophobic side chain; $X^{208}$ is selected from an amino acid; $X^{209}$ is selected from an amino acid comprising an acidic side chain; $X^{210}$ is selected from an amino acid; $X^{211}$ is selected from an amino acid; and $X^{212}$ is selected from an amino acid comprising a large hydrophobic side chain.

Aspect 75A. The IL-2Rβ ligand of aspect 74A, wherein, $X^{201}$ is selected from an amino acid; $X^{202}$ is selected from an amino acid; $X^{203}$ is selected from D and E; $X^{204}$ is selected from I, L, M, V, F, Y, and W; $X^{205}$ is selected from A, G, P, S, and T; $X^{206}$ is selected from D and E; $X^{207}$ is selected from I, L, M, V, F, Y, and W; $X^{208}$ is selected from an amino acid; $X^{209}$ is selected from D and E; $X^{210}$ is selected from an amino acid; $X^{211}$ is selected from an amino acid; and $X^{212}$ is selected from I, L, M, V, F, Y, and W.

Aspect 76A. The IL-2Rβ ligand of aspect 74A, wherein, $X^{201}$ is selected from C, F, L, S, and W; $X^{202}$ is selected from C, D, F, G, L, M, Q, S, V, W, and Y; $X^{203}$ is selected from A, C, D, E, L, M, N, S, W, and Y; $X^{204}$ is selected from A, D, I, M, V, and W; $X^{205}$ is selected from D, E, G, and I; $X^{206}$ is selected from C, D, G, H, L, Q, S, and T; $X^{207}$ is selected from C, D, I, L, V, W, and Y; $X^{208}$ is selected from C, D, L, V, and W; $X^{209}$ is selected from C, D, G, I, M, N, P, Q, and W; $X^{210}$ is selected from D. F. L. M. P, S, T, and Y; $X^{211}$ is selected from C, F, L, V, and W; and $X^{212}$ is selected from L, N, S, T, and V.

Aspect 77A. The IL-2Rβ ligand of aspect 76A, wherein $X^{201}$ is selected from C, F, L, S, and W.

Aspect 78A. The IL-2Rβ ligand of any one of aspects 76A to 77A, wherein $X^{202}$ is selected from C, D, F, G, L, M, Q, S, V, W, and Y.

Aspect 79A. The IL-2Rβ ligand of any one of aspects 76A to 78A, wherein $X^{203}$ is selected from D and E.

Aspect 80A. The IL-2Rβ ligand of any one of aspects 76A to 79A, wherein $X^{204}$ is V.

Aspect 81A. The IL-2Rβ ligand of any one of aspects 76A to 80A, wherein $X^{205}$ is G.

Aspect 82A. The IL-2Rβ ligand of any one of aspects 76A to 81A, wherein $X^{206}$ is D.

Aspect 83A. The IL-2Rβ ligand of any one of aspects 76A to 82A, wherein $X^{207}$ is selected from I, W, and Y.

Aspect 84A. The IL-2Rβ ligand of any one of aspects 76A to 83A, wherein $X^{208}$ is selected from C, D, L, V, and W.

Aspect 85A. The IL-2Rβ ligand of any one of aspects 76A to 84A, wherein $X^{209}$ is D.

Aspect 86A. The IL-2Rβ ligand of any one of aspects 76A to 85A, wherein $X^{210}$ is selected from D, F, L, M, P, S, T, and Y.

Aspect 87A. The IL-2Rβ ligand of any one of aspects 76A to 86A, wherein $X^{211}$ is selected from C, F, L, V, and W.

Aspect 88A. The IL-2Rβ ligand of any one of aspects 76A to 87A, wherein $X^{212}$ is selected from L and V.

Aspect 89A. The IL-2Rβ ligand of aspect 76A, wherein, $X^{201}$ is selected from an amino acid; $X^{202}$ is selected from an amino acid; $X^{203}$ is selected from D and E; $X^{204}$ is V; $X^{205}$ is G; $X^{206}$ is D; $X^{207}$ is selected from I, Y, and W; $X^{208}$ is selected from an amino acid; $X^{209}$ is D; $X^{210}$ is selected from an amino acid; $X^{211}$ is selected from an amino acid; and $X^{212}$ is selected from I, L, M, V, F, Y, and W.

Aspect 90A. The IL-2Rβ ligand of aspect 76A, wherein the IL-2Rβ ligand comprises an amino acid sequence selected from any one of SEQ ID NO: 1028 to SEQ ID NO: 1042 and SEQ ID NO: 1084.

Aspect 91A. The IL-2Rβ ligand of aspect 90A, wherein the IL-2Rβ ligand comprises an amino acid sequence selected from any one of SEQ ID NO: 1028 to SEQ ID NO: 1042 and SEQ ID NO: 1084, wherein the amino acid sequence is terminated with amino acids -G-G- on the N-terminus, on the C-terminus, or on both the N- and C-termini.

Aspect 92A. The IL-2Rβ ligand of any one of aspects 90 Å to 91A, wherein the IL-2Rβ ligand comprises an amino acid sequence selected from any one of SEQ ID NO: 1028 to SEQ ID NO: 1042 and SEQ ID NO: 1084, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

Aspect 93A. The IL-2Rβ ligand of any one of aspects 1A to 9A, wherein the IL-2Rβ ligand comprises an amino acid sequence selected from any one of SEQ ID NO: 1044 to SEQ ID NO: 1050.

Aspect 94A. The IL-2Rβ ligand of aspect 93A, wherein the IL-2Rβ ligand comprises an amino acid sequence selected from any one of SEQ ID NO: 1044 to SEQ ID NO: 1050, wherein the amino acid sequence is terminated with amino acids -G-G- on the N-terminus, on the C-terminus, or on both the N- and C-termini.

Aspect 95A. The IL-2Rβ ligand of any one of aspects 93A to 94A, wherein the IL-2Rβ ligand comprises an amino acid sequence selected from any one of SEQ ID NO: 1044 to SEQ ID NO: 1050, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

Aspect 96A. The IL-2Rβ ligand of any one of aspects 1A to 9A, wherein the IL-2Rβ ligand comprises the amino acid sequence of Formula (10) (SEQ ID NO: 578):

$$-X^{191}-X^{192}-X^{193}-X^{194}-X^{195}-C-X^{196}-X^{197}-X^{198}-X^{199}-X^{200}-X^{201}-X^{202}-X^{203}-X^{204}-X^{205}-X^{206}-X^{207}-X^{208}- \quad (10)$$

wherein, $X^{191}$ is selected from an amino acid comprising a large hydrophobic side chain or an aromatic side chain; $X^{192}$ is selected from an amino acid; $X^{193}$ is selected from an amino acid comprising a large hydrophobic side chain or an aromatic side chain; $X^{194}$ is selected from an amino acid comprising a large hydrophobic side chain or a basic side chain; $X^{195}$ is selected from an amino acid comprising an acidic side chain or a small hydrophobic side chain; $X^{196}$ is selected from an amino acid comprising a large hydrophobic side chain or a basic side chain; $X^{197}$ is selected from an amino acid comprising a large hydrophobic side chain; $X^{198}$ is selected from an amino acid comprising a small hydrophobic side chain; $X^{199}$ is selected from an amino acid comprising a polar/neutral side chain or a basic side chain; $X^{200}$ is selected from an amino acid comprising a large hydrophobic side chain; $X^{201}$ is selected from an amino acid comprising a small hydrophobic side chain; $X^{202}$ is selected from an amino acid comprising an acidic side chain or a polar/neutral side chain; $X^{203}$ is selected from an amino acid comprising a large hydrophobic side chain; $X^{204}$ is selected from an amino acid comprising an acidic side chain; $X^{205}$ is selected from an amino acid comprising a large hydrophobic side chain; $X^{206}$ is selected from an amino acid comprising an acidic side chain or an aromatic side chain; $X^{207}$ is selected from an amino acid comprising an amino acid; and $X^{208}$ is selected from an amino acid comprising an acidic side chain.

Aspect 97A. The IL-2Rβ ligand of aspect 96A, wherein, $X^{191}$ is selected from F, H, I, L, M, V, W, and Y; $X^{192}$ is selected from an amino acid; $X^{193}$ is selected from F, H, I, L, M, V, W, and Y; $X^{194}$ is selected from F, I, L, M, V, W, Y, H, K, and R; $X^{195}$ is selected from D, E, A, G, P, S, and T; $X^{196}$ is selected from F, I, L, M, V, W, Y, H, K, and R; $X^{197}$ is selected from F, I, L, M, V, and W; $X^{198}$ is selected from A, G, P, S, and T; $X^{199}$ is selected from H, N, Q, S, T, Y, H, K, and R; $X^{200}$ is selected from F, I, L, M, V, W, and Y; $X^{201}$ is selected from A, G, P, S, and T; $X^{202}$ is selected from D, E, H, N, Q, S, T, and Y; $X^{203}$ is selected from F, I, L, M, V, W, and Y; $X^{204}$ is selected from D and E; $X^{205}$ is selected from F, I, L, M, V, W, and Y; $X^{206}$ is selected from D, E, F, H, I, L, M, V, W, and Y; $X^{207}$ is selected from an amino acid; and $X^{208}$ is selected from D and E.

Aspect 98A. The IL-2Rβ ligand of aspect 97A, wherein $X^{191}$ is selected from F, H, W, and Y.

Aspect 99A. The IL-2Rβ ligand of any one of aspects 97A to 98A, wherein $X^{191}$ is W.

Aspect 100A. The IL-2Rβ ligand of any one of aspects 97A to 99A, wherein $X^{192}$ is selected from an amino acid.

Aspect 101A. The IL-2Rβ ligand of any one of aspects 97A to 100A, wherein $X^{193}$ is selected from F, H, W, and Y.

Aspect 102A. The IL-2Rβ ligand of any one of aspects 97A to 100A, wherein $X^{193}$ is selected from F, W, and Y.

Aspect 103A. The IL-2Rβ ligand of any one of aspects 97A to 102A, wherein $X^{194}$ is selected from H, L, and Y.

Aspect 104A. The IL-2Rβ ligand of any one of aspects 97A to 102A, wherein $X^{194}$ is L.

Aspect 105A. The IL-2Rβ ligand of any one of aspects 97A to 102A, wherein $X^{194}$ is Y.

Aspect 106A. The IL-2Rβ ligand of any one of aspects 97A to 105A, wherein $X^{195}$ is selected from D and P.

Aspect 107A. The IL-2Rβ ligand of any one of aspects 97A to 105A, wherein $X^{195}$ is D.

Aspect 108A. The IL-2Rβ ligand of any one of aspects 97A to 105A, wherein $X^{196}$ is P.

Aspect 109A. The IL-2Rβ ligand of any one of aspects 97A to 108A, wherein $X^{196}$ is selected from H and W.

Aspect 110A. The IL-2Rβ ligand of any one of aspects 97A to 108A, wherein $X^{196}$ is H.

Aspect 111A. The IL-2Rβ ligand of any one of aspects 97A to 108A, wherein $X^{196}$ is W.

Aspect 112A. The IL-2Rβ ligand of any one of aspects 97A to 111A, wherein $X^{197}$ is M.

Aspect 113A. The IL-2Rβ ligand of any one of aspects 97A to 112A, wherein $X^{198}$ is A.

Aspect 114A. The IL-2Rβ ligand of any one of aspects 97AA to 113, wherein $X^{199}$ is selected from H, K, R, and Q.

Aspect 115A. The IL-2Rβ ligand of any one of aspects 97A to 113A, wherein $X^{199}$ is Q.

Aspect 116A. The IL-2Rβ ligand of any one of aspects 97A to 113A, wherein $X^{199}$ is selected from H, K, and R.

Aspect 117A. The IL-2Rβ ligand of any one of aspects 97A to 116A, wherein $X^{200}$ is selected from L and V.

Aspect 118A. The IL-2Rβ ligand of any one of aspects 97A to 116A, wherein $X^{200}$ is L.

Aspect 119A. The IL-2Rβ ligand of any one of aspects 97A to 118A, wherein $X^{201}$ is G.

Aspect 120A. The IL-2Rβ ligand of any one of aspects 97A to 119A, wherein $X^{202}$ is selected from D, E, and Q.

Aspect 121A. The IL-2Rβ ligand of any one of aspects 97A to 119A, wherein $X^{202}$ is E.

Aspect 122A. The IL-2Rβ ligand of any one of aspects 97A to 121A, wherein $X^{203}$ is L.

Aspect 123A. The IL-2Rβ ligand of any one of aspects 97A to 122A, wherein $X^{204}$ is selected from D and E.

Aspect 124A. The IL-2Rβ ligand of any one of aspects 97A to 122A, wherein $X^{204}$ is D.

Aspect 125A. The IL-2Rβ ligand of any one of aspects 97A to 124A, wherein $X^{205}$ is L.

Aspect 126A. The IL-2Rβ ligand of any one of aspects 97A to 125A, wherein $X^{206}$ is selected from D and E.

Aspect 127A. The IL-2Rβ ligand of any one of aspects 97A to 126A, wherein $X^{207}$ is selected from an amino acid.

Aspect 128A. The IL-2Rβ ligand of any one of aspects 97A to 127A, wherein $X^{208}$ is selected from D and E.

Aspect 129A. The IL-2Rβ ligand of aspect 97A, wherein, $X^{191}$ is selected from F, H, W, and Y; $X^{192}$ is selected from an amino acid; $X^{193}$ is selected from F, H, W, and Y; $X^{194}$ is selected from H, L, and Y; $X^{195}$ is selected from D and P; $X^{196}$ is selected from H, R, and W; $X^{197}$ is M; $X^{198}$ is A; $X^{199}$ is selected from H, K, R, and Q; $X^{200}$ is selected from L and V; $X^{201}$ is G; $X^{202}$ is selected from D, E, and Q; $X^{203}$ is L; $X^{204}$ is selected from D and E; $X^{205}$ is L; $X^{206}$ is selected from D, E, H, F, W, and Y; $X^{207}$ is selected from an amino acid; and $X^{208}$ is selected from D and E.

Aspect 130A. The IL-2Rβ ligand of aspect 96A, wherein, $X^{191}$ is selected from F, H, W, and Y; $X^{192}$ is selected from an amino acid; $X^{193}$ is Y; $X^{194}$ is selected from H, L, and Y; $X^{195}$ is D; $X^{196}$ is W; $X^{197}$ is M; $X^{198}$ is A; $X^{199}$ is Q; $X^{200}$ is selected from L and V; $X^{201}$ is G; $X^{202}$ is selected from D, E, and Q; $X^{203}$ is L; $X^{204}$ is selected from D and E; $X^{205}$ is L; $X^{206}$ is selected from D and E; $X^{207}$ is selected from an amino acid; and $X^{208}$ is selected from D and E.

Aspect 131A. The IL-2Rβ ligand of aspect 96A, wherein, $X^{191}$ is selected from F, H, W, and Y; $X^{192}$ is selected from an amino acid; $X^{193}$ is Y; $X^{194}$ is selected from H, L, and Y; $X^{195}$ is D; $X^{196}$ is H; $X^{197}$ is M; $X^{1985}$ is A; $X^{199}$ is Q; $X^{200}$ is selected from L and V; $X^{201}$ is G; $X^{202}$ is selected from D, E, and Q; $X^{203}$ is L; $X^{204}$ is selected from D and E; $X^{205}$ is L; $X^{206}$ is selected from D and E; $X^{207}$ is selected from an amino acid; and $X^{208}$ is selected from D and E.

Aspect 132A. The IL-2Rβ ligand of aspect 96A, wherein, $X^{191}$ is selected from F, H, W, and Y; $X^{192}$ is selected from an amino acid; $X^{193}$ is Y; $X^{194}$ is selected from H, L, and Y; $X^{195}$ is D; $X^{196}$ is R; $X^{197}$ is M; $X^{198}$ is A; $X^{199}$ is Q; $X^{200}$ is selected from L and V; $X^{201}$ is G; $X^{202}$ is selected from D, E, and Q; $X^{203}$ is L; $X^{204}$ is selected from D and E; $X^{205}$ is L; $X^{206}$ is selected from D and E; $X^{207}$ is selected from an amino acid; and $X^{208}$ is selected from D and E.

Aspect 133A. The IL-2Rβ ligand of aspect 96A, wherein, $X^{191}$ is selected from F, H, W, and Y; $X^{192}$ is selected from an amino acid; $X^{193}$ is Y; $X^{194}$ is selected from H, L, and Y; $X^{195}$ is P; $X^{196}$ is W; $X^{197}$ is M; $X^{198}$ is A; $X^{199}$ is Q; $X^{200}$ is selected from L and V; $X^{201}$ is G; $X^{202}$ is selected from D, E, and Q; $X^{203}$ is L; $X^{204}$ is selected from D and E; $X^{205}$ is L; $X^{206}$ is selected from D and E; $X^{207}$ is selected from an amino acid; and $X^{208}$ is selected from D and E.

Aspect 134A. The IL-2Rβ ligand of aspect 96A, wherein, $X^{191}$ is selected from F, H, W, and Y; $X^{192}$ is selected from an amino acid; $X^{193}$ is Y; $X^{194}$ is selected from H, L, and Y; $X^{195}$ is D; $X^{196}$ is W; $X^{197}$ is M; $X^{198}$ is A; $X^{199}$ is selected from H, K, and R; $X^{200}$ is selected from L and V; $X^{201}$ is G; $X^{202}$ is selected from D, E, and Q; $X^{203}$ is L; $X^{204}$ is selected from D and E; $X^{205}$ is L; $X^{205}$ is selected from D and E; $X^{207}$ is selected from an amino acid; and $X^{208}$ is selected from D and E.

Aspect 135A. The IL-2Rβ ligand of aspect 96A, wherein, $X^{191}$ is selected from F, H, W, and Y; $X^{192}$ is selected from an amino acid; $X^{193}$ is Y; $X^{194}$ is selected from H, L, and Y; $X^{195}$ is D; $X^{196}$ is W; $X^{197}$ is M; $X^{198}$ is A; $X^{199}$ is Q; $X^{200}$ is selected from L and V; $X^{201}$ is G; $X^{202}$ is selected from D, E, and Q; $X^{203}$ is L; $X^{204}$ is selected from D and E; $X^{205}$ is L; $X^{206}$ is selected from F, H, W, and Y; $X^{207}$ is selected from an amino acid; and $X^{208}$ is selected from D and E.

Aspect 136A. The IL-2Rβ ligand of aspect 96A, wherein, $X^{191}$ is selected from A, D, E, F, G, H, I, K, L, N, M, P, Q, R, S, T, V, W, and Y; $X^{192}$ is selected from A, D, E, F, G, H, I, K, L, M, N, P, Q, R, S, T, V, W, and Y; $X^{193}$ is selected from A, C, D, F, G, H, I, L, M, N P, R, S, T, V, W, and Y; $X^{194}$ is selected from F, H, I, K, L, N, P, Q, R, S, T, V, W, and Y; $X^{195}$ is selected from A, D, E, F, G, H, K, L, M, N, P, Q, S, W, and Y; $X^{196}$ is selected from A, E, F, G, H, Q, R, S, W, and Y; $X^{197}$ is selected from A, D, E, F, I, K, L, M, N, Q, R, S, T, V, W, and Y; $X^{198}$ is A; $X^{199}$ is selected from A, D, H, K, L, N, P, Q, R, S, and Y; $X^{200}$ is selected from I, L, M, P, and V; $X^{201}$ is selected from G, H, and W; $X^{202}$ is selected from D, E, and Q; $X^{203}$ is L; $X^{204}$ is selected from A, D, E, H, I, L, T, V, and Y; $X^{205}$ is selected from F, I, L, M, V, W, and Y; $X^{206}$ is selected from A, D, E, F, G, H, I, K, L, M, N, P, Q, R, S, T, V, W, and Y; $X^{207}$ is selected from A, C, D, E, F, G, H, I, L, M, N, P, Q, R, S, T, V, W, and Y; and $X^{208}$ is selected from A, D, E, F, G, H, K, L, M, N, P, Q, R, S, T, V, W, and Y.

Aspect 137A. The IL-2Rβ ligand of aspect 136A, wherein, $X^{191}$ is selected from F, H, W, and Y; $X^{192}$ is selected from A, D, E, F, G, H, I, K, L, M, N, P, Q, R, S, T, V, W, and Y; $X^{193}$ is selected from F, H, W, and Y; $X^{194}$ is selected from F, H, I, L, V W, and Y; $X^{195}$ is selected from D, E, and P; $X^{196}$ is selected from F, H, R, S, W, and Y; $X^{197}$ is selected from F, I, L, M, and V; $X^{198}$ is A; $X^{199}$ is selected from H, K, N, Q, and R; $X^{200}$ is selected from I, L, and V; $X^{201}$ is G; $X^{202}$ is selected from D, E, and Q; $X^{203}$ is selected from F, I, L, M, V, and Y; $X^{204}$ is selected from D and E; $X^{205}$ is L; $X^{206}$ is selected from D, E, N, and Q; $X^{207}$ is selected from A, D, E, F, G, H, I, L, M, N, P, Q, R, S, T, V, W, and Y; and $X^{208}$ is selected from D and E.

Aspect 138A. The IL-2Rβ ligand of aspect 136A, wherein, $X^{191}$ is W; $X^{192}$ is selected from A, D, E, F, G, H, I, K, L, M, N, P, Q, R, S, T, V, W, and Y; $X^{193}$ is selected from F, H, W, and Y; $X^{194}$ is Y; $X^{195}$ is selected from D, E, and P; $X^{196}$ is selected from H, R, and W; $X^{197}$ is selected from I and M; $X^{198}$ is A; $X^{199}$ is selected from K, Q, and R; $X^{200}$ is selected from I, L, and V; $X^{201}$ is G; $X^{202}$ is E; $X^{203}$ is L; $X^{204}$ is D; $X^{205}$ is L; $X^{206}$ is selected from D and E; $X^{207}$ is selected from A, D, E, F, G, H, I, L, M, N, P, Q, R, S, T, V, W, and Y; and $X^{208}$ is selected from D and E.

Aspect 139A. The IL-2Rβ ligand of aspect 136A, wherein, $X^{191}$ is selected from A, D, E, F, G, H, I, K, L, N, M, P, Q, R, S, T, V, W, and Y; $X^{192}$ is selected from A, D, E, F, G, H, I, K, L, M, N, P, Q, R, S, T, V, W, and Y; $X^{193}$ is selected from F, H, W, and Y; $X^{194}$ is selected from F, H, L, W, and Y; $X^{195}$ is selected from D, E, and P; $X^{196}$ is selected from F, H, R, S, W, and Y; $X^{197}$ is selected from F, I, L, M, and V; $X^{198}$ is A; $X^{199}$ is selected from H, K, Q, N, and R; $X^{200}$ is selected from I, L, and V; $X^{201}$ is G; $X^{202}$ is selected from D, E, and Q; $X^{203}$ is L; $X^{204}$ is selected from D and E; $X^{205}$ is selected from F, I, L, M, V, and W; $X^{206}$ is selected from D, E, F, I, L, M, V, W, and Y; $X^{207}$ is selected from A, D, E, F, G, H, I, L, M, N, P, Q, R, S, T, V, W, and Y; and $X^{208}$ is selected from D and E.

Aspect 140A. The IL-2Rβ ligand of aspect 139A, wherein $X^{191}$ is selected from A, D, E, F, G, H, I, K, L, N, M, P, Q, R, S, T, V, W, and Y.

Aspect 141A. The IL-2Rβ ligand of any one of aspects 139A to 140A, wherein $X^{191}$ is selected from A, G, P, S, and T.

Aspect 142A. The IL-2Rβ ligand of any one of aspects 139A to 140A, wherein $X^{191}$ is selected from F, H, I, L, M, V, W, and Y.

Aspect 143A. The IL-2Rβ ligand of any one of aspects 139A to 140A, wherein $X^{191}$ is selected from F, H, W, and Y.

Aspect 144A. The IL-2Rβ ligand of any one of aspects 139A to 143A, wherein $X^{192}$ is selected from A, D, E, F, G, H, I, K, L, M, N, P, Q, R, S, T, V, W, and Y.

Aspect 145A. The IL-2Rβ ligand of any one of aspects 139A to 143A, wherein $X^{192}$ is selected from A, G, P, S, and T.

Aspect 146A. The IL-2Rβ ligand of any one of aspects 139A to 143A, wherein $X^{192}$ is selected from F, H, I, L, M, V, W, and Y.

Aspect 147A. The IL-2Rβ ligand of any one of aspects 139A to 146A, wherein $X^{193}$ is selected from F, H, W, and Y.

Aspect 148A. The IL-2Rβ ligand of any one of aspects 139A to 146A, wherein $X^{193}$ is W.

Aspect 149A. The IL-2Rβ ligand of any one of aspects 139A to 148A, wherein $X^{194}$ is selected from F, H, L, W, and Y.

Aspect 150A. The IL-2Rβ ligand of any one of aspects 139A to 148A, wherein $X^{194}$ is selected from H, L, and Y.

Aspect 151A. The IL-2Rβ ligand of any one of aspects 139A to 148A, wherein $X^{194}$ is Y.

Aspect 152A. The IL-2Rβ ligand of any one of aspects 139A to 151A, wherein $X^{195}$ is selected from D, E, and P.

Aspect 153A. The IL-2Rβ ligand of any one of aspects 139A to 151A, wherein $X^{195}$ is D.

Aspect 154A. The IL-2Rβ ligand of any one of aspects 139A to 151A, wherein $X^{195}$ is P.

Aspect 155A. The IL-2Rβ ligand of any one of aspects 139A to 154A, wherein $X^{196}$ is selected from F, H, R, S, W, and Y.

Aspect 156A. The IL-2Rβ ligand of any one of aspects 139A to 154A, wherein $X^{196}$ is selected from H, and W.

Aspect 157A. The IL-2Rβ ligand of any one of aspects 139A to 154A, wherein $X^{196}$ is W.

Aspect 158A. The IL-2Rβ ligand of any one of aspects 139A to 157A, wherein $X^{197}$ is selected from F, I, L, M, and V.

Aspect 159A. The IL-2Rβ ligand of any one of aspects 139A to 157A, wherein $X^{197}$ is selected from I and M.

Aspect 160A. The IL-2Rβ ligand of any one of aspects 139A to 157A, wherein $X^{197}$ is M.

Aspect 161A. The IL-2Rβ ligand of any one of aspects 139A to 160A, wherein $X^{198}$ is A.

Aspect 162A. The IL-2Rβ ligand of any one of aspects 139A to 161A, wherein $X^{199}$ is selected from H, K, Q, N, and R.

Aspect 163A. The IL-2Rβ ligand of any one of aspects 139A to 161A, wherein $X^{199}$ is selected from H, K, and R.

Aspect 164A. The IL-2Rβ ligand of any one of aspects 139A to 161A, wherein $X^{199}$ is Q.

Aspect 165A. The IL-2Rβ ligand of any one of aspects 139A to 164A, wherein $X^{200}$ is selected from I, L, and V.

Aspect 166A. The IL-2Rβ ligand of any one of aspects 139A to 164A, wherein $X^{200}$ is selected from L and V.

Aspect 167A. The IL-2Rβ ligand of any one of aspects 139A to 166A, wherein $X^{201}$ is G.

Aspect 168A. The IL-2Rβ ligand of any one of aspects 139A to 167A, wherein $X^{202}$ is selected from D, E, and Q.

Aspect 169A. The IL-2Rβ ligand of any one of aspects 139A to 167A, wherein $X^{202}$ is E.

Aspect 170A. The IL-2Rβ ligand of any one of aspects 139A to 169A, wherein $X^{203}$ is L.

Aspect 171A. The IL-2Rβ ligand of any one of aspects 139A to 170A, wherein $X^{204}$ is selected from D and E.

Aspect 172A. The IL-2Rβ ligand of any one of aspects 139A to 170A, wherein $X^{204}$ is D.

Aspect 173A. The IL-2Rβ ligand of any one of aspects 139A to 171A, wherein $X^{205}$ is selected from F, I, L, M, V, and W.

Aspect 174A. The IL-2Rβ ligand of any one of aspects 139A to 171A, wherein $X^{205}$ is L.

Aspect 175A. The IL-2Rβ ligand of any one of aspects 139A to 174A, wherein $X^{206}$ is selected from D and E.

Aspect 176A. The IL-2Rβ ligand of any one of aspects 139A to 174A, wherein $X^{206}$ is D.

Aspect 177A. The IL-2Rβ ligand of any one of aspects 139A to 174A, wherein $X^{206}$ is selected from F, I, L, M, V, W, and Y.

Aspect 178A. The IL-2Rβ ligand of any one of aspects 139A to 177A, wherein $X^{207}$ is selected from A, D, E, F, G, H, I, L, M, N, P, Q, R, S, T, V, W, and Y.

Aspect 179A. The IL-2Rβ ligand of any one of aspects 139A to 177A, wherein $X^{207}$ is selected from A, G, P, S, and T.

Aspect 180A. The IL-2Rβ ligand of any one of aspects 139A to 177A, wherein $X^{207}$ is selected from F, I, L, M, V, W, and Y.

Aspect 181A. The IL-2Rβ ligand of any one of aspects 139A to 180A, wherein $X^{208}$ is selected from D and E.

Aspect 182A. The IL-2Rβ ligand of aspect 139A, wherein, $X^{191}$ is selected from F, I, L, M, V, W, and Y; $X^{192}$ is selected from A, D, E, F, G, H, I, K, L, M, N, P, Q, R, S, T, V, W, and Y; $X^{193}$ is selected from F, H, W, and Y; $X^{194}$ is selected from H, L, and Y; $X^{195}$ is selected from D and P; $X^{196}$ is selected from H, R, and W; $X^{197}$ is selected from I and M; $X^{198}$ is A; $X^{199}$ is selected from H, K, Q, and R; $X^{200}$ is selected from L and V; $X^{201}$ is G; $X^{202}$ is selected from D, E, and Q; $X^{203}$ is L; $X^{204}$ is selected from D and E; $X^{205}$ is L; $X^{206}$ is selected from D, E, F, I, L, M, V, W, and Y; $X^{207}$ is selected from A, D, E, F, G, H, I, L, M, N, P, Q, R, S, T, V, W, and Y; and $X^{208}$ is selected from D and E.

Aspect 183A. The IL-2Rβ ligand of aspect 139A, wherein, $X^{191}$ is selected from F, I, L, M, V, W, and Y; $X^{192}$ is selected from A, D, E, F, G, H, I, K, L, M, N, P, Q, R, S, T, V, W, and Y; $X^{193}$ is W; $X^{194}$ is Y; $X^{195}$ is selected from D and P; $X^{196}$ is W; $X^{197}$ is M; $X^{198}$ is A; $X^{199}$ is Q; $X^{199}$ is selected from H, K, and R; $X^{200}$ is selected from L and V; $X^{201}$ is G; $X^{202}$ is E; $X^{203}$ is L; $X^{204}$ is selected from D and E; $X^{205}$ is L; $X^{206}$ is D; $X^{207}$ is selected from A, D, E, F, G, H, I, L, M, N, P, Q, R, S, T, V, W, and Y; and $X^{208}$ is selected from D and E.

Aspect 184A. The IL-2Rβ ligand of aspect 139A, wherein, $X^{191}$ is selected from F, I, L, M, V, W, and Y; $X^{193}$ is W; $X^{194}$ is Y; $X^{195}$ is selected from D and P; $X^{196}$ is selected from H, R, and W; $X^{197}$ is M; $X^{198}$ is A; $X^{199}$ is selected from H, K, Q, and R; $X^{200}$ is selected from L and V; $X^{201}$ is G; $X^{202}$ is E; $X^{203}$ is L; $X^{204}$ is D; $X^{205}$ is L; $X^{206}$ is D; $X^{207}$ is selected from A, D, E, F, G, H, I, L, M, N, P, Q, R, S, T, V, W, and Y; and $X^{208}$ is selected from D and E.

Aspect 185A. The IL-2Rβ ligand of aspect 97A, wherein the IL-2Rβ ligand comprises an amino acid sequence selected from any one of SEQ ID NO: 579 to SEQ ID NO: 808.

Aspect 186A. The IL-2Rβ ligand of aspect 185A, wherein the IL-2Rβ ligand comprises an amino acid sequence selected from any one of SEQ ID NO: 579 to SEQ ID NO: 808, wherein the amino acid sequence is terminated with amino acids -G-G- on the N-terminus, on the C-terminus, or on both the N- and C-termini.

Aspect 187A. The IL-2Rβ ligand of any one of aspects 185A to 186A, wherein the IL-2Rβ ligand comprises an amino acid sequence selected from any one of SEQ ID NO: 579 to SEQ ID NO: 808, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

Aspect 188A. The IL-20 ligand of any one of aspects 1A to 9A, wherein the IL-20 ligand comprises the amino acid sequence of Formula (11) (SEQ ID NO: 809):

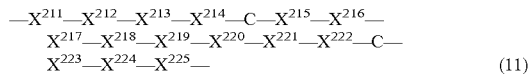

(11)

wherein, $X^{211}$ is selected from an amino acid; $X^{212}$ is selected from an amino acid comprising an aromatic side chain; $X^{213}$ is selected from an amino acid comprising a large hydrophobic side chain or an aromatic side chain; $X^{214}$ is P; $X^{215}$ is selected from an amino acid comprising an aromatic side chain; $X^{216}$ is selected from an amino acid comprising a large hydrophobic side chain; $X^{217}$ is A; $X^{218}$ is selected from an amino acid comprising a basic side chain or a polar/neutral side chain; $X^{219}$ is selected from an amino acid comprising a large hydrophobic side chain; $X^{220}$ is G; $X^{221}$ is selected from an amino acid comprising an acidic side chain or a polar/neutral side chain; $X^{222}$ is L; $X^{223}$ is D; $X^{224}$ is selected from an amino acid comprising a large hydrophobic side chain; and $X^{225}$ is selected from an amino acid comprising an acidic side chain.

Aspect 189A. The IL-2Rβ ligand of aspect 188A, wherein, $X^{211}$ is selected from an amino acid; $X^{212}$ is selected from F, H, W, and Y; $X^{213}$ is selected from F, H, I, L, M, V, W, and Y; $X^{214}$ is P; $X^{215}$ is selected from F, H, W, and Y; $X^{216}$ is selected from F, I, L, M, V, W, and Y; $X^{217}$ is A; $X^{218}$ is selected from K, R, H, N, Q, S, T, and Y; $X^{219}$ is selected from F, I, L, M, V, W, and Y; $X^{220}$ is G; $X^{221}$ is selected from D, E, H, N, Q, S, T, and Y; $X^{222}$ is L; $X^{223}$ is D; $X^{224}$ is selected from F, I, L, M, V, W, and Y; and $X^{225}$ is selected from D and E.

Aspect 190A. The IL-2Rβ ligand of aspect 189A, wherein $X^{211}$ is selected from an amino acid.

Aspect 191A. The IL-2Rβ ligand of any one of aspects 189A to 190A, wherein $X^{211}$ is selected from H, K, and R.

Aspect 192A. The IL-2Rβ ligand of any one of aspects 189A to 190A, wherein $X^{211}$ is selected from H and R.

Aspect 193A. The IL-2Rβ ligand of any one of aspects 189A to 192A, wherein $X^{212}$ is selected from F, H, W, and Y.

Aspect 194A. The IL-2Rβ ligand of any one of aspects 189A to 192A, wherein $X^{212}$ is W.

Aspect 195A. The IL-2Rβ ligand of any one of aspects 189A to 194A, wherein $X^{213}$ is selected from F, H, I, L, M, V, W, and Y.

Aspect 196A. The IL-2Rβ ligand of any one of aspects 189A to 194A, wherein $X^{213}$ is L.

Aspect 197A. The IL-2Rβ ligand of any one of aspects 189A to 194A, wherein $X^{213}$ is Y.

Aspect 198A. The IL-2Rβ ligand of any one of aspects 189A to 197A, wherein $X^{214}$ is P.

Aspect 199A. The IL-2Rβ ligand of any one of aspects 189A to 198A, wherein $X^{215}$ is selected from F, H, W, and Y.

Aspect 200A. The IL-2Rβ ligand of any one of aspects 189A to 198A, wherein $X^{215}$ is W.

Aspect 201A. The IL-2Rβ ligand of any one of aspects 189A to 200A, wherein $X^{216}$ is selected from F, I, L, M, V, W, and Y.

Aspect 202A. The IL-2Rβ ligand of any one of aspects 189A to 200A, wherein $X^{216}$ is M.

Aspect 203A. The IL-2Rβ ligand of any one of aspects 189A to 202A, wherein $X^{217}$ is A.

Aspect 204A. The IL-2Rβ ligand of any one of aspects 189A to 203A, wherein $X^{218}$ is selected from K, R, H, N, Q, S, T, and Y.

Aspect 205A. The IL-2Rβ ligand of any one of aspects 189A to 203A, wherein $X^{218}$ is selected from K and R.

Aspect 206A. The IL-2Rβ ligand of any one of aspects 189A to 203A, wherein $X^{211}$ is Q.

Aspect 207A. The IL-2Rβ ligand of any one of aspects 189A to 206A, wherein $X^{219}$ is selected from F, I, L, M, V, W, and Y.

Aspect 208A. The IL-2Rβ ligand of any one of aspects 189A to 206A, wherein $X^{219}$ is L.

Aspect 209A. The IL-2Rβ ligand of any one of aspects 189A to 208A, wherein $X^{220}$ is G.

Aspect 210A. The IL-2Rβ ligand of any one of aspects 189A to 209A, wherein $X^{221}$ is selected from D, E, H, N, Q, S, T, and Y.

Aspect 211A. The IL-2Rβ ligand of any one of aspects 189A to 209A, wherein $X^{221}$ is E.

Aspect 212A. The IL-2Rβ ligand of any one of aspects 189A to 211A, wherein $X^{222}$ is L.

Aspect 213A. The IL-2Rβ ligand of any one of aspects 189A to 212A, wherein $X^{223}$ is D.

Aspect 214A. The IL-2Rβ ligand of any one of aspects 189A to 213A, wherein $X^{224}$ is selected from F, I, L, M, V, W, and Y.

Aspect 215A. The IL-2Rβ ligand of any one of aspects 189A to 213A, wherein $X^{224}$ is L.

Aspect 216A. The IL-2Rβ ligand of any one of aspects 189A to 215A, wherein $X^{224}$ is selected from D and E.

Aspect 217A. The IL-2Rβ ligand of aspect 188A, wherein, $X^{211}$ is selected from H, K, and R; $X^{212}$ is W; $X^{213}$ is Y; $X^{214}$ is P; $X^{211}$ is W; $X^{216}$ is M; $X^{217}$ is A; $X^{211}$ is selected from L and V; $X^{220}$ is G; $X^{219}$ is selected N and Q; $X^{220}$ is G; $X^{221}$ is selected from E, D, and Q; $X^{222}$ is L; $X^{223}$ is D; $X^{224}$ is selected from L and M; and $X^{225}$ is selected from D and E.

Aspect 218A. The IL-2Rβ ligand of aspect 188A, wherein, $X^{211}$ is selected from A, D, E, G, H, L, M, N, Q, R, S, T, and V; $X^{212}$ is selected from C, F, W, and Y; $X^{213}$ is selected from F, H, K, L, N, Q, R, S, W, and Y; $X^{214}$ is P; $X^{215}$ is selected from W and Y; $X^{216}$ is selected from F, I, K, L, M, R, S, T, and V; $X^{217}$ is A; $X^{218}$ is selected from D, E, G, H, K, L, N, Q, R, S, and Y; $X^{219}$ is selected from L, P, and V; $X^{220}$ is selected from G, H, and W; $X^{221}$ is selected from D, E, and Q; $X^{222}$ is selected from L and M; $X^{223}$ is D; $X^{224}$ is selected from L, M, Q, and V; and $X^{225}$ is selected from A, D, E, F, G, H, L, N, Q, T, and V.

Aspect 219A. The IL-2Rβ ligand of aspect 218A, wherein, $X^{211}$ is selected from H an R; $X^{212}$ is selected from F and W; $X^{213}$ is selected from F, L, W, and Y; $X^{214}$ is P; $X^{215}$ is selected from W and Y; $X^{216}$ is selected from F, I, L, M, and V; $X^{217}$ is A; $X^{218}$ is selected from D, E, H, K, N, Q, and R; $X^{219}$ is selected from L and V; $X^{220}$ is G; $X^{221}$ is selected from D, E, and Q; $X^{222}$ is selected from L and M; $X^{223}$ is D; $X^{224}$ is selected L, M, and V; and $X^{225}$ is selected from D and E.

Aspect 220A. The IL-2Rβ ligand of aspect 218A, wherein, $X^{211}$ is selected from H and R; $X^{212}$ is W; $X^{213}$ is Y; $X^{214}$ is P; $X^{215}$ is W; $X^{216}$ is M; $X^{217}$ is A; $X^{218}$ is Q; $X^{219}$ is L; $X^{220}$ is G; $X^{221}$ is Q; $X^{222}$ is L; $X^{223}$ is D; $X^{224}$ is L; and $X^{225}$ is selected from D and E.

Aspect 221A. The IL-2Rβ ligand of aspect 218A, wherein, $X^{211}$ is selected from H and R; $X^{212}$ is W; $X^{213}$ is L; $X^{214}$ is P; $X^{215}$ is W; $X^{216}$ is M; $X^{217}$ is A; $X^{218}$ is Q; $X^{219}$ is L; $X^{220}$ is G; $X^{221}$ is Q; $X^{222}$ is L; $X^{223}$ is D; $X^{224}$ is L; and $X^{225}$ is selected from D and E.

Aspect 222A. The IL-2Rβ ligand of aspect 218A, wherein, $X^{211}$ is selected from H and R; $X^{212}$ is W; $X^{213}$ is Y; $X^{214}$ is P; $X^{215}$ is W; $X^{216}$ is M; $X^{217}$ is A; $X^{218}$ is selected from K and R; $X^{219}$ is L; $X^{200}$ is G; $X^{221}$ is Q; $X^{222}$ is L; $X^{223}$ is D; $X^{224}$ is L; and $X^{225}$ is selected from D and E.

Aspect 223A. The IL-2Rβ ligand of aspect 188A, wherein the IL-2Rβ ligand comprises an amino acid sequence selected from any one of SEQ ID NO: 810 to SEQ ID NO: 903.

Aspect 224A. The IL-2Rβ ligand of aspect 223A, wherein the IL-2Rβ ligand comprises an amino acid sequence selected from any one of SEQ ID NO: 810 to SEQ ID NO: 903, wherein the amino acid sequence is terminated with amino acids -G-G- on the N-terminus, on the C-terminus, or on both the N- and C-termini.

Aspect 225A. The IL-2Rβ ligand of any one of aspects 223A to 224A, wherein the IL-2Rβ ligand comprises an amino acid sequence selected from any one of SEQ ID NO: 810 to SEQ ID NO: 903, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); and amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

Aspect 226A. The IL-2Rβ ligand of aspect 1A, wherein the IL-2Rβ ligand comprises an amino acid sequence selected from any one of SEQ ID NO: 1 to SEQ ID NO: 193, SEQ ID NO: 578 to SEQ ID NO: 903, and SEQ ID NO: 1028 to SEQ ID NO: 1043, and SEQ ID NOS 1052-1064 and 1084.

Aspect 227A. The IL-2Rβ ligand of any one of aspects 1A to 226A, wherein the IL-2Rβ ligand does not comprise the amino acid sequence of SEQ ID NO: 268 and to SEQ ID NO: 374.

Aspect 228A. A compound comprising at least one IL-2Rβ ligand of any one of aspects 1A to 227A.

Aspect 229A. The compound of aspect 228A, wherein the compound further comprises at least one IL-2Rγc ligand of any one of SEQ ID NO: 194 to SEQ ID NO: 267 and SEQ ID NO: 904 to SEQ ID NO: 1027 and SEQ ID NOS 1065-1083.

Aspect 230A. The compound of any one of aspects 228A to 229A, wherein the compound comprises a least one IL-2Rγc ligand.

Aspect 231A. The compound of any one of aspects 228A to 230A, wherein the compound comprises an IL-2Rγc ligand, a linker, and an IL-2Rβ ligand.

Aspect 232A. The compound of aspect 231A, wherein the linker comprises a peptide linker.

Aspect 233A. The compound of aspect 231A, wherein the C-terminus of the IL-2Rγc ligand is covalently bound to the linker and the C-terminus of the IL-2Rβ ligand is bound to the linker.

Aspect 234A. The compound of aspect 231A, wherein the N-terminus of the IL-2Rγc ligand is covalently bound to the linker and the C-terminus of the IL-2Rβ ligand is bound to the linker.

Aspect 235A. The compound of aspect 231A, wherein the C-terminus of the IL-2Rγc ligand is covalently bound to the linker and the N-terminus of the IL-2Rβ ligand is bound to the linker.

Aspect 236A. The compound of aspect 231A, wherein the N-terminus of the IL-2Rγc ligand is covalently bound to the linker and the N-terminus of the IL-2Rβ ligand is bound to the linker.

Aspect 237A. The compound of any one of aspects 228A to 236A, wherein the compound is selected from a peptide, a conjugate, a fusion protein, and a single chain peptide.

Aspect 238A. The compound of any one of aspects 228A to 237A, wherein the compound comprises at least one moiety configured to modify a property of the conjugate.

Aspect 239A. The compound of aspect 238A, wherein the property is selected from aqueous solubility, polarity, lipophilicity, pharmacokinetic profile, targeting, bioavailability, pH-dependent binding, bioactivity, pharmacodynamics, cellular activity, metabolism, efficacy, caging (reversible incapacitation), and a combination of any of the foregoing.

Aspect 240A. The compound of any one of aspects 238A to 239A, wherein the at least one moiety comprises a small molecule, a polymer, a peptide, or an antibody.

Aspect 241A. The compound of any one of aspects 228A to 240A, comprising a pharmacokinetic moiety.

Aspect 242A. The compound of aspect 241A, wherein the pharmacokinetic moiety comprises a polyethylene glycol.

Aspect 243A. The compound of any one of aspects 228A to 242A, comprising a tumor-targeting moiety.

Aspect 244A. The compound of aspect 243A, wherein the tumor-targeting moiety comprises a tumor-specific antibody, a tumor-specific antibody fragment, a tumor-specific protein, or a tumor-specific peptide.

Aspect 245A. The compound of any one of aspects 228A to 244A, comprising an immune cell-targeting moiety.

Aspect 246A. The compound of any one of aspects 228A to 245A, wherein the compound is an IL-2R agonist.

Aspect 247A. The compound of any one of aspects 228A to 246A, wherein the compound is an IL-2R antagonist.

Aspect 248A. The compound of any one of aspects 228A to 247A, wherein the compound comprises a fusion protein, wherein the IL-2Rβ ligand is bound to a fusion partner.

Aspect 249A. The compound of aspect 248A, wherein the fusion protein partner comprises an IgG molecule, an IgG FAb fragment, or an Fc fragment, Aspect 250A. The compound of aspect 248A, wherein the protein fusion partner comprises an IL-2, a variant of IL-2, a mutant of IL-2, or an IL-2R agonist.

Aspect 251A. The compound of any one of aspects 228A to 250A, wherein the compound comprises a label.

Aspect 252A. The compound of aspect 251A, wherein the label is selected from a radioisotope, a fluorophore, or a combination thereof.

Aspect 253A. The compound of any one of aspects 228A to 252A, wherein the compound comprises a cage to protect peripheral tissues from toxicity of IL-2R activation.

Aspect 254A. The compound of any one of aspects 228A to 253A, wherein the compound comprises a moiety configured to target IL-2R-directed immuno-stimulation of the effector immune cells in the tumor.

Aspect 255A. The compound of any one of aspects 228A to 254A, wherein the compound comprises a cleavable moiety.

Aspect 256A. The compound of any one of aspects 228A to 240A, wherein the compound comprises a moiety that is toxic to cells expressing high levels of the IL-2Rβ subunit.

Aspect 257A. The compound of aspect 256A, wherein the cells expressing high levels of the IL-2Rβ subunit comprise cancer cells.

Aspect 258A. The compound of any one of aspects 228A to 257A, wherein the compound comprises an imaging agent, a diagnostic agent, a targeting agent, a therapeutic agent, or a combination of any of the foregoing.

Aspect 259A. The compound of any one of aspects 228A to 258A, wherein the compound comprises a moiety configured to target IL-2R-directed immuno-stimulation of effector immune cells in a tumor.

Aspect 260A. A pharmaceutical composition comprising; an IL-2Rβ ligand of any one of aspects 1A to 227A; a compound of any one of aspects 228A to 259A; or a combination thereof.

Aspect 261A. The pharmaceutical composition of aspect 260A, further comprising: an IL-2Rγc ligand of any one of SEQ ID NO: 194 to SEQ ID NO: 267 and SEQ ID NO: 904 to SEQ ID NO: 1027 and SEQ ID NOS 1065-1083; a compound comprising an IL-2Rγc ligand of any one of SEQ ID NO: 194 to SEQ ID NO: 267 and SEQ ID NO: 904 to SEQ ID NO: 1027 and SEQ ID NOS 1065-1083; or a combination thereof.

Aspect 262A. A method of treating cancer in a patient, comprising administering to a patient in need of such treatment, a therapeutically effective amount of the pharmaceutical composition of aspect 260A.

Aspect 263A. The method of aspect 262A, wherein the cancer comprises a solid tumor.

Aspect 264A. A method of treating an autoimmune disease in a patient, comprising administering to a patient in need of such treatment, a therapeutically effective amount of the pharmaceutical composition of any one of aspects 260A to 261A.

Aspect 265A. A method of screening compounds for IL-2Rβ activity, comprising: contacting a cell with, the IL-2Rβ ligand of any one of aspects 1A to 227A; the compound of any one of aspects 228A to 259A; or a combination of any of the foregoing; wherein the cell expresses the IL-2Rβ subunit; and contacting the cell with a test compound; and determining the activity of the test compound.

Aspect 266A. A method of activating the human IL-2 receptor, comprising contacting a cell expressing the human IL-2 receptor in vivo with a compound comprising: the IL-2Rβ ligand of any one of aspects 1A to 227A and an IL-2Rγc ligand of any one of SEQ ID NO: 194 to SEQ ID NO: 267 and SEQ ID NO: 904 to SEQ ID NO: 1027 and SEQ ID NOS 1065-1083, or a compound of any one of aspects 228A to 259A.

Aspect 267A. A method of activating the human IL-2 receptor in a patient, comprising contacting a cell expressing the human IL-2 receptor in vivo with a compound comprising: the IL-2Rβ ligand of any one of aspects 1A to 227A and an IL-2Rγc ligand of any one of SEQ ID NO: 194 to SEQ ID NO: 267 and SEQ ID NO: 904 to SEQ ID NO: 1027 and SEQ ID NOS 1065-1083, or a compound of any one of aspects 228A to 259A.

Aspect 268A. A method of treating a disease in a patient, wherein the IL-2 receptor signaling pathway is associated with the etiology of the disease, comprising administering to a patient in need of such treatment a therapeutically effective amount of a compound comprising the IL-2Rβ ligand of any one of aspects 1A to 227A, or a compound of any one of aspects 228A to 259A.

Aspect 269A. A method of treating a disease in a patient, wherein activation of the IL-2 receptor is effective in treating the disease, comprising administering to a patient in need of such treatment a therapeutically effective amount of a compound comprising the IL-2Rβ ligand of any one of aspects 1A to 227A, or a compound of any one of aspects 228A to 259A.

Aspect 270A. A method of treating a disease in a patient, wherein inhibition of the IL-2 receptor is effective in treating the disease, comprising administering to a patient in need of such treatment a therapeutically effective amount of a compound comprising the IL-2Rβ ligand of any one of aspects 1A to 227A, or a compound of any one of aspects 228A to 259A.

Aspect 271A. A method of treating a disease in a patient, wherein cells expressing the IL-2Rβ subunit are associated with the etiology of the disease, comprising administering to a patient in need of such treatment a therapeutically effective amount of a compound comprising the IL-2Rβ ligand of any one of aspects 1A to 227A, or a compound of any one of aspects 228A to 259A.

Aspect 272A. A method of treating a disease in a patient, wherein activation of IL-2R is effective in treating the disease, comprising administering to a patient in need of such treatment a therapeutically effective amount of a compound comprising the IL-2Rβ ligand of any one of aspects 1A to 227A, or a compound of any one of aspects 228A to 259A.

Aspect 273A. A method of treating a disease in a patient, wherein inhibiting IL-2R is effective in treating the disease, comprising administering to a patient in need of such treatment a therapeutically effective amount of a compound comprising the IL-2Rβ ligand of any one of aspects 1A to 227A, or a compound of any one of aspects 228A to 259A.

Aspect 274A. A method of treating a disease in a patient, wherein reducing the sensitivity of Treg cells to IL-2 is effective in treating the disease, comprising administering to a patient in need of such treatment a therapeutically effective amount of a compound comprising the IL-2Rβ ligand of any one of aspects 1A to 227A, or a compound of any one of aspects 228A to 259A.

Aspect 275A. A method of imaging cells expressing the IL-2Rβ subunit comprising administering to a patient an effective amount of a compound comprising the IL-2Rβ ligand of any one of aspects 1A to 227A, or a compound of any one of aspects 228A to 259A.

Aspect 276A. A method of diagnosing a disease in a patient wherein the disease is associated with cells expressing the IL-2Rβ subunit comprising: administering to a patient an effective amount of a compound comprising the IL-2Rβ ligand of any one of aspects 1A to 227A, or a compound of any one of aspects 228A to 259A; and determining a biodistribution of the compound comprising the IL-2Rβ ligand of any one of aspects 1A to 227A, or a compound of any one of aspects 228A to 259A.

Aspect 277A. A method of treating a disease in a patient, comprising: contacting a biological sample from a patient with an IL-2Rβ ligand of any one of aspects 1A to 227A or a compound comprising an IL-2Rβ ligand of any one of aspects 1A to 227A; determining at least one property associated with binding of the IL-2Rβ ligand to cells of the biological sample; and administering to the patient having the disease a compound comprising an IL-2Rβ ligand of any one of aspects 1A to 227A based on the at least one determined property.

Aspect 278A. The method of aspect 277A, wherein the at least one property comprises: an expression level of the IL-2Rβ subunit in cells of the biological sample; a characterization of cells of the biological sample expressing the IL-2Rβ subunit; and/or a binding affinity ($IC_{50}$) of cells of the biological sample expressing the IL-2Rβ subunit.

Aspect 279A. A method of targeting a compound to cells expressing the IL-2Rβ subunit comprising administering to a patient an effective amount of a compound comprising: the IL-2Rβ ligand of any one of aspects 1A to 227A; and a targeting moiety.

Aspect 280A. A method of delivering a cytotoxic compound to cells expressing the IL-2Rγc subunit comprising administering to a patient an effective amount of a compound comprising: an IL-2Rβ ligand of any one of aspects 1A to 227A; and cytotoxic moiety.

Aspect 281A. A binding site of the IL-2Rβ subunit, wherein the group of IL-2Rβ ligands having amino acid sequences of SEQ ID NOS: 1-163, 164-182, 578-808, 1028-1043, 1052-1060 and 1084, competitively bind to the binding site with each of the other IL-2Rβ ligands within the group; an IL-2Rβ ligand having amino acid sequence of SEQ ID NO: 1044 does not compete for binding to the binding site with the group of IL-2Rβ ligands; and IL-2 does not compete for binding to the binding site with the group of IL-2Rβ ligands.

Aspect 282A. The binding site of aspect 281A, wherein each IL-2Rβ ligand of the group of IL-2Rβ ligands has a binding affinity ($IC_{50}$) to the IL-2Rβ subunit of less than 100 μM.

Aspect 283A. The binding site of any one of aspects 281A to 282A, wherein each IL-2Rβ ligand of the group of IL-2Rβ ligands has a binding affinity ($IC_{50}$) to the IL-2Rγc subunit of greater than 100 μM.

Aspect 284A. The binding site of any one of aspects 281A to 283A, wherein an IL-2Rγc ligand having the amino acid sequence of SEQ ID NO: 224 does not compete for binding to the binding site with the group of IL-2Rβ ligands.

Aspect 285A. The binding site of any one of aspects 281A to 284A, wherein the group of IL-2Rβ ligands comprises IL-2Rβ ligands having the amino acid sequence of SEQ ID NOS: 58, 83, 142, 169, 170, and 1042.

Aspect 1B. An IL-2Rγc ligand, wherein the IL-2Rγc ligand exhibits a binding affinity ($IC_{50}$) to the human IL-2Rγc subunit of less than 100 μM.

Aspect 2B. The IL-2Rγc ligand of aspect 1B, wherein the IL-2Rγc ligand comprises from 5 to 30 amino acids.

Aspect 3B. The IL-2Rγc ligand of any one of aspects 1B to 2B, wherein the IL-2Rγc ligand exhibits a binding affinity ($IC_{50}$) to the human IL-2Rγc subunit in a range from 1 μM to 100 μM.

Aspect 4B. The IL-2Rγc ligand of any one of aspects 1B to 2B, wherein the IL-2Rγc ligand exhibits a binding affinity ($IC_{50}$) to the human IL-2Rγc subunit in a range from 0.1 μM to 50 μM.

Aspect 5B. The IL-2Rγc ligand of any one of aspects 1B to 2B, wherein the IL-2Rγc ligand exhibits a binding affinity ($IC_{50}$) to the human IL-2Rγc subunit of less than 100 μM.

Aspect 6B. The IL-2Rγc ligand of any one of aspects 1B to 2B, wherein the IL-2Rγc ligand exhibits a binding affinity ($IC_{50}$) to each of the human IL-2Rβ subunit and to the human IL-2Rγc subunit of less than 100 μM.

Aspect 7B. The IL-2Rγc ligand of any one of aspects 1B to 2B, wherein the IL-2Rγc ligand exhibits a binding affinity ($IC_{50}$) to the human IL-2Rα subunit of greater than 100 μM.

Aspect 8B. The IL-2Rγc ligand of any one of aspects 1B to 2B, wherein the IL-2Rγc ligand exhibits a binding affinity ($IC_{50}$) to the human IL-2Rγc subunit that is at least 10 times greater than the binding affinity ($IC_{50}$) of the IL-2Rγc ligand to the human IL-2Rα subunit.

Aspect 9B. The IL-2Rγc ligand of any one of aspects 1B to 8B, wherein the IL-2Rγc ligand comprises the amino acid sequence of Formula (4) (SEQ ID NO: 1069) or the amino acid sequence of Formula (4a) (SEQ ID NO: 1070):

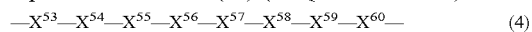

$$—X^{53}—X^{54}—X^{55}—X^{56}—X^{57}—X^{58}—X^{59}—X^{60}— \quad (4)$$

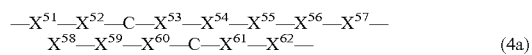

$$—X^{51}—X^{52}—C—X^{53}—X^{54}—X^{55}—X^{56}—X^{57}— \\ X^{58}—X^{59}—X^{60}—C—X^{61}—X^{62}— \quad (4a)$$

wherein, $X^{51}$ is selected from G, I, K, L, Q, R, T, Y, and V; $X^{52}$ is selected from A, D, E, H, I, L, M, R, S, T, V, and W; $X^{53}$ is selected from D, E, F, N, Q, S, and T; $X^{54}$ is selected from A, D, E, G, I, M, N, Q, R, S, and T; $X^{55}$ is selected from D, E, F, S, T, W, and Y; $X^{56}$ is selected from D, E, F, G, L, M, N, Q, and Y; $X^{57}$ is selected from E, G, N, S, and Q; $X^{58}$ is selected from I, K, M, P, T, and V; $X^{59}$ is selected from I, L, M, S, T, and V; $X^{60}$ is selected from F, I, and L; $X^{61}$ is selected from F, T, and W; and $X^{62}$ is selected from, E, F, G, I, K, L, M, N, P, Q, S, T, V, W, and Y.

Aspect 10B. The IL-2Rγc ligand of aspect 9B, wherein $X^{51}$ is selected from I, L, and V.

Aspect 11B. The IL-2Rγc ligand of any one of aspects 9B to 10B, wherein $X^{52}$ is selected from S and T.

Aspect 12B. The IL-2Rγc ligand of any one of aspects 9B to 11B, wherein $X^{53}$ is selected from D, E, N, and Q.

Aspect 13B. The IL-2Rγc ligand of any one of aspects 9B to 12B, wherein $X^{54}$ is selected from D, E, N, and Q.

Aspect 14B. The IL-2Rγc ligand of any one of aspects 9B to 13B, wherein $X^{55}$ is selected from F, W, and Y.

Aspect 15B. The IL-2Rγc ligand of any one of aspects 9B to 14B, wherein $X^{56}$ is selected from D, E, N, and Q.

Aspect 16B. The IL-2Rγc ligand of any one of aspects 9B to 15B, wherein $X^{57}$ is G.

Aspect 17B. The IL-2Rγc ligand of any one of aspects 9B to 16B, wherein $X^{58}$ is selected from I and V.

Aspect 18B. The IL-2Rγc ligand of any one of aspects 9B to 17B, wherein $X^{59}$ is selected from I, L, M, and V.

Aspect 19B. The IL-2Rγc ligand of any one of aspects 9B to 18B, wherein $X^{60}$ is selected from F, I, and L.

Aspect 20B. The IL-2Rγc ligand of any one of aspects 9B to 19B, wherein $X^{61}$ is W.

Aspect 21B. The IL-2Rγc ligand of any one of aspects 9B to 20B, wherein $X^{62}$ is selected from N and Q.

Aspect 22B. The IL-2Rγc ligand of aspect 9B, wherein, $X^{51}$ is selected from I, L, and V; $X^{52}$ is selected from S and T; $X^{53}$ is selected from D, E, N, and Q; $X^{54}$ is selected from D and N; $X^{55}$ is selected from F, W, and Y; $X^{56}$ is selected from D, E, N, and Q; $X^{57}$ is G; $X^{58}$ is selected from I and V; $X^{59}$ is selected from I, L, M, and V; $X^{60}$ is selected from F, I, and L; $X^{61}$ is W; and $X^{62}$ is selected from N and Q.

Aspect 23B. The IL-2Rγc ligand of aspect 9B, wherein the IL-2Rγc ligand comprises an amino acid sequence selected from any one of SEQ ID NO: 196 to SEQ ID NO: 210 and SEQ ID NO: 904 to SEQ ID NO: 913.

Aspect 24B. The IL-2Rγc ligand of aspect 23B, wherein the IL-2Rγc ligand comprises an amino acid sequence selected from any one of SEQ ID NO: 196 to SEQ ID NO: 210 and SEQ ID NO: 904 to SEQ ID NO: 913, wherein the amino acid sequence is terminated with amino acids -G-G- on the N-terminus, on the C-terminus, or on both the N- and C-termini.

Aspect 25B. The IL-2Rγc ligand of aspect 23B, wherein the IL-2Rγc ligand comprises an amino acid sequence selected from any one of SEQ ID NO: 196 to SEQ ID NO: 210 and SEQ ID NO: 904 to SEQ ID NO: 913, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

Aspect 26B. The IL-2Rγc ligand of any one of aspects 1B to 8B, wherein the IL-2Rγc ligand comprises the amino acid sequence of Formula (4) (SEQ ID NO: 1065) or the amino acid sequence of Formula (4a) (SEQ ID NO: 1066):

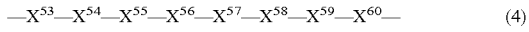  (4)

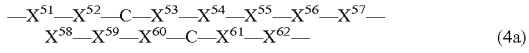  (4a)

wherein, $X^{51}$ is selected from an amino acid; $X^{52}$ is selected from an amino acid; $X^{53}$ is selected from an amino acid comprising a polar-neutral side chain or an acidic side chain; $X^{54}$ is selected from an amino acid comprising a polar-neutral side chain or an acidic side chain; $X^{55}$ is selected from an amino acid; $X^{56}$ is selected from an amino acid; $X^{57}$ is selected from an amino acid comprising a small hydrophobic side chain; $X^{58}$ is selected from an amino acid comprising a large hydrophobic side chain; $X^{59}$ is selected from an amino acid comprising a large hydrophobic side chain; $X^{60}$ is selected from an amino acid comprising a large hydrophobic side chain; $X^{61}$ is selected from an amino acid comprising a large hydrophobic side chain; and $X^{62}$ is selected from an amino acid.

Aspect 27B. The IL-2Rγc ligand of aspect 26B, wherein, $X^{51}$ is selected from an amino acid comprising a large hydrophobic side chain and a basic side chain; $X^{52}$ is selected from an amino acid comprising a hydroxyl-containing side chain and a large hydrophobic side chain; $X^{53}$ is selected from an amino acid comprising a polar-neutral side chain or an acidic side chain; $X^{54}$ is selected from an amino acid comprising a polar-neutral side chain or an acidic side chain; $X^{55}$ is selected from an amino acid comprising a large hydrophobic side chain; $X^{56}$ is selected from an amino acid comprising a polar-neutral side chain or an acidic side chain; $X^{57}$ is selected from an amino acid comprising a small hydrophobic side chain; $X^{58}$ is selected from an amino acid comprising a large hydrophobic side chain; $X^{59}$ is selected from an amino acid comprising a large hydrophobic side chain; $X^{60}$ is selected from an amino acid comprising a large hydrophobic side chain; $X^{61}$ is selected from an amino acid comprising a large hydrophobic side chain; and $X^{62}$ is selected from an amino acid comprising a polar-neutral side chain.

Aspect 28B. The IL-2Rγc ligand of any one of aspects 26B to 27B, wherein, $X^{51}$ is selected from R, K, H, F, I, L, M, V, Y, and W; $X^{52}$ is selected from S, T, F, I, L, M, V, Y, and W; $X^{53}$ is selected from D, E, H, N, Q, S, T, and Y; $X^{54}$ is selected from D, E, H, N, Q, S, T, and Y; $X^{55}$ is selected from F, I, L, M, V, Y, and W; $X^{56}$ is selected from D, E, H, N, Q, S, T, and Y; $X^{57}$ is selected from A, G, P, S, and T; $X^{58}$ is selected from F, I, L, M, V, Y, and W; $X^{59}$ is selected from F, I, L, M, V, Y, and W; $X^{60}$ is selected from F, I, L, M, V, Y, and W; $X^{61}$ is selected from F, I, L, M, V, Y, and W; and $X^{62}$ is selected from H, N, Q, S, T, and Y.

Aspect 29B. The IL-2Rγc ligand of aspect 28B, wherein $X^{51}$ is selected from I, L, and V.

Aspect 30B. The IL-2Rγc ligand of any one of aspects 28B to 29B, wherein $X^{52}$ is selected from S and T.

Aspect 31B. The IL-2Rγc ligand of any one of aspects 28B to 30B, wherein $X^{53}$ is selected from D, E, and Q.

Aspect 32B. The IL-2Rγc ligand of any one of aspects 28B to 31B, wherein $X^{54}$ is selected from D, E, and N.

Aspect 33B. The IL-2Rγc ligand of any one of aspects 28B to 32B, wherein $X^{55}$ is selected from F, Y, and W.

Aspect 34B. The IL-2Rγc ligand of any one of aspects 28B to 33B, wherein $X^{56}$ is selected from D, E, N, and Q.

Aspect 35B. The IL-2Rγc ligand of any one of aspects 28B to 34B, wherein $X^{57}$ is G.

Aspect 36B. The IL-2Rγc ligand of any one of aspects 28B to 35B, wherein $X^{58}$ is selected from I and V.

Aspect 37B. The IL-2Rγc ligand of any one of aspects 28B to 36B, wherein $X^{59}$ is selected from I, L, M, and V.

Aspect 38B. The IL-2Rγc ligand of any one of aspects 28B to 37B, wherein $X^{60}$ is selected from F, I, and L.

Aspect 39B. The IL-2Rγc ligand of any one of aspects 28B to 38B, wherein $X^{61}$ is W.

Aspect 40B. The IL-2Rγc ligand of any one of aspects 28B to 39B, wherein $X^{62}$ is selected from N and Q.

Aspect 41B. The IL-2Rγc ligand of aspect 28B, wherein, $X^{51}$ is selected from I, L, and V; $X^{52}$ is selected from S and T; $X^{53}$ is selected from D, E, and Q; $X^{54}$ is selected from D, E, and N; $X^{55}$ is selected from F, Y, and W; $X^{56}$ is selected from D, E, N, and Q; $X^{57}$ is G; $X^{58}$ is selected from I and V; $X^{59}$ is selected from I, L, M, and V; $X^{60}$ is selected from F, I, and L; $X^{61}$ is W; and $X^{62}$ is selected from N and Q.

Aspect 42B. The IL-2Rγc ligand of aspect 1B, wherein the IL-2Rγc ligand comprises the amino acid sequence of Formula (5) (SEQ ID NO: 211) or Formula (5a) (SEQ ID NO: 212):

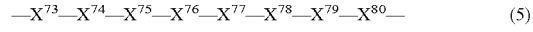  (5)

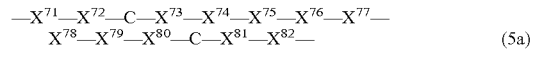  (5a)

wherein, $X^{71}$ is selected from F, G, I, L, P, Q, R, T, and V; $X^{72}$ is selected from A, D, E, I, M, R, S, T, and V; $X^{73}$ is selected from D, E, F, M, N, Q, S T, V, W, and Y; $X^{74}$ is selected from D, E, F, G, I, L, M, P, R, S, T, and V; $X^{75}$ is selected from F, H, L, W, and Y; $X^{76}$ is selected from D, E, H, L, N, Q, S, and T; $X^{77}$ is selected from G, T, Q, and E; $X^{78}$ is selected from I, L, M, Q, and V; $X^{79}$ is selected from D, E, N, Q, and R; $X^{80}$ is selected from D, F, I, and L; $X^{81}$ is selected from F, I, L, R, T, W, and Y; and $X^{82}$ is selected from A, F, G, H, I, L, N, P, Q, S, T, and W.

Aspect 43B. The IL-2Rγc ligand of aspect 42B, wherein $X^{71}$ is selected from I, L, and V.

Aspect 44B. The IL-2Rγc ligand of any one of aspects 42B to 43B, wherein $X^{72}$ is selected from A, D, E, I, M, and V.

Aspect 45B. The IL-2Rγc ligand of any one of aspects 42B to 44B, wherein $X^{73}$ is selected from E, Q, and N.

Aspect 46B. The IL-2Rγc ligand of any one of aspects 42B to 45B, wherein $X^{74}$ is selected from D and E.

Aspect 47B. The IL-2Rγc ligand of any one of aspects 42B to 46B, wherein $X^{75}$ is selected from F, W, and Y.

Aspect 48B. The IL-2Rγc ligand of any one of aspects 42B to 47B, wherein $X^{76}$ is selected from D, E, L, N, and Q.

Aspect 49B. The IL-2Rγc ligand of any one of aspects 42B to 48B, wherein $X^{77}$ is G.

Aspect 50B. The IL-2Rγc ligand of any one of aspects 42B to 49B, wherein $X^{78}$ is selected from I, M, and V.

Aspect 51B. The IL-2Rγc ligand of any one of aspects 42B to 50B, wherein $X^{79}$ is selected from D, E, Q, and R.

Aspect 52B. The IL-2Rγc ligand of any one of aspects 42B to 51B, wherein $X^{80}$ is selected from F, I, and L.

Aspect 53B. The IL-2Rγc ligand of any one of aspects 42B to 52B, wherein $X^{81}$ is W.

Aspect 54B. The IL-2Rγc ligand of any one of aspects 42B to 53B, wherein $X^{82}$ is selected from N and Q.

Aspect 55B. The IL-2Rγc ligand of aspect 42B, wherein, $X^{71}$ is selected from I, L, and V; $X^{72}$ is selected from A, D, E, I, M, and V; $X^{73}$ is selected from E, Q, and N; $X^{74}$ is selected from D and E; $X^{75}$ is selected from F, W, and Y; $X^{76}$ is selected from D, E, L, N, and Q; $X^{77}$ is G; $X^{78}$ is selected from I, M, and V; $X^{79}$ is selected from D, E, Q, and R; $X^{80}$ is selected from F, I, and L; $X^{81}$ is W; and $X^{82}$ is selected from N and Q.

Aspect 56B. The IL-2Rγc ligand of aspect 1B, wherein the IL-2Rγc ligand comprises the amino acid sequence of Formula (5) (SEQ ID NO: 1071) or Formula (5a) (SEQ ID NO: 1072):

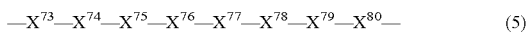

$$-X^{73}-X^{74}-X^{75}-X^{76}-X^{77}-X^{78}-X^{79}-X^{80}- \quad (5)$$

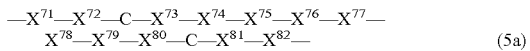

$$-X^{71}-X^{72}-C-X^{73}-X^{74}-X^{75}-X^{76}-X^{77}-X^{78}-X^{79}-X^{80}-C-X^{81}-X^{82}- \quad (5a)$$

wherein, $X^{71}$ is selected from an amino acid; $X^{72}$ is selected from an amino acid; $X^{73}$ is selected from an amino acid; $X^{74}$ is selected from an amino acid; $X^{75}$ is selected from an amino acid comprising a large hydrophobic side chain; $X^{76}$ is selected from an amino acid; $X^{77}$ is selected from a small hydrophobic side chain; $X^{78}$ is selected from an amino acid comprising a large hydrophobic side chain; $X^{79}$ is selected from an amino acid comprising a basic side chain, an acidic side chain, or a polar-neutral side chain; $X^{80}$ is selected from an amino acid comprising a large hydrophobic side chain; $X^{81}$ is selected from an amino acid comprising a large hydrophobic side chain; and $X^{82}$ is selected from an amino acid.

Aspect 57B. The IL-2Rγc ligand of aspect 56B, wherein, $X^{71}$ is selected from an amino acid comprising a large hydrophobic side chain; $X^{72}$ is selected from an amino acid comprising an acidic side chain or a large hydrophobic side chain; $X^{73}$ is selected from an amino acid comprising an acidic side chain, a hydroxyl-containing side chain, or a polar neutral side chain; $X^{74}$ is selected from an amino acid comprising an acidic side chain, a hydroxyl-containing side chain, or a large hydrophobic side chain; $X^{75}$ is selected from an amino acid comprising a large hydrophobic side chain; $X^{76}$ is selected from an amino acid comprising an acidic side chain, a hydroxyl-containing side chain, or a polar neutral side chain; $X^{77}$ is selected from a small hydrophobic side chain; $X^{78}$ is selected from an amino acid comprising a large hydrophobic side chain; $X^{79}$ is selected from an amino acid comprising a basic side chain, an acidic side chain, or a polar-neutral side chain; $X^{80}$ is selected from an amino acid comprising a large hydrophobic side chain; $X^{81}$ is selected from an amino acid comprising a large hydrophobic side chain; and $X^{82}$ is selected from an amino acid comprising a polar neutral side chain.

Aspect 58B. The IL-2Rγc ligand of any one of aspects 56B to 57B, wherein, $X^{71}$ is selected from F, I, L, M, V, Y, and W; $X^{72}$ is selected from D, E, F, I, L, M, V, Y, and W; $X^{73}$ is selected from D, E, S, T, H, N, Q, S, T, and Y; $X^{74}$ is selected from D, E, S, T, F, I, L, M, V, Y, and W; $X^{75}$ is selected from F, I, L, M, V, Y, and W; $X^{76}$ is selected from D, E, S, T, H, N, Q, S, T, and Y; $X^{77}$ is selected from A, G, P, S, and T; $X^{78}$ is selected from F, I, L, M, V, Y, and W; $X^{79}$ is selected from R, K, H, D, E, H, N, Q, S, T, and Y; $X^{80}$ is selected from F, I, L, M, V, Y, and W; $X^{81}$ is selected from F, I, L, M, V, Y, and W; and $X^{82}$ is selected from H, N, Q, S, T, and Y.

Aspect 59B. The IL-2Rγc ligand of aspect 58B, wherein $X^{71}$ is selected from I, L, and V.

Aspect 60B. The IL-2Rγc ligand of any one of aspects 58B to 59B, wherein $X^{72}$ is selected from D, E, I, M, and V.

Aspect 61B. The IL-2Rγc ligand of any one of aspects 58B to 60B, wherein $X^{73}$ is selected from E, N, and Q.

Aspect 62B. The IL-2Rγc ligand of any one of aspects 58B to 61B, wherein $X^{74}$ is selected from D and E.

Aspect 63B. The IL-2Rγc ligand of any one of aspects 58B to 62B, wherein $X^{75}$ is selected from F, W, and Y.

Aspect 64B. The IL-2Rγc ligand of any one of aspects 58B to 63B, wherein $X^{76}$ is selected from D, E, and N.

Aspect 65B. The IL-2Rγc ligand of any one of aspects 58B to 64B, wherein $X^{77}$ is selected from G.

Aspect 66B. The IL-2Rγc ligand of any one of aspects 58B to 65B, wherein $X^{78}$ is selected from I, M, and V.

Aspect 67B. The IL-2Rγc ligand of any one of aspects 58B to 66B, wherein $X^{79}$ is selected from D, E, N, Q, and R.

Aspect 68B. The IL-2Rγc ligand of any one of aspects 58B to 67B, wherein $X^{80}$ is selected from F, I, and L.

Aspect 69B. The IL-2Rγc ligand of any one of aspects 58B to 68B, wherein $X^{81}$ is W.

Aspect 70B. The IL-2Rγc ligand of any one of aspects 58B to 69B, wherein $X^{82}$ is selected from N and Q.

Aspect 71B. The IL-2Rγc ligand of aspect 58B, wherein, $X^{71}$ is selected from I, L, and V; $X^{72}$ is selected from D, E, I, M, and V; $X^{73}$ is selected from E, N, and Q; $X^{74}$ is selected from D and E; $X^{75}$ is selected from F, W, and Y; $X^{76}$ is selected from D, E, and N; $X^{77}$ is selected from G; $X^{78}$ is selected from I, M, and V; $X^{79}$ is selected from D, E, N, Q, and R; $X^{80}$ is selected from F, I, and L; $X^{81}$ is W; and $X^{82}$ is selected from N and Q.

Aspect 72B. The IL-2Rγc ligand of aspect 56B, wherein the IL-2Rγc ligand comprises an amino acid sequence selected from any one of SEQ ID NO: 213 to SEQ ID NO: 233 and SEQ ID NO: 914 to SEQ ID NO: 920.

Aspect 73B. The IL-2Rγc ligand of aspect 72B, wherein the IL-2Rγc ligand comprises an amino acid sequence selected from any one of SEQ ID NO: 213 to SEQ ID NO: 233 and SEQ ID NO: 914 to SEQ ID NO: 920, wherein the amino acid sequence is terminated with amino acids -G-G- on the N-terminus, on the C-terminus, or on both the N- and C-termini.

Aspect 74B. The IL-2Rγc ligand of aspect 72B, wherein the IL-2Rγc ligand comprises an amino acid sequence selected from any one of SEQ ID NO: 213 to SEQ ID NO: 233 and SEQ ID NO: 914 to SEQ ID NO: 920, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

Aspect 75B. The IL-2Rγc ligand of aspect 1B, wherein the IL-2Rγc ligand comprises the amino acid sequence of Formula (6) (SEQ ID NO: 234) or Formula (6a) (SEQ ID NO: 235):

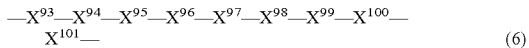

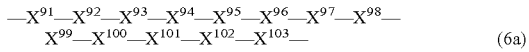

wherein, $X^{91}$ is selected from C, D, E, and L; $X^{92}$ is selected from C, L, M, R, S, V, and W; $X^{93}$ is selected from C, D, F, P, and R; $X^{94}$ is selected from A, D, L, Q, S, and W; $X^{95}$ is selected from D, E, F, L, and V; $X^{96}$ is selected from A, D, E, F, G, K, Q, and S; $X^{97}$ is selected from E, L, M, and W; $X^{98}$ is selected from G, I, L, W, and Y; $X^{99}$ is selected from E, I, R, T, and V; $X^{100}$ is W; $X^{101}$ is selected from C, A, I, L, P, and V; $X^{102}$ is selected from C, D, G, H; and $X^{103}$ is selected from C, D, E, H, S, and T.

Aspect 76B. The IL-2Rγc ligand of aspect 75B, wherein $X^{91}$ is selected from D and E.

Aspect 77B. The IL-2Rγc ligand of any one of aspects 75B to 76B, wherein $X^{92}$ is selected from L, M, R, S, V, and W.

Aspect 78B. The IL-2Rγc ligand of any one of aspects 75B to 77B, wherein $X^{93}$ is selected from D and F.

Aspect 79B. The IL-2Rγc ligand of any one of aspects 75B to 78B, wherein $X^{94}$ is S.

Aspect 80B. The IL-2Rγc ligand of any one of aspects 75B to 79B, wherein $X^{95}$ is selected from D and E.

Aspect 81B. The IL-2Rγc ligand of any one of aspects 75B to 80B, wherein $X^{96}$ is selected from D and E.

Aspect 82B. The IL-2Rγc ligand of any one of aspects 75B to 81B, wherein $X^{97}$ is selected from L, M, and W.

Aspect 83B. The IL-2Rγc ligand of any one of aspects 75B to 82B, wherein $X^{98}$ is G.

Aspect 84B. The IL-2Rγc ligand of any one of aspects 75B to 83B, wherein $X^{99}$ is E.

Aspect 85B. The IL-2Rγc ligand of any one of aspects 75B to 84B, wherein $X^{100}$ is W.

Aspect 86B. The IL-2Rγc ligand of any one of aspects 75B to 85B, wherein $X^{101}$ is selected from I, L, and V.

Aspect 87B. The IL-2Rγc ligand of any one of aspects 75B to 86B, wherein $X^{102}$ is selected from D and G.

Aspect 88B. The IL-2Rγc ligand of any one of aspects 75B to 87B, wherein $X^{103}$ is selected from S and T.

Aspect 89B. The IL-2Rγc ligand of aspect 75B, wherein, $X^{91}$ is selected from D and E; $X^{92}$ is selected from L, M, R, S, V, and W; $X^{93}$ is selected from D and F; $X^{94}$ is S; $X^{95}$ is selected from D and E; $X^{96}$ is selected from D and E; $X^{97}$ is selected from L, M, and W; $X^{98}$ is G; $X^{99}$ is E; $X^{100}$ is W; $X^{101}$ is selected from I, L, and V; $X^{102}$ is selected from D and G; and $X^{103}$ is selected from S and T.

Aspect 90B. The IL-2Rγc ligand of aspect 75B, wherein the IL-2Rγc ligand comprises an amino acid sequence selected from any one of SEQ ID NO: 236 to SEQ ID NO: 245:

Aspect 91B. The IL-2Rγc ligand of aspect 90B, wherein the IL-2Rγc ligand comprises an amino acid sequence selected from any one of SEQ ID NO: 236 to SEQ ID NO: 245, wherein the amino acid sequence is terminated with amino acids -G-G- on the N-terminus, on the C-terminus, or on both the N- and C-termini.

Aspect 92B. The IL-2Rγc ligand of aspect 90B, wherein the IL-2Rγc ligand comprises an amino acid sequence selected from any one of SEQ ID NO: 236 to SEQ ID NO: 245, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

Aspect 93B. The IL-2Rγc ligand of aspect 1B, wherein the IL-2Rγc ligand comprises the amino acid sequence of Formula (6) (SEQ ID NO: 1075) or Formula (6a) (SEQ ID NO: 1076):

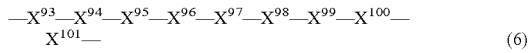

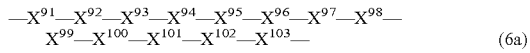

wherein, $X^{91}$ is selected from an amino acid comprising an acidic side chain or cysteine; $X^{92}$ is selected from an amino acid; $X^{93}$ is selected from an amino acid comprising an acidic side chain or large hydrophobic side chain; $X^{94}$ is selected from an amino acid; $X^{95}$ is selected from an amino acid; $X^{96}$ is selected from an amino acid; $X^{97}$ is selected from an amino acid comprising a large hydrophobic side chain; $X^{98}$ is selected from an amino acid comprising a small hydrophobic side chain or a large hydrophobic side chain; $X^{99}$ is selected from an amino acid; $X^{100}$ is selected from an amino acid comprising a large hydrophobic side chain; $X^{101}$ is selected from an amino acid comprising a large hydrophobic side chain; $X^{102}$ is selected from an amino acid comprising a small hydrophobic side chain or an acidic side chain or cysteine; and $X^{103}$ is selected from an amino acid comprising an acidic side chain or a hydroxyl-containing side chain or cysteine.

Aspect 94B. The IL-2Rγc ligand of aspect 93B, wherein, $X^{91}$ is selected from an amino acid comprising an acidic side chain; $X^{92}$ is selected from an amino acid; $X^{93}$ is selected from an amino acid comprising an acidic side chain or large hydrophobic side chain; $X^{94}$ is selected from an amino acid comprising an acidic side chain or a hydroxyl-containing side chain; $X^{95}$ is selected from an amino acid comprising an acidic side chain; $X^{96}$ is selected from an amino acid; $X^{97}$ is selected from an amino acid comprising a large hydrophobic side chain; $X^{98}$ is selected from an amino acid comprising a small hydrophobic side chain or a large hydrophobic side chain; $X^{99}$ is selected from an amino acid comprising an acidic side chain or large hydrophobic side chain; $X^{100}$ is selected from an amino acid comprising a large hydrophobic side chain; $X^{101}$ is selected from an amino acid comprising a large hydrophobic side chain; $X^{102}$ is selected from an amino acid comprising a small hydrophobic side chain or an acidic side chain; and $X^{103}$ is selected from an amino acid comprising an acidic side chain or a hydroxyl-containing side chain.

Aspect 95B. The IL-2Rγc ligand of any one of aspects 93B to 94B, wherein, $X^{91}$ is selected from D and E; $X^{92}$ is selected from an amino acid; $X^{93}$ is selected from D, E, F, I, L, M, V, Y, and W; $X^{94}$ is selected from D, E, S, and T; $X^{95}$ is selected from D and E; $X^{96}$ is selected from an amino acid; $X^{97}$ is selected from F, I, L, M, V, Y, and W; $X^{98}$ is selected from A, G, P, S, T, F, I, L, M, V, Y, and W; $X^{99}$ is selected from D, E, F, I, L, M, V, Y, and W; $X^{100}$ is selected from F, I, L, M, V, Y, and W; $X^{101}$ is selected from F, I, L, M, V, Y, and W; $X^{102}$ is selected from D, E, A, G, P, S, and T; and $X^{103}$ is selected from D, E, S, and T.

Aspect 96B. The IL-2Rγc ligand of aspect 95B, wherein $X^{91}$ is selected from D and E.

Aspect 97B. The IL-2Rγc ligand of any one of aspects 95B to 96B, wherein $X^{92}$ is selected from an amino acid.

Aspect 98B. The IL-2Rγc ligand of any one of aspects 95B to 97B, wherein $X^{93}$ is selected from D and F.

Aspect 99B. The IL-2Rγc ligand of any one of aspects 95B to 98B, wherein $X^{94}$ is S.

Aspect 100B. The IL-2Rγc ligand of any one of aspects 95B to 99B, wherein $X^{95}$ is selected from D and E.

Aspect 101B. The IL-2Rγc ligand of any one of aspects 95B to 100B, wherein $X^{96}$ is selected from an amino acid.

Aspect 102B. The IL-2Rγc ligand of any one of aspects 95B to 101B, wherein $X^{97}$ is selected from L, M, and W.

Aspect 103B. The IL-2Rγc ligand of any one of aspects 95B to 102B, wherein $X^{98}$ is G.

Aspect 104B. The IL-2Rγc ligand of any one of aspects 95B to 103B, wherein $X^{99}$ is E.

Aspect 105B. The IL-2Rγc ligand of any one of aspects 95B to 104B, wherein $X^{100}$ is W.

Aspect 106B. The IL-2Rγc ligand of any one of aspects 95B to 105B, wherein $X^{101}$ is selected from I, L, and V.

Aspect 107B. The IL-2Rγc ligand of any one of aspects 95B to 106B, wherein $X^{102}$ is selected from D and G.

Aspect 108B. The IL-2Rγc ligand of any one of aspects 95B to 107B, wherein $X^{103}$ is selected from S and T.

Aspect 109B. The IL-2Rγc ligand of aspect 95B, wherein, $X^{91}$ is selected from D and E; $X^{92}$ is selected from an amino acid; $X^{93}$ is selected from D and F; $X^{94}$ is S; $X^{95}$ is selected from D and E; $X^{96}$ is selected from an amino acid; $X^{97}$ is selected from L, M, and W; $X^{98}$ is G; $X^{99}$ is E; $X^{100}$ is W; $X^{101}$ is selected from I, L, and V; $X^{102}$ is selected from D and G; and $X^{103}$ is selected from S and T.

Aspect 110B. The IL-2Rγc ligand of aspect 1B, wherein the IL-2Rγc ligand comprises the amino acid sequence of Formula (7) (SEQ ID NO: 1081) or Formula (7a) (SEQ ID NO: 1082):

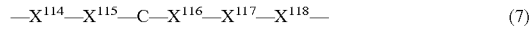

$$—X^{114}—X^{115}—C—X^{116}—X^{117}—X^{118}— \quad (7)$$

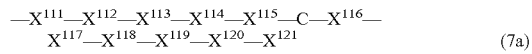

$$\begin{array}{c}—X^{111}—X^{112}—X^{113}—X^{114}—X^{115}—C—X^{116}—\\ X^{117}—X^{118}—X^{119}—X^{120}—X^{121}\end{array} \quad (7a)$$

wherein, $X^{111}$ is selected from D, G, I, and Q; $X^{112}$ is selected from D, I, and L; $X^{113}$ is selected from G, L, M, Q, R, S, and Y; $X^{114}$ is selected from D, E, G, L, S, T, and Y; $X^{115}$ is selected from E, L, P, and Q; $X^{116}$ is selected from D, E, K, L, S, and T; $X^{117}$ is selected from D, F, S, and W; $X^{118}$ is selected from F, N, W, and Y; $X^{119}$ is selected from F, I, L, R and W; $X^{120}$ is selected from A, E, L, and S; and $X^{121}$ is selected from H, L, K, N, Q, and V.

Aspect 111B. The IL-2Rγc ligand of aspect 110B, wherein $X^{111}$ is selected from D and Q.

Aspect 112B. The IL-2Rγc ligand of any one of aspects 110B to 111B, wherein $X^{112}$ is selected from I and L.

Aspect 113B. The IL-2Rγc ligand of any one of aspects 110B to 112B, wherein $X^{113}$ is selected from G, L, M, R, S, and Y.

Aspect 114B. The IL-2Rγc ligand of any one of aspects 110B to 113B, wherein $X^{114}$ is L.

Aspect 115B. The IL-2Rγc ligand of any one of aspects 110B to 114B, wherein $X^{15}$ is selected from E and Q.

Aspect 116B. The IL-2Rγc ligand of any one of aspects 110B to 115B, wherein $X^{116}$ is selected from D and E.

Aspect 117B. The IL-2Rγc ligand of any one of aspects 110B to 116B, wherein $X^{117}$ is selected from F and W.

Aspect 118B. The IL-2Rγc ligand of any one of aspects 110B to 117B, wherein $X^{118}$ is selected from F, W, and Y.

Aspect 119B. The IL-2Rγc ligand of any one of aspects 110B to 118B, wherein $X^{119}$ is selected from F, I, and L.

Aspect 120B. The IL-2Rγc ligand of any one of aspects 110B to 119B, wherein $X^{120}$ is S.

Aspect 121B. The IL-2Rγc ligand of any one of aspects 110B to 120B, wherein $X^{121}$ is selected from N and Q.

Aspect 122B. The IL-2Rγc ligand of aspect 110B, wherein, $X^{111}$ is selected from D and Q; $X^{112}$ is selected from I and L; $X^{113}$ is selected from G, L, M, R, S, and Y; $X^{114}$ is L; $X^{115}$ is selected from E and Q; $X^{116}$ is selected from D and E; $X^{117}$ is selected from F and W; $X^{118}$ is selected from F, W, and Y; $X^{119}$ is selected from F, I, and L; $X^{120}$ is S; and $X^{121}$ is selected from N and Q.

Aspect 123B. The IL-2Rγc ligand of aspect 110B, wherein the IL-2Rγc ligand comprises an amino acid sequence selected from any one of SEQ ID NO: 248 to SEQ ID NO: 254 and SEQ ID NO: 1051 and SEQ ID NO: 921 to SEQ ID NO: 922.

Aspect 124B. The IL-2Rγc ligand of aspect 123B, wherein the IL-2Rγc ligand comprises an amino acid sequence selected from any one of SEQ ID NO: 248 to SEQ ID NO: 254 and SEQ ID NO: 1051 and SEQ ID NO: 921 to SEQ ID NO: 922, wherein the amino acid sequence is terminated with amino acids -G-G- on the N-terminus, on the C-terminus, or on both the N- and C-termini.

Aspect 125B. The IL-2Rγc ligand of aspect 123B, wherein the IL-2Rγc ligand comprises an amino acid sequence selected from any one of SEQ ID NO: 248 to SEQ ID NO: 254 and SEQ ID NO: 1051 and SEQ ID NO: 921 to SEQ ID NO: 922, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

Aspect 126B. The IL-2Rγc ligand of aspect 1B, wherein the IL-2Rγc ligand comprises the amino acid sequence of Formula (7) (SEQ ID NO: 1077) or Formula (7a) (SEQ ID NO: 1078):

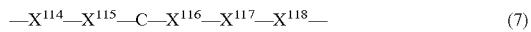

$$-X^{114}-X^{115}-C-X^{116}-X^{117}-X^{118}- \quad (7)$$

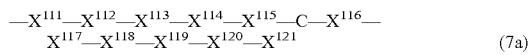

$$-X^{111}-X^{112}-X^{113}-X^{114}-X^{115}-C-X^{116}- X^{117}-X^{118}-X^{119}-X^{120}-X^{121} \quad (7a)$$

wherein, $X^{111}$ is selected from an amino acid; $X^{112}$ is selected from an amino acid comprising a large hydrophobic side chain or an acidic side chain; $X^{113}$ is selected from an amino acid; $X^{114}$ is selected from an amino acid comprising an acidic side chain or a hydroxyl-containing side chain; $X^{115}$ is selected from an amino acid; $X^{116}$ is selected from an amino acid; $X^{117}$ is selected from an amino acid comprising a large hydrophobic side chain; $X^{118}$ is selected from an amino acid comprising a large hydrophobic side chain; $X^{119}$ is selected from an amino acid comprising a large hydrophobic side chain; $X^{120}$ is selected from an amino acid; and $X^{121}$ is selected from an amino acid.

Aspect 127B. The IL-2Rγc ligand of aspect 125B, wherein, $X^{111}$ is selected from an amino acid; $X^{112}$ is selected from an amino acid comprising a large hydrophobic side chain or an acidic side chain; $X^{113}$ is selected from an amino acid; $X^{114}$ is selected from an amino acid comprising an acidic side chain or a hydroxyl-containing side chain; $X^{115}$ is selected from an amino acid comprising a large hydrophobic side chain; $X^{116}$ is selected from an amino acid comprising an acidic side chain; $X^{117}$ is selected from an amino acid comprising a large hydrophobic side chain; $X^{118}$ is selected from an amino acid comprising a large hydrophobic side chain; $X^{119}$ is selected from an amino acid comprising a large hydrophobic side chain; $X^{120}$ is selected from an amino acid; and $X^{121}$ is selected from an amino acid comprising a polar-neutral side chain.

Aspect 128B. The IL-2Rγc ligand of any one of aspects 126B to 127B, wherein, $X^{111}$ is selected from an amino acid; $X^{112}$ is selected from D, E, F, I, L, M, V, Y, and W; $X^{113}$ is selected from an amino acid; $X^{114}$ is selected from D, E, S, T, and Y; $X^{115}$ is selected from F, I, L, M, V, Y, and W; $X^{116}$ is selected from D and E; $X^{117}$ is selected from F, I, L, M, V, Y, and W; $X^{118}$ is selected from F, I, L, M, V, Y, and W; $X^{119}$ is selected from F, I, L, M, V, Y, and W; $X^{120}$ is selected from an amino acid; and $X^{121}$ is selected from H, N, Q, S, T, and Y.

Aspect 129B. The IL-2Rγc ligand of aspect 128B, wherein $X^{111}$ is selected from an amino acid.

Aspect 130B. The IL-2Rγc ligand of any one of aspects 128B to 129B, wherein $X^{112}$ is selected from I and L.

Aspect 131B. The IL-2Rγc ligand of any one of aspects 128B to 130B, wherein $X^{113}$ is selected from an amino acid.

Aspect 132B. The IL-2Rγc ligand of any one of aspects 128B to 131B, wherein $X^{114}$ is selected from D, E, and S.

Aspect 133B. The IL-2Rγc ligand of any one of aspects 128B to 132B, wherein $X^{115}$ is L.

Aspect 134B. The IL-2Rγc ligand of any one of aspects 128B to 133B, wherein $X^{116}$ is selected from D and E.

Aspect 135B. The IL-2Rγc ligand of any one of aspects 128B to 134B, wherein $X^{117}$ is selected from F and W.

Aspect 136B. The IL-2Rγc ligand of any one of aspects 128B to 135B, wherein $X^{118}$ is selected from F, W and Y.

Aspect 137B. The IL-2Rγc ligand of any one of aspects 128B to 136B, wherein $X^{119}$ is selected from F, I, and L.

Aspect 138B. The IL-2Rγc ligand of any one of aspects 128B to 137B, wherein $X^{120}$ is selected from an amino acid.

Aspect 139B. The IL-2Rγc ligand of any one of aspects 128B to 138B, wherein $X^{121}$ is selected from Q and N.

Aspect 140B. The IL-2Rγc ligand of aspect 128B, wherein, $X^{111}$ is selected from an amino acid; $X^{112}$ is selected from I and L; $X^{113}$ is selected from an amino acid; $X^{114}$ is selected from D, E, and S; $X^{115}$ is L; $X^{116}$ is selected from D and E; $X^{117}$ is selected from F and W; $X^{118}$ is selected from F, W and Y; $X^{119}$ is selected from F, I, and L; $X^{120}$ is selected from an amino acid; and $X^{121}$ is selected from Q and N.

Aspect 141B. The IL-2Rγc ligand of aspect 126B, wherein the IL-2Rγc ligand comprises an amino acid sequence selected from any one of SEQ ID NO: 255 to SEQ ID NO: 267 and SEQ ID NO: 923 to SEQ ID NO: 930.

Aspect 142B. The IL-2Rγc ligand of aspect 141B, wherein the IL-2Rγc ligand comprises an amino acid sequence selected from any one of SEQ ID NO: 255 to SEQ ID NO: 264 and SEQ ID NO: 923 to SEQ ID NO: 930, wherein the amino acid sequence is terminated with amino acids -G-G- on the N-terminus, on the C-terminus, or on both the N- and C-termini.

Aspect 143B. The IL-2Rγc ligand of aspect 141B, wherein the IL-2Rγc ligand comprises an amino acid sequence selected from any one of SEQ ID NO: 255 to SEQ ID NO: 264 and SEQ ID NO: 923 to SEQ ID NO: 930, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

Aspect 144B. The IL-2Rγc ligand of aspect 1B, wherein IL-2Rγc ligand comprises an amino acid sequence of Formula (8) (SEQ ID NO: 1083):

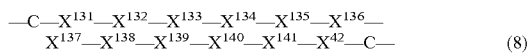

$$-C-X^{131}-X^{132}-X^{133}-X^{134}-X^{135}-X^{136}- X^{137}-X^{138}-X^{139}-X^{140}-X^{141}-X^{42}-C- \quad (8)$$

wherein, $X^{131}$ is selected from an amino acid comprising a large hydrophobic side chain; $X^{122}$ is selected from an amino acid comprising a large hydrophobic side chain; $X^{133}$ is selected from an amino acid comprising a large hydrophobic side chain; $X^{134}$ is selected from an amino acid comprising a large hydrophobic side chain; $X^{135}$ is selected from an amino acid comprising a basic side chain and an acidic or polar neutral side chain; $X^{136}$ is selected from an amino acid; $X^{137}$ is selected from an amino acid comprising a small hydrophobic side chain; $X^{138}$ is selected from an amino acid comprising an acidic or a polar neutral side chain; $X^{139}$ is selected from an amino acid comprising a large hydrophobic side chain; $X^{140}$ is selected from an amino acid comprising a small hydrophobic side chain or a hydroxyl-containing side chain; $X^{141}$ is selected from an amino acid comprising a large hydrophobic side chain; and $X^{142}$ is selected from an amino acid comprising a large hydrophobic side chain.

Aspect 145B. The IL-2Rγc ligand of aspect 144B, wherein, $X^{131}$ is selected from F, I, L, M, V, Y, and W; $X^{132}$ is selected from F, I, L, M, V, Y, and W; $X^{133}$ is selected from F, I, L, M, V, Y, and W; $X^{134}$ is selected from F, I, L, M, V, Y, and W; $X^{135}$ is selected from R, K, H, D, E, N, and Q; $X^{136}$ is selected from an amino acid; $X^{137}$ is selected from A, G, P, S, and T; $X^{138}$ is selected from D, E, N, and Q; $X^{139}$ is selected from F, I, L, M, V, Y, and W; $X^{140}$ is selected from A, G, P, S, and T; $X^{141}$ is selected from F, I, L, M, V, Y, and W; and $X^{142}$ is selected from F, I, L, M, V, Y, and W.

Aspect 146B. The IL-2Rγc ligand of any one of aspects 144B to 145B, wherein, $X^{131}$ is selected from G, G, A, E, F, G, L, and Y; $X^{132}$ is selected from I, S, N, L, I, and V; $X^{133}$ is selected from A, M, L, Y, R, M, A, Y, and I; $X^{134}$ is selected from Y, L, H, T, Y, F, K; $X^{135}$ is selected from R, Q, D, G, P, Y, L, I, K, and E; $X^{136}$ is selected from S, G, T, I, F, Q, R, H, N, and L; $X^{137}$ is selected from G, P, Q, T, D, G, N, and K; $X^{138}$ is selected from E, D, K, F, T; $X^{139}$ is selected from F, R, W, Y, V, L, and A; $X^{140}$ is selected from T, W, N, E, D, S, T, and L; $X^{141}$ is selected from M, W, Y, F, A, L, and I; and $X^{142}$ is selected from I, V, Y, L, V, Y, I, E, and M.

Aspect 147B. The IL-2Rγc ligand of aspect 146B, wherein $X^{131}$ is selected from F and Y.

Aspect 148B. The IL-2Rγc ligand of any one of aspects 146B to 147B, wherein $X^{132}$ is selected from I, V, and L.

Aspect 149B. The IL-2Rγc ligand of any one of aspects 146B to 147B, wherein $X^{132}$ is I.

Aspect 150B. The IL-2Rγc ligand of any one of aspects 146B to 149B, wherein $X^{133}$ is selected from M, L, Y, and I.

Aspect 151B. The IL-2Rγc ligand of any one of aspects 146B to 150B, wherein $X^{134}$ is selected from F, H, and Y.

Aspect 152B. The IL-2Rγc ligand of any one of aspects 146B to 150B, wherein $X^{134}$ is Y.

Aspect 153B. The IL-2Rγc ligand of any one of aspects 146B to 152B, wherein $X^{135}$ is selected from R, K, D, and E.

Aspect 154B. The IL-2Rγc ligand of any one of aspects 146B to 152B, wherein $X^{135}$ is R.

Aspect 155B. The IL-2Rγc ligand of any one of aspects 146B to 154B, wherein $X^{136}$ is selected from an amino acid.

Aspect 156B. The IL-2Rγc ligand of any one of aspects 146B to 155B, wherein $X^{137}$ is G.

Aspect 157B. The IL-2Rγc ligand of any one of aspects 146B to 156B, wherein $X^{138}$ is selected from D and E.

Aspect 158B. The IL-2Rγc ligand of any one of aspects 146B to 156B, wherein $X^{138}$ is E.

Aspect 159B. The IL-2Rγc ligand of any one of aspects 146B to 158B, wherein $X^{139}$ is selected from F, Y, and W.

Aspect 160B. The IL-2Rγc ligand of any one of aspects 146B to 158B, wherein $X^{139}$ is F.

Aspect 161B. The IL-2Rγc ligand of any one of aspects 146B to 160B, wherein $X^{140}$ is selected from S and T.

Aspect 162B. The IL-2Rγc ligand of any one of aspects 146B to 161B, wherein $X^{141}$ is selected from F, I, L, M, V, Y, and W.

Aspect 163B. The IL-2Rγc ligand of any one of aspects 146B to 161B, wherein $X^{141}$ is Y.

Aspect 164B. The IL-2Rγc ligand of any one of aspects 146B to 163B, wherein $X^{142}$ is selected from I, L, M, V, and Y.

Aspect 165B. The IL-2Rγc ligand of aspect 146B, wherein, $X^{131}$ is selected from F and Y; $X^{132}$ is I; $X^{133}$ is selected from M, L, Y, and I; $X^{134}$ is Y; $X^{135}$ is R; $X^{136}$ is selected from an amino acid; $X^{137}$ is G; $X^{138}$ is E; $X^{139}$ is F; $X^{140}$ is selected from S and T; $X^{141}$ is Y; and $X^{142}$ is selected from F, I, L, M, V, Y, and W.

Aspect 166B. The IL-2Rγc ligand of aspect 146B, wherein $X^{131}$ is F, $X^{132}$ is I, $X^{134}$ is Y, $X^{125}$ is R, $X^{137}$ is G, $X^{138}$ is E, $X^{139}$ is F, and $X^{141}$ is Y.

Aspect 167B. The IL-2Rγc ligand of aspect 144B, wherein the IL-2Rγc ligand comprises an amino acid sequence selected from any one of SEQ ID NO: 265 to SEQ ID NO: 267 and SEQ ID NO: 932 to SEQ ID NO: 940.

Aspect 168B. The IL-2Rγc ligand of aspect 167B, wherein the IL-2Rγc ligand comprises an amino acid sequence selected from any one of SEQ ID NO: 265 to SEQ ID NO: 267 and SEQ ID NO: 932 to SEQ ID NO: 940, wherein the amino acid sequence is terminated with amino acids -G-G- on the N-terminus, on the C-terminus, or on both the N- and C-termini.

Aspect 169B. The IL-2Rγc ligand of aspect 167B, wherein the IL-2Rγc ligand comprises an amino acid sequence selected from any one of SEQ ID NO: 265 to SEQ ID NO: 267 and SEQ ID NO: 932 to SEQ ID NO: 940, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

Aspect 170B. The IL-2Rγc ligand of aspect 1B, wherein IL-2Rγc ligand comprises the amino acid sequence of Formula (9) (SEQ ID NO: 941) or the amino acid sequence of Formula (9a) (SEQ ID NO: 942):

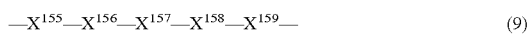

—$X^{155}$—$X^{156}$—$X^{157}$—$X^{158}$—$X^{159}$— (9)

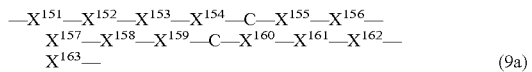

—$X^{151}$—$X^{152}$—$X^{153}$—$X^{154}$—C—$X^{155}$—$X^{156}$—$X^{157}$—$X^{158}$—$X^{159}$—C—$X^{160}$—$X^{161}$—$X^{162}$—$X^{163}$— (9a)

wherein, $X^{151}$ is selected from an amino acid comprising a small hydrophobic side chain or a hydroxyl-containing side chain; $X^{152}$ is selected from an amino acid comprising a large hydrophobic side chain; $X^{153}$ is selected from an amino acid comprising an acidic or polar neutral side chain; $X^{154}$ is selected from an amino acid comprising a basic side chain; $X^{155}$ is selected from an amino acid comprising a large hydrophobic side chain; $X^{156}$ is selected from an amino acid comprising a small hydrophobic side chain or a hydroxyl-containing side chain; $X^{157}$ is selected from an amino acid comprising a small hydrophobic side chain; $X^{158}$ is selected from an amino acid comprising a small hydrophobic side chain or a hydroxyl-containing side chain; $X^{159}$ is selected from an amino acid comprising a small hydrophobic side chain or a hydroxyl-containing side chain; $X^{160}$ is selected from an amino acid comprising a small hydrophobic side chain or a hydroxyl-containing side chain; $X^{161}$ is selected from an amino acid; $X^{162}$ is selected from an amino acid comprising a large hydrophobic side chain or a basic side chain; and $X^{163}$ is selected from an amino acid comprising a large hydrophobic side chain.

Aspect 171B. The IL-2Rγc ligand of aspect 170B, wherein, $X^{151}$ is selected from A, G, P, S, and T; $X^{152}$ is selected from F, I, L, M, V, Y, and W; $X^{153}$ is selected from D, E, N, and Q; $X^{154}$ is selected from H, K, and R; $X^{155}$ is selected from F, I, L, M, V, Y, and W; $X^{156}$ is selected from A, G, P, S, T, and Y; $X^{157}$ is selected from A, G, P, S, and T; $X^{158}$ is selected from A, G, P, S, T, and Y; $X^{159}$ is selected from A, G, P, S, T, and Y; $X^{160}$ is selected from A, G, P, S, T, and Y; $X^{161}$ is selected from an amino acid; $X^{162}$ is selected from F, I, L, M, V, Y, W, R, K, and H; and $X^{163}$ is selected from F, I, L, M, V, Y, and W.

Aspect 172B. The IL-2Rγc ligand of any one of aspects 170B to 171B, wherein, $X^{151}$ is selected from K, M, N, and K; $X^{152}$ is selected from M, L, and Y; $X^{153}$ is selected from N, Y, and L; $X^{154}$ is K; $X^{155}$ is selected from A, W, R, Y, and N; $X^{156}$ is selected from T, N, and S; $X^{157}$ is selected from P and A; $X^{158}$ is selected from S, R, F, and L; $X^{159}$ is selected from Q, S, E, and T; $X^{160}$ is selected from S, Q, and A; $X^{161}$ is selected from V, S, G, L, and N; $X^{162}$ is selected from I, K, R, and V; and $X^{163}$ is selected from F and L.

Aspect 173B. The IL-2Rγc ligand of aspect 172B, wherein $X^{151}$ is selected from S and T.

Aspect 174B. The IL-2Rγc ligand of any one of aspects 172B to 173B, wherein $X^{152}$ is selected from L and M.

Aspect 175B. The IL-2Rγc ligand of any one of aspects 172B to 173B, wherein $X^{152}$ is L.

Aspect 176B. The IL-2Rγc ligand of any one of aspects 172B to 175B, wherein $X^{153}$ is N.

Aspect 177B. The IL-2Rγc ligand of any one of aspects 172B to 176B, wherein $X^{154}$ is K.

Aspect 178B. The IL-2Rγc ligand of any one of aspects 172B to 177B, wherein $X^{155}$ is selected from W and Y.

Aspect 179B. The IL-2Rγc ligand of any one of aspects 172B to 178B, wherein $X^{156}$ is selected from S and T.

Aspect 180B. The IL-2Rγc ligand of any one of aspects 172B to 178B, wherein $X^{156}$ is S.

Aspect 181B. The IL-2Rγc ligand of any one of aspects 172B to 180B, wherein $X^{157}$ is P.

Aspect 182B. The IL-2Rγc ligand of any one of aspects 172B to 181B, wherein $X^{158}$ is S.

Aspect 183B. The IL-2Rγc ligand of any one of aspects 172B to 182B, wherein $X^{159}$ is selected from S and T.

Aspect 184B. The IL-2Rγc ligand of any one of aspects 172B to 182B, wherein $X^{159}$ is S.

Aspect 185B. The IL-2Rγc ligand of any one of aspects 172B to 183B, wherein $X^{160}$ is S.

Aspect 186B. The IL-2Rγc ligand of any one of aspects 172B to 184B, wherein $X^{161}$ is selected from an amino acid.

Aspect 187B. The IL-2Rγc ligand of any one of aspects 172B to 185B, wherein $X^{162}$ is selected from I, V, R, and K.

Aspect 188B. The IL-2Rγc ligand of any one of aspects 172B to 185B, wherein $X^{162}$ is selected from I and V.

Aspect 189B. The IL-2Rγc ligand of any one of aspects 172B to 185B, wherein $X^{162}$ is selected from R and K.

Aspect 190B. The IL-2Rγc ligand of any one of aspects 172B to 186B, wherein $X^{163}$ is selected from F and L.

Aspect 191B. The IL-2Rγc ligand of any one of aspects 172B to 186B, wherein $X^{163}$ is L.

Aspect 192B. The IL-2Rγc ligand of aspect 172B, wherein, $X^{151}$ is selected from S and T; $X^{152}$ is L; $X^{153}$ is N; $X^{154}$ is K; $X^{155}$ is selected from W and Y; $X^{156}$ is S; $X^{157}$ is P; $X^{158}$ is S; $X^{159}$ is S; $X^{160}$ is S T; $X^{161}$ is selected from an amino acid; $X^{162}$ is I; and $X^{163}$ is F.

Aspect 193B. The IL-2Rγc ligand of aspect 172B, wherein $X^{152}$ is L, $X^{153}$ is N, $X^{154}$ is K, $X^{156}$ is S, $X^{157}$ is P, $X^{158}$ is S, $X^{159}$ is S, $X^{160}$ is S, $X^{162}$ is I, and $X^{163}$ is F.

Aspect 194B. The IL-2Rγc ligand of aspect 170B, wherein the IL-2Rγc ligand comprises an amino acid sequence selected from any one of SEQ ID NO: 943 to SEQ ID NO: 948:

Aspect 195B. The IL-2Rγc ligand of aspect 194B, wherein the IL-2Rγc ligand comprises an amino acid sequence selected from any one of SEQ ID NO: 943 to SEQ ID NO: 948, wherein the amino acid sequence is terminated with amino acids -G-G- on the N-terminus, on the C-terminus, or on both the N- and C-termini.

Aspect 196B. The IL-2Rγc ligand of aspect 194B, wherein the IL-2Rγc ligand comprises an amino acid sequence selected from any one of SEQ ID NO: 943 to SEQ ID NO: 948, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

Aspect 197B. The IL-2Rγc ligand of aspect 1B, wherein the IL-2Rγc ligand comprises the amino acid sequence of Formula (12) (SEQ ID NO: 949):

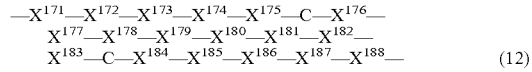

$$-X^{171}-X^{172}-X^{173}-X^{174}-X^{175}-C-X^{176}-X^{177}-X^{178}-X^{179}-X^{180}-X^{181}-X^{182}-X^{183}-C-X^{184}-X^{185}-X^{186}-X^{187}-X^{188}- \quad (12)$$

wherein, $X^{171}$ is selected from an amino acid comprising a basic side chain; $X^{172}$ is selected from an amino acid comprising a hydroxyl-containing side chain; $X^{173}$ is selected from an amino acid comprising an acidic side chain or a large hydrophobic side chain; $X^{174}$ is selected from an amino acid comprising a large hydrophobic side chain; $X^{175}$ is selected from an amino acid comprising an acidic side chain or a large hydrophobic side chain; $X^{176}$ is selected from an amino acid comprising an acidic side chain or a polar/neutral side chain; $X^{177}$ is selected from an amino acid comprising an acidic side chain; $X^{178}$ is selected from an amino acid comprising a large hydrophobic side chain or an aromatic side chain; $X^{179}$ is selected from an amino acid comprising an acidic side chain or a polar/neutral side chain; $X^{180}$ is G; $X^{181}$ is V; $X^{182}$ is E; $X^{183}$ is L;

$X^{184}$ is W; $X^{185}$ is selected from an amino acid comprising a large hydrophobic side chain; $X^{186}$ is E; $X^{187}$ is selected from an amino acid; and $X^{188}$ is selected from an amino acid comprising an acidic side chain.

Aspect 198B. The IL-2Rγc ligand of aspect 196B, wherein, $X^{171}$ is selected from H, K, and R; $X^{172}$ is selected from S, T, and Y; $X^{173}$ is selected from D, E, F, I, and V; $X^{174}$ is selected from I and V; $X^{175}$ is selected from E, I, L, M, and V; $X^{176}$ is selected from D, E, and Q; $X^{177}$ is selected from D and E; $X^{178}$ is selected from F and W; $X^{179}$ is selected from D, E, N, and Q; $X^{180}$ is G; $X^{181}$ is V; $X^{182}$ is selected from D and E; $X^{183}$ is L; $X^{184}$ is W; $X^{185}$ is selected from I, L, Q, and V; $X^{186}$ is selected from D and E; $X^{187}$ is selected from A, D, E, F, G, I, M, N, P, Q, R, S, T, V, W, and Y; and $X^{188}$ is selected from D, E, N, and Q.

Aspect 199B. The IL-2Rγc ligand of aspect 198B, wherein $X^{171}$ is selected from H, K, and R.

Aspect 200B. The IL-2Rγc ligand of any one of aspects 198B to 199B, wherein $X^{172}$ is selected from S, T, and Y.

Aspect 201B. The IL-2Rγc ligand of any one of aspects 198B to 200B, wherein $X^{173}$ is selected from D, E, F, I, L, M, V, W, and Y.

Aspect 202B. The IL-2Rγc ligand of any one of aspects 198B to 200B, wherein $X^{173}$ is selected from D and E.

Aspect 203B. The IL-2Rγc ligand of any one of aspects 198B to 200B, wherein $X^{173}$ is selected from F, I, L, M, V, W, and Y.

Aspect 204B. The IL-2Rγc ligand of any one of aspects 198B to 203B, wherein $X^{174}$ is selected from F, I, L, M, V, W, and Y.

Aspect 205B. The IL-2Rγc ligand of any one of aspects 198B to 203B, wherein $X^{174}$ is V.

Aspect 206B. The IL-2Rγc ligand of any one of aspects 198B to 205B, wherein $X^{175}$ is selected from D, E, F, I, L, M, V, W, and Y.

Aspect 207B. The IL-2Rγc ligand of any one of aspects 198B to 205B, wherein $X^{175}$ is selected from D and E.

Aspect 208B. The IL-2Rγc ligand of any one of aspects 198B to 205B, wherein $X^{175}$ is selected from F, I, L, M, V, W, and Y.

Aspect 209B. The IL-2Rγc ligand of any one of aspects 198B to 208B, wherein $X^{176}$ is selected from D, E, H, N, Q, S, T, and Y.

Aspect 210B. The IL-2Rγc ligand of any one of aspects 198B to 208B, wherein $X^{176}$ is selected from E and Q.

Aspect 211B. The IL-2Rγc ligand of any one of aspects 198B to 210B, wherein $X^{177}$ is selected from D and E.

Aspect 212B. The IL-2Rγc ligand of any one of aspects 198B to 211B, wherein $X^{178}$ is selected from F, H, I, L, M, V, W, and Y.

Aspect 213B. The IL-2Rγc ligand of any one of aspects 198B to 211B, wherein $X^{178}$ is selected from F, H, W, and Y.

Aspect 214B. The IL-2Rγc ligand of any one of aspects 198B to 211B, wherein $X^{178}$ is W.

Aspect 215B. The IL-2Rγc ligand of any one of aspects 198B to 214B, wherein $X^{179}$ is selected from D, E, H, N, Q, S, T, and Y.

Aspect 216B. The IL-2Rγc ligand of any one of aspects 198B to 214B, wherein $X^{179}$ is selected from D, E, and Q.

Aspect 217B. The IL-2Rγc ligand of any one of aspects 198B to 216B, wherein $X^{180}$ is G.

Aspect 218B. The IL-2Rγc ligand of any one of aspects 198B to 217B, wherein $X^{181}$ is V.

Aspect 219B. The IL-2Rγc ligand of any one of aspects 198B to 218B, wherein $X^{182}$ is E.

Aspect 220B. The IL-2Rγc ligand of any one of aspects 198B to 219B, wherein $X^{183}$ is L.

Aspect 221B. The IL-2Rγc ligand of any one of aspects 198B to 220B, wherein $X^{184}$ is W.

Aspect 222B. The IL-2Rγc ligand of any one of aspects 198B to 221B, wherein $X^{185}$ is selected from F, I, L, M, V, W, and Y.

Aspect 223B. The IL-2Rγc ligand of any one of aspects 198B to 221B, wherein $X^{185}$ is L.

Aspect 224B. The IL-2Rγc ligand of any one of aspects 198B to 223B, wherein $X^{186}$ is E.

Aspect 225B. The IL-2Rγc ligand of any one of aspects 198B to 224B, wherein $X^{187}$ is selected from an amino acid.

Aspect 226B. The IL-2Rγc ligand of any one of aspects 198B to 225B, wherein $X^{188}$ is selected from D and E.

Aspect 227B. The IL-2Rγc ligand of aspect 198B, wherein, $X^{171}$ is selected from H, K, and R; $X^{172}$ is selected from S, T, and Y; $X^{173}$ is selected from D, E, F, I, L, M, V, W, and Y; $X^{174}$ is selected from F, I, L, M, V, W, and Y; $X^{175}$ is selected from D, E, F, I, L, M, V, W, and Y; $X^{176}$ is selected from D, E, H, N, Q, S, T, and Y; $X^{177}$ is selected from D and E; $X^{178}$ is selected from F, H, I, L, M, V, W, and Y; $X^{179}$ is selected from D, E, H, N, Q, S, T, and Y; $X^{180}$ is G; $X^{181}$ is V; $X^{182}$ is E; $X^{183}$ is L; $X^{184}$ is selected from W; $X^{185}$ is selected from F, I, L, M, V, W, and Y; $X^{186}$ is E; $X^{187}$ is selected from an amino acid; and $X^{188}$ is selected from D and E.

Aspect 228B. The IL-2Rγc ligand of aspect 198B, wherein, $X^{171}$ is selected from H, K, and R; $X^{172}$ is selected from S, T, and Y; $X^{173}$ is selected from D, E, F, I, L, M, V, W, and Y; $X^{174}$ is V; $X^{175}$ is selected from D, E, F, I, L, M, V, W, and Y; $X^{176}$ is selected from D, E, H, N, Q, S, T, and Y; $X^{176}$ is selected from E and Q; $X^{177}$ is selected from D and E; $X^{178}$ is W; $X^{179}$ is selected from D, E, and Q; $X^{180}$ is G; $X^{181}$ is V; $X^{182}$ is E; $X^{183}$ is L; $X^{184}$ is W; $X^{185}$ is selected from F, I, L, M, V, W, and Y; $X^{185}$ is E; $X^{187}$ is selected from an amino acid; and $X^{188}$ is selected from D and E.

Aspect 229B. The IL-2Rγc ligand of aspect 196B, wherein IL-2Rγc ligand comprises the amino acid sequence any one of SEQ ID NO: 950 to SEQ ID NO: 1027.

Aspect 230B. The IL-2Rγc ligand of aspect 229B, wherein the IL-2Rγc ligand comprises an amino acid sequence selected from any one of SEQ ID NO: 950 to SEQ ID NO: 1027, wherein the amino acid sequence is terminated with amino acids -G-G- on the N-terminus, on the C-terminus, or on both the N- and C-termini.

Aspect 231B. The IL-2Rγc ligand of aspect 229B, wherein the IL-2Rγc ligand comprises an amino acid sequence selected from any one of SEQ ID NO: 950 to SEQ ID NO: 1027, wherein each amino acid independently comprises one or more of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

Aspect 232B. The IL-2Rγc ligand of aspect 1B, wherein the IL-2Rγc ligand comprises an amino acid sequence selected from any one of SEQ ID NO: 194 to SEQ ID NO: 267 and SEQ ID NO: 904 to SEQ ID NO: 1027 and SEQ ID NOS 1065-1082.

Aspect 233B. The IL-2Rγc ligand of any one of aspects 1B to 232B, wherein the IL-2Rγc ligand does not comprise the amino acid sequence of SEQ ID NO: 375 and to SEQ ID NO: 376.

Aspect 234B. A compound comprising at least one IL-2Rγc ligand of any one of aspects 1B to 233B.

Aspect 235B. The compound of aspect 234B, wherein the compound further comprises at least one IL-2Rβ ligand selected from any one of SEQ ID NO: 1 to SEQ ID NO: 193, SEQ ID NO. 578 to SEQ ID NO: 903, and SEQ ID NO: 1028 to SEQ ID NO: 1043, and SEQ ID NOS 1052-1064 and 1084.

Aspect 236B. The compound of any one of aspects 234B to 235B, wherein the compound comprises a least one IL-2Rγc ligand.

Aspect 237B. The compound of any one of aspects 234B to 235B, wherein the compound comprises a linker, wherein the linker couples the at least one IL-2Rγc ligand, at least one other IL-2Rγc ligand, at least one IL-2Rβ ligand, and/or a least one IL-2Rγc ligand.

Aspect 238B. The compound of any one of aspects 234B to 235B, wherein the compound comprises an IL-2Rγc ligand, a linker, and an IL-2Rβ ligand.

Aspect 239B. The compound of aspect 238B, wherein the linker comprises a peptide linker.

Aspect 240B. The compound of any one of aspects 238B to 239B, wherein the C-terminus of the IL-2Rγc ligand is covalently bound to the linker and the C-terminus of the IL-2Rβ ligand is bound to the linker.

Aspect 241B. The compound of any one of aspects 238B to 239B, wherein the N-terminus of the IL-2Rγc ligand is covalently bound to the linker and the C-terminus of the IL-2Rβ ligand is bound to the linker.

Aspect 242B. The compound of any one of aspects 238B to 239B, wherein the C-terminus of the IL-2Rγc ligand is covalently bound to the linker and the N-terminus of the IL-2Rβ ligand is bound to the linker.

Aspect 243B. The compound of any one of aspects 238B to 239B, wherein the N-terminus of the IL-2Rγc ligand is covalently bound to the linker and the N-terminus of the IL-2Rβ ligand is bound to the linker.

Aspect 244B. The compound of any one of aspects 234B to 243B, wherein the compound is selected from a peptide, a conjugate, a fusion protein, and a single chain peptide.

Aspect 245B. The compound of any one of aspects 234B to 244B, wherein the compound comprises at least one moiety configured to modify a property of the conjugate.

Aspect 246B. The compound of aspect 245B, wherein the property is selected from aqueous solubility, polarity, lipophilicity, pharmacokinetic profile, targeting, bioavailability, pH-dependent binding, bioactivity, pharmacodynamics, cellular activity, metabolism, efficacy, caging (reversible incapacitation), and a combination of any of the foregoing.

Aspect 247B. The compound of any one of aspects 245B to 246B, wherein the at least one moiety comprises a small molecule, a polymer, a peptide, or an antibody.

Aspect 248B. The compound of any one of aspects 234B to 247B, comprising a pharmacokinetic moiety.

Aspect 249B. The compound of aspect 248B, wherein the pharmacokinetic moiety comprises a polyethylene glycol.

Aspect 250B. The compound of any one of aspects 234B to 249B, comprising a tumor-targeting moiety.

Aspect 251B. The compound of aspect 250B, wherein the tumor-targeting moiety comprises a tumor-specific antibody, a tumor-specific antibody fragment, a tumor-specific protein, or a tumor-specific peptide.

Aspect 252B. The compound of any one of aspects 234B to 251B, comprising an immune cell-targeting moiety.

Aspect 253B. The compound of any one of aspects 234B to 252B, wherein the compound is an IL-2R agonist.

Aspect 254B. The compound of any one of aspects 234B to 253B, wherein the compound is an IL-2R antagonist.

Aspect 255B. The compound of any one of aspects 234B to 254B, wherein the compound comprises a fusion protein, wherein the IL-2Rα ligand is bound to a fusion partner.

Aspect 256B. The compound of aspect 255B, wherein the fusion protein partner comprises an IgG molecule, an IgG FAb fragment, or an Fc fragment, Aspect 257B. The compound of any one of aspects 255B to 256B, wherein the protein fusion partner comprises an IL-2, a variant of IL-2, a mutant of IL-2, or an IL-2R agonist.

Aspect 258B. The compound of any one of aspects 234B to 257B, wherein the compound comprises a label.

Aspect 259B. The compound of aspect 258B, wherein the label is selected from a radioisotope, a fluorophore, or a combination thereof.

Aspect 260B. The compound of any one of aspects 234B to 259B, wherein the compound comprises a cage to protect peripheral tissues from toxicity of IL-2R activation.

Aspect 261B. The compound of any one of aspects 234B to 260B, wherein the compound comprises a moiety configured to target IL-2R-directed immuno-stimulation of the effector immune cells in the tumor.

Aspect 262B. The compound of any one of aspects 234B to 261B, wherein the compound comprises a cleavable moiety.

Aspect 263B. The compound of any one of aspects 234B to 262B, wherein the compound comprises a moiety that is toxic to cells expressing high levels of the IL-2Rγc subunit.

Aspect 264B. The compound of aspect 263B, wherein the cells expressing high levels of the IL-2Rγc subunit comprise cancer cells.

Aspect 265B. The compound of any one of aspects 234B to 264B, wherein the compound comprises an imaging agent, a diagnostic agent, a targeting agent, a therapeutic agent, or a combination of any of the foregoing.

Aspect 266B. The compound of any one of aspects 234B to 265B, wherein the compound comprises a moiety configured to target IL-2R-directed immuno-stimulation of effector immune cells in a tumor.

Aspect 267B. A pharmaceutical composition comprising; an IL-2Rγc ligand of any one of aspects 1B to 233B; a compound of any one of aspects 234B to 266B; or a combination thereof.

Aspect 268B. The pharmaceutical composition of aspect 267B, further comprising: an IL-2Rβ ligand selected from any one of SEQ ID NO: 1 to SEQ ID NO: 193, SEQ ID NO: 578 to SEQ ID NO: 903, and SEQ ID NO: 1028 to SEQ ID NO: 1043, and SEQ ID NOS 1052-1064 and 1084; a compound comprising an IL-2Rβ ligand selected from any one of SEQ ID NO: 1 to SEQ ID NO: 193, SEQ ID NO: 578 to SEQ ID NO: 903, and SEQ ID NO: 1028 to SEQ ID NO: 1043, and SEQ ID NOS 1052-1064 and 1084; or a combination thereof.

Aspect 269B. A method of treating cancer in a patient, comprising administering to a patient in need of such treatment, a therapeutically effective amount of the pharmaceutical composition of any one of aspects 267B to 268B.

Aspect 270B. The method of aspect 269B, wherein the cancer comprises a solid tumor.

Aspect 271B. A method of treating an autoimmune disease in a patient, comprising administering to a patient in need of such treatment, a therapeutically effective amount of the pharmaceutical composition of any one of aspects 267B to 268B.

Aspect 272B. A method of screening compounds for IL-2Rγc activity, comprising: contacting a cell with, the IL-2Rγc ligand of any one of aspects 1B to 233B; the compound of any one of aspects 234B to 266B; or a combination of any of the foregoing; wherein the cell expresses the IL-2Rγc subunit; and contacting the cell with a test compound; and determining the activity of the test compound.

Aspect 273B. A method of activating the human IL-2 receptor, comprising contacting a cell expressing the human IL-2 receptor in vivo with a compound comprising: the IL-2Rγc ligand of any one of aspects 1B to 233B and an IL-2Rβ ligand selected from any one of SEQ ID NO: 1 to SEQ ID NO: 193, SEQ ID NO: 578 to SEQ ID NO: 903, and SEQ ID NO: 1028 to SEQ ID NO: 1043, and SEQ ID NOS 1052-1064 and 1084, or a compound of any one of aspects 234B to 266B.

Aspect 274B. A method of activating the human IL-2 receptor in a patient, comprising contacting a cell expressing the human IL-2 receptor in vivo with a compound comprising: the IL-2Rγc ligand of any one of aspects 1B to 233B and an IL-2Rβ ligand selected from any one of SEQ ID NO: 1 to SEQ ID NO: 193, SEQ ID NO: 578 to SEQ ID NO: 903, and SEQ ID NO: 1028 to SEQ ID NO: 1043, and SEQ ID NOS 1052-1064 and 1084, or a compound of any one of aspects 234B to 266B.

Aspect 275B. A method of treating a disease in a patient, wherein the IL-2 receptor signaling pathway is associated with the etiology of the disease, comprising administering to a patient in need of such treatment a therapeutically effective amount of a compound comprising the IL-2Rγc ligand of any one of aspects 1B to 233B, or a compound of any one of aspects 234B to 266B.

Aspect 276B. A method of treating a disease in a patient, wherein activation of the IL-2 receptor is effective in treating the disease, comprising administering to a patient in need of such treatment a therapeutically effective amount of a compound comprising the IL-2Rγc ligand of any one of aspects 1B to 233B, or a compound of any one of aspects 234B to 266B.

Aspect 277B. A method of treating a disease in a patient, wherein inhibition of the IL-2 receptor is effective in treating the disease, comprising administering to a patient in need of such treatment a therapeutically effective amount of a compound comprising the IL-2Rγc ligand of any one of aspects 1B to 233B, or a compound of any one of aspects 234B to 266B.

Aspect 278B. A method of treating a disease in a patient, wherein cells expressing the IL-2Rγc subunit are associated with the etiology of the disease, comprising administering to a patient in need of such treatment a therapeutically effective amount of a compound comprising the IL-2Rγc ligand of any one of aspects 1B to 233B, or a compound of any one of aspects 234B to 266B.

Aspect 279B. A method of treating a disease in a patient, wherein activation of IL-2R is effective in treating the disease, comprising administering to a patient in need of such treatment a therapeutically effective amount of a compound comprising the IL-2Rγc ligand of any one of aspects 1B to 233B, or a compound of any one of aspects 234B to 266B.

Aspect 280B. A method of treating a disease in a patient, wherein inhibiting IL-2R is effective in treating the disease, comprising administering to a patient in need of such treatment a therapeutically effective amount of a compound comprising the IL-2Rγc ligand of any one of aspects 1B to 233B, or a compound of any one of aspects 234B to 266B.

Aspect 281B. A method of treating a disease in a patient, wherein reducing the sensitivity of Treg cells to IL-2 is effective in treating the disease, comprising administering to a patient in need of such treatment a therapeutically effective amount of a compound comprising the IL-2Rγc ligand of any one of aspects 1B to 233B, or a compound of any one of aspects 234B to 266B.

Aspect 282B. A method of imaging cells expressing the IL-2Rγc subunit comprising administering to a patient an effective amount of a compound comprising the IL-2Rγc ligand of any one of aspects 1B to 233B, or a compound of any one of aspects 234B to 266B.

Aspect 283B. A method of diagnosing a disease in a patient wherein the disease is associated with cells expressing the IL-2Rγc subunit comprising: administering to a patient an effective amount of a compound comprising the IL-2Rγc ligand of any one of aspects 1B to 233B, or a compound of any one of aspects 234B to 266B; and determining a biodistribution of the compound comprising the IL-2Rγc ligand of any one of aspects 1B to 233B, or a compound of any one of aspects 234B to 266B.

Aspect 284B. A method of treating a disease in a patient, comprising: contacting a biological sample from a patient with an IL-2Rγc ligand of any one of aspects 1B to 233B or a compound comprising an IL-2Rγc ligand of any one of aspects 1B to 233B; determining at least one property associated with binding of the IL-2Rγc ligand to cells of the biological sample; and administering to the patient having the disease a compound comprising an IL-2Rγc ligand of any one of aspects 1B to 233B based on the at least one determined property.

Aspect 285B. The method of aspect 284B, wherein the at least one property comprises: an expression level of the IL-2Rγc subunit in cells of the biological sample; a characterization of cells of the biological sample expressing the IL-2Rγc subunit; and/or a binding affinity ($IC_{50}$) of cells of the biological sample expressing the IL-2Rγc subunit.

Aspect 286B. A method of targeting a compound to cells expressing the IL-2Rγc subunit comprising administering to a patient an effective amount of a compound comprising: the IL-2Rγc ligand of any one of aspects 1B to 233B; and a targeting moiety.

Aspect 287B. A method of delivering a cytotoxic compound to cells expressing the IL-2Rγc subunit comprising administering to a patient an effective amount of a compound comprising: an IL-2Rγc ligand of any one of aspects 1B to 233B; and cytotoxic moiety.

Aspect 288B. A binding site of the IL-2Rγc subunit, wherein, the group of IL-2Rγc ligands having amino acid sequences of SEQ ID NO: 194-210, 904-913, 211-233, 914-920, 234-245, 246-254, 921-922, 265-267, 932-940, and 1065-1082, competitively bind to the binding site with each of the other IL-2Rγc ligands within the group; an IL-2Rγc ligand having amino acid sequence of SEQ ID NO: 948 does not compete for binding to the binding site with the group of IL-2Rγc ligands; and IL-2 does not compete for binding to the binding site with the group of IL-2Rγc ligands.

Aspect 289B. The binding site of aspect 288B, wherein each IL-2Rγc ligand of the group of IL-2Rγc ligands has a binding affinity ($IC_{50}$) to the IL-2Rγc subunit of less than 100 μM.

Aspect 290B. The binding site of any one of aspects 288B to 289B, wherein each IL-2Rγc ligand of the group of IL-2Rγc ligands has a binding affinity (IC$_{50}$) to the IL-2Rβ subunit of greater than 100 μM.

Aspect 291B. The binding site of any one of aspects 288B to 290B, wherein an IL-2Rβ ligand having the amino acid sequence of SEQ ID NO: 58 does not compete for binding to the binding site with the group of IL-2Rγc ligands.

Aspect 292B. The binding site of any one of aspects 288B to 291B, wherein the group of IL-2Rγc ligands consists of peptides having the amino acid sequence of SEQ ID NOS: 198, 202, 224, 236, 248, and 1051.

Finally, it should be noted that there are alternative ways of implementing the embodiments disclosed herein. Accordingly, the present embodiments are to be considered as illustrative and not restrictive, and the claims are not to be limited to the details given herein but may be modified within the scope and equivalents thereof.

What is claimed is:

1. An IL-2Rβ ligand, wherein the IL-2Rβ ligand comprises an amino acid sequence selected from any one of SEQ ID NOS: 589 and 808:

```
                                    SEQ ID NO: 589
L V G W N H Y D C S V A R V G E L C D L

SEQ ID NO: 808
W Y P C W M A Q L G E L C D L D
``` wherein each amino acid sequence independently comprises from 1 to 5 of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

2. The IL-2β ligand of claim 1, wherein the IL-2Rβ ligand exhibits a binding affinity ($IC_{50}$) to the human IL-2Rβ subunit of less than 100 μM.

3. The IL-2Rβ ligand of claim 1, wherein the amino acid sequence is terminated with amino acids -G-G- on the N-terminus, on the C-terminus, or on both the N- and C-termini.

4. A pharmaceutical composition comprising the IL-2Rβ ligand of claim 1.

5. A compound comprising at least one IL-2Rβ ligand of claim 1.

6. The compound of claim 5, wherein the compound is selected from a peptide comprising the IL-2Rβ ligand, a conjugate, and a fusion protein.

7. The compound of claim 5, wherein the compound comprises an IL-2Rα ligand, an IL-2Rγc ligand, or both an IL-2Rα ligand and an IL-2Rγc ligand.

8. A pharmaceutical composition comprising the compound of claim 5.

9. An IL-2β ligand comprising the amino acid sequence of Formula (10) (SEQ ID NO: 578):

$$-X^{191}-X^{192}-X^{193}-X^{194}-X^{195}-C-X^{196}-X^{197}-X^{198}-X^{199}-X^{200}-X^{201}-X^{202}-X^{203}-X^{204}-X^{205}-X^{206}-X^{207}-X^{208}- \quad (10)$$

wherein,
$X^{191}$ is selected from F, H, I, L, M, V, W, and Y;
$X^{192}$ is selected from A, D, E, F, G, H, I, K, L, M, N, P, Q, R, S, T, V, W, and Y;
$X^{193}$ is selected from F, H, I, L, M, V, W, and Y;
$X^{194}$ is selected from F, H, L, W, and Y;
$X^{195}$ is selected from D, E, and P;
$X^{196}$ is selected from F, H, R, W, and Y;
$X^{197}$ is selected from F, I, L, M, and V;
$X^{198}$ is A;
$X^{199}$ is selected from H, K, Q, N, and R;
$X^{200}$ is selected from I, L, and V;
$X^{201}$ is G;
$X^{202}$ is selected from D, E, and Q;
$X^{203}$ is L;
$X^{204}$ is selected from D and E;
$X^{205}$ is selected from F, I, L, M, V, and W;
$X^{206}$ is selected from D, E, F, H, I, L, M, V, W, and Y;
$X^{207}$ is selected from A, C, D, E, F, G, H, I, L, M, N, P, Q, R, S, T, V, W, and Y; and
$X^{208}$ is selected from D and E.

10. The IL-2β ligand of claim 9, wherein the IL-2Rβ ligand exhibits a binding affinity ($IC_{50}$) to the human IL-2Rβ subunit of less than 100 μM.

11. A pharmaceutical composition comprising the IL-2Rβ ligand of claim 9.

12. A compound comprising at least one IL-2Rβ ligand of claim 9.

13. The compound of claim 12, wherein the compound comprises an IL-2Rα ligand, an IL-2Rγc ligand, or both an IL-2Rα ligand and an IL-2Rγc ligand.

14. A pharmaceutical composition comprising the compound of claim 12.

15. An IL-2β ligand comprising the amino acid sequence of Formula (10) (SEQ ID NO: 578):

$$-X^{191}-X^{192}-X^{193}-X^{194}-X^{195}-C-X^{196}-X^{197}-X^{198}-X^{199}-X^{200}-X^{201}-X^{202}-X^{203}-X^{204}-X^{205}-X^{206}-X^{207}-X^{208}- \quad (10)$$

wherein,
$X^{191}$ is selected from F, H, I, L, M, V, W, and Y;
$X^{192}$ is selected from A, D, E, F, G, H, I, K, L, M, N, P, Q, R, S, T, V, W, and Y;
$X^{193}$ is selected from F, H, I, L, M, V, W, and Y;
$X^{194}$ is selected from H, L, and Y;
$X^{195}$ is selected from D and P;
$X^{196}$ is selected from H, R, and W;
$X^{197}$ is selected from I and M;
$X^{198}$ is A;
$X^{199}$ is selected from H, K, Q, and R;
$X^{200}$ is selected from L and V;
$X^{201}$ is G;
$X^{202}$ is selected from D, E, and Q;
$X^{203}$ is L;
$X^{204}$ is selected from D and E;
$X^{205}$ is L;
$X^{206}$ is selected from D, E, F, H, I, L, M, V, W, and Y;
$X^{207}$ is selected from A, C, D, E, F, G, H, I, L, M, N, P, Q, R, S, T, V, W, and Y; and
$X^{208}$ is selected from D and E.

16. The IL-2Rβ ligand of claim 15, wherein,
$X^{194}$ is Y;
$X^{195}$ is selected from D and P;
$X^{196}$ is W;
$X^{197}$ is M;
$X^{198}$ is A;
$X^{199}$ is Q;
$X^{199}$ is selected from H, K, and R;
$X^{200}$ is selected from L and V;
$X^{201}$ is G;
$X^{202}$ is E;
$X^{203}$ is L;
$X^{204}$ is selected from D and E; and
$X^{205}$ is L.

17. The IL-2Rβ ligand of claim 15, wherein,
$X^{194}$ is Y;
$X^{195}$ is selected from D and P;
$X^{196}$ is selected from H, R, and W;
$X^{197}$ is M;
$X^{198}$ is A;
$X^{199}$ is selected from H, K, Q, and R;

$X^{200}$ is selected from L and V;
$X^{201}$ is G;
$X^{202}$ is E;
$X^{203}$ is L;
$X^{204}$ is D; and
$X^{205}$ is L.

18. A pharmaceutical composition comprising the IL-2Rβ ligand of claim 15.

19. A compound comprising at least one IL-2Rβ ligand of claim 15.

20. The compound of claim 19, wherein the compound comprises an IL-2Rα ligand, an IL-2Rγc ligand, or both an IL-2Rα ligand and an IL-2Rγc ligand.

21. A pharmaceutical composition comprising the compound of claim 19.

22. An IL-2Rβ ligand, wherein the IL-2Rβ ligand comprises an amino acid sequence selected from any one of SEQ ID NOS: 580-583, 587, 590, 593, 595, 598, 599, 601-603, 605-607, 610-613, 618-620, 626-628, 631, 633, 635, 637, 639, 642, 644, 646-648, 654-656, 659, 661, 663, 665, 666, 669, 674, 681, 682-684, 692, 695, 701, 706, 710, 711, 714-719, 724, 725, 728, 730, 731, 733, 734, 737, 738, 740-742, 747-749, 752-757, 759, 760, 763, 766, 769, 771, 772, 776, 779, 782, 783, 785, 791-793, 795, 796, 798-800, and 803:

```
                                        SEQ ID NO: 580
L P C W I A Q V G E L C D L

SEQ ID NO: 581
L P C H M A Q L G E L C D L

SEQ ID NO: 582
H P C W M A K V G E L C D L

SEQ ID NO: 583
Y P C H M A N V G E L C D L

SEQ ID NO: 587
G R A D Q V L P C W M A Q L G E L C E L

SEQ ID NO: 590
Y P C W M A Q I G E L C D L

SEQ ID NO: 593
Y D C R F A Q L G E L C D L

SEQ ID NO: 595
T M A S N W Y D C H M A Q V G E L C D L

SEQ ID NO: 598
A Q A R F W H D C S I A H V G E L C D L

SEQ ID NO: 599
T A A E Y W Y P C W M A Q V G E L C D L

SEQ ID NO: 601
Y F C H I A K L G E L C D L

SEQ ID NO: 602
L A C R F A K L G E L C D L

SEQ ID NO: 603
L P C W M A Q L G D L C D L

SEQ ID NO: 605
K L G K G W H D C S V A Q V G E L C D L

SEQ ID NO: 606
D V F K N W Y D C R I A K L G E L C D L

SEQ ID NO: 607
E Y V L K W P D C S S A Q L G E L C E L
```

-continued
```
                                        SEQ ID NO: 610
Y P C R M A K L G E L C D L

SEQ ID NO: 611
Y P C W L A H V G E L C D L

SEQ ID NO: 612
Y P C W M A Q L G E L C D L

SEQ ID NO: 613
Y D C S I A Q L G E L C D L

SEQ ID NO: 618
K V K L S W Y D C S V A Q V G E L C D L

SEQ ID NO: 619
G F L L E W Y D C R I A Q V G E L C D L

SEQ ID NO: 620
Y D S R S Y L P C H M A Q L G D L C D L

SEQ ID NO: 626
L P C W L A K V G D L C D L

SEQ ID NO: 627
D H L Q R W W P C R L A R L G E L C D L

SEQ ID NO: 628
K S G Q R Y Y D C S M A Q L G E L C D L

SEQ ID NO: 631
L P R S G W Y D C S I A H V G E L C D L

SEQ ID NO: 633
Y P C W I A Q V G E L C D L

SEQ ID NO: 635
L D C R F A Q V G D L C D I

SEQ ID NO: 637
Y P C W V A K L G E L C D F

SEQ ID NO: 639
L D E T Y W Y D C H V A Q V G E L C D L

SEQ ID NO: 642
R T Y D P G Q D C R L A Q L G E L C E L

SEQ ID NO: 643
L M C W L A Q L G E L C E L

SEQ ID NO: 644
Y P C W I A K V G E L C D L

SEQ ID NO: 646
Y E C H L A K L G E L C D L

SEQ ID NO: 647
R G R W E W Y D C S I A Q V G E L C D V

SEQ ID NO: 648
R S F E N W Y D C R I A Q L G E L C D L

SEQ ID NO: 654
Y P C H I A Q V G E L C D L

SEQ ID NO: 655
Y P C H V A Q L G E L C D L

SEQ ID NO: 656
Y D C S M A Q L G E L C D L

SEQ ID NO: 659
T R N E F V Y P C W L A Q V G E L C D L

SEQ ID NO: 661
E V N W L Y Y D C R F A H L G E L C D L

SEQ ID NO: 663
Y D C R I A Q V G E L C D L
```

-continued

SEQ ID NO: 665
F D C R F A Q V G D L C D L W S P E H I

SEQ ID NO: 666
L P C W L A N V G E L C D L P G K F E R

SEQ ID NO: 669
Y E C W M A K L G E L C D M Y L E G E I

SEQ ID NO: 674
M S W Y D C W M A Q V G E L C D L H V L

SEQ ID NO: 681
W S W Y D C R I A Q I G E L C D L I T M

SEQ ID NO: 682
W L F Y D C R W A Q V G E L C D L S G D

SEQ ID NO: 683
Y P C W I A Q I G E L C D M D P R A N M

SEQ ID NO: 684
Y D C R F A Q L G E L C D L Y E T D G R

SEQ ID NO: 692
A G W H P C H L A Q V G E L C D L D A L

SEQ ID NO: 694
Y S C G I A K V G E L C D L V D Q E P D

SEQ ID NO: 695
H P C H M A R L G E L C D L H S G V Y D

SEQ ID NO: 701
S K F Y D C R I A K L G E L C D L R S G

SEQ ID NO: 706
Y D C S I A Q L G E L C D V E P W E S M

SEQ ID NO: 710
R H F L D C R I A Q I G D L C D L I G F

SEQ ID NO: 711
P A Y Y D C S I A K V G E L C D L S M M

SEQ ID NO: 714
E Y S L D C R I A Q L G Q L C D L M R W

SEQ ID NO: 715
Y D C R M A K V G E L C D L W W D T L Y

SEQ ID NO: 716
Y D C H M A K L G E L C D L M L G D V T

SEQ ID NO: 717
Y P C H L A H V G E L C D L E G G T E F

SEQ ID NO: 718
Y D C S I A R V G E L C D L L Q D W W P

SEQ ID NO: 719
L P C W L A Q V G E L C D L Q E E T G S

SEQ ID NO: 724
G L T L P C W M A Q L G E L C D L N N A

SEQ ID NO: 725
N L H Y D C R I A Q V G E L C D L T Y E

SEQ ID NO: 728
L P C H L A Q V G E L C D L P S S M L T

SEQ ID NO: 730
T S F H D C R I A N V G E L C D L S I L

SEQ ID NO: 731
V S W Y P C H M A Q V G E L C D L G F S

SEQ ID NO: 733
A V W Y D C R I A Q V G E L C D L V H P

SEQ ID NO: 734
Y D C F F A H V G E L C D L M G N S G T

SEQ ID NO: 737
Y D C S L A Q L G E L C D L T G P S Y G

SEQ ID NO: 738
Y P C H V A Q V G E L C D L S P G L H G

SEQ ID NO: 740
S G W Y P C R I A R L G E L C D L W E G

SEQ ID NO: 741
Q V H Y D C S M A Q L G E L C D L Y D E

SEQ ID NO: 742
L W F Y D C R F A H V G E L C D L E Q T

SEQ ID NO: 747
L H I L K N Y P C Y L A Q V G E L C D L

SEQ ID NO: 748
H I M R T W Y D C S I A Q I G E L C D L

SEQ ID NO: 749
P E R G G W Y D C R F A K L G E L C D L

SEQ ID NO: 752
I S G L G I Y P C W M A H L G E L C D L

SEQ ID NO: 753
G V T Y Q W Y D C S I A L V G E L C D I

SEQ ID NO: 754
Y P C H L A L L G E L C D L

SEQ ID NO: 755
R P W R Q W Y D C S I A R L G E L C D I

SEQ ID NO: 756
Y P C W M A Q V G E L C D L

SEQ ID NO: 757
Y D C S I A K L G E L C D L

SEQ ID NO: 759
N E Q M I P W P C H L A Q L G D L C D L

SEQ ID NO: 760
F P C W L A K L G D L C D L

SEQ ID NO: 763
W S I A N F Y D C R F A H L G E L C D L

SEQ ID NO: 766
Y P C W I A K L G E L C D F

SEQ ID NO: 769
Y P C W L A R V G E L C D L D S G D V H

SEQ ID NO: 771
Y P C W M A H V G E L C D L E G W F G V

SEQ ID NO: 772
G V F Y D C R I A Q L G E L C D L W A S

SEQ ID NO: 776
H P C H M A Q V G E L C D L N F P Y V E

SEQ ID NO: 779
Y P C H M A Q L G E L C D L W S W G D I

SEQ ID NO: 782
K T W Y D C R F A Q L G E L C D L N M N

SEQ ID NO: 783
L P C W L A R L G E L C D L Q Y E Y N D

SEQ ID NO: 785
Y P C R I A K L G E L C D L S E W Q Q L

-continued

```
                              SEQ ID NO: 791
K V W Y P C R I A Q V G E L C D L D Q F

SEQ ID NO: 792
G E W Y D C R I A Q V G E L C D L W P V

SEQ ID NO: 793
Y P C W F A K L G E L C D L G L T D T K

SEQ ID NO: 795
Q F W L G C W M A Q V G E L C D L D Q P

SEQ ID NO: 796
Y T W L D C S V A Q L G Q L C D L W S M

SEQ ID NO: 798
G D L V M F Y D C R F A R V G E L C D L

SEQ ID NO: 799
R L F D P D Q N C R F A L L G E L C L L

SEQ ID NO: 800
G S V W E F Y D C F I A R V G E L C D L

SEQ ID NO: 803
Y P C W M A Q V G E L C D L F L E S V P.
```

23. The IL-2Rβ ligand of claim 22, wherein the amino acid sequence is terminated with amino acids -G-G- on the N-terminus, on the C-terminus, or on both the N- and C-termini.

24. The IL-2Rβ ligand of claim 22, wherein each amino acid sequence independently comprises from 1 to 5 of the following conservative substitutions: amino acids having a small hydrophobic side chain comprising alanine (A), glycine (G), proline (P), serine (S), or threonine (T); amino acids having a hydroxyl-containing side chain comprising serine (S), threonine (T), or tyrosine (Y); amino acids having an acidic side chain comprising aspartate (D) or glutamate (E); amino acids having a polar-neutral side chain comprising histidine (H), asparagine (N), glutamine (Q), serine (S), threonine (T), or tyrosine (Y); amino acids having a basic side chain comprising arginine (R), lysine (K), or histidine (H); amino acids having a large hydrophobic side chain comprising isoleucine (I), leucine (L), methionine (M), valine (V), phenylalanine (F), tyrosine (Y), or tryptophan (W); and amino acids having an aromatic side chain comprising phenylalanine (F), histidine (H), tryptophan (W), or tyrosine (Y).

25. The IL-2β ligand of claim 24, wherein the IL-2Rβ ligand exhibits a binding affinity ($IC_{50}$) to the human IL-2Rβ subunit of less than 100 μM.

26. A pharmaceutical composition comprising the IL-2Rβ ligand of claim 22.

27. A compound comprising at least one IL-2Rβ ligand of claim 22.

28. The compound of claim 27, wherein the compound is selected from a peptide comprising the IL-2Rβ ligand, a conjugate, and a fusion protein.

29. The compound of claim 27, wherein the compound comprises an IL-2Rα ligand, an IL-2Rγc ligand, or both an IL-2Rα ligand and an IL-2Rγc ligand.

30. A pharmaceutical composition comprising the compound of claim 27.

* * * * *

UNITED STATES PATENT AND TRADEMARK OFFICE
CERTIFICATE OF CORRECTION

PATENT NO. : 11,358,986 B2
APPLICATION NO. : 16/884661
DATED : June 14, 2022
INVENTOR(S) : William J. Dower et al.

It is certified that error appears in the above-identified patent and that said Letters Patent is hereby corrected as shown below:

In the Specification

At Column 36, Line number 32, delete "$X^{203}—X^{204}—X^{205}—X^{206}—X^{207}—X^{208}—$" and insert -- $X^{203}—C—X^{204}—X^{205}—X^{206}—X^{207}—X^{208}—$ --

At Column 189, Line number 28, delete "$X^{203}—X^{204}—X^{205}—X^{206}—X^{207}—X^{208}—$" and insert -- $X^{203}—C—X^{204}—X^{205}—X^{206}—X^{207}—X^{208}—$ --

In the Claims

At Column 711, Claim number 9, Line number 53, delete "$X^{203}—X^{204}—X^{205}—X^{206}—X^{207}—X^{208}—$" and insert -- $X^{203}—C—X^{204}—X^{205}—X^{206}—X^{207}—X^{208}—$ --

At Column 712, Claim number 15, Line number 24, delete "$X^{203}—X^{204}—X^{205}—X^{206}—X^{207}—X^{208}—$" and insert -- $X^{203}—C—X^{204}—X^{205}—X^{206}—X^{207}—X^{208}—$ --

Signed and Sealed this
Twenty-sixth Day of December, 2023

Katherine Kelly Vidal
*Director of the United States Patent and Trademark Office*